US012655147B1

(12) United States Patent
Sumikawa et al.

(10) Patent No.: US 12,655,147 B1
(45) Date of Patent: Jun. 16, 2026

(54) FUSED RING COMPOUND AND PHARMACEUTICAL CONTAINING SAME

(71) Applicant: KAKEN PHARMACEUTICAL CO., LTD., Tokyo (JP)

(72) Inventors: Yoshitake Sumikawa, Kyoto (JP); Issei Akahoshi, Kyoto (JP); Masaya Kato, Kyoto (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 19/207,932

(22) Filed: May 14, 2025

Related U.S. Application Data

(63) Continuation of application No. 19/116,232, filed as application No. PCT/JP2023/036453 on Sep. 29, 2023.

(30) Foreign Application Priority Data

Sep. 30, 2022 (JP) ................................ 2022-158409

(51) Int. Cl.

| | |
|---|---|
| *C07D 471/04* | (2006.01) |
| *A61K 31/404* | (2006.01) |
| *A61K 31/4184* | (2006.01) |
| *A61K 31/4192* | (2006.01) |
| *A61K 31/4196* | (2006.01) |
| *A61K 31/4245* | (2006.01) |
| *A61K 31/427* | (2006.01) |
| *A61K 31/433* | (2006.01) |
| *A61K 31/437* | (2006.01) |
| *A61K 31/4439* | (2006.01) |
| *A61K 31/444* | (2006.01) |
| *A61K 31/4725* | (2006.01) |
| *A61K 31/501* | (2006.01) |
| *A61K 31/513* | (2006.01) |
| *A61K 31/5377* | (2006.01) |
| *C07D 235/14* | (2006.01) |
| *C07D 401/04* | (2006.01) |
| *C07D 401/14* | (2006.01) |
| *C07D 403/04* | (2006.01) |
| *C07D 403/10* | (2006.01) |
| *C07D 403/14* | (2006.01) |
| *C07D 405/04* | (2006.01) |
| *C07D 413/10* | (2006.01) |
| *C07D 417/14* | (2006.01) |

(52) U.S. Cl.

CPC .......... *C07D 471/04* (2013.01); *A61K 31/404* (2013.01); *A61K 31/4184* (2013.01); *A61K 31/4192* (2013.01); *A61K 31/4196* (2013.01); *A61K 31/4245* (2013.01); *A61K 31/427* (2013.01); *A61K 31/433* (2013.01); *A61K 31/437* (2013.01); *A61K 31/4439* (2013.01); *A61K 31/444* (2013.01); *A61K 31/4725* (2013.01); *A61K 31/501* (2013.01); *A61K 31/513* (2013.01); *A61K 31/5377* (2013.01); *C07D 235/14* (2013.01); *C07D 401/04* (2013.01); *C07D 401/14* (2013.01); *C07D 403/04* (2013.01); *C07D 403/10* (2013.01); *C07D 403/14* (2013.01); *C07D 405/04* (2013.01); *C07D 413/10* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 7,223,785 | B2 | 5/2007 | Beaulieu et al. |
| 7,671,058 | B2 | 3/2010 | Tokuyama et al. |
| 7,888,363 | B2 | 2/2011 | Beaulieu et al. |

(Continued)

FOREIGN PATENT DOCUMENTS

| | | |
|---|---|---|
| CN | 115364223 A | 11/2022 |
| EP | 1960398 B1 | 9/2010 |

(Continued)

OTHER PUBLICATIONS

International Search Report and Written Opinion for International Application No. PCT/JP2023/036453 mailed Dec. 19, 2023, 17 pages.

(Continued)

*Primary Examiner* — Leslie A. Royds Draper
(74) *Attorney, Agent, or Firm* — Lathrop GPM LLP; Brian C. Trinque

(57) ABSTRACT

The present invention provides a novel compound that has STAT6 inhibitory activity and is effective for treatment of inflammatory diseases such as atopic dermatitis and for allergic diseases. A compound pharmaceutically acceptable salt thereof expressed by general formula (I) having STAT6 inhibitory activity.

(I)

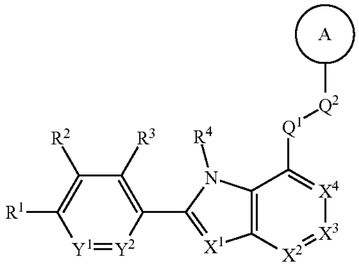

30 Claims, No Drawings

(56) References Cited

U.S. PATENT DOCUMENTS

| | | | |
|---|---|---|---|
| 8,263,612 | B2 | 9/2012 | Bondy et al. |
| 8,722,677 | B2 | 5/2014 | Bondy et al. |
| 9,242,983 | B2 | 1/2016 | Bondy et al. |
| 9,567,339 | B2 | 2/2017 | Bonafoux et al. |
| 9,593,108 | B2 | 3/2017 | Maccoss et al. |
| 10,479,802 | B2 | 11/2019 | Dominguez et al. |
| 10,981,908 | B2 | 4/2021 | Steeneck et al. |
| 11,053,241 | B2 | 7/2021 | Greenwood et al. |
| 11,059,836 | B2 | 7/2021 | Dominguez et al. |
| 11,376,241 | B2 | 7/2022 | Steeneck et al. |
| 11,834,449 | B2 | 12/2023 | Greenwood et al. |
| 2023/0212190 | A1 | 7/2023 | Dominguez et al. |

FOREIGN PATENT DOCUMENTS

| | | | | | |
|---|---|---|---|---|---|
| EP | 2094702 | B1 | | 9/2015 | |
| EP | 3013337 | B1 | | 10/2018 | |
| EP | 3577112 | B1 | | 12/2020 | |
| EP | 3577115 | B1 | | 12/2020 | |
| EP | 3186233 | B1 | | 8/2021 | |
| EP | 3886843 | A1 | | 10/2021 | |
| EP | 4008328 | A1 | | 6/2022 | |
| JP | 2006-241089 | A | | 9/2006 | |
| JP | 2008-208103 | A | | 9/2008 | |
| JP | 2025-156167 | A | | 10/2025 | |
| WO | WO 2007/083978 | A1 | | 7/2007 | |
| WO | WO 2010/003048 | A1 | | 1/2010 | |
| WO | WO 2011/130595 | A2 | | 10/2011 | |
| WO | WO 2014/182928 | A2 | | 11/2014 | |
| WO | WO 2016/033445 | A1 | | 3/2016 | |
| WO | WO 2018/141857 | A1 | | 8/2018 | |
| WO | WO 2020/112937 | A1 | | 6/2020 | |
| WO | WO 2023/115165 | A1 | | 6/2023 | |
| WO | WO 2023/115203 | A1 | | 6/2023 | |
| WO | WO-2024071439 | A1 | * | 4/2024 | ........... C07D 471/04 |
| WO | WO 2024/107017 | A1 | | 5/2024 | |

OTHER PUBLICATIONS

Lee et al., "Design, synthesis and biological evaluation of novel imidazopyridines as potential antidiabetic GSK3β inhibitors", *Bioorganic & Medicinal Chemistry Letters* 22(13):4221-4224 (2012).

Akimoto et al., "Abrogation of Bronchial Eosinophilic Inflammation and Airway Hyperreactivity in Signal Transducers and Activators of Transcription (STAT)6-deficient Mice", *Journal of Experimental Medicine* 187(9):1537-1542 (1998).

Cardoso et al., "The signal transducer and activator of transcription 6 (STAT-6) mediates Th2 inflammation and tissue damage in a murine model of peanut-induced food allergy", *Allergology and immunopathology* 47(6):535-543 (2019).

Igawa et al., "A therapeutic effect of STAT6 decoy oligodeoxynucleotide ointment in aptopic dermatitis: a pilot study in adults", *British Association of Dermatologists, British Journal of Dermatology* 160:1124-1126 (2009).

Kaplan et al., "Stat6 Is Required for Mediating Responses to IL-4 and for the Development of Th2 Cells", *Immunity* 4:313-319 (1996).

Kasaian et al., "An IL-4/IL-13 Dual Antagonist Reduced Lung Inflammation, Airway Hyperresponsiveness, and IgE Production in Mice", American Journal of Respiratory Cell and Molecular Biology 49:37-46 (2013).

Knight et al., "Small molecular targeting of the STAT5/6 Src homology 2 (SH2) domains to inhibit allergic airway disease", *Journal of Biological Chemistry* 293(26):10026-10040 (2018).

Shimoda et al., "Lack of IL-4-induced Th2 response and IgE class switching in mice with disrupted Stat6 gene", *Nature* 380:630-633 (1996).

Takeda et al., "Essential role of Stat6 in IL-4 signalling", *Nature* 380:627-630 (1996).

Takeshita et al., "Essential role of MHC II-independent CD4+ T cells, IL-4 and STAT6 in contact hypersensitivity induced by fluorescein isothiocyanate in the mouse", *International Immunology* 16(5):685-695 (2004).

* cited by examiner

FUSED RING COMPOUND AND PHARMACEUTICAL CONTAINING SAME

CROSS REFERENCE TO RELATED APPLICATIONS

This application is a continuation of U.S. patent application Ser. No. 19/116,232, filed Mar. 27, 2025, which is a 35 U.S.C. § 371 filing of International Patent Application No. PCT/JP2023/036453, filed Sep. 29, 2023, which claims priority to Japanese Patent Application No. 2022-158409, filed Sep. 30, 2022, the contents of each of which are incorporated herein by reference in their entirety.

TECHNICAL FIELD

The present invention relates to a novel fused ring compound, and to a medicament containing the same as an active ingredient. More specifically, the present invention relates to a novel compound having an inhibitory effect on Signal Transducer and Activator of Transcription 6 (hereinafter referred to as STAT6).

BACKGROUND ART

Interleukin 4 (IL-4) and interleukin 13 (IL-13) are cytokines that transmit signals into cells by binding to receptors expressed on the cell membrane. These two cytokines are deeply involved in the induction of type 2 inflammatory responses, which are thought to play an important role in the pathogenesis of inflammatory and allergic diseases such as bronchial asthma, atopic dermatitis, and the like, and are important in the pathogenesis of mouse airway hyperresponsiveness models and mouse contact dermatitis models (Non-Patent Document 1). In other words, suppression of intracellular signal transduction by IL-4 and IL-13 is expected to lead to the treatment of various diseases caused by type 2 inflammatory responses. In fact, dupilumab (human IgG4 monoclonal antibody), an antibody drug that binds to the IL-4 receptor α subunit (IL-4Rα), which mediates intracellular signal transduction by IL-4 and IL-13, has excellent therapeutic effects against inflammatory diseases and allergic diseases, such as atopic dermatitis, bronchial asthma, and chronic sinusitis accompanied by nasal polyps.

STAT6 is a transcription factor responsible for intracellular signal transduction of IL-4 and IL-13. When IL-4 and IL-13 bind to receptors on the cell membrane, the receptor common subunit for these two cytokines IL-4Rα is phosphorylated. STAT6 then binds to the phosphorylated IL-4Rα, and STAT6 is phosphorylated. The phosphorylated STAT6 forms a dimer and moves into the nucleus to promote the expression of various genes as transcription factors. As described above, STAT6 plays important roles in signal transduction into cells by IL-4 and IL-13, and inhibition of activation and function of STAT6 is expected to lead to treatment of inflammatory diseases and allergic diseases in which IL-4 and IL-13 are involved. Actually, it has been reported that the IL-4 signal cannot be transmitted and allergic response is suppressed in STAT6 knockout mice (Non-Patent Documents 2, 3, and 4), and that pathological conditions such as contact dermatitis induced by various inflammatory and allergenic substances (Non-Patent Document 5), bronchial asthma (Non-Patent Document 6), and food allergy (Non-Patent Document 7) are alleviated. In addition, a clinical study in which a decoy oligonucleotide against STAT6 was administered to atopic dermatitis patients reported an improving effect on erythematous and pruritic symptoms (Non-Patent Document 8). Furthermore, it has been reported that a compound that inhibits binding between phosphorylated IL-4Rα and STAT6 reduces the pathology of a mouse allergic lung disease model (Non-Patent Document 9 and Patent Document 1).

Based on the above, STAT6 inhibitors that inhibit the activation and function of STAT6 are considered to be very useful as prophylactic or therapeutic agents for various pathological conditions where IL-4 and IL-13 are involved. Compounds of general formula (I) of the present invention which are described below are neither disclosed nor suggested in any of the conventional technology documents.

Incidentally, the following compounds are known 5,6-fused ring derivatives which are in a different technical field as the present invention. Patent Document 2 discloses a compound, which is a sirtuin modulator, that is expressed by the formula:

[Chem. Fig. 1]

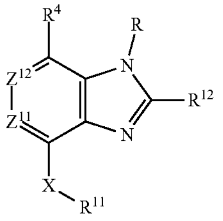

(where each symbol is as defined in Patent Document 2). Patent Document 3 discloses a material used for imaging huntingtin protein, that is expressed by the formula:

[Chem. Fig. 2]

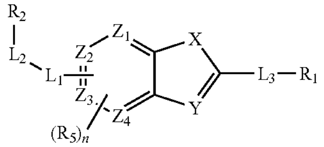

(where each symbol is as defined in Patent Document 3).

However, Patent Document 2 and Patent Document 3 do not specifically disclose the compound of the general formula (I) of the present invention, and neither document describes nor suggests that the compound has a STAT6 inhibitory activity, nor that the compound is useful for treating diseases associated with STAT6.

PRIOR ART DOCUMENTS

Patent Documents

Patent Document 1: International Patent Publication No. 2014/182928
Patent Document 2: International Patent Publication No. 2010/003048
Patent Document 3: International Patent Publication No. 2016/033445

Non-Patent Documents

Non Patent Document 1: American journal of respiratory cell and molecular biology. 2013:49, p. 37 to 46.
Non-Patent Document 2: Nature. 1996:380, p. 627 to 630.
Non-Patent Document 3: Nature. 1996:380, p. 630 to 633.

Non-Patent Document 4: Immunity. 1996:4, p. 313 to 319.
Non-Patent Document 5: International Immunology. 2004: 16, p. 685 to 695.
Non-Patent Document 6: Journal of experimental medicine. 1998:187, p. 1537 to 1542.
Non-Patent Document 7: Allergologia et Immunopathologia. 2019:47, p. 535 to 543.
Non-Patent Document 8: British Journal of Dermatology. 2009:160, p. 1124 to 1126.
Non-Patent Document 9: Journal of Biological Chemistry. 2018:293, p. 10026 to 10040.

SUMMARY OF THE INVENTION

Problem to be Solved by the Invention

An object of the present invention is to provide a new compound that has STAT6 inhibitory activity and is effective for the treatment of inflammatory diseases such as atopic dermatitis and for allergic diseases.

Means for Solving the Problems

As a result of intensive studies to solve the above problems, the present inventors found that a novel compound expressed by the following general formula (I) has excellent STAT6 inhibitory activity, and achieved the present invention on the basis of this finding.

In other words, the present invention is:

(1) A compound expressed by general formula (I):

[Chem. Fig. 3]

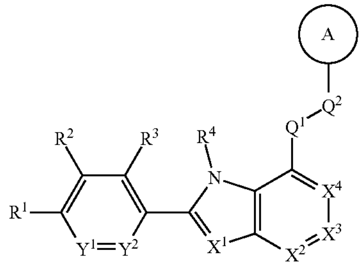

(I)

[where $R^1$ is an optionally substituted 5-membered heteroaryl group, an optionally substituted 5- to 6-membered non-aromatic heterocyclic group, an optionally substituted pyridonyl group, —C(═O)—$NR^aR^b$, or —$NR^c$—C(═O)$R^d$, where $R^a$, $R^b$, $R^c$, and $R^d$ each independently represents a hydrogen atom or a $C_1$-$C_6$ alkyl group;

$R^2$ is a hydrogen atom, an optionally substituted $C_1$-$C_6$ alkyl group, or an optionally substituted $C_1$-$C_6$ haloalkyl group;

or $R^1$ and $R^2$ may together with the carbon atoms to which they are attached form an optionally substituted 5- to 6-membered non-aromatic heterocyclic group;

$R^3$ is a hydrogen atom, an optionally substituted $C_1$-$C_6$ alkyl group, or an optionally substituted $C_1$-$C_6$ haloalkyl group;

$R^4$ is a hydrogen atom, an optionally substituted $C_1$-$C_6$ alkyl group, an optionally substituted $C_1$-$C_6$ haloalkyl group, an optionally substituted $C_1$-$C_3$ alkoxy-$C_2$-$C_6$ alkyl group, an optionally substituted $C_1$-$C_3$ haloalkoxy-$C_2$-$C_6$ alkyl group, or an optionally substituted $C_3$-$C_6$ cycloalkyl-$C_1$-$C_6$ alkyl group;

$Q^1$ is C(═O) or $CH_2$;

$Q^2$ is NH or O;

$X^1$ is N or $CR^5$, where $R^5$ is a hydrogen atom or a halogen atom;

$X^2$, $X^3$, and $X^4$ are each independently N or $CR^6$, where $R^6$ is a hydrogen atom, a halogen atom, a cyano group, an optionally substituted $C_1$-$C_6$ alkyl group, an optionally substituted $C_1$-$C_6$ haloalkyl group, an optionally substituted hydroxy-$C_1$-$C_6$ alkyl group, an optionally substituted cyano-$C_1$-$C_6$ alkyl group, an optionally substituted $C_3$-$C_6$ cycloalkyl group, an optionally substituted $C_1$-$C_6$ alkoxy-$C_1$-$C_6$ alkyl group, an optionally substituted $C_2$-$C_6$ alkenyl group, an optionally substituted $C_2$-$C_6$ alkynyl group, or an optionally substituted phenyl group;

$Y^1$ and $Y^2$ are each independently N or $CR^7$, where $R^7$ is a hydrogen atom, an optionally substituted $C_1$-$C_6$ alkyl group, or an optionally substituted $C_1$-$C_6$ haloalkyl group; and ring A is an optionally substituted phenyl group or an optionally substituted 5-to 6-membered heteroaryl group, where the phenyl group or the 5- to 6-membered heteroaryl group may be further fused with another ring to form an optionally substituted 8- to 10-membered fused ring.]

or a pharmaceutically acceptable salt thereof.

(2) The compound or pharmaceutically acceptable salt thereof according to (1), wherein in general formula (I), $Q^1$ is C(═O) and $Q^2$ is NH.

(3) The compound or pharmaceutically acceptable salt thereof according to (1) or (2), wherein, in general formula (I), $X^1$, $X^2$, and $X^4$ are each independently CH or N.

(4) The compound or pharmaceutically acceptable salt thereof according to any one of (1) to (3), wherein in general formula (I), (i) $X^1$ is CH, $X^2$ is CH, and $X^4$ is CH;

(ii) $X^1$ is N, $X^2$ is CH, and $X^4$ is CH; or (iii) $X^1$ is CH, $X^2$ is CH, and $X^4$ is N.

(5) The compound or pharmaceutically acceptable salt thereof according to any one of (1) to (4), wherein in general formula (I), $Y^1$ and $Y^2$ are each independently CH or N.

(6) The compound or pharmaceutically acceptable salt thereof according to any one of (1) to (5), wherein in general formula (I), (i) $Y^1$ is CH and $Y^2$ is CH;

(ii) $Y^1$ is N and $X^2$ is CH; or (iii) $Y^1$ is CH and $Y^2$ is N.

(7) The compound or pharmaceutically acceptable salt thereof according to any one of (1) to (6), wherein in the general formula (I), ring A is an optionally substituted phenyl group, an optionally substituted pyridinyl group, an optionally substituted pyrazolyl group, or an optionally substituted thiadiazolyl group.

(8) The compound or pharmaceutically acceptable salt thereof according to any one of (1) to (7), wherein in general formula (I), ring A is a ring selected from a group consisting of rings expressed by the following formula

[Chem. Fig. 4]

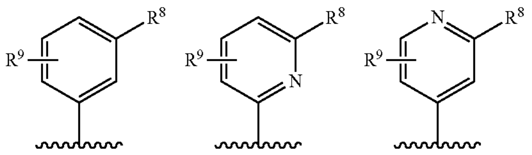

-continued

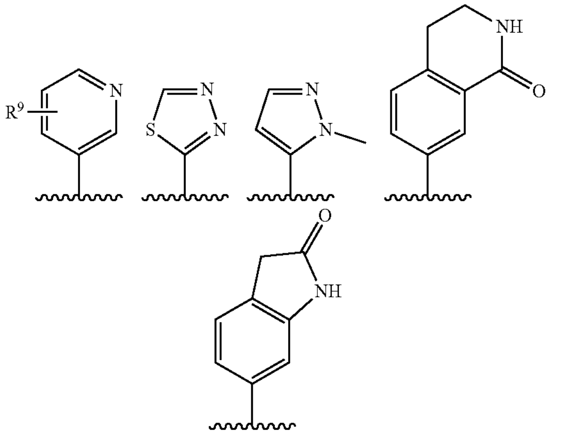

(wherein $R^8$ is a hydrogen atom, a cyano group, a hydroxyl group, an amino group, a methanesulfonylamino group, a sulfonamide group, a $C_1$-$C_6$ alkyl group, a $C_1$-$C_6$ haloalkyl group, a hydroxy-$C_1$-$C_6$ alkyl group, a $C_1$-$C_6$ alkoxy group, a $C_1$-$C_6$ alkoxy-$C_1$-$C_6$alkyl group, a $C_1$-$C_6$ alkylcarbonyl group, an amino-$C_1$-$C_6$ alkyl group, an N-acetylamino-$C_1$-$C_6$ alkyl group, a $C_1$-$C_6$ alkylcarbamoyl group, an N-methyl-$C_1$-$C_6$ alkylcarbamoyl group, an imidazolyl group, a thiazolyl group, or a —C(═O)NHR$^e$ group, where R$^e$ is a $C_1$-$C_6$ alkyl group which may be substituted with a hydrogen atom or a cyano group, a $C_1$-$C_6$ alkylcarbonyl group optionally substituted with a dimethylamino group, or an optionally substituted 5- to 6-membered heteroaryl group; and $R^9$ is a hydrogen atom, a halogen atom, or a $C_1$-$C_6$ alkyl group.)

(9) The compound or pharmaceutically acceptable salt thereof according to any one of (1) to (7), wherein in general formula (I), ring A is a ring selected from a group consisting of rings expressed by the following formula

[Chem. Fig. 5]

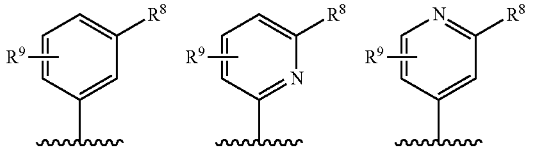

wherein $R^8$ and $R^9$ are as defined above.)

(10) The compound or pharmaceutically acceptable salt thereof according to any one of (1) to (7), wherein in general formula (I), ring A is a ring selected from a group consisting of rings expressed by the following formula

[Chem. Fig. 6]

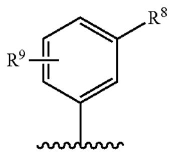

[where $R^8$ is a hydrogen atom, a cyano group, a $C_1$-$C_6$ alkyl group, an imidazolyl group, a thiazolyl group or a —C(═O)—NHR$^e$ group; and R$^e$ is a hydrogen atom, a $C_{16}$ alkyl group which may be substituted with a cyano group, a $C_{16}$ alkylcarbonyl group which may be substituted with a dimethylamino group, or a ring selected from rings expressed by the following formula:

[Chem. Fig. 7]

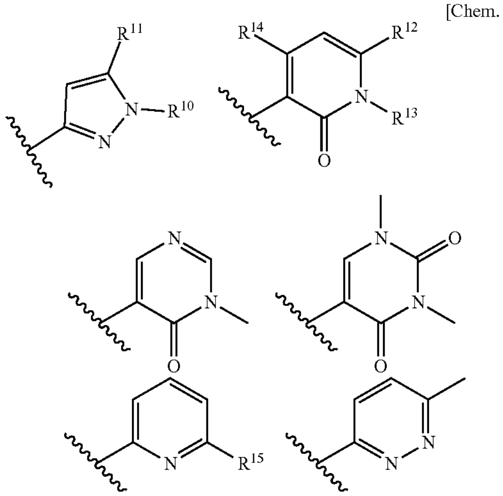

{where $R^{10}$ is a hydrogen atom, a $C_1$-$C_6$ alkyl group optionally substituted with a cyano group, a $C_1$-$C_6$ alkyl group optionally substituted with a $C_3$-$C_6$cycloalkyl group, a $C_1$-$C_6$ alkoxy-$C_1$-$C_6$ alkylcarbonyl group, or a $C_3$-$C_6$ cycloalkyl group; $R^{11}$ is a hydrogen atom, a halogen atom or a cyano group; $R^{12}$ is a hydrogen atom or $C_1$-$C_6$ alkyl group; $R^{13}$ is a hydrogen atom, a $C_1$-$C_6$ alkyl group, or a $C_1$-$C_6$ alkyl group optionally substituted with a halogen atom; $R^{14}$ is a hydrogen atom or a $C_1$-$C_6$ alkyl group; and $R^{15}$ is a hydrogen atom, $C_1$-$C_6$ alkyl group or a $C_1$-$C_6$ alkoxy-$C_1$-$C_6$ alkyl group}].

(11) The compound or a pharmaceutically acceptable salt thereof according to any one of (1) to (10), wherein in general formula (I), $R^1$ is a ring selected from a group consisting of rings expressed by the following formula

[Chem. Fig. 8]

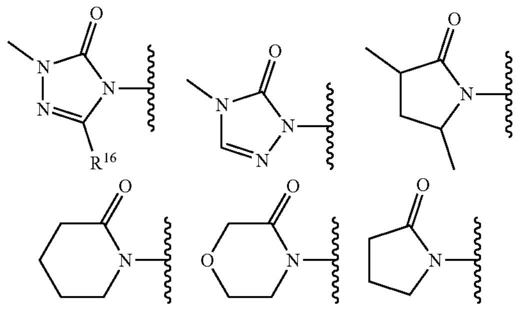

{where, $R^{16}$ is a hydrogen atom, a $C_1$-$C_6$ alkyl group, or a $C_1$-$C_6$ haloalkyl group} a —C(═O—NR$^a$R$^b$ group, or an —NR$^c$—C(═O)R$^d$ group, where R$^a$, R$^b$, R$^c$ and R$^d$ are each independently a hydrogen atom or a $C_1$-$C_6$ alkyl group;

or $R^{12}$ together with the carbon atom to which they are attached form a ring expressed by the formula

[Chem. Fig. 9]

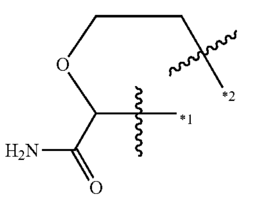

{where, $*^1$ is a carbon atom to which $R^1$ is bonded, $*^2$ is a carbon atom to which $R^2$ is bonded}.

(12) The compound or pharmaceutically acceptable salt thereof according to any one of (1) to (11), wherein in general formula (I), $R^4$ is a $C_1$-$C_6$ alkyl group, $C_1$-$C_6$ haloalkyl group, $C_1$-$C_3$ alkoxy-$C_2$-$C_6$ alkyl group, $C_1$-$C_3$ haloalkoxy-$C_2$-$C_6$ alkyl group, or a $C_3$-$C_6$ cycloalkyl-$C_1$-$C_6$ alkyl group which may be substituted with a cyano group.

(13) The compound or pharmaceutically acceptable salt thereof according to any one of (1) to (12), wherein in general formula (I), $X^2$ is a CH group, and $X^3$ is a $CR^6$ group, where $R^6$ is a hydrogen atom, a halogen atom, a cyano group, a $C_1$-$C_6$ alkyl group, a $C_1$-$C_6$ haloalkyl group, a hydroxy-$C_1$-$C_6$ alkyl group, a cyano-$C_1$-$C_6$ alkyl group, a $C_3$-$C_6$ cycloalkyl group, a $C_1$-$C_6$ alkoxy-$C_1$-$C_6$ alkyl group, a $C_1$-$C_6$ alkenyl group, a $C_1$-$C_6$ alkynyl group or a phenyl group.

(14) The compound or pharmaceutically acceptable salt thereof according to (1), wherein the compound expressed by general formula (I) is either:

[Chem. Fig. 10-1]

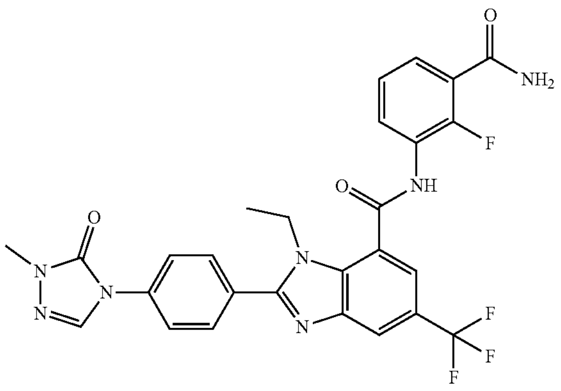

-continued

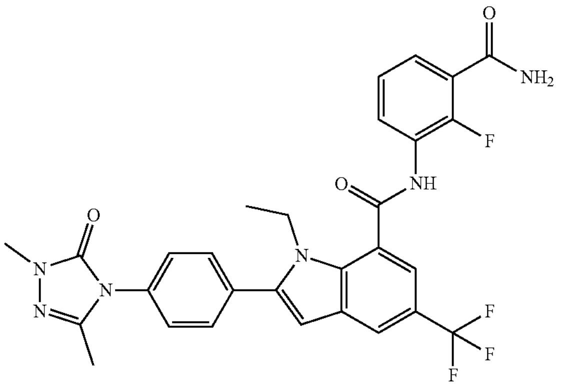

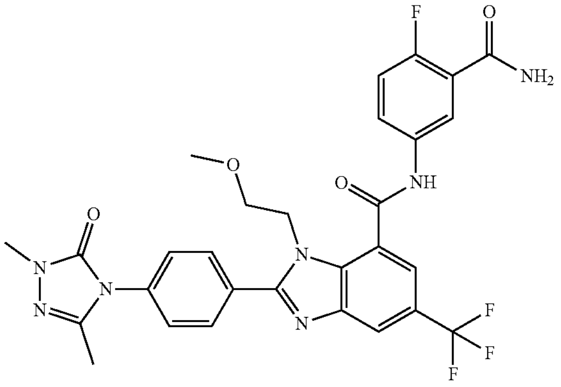

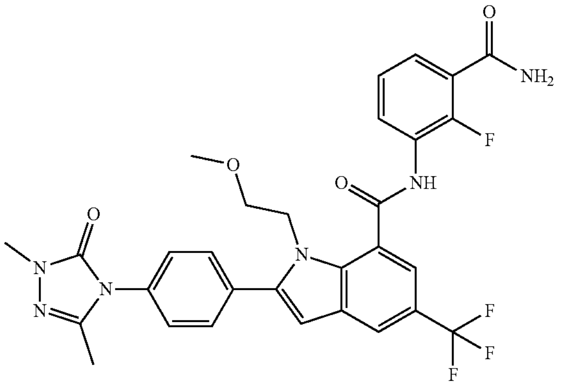

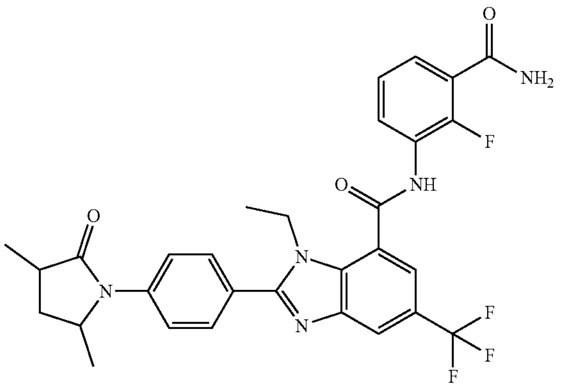

-continued
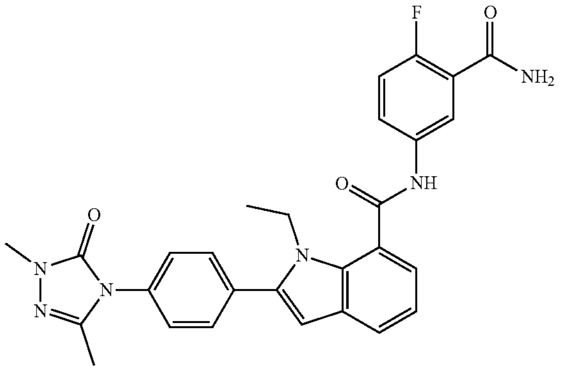
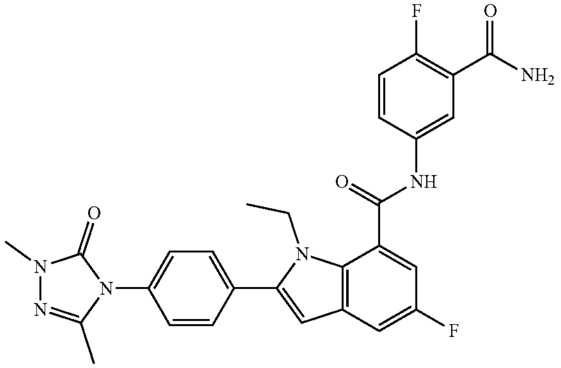
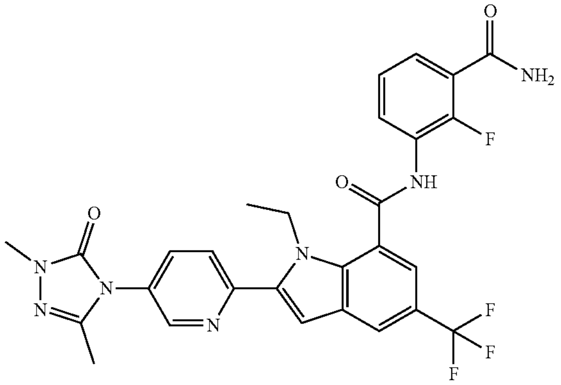
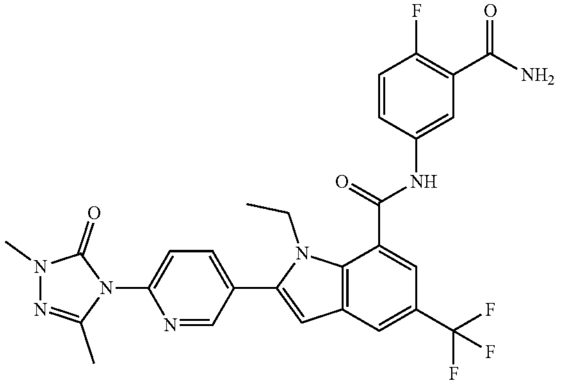
-continued
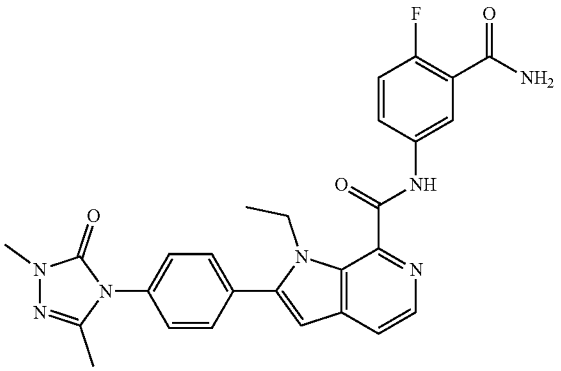
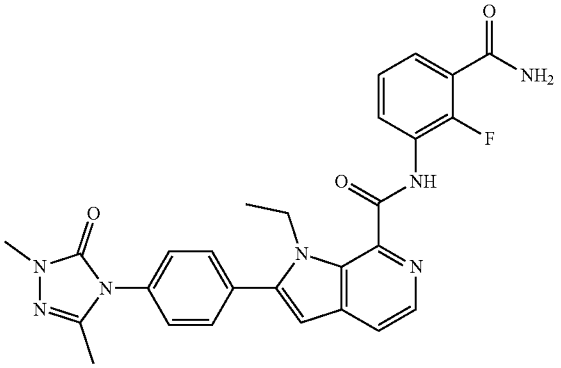
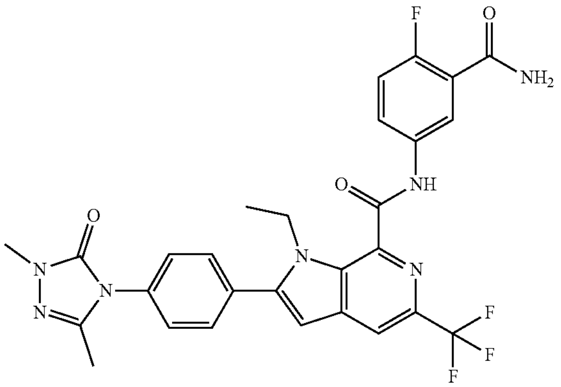
or
[Chem. Fig. 10-2]
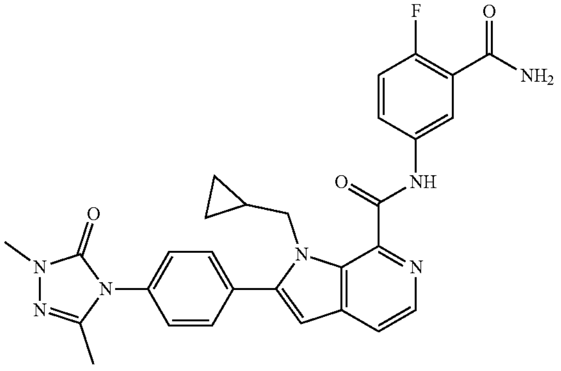

-continued
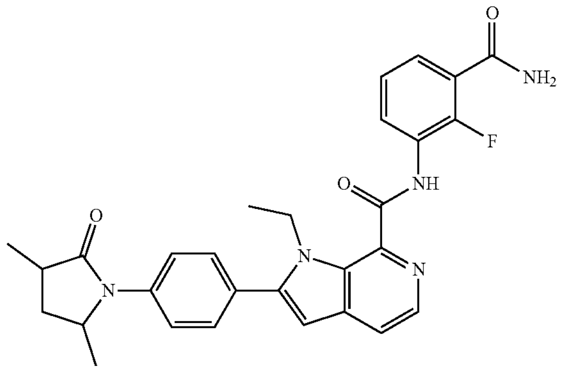
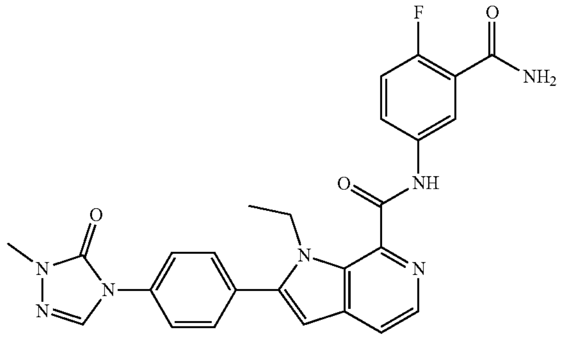
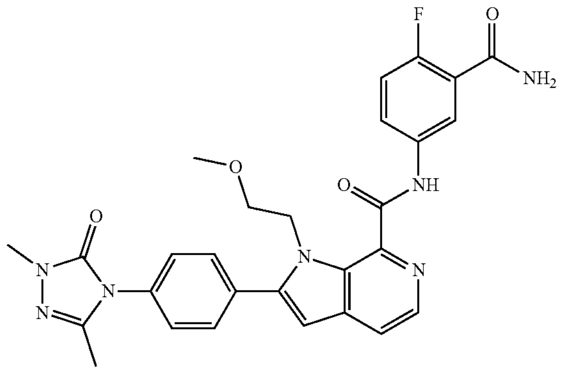
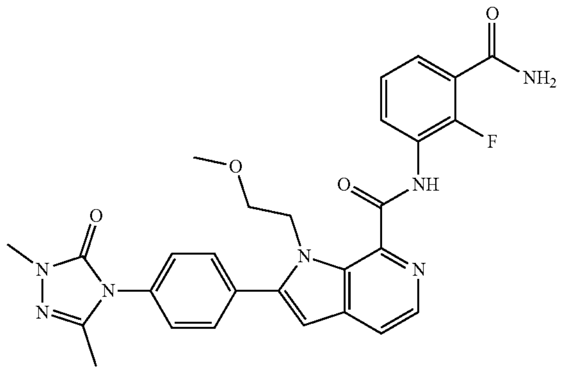
-continued
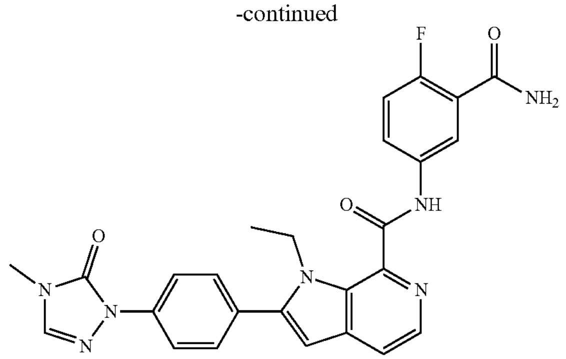
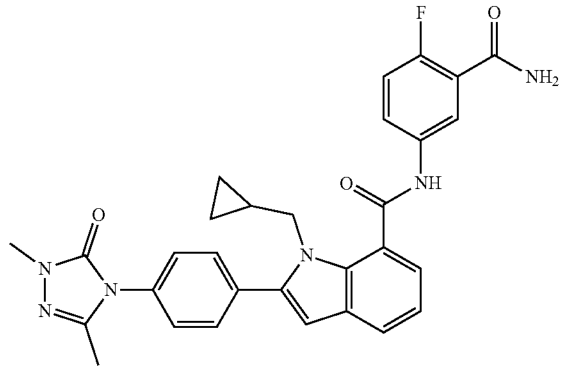
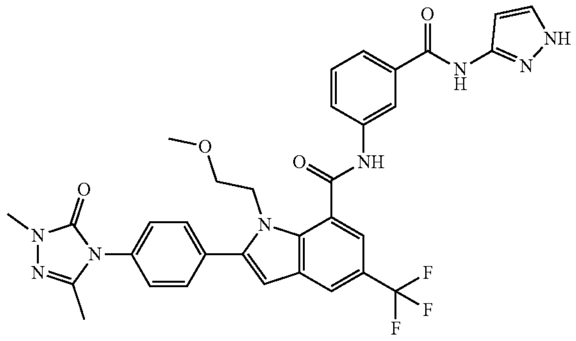
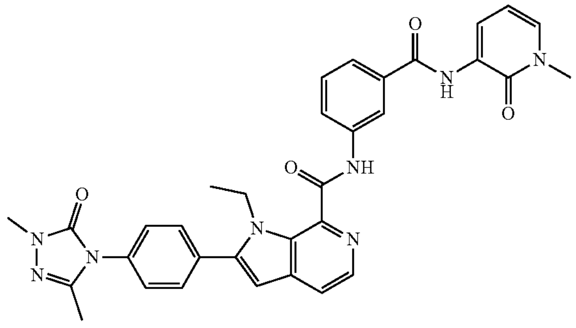
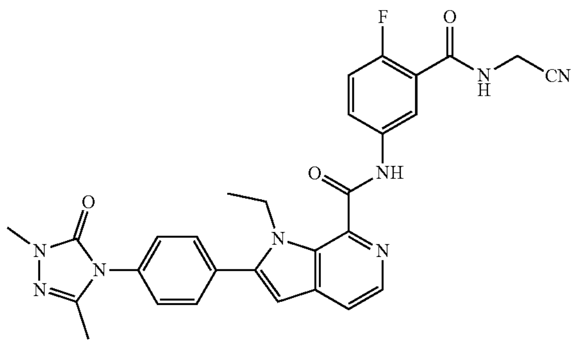

-continued

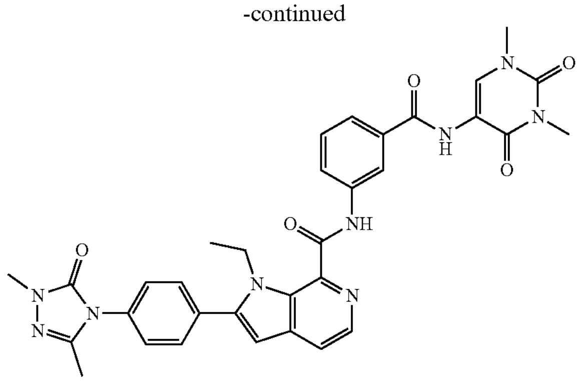

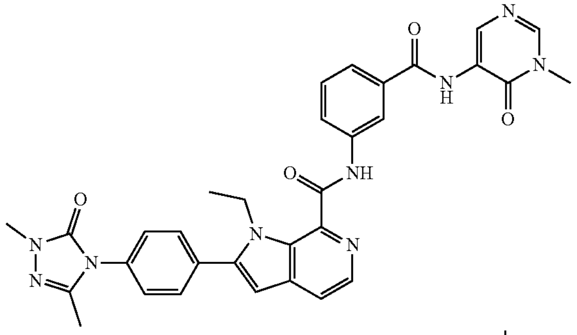

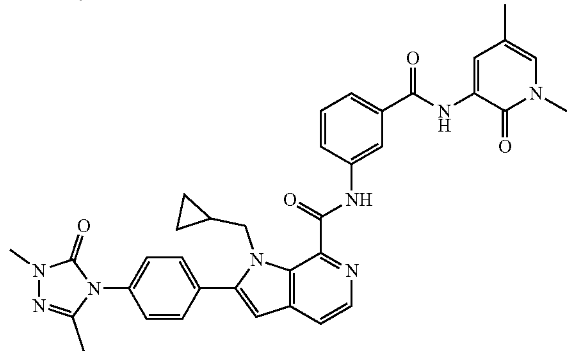

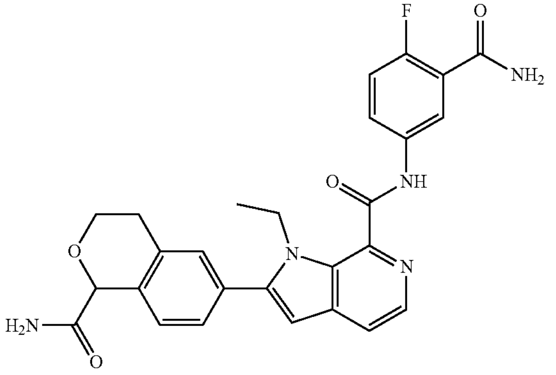

(15) A medicament, comprising the compound according to any one of (1) to (14) or a pharmaceutically acceptable salt thereof as an active ingredient.

(16) A medicament, comprising the compound according to any one of (1) to (14) or pharmaceutically acceptable salts thereof as an active ingredient, which is a prophylactic or therapeutic agent for diseases associated with STAT6.

(17) The medicament according to (16), wherein the diseases associated with STAT6 are allergic diseases and inflammatory diseases.

(18) The medicament according to (16) or (17), wherein the diseases associated with STAT6 are one or more diseases selected from the group consisting of chronic obstructive pulmonary disease, atopic dermatitis, bronchial asthma, bullous pemphigoid, nasal polyps, chronic rhinosinusitis, allergic rhinitis, eosinophilic esophagitis, prurigo, and urticaria.

(19) A method for preventing or treating one or more diseases selected from the group consisting of chronic obstructive pulmonary disease, atopic dermatitis, bronchial asthma, bullous pemphigoid, nasal polyps, chronic rhinosinusitis, allergic rhinitis, eosinophilic esophagitis, prurigo, and urticaria, the method comprising: administering the compound or pharmaceutically acceptable salt thereof according to any one of (1) to (14) to a subject in need thereof.

(20) Use of the compound or pharmaceutically acceptable salt thereof according to any one of (1) to (14) for the manufacture of a prophylactic or therapeutic agent for diseases associated with STAT6.

(21) The use according to (20), wherein the diseases involving STAT6 are allergic and inflammatory diseases.

(22) The use according to (20) or (21), wherein the diseases involving STAT6 are one or more diseases selected from the group consisting of chronic obstructive pulmonary disease, atopic dermatitis, bronchial asthma, bullous pemphigoid, nasal polyps, chronic rhinosinusitis, allergic rhinitis, eosinophilic esophagitis, prurigo, and urticaria.

Effects of the Invention

The present invention can provide a novel compound which has excellent STAT6 inhibitory activity, and is particularly effective for treatment of allergic diseases and inflammatory diseases associated with STAT6.

DESCRIPTION OF THE PREFERRED EMBODIMENTS

The present invention will hereinafter be described.

In the present specification, "n-" refers to normal, "sec-" refers to secondary, and "tert-" refers to tertiary.

First, each substituent in general formula (I) will be described, but the present invention is not limited to substituents exemplified as specific examples.

Specific examples of "halogen atom" include fluorine atoms, chlorine atoms, bromine atoms, and iodine atoms.

"$C_1$-$C_6$ alkyl group" refers to a linear or branched alkyl group having 1 to 6 carbon atoms, and specific examples thereof include methyl groups, ethyl groups, n-propyl groups, isopropyl groups, n-butyl groups, isobutyl groups, tert-butyl groups, sec-butyl groups, n-pentyl groups, tert-pentyl groups, 3-methylbutyl groups (isopentyl groups), neopentyl groups, n-hexyl groups, and the like.

"$C_2$-$C_6$ alkyl group" refers to a linear or branched alkyl group having 2 to 6 carbon atoms, and specific examples thereof include ethyl groups, n-propyl groups, isopropyl groups, n-butyl groups, isobutyl groups, tert-butyl groups, sec-butyl groups, n-pentyl groups, tert-pentyl groups, 3-methylbutyl groups (isopentyl groups), neopentyl groups, n-hexyl groups, and the like.

"$C_1$-$C_6$ haloalkyl group" is a group obtained by substituting one or a plurality of hydrogen atoms of the aforementioned "$C_1$-$C_6$ alkyl group" with a halogen atom. The halogen atom may be bonded at any substitutable position. Specific examples thereof include trifluoromethyl groups, difluoromethyl groups, monofluoromethyl groups, 2-fluoroethyl groups, 2,2-difluoroethyl groups, 1,1-difluoroethyl groups, 2,2,2-trifluoroethyl groups, 1,1,2-trifluoroethyl groups, 1,1,2,2,2-pentafluoroethyl groups, 2-bromo-1,1-difluoroethyl groups, 1,1,1-trifluoropropan-2-yl groups, 1,1-difluoropropan-2-yl groups, 3,3,3-trifluoro-2-methylpropyl groups, 1,1-difluoro-2-methylpropyl groups, and the like.

The term "hydroxy-$C_1$-$C_6$ alkyl group" refers to a group obtained by substituting one of the hydrogen atoms of the aforementioned "$C_1$-$C_6$ alkyl group" with a hydroxy group. The hydroxy group may be attached at any substitutable position. Specific examples thereof include hydroxymethyl groups, 1-hydroxyethyl groups, 2-hydroxyethyl groups, 1-hydroxy-n-propyl groups, 2-hydroxy-n-propyl groups, 3-hydroxy-n-propyl groups, 2-hydroxy-2-methyl-n-propyl groups, 3-hydroxy-2, 2-dimethyl-n-propyl groups, 1-hydroxy-n-propan-2-yl groups, 1-hydroxy-2-methyl-n-propan-2-yl groups, 2-hydroxy-n-propan-2-yl groups, 4-hydroxy-n-butyl groups, 3-hydroxy-n-butyl groups, 3-hydroxy-2-methyl-n-butyl groups, 2-hydroxy-n-butyl groups, 2-hydroxy-2-methyl-n-butyl groups, 2-hydroxy-2-ethyl-n-butyl groups, 3-hydroxy-n-butan-2-yl groups, 3-hydroxy-3-methyl-n-butan-2-yl groups, 3-hydroxy-2,3-dimethyl-n-butan-2-yl groups, and the like.

The term "cyano-$C_1$-$C_6$ alkyl group" refers to the aforementioned "$C_1$-$C_6$ alkyl group" in which one of the hydrogen atoms has been substituted with a cyano group. The hydroxy group may be attached at any substitutable position. Specific examples thereof include cyanomethyl groups, 1-cyanoethyl groups, 2-cyanoethyl groups, 1-cyano-n-propyl groups, 2-cyano-n-propyl groups, 3-cyano-n-propyl groups, 2-cyano-2-methyl-n-propyl groups, 3-cyano-2,2-dimethyl-n-propyl groups, 1-cyano-n-propan-2-yl groups, 1-cyano-2-methyl-n-propan-2-yl groups, 2-cyano-n-propan-2-yl groups, 4-cyano-n-butyl groups, 3-cyano-n-butyl groups, 3-cyano-2-methyl-n-butyl groups, 2-cyano-n-butyl groups, 2-cyano-2-methyl-n-butyl groups, 2-cyano-2-ethyl-n-butyl groups, 3-cyano-n-butan-2-yl groups, 3-cyano-3-methyl-n-butan-2-yl groups and 3-cyano-2,3-dimethyl-n-butan-2-yl groups.

The "$C_3$-$C_6$ cycloalkyl group" represents a monocyclic or bridged cyclic saturated carbocyclic group having 3 to 6 carbon atoms. Specific examples thereof include cyclopropyl groups, cyclobutyl groups, cyclopentyl groups, cyclohexyl groups, bicyclo[1.1.1]pentyl groups, and the like.

The "5- to 6-membered non-aromatic heterocyclic group" refers to a monovalent substituent obtained by removing one hydrogen atom at an arbitrary position from a 5- to 6-membered monocyclic, bridged cyclic, or spirocyclic non-aromatic heterocycle containing 1 to 2 heteroatoms selected from oxygen atoms, sulfur atoms, and nitrogen atoms as ring-forming atoms. Specific examples of such a non-aromatic heterocycle include azetidine, pyrrolidine, piperidine, oxazolidine, isoxazolidine, thiazolidine, isothiazolidine, piperazine, morpholine, thiomorpholine, azepine, diazepine, oxetane, tetrahydrofuran, 1,3-dioxolane, tetrahydropyran, dihydropyran, 1,4-dioxane, and the like.

The "$C_2$-$C_6$ alkenyl group" refers to a linear or branched alkenyl group having 2 to 6 carbon atoms and having one or more double bonds. Specific examples thereof include vinyl groups, 1-propenyl groups, isopropenyl groups, 1-butenyl groups, isobutenyl groups, 2-methyl-1-propenyl groups, 1-methyl-1-propenyl groups, 1-pentenyl groups, 1-hexenyl groups, and the like. The "$C_2$-$C_6$ alkynyl group" refers to a linear or branched alkynyl group having 2 to 6 carbon atoms and having one or more triple bonds. Specific examples thereof include ethynyl groups, 1-propynyl groups, 1-butynyl groups, 3-methyl-1-butynyl groups, 1-pentynyl groups, 3-methyl-1-pentynyl groups, 1-hexynyl groups, and the like.

The "5- to 6-membered heteroaryl group" refers to a monovalent substituent obtained by removing one hydrogen atom at an arbitrary position from a 5- to 6-membered aromatic hetero ring containing 1 to 4 hetero atoms selected from oxygen atoms, sulfur atoms, and nitrogen atoms, as ring-forming atoms. Specific examples of such an aromatic heterocycle include pyrrole, pyrazole, imidazole, 1,2,3-triazole, 1,2,4-triazole, tetrazole, pyridine, pyridone, pyridazine, pyrimidine, pyrazine, uracil, 1,2,3-triazine, 1,2,4-triazine, 1,3,5-triazine, furan, thiophene, thiazole, isothiazole, oxazole, isoxazole, 1,2,4-oxadiazole, 134-oxadiazole, 1,2,4-thiadiazole, 1,3,4-thiadiazole and the like. "5-membered heteroaryl group" refers to a monovalent substituent obtained by removing one hydrogen atom at an arbitrary position from a 5-membered aromatic hetero ring in the "5- to 6-membered heteroaryl group". Specific examples of such an aromatic heterocycle include pyrrole, pyrazole, imidazole, 1,2,3-triazole, 1,2,4-triazole, tetrazole, furan, thiophene, thiazole, isothiazole, oxazole, isoxazole, 1,2,4-oxadiazole, 1,3,4-oxadiazole, 1,2,4-thiadiazole, 1,3,4-thiadiazole, and the like.

"$C_1$-$C_6$ alkoxy group" refers to an alkoxy group in which the alkyl moiety is the aforementioned "$C_1$-$C_6$ alkyl group", and specific examples thereof include methoxy groups, ethoxy groups, n-propoxy groups, isopropoxy groups, n-butoxy groups, sec-butoxy groups, tert-butoxy groups, n-pentyloxy groups, n-hexyloxy groups, and the like.

"$C_1$-$C_3$ alkoxy group" refers to an alkoxy group in which the alkyl moiety is a linear or branched alkyl having 1 to 3 carbon atoms, and specific examples thereof include methoxy groups, ethoxy groups, n-propoxy groups, isopropoxy groups, and the like.

"$C_1$-$C_3$ haloalkoxy group" refers to a group obtained by substituting one or a plurality of hydrogen atoms of the aforementioned "$C_1$-$C_3$ alkoxy group" with a halogen atom. The halogen atom may be bonded at any substitutable position. Specific examples thereof include trifluoromethoxy groups, difluoromethoxy groups, 2,2,2-trifluoroethoxy groups, 2,2-difluoroethoxy groups, 3,3,3-trifluoro-n-propoxy groups, 3,3-difluoro-n-propoxy groups, 2,2-difluoro-n-propoxy groups, and the like.

"$C_1$-$C_6$ alkoxy-$C_1$-$C_6$ alkyl group" refers to the aforementioned "$C_1$-$C_6$ alkyl group" substituted with a "$C_1$-$C_6$ alkoxy group". The alkoxy group may be bonded at any substitutable position. Specific examples thereof include methoxymethyl groups, ethoxymethyl groups, n-propoxymethyl groups, 2-methoxyethyl groups, 2-ethoxyethyl groups, 2-n-propoxyethyl groups, 2-isopropoxyethyl groups, 3-methoxy-n-propyl groups, 2-methoxy-n-propyl groups, and the like.

"$C_1$-$C_3$ alkoxy-$C_2$-$C_6$ alkyl group" refers to the aforementioned "$C_2$-$C_6$ alkyl group" substituted with a "$C_1$-$C_3$ alkoxy group". The alkoxy group atom may be bonded at any substitutable position. Specific examples thereof include 2-methoxyethyl groups, 2-ethoxyethyl groups, 2-n-propoxyethyl groups, 2-isopropoxyethyl groups, 3-methoxy-n-propyl groups, 2-methoxy-n-propyl groups, and the like.

"$C_1$-$C_3$ haloalkoxy-$C_2$-$C_6$ alkyl group" refers to the aforementioned "$C_2$-$C_6$ alkyl group" substituted with a "$C_1$-$C_3$ haloalkoxy group". The haloalkoxy group may be bonded at any substitutable position. Specific examples thereof include 2-(trifluoromethoxy) ethyl groups, 2-(difluoromethoxy) ethyl groups, 2-(2,2,2-trifluoroethoxy) ethyl groups, 2-(2, 2-difluoromethoxy) ethyl groups, 2-(3,3,3-trifluoro-n-propoxy) ethyl groups, 2-(3,3-difluoro-n-propoxy) ethyl groups, 2-(2,2-difluoro-n-propoxy) ethyl groups, and the like.

"$C_3$-$C_6$ cycloalkyl-$C_1$-$C_6$ alkyl group" refers to the aforementioned "$C_1$-$C_6$ alkyl group" substituted with a "$C_3$-$C_6$ cycloalkyl group". The cycloalkyl group may be bonded at any substitutable position. Specific examples thereof include cyclopropylmethyl groups, cyclobutylmethyl groups, cyclopentylmethyl groups, cyclohexylmethyl groups, 2-cyclopropylethyl groups, 3-cyclopropylpropyl groups, and the like.

"$C_1$-$C_6$" alkylcarbonyl group" refers to the aforementioned "$C_1$-$C_6$ alkyl group" substituted with a carbonyl group, and specific examples thereof include formyl groups, acetyl groups, 2-oxoethyl groups, propionyl groups, 2-oxopropyl groups, 3-oxopropyl groups, and the like.

"$C_1$-$C_6$ alkoxy-$C_1$-$C_6$ alkylcarbonyl group" refers to the aforementioned "$C_1$-$C_6$ alkylcarbonyl group" substituted with the aforementioned "$C_1$-$C_6$ alkoxy group". The alkoxy group may be bonded at any substitutable position. Specific examples thereof include methoxycarbonyl groups, ethoxycarbonyl groups, 2-methoxy-2-oxoethyl groups, and the like.

In the present specification, the "8- to 10-membered fused ring" refers to any ring structure formed from a phenyl group or a "5- to 6-membered heteroaryl group" and a ring structure of a group consisting of "$C_3$-$C_6$ cycloalkyl groups", "5- to 6-membered non-aromatic heterocyclic groups", "5- to 6-membered heteroaryl groups", and phenyl groups, that share two atoms forming each ring. The combination of two types of ring structures may be the same or different, and may be, for example, a fused ring containing two phenyl groups, a fused ring containing a phenyl group and "5- to 6-membered non-aromatic heterocyclic group", or a fused ring containing a phenyl group and a "5- to 6-membered heteroaryl group". Specific examples thereof include naphthalene, tetrahydronaphthalene, quinoline, chroman, isochroman, indoline, isoindoline, tetrahydroquinoline, tetrahydroisoquinoline, and the like.

The substituent of the "optionally substituted 5-membered heteroaryl group", "optionally substituted 5- to 6-membered non-aromatic heterocyclic group", and "optionally substituted pyridonyl group" of $R^1$ in general formula (I) is a substituent selected from a group consisting of deuterium, halogen atoms, cyano groups, hydroxyl groups, amino groups, $C_1$-$C_6$ alkyl groups, $C_1$-$C_6$ haloalkyl groups, and oxo groups. One or more of these substituents may be substituted at all substitutable positions.

In the general formula (I), the substituent of the "optionally substituted $C_1$-$C_6$ alkyl group" and the "optionally substituted $C_1$-$C_6$ haloalkyl group" in $R^2$ and $R^3$ is a substituent selected from the group consisting of deuterium, cyano groups, hydroxyl groups, amino groups, and oxo groups. One or more of these substituents may be substituted at all substitutable positions.

In general formula (I), the substituent of the "optionally substituted $C_1$-$C_6$ alkyl group", "optionally substituted $C_1$-$C_6$ haloalkyl group", "optionally substituted $C_1$-$C_3$ alkoxy-$C_2$-$C_6$ alkyl group", "optionally substituted $C_1$-$C_3$ haloalkoxy-$C_2$-$C_6$ alkyl group", and "optionally substituted $C_3$-$C_6$ cycloalkyl-$C_1$-$C_6$ alkyl group" of $R^4$ is a substituent selected from a group consisting of deuterium, halogen atoms, cyano groups, hydroxyl groups, amino groups, $C_1$-$C_6$ alkyl groups, $C_1$-$C_6$ haloalkyl groups, and oxo groups. One or more of these substituents may be substituted at all substitutable positions. However, if the substituent is an "optionally substituted $C_1$-$C_6$ alkyl group", "optionally substituted $C_1$-$C_6$ haloalkyl group", "optionally substituted $C_1$-$C_3$ alkoxy-$C_2$-$C_6$ alkyl group" or "optionally substituted $C_1$-$C_3$ haloalkoxy-$C_2$-$C_6$ alkyl group", halogen atoms, $C_1$-$C_6$ alkyl groups and $C_1$-$C_6$ haloalkyl groups are excluded from the substituents.

In general formula (I), the substituent of the "optionally substituted $C_1$-$C_6$ alkyl group", "optionally substituted $C_1$-$C_6$ haloalkyl group", "optionally substituted hydroxy-$C_1$-$C_6$ alkyl group", "optionally substituted cyano-$C_1$-$C_6$ alkyl group", "optionally substituted $C_3$-$C_6$" cycloalkyl group", "optionally substituted $C_1$-$C_6$ alkoxy-$C_1$-$C_6$ alkyl group", "optionally substituted $C_2$-$C_6$ alkenyl group", and "optionally substituted $C_2$-$C_6$ alkynyl group" of $R^6$ is selected from a group consisting of deuterium, halogen atoms, cyano groups, hydroxyl groups, amino groups, $C_1$-$C_6$ alkyl groups, $C_1$-$C_6$ haloalkyl groups, and oxo groups. One or more of these substituents may be substituted at all substitutable positions. However, if the substituent is an "optionally substituted $C_1$-$C_6$ alkyl group", "optionally substituted $C_1$-$C_6$ haloalkyl group", or "optionally substituted $C_1$-$C_3$ alkoxy-$C_2$-$C_6$ alkyl group", halogen atoms, $C_1$-$C_6$ alkyl groups, and $C_1$-$C_6$ haloalkyl groups are excluded from the substituents.

In general formula (I), the substituent of the "optionally substituted phenyl group" and the "optionally substituted 5- to 6-membered heteroaryl group" of $R^6$ is a substituent selected from the group consisting of deuterium, halogen atoms, cyano groups, hydroxyl groups, amino groups, $C_1$-$C_6$ alkyl groups, and $C_1$-$C_6$ haloalkyl groups. One or more of these substituents may be substituted at all substitutable positions.

In general formula (I), the substituent of the "optionally substituted $C_1$-$C_6$ alkyl group" and the "optionally substituted $C_1$-$C_6$ haloalkyl group" of $R^7$ is a substituent selected from the group consisting of deuterium, cyano groups, hydroxyl groups, and amino groups. One or more of these substituents may be substituted at all substitutable positions.

In general formula (I), the substituents of the "optionally substituted phenyl group" and the "optionally substituted 5- to 6-membered heteroaryl group" in ring A are substituents selected from the group consisting of deuterium, halogen atoms, cyano groups, hydroxyl groups, amino groups, methanesulfonylamino groups, sulfonamide groups, $C_1$-$C_6$ alkyl groups, $C_1$-$C_6$ haloalkyl groups, hydroxy-$C_1$-$C_6$ alkyl groups, $C_1$-$C_6$ alkoxy groups, $C_1$-$C_6$ alkoxy-$C_1$-$C_6$ alkyl groups, $C_1$-$C_6$ alkylcarbonyl groups, amino-$C_1$-$C_6$ alkyl groups, N-acetylamino-$C_1$-$C_6$ alkyl groups, $C_1$-$C_6$ alkylcarbamoyl groups, N-methyl-$C_1$-$C_6$ alkylcarbamoyl groups, imidazolyl groups, thiazolyl groups, and —C(=O)NHR$^e$ ($R^e$ represents a hydrogen atom, deuterium, cyano-$C_1$-$C_6$ alkyl groups, dimethylamino-$C_1$-$C_6$ alkylcarbonyl groups or an optionally substituted 5- to 6-membered heteroaryl groups). One or more of these substituents may be substituted at all substitutable positions.

In general formula (I), the substituent of the "optionally substituted fused ring" is a substituent selected from a group consisting of deuterium, halogen atoms, cyano groups, hydroxyl groups, amino groups, $C_1$-$C_6$ alkyl groups, $C_1$-$C_6$ haloalkyl groups, and oxo groups. One or more of these substituents may be substituted at all substitutable positions.

The substituent of the "optionally substituted 5- to 6-membered heteroaryl group" of $R^e$ is a substituent selected from a group consisting of deuterium, halogen atoms, cyano groups, hydroxyl groups, $C_1$-$C_6$ alkyl groups, $C_1$-$C_6$ haloalkyl groups, hydroxy-$C_1$-$C_6$ alkyl groups, cyano-$C_1$-$C_6$ alkyl groups, $C_3$-$C_6$ cycloalkyl groups, $C_3$-$C_6$ cycloalkyl-$C_1$-$C_6$ alkyl groups, $C_1$-$C_6$ alkoxy groups, $C_1$-$C_6$ alkoxy-$C_1$-$C_6$ alkyl groups, and $C_1$-$C_6$ alkoxy-$C_1$-$C_6$ alkylcarbonyl groups. One or more of these substituents may be substituted at all substitutable positions.

When an asymmetric carbon is present in the compound expressed by general formula (I), all of the racemates, diastereoisomers, and individual optically active forms are included in the present invention.

Furthermore, the compound expressed by general formula I or a pharmaceutically acceptable salt thereof can form a hydrate or a solvate, which are also included in the scope of the present invention.

Preferred atoms or substituents of the compounds of general formula I or pharmaceutically acceptable salts thereof of the present invention are described below.

A preferred example of $Q^1$ is C(═O).

A preferred example of $Q^2$ is NH.

A more preferable example is where $Q^1$ is C(═O) and $Q^2$ is NH.

Preferred examples of $X^1$ are CH and N.

Preferred examples of $X^2$ are CH and N.

Preferred examples of $X^3$ are $CR^6$ or N, where $R^6$ is a hydrogen atom, a halogen atom, a cyano group, a $C_1$-$C_6$ alkyl group, a $C_1$-$C_6$ haloalkyl group, a hydroxy-$C_1$-$C_6$ alkyl group, a cyano-$C_1$-$C_6$ alkyl group, a $C_3$-$C_6$ cycloalkyl group, a $C_1$-$C_6$ alkoxy-$C_1$-$C_6$ alkyl group, a $C_2$-$C_6$ alkenyl group, a $C_2$-$C_6$ alkynyl group, or a phenyl group.

Preferred examples of $X^4$ are CH and N.

Preferred examples of $Y^1$ are N or $CR^7$, where $R^7$ is a hydrogen atom, a $C_1$-$C_6$ alkyl group, or a $C_1$-$C_6$ haloalkyl group.

Preferred examples of $Y^2$ are N and $CR^7$, where $R^7$ is a hydrogen atom, a $C_1$-$C_6$ alkyl group, or a $C_1$-$C_6$ haloalkyl group.

More preferred examples are cases where:

(i) $Y^1$ is CH and $Y^2$ is CH;

(ii) $Y^1$ is N and $X^2$ is CH; or (iii) $Y^1$ is CH and $Y^2$ is N.

An even more preferred example is when $Y^1$ is CH and $Y^2$ is CH. Preferred examples of ring A include rings selected from rings expressed by the following formula

[Chem. Fig. 11]

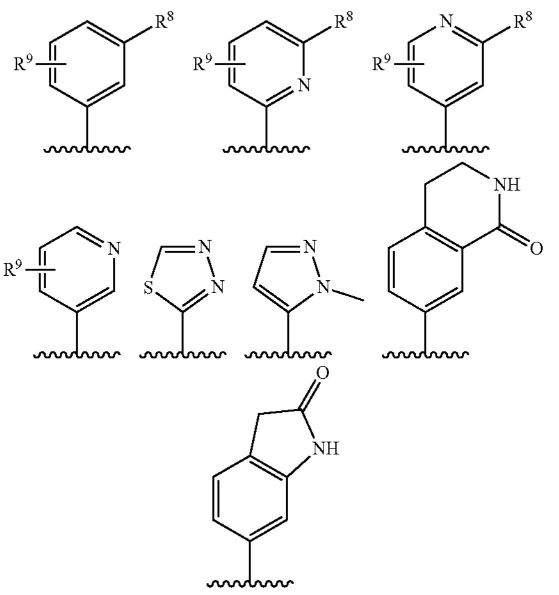

(where $R^8$ is a hydrogen atom, a cyano group, a hydroxyl group, an amino group, a methanesulfonylamino group, a sulfonamide group, a $C_1$-$C_6$ alkyl group, a $C_1$-$C_6$ haloalkyl group, a hydroxy-$C_1$-$C_6$ alkyl group, a $C_1$-$C_6$ alkoxy group, a $C_1$-$C_6$ alkoxy-$C_1$-$C_6$ alkyl group, a $C_1$-$C_6$ alkylcarbonyl group, an amino-$C_1$-$C_6$ alkyl group, an N-acetylamino-$C_1$-$C_6$ alkyl group, a $C_1$-$C_6$ alkylcarbamoyl group, an N-methyl-$C_1$-$C_6$ alkylcarbamoyl group, an imidazolyl group, a thiazolyl group, or a —C(═O)NHR$^e$ group, where $R^e$ is a $C_1$-$C_6$ alkyl group which may be substituted with a hydrogen atom or a cyano group, a $C_1$-$C_6$ alkylcarbonyl group optionally substituted with a dimethylamino group; or

[Chem. Fig. 12]

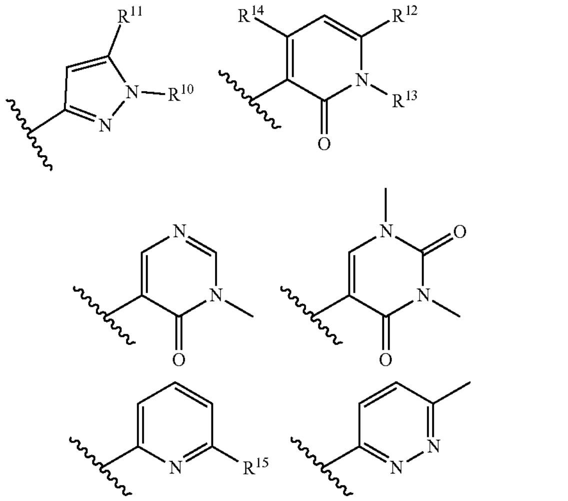

{where $R^{10}$ is a hydrogen atom, a $C_1$-$C_6$ alkyl group optionally substituted with a cyano group, a $C_1$-$C_6$ alkyl group optionally substituted with a $C_3$-$C_6$ cycloalkyl group, a $C_1$-$C_6$ alkoxy-$C_1$-$C_6$ alkylcarbonyl group, or a $C_3$-$C_6$ cycloalkyl group; $R^{11}$ is a hydrogen atom, a halogen atom or a cyano group; $R^{12}$ is a hydrogen atom or $C_1$-$C_6$ alkyl group; $R^{13}$ is a hydrogen atom, a $C_1$-$C_6$ alkyl group, or a $C_1$-$C_6$ alkyl group optionally substituted with a halogen atom; $R^{14}$ is a hydrogen atom or a $C_1$-$C_6$ alkyl group; and $R^{15}$ is a hydrogen atom, $C_1$-$C_6$ alkyl group or a $C_1$-$C_6$ alkoxy-$C_1$-$C_6$ alkyl group}; $R^9$ is a hydrogen atom, a halogen atom, or a $C_1$-$C_6$ alkyl group).

More preferable are rings selected from rings expressed by the following formula:

[Chem. Fig. 13]

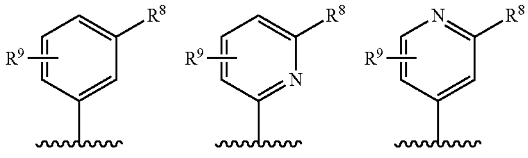

-continued

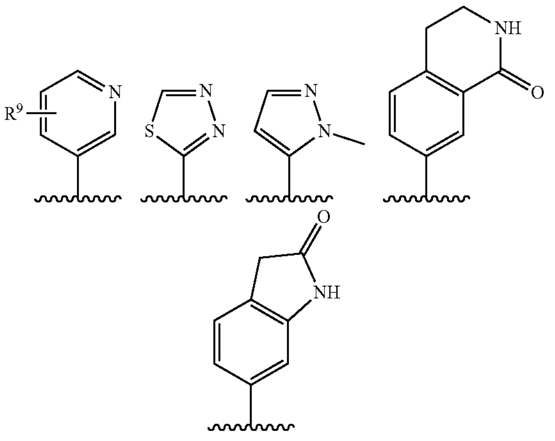

(where $R^8$ is an imidazolyl group, a thiazolyl group or a —C(═O)NHR$^e$ group, wherein R$^e$ is a hydrogen atom, a $C_1$-$C_6$ alkyl group optionally substituted with a cyano group, a $C_1$-$C_6$ alkylcarbonyl group optionally substituted with a dimethylamino group, or a group expressed by the following formula

[Chem. Fig. 14]

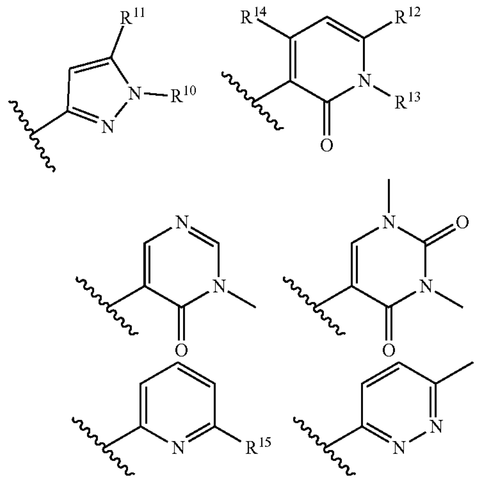

{where $R^{10}$ is a hydrogen atom, a $C_1$-$C_6$ alkyl group optionally substituted with a cyano group, a $C_1$-$C_6$ alkyl group optionally substituted with a $C_3$-$C_6$ cycloalkyl group, a $C_1$-$C_6$ alkoxy-$C_1$-$C_6$ alkylcarbonyl group, or a $C_3$-$C_6$ cycloalkyl group; $R^{11}$ is a hydrogen atom, a halogen atom or a cyano group; $R^{12}$ is a hydrogen atom or $C_1$-$C_6$ alkyl group; $R^{13}$ is a hydrogen atom, a $C_1$-$C_6$ alkyl group, or a $C_1$-$C_6$ alkyl group optionally substituted with a halogen atom; $R^{14}$ is a hydrogen atom or a $C_1$-$C_6$ alkyl group; and $R^{15}$ is a hydrogen atom, $C_1$-$C_6$ alkyl group or a $C_1$-$C_6$ alkoxy-$C_1$-$C_6$ alkyl group}; $R^9$ is a hydrogen atom or a halogen atom.)

In addition, in another embodiment of the present invention, preferred examples of ring A are rings selected from a group consisting of rings expressed by the following formula

[Chem. Fig. 15]

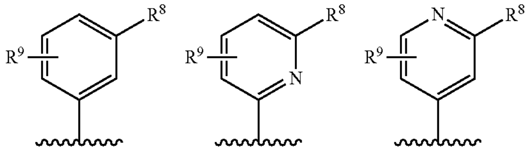

(where $R^8$ is a hydrogen atom, a cyano group, a hydroxyl group, an amino group, a methanesulfonylamino group, a sulfonamide group, a $C_1$-$C_6$ alkyl group, a $C_1$-$C_6$ haloalkyl group, a hydroxy-$C_1$-$C_6$ alkyl group, a $C_1$-$C_6$ alkoxy group, a $C_1$-$C_6$ alkoxy-$C_1$-$C_6$ alkyl group, a $C_1$-$C_6$ alkylcarbonyl group, an amino-$C_1$-$C_6$ alkyl group, an N-acetylamino-$C_1$-$C_6$ alkyl group, a $C_1$-$C_6$ alkylcarbamoyl group, an N-methyl-$C_1$-$C_6$ alkylcarbamoyl group, an imidazolyl group, a thiazolyl group, or a —C(═O)NHR$^e$ group, where R$^e$ is a $C_1$-$C_6$ alkyl group which may be substituted with a hydrogen atom or a cyano group, a $C_1$-$C_6$ alkylcarbonyl group optionally substituted with a dimethylamino group; or

[Chem. Fig. 16]

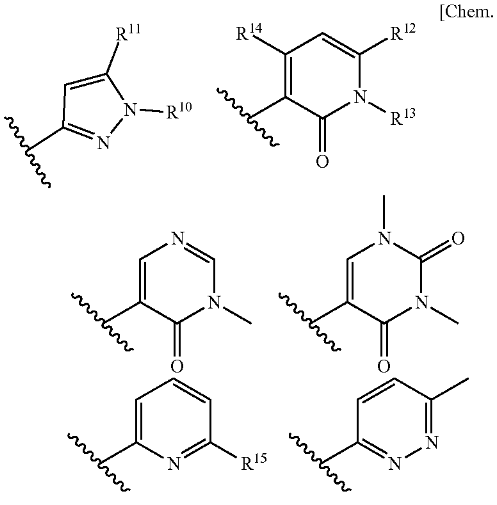

{where $R^{10}$ is a hydrogen atom, a $C_1$-$C_6$ alkyl group optionally substituted with a cyano group, a $C_1$-$C_6$ alkyl group optionally substituted with a $C_3$-$C_6$ cycloalkyl group, a $C_1$-$C_6$ alkoxy-$C_1$-$C_6$ alkylcarbonyl group, or a $C_3$-$C_6$ cycloalkyl group; $R^{11}$ is a hydrogen atom, a halogen atom or a cyano group; $R^{12}$ is a hydrogen atom or $C_1$-$C_6$ alkyl group; $R^{13}$ is a hydrogen atom, a $C_1$-$C_6$ alkyl group, or a $C_1$-$C_6$ alkyl group optionally substituted with a halogen atom; $R^{14}$ is a hydrogen atom or a $C_1$-$C_6$ alkyl group; and $R^{15}$ is a hydrogen atom, $C_1$-$C_6$ alkyl group or a $C_1$-$C_6$ alkoxy-$C_1$-$C_6$ alkyl group}; $R^9$ is a hydrogen atom, a halogen atom, or a $C_1$-$C_6$ alkyl group).

More preferable are rings selected from rings expressed by the following formula:

[Chem. Fig. 17]

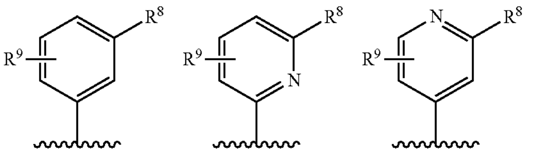

(where $R^8$ is an imidazolyl group, a thiazolyl group or a —C(═O)NHR$^e$ group, wherein R$^e$ is a hydrogen atom, a $C_1$-$C_6$ alkyl group optionally substituted with a cyano group, a $C_1$-$C_6$ alkylcarbonyl group optionally substituted with a dimethylamino group, or a group expressed by the following formula

[Chem. Fig. 18]

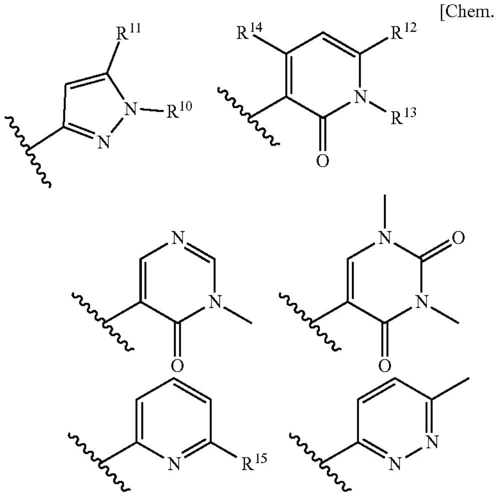

{where $R^{10}$ is a hydrogen atom, a $C_1$-$C_6$ alkyl group optionally substituted with a cyano group, a $C_1$-$C_6$ alkyl group optionally substituted with a $C_3$-$C_6$cycloalkyl group, a $C_1$-$C_6$ alkoxy-$C_1$-$C_6$ alkylcarbonyl group, or a $C_3$-$C_6$ cycloalkyl group; $R^{11}$ is a hydrogen atom, a halogen atom or a cyano group; $R^{12}$ is a hydrogen atom or $C_1$-$C_6$ alkyl group; $R^{13}$ is a hydrogen atom, a $C_1$-$C_6$ alkyl group, or a $C_1$-$C_6$ alkyl group optionally substituted with a halogen atom; $R^{14}$ is a hydrogen atom or a $C_1$-$C_6$ alkyl group; and $R^{15}$ is a hydrogen atom, $C_1$-$C_6$ alkyl group or a $C_1$-$C_6$ alkoxy-$C_1$-$C_6$ alkyl group}; $R^9$ is a hydrogen atom or a halogen atom.)

In addition, in another embodiment of the present invention, preferred examples of ring A are rings selected from a group consisting of rings expressed by the following formula

[Chem. Fig. 19]

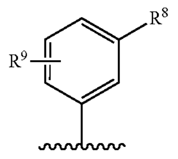

(where $R^8$ is an imidazolyl group, a thiazolyl group or a —C(═O)—NHR$^e$ group, wherein R$^e$ is a hydrogen atom, a $C_1$-$C_6$ alkyl group optionally substituted with a cyano group, a $C_1$-$C_6$ alkylcarbonyl group optionally substituted with a dimethylamino group, or a group expressed by the following formula

[Chem. Fig. 20]

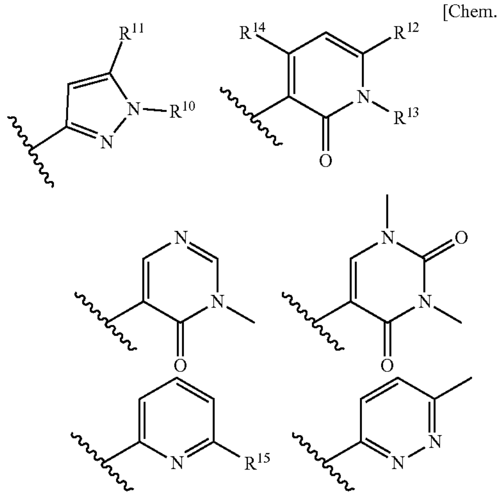

{where $R^{10}$ is a hydrogen atom, a $C_1$-$C_6$ alkyl group optionally substituted with a cyano group, a $C_1$-$C_6$ alkyl group optionally substituted with a $C_3$-$C_6$cycloalkyl group, a $C_1$-$C_6$ alkoxy-$C_1$-$C_6$ alkylcarbonyl group, or a $C_3$-$C_6$ cycloalkyl group; $R^{11}$ is a hydrogen atom, a halogen atom or a cyano group; $R^{12}$ is a hydrogen atom or $C_1$-$C_6$ alkyl group; $R^{13}$ is a hydrogen atom, a $C_1$-$C_6$ alkyl group, or a $C_1$-$C_6$ alkyl group optionally substituted with a halogen atom; $R^{14}$ is a hydrogen atom or a $C_1$-$C_6$ alkyl group; and $R^{15}$ is a hydrogen atom, $C_1$-$C_6$ alkyl group or a $C_1$-$C_6$ alkoxy-$C_1$-$C_6$ alkyl group}; $R^9$ is a hydrogen atom or a halogen atom.)

Preferred examples of $R^1$ are rings selected from a group consisting of rings expressed by the following formula

[Chem. Fig. 21]

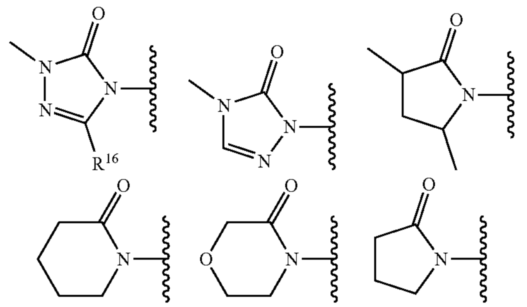

{where $R^{16}$ is a hydrogen atom, a $C_1$-$C_6$ alkyl group, or a $C_1$-$C_6$ haloalkyl group} and a —C(═O—NR$^a$R$^b$ group, or an —NR$^c$—C(═O)R$^d$ group, where R$^a$, R$^b$, R$^c$, and R$^d$ are each independently a hydrogen atom or a $C_1$-$C_6$ alkyl group.

A preferred example of $R^2$ is a hydrogen atom.

Alternatively, a preferred example is where $R^1$ and $R^2$ together with the carbon atom to which they are attached form a ring expressed by the formula

[Chem. Fig. 22]

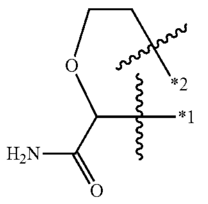

{where $*^1$ is a carbon atom to which $R^1$ is bonded, $*^2$ is a carbon atom to which $R^2$ is bonded}.

A preferred example of $R^3$ is a hydrogen atom.

Preferred examples of $R^4$ are $C_1$-$C_6$ alkyl groups, $C_1$-$C_6$ haloalkyl groups, $C_1$-$C_3$ alkoxy-$C_2$-$C_6$ alkyl groups, $C_1$-$C_3$ haloalkoxy-$C_2$-$C_6$ alkyl groups, and $C_3$-$C_6$ cycloalkyl-$C_1$-$C_6$ alkyl groups optionally substituted with a cyano group. More preferable examples are $C_1$-$C_6$ alkyl groups, $C_1$-$C_3$ alkoxy-$C_2$-$C_6$ alkyl groups, and $C_3$-$C_6$ cycloalkyl-$C_1$-$C_6$ alkyl groups which may be substituted with a cyano group. In particular, compounds selected from the following are particularly preferred.

[Chem. Fig. 23-1]

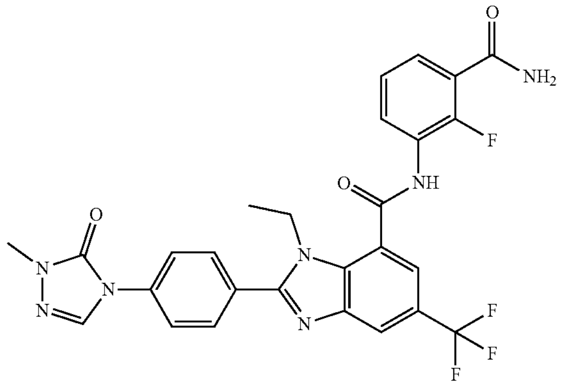

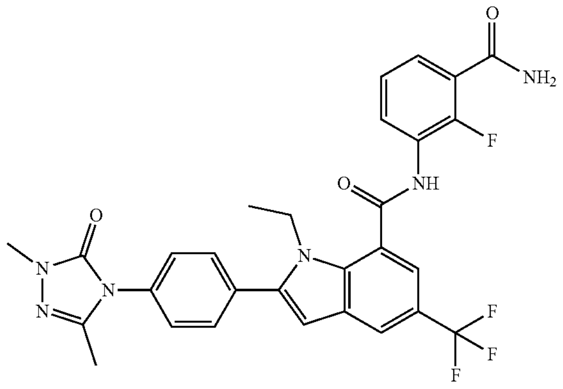

-continued

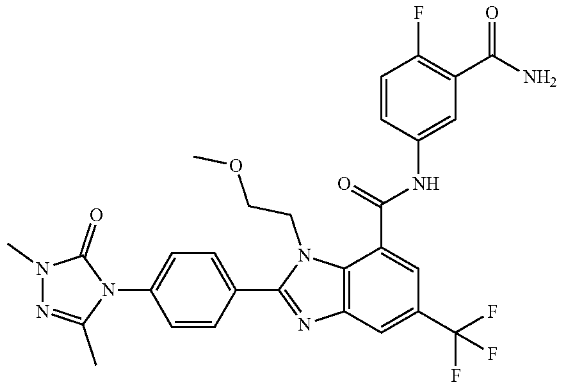

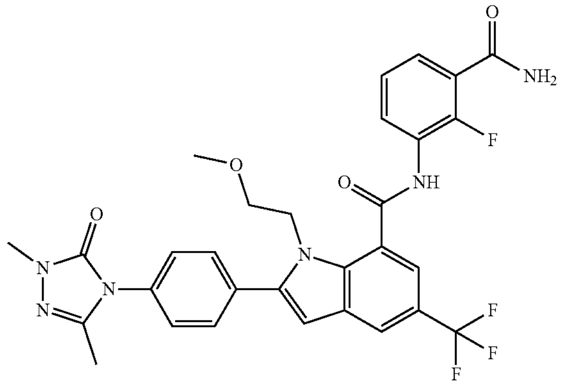

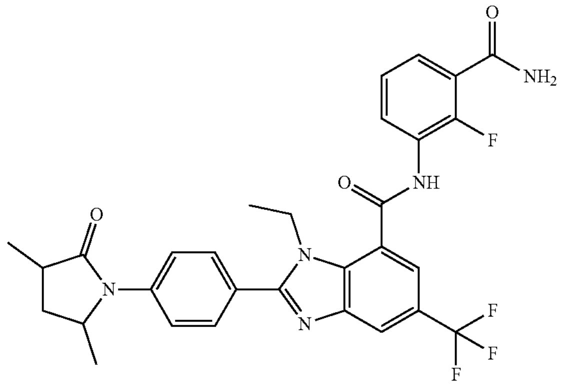

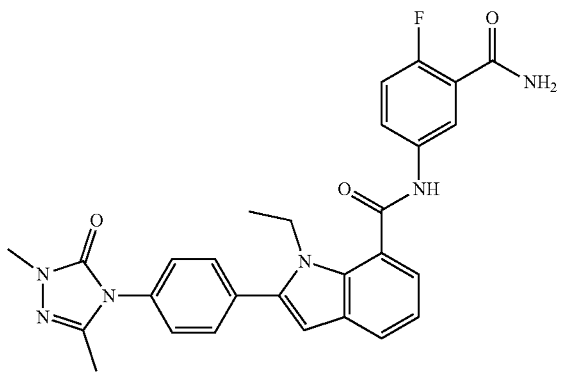

[Chem. Fig. 23-2]
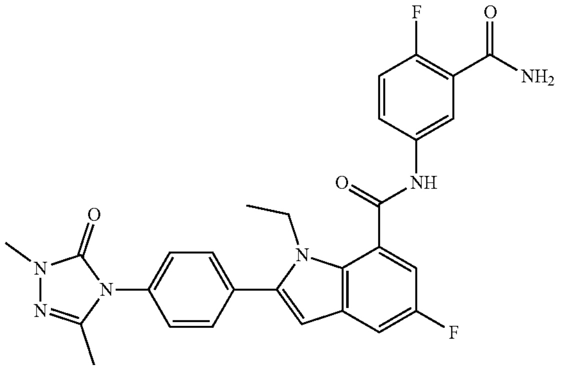
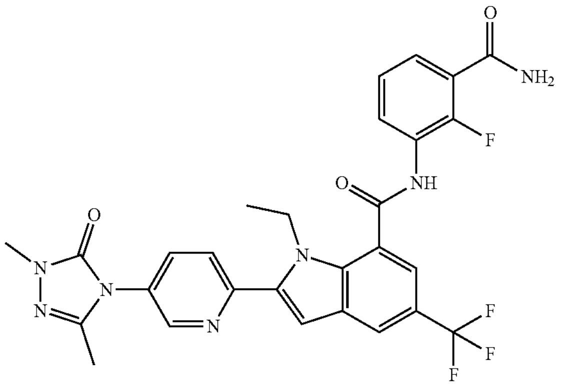
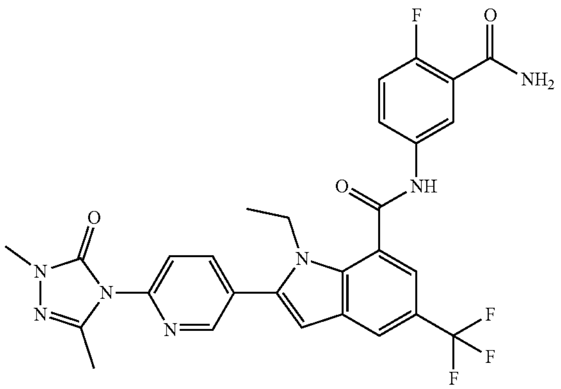
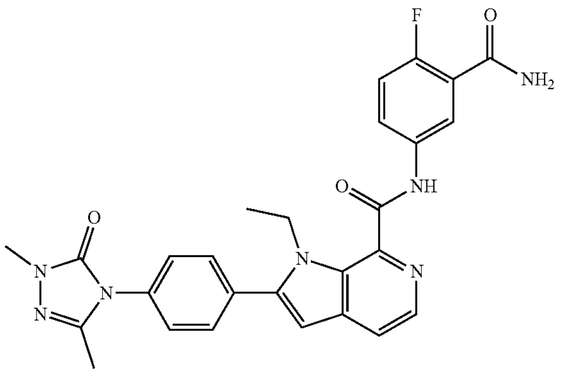
-continued
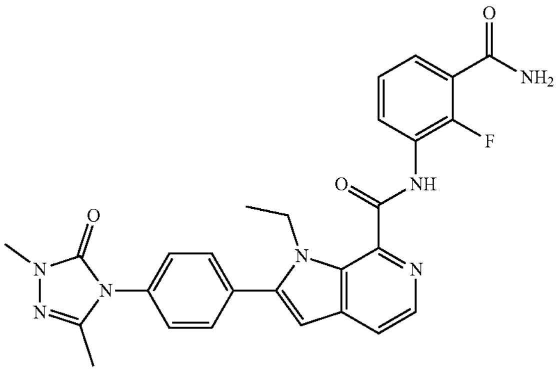
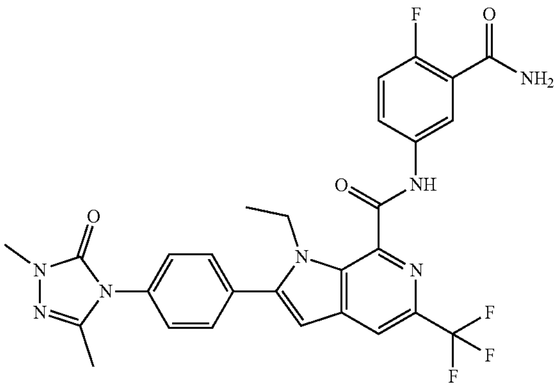
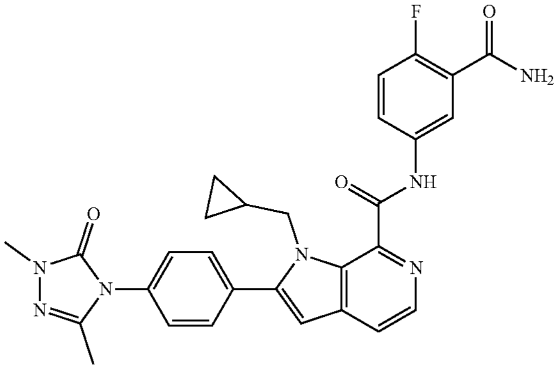
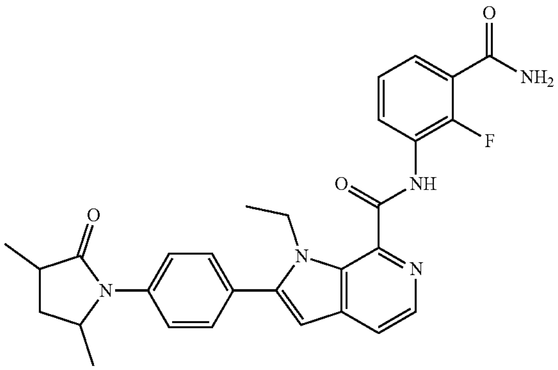

-continued

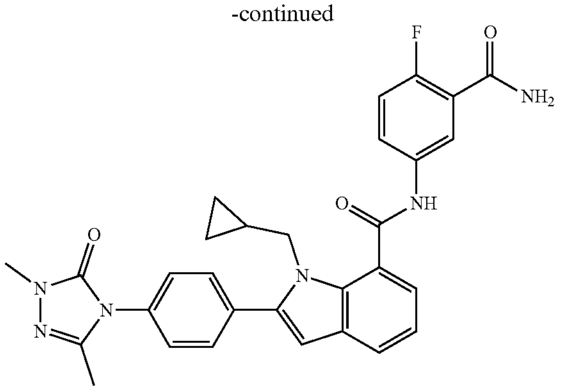

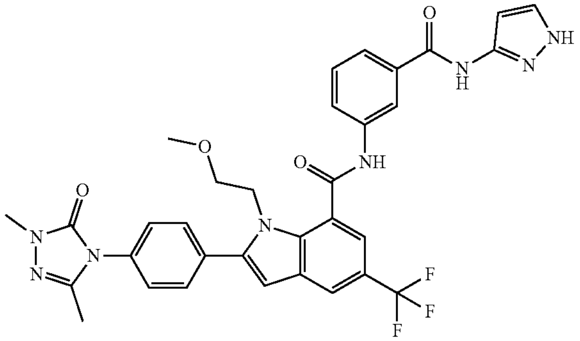

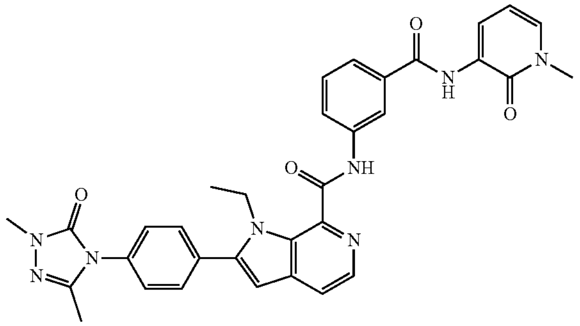

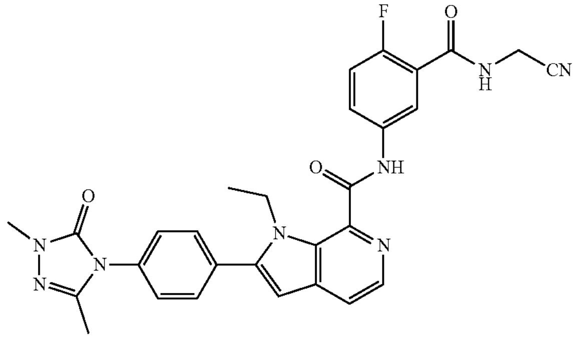

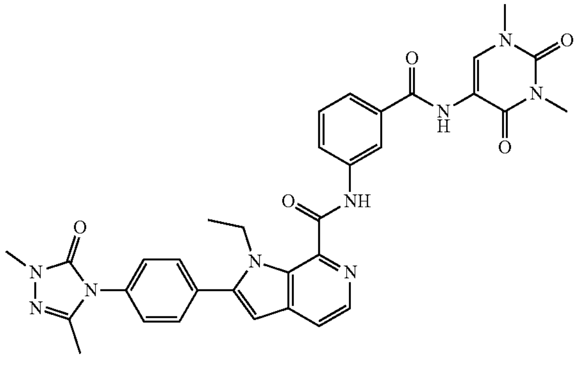

-continued

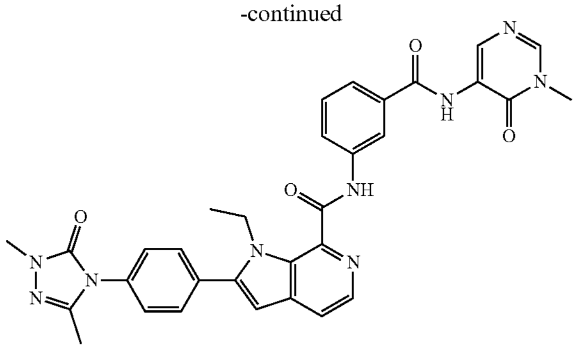

[Chem. Fig. 23-3]

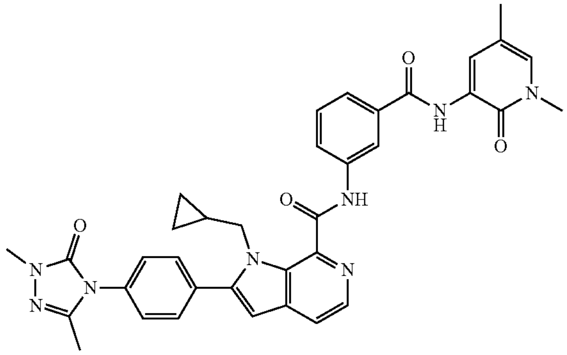

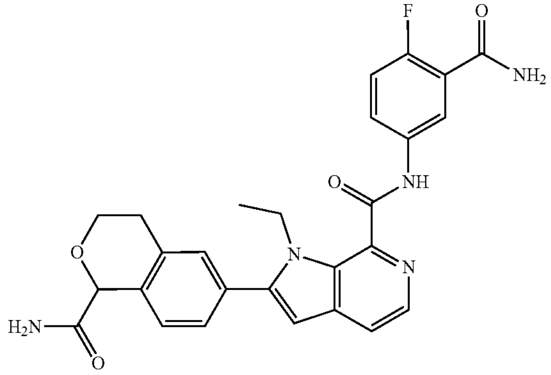

The "salt" of compound (I) is not particularly limited as long as the salt is a pharmaceutically acceptable salt, and examples thereof include inorganic acid salts such as hydrochloride, hydrobromide, nitrate, sulfate, and phosphate; organic carboxylates such as acetate, oxalate, fumarate, maleate, malonate, citrate, succinate, and malate; organic sulfonates such as methanesulfonate, benzenesulfonate, and p-benzenesulfonate; alkali metal salts such as lithium, sodium, and potassium salts; alkaline earth metal salts such as calcium and magnesium salts; and the like.

The compound (I) of the present invention or a pharmaceutically acceptable salt thereof can be produced by various methods, for example, the general synthetic methods described in the following production methods 1 to 27, methods similar to the following production methods, or synthetic methods well known to those skilled in the art can be suitably combined. For example, other compounds of the general formula I or pharmaceutically acceptable salts thereof can be derived by performing a known reaction such as condensation reaction, addition reaction, oxidation reaction, reduction reaction, substitution reaction, halogenation reaction, dehydration reaction, or hydrolysis reaction, or by appropriately combining these reactions. In addition, the salt of compound (I) can be appropriately selected from the aforementioned "salts" for each of the following production methods unless otherwise specified, and the salt can be produced by a method well known to those skilled in the art.

If compound (I) has one or more asymmetric carbon atoms, an operation of resolving stereoisomers may be included in any of the steps described in Production Methods 1 to 27. The method for separating stereoisomers can be any method generally used by those skilled in the art, and for example, separation by column chromatography can be suggested. All starting materials and reagents used for synthesis are either commercially available or can be prepared by methods well known to those skilled in the art using commercially available compounds.

Treatments such as extraction and purification of the compound of the present invention may be carried out by conventional organic chemistry procedures. In each step of producing an intermediate for producing the compound (I), the product may be transferred to the next step as a crude product containing impurities without purification, or a plurality of steps may be continuously performed as in a one pot reaction. Furthermore, compound (I) or the product of each step for producing compound (I) may be obtained in the form of a salt, a solvate or the like. In addition, in all the steps described below, the order of the steps to be performed may be appropriately changed. Note that the method for producing compound (I) of the present invention is not limited to the following examples.

Abbreviations in the respective production methods and examples of the present specification are as follows.

Pin: pinacol

MIDA: N-methyliminodiacetic acid

THF: Tetrahydrofuran

DMF: N, N-Dimethylformamide

DMAc: N,N-Dimethylacetamide

DMSO: Dimethyl sulfoxide tert: tertiary

DABCO: 1,4-diazabicyclo[2.2.2.] octane

DBU: 1,8-diazabicyclo[5.4.0]-7-undecene

DCC: N,N'-dicyclohexylcarbodiimide

DIC: N,N'-diisopropylcarbodiimide

EDC: 1-ethyl-3-(3-dimethylaminopropyl) carbodiimide hydrochloride

HBTU: 1-[bis(dimethylamino)methylene]-1H-benzotriazolium 3-oxide hexafluorophosphate HATU: 1-[bis(dimethylamino)methylene]-1H-1,2,3-triazolo[4,5-b]pyridinium 3-oxide hexafluorophosphate COMU: (1-cyano-2-ethoxy-2-oxoethylidenaminooxy) dimethylamino-morpholino-carbenium hexafluorophosphate TCFH: Chloro-N, N,N',N'-tetramethylformamidinium hexafluorophosphate BOP: Benzotriazol-1-yloxytris(dimethylamino)phosphonium hexafluorophosphate PyBOP: (benzotriazol-1-yloxy)tripyrrolidinophosphonium hexafluorophosphate PyBrop: Bromotripyrrolidino phosphonium hexafluorophosphate DMT-MM: 4-(4,6-dimethoxy-1,3,5-triazin-2-yl)-4-methylmorpholinium chloride T3P: 2,4,6,-tripropyl-1,3,5,2,4,6,-trioxatriphosphorinane-2,4,6-trioxide HOBt: 1-hydroxybenzotriazole HOAt: 1-hydroxy-7-azabenzotriazole Oxyma: Ethyl cyano (hydroxyimino) acetate DIPEA: N,N-diisopropylethylamine DMAP: 4-dimethylaminopyridine DEAD: Diethyl azodicarboxylate DIAD: Diisopropyl azodicarboxylate TMAD: 1,1'-azobis(N, N-dimethylformamide)

ADDP: 1,1'-(azodicarbonyl) dipiperidine

XPhos: 2-dicyclohexylphosphino-2',4',6'-triisopropylbiphenyl

Aphos-PD-G3: [4-(di-tert-butylphosphino)-N, N-dimethylaniline-2-(2'-aminobiphenyl)]palladium (II) methanesulfonic acid Xantphos-PD-G3: [(4,5-bis(diphenylphosphino)-9,9-dimethylxanthene)-2-(2'-amino-1,1'-biphenyl)]palladium (II) methanesulfonate SPhos-PD-G3: (2-dicyclohexylphosphino-2',6'-dimethoxybiphenyl) [2-(2'-amino-1,1'-biphenyl)]palladium (II) methane sulfonic acid BINAP: 2,2'-bis(diphenylphosphino)-1,1'-binaphthalene SPhos: 2-dicyclohexylphosphino-2',6'-dimethoxybiphenyl tBuXPhos: 2-di-tert-butylphosphino-2',4',6'-triisopropylbiphenyl DavePhos: 2-dicyclohexylphosphino-2'-(N, N-dimethylamino) biphenyl XantPhos: 4,5-bis(diphenylphosphino)-9,9-dimethylxanthene BrettPhos: 2-(dicyclohexylphosphino)-3, 6-dimethoxy-2',4',6'-triisopropyl-1,1'-biphenyl QPhos: 1,2,3,4,5-pentaphenyl-1'-(di-tertiary-butylphosphino)ferrocene LDA: Lithium diisopropylamide MTBE: Methyl tertiary butyl ether Boc: Tertiary-butoxycarbonyl Cbz: Benzyloxycarbonyl Fmoc: 9-fluorenylmethyloxycarbonyl TMS: Trimethylsilyl LC: Liquid chromatography MS: Mass spectrometry ESI: Electrospray ionization UV: Ultraviolet light NMR: Nuclear magnetic resonance TEA: Triethylamine TFA: Trifluoroacetic acid NIS: N-iodosuccinimide NMP: N-methylpyrrolidone TBAF: tetrabutylammonium fluoride NBS: N-bromosuccinimide NCS: N-chlorosuccinimide DTT: Dithiothreitol EDTA: Ethylenediaminetetraacetic acid Compound (I) can be produced, for example, by the following production method 1.

<Production Method 1>

[Chem. Fig. 24]

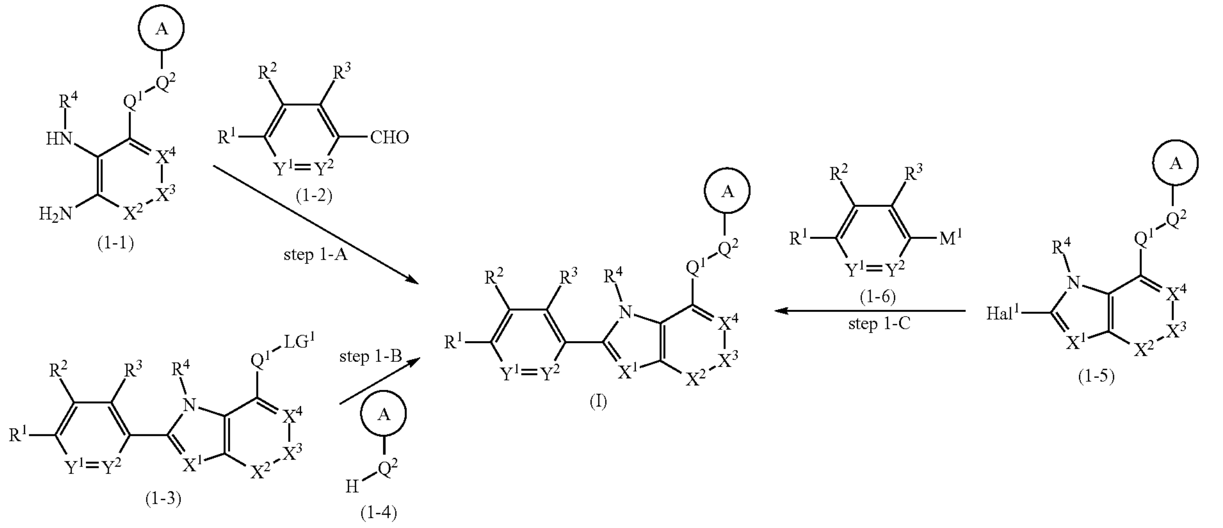

[where $R^1$, $R^2$, $R^3$, $R^4$, $X^1$, $X^2$, $X^3$, $X^4$, $Y^1$, $Y^2$, $Q^1$, $Q^2$, and ring A are as defined above. Furthermore, $LG^1$ is a hydroxyl group or a chloro group, $M^1$ is a boronic acid or a boronic acid-related structure such as $B(OH)_2$, $B(OMe)_2$, B(pin), B(MIDA), or $BF_3K$, and $Hal^1$ is a chloro group, a bromo group, or an iodo group.]

(Step 1-A)

(Step 1-A) can produce Compound (I) by subjecting compound (1-1) to a cyclization reaction with compound (1-2) in air or in an oxygen environment. An acid may be present in order to facilitate the reaction, and examples of the acid include, but are not limited to, acetic acid, trifluoroacetic acid, ammonium acetate, p-toluenesulfonic acid, hydrochloric acid, phosphoric acid, and the like.

Examples of the reaction solvent include, but are not limited to, aromatic hydrocarbons such as benzene, toluene, chlorobenzene, xylene, and the like; halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; aprotic polar solvents such as DMF, DMAc, N-methylpyrrolidone, DMSO, and the like; alcohols such as methanol, ethanol, and the like; water; and mixed solvents thereof, and the reaction can be performed under solvent-free conditions.

The reaction temperature is not particularly limited, and the reaction is usually carried out at room temperature to 200° C. The reaction time is not particularly limited, and is preferably 1 to 24 hours.

(Step 1-B)

In (Step 1-B), compound (I) can be synthesized by subjecting compound (1-3) and compound (1-4) to an addition elimination reaction or substitution reaction in the presence or absence of a base.

Examples of the reaction solvent include, but are not limited to, aromatic hydrocarbons such as benzene, toluene, chlorobenzene, xylene, and the like; halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; aprotic polar solvents such as DMF, DMAc, N-methylpyrrolidone, DMSO, and the like; and mixed solvents thereof.

Examples of the base include, but are not limited to, metal bases such as potassium carbonate, potassium bicarbonate, potassium acetate, sodium acetate, sodium carbonate, sodium bicarbonate, cesium carbonate, lithium carbonate, tripotassium phosphate, potassium tert-butoxide, sodium methoxide, sodium ethoxide, sodium tert-butoxide, potassium fluoride, potassium bis(trimethylsilyl)amide, sodium hydride, and the like; and organic bases such as trimethylamine, triethylamine, diisopropylethylamine, tripropylamine, triisopropylamine, tributylamine, N-methylmorpholine, 1-methylimidazole, pyridine, 4-(N, N-dimethylamino)pyridine, 2,6-dimethylpyridine, 2,6-di-tert-butylpyridine, N, N-dimethylaniline, N,N-diethylaniline, 1,5-diazabicyclo[4.3.0]non-5-ene, 1,4-diazabicyclo[2.2.2]octane (DABCO), 1,1,3,3-tetramethylguanidine, 1,8-diazabicyclo[5.4.0]-7-undecene (DBU), and the like. If $Q^1$ is a carbonyl group and $LG^1$ is a hydroxyl group, the reaction is carried out in the presence of a condensing agent. Examples of the condensing agent include, but are not limited to, DCC, DIC, EDC, HBTU, HATU, COMU, TCFH, BOP, PyBOP, PyBrOP, DMT-MM or T3P. Furthermore, an additive may be added to facilitate the reaction, and examples of the additive include HOBt, HOAt, Oxyma, DMAP, and the like.

If $Q^1$ is a methylene group ($—CH_2—$) and $LG^1$ is a hydroxyl group, the Mitsunobu reaction is performed in the presence of an azodicarboxylic acid derivative and a phosphine derivative. Examples of azodicarboxylic acid derivatives include, but are not limited to, diethyl azodicarboxylate (DEAD), diisopropyl azodicarboxylate (DIAD), N,N,N',N'-tetramethylazodicarboxamide (TMAD), 1,1'-(azodicarbonyl) dipiperidine (ADDP), and the like. Examples of the phosphine derivative include, but are not limited to, triphenylphosphine and tri-n-butylphosphine.

The reaction temperature is not particularly limited, and is usually 0° C. to 150° C.

The reaction time is not particularly limited and is preferably 0.5 hours to 24 hours.

(Step 1-C)

In (Step 1-C), compound (I) can be produced by subjecting compound (1-5) and compound (1-6) to a Suzuki-Miyaura coupling reaction in the presence of a palladium catalyst and a base.

Examples of palladium catalysts include, but are not limited to metallic palladium such as palladium-carbon, palladium black, and the like; palladium salts such as palladium chloride, palladium acetate, and the like; organic palladium complexes such as tetrakis(triphenylphosphine) palladium, dichlorobis(triphenylphosphine) palladium, palladium-1,1'-bis (diphenylphosphino)ferrocene chloride, tris (dibenzylideneacetone) dipalladium, bis[di-tert-butyl(4-dimethylaminophenyl)phosphine]dichloropalladium, bis (acetonitrile)dichloropalladium, chloro(crotyl)(tri-tert-butylphosphine) palladium, XPhos-palladium(crotyl) chloride, and the like; palladacycle complexes such as APhos-Pd-G3, Xantphos-PD-G3, SPhos-PD-G3, and the like; and polymer-immobilized organic palladium complexes such as polymer-supported bis(acetate)triphenylphosphine palladium, polymer-supported di(acetate)dicyclohexylphenylphosphine palladium, and the like. These may be used in combination.

Examples of the base include, but are not limited to, metal bases such as potassium carbonate, potassium bicarbonate, potassium acetate, sodium acetate, sodium carbonate, sodium bicarbonate, cesium carbonate, lithium carbonate, tripotassium phosphate, potassium tert-butoxide, sodium methoxide, sodium ethoxide, sodium tert-butoxide, potassium fluoride, potassium bis(trimethylsilyl)amide, sodium hydride, and the like; and organic bases such as trimethylamine, triethylamine, diisopropylethylamine, tripropylamine, triisopropylamine, tributylamine, N-methylmorpholine, pyridine, 4-(N, N-dimethylamino)pyridine, 2,6-dimethylpyridine, 2,6-di-tert-butylpyridine, N,N-1,5-diazabicyclo [4.3.0]non-5-ene, 1,4-dimethylaniline, N,N-diethylaniline, diazabicyclo[2.2.2]octane (DABCO), 1,1,3,3-tetramethylguanidine, 1,8-diazabicyclo[5.4.0]-7-undecene (DBU), and the like.

Additives may be present to facilitate the reaction, and include, but are not limited to, trialkylphosphines such as trimethylphosphine, tri-tert-butylphosphine, and the like; tricycloalkylphosphines such as tricyclohexylphosphine, and the like; triarylphosphines such as triphenylphosphine, tritolylphosphine, and the like; trialkylphosphites such as trimethylphosphite, triethylphosphite, tributylphosphite, and the like; tricycloalkylphosphites such as tricyclohexylphosphite and the like; triarylphosphites such as triphenylphosphite and the like; imidazolium salts such as 1,3-bis(2,4,6-trimethylphenyl) imidazolium chloride and the like; diketones such as acetylacetone, octafluoroacetylacetone, and the like; amines such as trimethylamine, triethylamine, tripropylamine, triisopropylamine, tributylamine, and the like; 1,1'-bis(diphenylphosphino) ferrocene; 1,4-bis(diphenylphosphino) butane; 2,2'-bis(diphenylphosphino)-1,1'-binaphthyl (BINAP); 2-dicyclohexylphosphino-2',6'-dimethoxybiphenyl (SPhos); 2-dicyclohexylphosphino-2',4',6'-triisopropylbiphenyl (XPhos); 2-(di-tert-butylphosphino)-2', 4',6'-triisopropylbiphenyl (DavePhos); 4,5-(Xantphos); 2-bis(diphenylphosphino)-9, 9-dimethylxanthene (dicyclohexylphosphino)-3,6-dimethoxy-2',4',6'-triisopropyl-1,1'-biphenyl (BrettPhos); 1,2,3,4,5-pentaphenyl-1'-(di-tert-butylphosphino)ferrocene (QPhos); and 2-(di-tert-butylphosphino) biphenyl. These additives may be used alone or in combination.

Examples of the reaction solvent include, but are not limited to, aromatic hydrocarbons such as benzene, toluene, xylene, and the like; aliphatic hydrocarbons such as hexane, heptane, and the like; halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; aprotic polar solvents such as DMF, DMAC, N-methylpyrrolidone, DMSO, and the like; alcohols such as methanol, ethanol, and the like; water; and mixed solvents thereof.

The reaction temperature is not particularly limited, and is usually room temperature to 150° C. The reaction time is not particularly limited and is preferably 0.1 hours to 24 hours.

Compound (2-6), which is one of the aforementioned compounds (1-1), can be produced, for example, by the following production method 2.

<Production Method 2>

[Chem. Fig. 25]

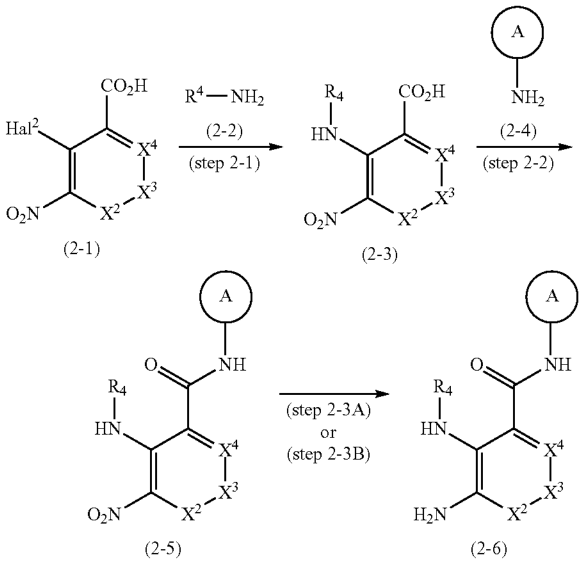

[where $R^4$, $X^2$, $X^3$, $X^4$, and ring A are as defined above.

Furthermore, Hal2 is a fluoro group or a chloro group.]

(Step 2-1)

In (Step 2-1), compound (2-3) can be produced by subjecting compound (2-1) and compound (2-2) to an aromatic nucleophilic substitution reaction in the presence of a base.

Examples of the base include, but are not limited to, metal bases such as potassium carbonate, potassium bicarbonate, potassium acetate, sodium acetate, sodium carbonate, sodium bicarbonate, cesium carbonate, lithium carbonate, tripotassium phosphate, potassium tert-butoxide, sodium tert-butoxide, potassium fluoride, potassium bis(trimethylsilyl)amide, sodium hydride, and the like; and organic bases such as trimethylamine, triethylamine, diisopropylethylamine, tripropylamine, triisopropylamine, tributylamine, N-methylmorpholine, pyridine, 4-(N, N-dimethylamino) pyridine, 2,6-dimethylpyridine, 2,6-di-tert-butylpyridine, N,N-dimethylaniline, N,N-diethylaniline, 1,5-diazabicyclo [4.3.0]non-5-ene, 1,4-diazabicyclo[2.2.2]octane (DABCO), 1,1,3,3-tetramethylguanidine, 1,8-diazabicyclo[5.4.0]-7-undecene (DBU), and the like.

Examples of the reaction solvent include, but are not limited to, aromatic hydrocarbons such as benzene, toluene, chlorobenzene, xylene, and the like; halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; aprotic polar solvents such as DMF, DMAc, N-methylpyrrolidone, DMSO, and the like; water; and mixed solvents thereof, and the reaction can be performed under solvent-free conditions.

The reaction temperature is not particularly limited, and is usually room temperature to 200° C. The reaction time is not particularly limited and is preferably 0.5 hours to 24 hours.

(Step 2-2)

In (Step 2-2), compound (2-5) can be produced by subjecting compound (2-3) and compound (2-4) to a condensation reaction using a condensing agent in the presence or absence of a base.

Examples of the condensing agent include, but are not limited to, DCC, DIC, EDC, HBTU, HATU, COMU, TCFH, BOP, PyBOP, PyBrOP, DMT-MM, T3P, and the like. An additive may be added to facilitate the reaction, and examples of the additive include HOBt, HOAt, Oxyma, DMAP and the like.

Examples of the base include: organic bases such as trimethylamine, triethylamine, diisopropylethylamine, tripropylamine, triisopropylamine, tributylamine, N-methylmorpholine, 1-methylimidazole, pyridine, 4-(N, N-dimethylamino)pyridine, 2,6-dimethylpyridine, 2,6-di-tert-butylpyridine, N,N-dimethylaniline, N, N-diethylaniline, 1,5-diazabicyclo[4.3.0]non-5-ene, 1,4-diazabicyclo[2.2.2]octane (DABCO), 1,1,3,3-tetramethylguanidine, 1,8-diazabicyclo[5.4.0]-7-undecene (DBU), and the like.

Examples of the reaction solvent include, but are not limited to, aromatic hydrocarbons such as benzene, toluene, chlorobenzene, xylene, and the like; halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; aprotic polar solvents such as DMF, DMAc, N-methylpyrrolidone, DMSO, and the like; and mixed solvents thereof.

The reaction temperature is not particularly limited, and is usually room temperature to 100° C. The reaction time is not particularly limited and is preferably 0.5 hours to 24 hours.

(Step 2-3A)

In (Step 2-3A), compound (2-6) can be produced by subjecting compound (2-5) to a catalytic reductive reaction in the presence of a transition metal catalyst and hydrogen gas.

Examples of the transition metal catalyst include, but are not limited to, palladium/carbon, palladium hydroxide/carbon, palladium/fibroin, Raney nickel, platinum oxide, and the like.

Examples of the reaction solvent include, but are not limited to, alcohols such as methanol, ethanol, 2-propanol, tert-butanol, and the like; esters such as methyl acetate, ethyl acetate, and the like; ethers such as diethyl ether, THF, 1,4-dioxane, 1,2-dimethoxyethane, and the like; aprotic polar solvents such as DMF, DMAc, N-methylpyrrolidone, DMSO, and the like; protic polar solvents such as acetic acid, and the like; water; and mixed solvents thereof. The reaction temperature is not particularly limited and is usually between room temperature and 100° C., and the reaction is carried out under ambient pressure or increased pressure. The reaction time is not particularly limited and is preferably 0.5 hours to 24 hours.

(Step 2-3B)

In (Step 2-3B), compound (2-6) can be produced by subjecting compound (2-5) to a reducing reaction, in the presence of reduced iron or zinc. In order to facilitate the reaction, an additive may be present, and examples of the additive include, but are not limited to, acetic acid, hydrochloric acid, ammonium chloride, and the like.

Examples of the reaction solvent include, but are not limited to, alcohols such as methanol, ethanol, 2-propanol, tert-butyl alcohol, and the like; ethers such as diethyl ether, THF, 1,4-dioxane, 1,2-dimethoxyethane, and the like; protic polar solvents such as acetic acid and the like; water; and mixed solvents thereof.

The reaction temperature is not particularly limited, and is usually 0° C. to 100° C.

The reaction time is not particularly limited and is preferably 0.5 hours to 24 hours.

Compound (1-2) can be produced, for example, by the following production method 3.

<Production Method 3>

[Chem. Fig. 26]

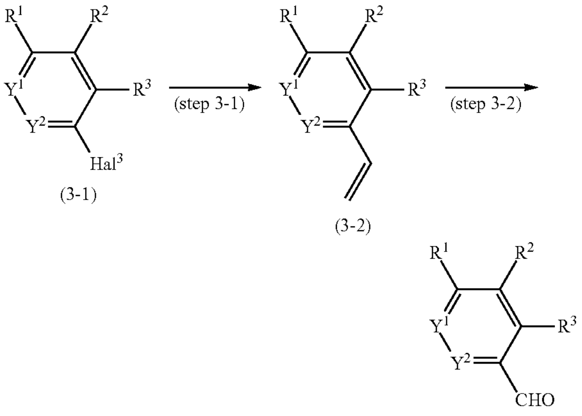

(3-1) (3-2) (1-2)

[where $R^1$, $R^2$, $R^3$, $Y^1$, and $Y^2$ are as defined above. Furthermore, $Hal^3$ is a chloro group, a bromo group or an iodo group.]

(Step 3-1)

In (Step 3-1), compound (3-2) can be produced by subjecting compound (3-1) and vinylboronic acid or a vinylboronic acid derivative to a Suzuki-Miyaura coupling reaction in the presence of a palladium catalyst and a base.

Examples of the vinylboronic acid derivative include vinylboronic acid pinacol ester, dibutyl vinylboronate, MIDA vinylboronate MIDA, potassium vinyltetrafluoroborate, and the like.

Examples of the palladium catalyst and base include the palladium catalysts and bases described in (Step 1-C) of Production Method 1.

Additives may be present to facilitate the reaction, and examples of the additives include the additives described in (Step 1-C) of Production Method 1.

Examples of the reaction solvent include the solvents described in (Step 1-C) of Production Method 1.

The reaction temperature is not particularly limited, and is usually room temperature to 150° C. The reaction time is not particularly limited and is preferably 0.1 hours to 24 hours.

(Step 3-2)

In (Step 3-2), compound (1-2) can be produced by subjecting compound (3-2) to a double bond cleavage reaction using osmium tetroxide and sodium periodate.

In order to facilitate the reaction, an additive may be present, and examples of the additive include 2,6-lutidine and the like.

Examples of the reaction solvent include, but are not limited to, halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; acetone; water; and mixed solvents thereof.

The reaction temperature is not particularly limited, and is usually 0° C. to 100° C.

The reaction time is not particularly limited and is preferably 1 hour to 24 hours.

Compound (4-3), which is one of the aforementioned compounds (3-1), can be produced, for example, by the following production method 4.

<Production Method 4>

[Chem. Fig. 27]

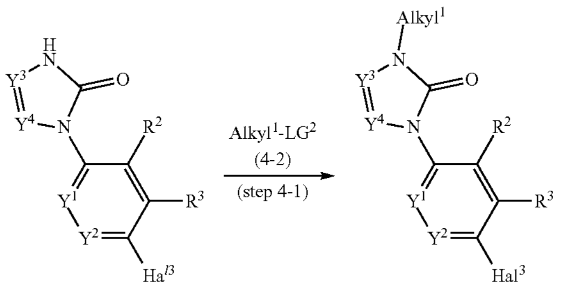

(4-1) (4-3)

[where $R^2$, $R^3$, $R^4$, $Y^1$, $Y^2$, and $Hal^3$ are as defined above. In addition, $Y^3$ and $Y^4$ are each independently CH, C-Alkyl$^2$ or N, Alkyl$^1$ and Alkyl$^2$ are each independently an optionally substituted $C_1$-$C_6$ alkyl group, and $LG^2$ is a bromo group, an iodo group, or a trifluoromethanesulfonyloxy group.]

(Step 4-1)

In (Step 4-1), compound (4-3) can be produced by subjecting compound (4-1) and compound (4-2) to a substitution reaction in the presence of a base.

Examples of the base include the bases described in (Step 2-1), with sodium hydride, tripotassium phosphate, and potassium tert-butoxide being preferred.

Examples of the reaction solvent include, but are not limited to, aromatic hydrocarbons such as benzene, toluene, chlorobenzene, xylene, and the like; nitriles such as acetonitrile, propionitrile, and the like; ethers such as diethyl ether, THF, 1,4-dioxane, 1,2-dimethoxyethane, and the like; aprotic polar solvents such as DMF, DMAc, N-methylpyrrolidone, DMSO, and the like; and mixed solvents thereof.

The reaction temperature is not particularly limited, and is usually 0° C. to 100° C.

The reaction time is not particularly limited and is preferably 0.5 hours to 24 hours.

Compound (5-5), which is one of the aforementioned compounds (4-1), can be produced, for example, by the following production method 5.

<Production Method 5>

[Chem. Fig. 28]

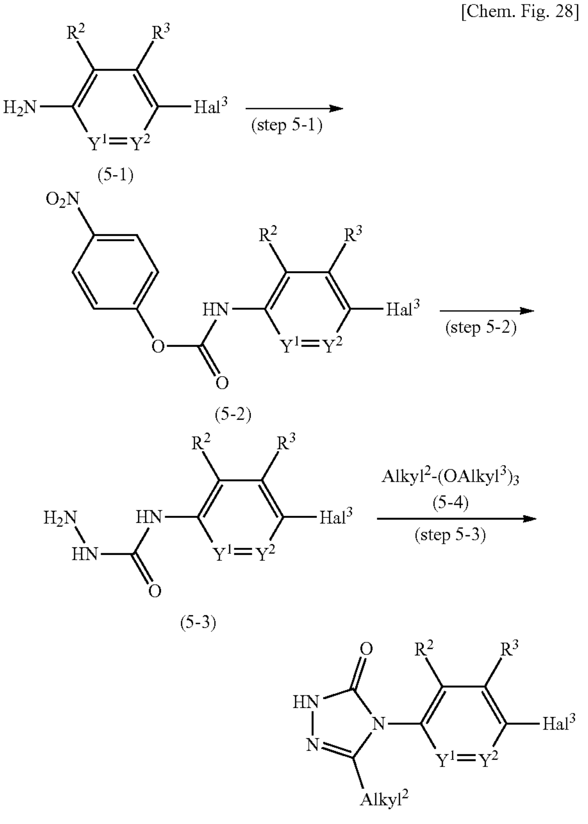

(5-1) (5-2) (5-3) (5-5)

[where $R^2$, $R^3$, $Y^1$, $Y^2$, $Hal^3$, and Alkyl$^2$ are as defined above.

Furthermore, Alkyl$^3$ is an optionally substituted $C_1$-$C_3$ alkyl group.]

(Step 5-1)

In (Step 5-1), compound (5-2) can be produced by subjecting compound (5-1) to a carbamation reaction with 4-nitrophenyl chloroformate in the presence of a base.

Examples of the base include the bases described in (Step 2-2).

Examples of the reaction solvent include, but are not limited to, aromatic hydrocarbons such as benzene, toluene, chlorobenzene, xylene, and the like; halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; and mixed solvents thereof.

The reaction temperature is not particularly limited, and is usually 0° C. to 100° C.

The reaction time is not particularly limited and is preferably 0.5 hours to 24 hours.

(Step 5-2)

In (Step 5-2), compound (5-3) can be produced by subjecting compound (5-2) to an addition-elimination reaction with hydrazine or hydrazine monohydrate in the presence or absence of a base.

Examples of the base include the bases described in (Step 2-2).

Examples of the reaction solvent include the solvents described in (Step 5-1).

The reaction temperature is not particularly limited, and is usually 0° C. to 100° C.

The reaction time is not particularly limited and is preferably 0.5 hours to 24 hours.

(Step 5-3)

In (Step 5-3), compound (5-5) can be produced by subjecting compound (5-3) and compound (5-4) to a triazolone cyclization reaction in the presence of an acid.

Examples of the acid include, but are not limited to, para-toluenesulfonic acid.

Examples of the reaction solvent include, but are not limited to, aromatic hydrocarbons such as benzene, toluene, xylene, and the like; aliphatic hydrocarbons such as hexane, heptane, and the like; halogenated hydrocarbons such as dichloromethane, chloroform, 1,2-dichloroethane, and the like; ethers such as diethyl ether, THF, 1,4-dioxane, 1,2-dimethoxyethane, and the like; alcohols such as methanol, ethanol, n-butyl alcohol, tert-butyl alcohol, and the like; and mixed solvents thereof.

The reaction temperature is not particularly limited, and is usually 0° C. to 100° C. The reaction time is not particularly limited and is preferably 0.5 hours to 24 hours.

Compound (6-3), which is one of the aforementioned compounds (3-1), can be produced, for example, by the following production method 6.

<Production Method 6>

[Chem. Fig. 29]

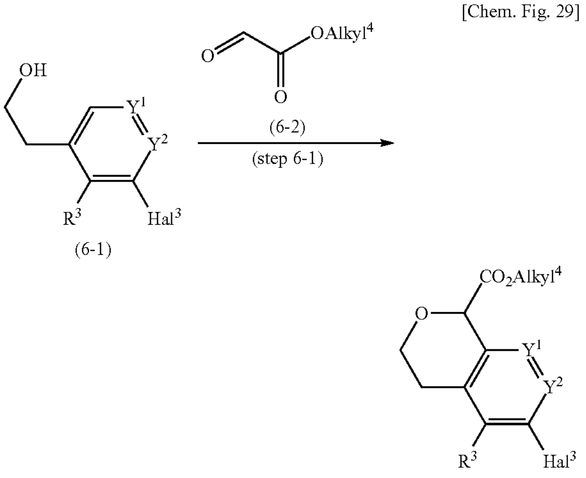

(6-1)
(6-2)
(6-3)

[where $R^3$, $Y^1$, $Y^2$, and $Hal^3$ are as defined above. Furthermore, $Alkyl^4$ is an optionally substituted $C_1$-$C_6$ alkyl group.]

(Step 6-1)

In (Step 6-1), compound (6-3) can be produced by subjecting compound (6-1) and compound (6-2) to an oxa-Pictet-Spengler reaction in the presence of an acid.

Acids include, but are not limited to, hydrochloric acid, sulfuric acid, trifluoroacetic acid, titanium chloride (IV), boron trifluoride, and the like.

Examples of the reaction solvent include, but are not limited to, aromatic hydrocarbons such as benzene, toluene, xylene, and the like; aliphatic hydrocarbons such as hexane, heptane, and the like; halogenated hydrocarbons such as dichloromethane, chloroform, 1,2-dichloroethane, and the like; ethers such as diethyl ether, THF, 1,4-dioxane, 1,2-dimethoxyethane, and the like; alcohols such as methanol, ethanol, tert-butyl alcohol, and the like; nitromethane; water; and mixed solvents thereof, and the reaction can also be performed under solvent-free conditions.

The reaction temperature is not particularly limited, and is usually 0° C. to 100° C.

The reaction time is not particularly limited and is preferably 1 hour to 100 hours.

Compound (7-3), which is one of the aforementioned compounds (3-1), can be produced, for example, by the following production method 7.

<Production Method 7>

[Chem. Fig. 30]

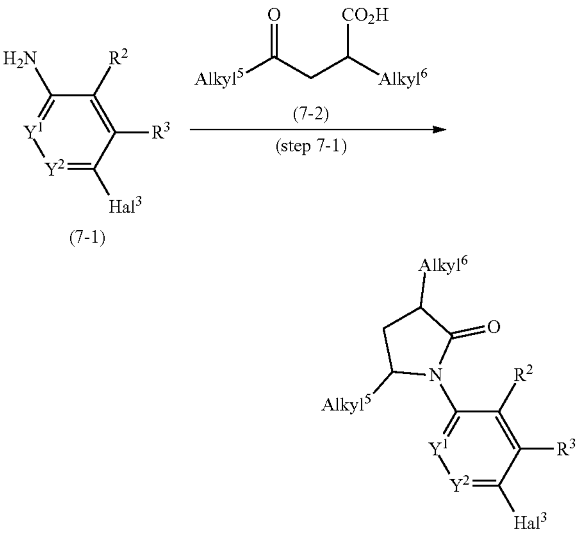

(7-1)
(7-2)
(7-3)

[Where $R^2$, $R^3$, $Y^1$, $Y^2$, and $Hal^3$ are as defined above. Furthermore, $Alkyl^5$ and $Alkyl^6$ are each independently a hydrogen atom or an optionally substituted $C_1$-$C_6$ alkyl group.]

(Step 7-1)

In (Step 7-1), compound (7-3) can be produced by subjecting compound (7-1) and compound (7-2) to a lactam cyclization reaction in the presence of phenylsilane and indium acetate.

The lactam cyclization can be carried out, for example, according to the method described in Angewandte Chemie-International Edition 2016, 55, p 1864 to 1867.

Compound (8-2), which is one of the aforementioned compounds (1-2), can be produced, for example, by the following production method 8.

<Production Method 8>

[Chem. Fig. 31]

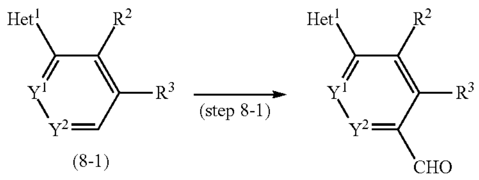

(8-1)
(8-2)

[Where $R^2$, $R^3$, $Y^1$ and $Y^2$ are as defined above. Furthermore, $Het^1$ is an optionally substituted amino group or an optionally substituted alkoxy group. $R^2$ and $Het^1$ may form an optionally substituted ring together with the carbon atoms to which each is bonded.]

(Step 8-1)

In (Step 8-1), compound (8-2) can be produced by subjecting compound (8-1) to a Duff reaction using an acid and hexamethylenetetramine.

Examples of the acid include, but are not limited to, acetic acid; trifluoroacetic acid; methanesulfonic acid; trifluoromethanesulfonic acid; and the like.

Examples of the reaction solvent include halogenated hydrocarbons such as dichloromethane and the like; alcohols such as ethanol and the like; water; and mixed solvents thereof, but the reaction may be carried out under solvent-free conditions.

The reaction temperature is not particularly limited, and is usually 0° C. to 100° C.

The reaction time is not particularly limited and is preferably 0.5 hours to 24 hours.

Compound (9-3), which is one of the aforementioned compounds (1-2), can be produced, for example, by the following production method 9.

<Production Method 9>

[Chem. Fig. 32]

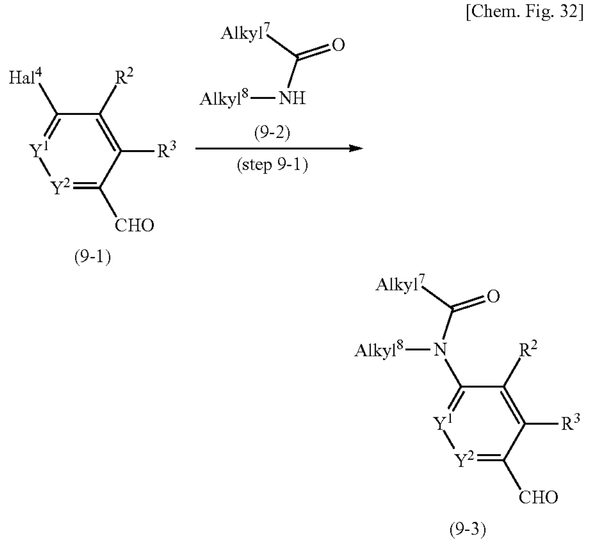

(9-1) (9-3)

[Where $R^2$, $R^3$, $Y^1$, and $Y^2$ are as defined above. $Hal^4$ is a chloro group, a bromo group or an iodo group.] In addition, $Alkyl^7$ is an optionally substituted $C_1$-$C_6$ alkyl group; $Alkyl^8$ is a hydrogen atom or an optionally substituted $C_1$-$C_6$ alkyl group; and $Alkyl^7$ and $Alkyl^8$ may form an optionally substituted ring together with the carbon atom to which each is bonded.]

(Step 9-1)

In (Step 9-1), compound (9-3) can be produced by subjecting compound (9-1) and compound (9-2) to a Goldberg amination reaction under the presence of a copper-catalyst and a base.

Examples of the copper catalyst include, but are not limited to, copper(I) iodide, copper(I) chloride, copper(II) chloride, copper(I) oxide, copper(I) thiocyanate, copper(II) sulfate pentahydrate, copper(II) acetate, copper(II) acetylacetonate, and the like.

Examples of the base include, but are not limited to, metal bases such as potassium carbonate, sodium carbonate, cesium carbonate, tripotassium phosphate, potassium tert-butoxide, sodium tert-butoxide, and the like.

In order to facilitate the reaction, an additive may coexist, and examples of the additive include N,N'-dimethylethylenediamine and the like.

Examples of the reaction solvent include, but are not limited to, aromatic hydrocarbons such as toluene and the like; ethers such as THF, 1,4-dioxane, and the like; aprotic polar solvents such as DMF, N-methylpyrrolidone, and the like; and mixed solvents thereof.

The reaction temperature is not particularly limited, and is usually room temperature to 150° C. The reaction time is not particularly limited and is preferably 0.5 hours to 24 hours.

Compound (10-3), which is one of the aforementioned compounds (1-6), and compound (10-6), which is one of the aforementioned compounds (1-3), can be produced, for example, by the following production method 10.

<Production Method 10>

[Chem. Fig. 33]

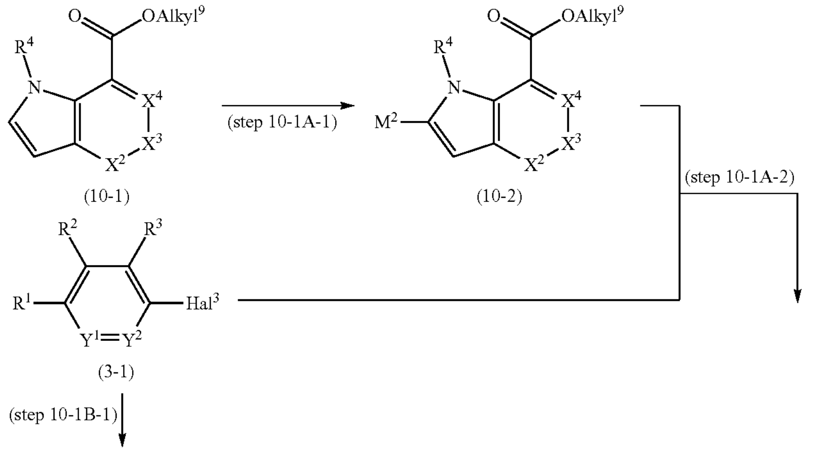

(10-1) (10-2) (3-1)

-continued

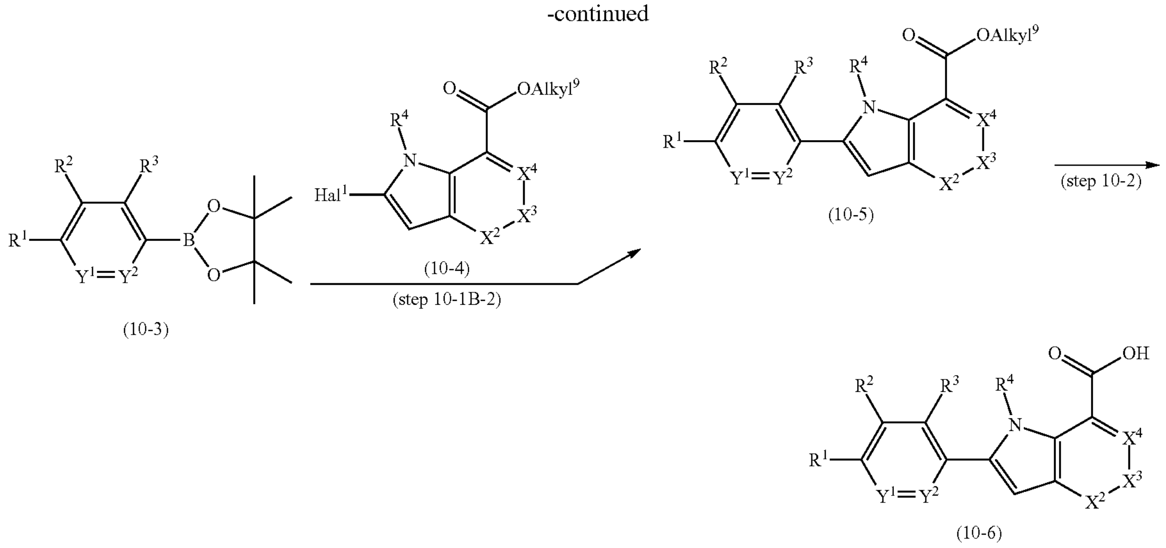

(10-3) (10-5) (10-6)

[Where $R^1$, $R^2$, $R^3$, $R^4$, $X^2$, $X^3$, $X^4$, $Y^1$, $Y^2$, $Hal^1$, and $Hal^3$ are as defined above. Furthermore, $M^2$ is boronic acid or a boronic acid ester, and $Alkyl^9$ is a methyl group, an ethyl group, or a benzyl group.]

(Step 10-1A-1)

In (Step 10-1A-1), compound (10-2) can be produced by subjecting compound (10-1) to a borylation reaction using a borate ester under the presence of LDA.

Examples of the borate acid ester include, but are not limited to, trimethyl borate, triethyl borate, triisopropyl borate, and the like.

Examples of the reaction solvent include, but are not limited to, aromatic hydrocarbons such as toluene and the like; ethers such as THF, 1,4-dioxane, and the like; and mixed solvents thereof.

The reaction temperature is not particularly limited, and is usually −78° C. to room temperature. The reaction time is not particularly limited and is preferably 0.5 hours to 24 hours.

(Step 10-1A-2)

In (Step 10-1A-2), compound (10-5) can be produced by subjecting compound (10-2) and compound (3-1) to a Suzuki-Miyaura coupling reaction by the same method as in step (1-C).

(Step 10-1B-1)

In (step 10-1B-1), compound (10-3) can be produced by subjecting compound (3-1) and bis(pinacolato)diboron to a Miyaura borylation reaction under the presence of a palladium catalyst and potassium acetate.

Examples of the palladium catalyst include the palladium catalysts described in (Step 1-C) of Production Method 1.

Additives may be present to facilitate the reaction, and examples of the additives include the additives described in (Step 1-C) of Production Method 1.

Examples of the reaction solvent include, but are not limited to, aromatic hydrocarbons such as benzene, toluene, chlorobenzene, xylene, and the like; aliphatic hydrocarbons such as hexane, heptane, and the like; halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; aprotic polar solvents such as DMF, DMAc, N-methylpyrrolidone, DMSO, and the like; and mixed solvents thereof.

The reaction temperature is not particularly limited, and is usually 80° C. to 150° C.

The reaction time is not particularly limited and is preferably 0.1 hours to 24 hours.

(Step 10-1B-2)

In Step 10-1B-2, compound (10-5) can be produced by subjecting compound (10-3) and compound (10-4) to a Suzuki-Miyaura coupling reaction by the same method as in (Step 1-C) of Production Method 1.

(Step 10-2)

In step (10-2), compound (10-6) can be produced by subjecting compound (10-5) to a hydrolysis reaction in the presence of a base.

Examples of the base include lithium hydroxide, sodium hydroxide, potassium hydroxide, and the like.

Examples of the reaction solvent include, but are not limited to, ethers such as diethyl ether, THF, 1,4-dioxane, 1,2-dimethoxyethane, and the like; alcohols such as methanol, ethanol, 2-propanol, tert-butyl alcohol, and the like; water; and mixed solvents thereof.

The reaction temperature is not particularly limited, and is usually 0° C. to 100° C.

The reaction time is not particularly limited and is preferably 0.5 hours to 24 hours.

Compound (10-6) can be produced, for example, by the following production method 11.

<Production Method 11>

[Chem. Fig. 34]

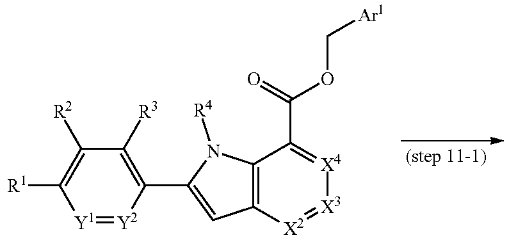

(11-1)

-continued

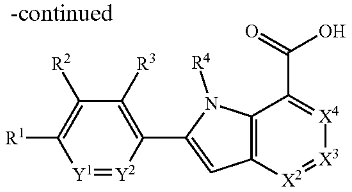

(10-6)

[Wherein $R^1$, $R^2$, $R^3$, $R^4$, $X^2$, $X^3$, $X^4$, $Y^1$, and $Y^2$ are as defined above. Furthermore, $Ar^1$ is an optionally substituted phenyl group.]

(Step 11-1)

In (step 11-1), compound (10-6) can be produced by subjecting compound (11-1) to a catalytic reduction reaction in the presence of a transition metal catalyst and in the presence of hydrogen.

The reaction may be carried out under the same conditions as in the method described in (Step 2-3A) of Production Method 2.

Compound (10-4) can be produced, for example, by the following production method 12.

<Production Method 12>

[Chem. Fig. 35]
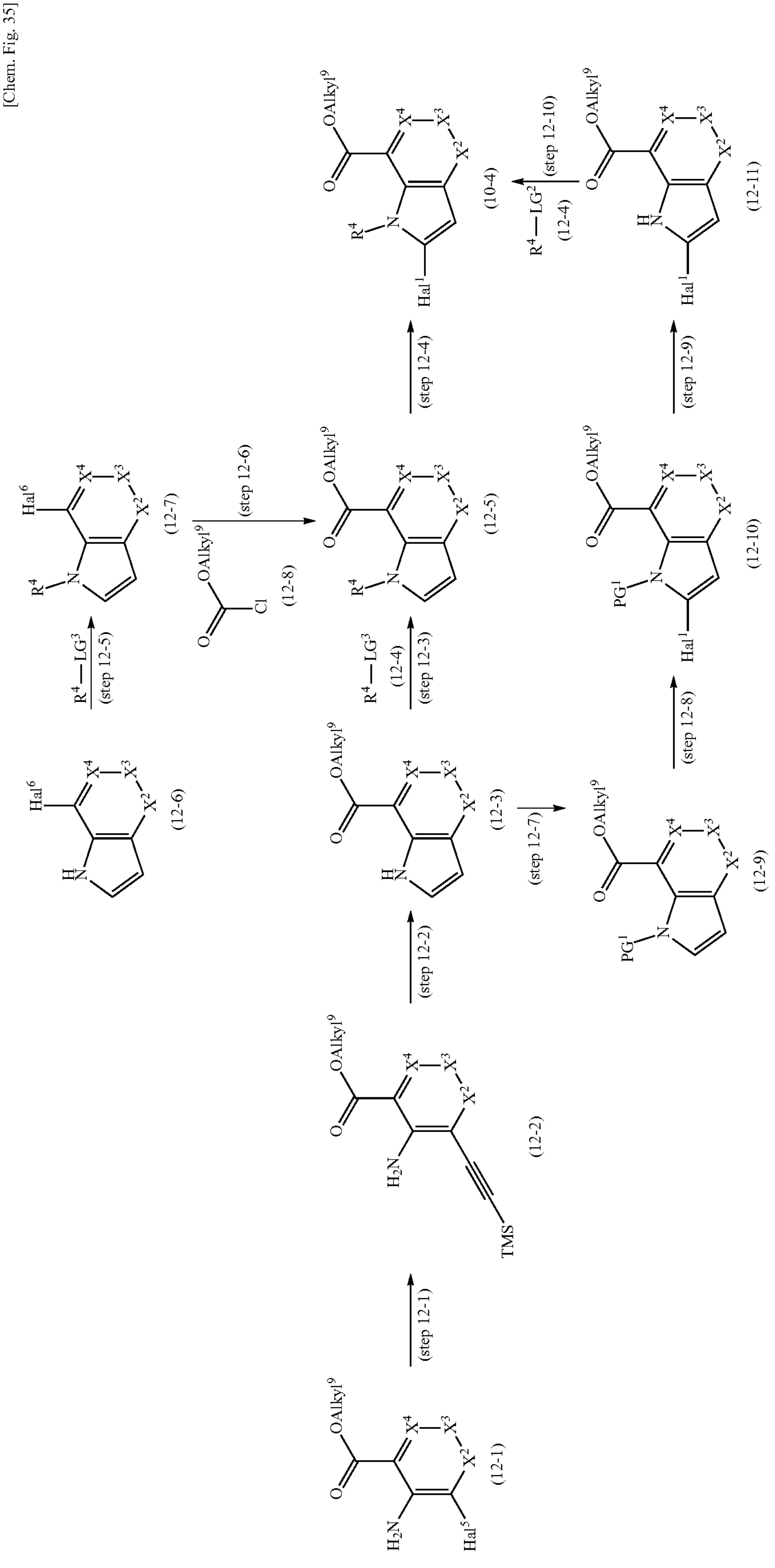
(12-1) (12-2) (12-3) (12-5) (10-4) (12-6) (12-7) (12-9) (12-10) (12-11)

[Where $R^1$, $R^2$, $R^3$, $R^4$, $X^2$, $X^3$, $X^4$, $Y^1$, $Y^2$, $Hal^1$, and $Alkyl^9$ are as defined above. $Hal^5$ is a chloro group, a bromo group or an iodo group.] Furthermore, $LG^3$ is a leaving group such as a chloro group, a bromo group, an iodo group, a trifluoromethanesulfonyloxy group, or the like; and $PG^1$ is a protecting group selected from carbamate-based protecting groups such as a Boc group or the like; an amide-based protecting group such as an acetyl group and the like; a sulfonamide-based protecting group such as a paratoluenesulfonyl group; and the like.]

(Step 12-1)

In (step 12-1), compound (12-2) can be produced by subjecting compound (12-1) and trimethylsilylacetylene to a Sonogashira coupling reaction in the presence of a palladium catalyst and a base.

Examples of the palladium catalyst include the palladium catalysts described in (Step 1-C).

Examples of the base include the bases described in (Step 1-C).

An additive may be added in order to facilitate the reaction, and examples of the additive include the additives described in (Step 1-C), and copper salts such as copper(I) iodide, and these additives may be used alone or in combination.

Examples of the reaction solvent include, but are not limited to, aromatic hydrocarbons such as benzene, toluene, xylene, and the like; aliphatic hydrocarbons such as hexane, heptane, and the like; halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; aprotic polar solvents such as DMF, DMAc, N-methylpyrrolidone, DMSO, and the like; alcohols such as methanol, ethanol, and the like; and mixed solvents thereof.

(Step 12-2)

In (Step 12-2), compound (12-3) can be produced by subjecting compound (12-2) to an indole cyclization reaction in the presence of a base or in the presence of a transition metal catalyst.

Examples of the base include, but are not limited to, sodium tert-butoxide, sodium hydride, and the like.

Examples of the transition metal catalyst include, but are not limited to, copper salts such as copper(I) iodide and the like; silver complexes such as silver bis(trifluoromethanesulfonyl)imide and the like; and gold salts such as gold(I) chloro(2-dicyclohexylphosphino-2',6'-dimethoxy-1,1'-biphenyl), gold(I) chloro(triphenylphosphine), and the like. Furthermore, these catalysts may be used in combination.

Examples of the reaction solvent include, but are not limited to, aromatic hydrocarbons such as benzene, toluene, xylene, and the like; aliphatic hydrocarbons such as hexane, heptane, and the like; ethers such as diethyl ether, THF, 1,4-dioxane, 1,2-dimethoxyethane, and the like; aprotic polar solvents such as DMF, DMAc, N-methylpyrrolidone, DMSO, and the like; alcohols such as methanol, ethanol, and the like; acetonitrile; and mixed solvents thereof.

The reaction temperature is not particularly limited, and is usually room temperature to 150° C. The reaction time is not particularly limited and is preferably 1 hour to 24 hours.

(Step 12-3)

In (step 12-3), compound (12-5) can be produced by subjecting compound (12-3) and compound (12-4) to a substitution reaction in the presence of a base.

Examples of the base include the bases described in (Step 1-B).

Examples of the reaction solvent include the reaction solvents described in (Step 1-B).

The reaction temperature is not particularly limited, and is usually 0° C. to 150° C.

The reaction time is not particularly limited and is preferably 1 hour to 24 hours.

(Step 12-4)

In (step 12-4), compound (10-4) can be produced by subjecting compound (12-5) to a halogenation reaction using LDA and a halogenating agent.

Examples of the halogenating agent include iodinating agents such as N-iodosuccinimide, N-iodophthalimide, N-iodosaccharin, 1,3-diiodo-5,5-dimethylhydantoin, iodine, and the like; brominating agents such as N-bromosuccinimide, N-bromophthalimide, N-bromosaccharin, 1,3-dibromo-5,5-dimethylhydantoin, carbon tetrabromide, bromine, and the like; and chlorinating agents such as N-chlorosuccinimide, N-chlorophthalimide, N-chlorosaccharin, 1,3-dichloro-5,5-dimethylhydantoin, and the like.

Examples of the reaction solvent include, but are not limited to, ethers such as diethyl ether, THF, 1,4-dioxane, 1,2-dimethoxyethane, and the like.

The reaction temperature is not particularly limited, and is usually −78° C. to room temperature. The reaction time is not particularly limited and is preferably 1 hour to 24 hours.

(Step 12-5)

In (Step 12-5), Compound (12-7) can be produced by subjecting Compound (12-6) and Compound (12-4) to a substitution reaction by the same method as in (Step 12-3).

(Step 12-6)

In (Step 12-6), compound (12-5) can be produced by subjecting compound (12-7) to an esterification reaction using n-butyl lithium and compound (12-8).

Examples of the reaction solvent include, but are not limited to, ethers such as diethyl ether, THF, 1,4-dioxane, 1,2-dimethoxyethane, MTBE, and the like. The reaction temperature is not particularly limited, and is usually −78° C. to room temperature. The reaction time is not particularly limited and is preferably 1 hour to 24 hours.

(Step 12-7)

In (step 12-7), compound (12-9) can be produced by protecting the nitrogen forming the azole ring of compound (12-3) with a protecting group $PG^1$. The reaction may be carried out by a method well known to those skilled in the art (for example, the method described in "Protective Groups in Organic Synthesis (5th ed., 2014)" by Green and Wuts, and the like).

(Step 12-8)

In (Step 12-8), Compound (12-10) can be produced by subjecting Compound (12-9) to a hydrogenation reaction by the same method as in (Step 12-4).

(Step 12-9)

In (step 12-9), compound (12-11) can be produced by subjecting compound (12-10) to a deprotection reaction for removing the protecting group $PG^1$. The deprotection reaction may be carried out according to a method well known to those skilled in the art (for example, the method described in "Protective Groups in Organic Synthesis (5th edition, 2014)" by Green and Wuts, and the like).

(Step 12-10)

In (Step 12-10), Compound (10-4) can be produced by subjecting Compound (12-11) and Compound (12-4) to a substitution reaction by the same method as in (Step 12-3).

Compound (10-5) can be produced, for example, by the following production method 13.

<Production Method 13>

[Chem. Fig. 36]
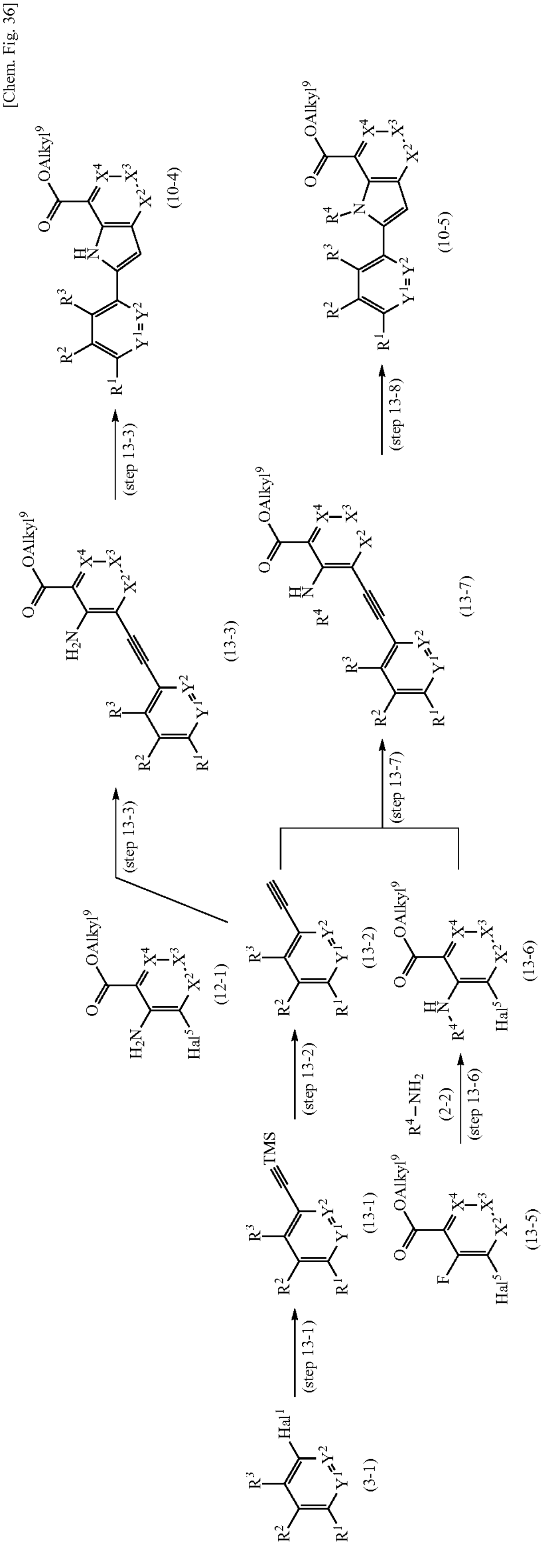
(3-1) (13-1) (13-2) (13-5) (13-6) (12-1) (13-3) (13-7) (10-4) (10-5)

[Where $R^1$, $R^2$, $R^3$, $R^4$, $X^2$, $X^3$, $X^4$, $Y^1$, $Y^2$, $Hal^1$, $Hal^5$, $LG^3$, and $Alkyl^9$ are as defined above.]

(Step 13-1)

In (step 13-1), compound (13-1) can be produced by subjecting compound (3-1) and trimethylsilylacetylene to a Sonogashira coupling reaction by the same method as (Step 12-1).

(Step 13-2)

In (step 13-2), compound (13-2) can be produced by subjecting compound (13-1) to a detrimethylsilylation reaction. The detrimethylsilylation reaction may be carried out according to a method well known to those skilled in the art (for example, the method described in "Protective Groups in Organic Synthesis (5th edition, 2014)" by Green and Wuts, and the like).

(Step 13-3)

In (Step 13-3), Compound (13-3) can be produced by subjecting Compound (13-2) and Compound (12-1) to a substitution reaction by the same method as in (Step 12-1).

(Step 13-4)

In (Step 13-4), compound (13-4) can be produced by subjecting compound (13-3) to an indole cyclization reaction in the presence of a transition metal catalyst.

Examples of the transition metal catalyst include, but are not limited to, copper salts such as copper(I) iodide and the like; silver complexes such as silver bis(trifluoromethanesulfonyl)imide and the like; and gold salts such as gold(I) chloro(2-dicyclohexylphosphino-2',6'-dimethoxy-1, 1'-biphenyl), gold(I) chloro(triphenylphosphine), and the like.

Examples of the reaction solvent include, but are not limited to, aromatic hydrocarbons such as benzene, toluene, xylene, and the like; aliphatic hydrocarbons such as hexane, heptane, and the like; ethers such as diethyl ether, THF, 1,4-dioxane, 1,2-dimethoxyethane, and the like; alcohols such as methanol, ethanol, and the like; and mixed solvents thereof.

The reaction temperature is not particularly limited, and is usually room temperature to 150° C. The reaction time is not particularly limited and is preferably 1 hour to 24 hours.

(Step 13-5)

In (Step 13-5), Compound (10-5) can be produced by subjecting Compound (13-4) and Compound (12-4) to a substitution reaction by the same method as in (Step 12-3).

(Step 13-6)

In (Step 13-6), Compound (13-6) can be produced by subjecting Compound (13-5) and Compound (2-2) to an aromatic nucleophilic substitution reaction by the same method as in (Step 2-1).

(Step 13-7)

In (Step 13-7), Compound (13-7) can be produced by subjecting Compound (13-6) and Compound (13-2) to a substitution reaction by the same method as in (Step 12-1).

(Step 13-8)

In (Step 13-8), Compound (10-5) can be produced by subjecting Compound (13-7) to an indole cyclization reaction by the same method as in (Step 13-4).

Compound (13-4) can be produced, for example, by the following production method 14.

<Production Method 14>

[Chem. Fig. 37]

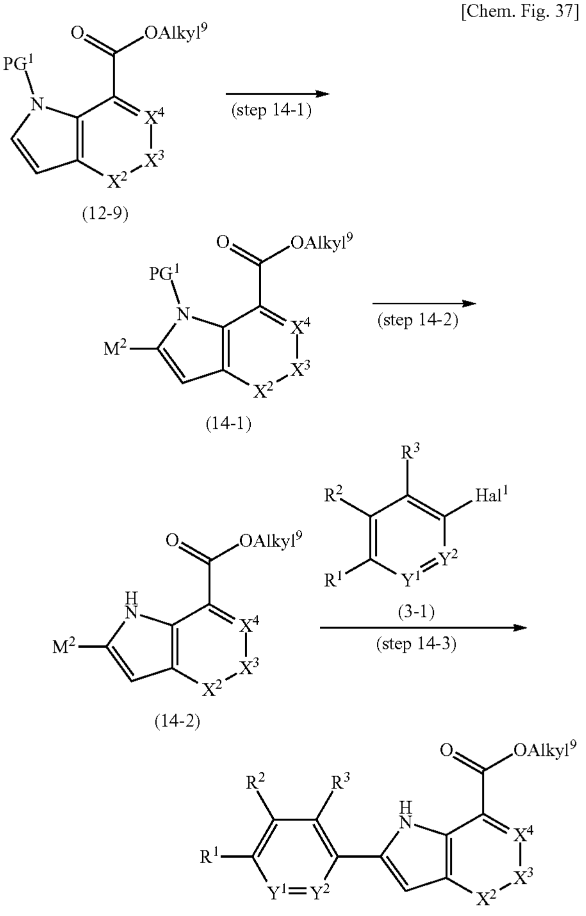

(12-9)
(14-1)
(3-1)
(14-2)
(13-4)

[Where $R^1$, $R^2$, $R^3$, $R^4$, $X^2$, $X^3$, $X^4$, $Y^1$, $Y^2$, $Hal^1$, $PG^1$, $M^2$, and $Alkyl^9$ are as defined above.]

(Step 14-1)

In (Step 14-1), Compound (14-1) can be produced by subjecting Compound (12-9) to a borylation reaction by the same method as in (Step 10-1A-1).

(Step 14-2)

In (Step 14-2), compound (14-2) can be produced by subjecting compound (14-1) to a deprotection reaction for removing protecting group $PG^1$ by the same method as in (Step 12-9).

(Step 14-3)

In (Step 14-3), compound (13-4) can be produced by subjecting compound (14-2) and compound (3-1) to a Suzuki-Miyaura coupling reaction by the same method as in (Step 1-C).

Compound (15-2), which is one of the aforementioned compounds (1-3), can be produced, for example, by the method of Production Method 15 shown below.

<Production Method 15>

[Chem. Fig. 38]

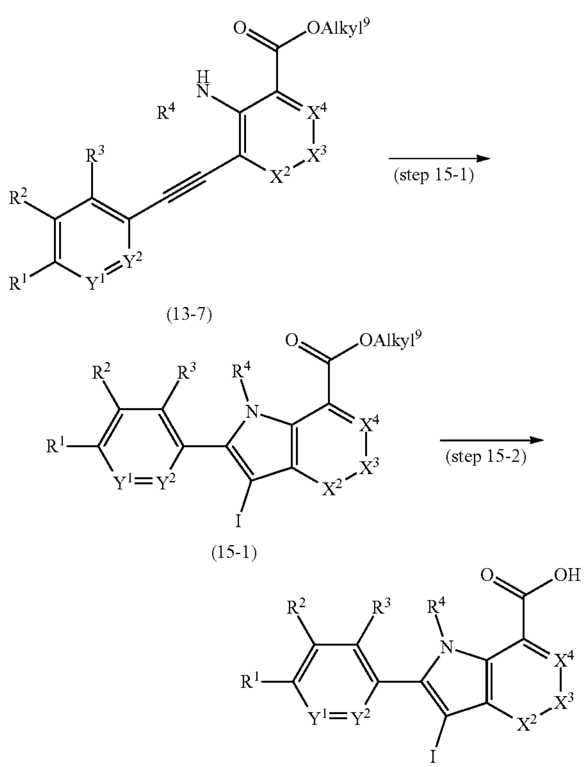

(13-7)

(15-1)

(15-2)

[Where $R^1$, $R^2$, $R^3$, $R^4$, $X^2$, $X^3$, $X^4$, $Y^1$, $Y^2$, and $Alkyl^9$ are as defined above.]

(Step 15-1)

In (step 15-1), compound (15-1) can be produced by subjecting compound (13-7) to an indole cyclization reaction in the presence of copper(I) iodide.

Examples of the reaction solvent include, but are not limited to, aromatic hydrocarbons such as benzene, toluene, xylene, and the like; aliphatic hydrocarbons such as hexane, heptane, and the like; ethers such as diethyl ether, THF, 1,4-dioxane, 1,2-dimethoxyethane, and the like; alcohols such as methanol, ethanol, and the like; and mixed solvents thereof.

The reaction temperature is not particularly limited, and is usually room temperature to 150° C. The reaction time is not particularly limited and is preferably 1 hour to 24 hours.

(Step 15-2)

In (Step 15-2), compound (15-2) can be produced by subjecting compound (15-1) to a hydrolysis reaction by the same method as in (Step 10-2).

Compound (16-2), which is one of the aforementioned compounds (1-3), can be produced, for example, by the method of Production Method 16 shown below.

<Production Method 16>

[Chem. Fig. 39]

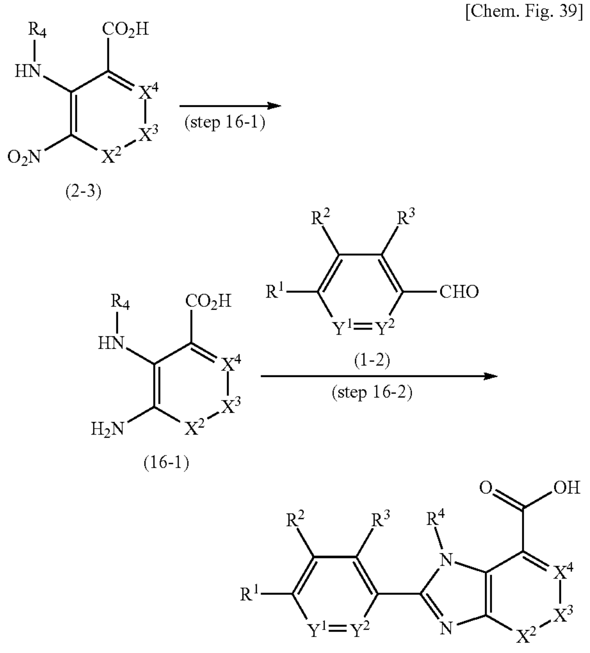

(2-3)

(16-1)

(1-2)

(16-2)

[Wherein $R^1$, $R^2$, $R^3$, $R^4$, $X^2$, $X^3$, $X^4$, $Y^1$, and $Y^2$ are as defined above.]

(Step 16-1)

In (Step 16-1), compound (16-1) can be produced by subjecting compound (2-3) to a nitro group-reduction reaction by the same method as in (Step 2-3A) or (Step 2-3B) of Production Method 2.

(Step 16-2)

In (Step 16-2), compound (16-2) can be produced by subjecting compound (16-1) to a cyclization reaction with compound (1-2) by the same method as in (Step 1-A) of Production Method 1.

Compound (17-1), which is one of the aforementioned compounds (1-3), can be produced, for example, by the following production method 17.

<Production Method 17>

[Chem. Fig. 40]

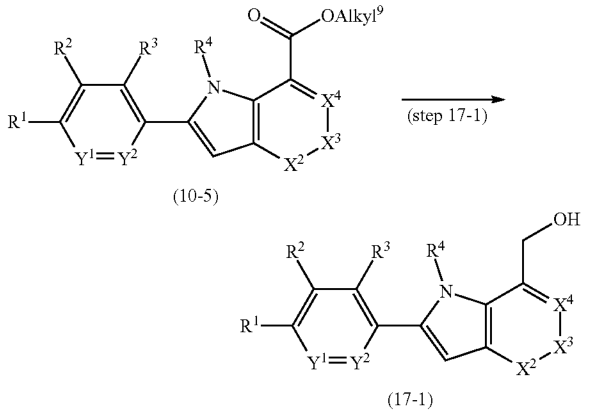

(10-5)

(17-1)

[Where $R^1$, $R^2$, $R^3$, $R^4$, $X^2$, $X^3$, $X^4$, $Y^1$, $Y^2$, and $Alkyl^9$ are as defined above.]

(Step 17-1)

In (step 17-1), compound (17-1) can be produced by reducing the alkoxycarbonyl group (—$CO_2$ $Alkyl^9$) of compound (10-5) to a hydroxymethyl group using a reducing agent.

Examples of the reducing agent include sodium borohydride, lithium borohydride, lithium aluminum hydride, isobutylaluminum hydride, sodium bis(2-methoxyethoxy) aluminum hydride, and the like.

Examples of the reaction solvent include, but are not limited to, aromatic hydrocarbons such as benzene, toluene, chlorobenzene, xylene, and the like; alcohols such as methanol, ethanol, 2-propanol, tert-butanol, and the like; ethers such as diethyl ether, THF, 1,4-dioxane, and the like; and mixed solvents thereof.

The reaction temperature is not particularly limited, and is usually 0° C. to 100° C.

The reaction time is not particularly limited and is preferably 1 hour to 24 hours.

Compound (18-1), which is one of the aforementioned compounds (1-3), can be produced, for example, by the following production method 18.

<Production Method 18>

[Chem. Fig. 41]

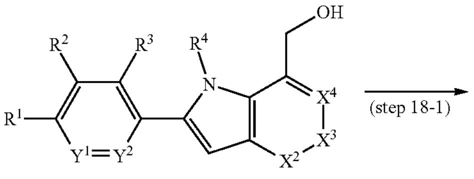

(17-1)

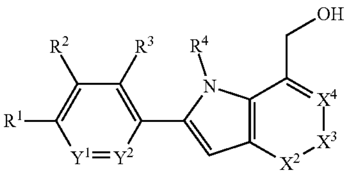

(18-1)

[Wherein $R^1$, $R^2$, $R^3$, $R^4$, $X^2$, $X^3$, $X^4$, $Y^1$, and $Y^2$ are as defined above.]

(Step 18-1)

In (step 18-1), compound (18-1) can be produced by converting the hydroxymethyl group of compound (17-1) to a chloromethyl group using methanesulfonyl chloride in the presence of a base.

Examples of the base include organic bases such as triethylamine, diisopropylethylamine, pyridine, 4-(N, N-dimethylamino)pyridine, and the like.

Examples of the reaction solvent include, but are not limited to, aromatic hydrocarbons such as benzene, toluene, chlorobenzene, xylene, and the like;

halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; and mixed solvents thereof.

The reaction temperature is not particularly limited, and is usually 0° C. to 50° C.

The reaction time is not particularly limited and is preferably 0.5 hours to 24 hours.

Compound (19-5), which is one of the aforementioned compounds (1-3), can be produced, for example, by the method of Production Method 19 shown below.

<Production Method 19>

[Chem. Fig. 42]

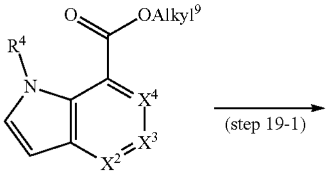

(12-5)

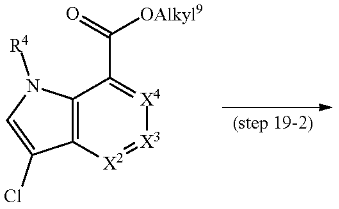

(19-1)

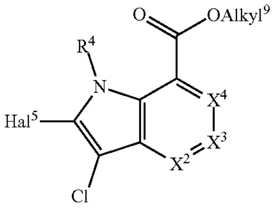

(19-2)

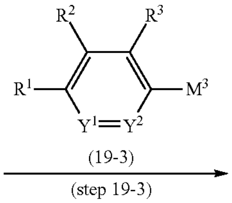

(19-3)

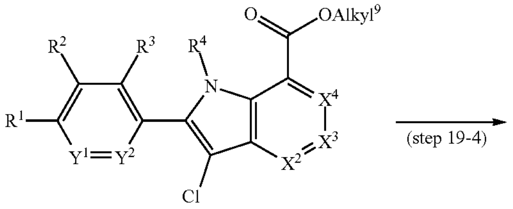

(19-4)

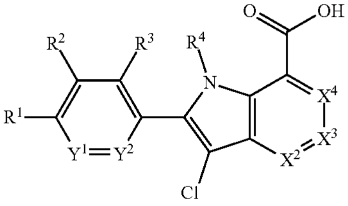

(19-5)

[Where $R^1$, $R^2$, $R^3$, $R^4$, $X^2$, $X^3$, $X^4$, $Y^1$, $Y^2$, and $Alkyl^9$ are as defined above. In addition, $Hal^5$ is a bromo group or an iodo group, and $M^3$ is a boronic acid or a boronic acid-related structure such as $B(OH)_2$, $B(OMe)_2$, B(pin), B(MIDA), or $BF_3K$.]

(Step 19-1)

In (step 19-1), compound (19-1) can be produced by subjecting compound (12-5) to a chlorination reaction using a chlorinating agent.

Examples of the chlorinating agent include N-chlorosuccinimide, N-chlorophthalimide, N-chlorosaccharin, and 1,3-dichloro-5,5-dimethylhydantoin.

Examples of the reaction solvent include, but are not limited to, aromatic hydrocarbons such as benzene, toluene, chlorobenzene, xylene, and the like; halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; aprotic polar solvents such as DMF, DMAc, N-methylpyrrolidone, DMSO, and the like; and mixed solvents thereof.

The reaction temperature is not particularly limited, and is usually 0° C. to 100° C.

The reaction time is not particularly limited and is preferably 1 hour to 24 hours.

(Step 19-2)

In (step 19-2), compound (19-2) can be produced by subjecting compound (19-1) to a halogenation reaction using a halogenating agent.

Examples of the halogenating agent include iodinating agents such as N-iodosuccinimide, N-iodophthalimide, N-iodosaccharin, 1,3-diiodo-5,5-dimethylhydantoin, and the like; and brominating agents such as N-bromosuccinimide, N-bromophthalimide, N-bromosaccharin, 1,3-dibromo-5,5-dimethylhydantoin, bromine, and the like.

Examples of the reaction solvent include, but are not limited to, aromatic hydrocarbons such as benzene, toluene, chlorobenzene, xylene, and the like; halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; aprotic polar solvents such as DMF, DMAc, N-methylpyrrolidone, DMSO, and the like; and mixed solvents thereof.

The reaction temperature is not particularly limited, and is usually 0° C. to 100° C.

The reaction time is not particularly limited and is preferably 1 hour to 24 hours.

(Step 19-3)

In (Step 19-3), compound (19-4) can be produced by subjecting compound (19-2) and compound (19-3) to a Suzuki-Miyaura coupling reaction by the same method as in (Step 1-C) of Production Method 1.

(Step 19-4)

In (Step 19-4), compound (19-5) can be produced by subjecting compound (19-4) to a hydrolysis reaction by the same method as in (Step 10-2) of Production Method 10.

Compound (20-2) which is one of compounds (1-5) can be produced, for example, by the method of Production Method 20 shown below.

<Production Method 20>

[Chem. Fig. 43]

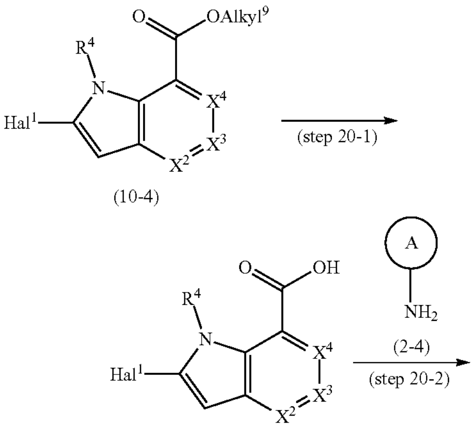

(10-4)

(20-1)

-continued

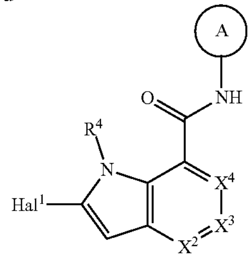

(20-2)

[Where $R^4$, $X^2$, $X^3$, $X^4$, $Hal^1$, $Alkyl^9$, and ring A are as defined above.]

(Step 20-1)

In (Step 20-1), compound (20-1) can be produced by subjecting compound (10-4) to a hydrolysis reaction by the same method as in (Step 10-2) of Production Method 10.

(Step 20-2)

In (Step 20-2), compound (20-2) can be produced by subjecting compound (20-1) and compound (2-4) to a condensation reaction by the same method as in (Step 2-2) of Production Method 2.

Compound (21-4), which is one of the aforementioned compounds (2-4), can be produced, for example, by the method shown in Production Method 21.

<Production Method 21>

[Chem. Fig. 44]

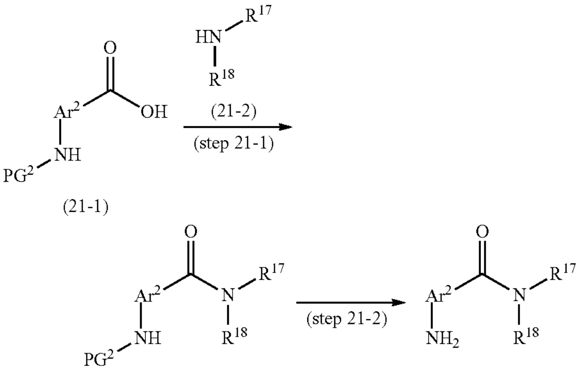

(21-1)

(21-3)

(21-4)

[Where $Ar^2$ is an optionally substituted phenyl group or an optionally substituted 5- to 6-membered heteroaryl group. $PG^2$ is a protecting group for an amino group, and examples thereof include carbamate-based protecting groups such as a Boc group, a Cbz group, an Fmoc group, and the like; and amide-based protecting groups such as a trifluoroacetyl group, and the like. $R^{17}$ and $R^{18}$ are each independently a hydrogen atom, an optionally substituted $C_1$-$C_6$ alkyl group, an optionally substituted phenyl group, or an optionally substituted 5- to 6-membered heteroaryl group.]

(Step 21-1)

In (Step 21-1), compound (21-3) can be produced by subjecting compound (21-1) and compound (21-2) to a condensation reaction by the same method as in (Step 2-2) of Production Method 2.

(Step 21-2)

In (step 21-2), compound (21-4) can be produced by subjecting compound (21-3) to a deprotection reaction for removing the protecting group PG 2. The deprotection reaction may be carried out according to a method well known to those skilled in the art (for example, the method described in "Protective Groups in Organic Synthesis (5th edition, 2014)" by Green and Wuts, and the like).

Compound (22-1), which is one of the aforementioned compound (I), can be produced, for example, by the method shown in Production Method 22, and then the functional group can be converted.

<Production Method 22>

[Chem. Fig. 45]

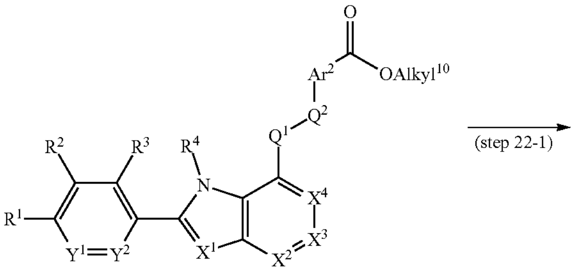

(22-1)

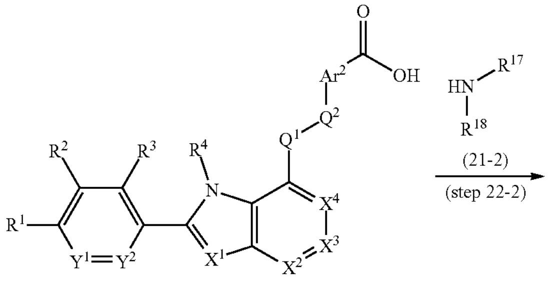

(22-2)

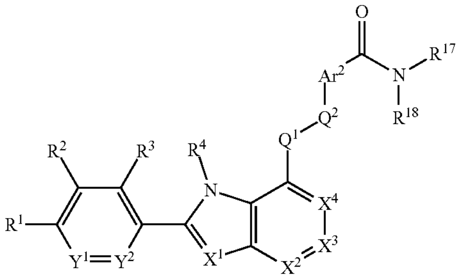

(22-3)

[where $R^1$, $R^2$, $R^3$, $R^4$, $X^1$, $X^2$, $X^3$, $X^4$, $Y^1$, $Y^2$, $Q^1$, $Q^2$, $Ar^2$, $R^{17}$, and $R^{18}$ are as defined above. Furthermore, $Alkyl^{10}$ is an optionally substituted $C_1$-$C_6$ alkyl group.]

(Step 22-1)

In (Step 22-1), compound (22-2) can be produced by subjecting compound (22-1) to a hydrolysis reaction by the same method as in (Step 10-2) of Production Method 10.

(Step 22-2)

In (Step 22-2), compound (22-3) can be produced by subjecting compound (22-2) and compound (21-2) to a condensation reaction by the same method as in (Step 2-2) of Production Method 2.

Compound (23-1), which is one of the aforementioned compounds (I), can be produced, for example, by the method shown in Production Method 23, and then the functional group can be converted.

<Production Method 23>

[Chem. Fig. 46]

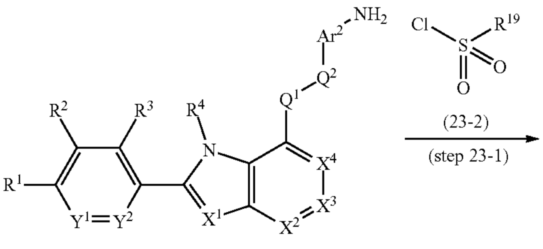

(23-1)

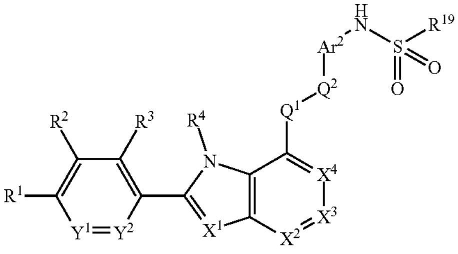

(23-3)

[where $R^1$, $R^2$, $R^3$, $R^4$, $X^1$, $X^2$, $X^3$, $X^4$, $Y^1$, $Y^2$, $Q^1$, $Q^2$, and $Ar^2$ are as defined above. Furthermore, $R^{19}$ is an optionally substituted $C_1$-$C_6$ alkyl group, an optionally substituted phenyl group, or an optionally substituted 5-to 6-membered heteroaryl group.]

(Step 23-1)

In (step 23-1), compound (23-3) can be produced by a sulfonylation reaction using compound (23-1) and compound (23-2) in the presence of a base.

Examples of the base include the bases described in (Step 2-2) of Production Method 2.

Examples of the reaction solvent include, but are not limited to, aromatic hydrocarbons such as benzene, toluene, chlorobenzene, xylene, and the like; halogenated hydrocarbons such as dichloromethane, chloroform, 1,2-dichloroethane, and the like; nitriles such as acetonitrile, propionitrile, and the like; ethers such as diethyl ether, THF, 1,4-dioxane, 1,2-dimethoxyethane, and the like; and mixed solvents thereof.

The reaction temperature is not particularly limited, and is usually 0° C. to 100° C.

The reaction time is not particularly limited and is preferably 0.5 hours to 24 hours.

Compound (24-1), which is one of the aforementioned compounds (I), can be produced, for example, by the method shown in Production Method 24, and then the functional group can be converted.

<Production Method 24>

[Chem. Fig. 47]

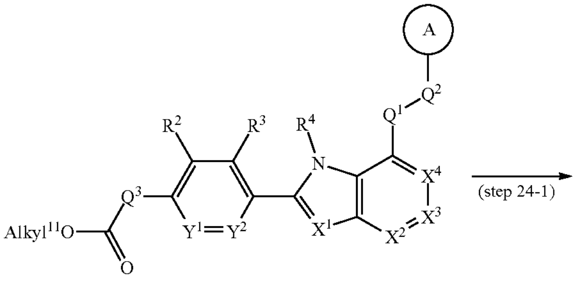

(24-1)

-continued

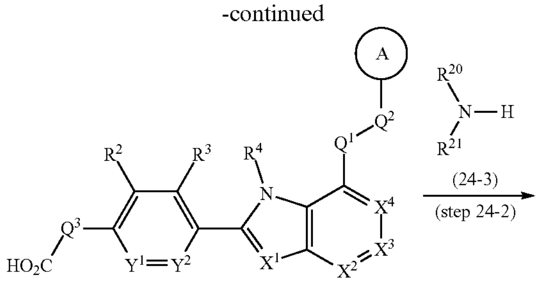

(24-2)

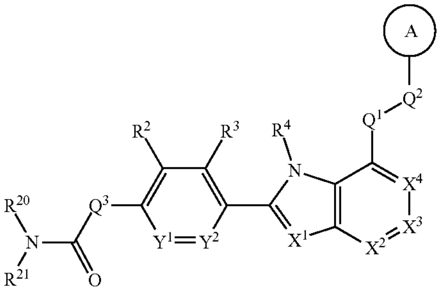

(24-4)

[Where $R^2$, $R^3$, $R^4$, $X^1$, $X^2$, $X^3$, $X^4$, $Y^1$, $Y^2$, $Q^1$, $Q^2$, and ring A are as defined above. $Alkyl^{11}$ is an optionally substituted $C_1$-$C_6$ alkyl group. $Q^3$ is absent or is an optionally substituted $C_1$-$C_3$ alkyl group, or $Q^3$ and $R^2$, together with the carbon atom to which they are attached, can form an optionally substituted non-aromatic heterocyclic group. $R^{20}$ and $R^{21}$ are each independently a hydrogen atom or an optionally substituted $C_1$-$C_6$ alkyl group.]

(Step 24-1)

In (Step 24-1), compound (24-2) can be produced by subjecting compound (24-1) to a hydrolysis reaction by the same method as in (Step 10-2) of Production Method 10.

(Step 24-2)

In (Step 24-2), compound (24-4) can be produced by subjecting compound (24-2) and compound (24-3) to a condensation reaction by the same method as in (Step 2-2) of Production Method 2.

Compound (25-1), which is one of the aforementioned compounds (I), can be produced, for example, by the method shown in Production Method 25, and then the functional group can be converted.

<Production Method 25>

[Chem. Fig. 48]

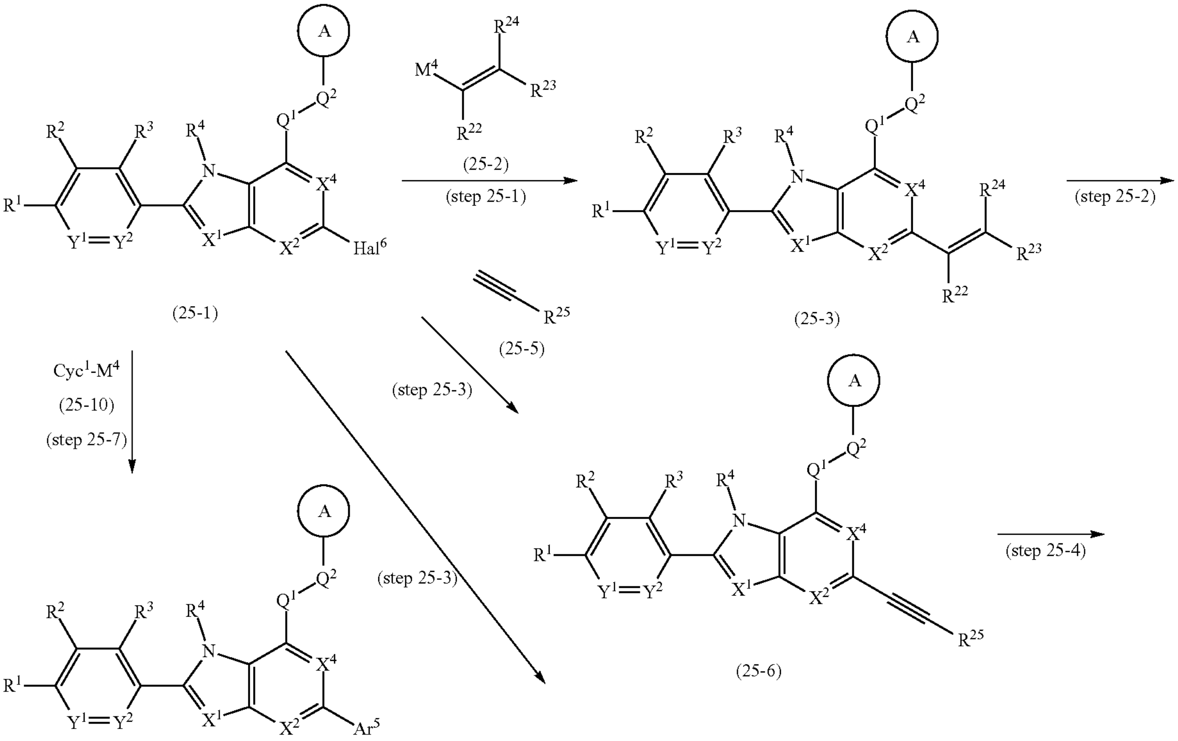

(25-11)

-continued

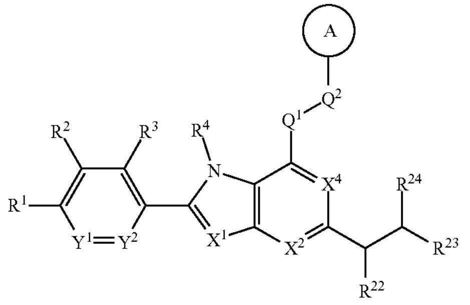

(25-4)

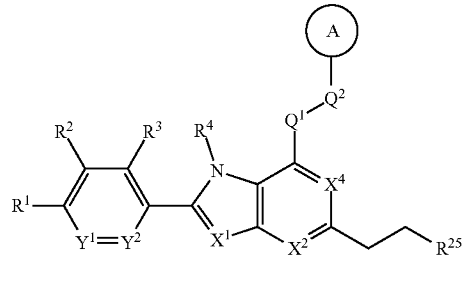

(25-7)

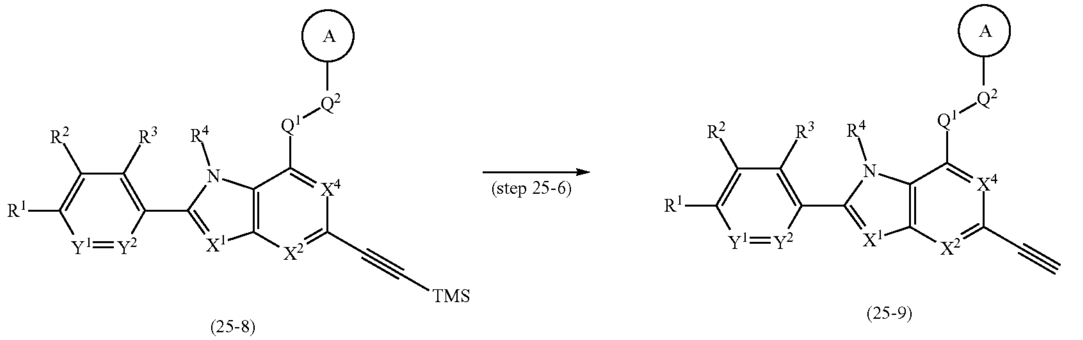

(25-8) (25-9)

[where $R^1$, $R^2$, $R^3$, $R^4$, $X^1$, $X^2$, $X^3$, $X^4$, $Y^1$, $Y^2$, $Q^1$, $Q^2$, and ring A are as defined above. $Hal^6$ is a chloro group, a bromo group or an iodo group.] $R^{22}$, $R^{23}$, $R^{24}$, and $R^{25}$ are each independently an optionally substituted $C_1$-$C_6$ alkyl group, and $R^{22}$ and $R^{23}$ may together with the carbon atom to which they are attached, form an optionally substituted cycloalkyl group. $Cyc^1$ is an optionally substituted phenyl group or an optionally substituted cyclopropyl group. $M^4$ is boronic acid or a boronic acid-related structure such as $B(OH)_2$, $B(OMe)_2$, B(pin), B(MIDA), $BF_3K$, or the like.]

(Step 25-1)

In (Step 25-1), compound (25-3) can be produced by subjecting compound (25-1) and compound (25-2) to a Suzuki-Miyaura coupling reaction by the same method as in (Step 1-C) of Production Method 1.

(Step 25-2)

In (step 25-2), compound (25-4) can be produced by subjecting compound (25-3) to a catalytic reduction reaction in the presence of a transition metal catalyst and in the presence of hydrogen gas.

The reaction may be carried out under the same conditions as in the method described in (Step 2-3A) of Production Method 2.

(Step 25-3)

In (Step 25-3), compound (25-6) can be produced by subjecting compound (25-1) and compound (25-5) to a Sonogashira coupling reaction by the same method as in (Step 12-1) of Production Method 12.

(Step 25-4)

In (step 25-4), compound (25-7) can be produced by subjecting compound (25-6) to a catalytic reduction reaction by the same method as in (step 25-2).

(Step 25-5)

In (step 25-5), compound (25-8) can be produced by subjecting compound (25-1) and trimethylsilylacetylene to a Sonogashira coupling reaction by the same method as in (step 12-1) of Production Method 12.

(Step 25-6)

In (step 25-6), compound (25-9) can be produced by subjecting compound (25-8) to a detrimethylsilylation reaction. The detrimethylsilylation reaction may be carried out according to a method well known to those skilled in the art (for example, the method described in "Protective Groups in Organic Synthesis (5th edition, 2014)" by Green and Wuts, and the like).

(Step 25-7)

In (Step 25-7), compound (25-11) can be produced by subjecting compound (25-1) and compound (25-10) to a Suzuki-Miyaura coupling reaction by the same method as in (Step 1-C) of Production Method 1.

Compound (26-1), which is one of the aforementioned compounds (25-3), can be produced, for example, by the method shown in Production Method 26, and then the functional group can be converted.

<Production Method 26>

[Chem. Fig. 49]

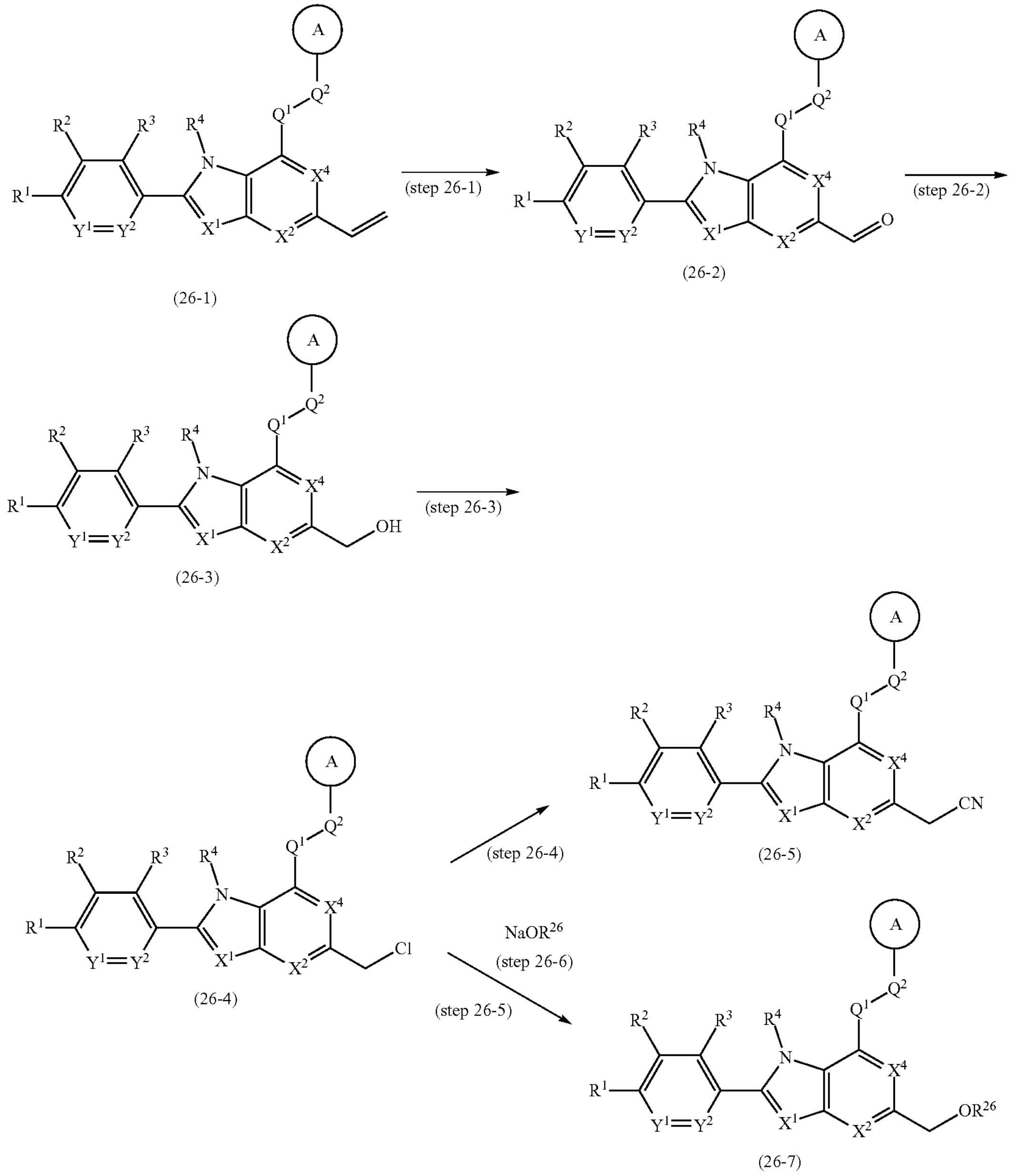

[where $R^1$, $R^2$, $R^3$, $R^4$, $X^1$, $X^2$, $X^3$, $X^4$, $Y^1$, $Y^2$, $Q^1$, $Q^2$, and ring A are as defined above. $R^{26}$ is an optionally substituted $C_1$-$C_6$ alkyl group.]

(Step 26-1)

In (Step 26-1), compound (26-2) can be produced by subjecting compound (26-1) to a double bond cleavage reaction by the same method as in (Step 3-2) of Production Method 3.

(Step 26-2)

In (step 26-2), compound (26-3) can be produced by reducing the formyl group of compound (26-2) to a hydroxymethyl group using a reducing agent.

Examples of the reducing agent include sodium borohydride, lithium borohydride, and the like.

Examples of the reaction solvent include, but are not limited to, aromatic hydrocarbons such as benzene, toluene, chlorobenzene, xylene, and the like; alcohols such as methanol, ethanol, 2-propanol, tert-butanol, and the like; ethers such as diethyl ether, THF, 1,4-dioxane, and the like; and mixed solvents thereof.

The reaction temperature is not particularly limited, and is usually 0° C. to 100° C.

The reaction time is not particularly limited and is preferably 0.5 hours to 24 hours.

(Step 26-3)

In (Step 26-3), compound (26-4) can be produced by converting the hydroxymethyl group of compound (26-3) to a chloromethyl group by the same method as in (Step 18-1) of Production Method 18.

(Step 26-4)

In (Step 26-4), compound (26-5) can be produced by substituting the chloro group of compound (26-4) with a cyano group using a cyanide.

Examples of the cyanide include sodium cyanide, potassium cyanide and the like.

Examples of the reaction solvent include, but are not limited to, aromatic hydrocarbons such as benzene, toluene, chlorobenzene, xylene, and the like; ethers such as diethyl ether, THF, 1,4-dioxane, 1,2-dimethoxyethane, and the like; aprotic polar solvents such as DMF, DMAc, N-methylpyrrolidone, DMSO, and the like; and mixed solvents thereof.

The reaction temperature is not particularly limited, and is usually 0° C. to 100° C.

The reaction time is not particularly limited and is preferably 0.5 hours to 24 hours.

(Step 26-5)

In (step 26-5), compound (26-7) can be produced by substituting the chloro group of compound (26-4) with an alkoxy group using compound (26-6). The reaction solvent is preferably an alcohol expressed by the formula ($R^{26}$—OH). The reaction temperature is not particularly limited, and is usually 0° C. to 100° C. The reaction time is not particularly limited and is preferably 0.5 hours to 24 hours.

Compound (27-1), which is one of the aforementioned compounds (I), can be produced, for example, by the method shown in Production Method 27, and then the functional group can be converted.

<Production Method 27>

[Chem. Fig. 50]

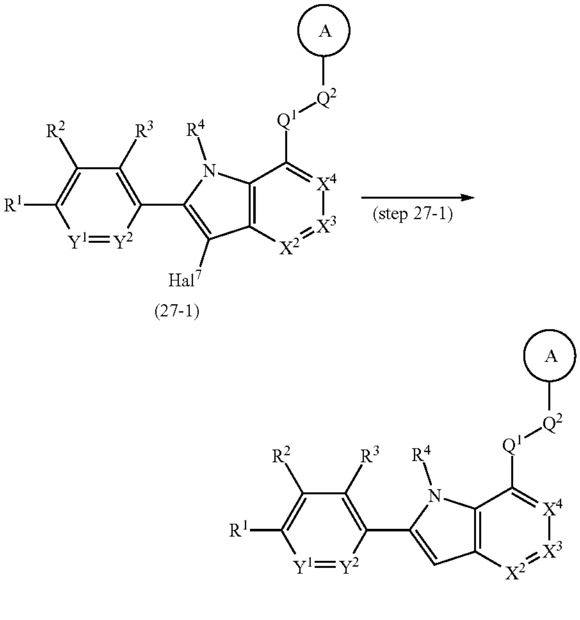

(27-1)

(27-2)

[where $R^1$, $R^2$, $R^3$, $R^4$, $X^1$, $X^2$, $X^3$, $X^4$, $Y^1$, $Y^2$, $Q^1$, $Q^2$, and ring A are as defined above. $Hal^7$ is a chloro group, a bromo group or an iodo group.]

(Step 27-1)

In (step 27-1), compound (27-2) can be produced by subjecting compound (27-1) to a catalytic reduction reaction in the presence of a transition metal catalyst and in the presence of hydrogen gas.

The reaction may be carried out under the same conditions as in the method described in (Step 2-3A) of Production Method 2.

The compound of the present invention produced by the aforementioned method may be a free compound, a salt thereof, a hydrate thereof or various solvates such as an ethanolate, and the compound of the present invention may be isolated and purified as an oily substance, an amorphous substance, or a substance composed of any crystal polymorph. Pharmaceutically acceptable salts of the compounds of the present invention may be prepared by conventional salt forming reactions. Isolation and purification may be carried out by applying chemical operations such as extraction fractionation, crystallization, and various types of fractional chromatography. Furthermore, optical isomers may be obtained as stereochemically pure isomers by selecting appropriate starting compounds or by optical separation of racemic compounds.

Compound (I) of the present invention and pharmaceutically acceptable salts thereof exhibit excellent STAT6 inhibitory activity. Therefore, a medicament containing these compounds as an active ingredient is useful as a prophylactic or therapeutic agent for diseases associated with STAT6 of mammals including humans. Diseases involving STAT6 include, for example, inflammatory diseases and allergic diseases. Inflammatory diseases and allergic diseases include, for example, chronic obstructive pulmonary disease, atopic dermatitis, bronchial asthma, bullous pemphigoid, nasal polyps, chronic rhinosinusitis, allergic rhinitis, eosinophilic esophagitis, prurigo, and urticaria.

A medicament containing compound I of the present invention or a pharmaceutically acceptable salt as an active ingredient can be prepared by a conventional method known in the art using the compound alone or in an admixture with pharmaceutically acceptable liquid or solid carriers such as excipients, binders, diluents, extenders, disintegrants, stabilizers, preservatives, buffers, emulsifiers, aromatics, colorants, sweeteners, thickeners, corrigents, solubilizing agents, and the like.

The medicament according to the present invention may be in any form including a solid composition, a liquid composition, and other compositions, and an optimum form is selected as necessary.

The medicament of the present invention can be administered orally or parenterally to mammals (e.g., humans, monkeys, cows, horses, pigs, dogs, cats, rabbits, rodents, rats, mice, and the like) in the form of tablets (including sugar-coated tablets and film-coated tablets), powders, granules, capsules, oral solutions, injections, suppositories, sustained-release preparations, lotions, liniments, ointments, patches, suspensions, emulsions, percutaneous absorption preparations, external solutions, creams, aerosols, and the like. In addition, other drugs may be added as necessary.

The administration route of the medicament of the present invention is not limited. In the case of oral administration, dosage forms such as tablets, orally disintegrating tablets, capsules, granules, powders, oral liquids, syrups, oral jellies, oral sprays, or the like can be prepared. Each of these compounds can be prepared by a conventional method known in the art. The dosage of the medicament of the present invention is not limited. For example, in the case of oral administration to adult patients, the present compound can be administered as an active ingredient at a dose of about 0.1 to 100 mg/kg once a day or more.

EXAMPLES

Hereinafter, the features of the present invention will be described in more detail with reference to Examples and Test Examples.

Materials, amounts used, ratios, treatment contents, treatment procedures and the like shown in the following Examples can be appropriately changed without departing from the gist of the present invention. Therefore, the scope of the present invention should not be construed as being limited to the specific examples shown below.

$^1$H-NMR spectra and mass spectrometry in the following examples were measured under the following conditions.

When describing $^1$H-NMR, deuterochloroform ($CDCl_3$), deuterodimethylsulfoxide (DMSO-$d_6$), or deuteromethanol ($CD_3OD$) are used as solvents, and tetramethylsilane as an internal standard was measured using an AVANCEIII HD400 type (400 MHz, manufactured by Bruker BioSpin K. K.).

In the measurement results for the chemical shift of $^1$H-NMR spectra, o values were expressed in ppm and J values for coupling constants were expressed in Hz. The meanings of the abbreviations are s: singlet, d: doublet, t: triplet, q: quartet, m: multiplet, and br: broad.

LC/MS was measured using an ESI (electrospray ionization) method under the following conditions, where "$[M+H]^+$" refers to ESI positive ion mode, and "$[M-H]^-$" refers to ESI negative ion mode. In each chromatographic and experimental procedure, "number/number" refers to the volume ratio of each solvent unless otherwise indicated.

Device: mass spectrometer (Exactive) (manufactured by Thermo Fisher Scientific Inc.) (LC portion: nanospace SI-2/NASCA (manufactured by Shiseido Company, Limited.))

Column: none

Solvent:

Liquid A: Distilled water

Liquid B: Acetonitrile

The mixing ratio of Liquid A to liquid B was fixed at 50/50.

Flow rate: 0.2 mL/min

Detector (wavelength): UV detector (254 nm)

The microwave reaction device that was used was an Initiator sixty manufactured by Biotage Japan.

Also, in the following figures, Ref.-numbers refer to reference synthesis example compounds, and Ex.-numbers refer to Example compounds. In addition, an example number refers to the preparation of an example compound having the same number.

Example 1

[Chem. Fig. 51]

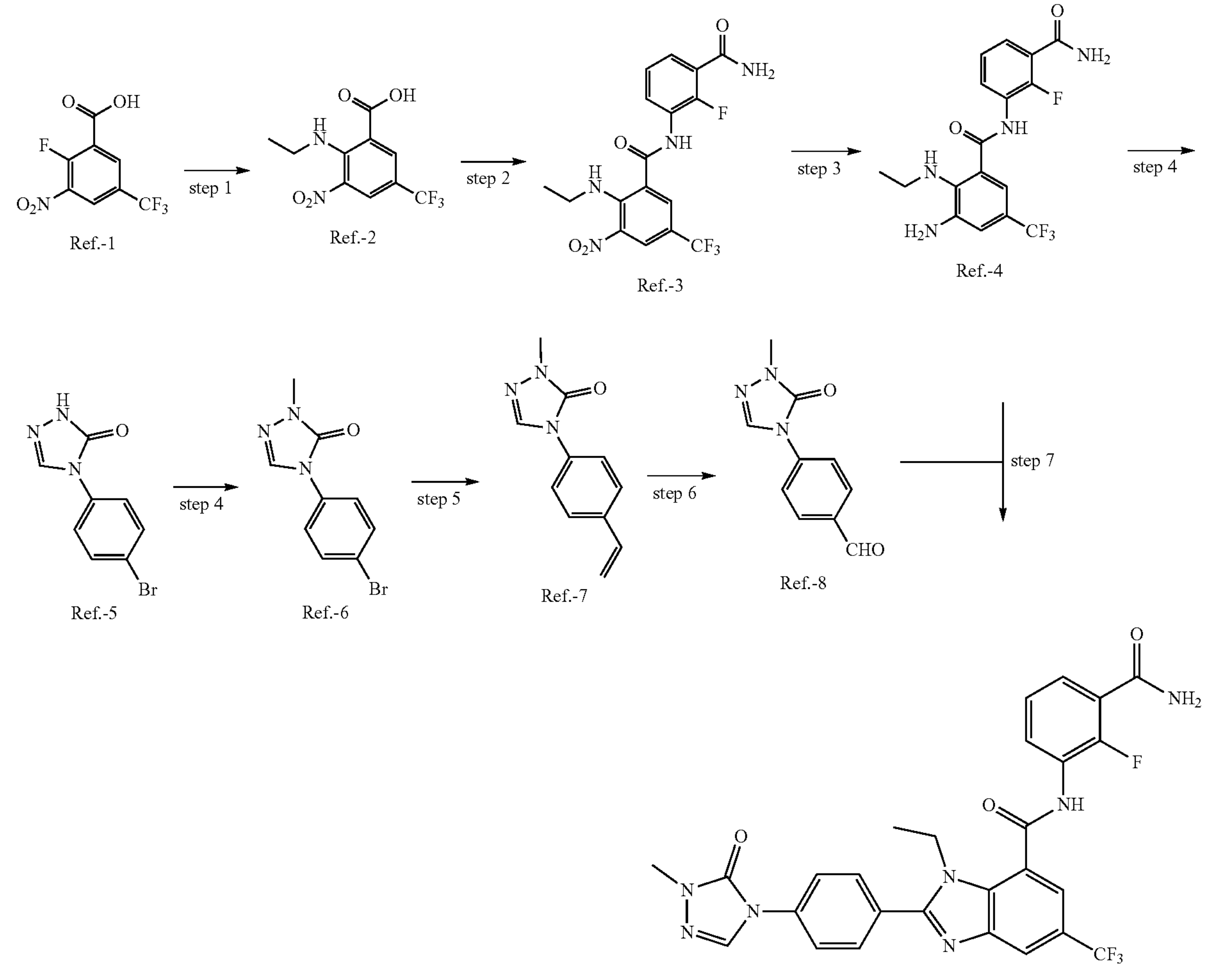

Ref.-1 Ref.-2 Ref.-3 Ref.-4 Ref.-5 Ref.-6 Ref.-7 Ref.-8

Ex.-1

Step 1

Under ice-cooling, reference synthesis example compound 1 (5.00 g, 18.5 mmol) and THF (90 mL) were mixed, potassium carbonate (4.10 g, 29.7 mmol) and ethyl amine/THF solution (2.0 mol/L, 12 mL) were added, the temperature was raised to 50° C., and the mixture was stirred for 4 hours. Water and a mixed solution of ethyl acetate/n-hexane (3/1) were added to the cooled reaction solution and stirred, and the aqueous layer was separated. 2 mol/L of hydrochloric acid (40 mL) was added to the separated aqueous layer, followed by extraction using ethyl acetate. The extract was dried over anhydrous sodium sulfate and evaporated under reduced pressure to obtain reference synthetic example compound 2 (yield 4.22 g).

Step 2

Reference synthesis example compound 2 (4.22 g, 15.2 mmol) and acetonitrile (80 mL) were mixed, 3-amino-2-fluorobenzamide (2.69 g, 17.5 mmol) and 1-methylimidazole (2.87 mL, 36.4 mmol) were added, ice-cooled, TCFH (5.11 g, 18.2 mmol) was added, and the mixture was stirred at room temperature for 15 hours. Water was added to the reaction solution, and the precipitate was collected by filtration. The obtained solid was purified by silica gel column chromatography to obtain reference synthesis example compound 3 (yield 5.56 g).

Step 3

Reference synthesis example compound 3 (1.05 g, 2.53 mmol) and methanol (50 mL) were mixed, 10% palladium-carbon (250 mg) was added, and the mixture was stirred at room temperature for 1 hour under a hydrogen environment. The reaction solution was filtered through Celite®, and the solvent was distilled off under reduced pressure. A chloroform/methanol mixed solution was added to the residue, and the precipitated solid was collected by filtration (A). The filtrate was concentrated under reduced pressure and the residue was purified by silica gel column chromatography (B). The solid A collected by filtration and the fraction B purified by column chromatography were combined to obtain reference synthesis example compound 4 (yield 910 mg).

Step 4

Reference synthesis example compound 5 (5.00 g, 20.8 mmol) and DMF (104 mL) were mixed, sodium hydride (60% in oil) (1.25 g, 31.3 mmol) was added, and the mixture was stirred for 10 minutes. Methyl iodide (2.6 mL, 42 mmol) was added to the reaction solution, and the mixture was stirred at room temperature for 23 hours. Saturated ammonium chloride aqueous solution and water was added to the reaction solution, the precipitate was collected by filtration to obtain reference synthesis example compound 6 (yield 4.98 g).

Step 5

Reference synthesis example compound 6 (4.98 g, 19.6 mmol), potassium vinyltrifluoroborate (5.25 g, 39.2 mmol), cesium carbonate (12.8 g, 39.3 mmol), and 1,4-dioxane/water (5/1) (98 mL) were mixed and degassed, and bis[di-tert-butyl(4-dimethylaminophenyl)phosphine] dichloropalladium (II) (695 mg, 0.981 mmol) was added and stirred at 90° C. for 4 hours under an argon environment. The solution was allowed to cool and then filtered through Celite®. Water was added to the filtrate, and the mixture was extracted using ethyl acetate and washed with saturated brine. The filtrate was dried over anhydrous sodium sulfate, and the solvent was distilled off under reduced pressure. The residue was purified by silica gel column chromatography to obtain reference synthesis example compound 7 (yield 2.04 g).

Step 6

Reference synthesis example compound 7 (2.04 g, 10.1 mmol) and 1,4-dioxane (101 mL) were mixed under ice-cooling, and then water (34 mL), 2,6-dimethylpyridine (2.35 mL, 20.2 mmol), sodium periodate (8.66 g, 40.5 mmol), and osmium tetraoxide/tert-butyl alcohol solution (2.5 w/v %) (5.15 mL, 0.51 mmol) were added in this order, followed by stirring at room temperature for 2 hours. The reaction solution was ice-cooled, saturated aqueous sodium thiosulfate solution and water were sequentially added, and the mixture was extracted using ethyl acetate. The solvent was distilled off under reduced pressure, and then the residue was purified by silica gel column chromatography to obtain reference synthesis example compound 8 (yield 1.88 g).

Step 7

Reference synthesis example compound 4 (100 mg, 0.260 mmol) and ethanol (5 mL) were mixed, and then reference synthesis example compound 8 (69 mg, 0.34 mmol) and acetic acid (149 μL, 2.60 mmol) were added, followed by stirring at 85° C. for 18 hours under an oxygen environment. A saturated aqueous solution of sodium hydrogen carbonate was added to the cooled reaction solution, and the precipitate was collected by filtration. The obtained solid was purified by silica gel column chromatography to obtain Example Compound 1 (yield 106 mg).

Example 2

[Chem. Fig. 52]

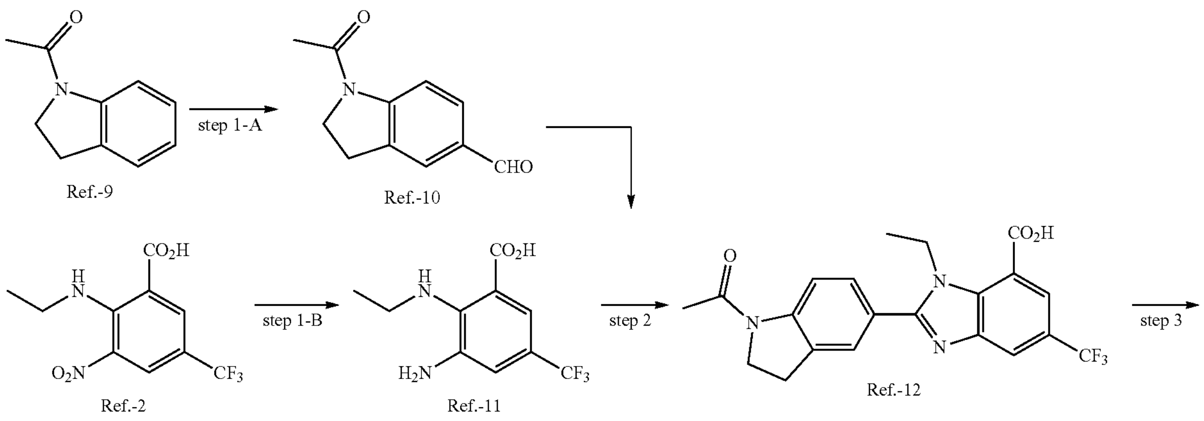

Ref.-9 Ref.-10 Ref.-2 Ref.-11 Ref.-12

-continued

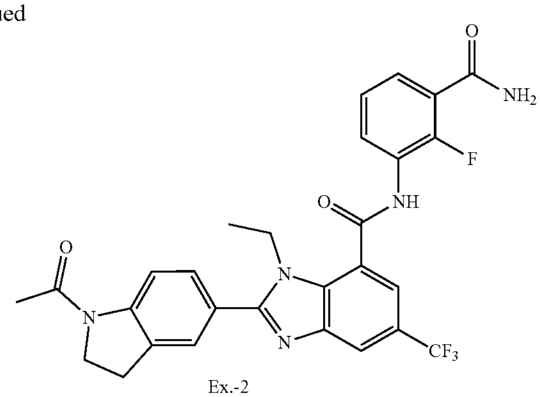

Ex.-2

Step 1-A

Reference synthesis example compound 9 (1.00 g, 6.20 mmol) and TFA (5.2 mL) were mixed, and then hexamethylenetetramine (957 mg, 6.83 mmol) was added, followed by stirring at 90° C. for 24 hours. The cooled reaction solution was diluted with water and extracted using ethyl acetate. The extract was washed with saturated brine and dried over anhydrous sodium sulfate. The solvent was distilled off under reduced pressure, and then the residue was purified by silica gel column chromatography to obtain reference synthesis example compound 10 (yield 826 mg).

Step 1-B

Reference synthesis example compound 2 (500 mg, 1.80 mmol) and methanol (20 mL) were mixed, 20% palladium hydroxide/charcoal (50 mg, 0.071 mmol) was added, and the mixture was stirred at room temperature for 4 hours under a hydrogen environment (0.3 MPa). The reaction solution was filtered, and the solvent was distilled off under reduced pressure. The residue was purified by silica gel column chromatography to obtain reference synthesis example compound 11 (yield 410 mg).

Step 2

Reference synthesis example compound 11 (100 mg, 0.403 mmol) and ethanol (4 mL) were mixed, and then reference synthesis example compound 10 (114 mg, 0.603 mmol) and acetic acid (231 μL, 4.03 mmol) were added, followed by stirring at 70° C. for 2 hours under an oxygen environment. The reaction solution was allowed to cool, and the precipitated solid was collected by filtration and washed with methanol to obtain reference synthetic example compound 12 (yield 86.7 mg).

Step 3

Reference synthesis example compound 12 (15 mg, 0.0359 mmol) and acetonitrile (500 μL) were mixed, and then 3-amino-2-fluorobenzamide (6.6 mg, 0.043 mmol), 1-methylimidazole (7.0 μL, 0.089 mmol), and TCFH (12.2 mg, 0.0435 mmol) were added, followed by stirring at room temperature for 5 hours. Water was added to the reaction solution, and the precipitated solid was collected by filtration and washed with water. The obtained solid was purified by silica gel column chromatography to obtain Example Compound 2 (yield 5.7 mg).

Examples 3 to 10

Example compounds 3 to 10 were produced according to the methods shown in Examples 1 and 2 described above or Examples 11 to 14 described below, or similar methods.

Example 11

[Chem. Fig. 53]

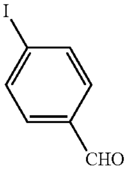

Ref.-13

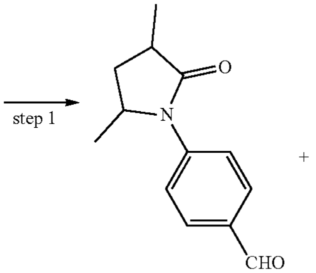

Ref.-14
(1st peak diastereomeric pure racemate)

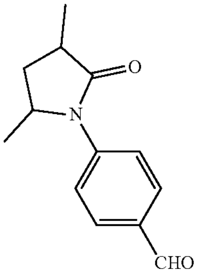

Ref.-15
(2nd peak diastereomeric pure racemate)

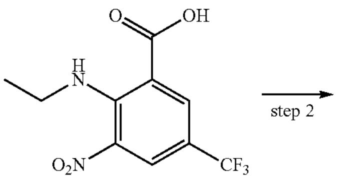

Ref.-2

-continued

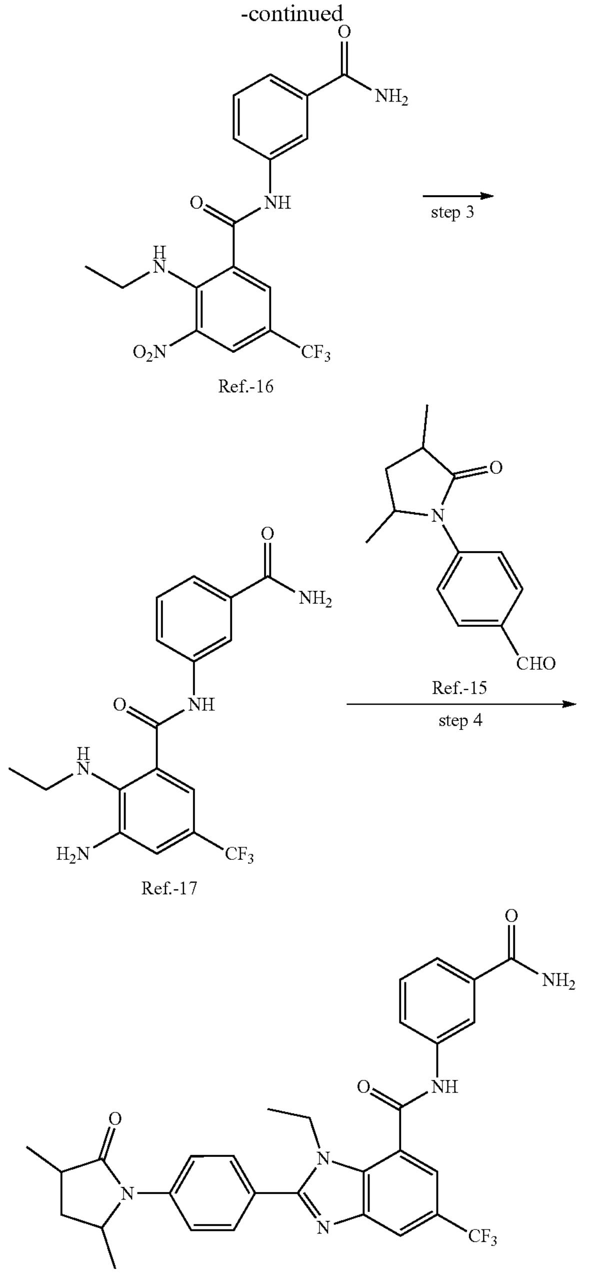

Ex.-11
(diasrtereomeric pure, racemate)

Step 1

Reference synthesis example compound 13 (246 mg, 1.06 mmol), 3,5-dimethylpyrrolidin-2-one (100 mg, 0.884 mmol), cuprous iodide (8.4 mg, 0.044 mmol) and tripotassium phosphate (375 mg, 1.77 mmol) were added with 1,4-dioxane (8 mL) and N,N'-dimethylethylenediamine (10 μL, 0.093 mmol), and stirred under an argon environment at 120° C. for 14 hours. The reaction solution was allowed to cool, water and ethyl acetate were added and stirred, and then the organic layer was separated. The separated organic layer was dried over anhydrous sodium sulfate, and the solvent was distilled off under reduced pressure. The residue was purified by silica gel column chromatography and, at the same time, diastereomers were separated to obtain reference synthesis example compound 14 (diastereomer of the first peak) (yield 101 mg) and reference synthesis example compound 15 (diastereomer of the second peak) (yield 80.2 mg).

Step 2

Reference synthesis example compound 2 (1.50 g, 5.39 mmol) and acetonitrile (25 mL) were mixed, and then 3-aminobenzamide (881 mg, 6.47 mol), 1-methylimidazole (1.02 mL, 12.9 mmol), and TCFH (1.82 g, 6.49 mmol) were added, followed by stirring at room temperature for 5 hours. Water was added to the reaction solution, and the precipitated solid was collected by filtration to obtain reference synthesis example compound 16 (yield 1.76 g).

Step 3

Reference synthesis example compound 16 (156 mg, 0.394 mmol) and methanol (3.9 mL) were mixed, 20% palladium hydroxide/charcoal (15.6 mg) was added, and the mixture was stirred at room temperature for 2 hours under a hydrogen environment. The reaction solution was filtered and the solvent was evaporated under reduced pressure. The residue was purified by silica gel column chromatography to obtain reference synthesis example compound 17 (yield 133 mg).

Step 4

Reference synthesis example compound 15 (10 mg, 0.046 mmol) and acetic acid (23 μL) were added to a solution of reference synthesis example compound 17 (15 mg, 0.041 mmol) in ethanol (1 mL), and the solution was stirred at 80° C. for 17 hours under an oxygen environment. A saturated aqueous sodium hydrogen carbonate solution was added to the reaction solution, and the precipitate was collected by filtration. The obtained solid was purified by silica gel column chromatography to obtain Example Compound 11 (yield 16.8 mg).

Examples 12 and 13

[Chem. Fig. 54]

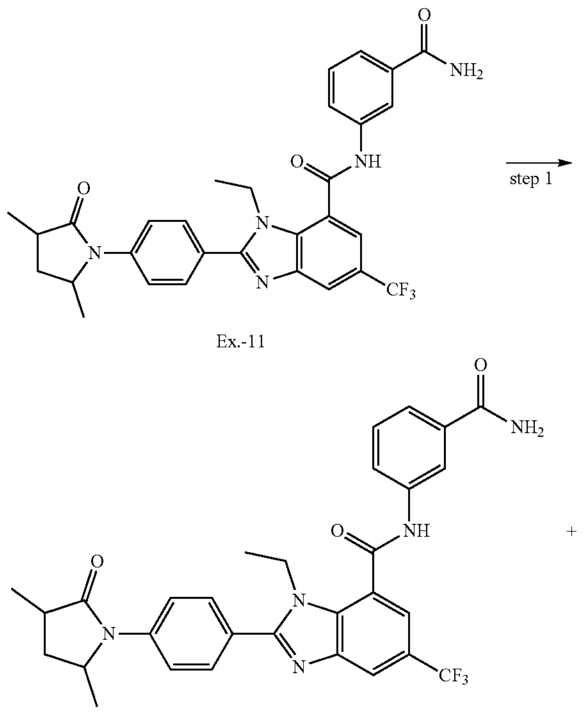

Ex.-12
(1st peak,
diasrtereomeric pure,
enantiomeric pure)

-continued

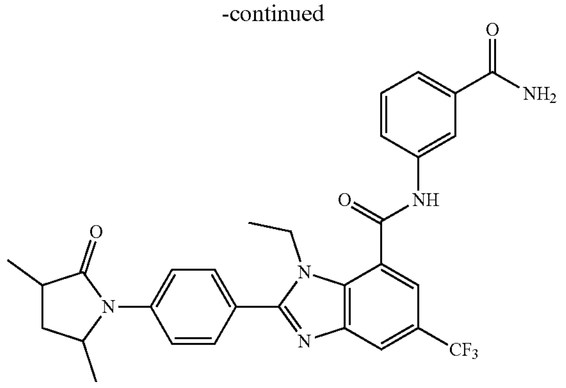

Ex.-13
(2nd peak,
diasrtereomeric pure,
enantiomeric pure)

Step 1

A preparative chiral column (CHIRALPAK IC, manufactured by Daicel Corporation) was attached to a preparative LC system (LC-Forte/R, manufactured by YMC Co., Ltd.), and a mixed solution of ethanol/normal hexane (1/1) was passed through the column at room temperature and a flow rate of 8.0 mL/min for equilibration. Example Compound 11 (12.0 mg, 0.0213 mmol) was dissolved in ethanol (7 mL) to obtain Solution A. Solution A (3.5 mL) was injected, and the first peak (retention time: about 18 minutes) and the second peak (retention time: about 19 minutes) were collected while observing with a UV detector (detection wave length: 254 nm) (the operation was performed two times). Example Compound 12 (yield 5.8 mg) was obtained from the fraction derived from the first peak, and Example Compound 13 (yield 5.1 mg) was obtained from the fraction derived from the second peak, by distilling off the solvents contained in the respective fractions under reduced pressure.

Example 14

[Chem. Fig. 55]

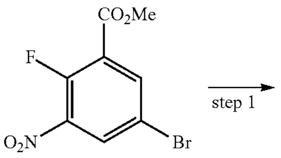

Ref.-18

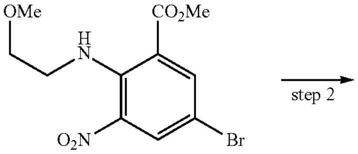

Ref.-19

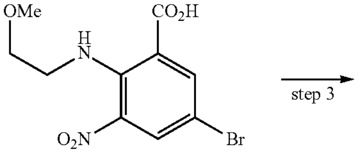

Ref.-20

-continued

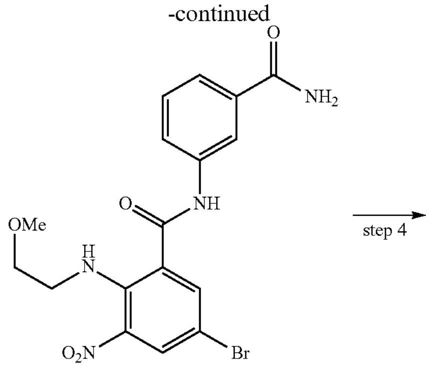

Ref.-21

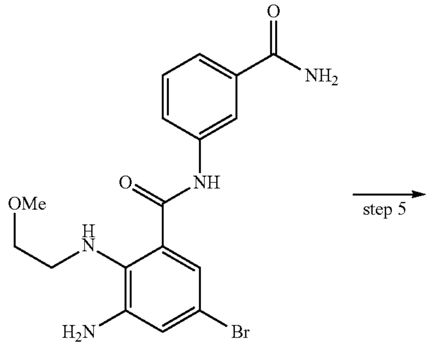

Ref.-22

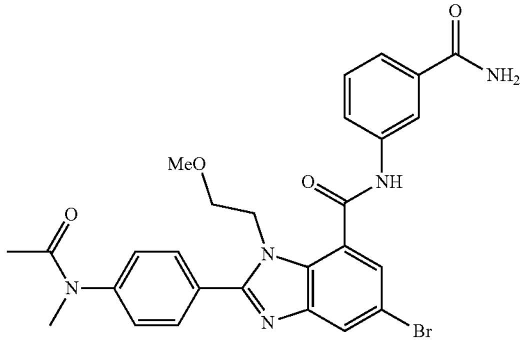

Ex.-14

Step 1

Reference synthesis example compound 18 (3.00 g, 10.8 mmol) and THF (54 mL) were mixed, then potassium carbonate (2.39 g, 17.3 mmol) and 2-methoxyethylamine (1.2 mL, 14 mmol) were added, and the mixture was stirred at room temperature for 3 hours. Water was added to the reaction solution, followed by extraction using chloroform. The extract was dried over anhydrous sodium sulfate and evaporated under reduced pressure to obtain reference synthetic example compound 19 in a partially impure state (yield 3.65 g).

Step 2

The impurity-containing reference synthesis example compound 19 (3.65 g) obtained by the method described in Step 1 and methanol (110 mL) were mixed, and then 4 mol/L aqueous sodium hydroxide (21 mL) was added, followed by stirring at room temperature for 2 hours. The reaction solution was ice-cooled, 6 mol/L of hydrochloric acid was added, and the mixture was extracted using chloroform. The extract was dried over anhydrous sodium sulfate, and evaporation was performed under reduced pressure to obtain reference synthetic example compound 20 in a partially impure state (yield 3.47 g).

Step 3

Reference synthesis example compound 20 (3.47 g) containing impurity obtained by the method described in Step 2 was mixed with acetonitrile (54.4 mL), and then 3-aminobenzamide (1.78 g, 13.1 mmol), 1-methylimidazole (2.1 mL, 27 mmol), and TCFH (3.66 g, 13.0 mmol) were added, followed by stirring at room temperature for 18 hours. Water was added to the reaction solution, the precipitated solid was collected by filtration and washed with water to obtain reference synthesis example compound 21 (yield 4.53 g).

Step 4

Reference synthesis example compound 21 (4.45 g, 10.1 mmol) and ethanol (101 mL) were mixed, and then acetic acid (5.8 mL) and reduced iron (2.83 g, 50.6 mmol) were added, followed by stirring at 50° C. for 20 hours. The reaction solution was allowed to cool, and then filtered through Celite®. The filtrate was concentrated under reduced pressure, and the residue was purified by silica gel column chromatography to obtain reference synthesis example compound 22 (yield 1.68 g).

Step 5

Reference synthesis example compound 22 (1.15 g, 2.81 mmol) and ethanol (56 mL) were mixed, then N-(4-formylphenyl)-N-methyl-acetamide (503 mg, 2.84 mmol) and acetate (1.6 mL, 28 mmol) were added, and the mixture was stirred at 70° C. for 3 hours under an oxygen environment. Water and saturated aqueous sodium hydrogen carbonate solution were added to the reaction solution, and the mixture was extracted using chloroform. The extracted solution was concentrated under reduced pressure, and the residue was purified by silica gel column chromatography to obtain Example Compound 14 (yield 1.13 g).

Example compounds 1 to 14 in the following table were produced according to the methods shown in Examples 1 and 2 and Examples 11 to 14 described above, or similar methods. Furthermore, $^1$H-NMR data and/or LC/MS data of these Example compounds are shown in the table.

TABLE 1-1

| Ex. | Structure | Data |
|---|---|---|
| 1 | 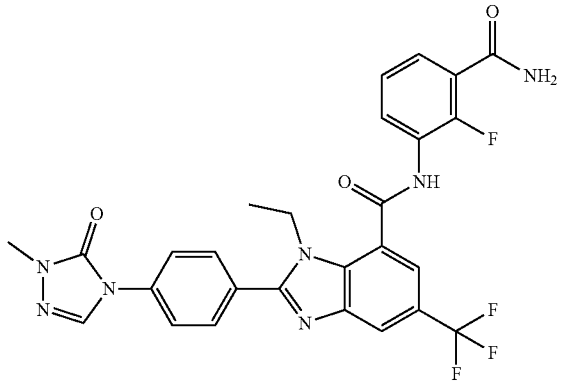 [SMILES: CCn1c(-c2ccc(-n3cnn(C)c3=O)cc2)nc2cc(C(F)(F)F)cc(C(=O)Nc3cccc(C(N)=O)c3F)c21] | $^1$H-NMR (400 MHz, DMSO-$d_6$) δ: 1.20 (3H, t, J = 7.1 Hz), 3.43 (3H, s), 4.45 (2H, q, J = 7.0 Hz), 7.32 (1H, t, J = 7.8 Hz), 7.51 (1H, t, J = 6.2 Hz), 7.68 (1H, s), 7.83-8.00 (7H, m), 8.29 (1H, s), 8.64 (1H, s), 10.89 (1H, s). ESI-MS m/z: 568 [M + H]$^+$ |
| 2 | 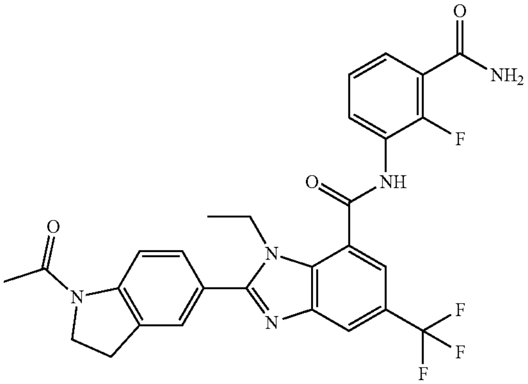 [SMILES: CCn1c(-c2ccc3c(c2)CCN3C(C)=O)nc2cc(C(F)(F)F)cc(C(=O)Nc3cccc(C(N)=O)c3F)c21] | $^1$H-NMR (400 MHz, DMSO-$d_6$) δ: 1.13-1.20 (3H, m), 2.20 (3H, s), 3.23-3.30 (2H, m), 4.18-4.21 (2H, m), 4.41-4.48 (2H, m), 7.30-7.37 (1H, m), 7.50-7.70 (4H, m), 7.82-7.91 (3H, m), 8.21-8.27 (2H, m), 10.88 (1H, s). ESI-MS m/z: 554 [M + H]$^+$ |

TABLE 1-1-continued
| Ex. | Structure | Data |
| --- | --- | --- |
| 3 | 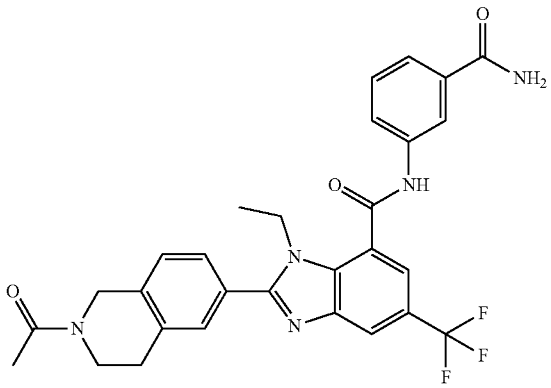 [SMILES: CCn1c(-c2ccc3c(c2)CCN(C(C)=O)C3)nc2cc(C(F)(F)F)cc(C(=O)Nc3cccc(C(N)=O)c3)c21] | ESI-MS m/z: 550 [M + H]$^+$ |
| 4 | 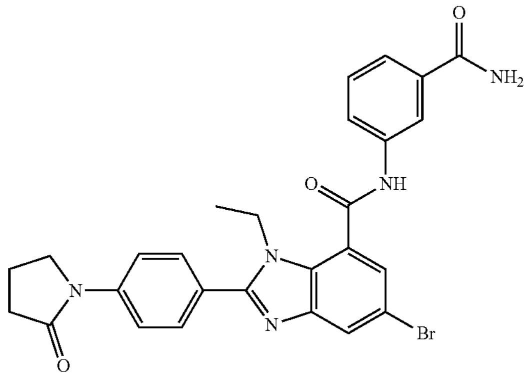 [SMILES: CCn1c(-c2ccc(N3CCCC3=O)cc2)nc2cc(Br)cc(C(=O)Nc3cccc(C(N)=O)c3)c21] | ESI-MS m/z: 546, 548 [M + H]$^+$ |
| 5 | 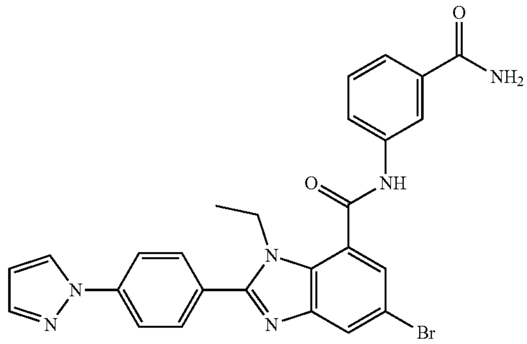 [SMILES: CCn1c(-c2ccc(-n3cccn3)cc2)nc2cc(Br)cc(C(=O)Nc3cccc(C(N)=O)c3)c21] | ESI-MS m/z: 529, 531 [M + H]$^+$ |
| 6 | 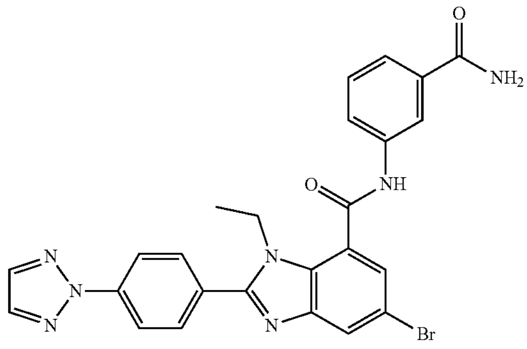 [SMILES: CCn1c(-c2ccc(-n3nccn3)cc2)nc2cc(Br)cc(C(=O)Nc3cccc(C(N)=O)c3)c21] | ESI-MS m/z: 530, 532 [M + H]$^+$ |

TABLE 1-2
| | | |
|---|---|---|
| 7 | 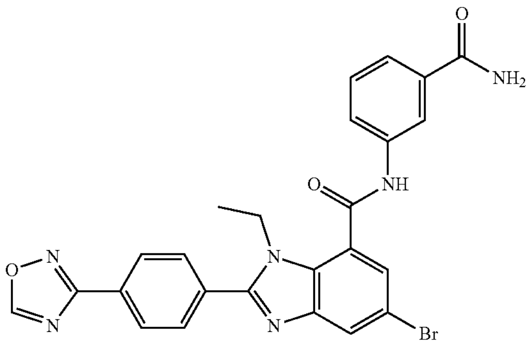 [SMILES: CCn1c(-c2ccc(-c3ncon3)cc2)nc2cc(Br)cc(C(=O)Nc3cccc(C(N)=O)c3)c21] | ESI-MS m/z: 531, 533 $[M + H]^+$ |
| 8 | 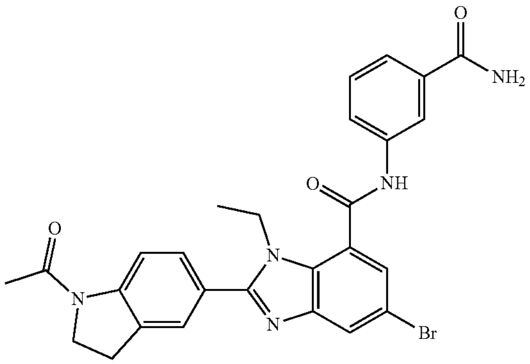 [SMILES: CCn1c(-c2ccc3c(c2)CCN3C(C)=O)nc2cc(Br)cc(C(=O)Nc3cccc(C(N)=O)c3)c21] | ESI-MS m/z: 546, 548 $[M + H]^+$ |
| 9 | 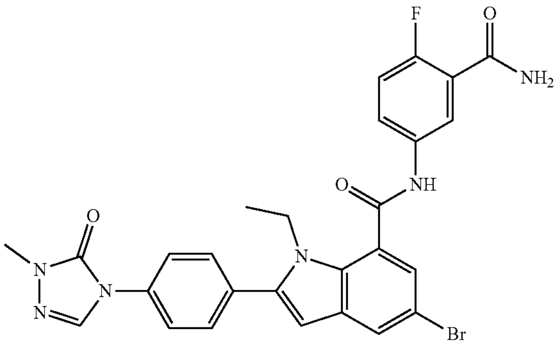 [SMILES: CCn1c(-c2ccc(-n3cnn(C)c3=O)cc2)cc2cc(Br)cc(C(=O)Nc3ccc(F)c(C(N)=O)c3)c21] | ESI-MS m/z: 578, 580 $[M + H]^+$ |
| 10 | 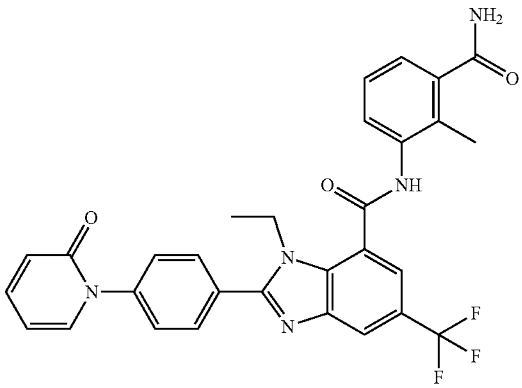 [SMILES: CCn1c(-c2ccc(-n3ccccc3=O)cc2)nc2cc(C(F)(F)F)cc(C(=O)Nc3cccc(C(N)=O)c3C)c21] | $^1$H-NMR (400 MHz, DMSO-$d_6$) δ: 1.25 (3H, t, J = 7.1 Hz), 2.36 (3H, s), 4.47-4.52 (2H, m), 6.37-6.40 (1H, m), 6.52-6.58 (1H, m), 7.26-7.32 (2H, m), 7.46 (1H, br s), 7.51-7.58 (2H, m), 7.67-7.70 (2H, m), 7.78-7.80 (1H, m), 7.84 (1H, br s), 7.90-7.97 (3H, m), 8.31 (1H, m), 10.55 (1H, s).<br>ESI-MS m/z: 558, 560 $[M + H]^+$ |

TABLE 1-2-continued

| | | |
|---|---|---|
| 11 | 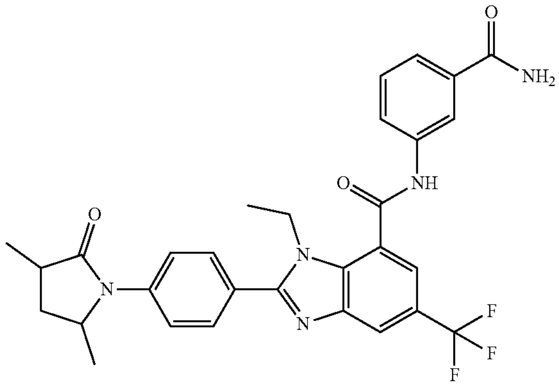 [SMILES: CCn1c(-c2ccc(N3C(=O)C(C)CC3C)cc2)nc2cc(C(F)(F)F)cc(C(=O)Nc3cccc(C(N)=O)c3)c21]<br>(diasrtereomeric pure, racemate) | $^1$H-NMR (400 MHz, DMSO-$d_6$) δ: 1.14-1.35 (10H, m), 2.55-2.68 (2H, m), 4.35-4.45 (3H, m), 7.41 (1H, br s), 7.47 (1H, t, J = 7.9 Hz), 7.61-7.66 (3H, m), 7.80-7.84 (3H, m), 7.91-7.94 (1H, m), 7.99 (1H, br s), 8.25 (2H, s), 11.05 (1H, s).<br>ESI-MS m/z: 564 $[M + H]^+$ |
| 12 | 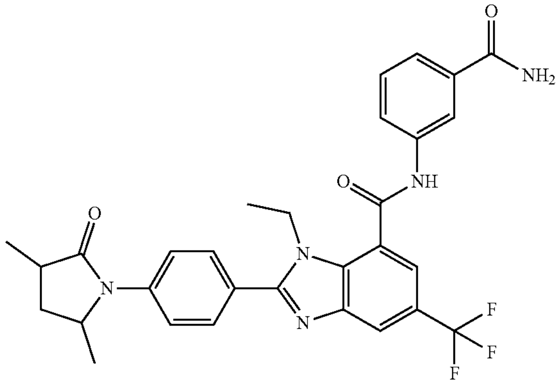 [SMILES: CCn1c(-c2ccc(N3C(=O)C(C)CC3C)cc2)nc2cc(C(F)(F)F)cc(C(=O)Nc3cccc(C(N)=O)c3)c21]<br>(diasrtereomeric pure, enantiomeric pure, 1st peak) | $^1$H-NMR (400 MHz, DMSO-$d_6$) δ: 1.14-1.39 (10H, m), 2.56-2.69 (2H, m), 4.35-4.46 (3H, m), 7.41 (1H, br s), 7.47 (1H, t, J = 7.9 Hz), 7.61-7.67 (3H, m), 7.80-7.84 (3H, m), 7.91-7.94 (1H, m), 8.00 (1H, br s), 8.25 (2H, s), 11.04 (1H, s).<br>ESI-MS m/z: 564 $[M + H]^+$ |

TABLE 1-3

| | | |
|---|---|---|
| 13 | 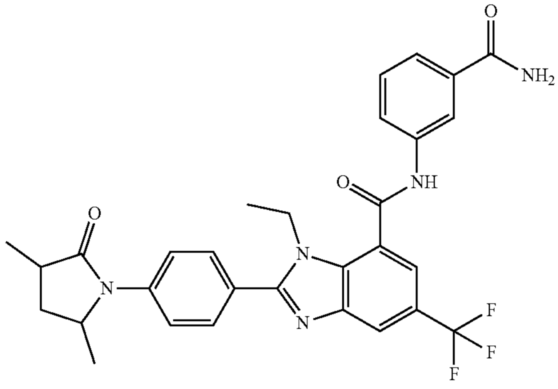 [SMILES: CCn1c(-c2ccc(N3C(=O)C(C)CC3C)cc2)nc2cc(C(F)(F)F)cc(C(=O)Nc3cccc(C(N)=O)c3)c21]<br>(diasrtereomeric pure,<br>enantiomeric pure, 2nd peak) | $^1$H-NMR (400 MHz, DMSO-$d_6$) δ: 1.14-1.39 (10H, m), 2.56-2.69 (2H, m), 4.35-4.46 (3H, m), 7.41 (1H, br s), 7.47 (1H, t, J = 7.9 Hz), 7.61-7.67 (3H, m), 7.80-7.84 (3H, m), 7.91-7.94 (1H, m), 8.00 (1H, br s), 8.25 (2H, s), 11.04 (1H, s).<br>ESI-MS m/z: 564 $[M + H]^+$ |

TABLE 1-3-continued

| | | |
|---|---|---|
| 14 | 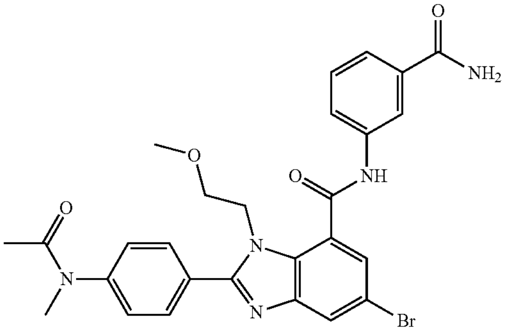 [SMILES: COCCn1c(-c2ccc(N(C)C(C)=O)cc2)nc2cc(Br)cc(C(=O)Nc3cccc(C(N)=O)c3)c21] | ESI-MS m/z: 564, 566 [M + H]+ |

Example 15

[Chem. Fig. 56]

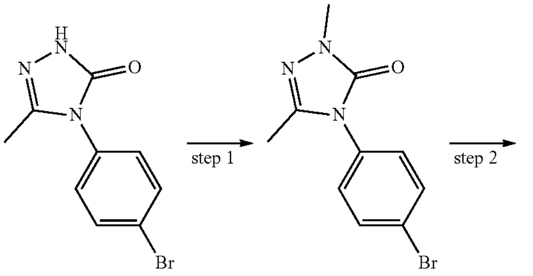

Ref.-23 Ref.-24

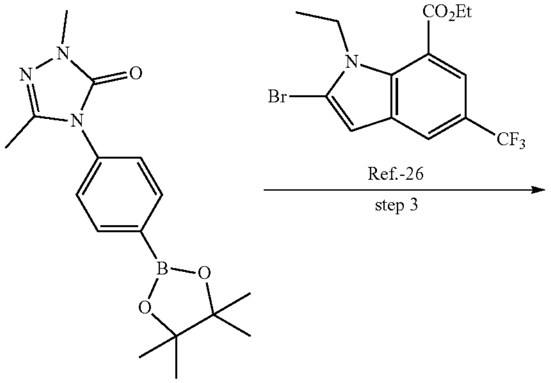

Ref.-25

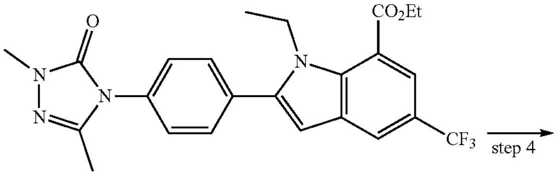

Ref.-27

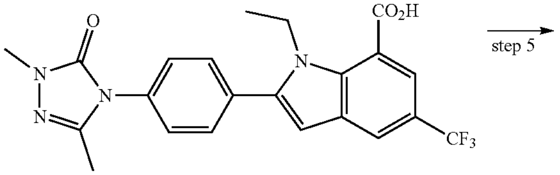

Ref.-28

-continued

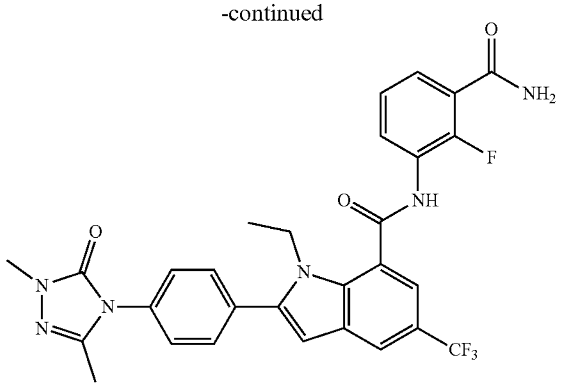

Ex.-15

Step 1

Reference synthesis example compound 23 (4.02 g, 15.8 mmol) and DMF (70 mL) were mixed, sodium hydride (60% in oil) (949 mg, 23.7 mmol) was added under ice-cooling, and the mixture was stirred for 30 minutes. Methyl iodide (2.95 mL, 47.4 mmol) was added and stirred at room temperature for 18 hours. A saturated aqueous ammonium chloride solution was added to the reaction solution under ice-cooling, followed by extraction using ethyl acetate. The extract was washed with saturated brine and dried over anhydrous sodium sulfate. The solvent was distilled under reduced pressure, and the residue was purified by silica gel column chromatography to obtain reference synthesis example compound 24 (yield 3.83 g).

Step 2

Reference synthesis example compound 24 (250 mg, 0.932 mmol) and 1,4-dioxane (5 mL) were mixed, and then bis(pinacolato)diboron (355 mg, 1.40 mmol), potassium acetate (183 mg, 1.87 mmol), and [1,1'-bis(diphenylphosphino)ferrocene]dichloropalladium (II) (68.2 mg, 0.932 mmol) were added and stirred at 100° C. for 3 hours. The reaction solution was allowed to cool and filtered through Celite®. Water and ethyl acetate were added, the mixture was stirred, and the organic layer was separated. The separated organic layer was sequentially washed with water and saturated brine, and dried over anhydrous sodium sulfate. The solvent was distilled off under reduced pressure, and then the residue was purified by silica gel column chromatography to obtain reference synthesis example compound 25 (yield 90 mg).

Step 3

Reference synthesis example compound 26 (75 mg, 0.21 mmol), reference synthesis example compound 25 (85 mg, 0.27 mmol), and 1,4-dioxane (3 mL) were mixed, and then water (600 μL), cesium carbonate (134 mg, 0.411 mmol), and [1,1'-bis(diphenylphosphino)ferrocene]dichloropalladium (II) (7.3 mg, 0.010 mmol) were added, followed by stirring at 100° C. for 3 hours. The mixture was allowed to cool, diluted with water, and extracted using ethyl acetate. The extract was dried over anhydrous sodium sulfate, and the solvent was distilled off under reduced pressure. The residue was purified by silica gel column chromatography to obtain reference synthetic example compound 27 (yield 59.8 mg).

Step 4

Reference synthesis example compound 27 (58 mg, 0.12 mmol) and THF (2 mL) were mixed, methanol (3 mL) and 4 mol/L aqueous sodium hydroxide (3 mL, 12 mmol) were added, and the mixture was stirred at 60° C. for 4 hours. The reaction solution was allowed to cool, and 2 mol/L of hydrochloric acid (2.2 mL) was added to the mixture, which was then diluted with water and extracted using ethylacetate/methanol (10/1). The extract was dried over anhydrous sodium sulfate and the solvent was evaporated under reduced pressure to obtain reference synthesis example compound 28 (yield 55 mg).

Step 5

Reference synthesis example compound 28 (12 mg, 0.027 mmol) and acetonitrile (300 μL) were mixed, and then 3-amino-2-fluorobenzamide (6.5 mg, 0.042 mmol), 1-methylimidazole (6.0 μL, 0.076 mmol) and TCFH (9.1 mg, 0.032 mmol) were added, followed by stirring at room temperature for 15 hours. The reaction solution was diluted with water, and the precipitate was collected by filtration. The obtained solid was purified by silica gel column chromatography to obtain Example Compound 15 (yield 3.2 mg).

Example 16

[Chem. Fig. 57]

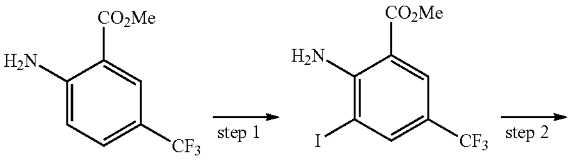

Ref.-29 Ref.-30

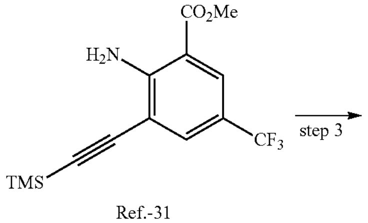

Ref.-31

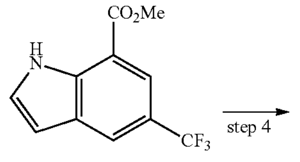

Ref.-32

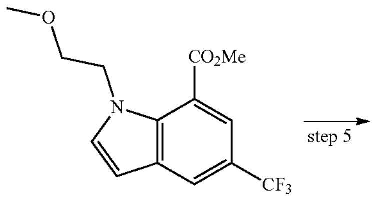

Ref.-33

-continued

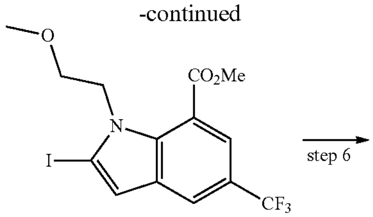

Ref.-34

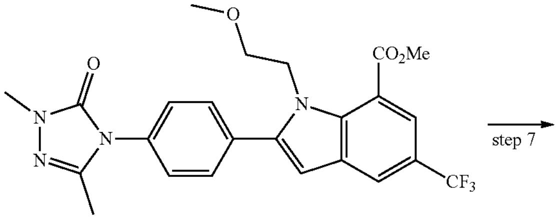

Ref.-35

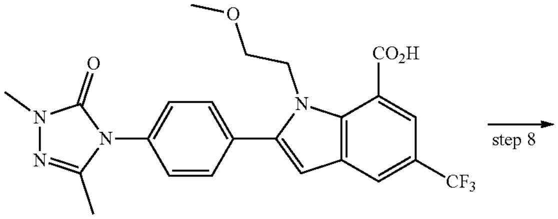

Ref.-36

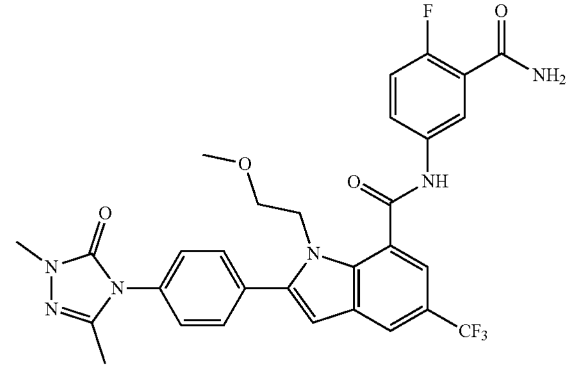

Ex.-16

Step 1

Reference synthesis example compound 29 (5.14 g, 23.5 mmol) and TFA (40 mL) were mixed, and then NIS (5.80 g, 25.8 mmol) was added, followed by stirring at room temperature for 5 hours. After the reaction solution was concentrated under reduced pressure, a saturated aqueous solution of sodium hydrogen carbonate and ethyl acetate were added and stirred, and then the organic layer was separated. The separated organic layer was dried over anhydrous sodium sulfate, and the solvent was distilled off under reduced pressure. The residue was purified by silica gel column chromatography to obtain reference synthetic example compound 30 (yield 7.64 g).

Step 2

Reference synthesis example compound 30 (5.49 g, 15.9 mmol) and TEA (59 mL) were mixed, then dichlorobis (triphenylphosphine) palladium (II) (558 mg, 0.795 mmol), cuprous iodide (152 mg, 0.798 mmol) and trimethylsilylacetylene (2.81 mL, 19.9 mmol) were added, and the mixture was stirred under an argon environment at room temperature for 3 hours. Chloroform and water were added to the reaction solution and stirred, and the organic layer was separated. The separated organic layer was dried over anhydrous sodium sulfate, and the solvent was distilled off under reduced pressure. The residue was purified by silica gel column chromatography to obtain reference synthetic example compound 31 (yield 4.82 g).

Step 3

Potassium tert-butoxide (1.35 g, 12.0 mmol) and NMP (18 mL) were mixed, and a solution of reference synthesis example compound 31 (1.80 g, 5.71 mmol) in NMP (18 mL) was added dropwise under ice-cooling, and then the mixture was stirred under ice-cooling for 1 hour and then at room temperature for 4 hours. The reaction solution was added dropwise to an ice-cooled saturated aqueous ammonium chloride solution, followed by extraction using ethyl acetate. Normal hexane was added to the extract, and the mixture was washed successively with water and saturated brine, and dried over anhydrous sodium sulfate. The solvent was distilled off under reduced pressure, and then the residue was purified by silica gel column chromatography to obtain reference synthesis example compound 32 (yield 981 mg).

Step 4

Reference synthesis example compound 32 (410 mg, 1.69 mmol) and DMF (10 mL) were mixed, sodium hydride (60% in oil) (88 mg, 2.20 mmol) was added under ice-cooling, and the mixture was stirred for 10 minutes. 2-Bromoethyl methyl ether (475 μL, 5.06 mmol) was added and the mixture was stirred at 60° C. for 16 hours. The reaction solution was added dropwise to an ice-cooled saturated aqueous ammonium chloride solution, diluted with water, and extracted using ethyl acetate. Normal hexane was added to the extract, and the mixture was washed successively with water and saturated brine. The filtrate was dried over anhydrous sodium sulfate, and the solvent was distilled off under reduced pressure. The residue was purified by silica gel column chromatography to obtain reference synthesis example compound 33 (yield 407 mg).

Step 5

Reference synthesis example compound 33 (554 mg, 1.84 mmol) and THF (8 mL) were mixed and cooled to −78° C., and 1.0 mol/L of LDA in normal hexane/THF (about 1/7) (2.8 mL, 2.8 mmol) was added and stirred for 1 hour. Carbontetrabromide (976 mg, 2.94 mmol) in THF (368 μL) was added dropwise, and the mixture was stirred at −78° C. for 3 hours. The reaction solution was added dropwise to an ice-cooled saturated aqueous ammonium chloride solution, diluted with water, and extracted using ethyl acetate. The organic layer was dried over anhydrous sodium sulfate, and the solvent was distilled off under reduced pressure. The residue was purified by silica gel column chromatography to obtain reference synthesis example compound 34 (yield 304 mg).

Step 6

Reference synthesis example compound 34 (120 mg, 0.316 mmol), reference synthesis example compound 25 (98 mg, 0.31 mmol), and 1,4-dioxane (4 mL) were mixed, and then water (800 μL), cesium carbonate (206 mg, 0.632 mmol), and [1,1'-bis(diphenylphosphino)ferrocene]dichloropalladium (II) (11.2 mg, 0.0158 mmol) were added, followed by stirring at 100° C. for 18 hours. The mixture was allowed to cool, diluted with water, and extracted using ethyl acetate. The extract was dried using anhydrous sodium sulfate, the solvent was distilled off under reduced pressure, and then the residue was purified by silica gel column chromatography to obtain reference synthetic example compound 35 (yield 60.3 mg).

Step 7

Reference synthesis example compound 35 (60.3 mg, 0.123 mmol) and methanol (1.5 mL) were mixed, and then 4 mol/L aqueous sodium hydroxide (3 mL, 12 mmol) was added, followed by stirring at 60° C. for 4 hours. After allowing to cool, 2 mol/L hydrochloric acid was added, and the mixture was extracted using ethylacetate/methanol (10/1). The extract was dried over anhydrous sodium sulfate and evaporated under reduced pressure to obtain reference synthetic example compound 36 (yield 41.0 mg).

Step 8

Reference synthetic example compound 36 (10 mg, 0.021 mmol) and acetonitrile (500 μL) were mixed, and then 5-amino-2-fluorobenzamide (6.5 mg, 0.042 mmol), 1-methylimidazole (7 μL, 0.09 mmol), and TCFH (11.8 mg, 0.0421 mmol) were sequentially added, followed by stirring at room temperature for 15 hours. The mixture was diluted with 2 mol/L HCl and extracted using EtOAc. The extract was dried over anhydrous sodium sulfate, and the solvent was distilled off under reduced pressure. The residue was purified by silica gel column chromatography to obtain Example Compound 16 (yield 8.9 mg).

Example 17

[Chem. Fig. 58]

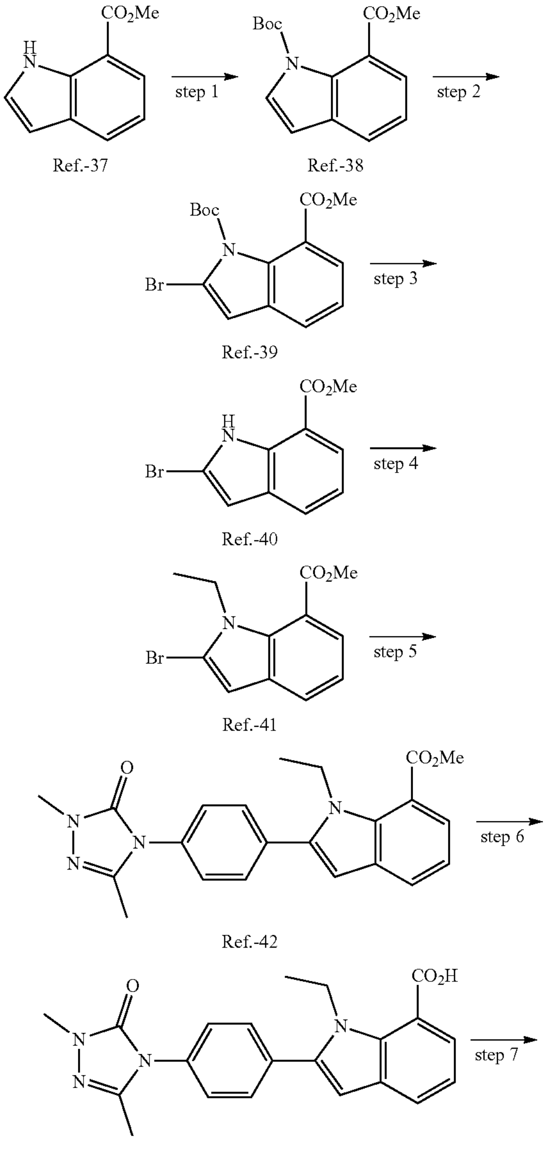

Ref.-37 Ref.-38 Ref.-39 Ref.-40 Ref.-41 Ref.-42 Ref.-43

-continued

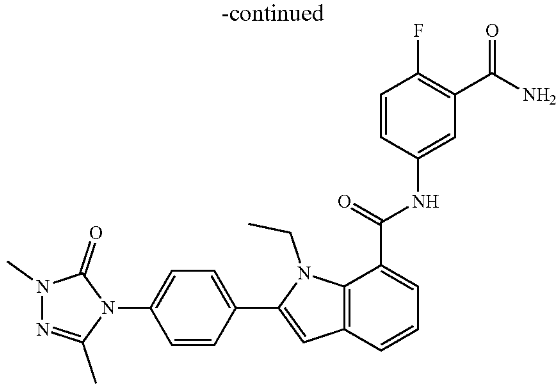

Ex.-17

Step 1

Reference synthesis example compound 37 (5.4 g, 31 mmol) and THF (100 mL) were mixed, sodium hydride (60% in oil) (1.59 g, 39.8 mmol) and di-tert-butyl dicarbonate (9.1 mL, 40 mmol) were sequentially added under ice-cooling, and the mixture was stirred at room temperature for 1 hour. Water was added to the reaction solution, followed by extraction using ethyl acetate. The solvent was distilled off under reduced pressure, and then the residue was purified by silica gel column chromatography to obtain reference synthesis example compound 38 (yield 7.11 g).

Step 2

Diisopropylamine (10.8 mL, 77.5 mmol) and THF (103 mL) were mixed and cooled to −78° C., 2.56 mol/L n-butyllithium/n-hexane solution (20.2 mL, 51.7 mmol) was added, the temperature was raised to 0° C., and the mixture was stirred for 15 minutes. The reaction solution was cooled to −78° C., and reference synthetic example compound 38 (7.11 g, 25.8 mmol) was added, followed by stirring for 1 hour. Carbontetrabromide (8.7 g, 26 mmol) in THF (5.5 mL) was added dropwise, and the mixture was warmed to room temperature and stirred for 3 hours. The reaction solution was added dropwise to an ice-cooled saturated aqueous ammonium chloride solution, water was added, and the mixture was extracted using ethyl acetate. The extract was dried over anhydrous sodium sulfate, and the solvent was distilled off under reduced pressure. The residue was purified by silica gel column chromatography to obtain reference synthetic example compound 39 (yield 7.7 g).

Step 3

Reference synthesis example compound 39 (7.7 g, 22 mmol) and dichloromethane (25 mL) were mixed, and then 4 mol/L hydrochloric acid-ethyl acetate (72 mL, 288 mmol) was added, followed by stirring at room temperature for 1 hour. The solvent was distilled off under reduced pressure, and then the residue was purified by silica gel column chromatography to obtain reference synthesis example compound 40 (yield 2.6 g).

Step 4

Reference synthesis example compound 40 (1.1 g, 4.3 mmol) and DMF (8.8 mL) were mixed, and sodium hydride (60% in oil) (0.35 g, 8.8 mmol) was added under ice-cooling, followed by stirring for 10 minutes. Ethyl iodide (0.7 mL, 9 mmol) was added to the reaction solution, and the mixture was stirred at room temperature for 12 hours. The reaction solution was added dropwise to an ice-cooled saturated aqueous ammonium chloride solution, diluted with water, and extracted using ethyl acetate. Normal hexane was added to the extract, and the mixture was washed successively with water and saturated brine. The filtrate was dried over anhydrous sodium sulfate, and the solvent was distilled off under reduced pressure. The residue was purified by silica gel column chromatography to obtain reference synthetic example compound 41 (yield 1.0 g).

Step 5

Reference synthesis example compound 41 (180 mg, 0.38 mmol), reference synthesis example compound 25 (300 mg, 0.952 mmol), and 1,4-dioxane (6.4 mL) were mixed, and then cesium carbonate (416 mg, 1.28 mmol) and APhos-Pd-G3 (20 mg, 0.031 mmol) were added, followed by stirring at 140° C. for 1 hour under microwave irradiation. After allowing to cool, water was added, and the mixture was stirred, followed by extraction using ethyl acetate. The extract was dried over anhydrous sodium sulfate, and the solvent was distilled off under reduced pressure. The residue was purified by silica gel column chromatography to obtain reference synthesis example compound 42 (yield 198 mg).

Step 6

Reference synthesis example compound 42 (198 mg, 0.507 mmol), THF (0.9 mL) and methanol (3.2 mL) were mixed, and then 4 mol/L aqueous sodium hydroxide (2.5 mL, 10 mmol) was added under ice-cooling, followed by stirring at room temperature for 1 hour. After the reaction solution was neutralized, the solvent was distilled off under reduced pressure. The residue was purified by silica gel column chromatography to obtain reference synthesis example compound 43 (yield 139 mg).

Step 7

Reference synthesis example compound 43 (68 mg, 0.18 mmol), 5-amino-2-fluorobenzamide (42 mg, 0.27 mmol) and acetonitrile (2 mL) were mixed, 1-methylimidazole (0.043 mL, 0.54 mmol) and TCFH (81 mg, 0.29 mmol) were added, and the mixture was stirred at room temperature for 4 hours. Water was added, and then the mixture was stirred and extracted using ethyl acetate. The extract was dried over anhydrous sodium sulfate, and the solvent was distilled off under reduced pressure. The residue was purified by silica gel column chromatography to obtain Example Compound 17 (yield 71.6 mg).

Example 18

[Chem. Fig. 59]

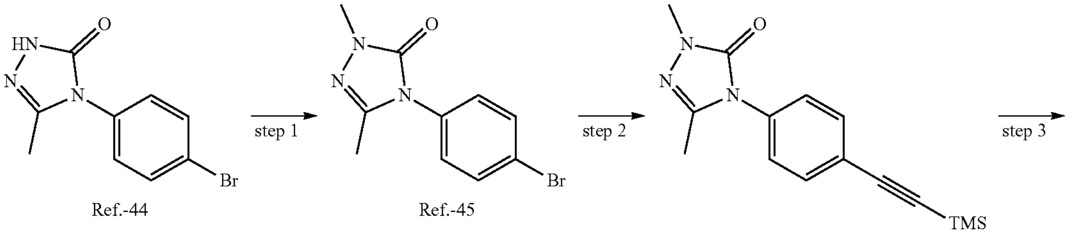

Ref.-44 Ref.-45 Ref.-46

-continued

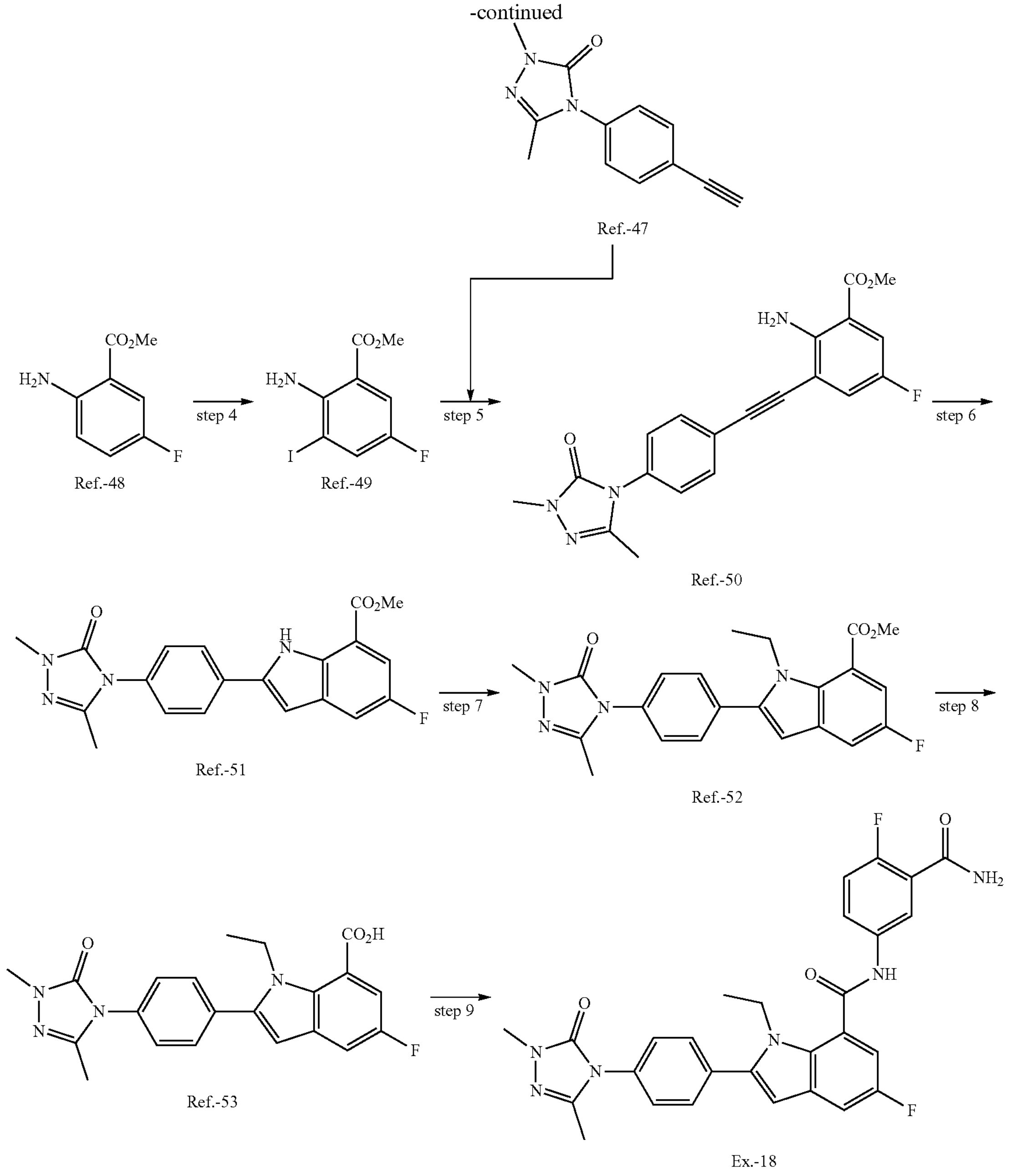

Step 1

Reference synthesis example compound 44 (10 g, 39 mmol) and DMF (196 mL) were mixed, sodium hydride (60% in oil) (2.4 g, 60 mmol) and methyl iodide (7.4 mL, 120 mmol) were sequentially added under ice-cooling, and then the mixture was stirred at room temperature for 3 hours. The reaction solution was ice-cooled, saturated aqueous ammonium chloride solution and water were added, and the mixture was extracted using ethyl acetate. The extract was washed successively with water and saturated brine, and then dried over anhydrous sodium sulfate. The solvent was distilled off under reduced pressure, then MTBE was added to the residue to perform slurry washing, and the solid was collected by filtration to obtain reference synthesis example compound 45 (yield 7.78 g).

Step 2

Reference synthesis example compound 45 (4.47 g, 16.7 mmol), THF (0.080 L) and triethyl amine (7.0 mL, 50 mmol) were mixed and then degassed. [1,1'-bis(diphenylphosphino)ferrocene]dichloropalladium (II) (1.22 g, 1.67 mmol), cuprous iodide (0.318 g, 1.67 mmol) and trimethylsilylacetylene (3.0 mL, 21 mmol) were added, and the mixture was stirred at 75° C. for 1.5 hours under an argon environment. After cooling, the solvent was distilled off under reduced pressure. Chloroform and water were added to the residue, the mixture was stirred and then filtered through Celite®, and the organic layer of the filtrate was separated. The filtrate was dried over anhydrous sodium sulfate, and the solvent was distilled off under reduced pressure. The residue was purified by silica gel column chromatography to obtain reference synthetic example compound 46 (yield 4.76 g).

Step 3

Reference synthesis example compound 46 (4.76 g, 16.7 mmol) and THF (0.067 L) were mixed, and then 1 mol/L TBAF/THE solution (0.028 L, 28 mmol) were added, followed by stirring at room temperature for 30 minutes. The solvent was distilled off under reduced pressure, and then the residue was purified by silica gel column chromatography to obtain reference synthesis example compound 47 (yield 2.83 g).

Step 4

Reference synthesis example compound 48 (2.00 g, 11.8 mmol) and acetic acid (40 mL) were mixed, NIS (2.9 g, 13 mmol) was added, and then the mixture was stirred at room temperature for 2 hours. The reaction solution was concentrated under reduced pressure, a saturated aqueous sodium hydrogen carbonate solution and chloroform were added and stirred, and the organic layer was separated. The organic layer was dried over anhydrous sodium sulfate, and the solvent was distilled off under reduced pressure. The residue was purified by silica gel column chromatography to obtain reference synthetic example compound 49 (yield 3.4 g).

Step 5

Reference synthesis example compound 49 (1.0 g, 3.4 mmol) and acetonitrile (10 mL) were mixed, and then potassium carbonate (1.4 g, 10 mmol), palladium (II) acetate (38 mg, 0.17 mmol), 1,4-bis(diphenylphosphino) butane (144 mg, 0.338 mmol) and reference synthesis example compound 47 (882 mg, 4.14 mmol) were added, the reactor was purged with argon and sealed, and then the reaction mixture was stirred for 1 hour at 140° C. under microwave radiation. After allowing to cool, water was added to the reaction solution, and the mixture was extracted using chloroform. The organic layer was dried using anhydrous sodium sulfate, and the solvent was distilled off under reduced pressure. The residue was purified by silica gel column chromatography to obtain reference synthesis example compound 50 (yield 284 mg).

Step 6

Reference synthesis example compound 50 (284 mg, 0.746 mmol) and acetonitrile (6 mL) were mixed, then degassed, the reactor was purged with argon, bis(acetonitrile)dichloropalladium (II) (212 mg, 0.817 mmol) was added, and the mixture was stirred at 100° C. for 2 hours. After allowing to cool, the mixture was filtered through Celite®. Ethyl acetate, water, and a small amount of solution were added to the filtrate and stirred, and the organic layer was separated. The organic layer was washed successively with water, a saturated aqueous solution of sodium thiosulfate, and saturated brine, and then dried over anhydrous sodium sulfate. The solvent was distilled off under reduced pressure, and then the residue was purified by silica gel column chromatography to obtain reference synthesis example compound 51 (yield 144 mg).

Step 7

Reference synthetic example compound 51 (144 mg, 0.378 mmol) and DMF (1 mL) were mixed, and sodium hydride (60% in oil) (30 mg, 0.75 mmol) was added under ice-cooling, followed by stirring for 10 minutes. Ethyl iodide (0.061 mL, 0.76 mmol) was added and the mixture was stirred at room temperature for 12 hours. The reaction solution was added dropwise to an ice-cooled saturated aqueous ammonium chloride solution, then water and ethyl acetate were added, the mixture was stirred, and the organic layer was separated. Normal hexane was added to the organic layer, and the mixture was washed successively with water and saturated brine. The filtrate was dried over anhydrous sodium sulfate, and the solvent was distilled off under reduced pressure. The residue was purified by silica gel column chromatography to obtain reference synthetic example compound 52 (yield 70.7 mg).

Step 8

Reference synthesis example compound 52 (70 mg, 0.17 mmol), methanol (1.6 mL) and THF (0.3 mL) were mixed, and then 4 mol/L aqueous sodium hydroxide (0.86 mL, 3.4 mmol) was added under ice-cooling, followed by stirring at room temperature for 1 hour. The reaction solution was concentrated under reduced pressure to obtain reference synthesis example compound 53 as a mixture with sodium chloride (yield 0.27 g).

Step 9

5-Amino-2-fluorobenzamide (19 mg, 0.12 mmol), DMF (1 mL), DIPEA (0.043 mL, 0.25 mmol) and HATU (47 mg, 0.12 mmol) were sequentially added to a sodium chloride mixture (0.13 g) of reference synthesis example compound 53 obtained by the method described in Step 8, and then the mixture was stirred at room temperature for 4 hours. Water was added to the reaction solution, followed by extraction using ethyl acetate. The organic layer was dried over anhydrous sodium sulfate, and the solvent was distilled off under reduced pressure. The residue was purified by silica gel column chromatography to obtain Example Compound 18 (yield 12.2 mg).

Example 19

[Chem. Fig. 60]

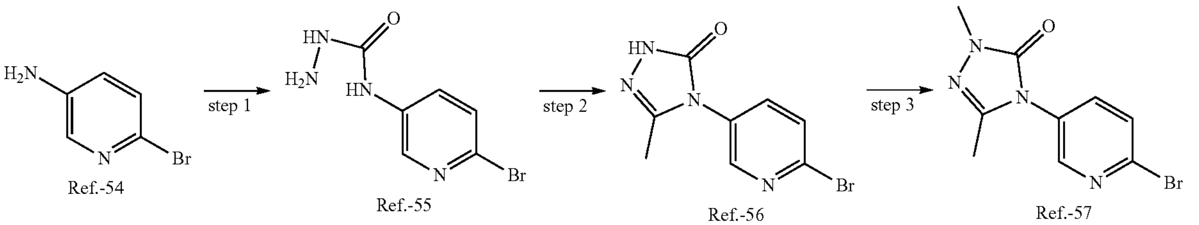

Ref.-54 Ref.-55 Ref.-56 Ref.-57

-continued

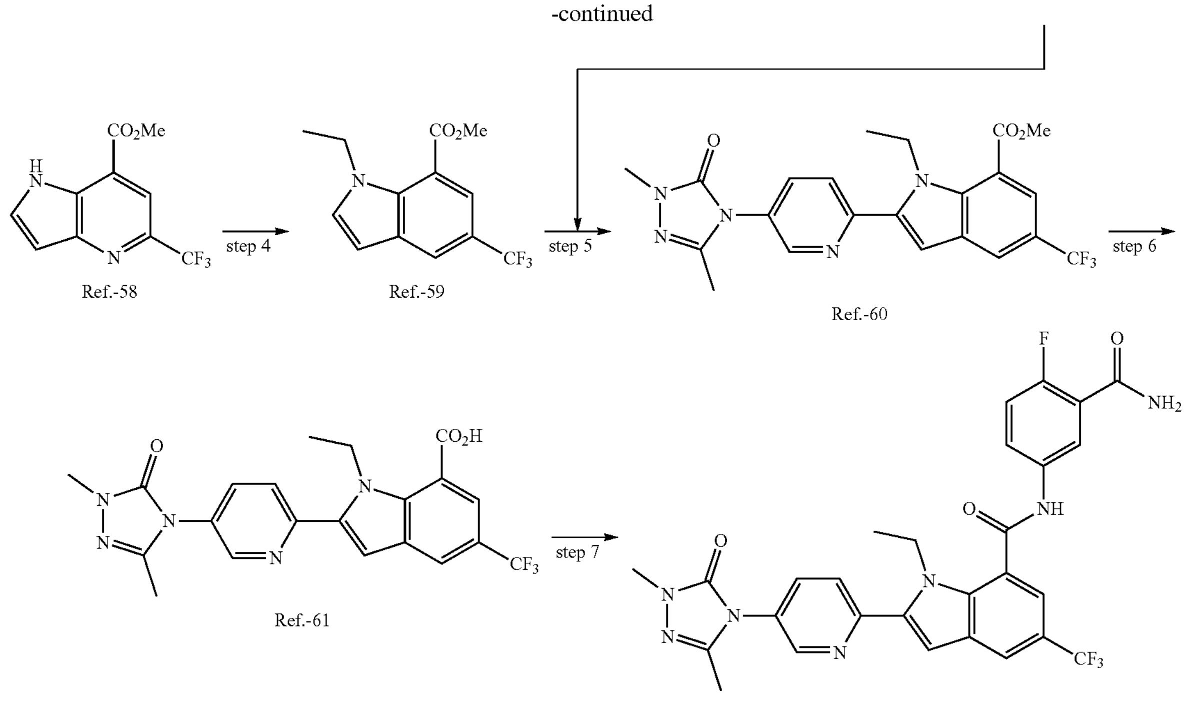

Ref.-58 Ref.-59 Ref.-60 Ref.-61 Ex.-19

Step 1

Reference synthesis example compound 54 (10.0 g, 57.8 mmol) and THF (289 mL) were mixed, ice-cooled, then 4-nitrophenyl chloroformate (11.7 g, 58.0 mmol) and pyridine (7.0 mL, 87 mmol) were added, and the mixture was stirred at room temperature for 4 hours. The solvent was distilled off under reduced pressure, and then 1,4-dioxane (289 mL) and hydrazine hydrate (8.4 mL, 170 mmol) was added to the residue to make a suspension, which was then stirred at 70° C. for 2 hours. The reaction solution was allowed to cool, water was added and stirred, and then the precipitate was collected by filtration to obtain reference synthesis example compound 55 (yield 11.7 g).

Step 2

Reference synthesis example compound 55 (9.00 g, 39.0 mmol) and ethanol (97 mL) were mixed, then triethyl orthoacetate (8.6 mL, 47 mmol) and p-toluenesulfonic acid monohydrate (741 mg, 3.90 mmol) were added, and then the mixture was stirred under reflux for 16 hours. The reaction solution was allowed to cool, water was added, and the mixture was stirred. The precipitate was collected by filtration to obtain reference synthetic example compound 56 (yield 3.48 g).

Step 3

Reference synthesis example compound 56 (3.00 g, 11.8 mmol) and DMF (30 mL) were mixed, then potassium-tert-butoxide (1.98 g, 17.7 mmol) and methyl iodide (2.2 mL, 35 mmol) were sequentially added under ice-cooling, and then the mixture was stirred at room temperature for 4 hours. Water was added to the reaction solution under ice-cooling, and the mixture was stirred and extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 57 (yield 1.85 g).

Step 4

Reference synthesis example compound 58 (10.0 g, 41.1 mmol) and DMF (164 mL) were mixed, sodium hydride (60% in oil) (2.14 g, 53.5 mmol) was added under ice-cooling, and the mixture was stirred for 20 minutes. Ethyl iodide (4.9 mL, 61 mmol) was added and stirred at room temperature for 3 hours. A saturated aqueous ammonium chloride solution was added to the reaction solution under ice-cooling and stirred, followed by extraction using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 59 (yield 7.34 g).

Step 5

Reference synthesis example compound 59 (3.27 g, 12.1 mmol), THF (13 mL) and isopropyl borate (3.1 mL, 13 mmol) were mixed, 1.09 mol/L LDA in normal hexane/THF (8.6 mL, 9.4 mmol) was added under ice-cooling, and the mixture was then stirred for 30 minutes. An aqueous solution (13 mL) of tripotassium phosphate (2.13 g, 10.0 mmol), reference synthesis example compound 57 (1.80 g, 6.69 mmol) and a THF (13 mL) solution of chloro(crotyl) (tri-tert-butylphosphine) palladium (II) (267 mg, 0.669 mmol) were added, and the mixture was stirred at 50° C. for 2 hours. The reaction solution was allowed to cool, water was added, and the mixture was stirred and then extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 60 (yield 2.58 g).

Step 6

Reference synthesis example compound 60 (500 mg, 1.09 mmol), THF (2.7 mL) and methanol (2.7 mL) were mixed, and then a 4 mol/L aqueous sodium hydroxide solution (2.7 mL, 10.8 mmol) was added, followed by stirring at 50° C. for 2 hours. 1 mol/L hydrochloric acid was added to the reaction solution under ice-cooling, and the precipitate was collected by filtration to obtain reference synthetic example compound 61 (yield 300 mg).

Step 7

Reference synthesis example compound 61 (100 mg, 0.225 mmol), 3-amino-2-fluorobenzamide (51.9 mg, 0.337 mmol) and acetonitrile (1.1 mL) were mixed, and then 1-methylimidazole (71 μL, 0.90 mmol) and TCFH (126 mg, 0.449 mmol) were added, followed by stirring at room temperature for 16 hours. Water was added to the reaction solution and stirred, and then the precipitate was collected by filtration to obtain Example Compound 19 (yield 58.9 mg).

Example 20

[Chem. Fig. 61]

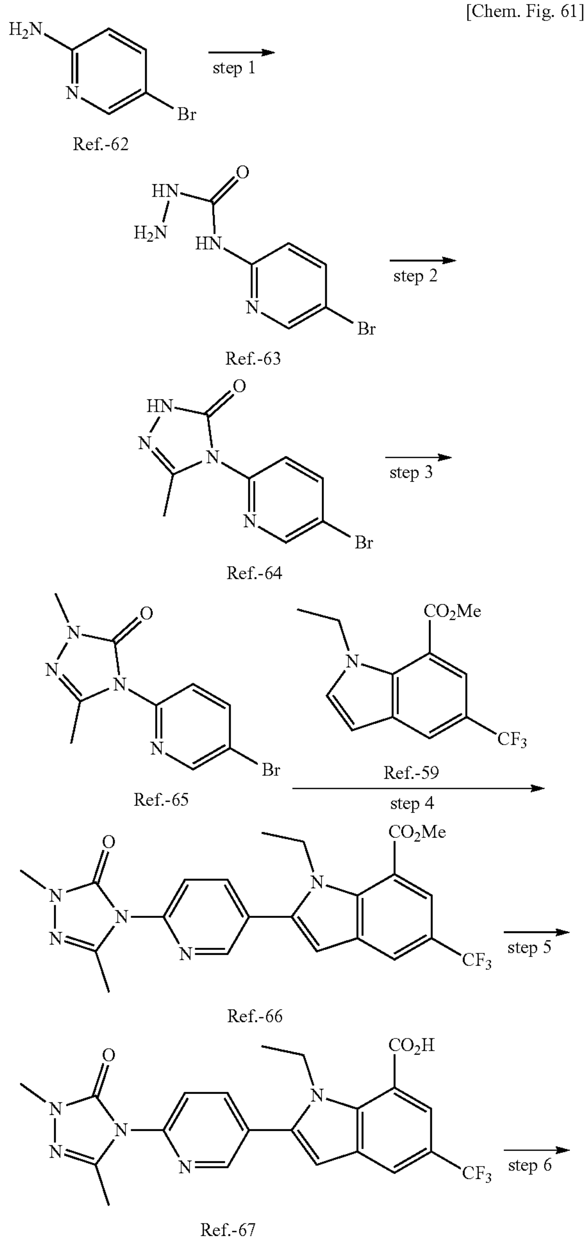

-continued

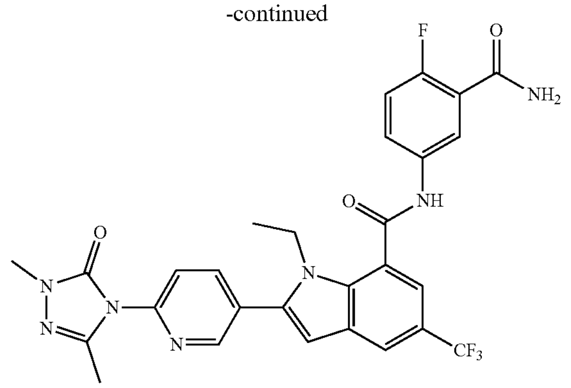

Ex.-20

Step 1

Reference synthesis example compound 62 (4.00 g, 23.1 mmol) and THF (116 mL) were mixed, 4-nitrophenyl chloroformate (4.66 g, 23.1 mmol) and pyridine (2.8 mL, 35 mmol) were added under ice-cooling, and then the mixture was stirred at room temperature for 17 hours. The solvent was distilled off under reduced pressure, and then the residue was dissolved in 1,4-dioxane (116 mL), hydrazine hydrate (3.37 mL, 69.3 mmol) was added, and the mixture was stirred at 70° C. for 5 hours. The cooled reaction solution was poured into ice-cooled water (500 mL) and stirred for 30 minutes. The precipitate was filtered, washed with water, and dried under reduced pressure to obtain reference synthesis example compound 63 (yield 4.43 g).

Step 2

Reference synthesis example compound 63 (4.43 g, 19.2 mmol) and ethanol (48 mL) were mixed, then triethyl orthoacetate (5.7 mL, 39 mmol) and p-toluenesulfonic acid monohydrate (365 mg, 1.92 mmol) were added, and the mixture was stirred at 80° C. for 6 hours. The reaction solution was poured into ice-cooled water (500 mL) and stirred for 30 minutes. The precipitate was collected by filtration, washed with water, and dried under reduced pressure to obtain reference synthesis example compound 64 (yield 4.61 g).

Step 3

Reference synthesis example compound 64 (4.61 g, 18.1 mmol) and DMF (60 mL) were mixed, then tripotassium phosphate (5.75 g, 27.1 mmol) was added under ice-cooling, and the mixture was stirred for 10 minutes. Methyl iodide (1.69 mL, 27.1 mmol) was added, followed by stirring at room temperature for 4 hours. The reaction solution was poured into ice-cooled water (500 mL) and stirred for 30 minutes. The precipitate was collected by filtration and washed with water to obtain reference synthesis example compound 65 (yield 3.33 g).

Step 4

Reference synthesis example compound 59 (1.09 g, 4.02 mmol), THF (4.5 mL) and isopropyl borate (1.03 mL, 4.46 mmol) were mixed and degassed, and then 1.09 mol/L of LDA in normal hexane/THF (2.86 mL, 3.12 mmol) was added under ice-cooling and stirred for 30 minutes. Tripotassium phosphate (710 mg, 3.34 mmol) in water (4.5 mL), reference synthesis example compound 65 (600 mg, 2.23 mmol) and chloro(crotyl) (tri-tert-butylphosphine) palladium (II) (80.9 mg, 0.203 mmol) in THF (11 mL) were sequentially added and stirred at 40° C. for 2.5 hours. The reaction solution was allowed to cool, diluted with water, and extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 66 (yield 664 mg).

Step 5

Reference synthesis example compound 66 (945 mg, 2.06 mmol), methanol (5.1 mL) and THF (5.1 mL) were mixed, and then 4 mol/L aqueous sodium hydroxide (2.57 mL, 10.3 mmol) was added, followed by stirring at room temperature for 5 hours. The reaction solution was acidified with 6 mol/L-hydrochloric acid under ice-cooling and extracted using a mixture of chloroform/methanol (4/1). The extract was washed with saturated brine and dried over anhydrous sodium sulfate. The solvent was distilled off under reduced pressure to obtain reference synthesis example compound 67 (yield 1.06 g) as a solvent mixture.

Step 6

The solvent mixture (1.06 g) of reference synthesis example compound 67 obtained by the method described in Step 5 and acetonitrile (21 mL) was mixed, and then 5-amino-2-fluorobenzamide (634 mg, 4.11 mmol), TCFH (1.15 g, 4.10 mmol) and 1-methylimidazole (649 μL, 8.22 mmol) were sequentially added, followed by stirring at room temperature overnight. The reaction solution was diluted with water and extracted using chloroform. The extract was washed with saturated brine and dried over anhydrous sodium sulfate. The solvent was distilled off under reduced pressure, and then 2-propanol (30 mL) was added to the residue to perform slurry washing, and then the solid was collected by filtration and dried under reduced pressure to obtain Example Compound 20 (yield 1.24 g).

Example 21

[Chem. Fig. 62]

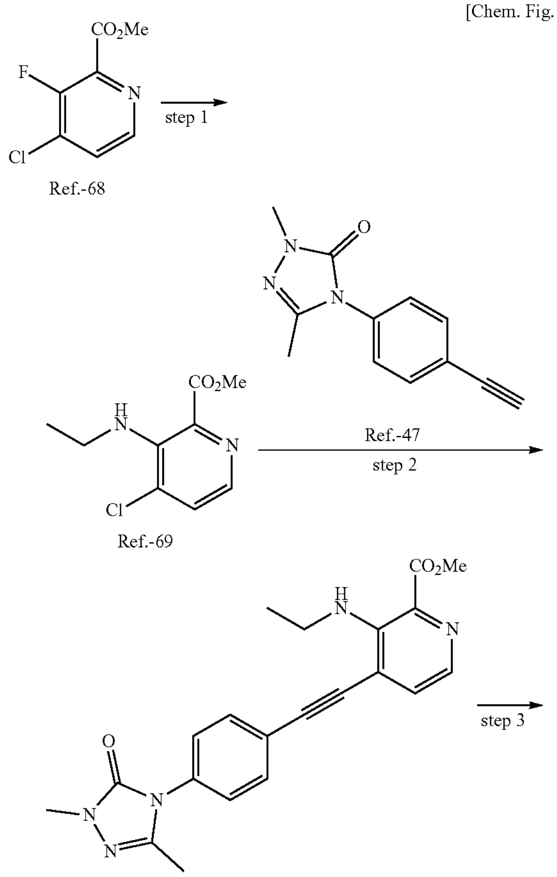

Ref.-70

-continued

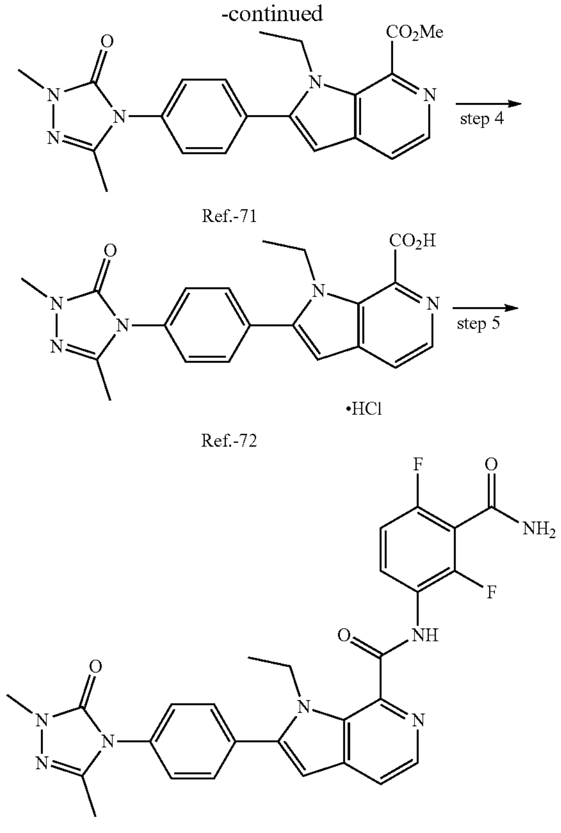

Ex.-21

Step 1

Reference synthesis example compound 68 (694 mg, 3.66 mmol) and DMSO (10 mL) were mixed, and then DIPEA (1.89 mL, 11.0 mmol) and 2.0 mol/L ethyl amine/THF (2.2 mL, 4.4 mmol) were added, followed by stirring at 50° C. for 3 hours and then at room temperature for 16 hours. Water and ethyl acetate were added to the reaction solution, stirred, and then the organic layer was separated. The separated organic layer was washed with saturated brine and then dried over anhydrous sodium sulfate. The solvent was distilled off under reduced pressure to obtain reference synthesis example compound 69 (yield 694 mg).

Step 2

Reference synthesis example compound 69 (300 mg, 1.40 mmol) and acetonitrile (5 mL) were mixed, and then potassium carbonate (580 mg, 4.20 mmol), palladium acetate (II) (15.7 mg, 0.0699 mmol), 1,4-bis(diphenylphosphino) butan (60.0 mg, 0.141 mmol), and reference synthesis example compound 47 (447 mg, 2.10 mmol) were added. The reactor was purged with argon and sealed, and then the reaction mixture was stirred at 140° C. for 1.5 hours under microwave irradiation. After allowing to cool, water was added to the reaction solution, and the mixture was extracted using chloroform. The extract was dried over anhydrous sodium sulfate, and the solvent was distilled off under reduced pressure. The residue was purified by silica gel column chromatography to obtain reference synthesis example compound 70 (yield 244 mg).

Step 3

Reference synthesis example compound 70 (5.81 g, 14.8 mmol) and methanol (0.037 L) were mixed and degassed, and the reactor was purged with argon. Then, chloro(triphenylphosphine) gold(I) (1.47 g, 2.97 mmol) and silver bis(trifluoromethanesulfonyl)imide (1.15 g, 2.96 mmol) were added, and the mixture was stirred at 80° C. for 2 hours. After cooling, the solvent was distilled off under reduced pressure. The residue was purified by silica gel column chromatography to obtain reference synthesis example compound 71 (yield 5.38 g).

Step 4

Reference synthesis example compound 71 (23.3 mg, 0.0595 mmol), methanol (0.5 mL) and THF (0.5 mL) were mixed, then 4 mol/L aqueous sodium hydroxide (150 μL, 0.6 mmol) was added, and the mixture was stirred at room temperature for 18 hours. 2 mol/L hydrochloric acid (0.5 mL) was added to the reaction solution, and the solvent was distilled off under reduced pressure to obtain reference synthesis example compound 72 as a sodium chloride mixture (yield 62.3 mg).

Step 5

A sodium chloride mixture (30 mg) of reference synthesis example compound 72 obtained by the method described in Step 4 was mixed with acetonitrile (1 mL), and then 5-amino-2-fluorobenzamide (9.2 mg, 0.060 mmol), 1-methylimidazole (14 μL, 0.18 mmol), and TCFH (16.9 mg, 0.0602 mmol) were sequentially added, followed by stirring at 40° C. for 15 hours. 1 mol/L HCl and EtOAc were added to the reaction solution and stirred, and then the organic layer was separated. The separated organic layer was dried over anhydrous sodium sulfate, and the solvent was distilled off under reduced pressure. The residue was purified by silica gel column chromatography, followed by slurry washing with a mixed solution of n-hexane/ethyl acetate (3/1), and then the solid was collected by filtration and dried under reduced pressure to obtain Example Compound 21 (yield 9.2 mg).

Example 22

[Chem. Fig. 63]

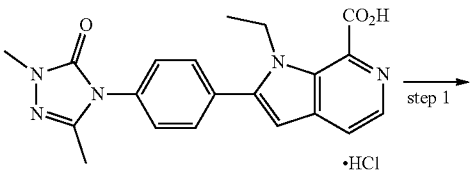

Ref.-72

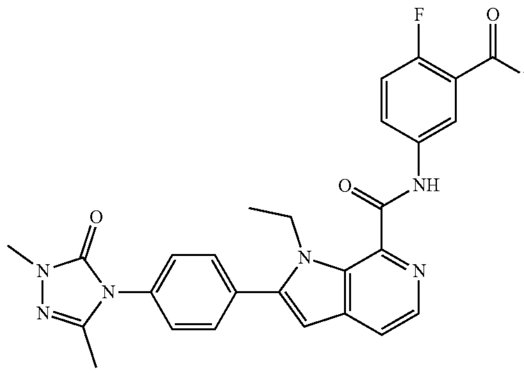

Ex.-22

Step 1

A sodium chloride mixture (30 mg) of reference synthesis example compound 72 obtained by the method described in Step 4 of Example 21 was mixed with acetonitrile (1 mL), and then 3-amino-2-fluorobenzamide (9.2 mg, 0.060 mmol), 1-methylimidazole (14 μL, 0.18 mmol), and TCFH (16.9 mg, 0.0602 mmol) were sequentially added, followed by stirring at 40° C. for 15 hours. 1 mol/L HCl and EtOAc were added to the reaction solution and stirred, and then the organic layer was separated. The separated organic layer was dried over anhydrous sodium sulfate, and the solvent was distilled off under reduced pressure. The residue was purified by silica gel column chromatography to obtain Example Compound 22 (yield 9.3 mg).

Example 23

[Chem. Fig. 64]

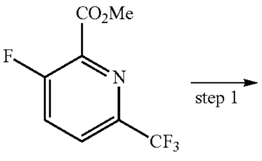

Ref.-73

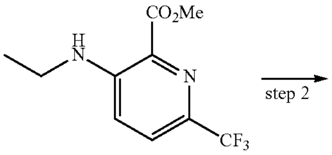

Ref.-74

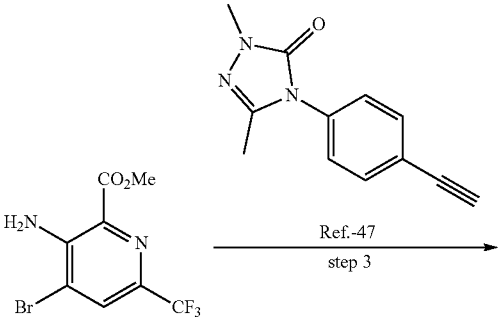

Ref.-75

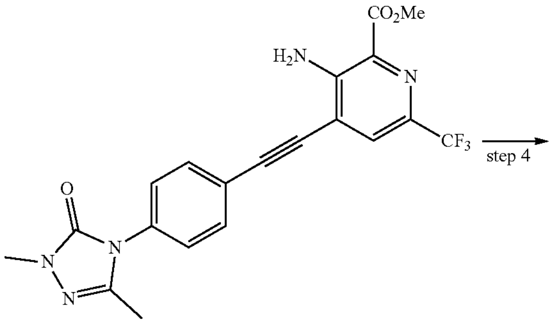

Ref.-76

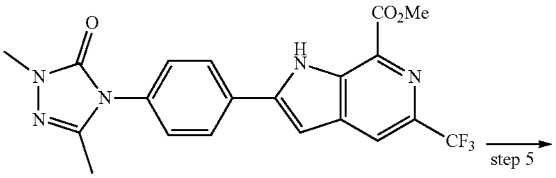

Ref.-77

-continued

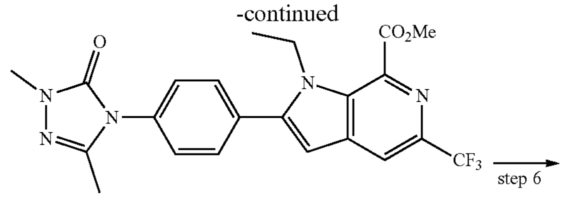

Ref.-78

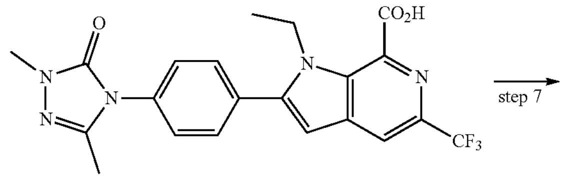

Ref.-79

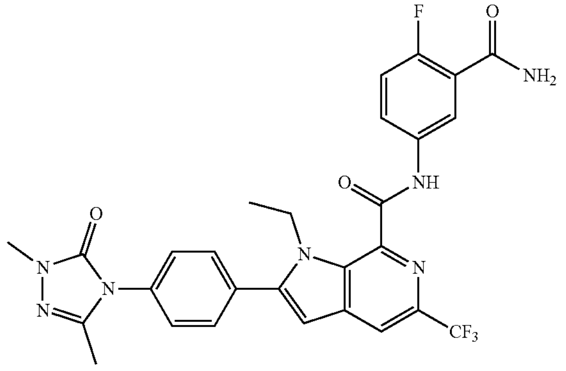

Ex.-23

Step 1

Reference synthesis example compound 73 (509 mg, 2.28 mmol) and THF (8 mL) were mixed, and potassium carbonate (619 mg, 4.48 mmol) and 2.0 mol/L ethyl amine/THF solution (1.3 mL, 2.6 mmol) were added, followed by stirring at 70° C. for 3 hours. Water and ethyl acetate were added to the cooled reaction solution and stirred, and the organic layer was separated. The separated organic layer was washed with saturated brine and then dried over anhydrous sodium sulfate. The solvent was distilled off under reduced pressure to obtain reference synthesis example compound 74 partially containing an impurity (yield 610 mg).

Step 2

Reference synthesis example compound 74 (300 mg) containing an impurity obtained by the method described in Step 1 was mixed with acetonitrile (10 mL), and then NBS (323 mg, 1.81 mmol) and acetic acid (69 μL, 1.21 mmol) were added, followed by stirring at 85° C. for 17 hours. Ethyl acetate, a saturated aqueous sodium hydrogen carbonate solution, and saturated brine were sequentially added to the cooled reaction solution and stirred, and then the organic layer was separated. The separated organic layer was dried over anhydrous sodium sulfate, and the solvent was distilled off under reduced pressure. The residue was purified by silica gel column chromatography to obtain reference synthesis example compound 75 (yield 118 mg). In this step, unexpected deethylation of the amino group also occurred simultaneously.

Step 3

Reference synthesis example compound 75 (116 mg, 0.388 mmol) and THF (5 mL) were mixed, and then reference synthesis example compound 47 (165 mg, 0.774 mmol), triethyl amine (162 μL, 1.17 mmol), cuprous iodide (3.7 mg, 0.019 mmol), and [1,1'-bis(diphenylphosphino) ferrocene] dichloropalladium (II) (14.2 mg, 0.0194 mmol) were added, followed by stirring at 90° C. for 3 hours under an argon environment. After cooling, the reaction solution was diluted with water, and extracted using ethyl acetate. The organic layer was dried over anhydrous sodium sulfate, and the solvent was distilled off under reduced pressure. The residue was purified by silica gel column chromatography to obtain reference synthesis example compound 76 (yield 104 mg).

Step 4

Reference synthesis example compound 76 (103 mg, 0.238 mmol) and ethanol (1.5 mL) were mixed, degassed, the reactor was purged with argon, chloro(2-dicyclohexylphosphino-2',6'-dimethoxy-1,1'-biphenyl) gold(I) (30.6 mg, 0.0476 mmol) and silver bis(trifluoromethanesulfonyl) imide (18.4 mg, 0.0474 mmol) were added, and the mixture was stirred at 100° C. for 3 hours. The reaction solution was allowed to cool at room temperature and filtered, and the filtrate was concentrated under reduced pressure. The residue was purified by silica gel column chromatography to obtain reference synthesis example compound 77 (yield 98 mg).

Step 5

Reference synthetic example compound 77 (50 mg, 0.12 mmol) and DMF (1 mL) were mixed, sodium hydride (60% in oil) (7.0 mg, 0.18 mmol) was added under ice-cooling, and the mixture was stirred for 10 minutes. Ethyl iodide (46 μL, 0.58 mmol) was added to the reaction solution, and the mixture was stirred at room temperature for 16 hours. The reaction solution was added dropwise to an ice-cooled saturated aqueous ammonium chloride solution, diluted with water, and extracted using ethyl acetate. The extract was washed successively with water and saturated brine, dried over anhydrous sodium sulfate, and the solvent was evaporated under reduced pressure. The residue was purified by silica gel column chromatography to obtain reference synthetic example compound 78 (yield 32.0 mg).

Step 6

Reference synthesis example compound 78 (32 mg, 0.070 mmol), methanol (1 mL) and THF (0.5 mL) were mixed, and then 4 mol/L aqueous sodium hydroxide (174 μL, 0.696 mmol) was added, followed by stirring at 40° C. for 5 hours. 2 mol/L HCl (0.5 mL) and water were sequentially added to the reaction solution, and then the solvent was distilled off under reduced pressure to obtain a NaCl mixture of reference synthesis example compound 79 (yield 74.3 mg).

Step 7

A sodium chloride mixture (37 mg) of reference synthesis example compound 79 obtained by the method described in Step 6 was mixed with acetonitrile (1 mL), and then 5-amino-2-fluorobenzamide (8.0 mg, 0.052 mmol), 1-methylimidazole (17 μL, 0.22 mmol), and TCFH (19.5 mg, 0.0695 mmol) were added, followed by stirring at 40° C. for 15 hours. Water and ethyl acetate were added to the reaction solution, stirred, and then the organic layer was separated. The separated organic layer was dried over anhydrous sodium sulfate, and the solvent was distilled off under reduced pressure. The residue was purified by silica gel column chromatography, followed by slurry washing with a mixed solvent of n-hexane/ethyl acetate (3/1), and the solid was collected by filtration. The obtained solid was dried under reduced pressure to obtain Example Compound 23 (yield 9.7 mg).

Example 24

[Chem. Fig. 65]

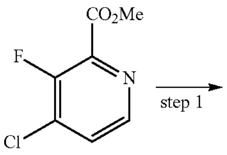

Ref.-68

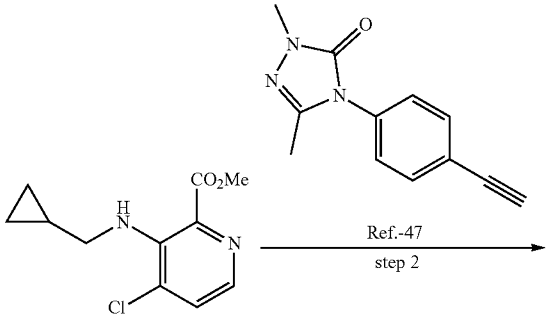

Ref.-80

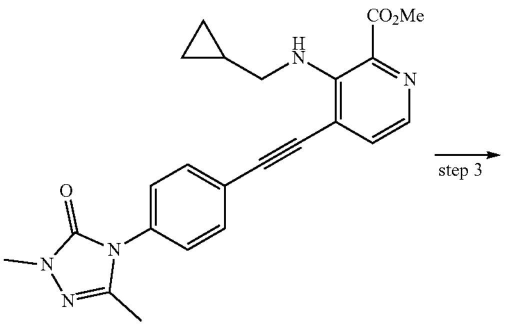

Ref.-81

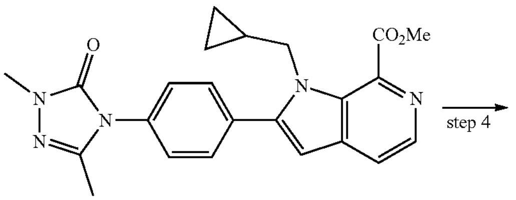

Ref.-82

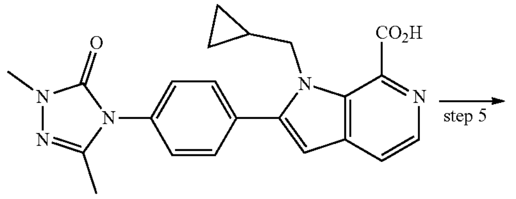

Ref.-83

-continued

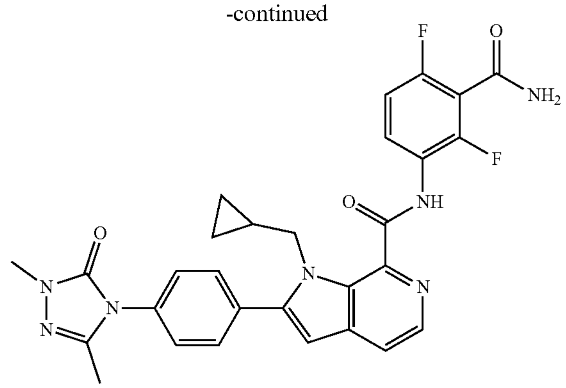

Ex.-24

Step 1

Reference synthesis example compound 68 (3.00 g, 15.8 mmol) and DMSO (40 mL) were mixed, and then DIPEA (8.2 mL, 48 mmol) and cyclopropylmethylamine (1.7 mL, 20 mmol) were added, followed by stirring at 80° C. for 4 hours. After allowing to cool, water was added to the reaction solution, and the mixture was extracted using ethyl acetate. The organic layer was washed successively with water and saturated brine, and dried over anhydrous sodium sulfate. The solvent was distilled off under reduced pressure, and then the residue was purified by silica gel column chromatography to obtain reference synthesis example compound 80 (yield 2.83 g).

Step 2

Palladium (II) acetate (113 mg, 0.499 mmol), XPhos (476 mg, 0.999 mmol) and acetonitrile (25 mL) were mixed, degassed, and then stirred under an argon environment at room temperature for 5 minutes. Reference synthesis example compound 47 (2.66 g, 12.5 mmol), cesium carbonate (6.50 g, 19.9 mmol), and reference synthesis example compound 80 (2.40 g, 9.97 mmol) were added and stirred at 90° C. for 2 hours. The reaction solution was allowed to cool, water was added, and the mixture was extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 81 (yield 3.05 g).

Step 3

Reference synthesis example compound 81 (3.00 g, 7.19 mmol) and methanol (18 mL) were mixed, degassed, and the reactor was purged with argon. Then, chloro(triphenylphosphine) gold(I) (711 mg, 1.44 mmol) and silver bis(trifluoromethanesulfonyl)imide (558 mg, 1.44 mmol) were added, and the mixture was stirred at 80° C. for 2 hours. After cooling, the solvent was distilled off under reduced pressure. The residue was purified by silica gel column chromatography to obtain reference synthesis example compound 82 (yield 2.89 g).

Step 4

Reference synthesis example compound 82 (2.89 g, 6.92 mmol), THF (17 mL), and methanol (17 mL) were mixed, and then 4 mol/L aqueous sodium hydroxide (8.7 mL, 35 mmol) was added, followed by stirring at 50° C. for 4 hours. The reaction solution was acidified using a 10% aqueous citric acid solution, and the organic solvent was distilled off under reduced pressure. Ethanol (2 mL) was added to the residue, and the mixture was stirred under ice-cooling for 1 hour. The precipitate was collected by filtration to obtain reference synthesis example compound 83 (yield 1.37 g).

Step 5

Reference synthesis example compound 83 (1.00 g, 2.48 mmol), 5-amino-2-fluorobenzamide (573 mg, 3.72 mmol) and acetonitrile (12 mL) were mixed, 1-methylimidazole (783 μL, 9.92 mmol) and TCFH (1.39 g, 4.95 mmol) were added, and the mixture was stirred at room temperature for 16 hours. Water was added to the reaction solution and stirred, and the precipitate was filtered off. The solid collected by filtration was dried under reduced pressure, and then purified by silica gel column chromatography to obtain Example Compound 24 (yield 808 mg).

Example 25

[Chem. Fig. 66]

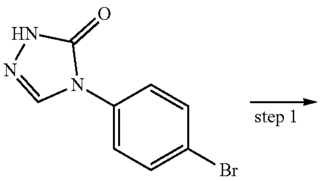

Ref.-84

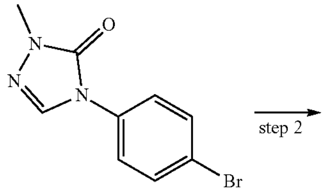

Ref.-85

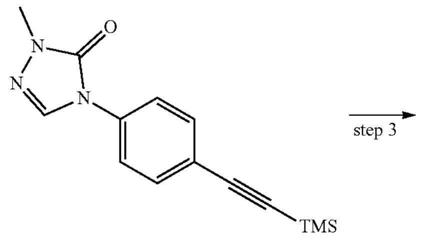

Ref.-86

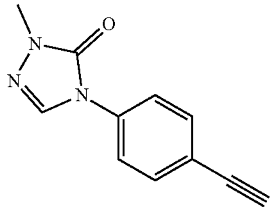

Ref.-87

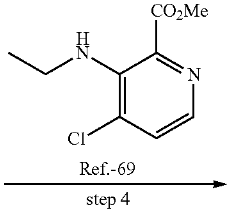

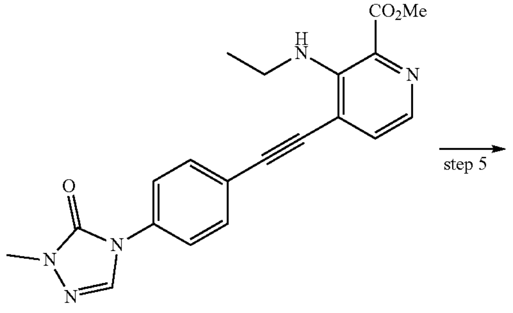

Ref.-88

-continued

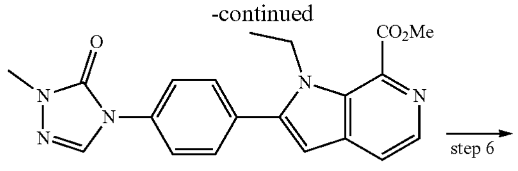

Ref.-89

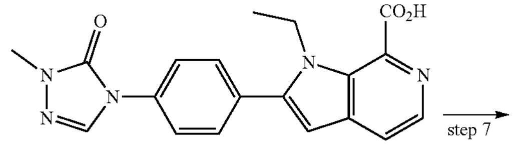

•HCl

Ref.-90

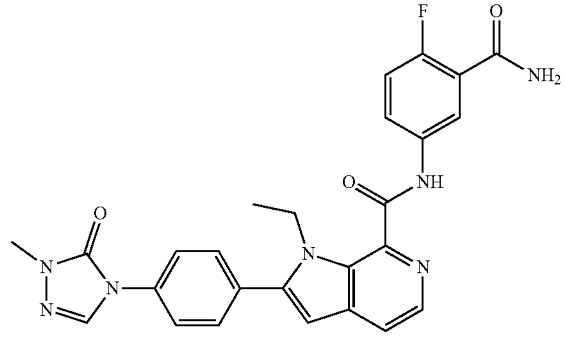

Ex.-25

Step 1

Reference synthesis example compound 84 (10.0 g, 41.7 mmol) and DMF (0.10 L) were mixed, sodium hydride (60% in oil) (2.50 g, 62.5 mmol) was added, and the mixture was stirred at room temperature for 10 minutes. Methyl iodide (7.9 mL, 130 mmol) was added and stirred at room temperature for 2.5 hours. Sodium hydride (60% in oil) (1.50 g, 37.5 mmol) was added, followed by stirring at room temperature for 30 minutes. Water (200 mL) was added and stirred, and then the precipitated solid was collected by filtration. The solid collected by filtration was dried under reduced pressure to obtain reference synthesis example compound 85 (yield 10.6 g).

Step 2

Reference synthesis example compound 85 (3.00 g, 11.8 mmol), THF (0.060 L), and triethyl amine (4.92 mL, 35.4 mmol) were mixed, and the mixture was degassed and purged with argon. [1,1'-bis(diphenylphosphino)ferrocene] dichloropalladium (II) (0.864 g, 1.18 mmol), cuprous iodide (0.225 g, 1.18 mmol), and trimethylsilylacetylene (2.1 mL, 15 mmol) were added, and the mixture was stirred at 50° C. for 4 hours under an argon environment. After allowing to cool, the mixture was diluted with ethyl acetate, and then filtered through Celite®. The solvent in the filtrate was distilled off under reduced pressure, and then the residue was purified by silica gel column chromatography to obtain reference synthesis example compound 86 (yield 2.71 g).

Step 3

Reference synthesis example compound 86 (2.71 g, 9.99 mmol) and THF (0.038 L) were mixed, and then 1 mol/L TBAF/THF solution (0.016 L, 16 mmol) was added, followed by stirring at room temperature for 30 minutes. The solvent was distilled off under reduced pressure, and then the residue was purified by silica gel column chromatography to obtain reference synthesis example compound 87 (yield 1.74 g).

Step 4

XPhos (0.289 g, 0.606 mmol), palladium (II) acetate (68.6 mg, 0.303 mmol), and acetonitrile (0.015 L) were mixed, and then reference synthesis example compound 87 (1.51 g, 7.58 mmol), cesium carbonate (3.95 g, 12.1 mmol), and reference synthesis example compound 69 (1.30 g 6.06 mmol) were added, followed by stirring at 95° C. for 1.5 hours under an argon environment. The mixture was allowed to cool, diluted with chloroform and water, and then filtered through Celite®. The organic layer was separated and dried over anhydrous sodium sulfate. The solvent was distilled off under reduced pressure, and then the residue was purified by silica gel column chromatography and then slurry-washed with a mixed solution of n-hexane/ethylacetate (1/1) (25 mL). The solid was collected by filtration, and then dried under reduced pressure to obtain reference synthesis example compound 88 (yield 1.40 g).

Step 5

Reference synthesis example compound 88 (1.40 g, 3.71 mmol) and methanol (9.3 mL) were mixed, then degassed, the reactor was purged with argon, chloro(triphenylphosphine) gold(I) (0.367 g, 0.742 mmol) and silver bis(trifluoromethanesulfonyl)imide (0.288 g, 0.742 mmol) were added, and the mixture was stirred at 80° C. for 2 hours. After cooling, the solvent was distilled off under reduced pressure. The residue was purified by silica gel column chromatography to obtain reference synthetic example compound 89 (yield 1.23 g).

Step 6

Reference synthesis example compound 89 (1.20 g, 3.18 mmol) and THF (0.012 L) were mixed, methanol (0.012 L) and 4 mol/L aqueous sodium hydroxide (3.2 mL, 13 mmol) were added, and the mixture was stirred at room temperature for 3 hours. 2 mol/L hydrochloric acid (10 mL) was added dropwise to the reaction solution, and the mixture was distilled under reduced pressure. About 10 mL of toluene was added to the residue, and the mixture was distilled under reduced pressure. This operation was repeated twice, followed by drying under reduced pressure to obtain reference synthesis example compound 90 as a mixture of sodium chloride (yield 2.01 g).

Step 7

A sodium chloride mixture (1.20 g) of reference synthesis example compound 90 obtained by the method described in Step 6 and acetonitrile (0.019 L) were mixed, and then 5-amino-2-fluorobenzamide (0.584 g, 3.79 mmol), 1-methylimidazole (0.75 mL, 9.5 mmol), and TCFH (1.06 g, 3.78 mmol) were added, followed by stirring at room temperature for 15 hours. The solvent was distilled off under reduced pressure, the residue was diluted with water and chloroform, and filtered. The filtrate was extracted using chloroform, and the extract was dried over anhydrous sodium sulfate. The solvent was distilled off under reduced pressure, the residue was purified by silica gel column chromatography, ethanol (15 mL) was added to perform slurry washing, and then the solid was collected by filtration and dried under reduced pressure to obtain Example Compound 25 (yield 0.727 g).

Example 26

[Chem. Fig. 67]

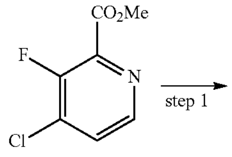

Ref.-68

-continued

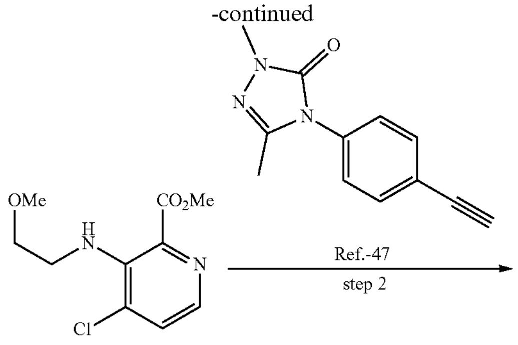

Ref.-91

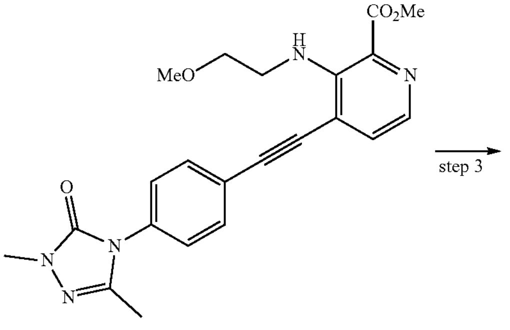

Ref.-92

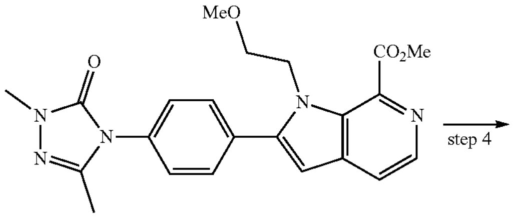

Ref.-93

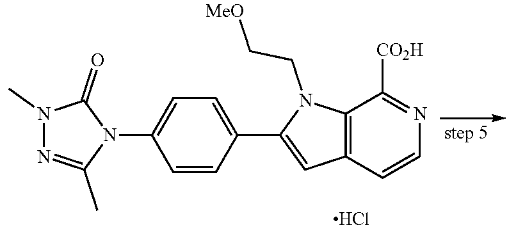

Ref.-94

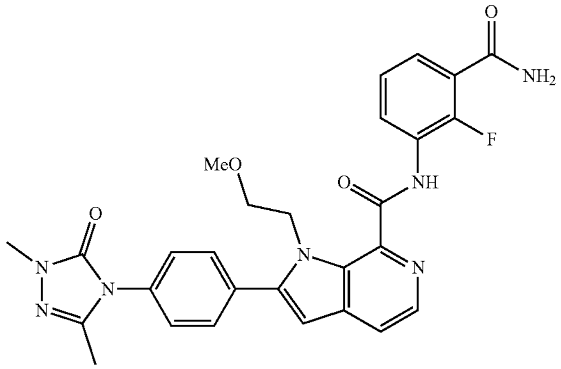

Ex.-26

Step 1

Reference synthesis example compound 69 (500 mg, 2.63 mmol) and DMSO (6.6 mL) were mixed, DIPEA (1.36 mL, 7.91 mmol) and 2-methoxymethylamine (396 mg, 5.27 mmol) were added, and the mixture was stirred at 80° C. for 4 hours. Water and ethyl acetate were added to the reaction solution, stirred, and then the organic layer was separated. The separated organic layer was washed with saturated brine, dried over anhydrous sodium sulfate, and evaporated to obtain reference synthesis example compound 91 (yield 566 mg).

Step 2

Reference synthesis example compound 91 (197 mg, 0.805 mmol) and acetonitrile (2 mL) were mixed, and then palladium (II) acetate (9.2 mg, 0.041 mmol), XPhos (39.0 mg, 0.041 mmol), reference synthesis example compound 47 (180 mg, 0.844 mmol), and cesium carbonate (799 mg 2.45 mmol) were added, followed by stirring at 100° C. for 3.5 hours under an argon environment. After allowing to cool, water and ethyl acetate were added, stirred, and filtered. The organic layer of the filtrate was separated and dried over anhydrous sodium sulfate, and then the solvent was distilled off under reduced pressure. The residue was purified by silica gel column chromatography to obtain reference synthetic example compound 92 (yield 99.9 mg).

Step 3

Reference synthesis example compound 92 (99.9 mg, 0.237 mmol) and ethanol (3 mL) were mixed, degassed, and the reactor was purged with argon. Then, chloro(triphenylphosphine) gold(I) (30.5 mg, 0.0474 mmol) and silver bis(trifluoromethanesulfonyl)imide (18.4 mg, 0.0474 mmol) were added, and the mixture was stirred at 100° C. for 16 hours. After allowing to cool, the mixture was filtered and concentrated under reduced pressure. The residue was purified by silica gel column chromatography to obtain reference synthetic example compound 93 (yield 80.1 mg).

Step 4

Reference synthesis example compound 93 (77.7 mg, 0.184 mmol), methanol (1 mL), and THF (1 mL) were mixed, and then 4 mol/L aqueous sodium hydroxide (460 μL, 1.84 mmol) was added, followed by stirring at 40° C. for 3 hours. 2 mol/L hydrochloric acid (1.5 mL) was added to the reaction solution, and the solvent was distilled off under reduced pressure to obtain reference synthesis example compound 94 as a mixture of sodium chlorides (yield 194 mg).

Step 5

Acetonitrile (1 mL), 3-amino-2-fluorobenzamide (12.0 mg, 0.0779 mmol), 1-methylimidazole (19 μL, 0.241 mmol), and TCFH (21.8 mg, 0.0777 mmol) were sequentially added to a sodium chloride mixture (40 mg) of reference synthesis example compound 94 obtained by the method described in Step 4, and the mixture was stirred at 40° C. for 15 hours. Water and ethyl acetate were added to the reaction solution, stirred, and then the organic layer was separated. The separated organic layer was dried over anhydrous sodium sulfate, and the solvent was distilled off under reduced pressure. After the residue was purified by silica gel column chromatography, slurry washing was performed by adding a mixed solution of n-hexane/ethyl acetate (3/1), and then the solid was collected by filtration. The solid collected by filtration was dried under reduced pressure to obtain Example Compound 26 (yield 11.0 mg).

Example 27

[Chem. Fig. 68]

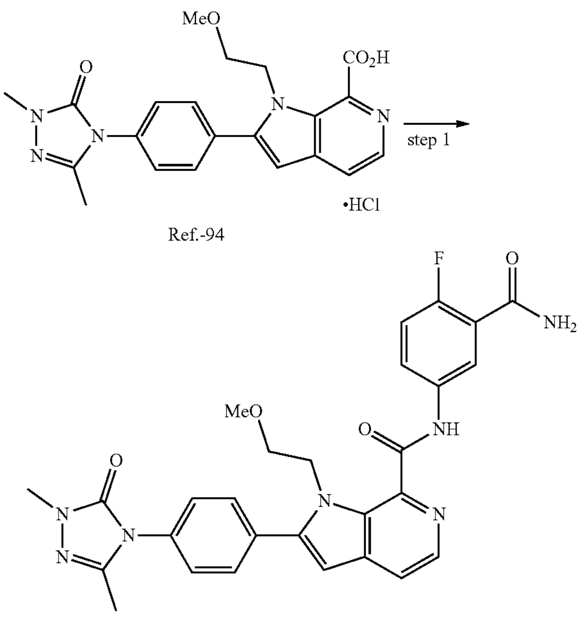

Ref.-94

Ex.-27

Acetonitrile (1 mL), 5-amino-2-fluorobenzamide (12.0 mg, 0.0779 mmol), 1-methylimidazole (19 μL, 0.241 mmol), and TCFH (21.8 mg, 0.0777 mmol) were sequentially added to a sodium chloride mixture (40 mg) of reference synthesis example compound 94 obtained by the method described in Step 4 of Example 26, followed by stirring at 40° C. for 15 hours. Water and ethyl acetate were added to the reaction solution, stirred, and then the organic layer was separated. The separated organic layer was dried over anhydrous sodium sulfate, and the solvent was distilled off under reduced pressure. After the residue was purified by silica gel column chromatography, slurry washing was performed by adding a mixed solution of n-hexane/ethyl acetate (3/1), and then the solid was collected by filtration. The solid collected by filtration was dried under reduced pressure to obtain Example Compound 27 (yield 11.2 mg).

Example 28

[Chem. Fig. 69]

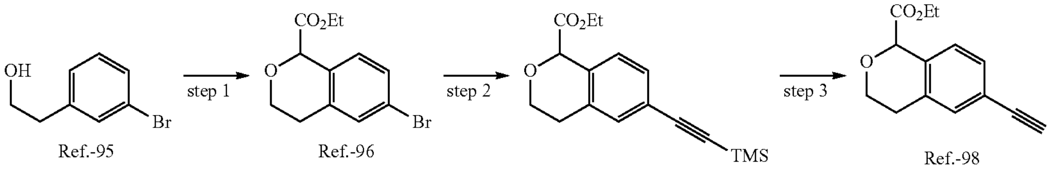

Ref.-95 Ref.-96 Ref.-97 Ref.-98

-continued
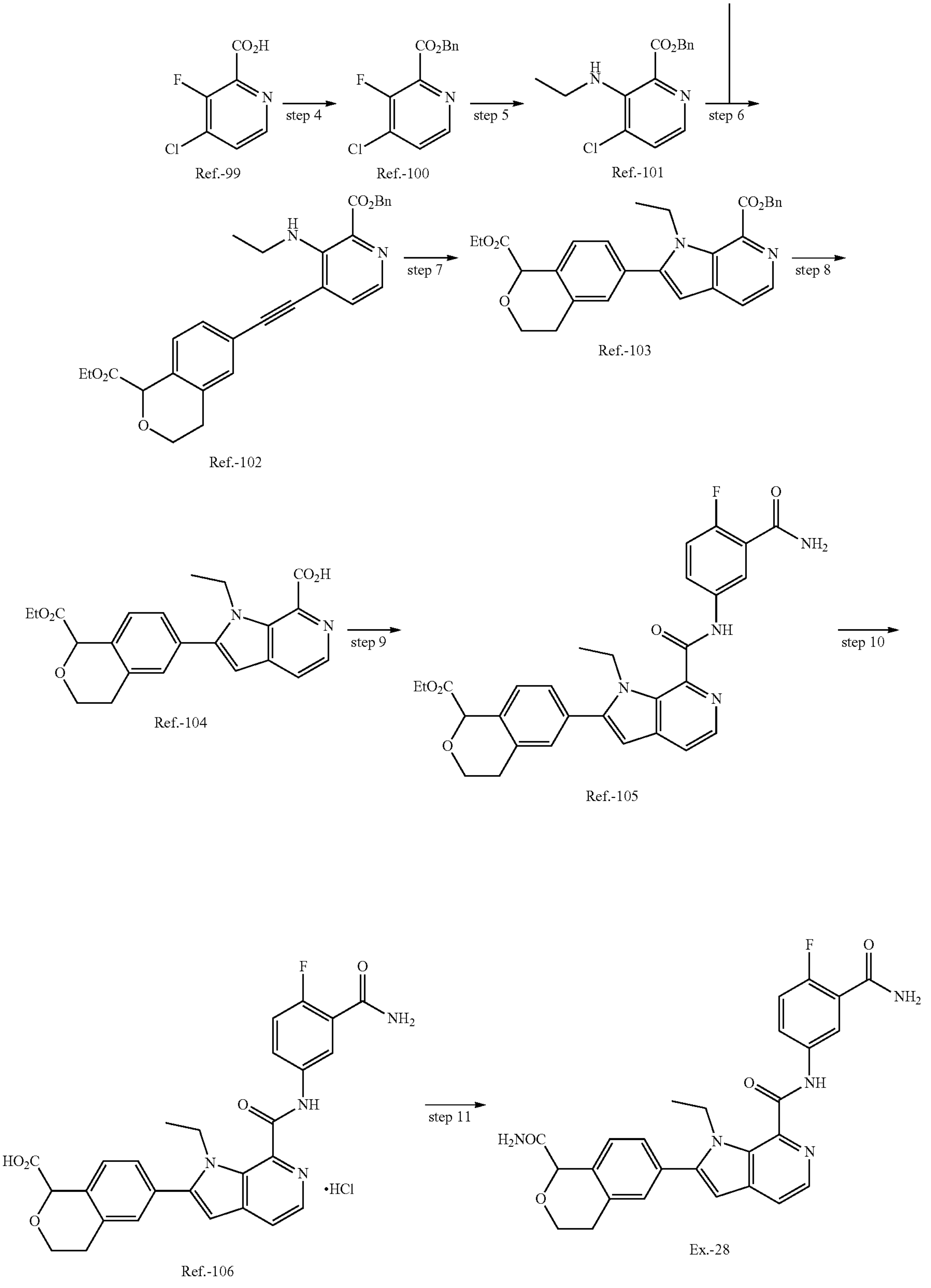

Step 1

Nitromethane (20 mL) and ethyl 2,2-diethoxyacetate (2.52 g, 14.3 mmol) were added to reference synthesis example compound 95 (2.4 g, 12 mmol), the mixture was cooled with ice, titanium chloride (IV) (4.38 mL, 39.9 mmol) was added dropwise, and then the mixture was stirred at room temperature for 20 hours. Water and ethyl acetate were sequentially added and stirred, and the organic layer was separated. The separated organic layer was dried over anhydrous sodium sulfate, and the solvent was distilled off under reduced pressure. The residue was purified by silica gel column chromatography to obtain reference synthetic example compound 96 (yield 2.71 g).

Step 2

THF (25 mL) and triethyl amine (2.2 mL, 16 mmol), [1,1'-bis(diphenylphosphino) ferrocene]dichloropalladium (II) dichloromethane complex (0.43 g, 0.53 mmol), cuprous iodide (100 mg, 0.525 mmol), and trimethylacetylene (1.1 mL, 7.8 mmol) were added to the reference synthesis example compound 96 (1.5 g, 5.3 mmol) and the mixture was stirred at 75° C. for 1.5 hours under an argon environment. After allowing to cool, the reaction solution was diluted with chloroform and filtered through Celite®. The filtrate was concentrated under reduced pressure, and the residue was purified by silica gel column chromatography to obtain reference synthetic example compound 97 (yield 1.64 g).

Step 3

THF (25 mL) and 1 mol/L TBAF/THF solution (10.8 mL, 10.8 mmol) were sequentially added to reference synthesis example compound 97 (1.64 g, 5.42 mmol), and the mixture was stirred at room temperature for 30 minutes. The solvent was distilled off under reduced pressure, and the residue was purified by silica gel column chromatography to obtain reference synthesis example compound 98.

Step 4

Reference synthesis example compound 99 (1.05 g, 5.98 mmol) and DMSO (30 mL) were mixed, and then potassium carbonate (1.24 g, 8.97 mmol) was added under ice-cooling, followed by stirring for 10 minutes. Benzylbromide (853 μL, 7.18 mmol) was added and stirred at room temperature for 21 hours. Water and ethyl acetate were added, the mixture was stirred, and the organic layer was separated. The separated organic layer was washed with saturated brine, and the solvent was distilled off under reduced pressure. The residue was purified by silica gel column chromatography to obtain reference synthesis example compound 100 (yield 1.01 g).

Step 5

DMSO (10 mL), DIPEA (1.96 mL, 11.4 mmol), and 2.0 mol/L ethyl amine/THF (2.3 mL, 4.6 mmol) were sequentially added to reference synthesis example compound 100 (1.01 g, 3.80 mmol), and the mixture was stirred at 80° C. for 4 hours. Ethyl acetate and water were added and stirred under water-cooling, and the organic layer was separated. The separated organic layer was sequentially washed with water and saturated brine, and dried over anhydrous sodium sulfate. The solvent was distilled off under reduced pressure, and then the residue was purified by silica gel column chromatography to obtain reference synthesis example compound 101 (yield 980 mg).

Step 6

Palladium (II) acetate (23.7 mg, 0.105 mmol), XPhos (99.8 mg, 0.209 mmol), and degassed acetonitrile (10 mL) were mixed, and then reference synthesis example compound 98 (0.482 g, 2.09 mmol), cesium carbonate (1.36 g, 4.17 mmol), and reference synthesis example compound 101 (0.980 g 3.37 mmol) were added, followed by stirring at 95° C. for 1.5 hours under an argon environment. After allowing to cool, water was added to the reaction solution, and the mixture was extracted using ethyl acetate. The extract was dried over anhydrous sodium sulfate, and the solvent was distilled off under reduced pressure. The residue was purified by silica gel column chromatography to obtain reference synthetic example compound 102 (yield 0.554 g).

Step 7

Reference synthesis example compound 102 (554 mg, 1.14 mmol) and ethanol (10 mL) were mixed, degassed, the reactor was purged with argon, and then chloro(2-dicyclohexylphosphino-2',6'-dimethoxy-1,1'-biphenyl) gold (I) (73.5 mg, 0.114 mmol) and silver bis(trifluoromethanesulfonyl)imide (44.3 mg, 0.114 mmol) were added, followed by stirring at 100° C. for 3 hours. After allowing to cool, the mixture was filtered and concentrated under reduced pressure. The residue was purified by silica gel column chromatography to obtain reference synthesis example compound 103 (yield 272 mg).

Step 8

THF (5 mL) and 10% palladium/carbon (40 mg) were sequentially added to reference synthesis example compound 103 (270 mg, 0.557 mmol), and the mixture was stirred at room temperature for 17 hours under a hydrogen environment. The reaction solution was filtered, and the solvent was distilled off under reduced pressure. The residue was purified by silica gel column chromatography to obtain reference synthesis example compound 104 (yield 135 mg).

Step 9

Acetonitrile (1 mL), 5-amino-2-fluorobenzamide (20 mg, 0.13 mmol), 1-methylimidazole (30 μL, 0.38 mmol), and TCFH (35.6 mg, 0.127 mmol) were sequentially added to reference synthetic example compound 104 (25 mg, 0.063 mmol), and stirred at 40° C. for 15 hours. Water and ethyl acetate were added to the reaction solution, stirred, and then the organic layer was separated. The separated organic layer was dried over anhydrous sodium sulfate, and the solvent was distilled off under reduced pressure. The residue was purified by silica gel column chromatography, a mixed solution of n-hexane/ethylacetate (3/1) was added to perform slurry washing, and then the solid was collected by filtration to obtain reference synthesis example compound 105 partially containing an impurity (yield 43 mg).

Step 10

Reference synthesis example compound 105 (43 mg) containing an impurity obtained by the method described in Step 9 was mixed with methanol (500 μL) and THF (500 μL), 4 mol/L aqueous sodium hydroxide (203 μL) was added, and the mixture was stirred at 40° C. for 2 hours. HCl was added to neutralize the reaction solution, and then the mixture was concentrated and dried under reduced pressure to obtain reference synthesis example compound 106 as a sodium chloride mixture (yield 91 mg).

Step 11

Ammonium chloride (145 mg, 2.71 mmol), DMF (3 mL), DIPEA (467 μL, 2.72 mmol), and HATU (138 mg, 0.363 mmol) were sequentially added to a sodium chloride mixture (91 mg) of reference synthesis example compound 106 obtained by the method described in Step 10, followed by stirring at room temperature for 18 hours. Water and ethyl acetate were added, the mixture was stirred, and the organic layer was separated. The separated organic layer was dried over anhydrous sodium sulfate, and the solvent was distilled off under reduced pressure. The residue was purified by silica gel column chromatography, followed by slurry washing with a mixed solution of ethyl acetate/n-hexane (1/3), and then the solid was collected by filtration to obtain Example Compound 28 (yield 19.8 mg).

Example 29

[Chem. Fig. 70]

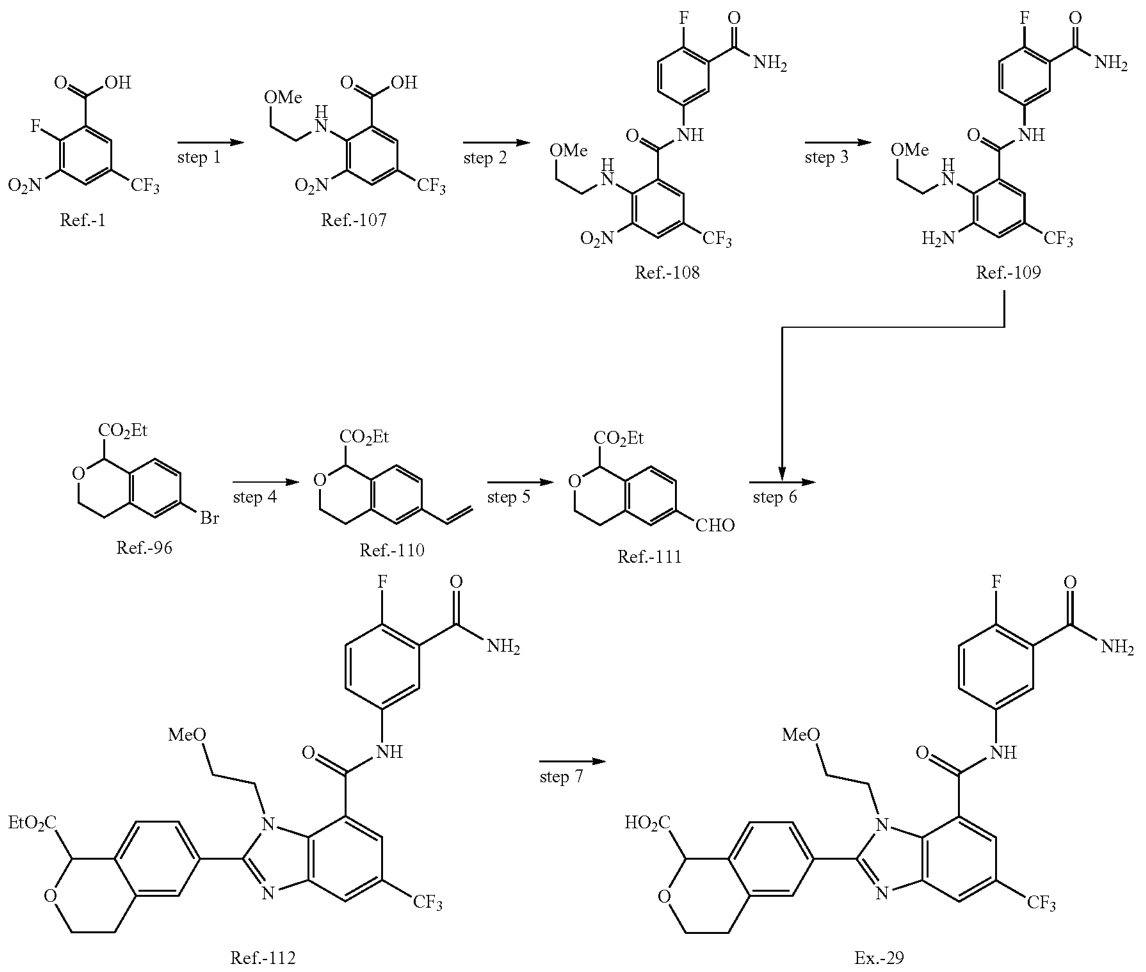

Step 1-3

Reference synthesis example compound 109 was obtained from reference synthesis example compound 1 by the same method as in steps 1 to 3 of Example 1.

Step 4

A suspension containing reference synthesis example compound 96 (300 mg, 1.05 mmol), potassium vinyltrifluoroborate (281 mg, 2.10 mmol), and cesium carbonate (686 mg, 2.11 mmol) in a 1,4-dioxane/water (5/1) mixture (4 mL) was degassed, and bis(di-tert-butyl(4-dimethylaminophenyl)phosphine) dichloropalladium(II) (38 mg, 0.054 mmol) was added, followed by stirring at 90° C. for 5 hours under an argon environment. The reaction solution was cooled and filtered. Water was added to the filtrate, and the mixture was extracted using ethyl acetate and washed with saturated brine. The filtrate was dried over anhydrous sodium sulfate, and the solvent was distilled off under reduced pressure. The residue was purified by silica gel column chromatography to obtain reference synthesis example compound 110 (yield 213 mg).

Step 5

Reference synthesis example compound 110 (212 mg, 0.913 mmol) was mixed with 1,4-dioxane (9 mL), and then water (3 mL), 2,6-dimethylpyridine (212 μL, 1.83 mmol), sodium periodate (781 mg, 3.65 mmol), and tert-butyl alcohol (2.5 w/v %) (460 μL, 0.045 mmol) were sequentially added, followed by stirring at room temperature for 2 hours. Water and ethyl acetate were added to the reaction solution, and the organic layer was separated. The separated organic layer was washed with saturated brine and then dried over anhydrous sodium sulfate. The solvent was distilled off under reduced pressure, and then the residue was purified by silica gel column chromatography to obtain reference synthesis example compound 111 (yield 187 mg).

Step 6

Reference synthesis example compound 111 (71 mg, 0.30 mmol) and acetic acid (86 μL, 1.50 mmol) were added to a mixture of reference synthesis example compound 109 (100 mg, 0.252 mmol) in ethanol (4 mL), and the mixture was stirred at 80° C. for 17 hours in an oxygen environment. The reaction solution was allowed to cool, a saturated aqueous sodium hydrogen carbonate solution and ethyl acetate were added and stirred, and then the organic layer was separated. The separated organic layer was dried over anhydrous sodium sulfate, and the residue was purified by silica gel column chromatography to obtain reference synthesis example compound 112 (yield 135 mg).

Step 7

Reference synthesis example compound 112 (122 mg, 0.200 mmol) and methanol (2 mL) were mixed, and then 4 mol/L aqueous sodium hydroxide (300 μL) was added, followed by stirring at 50° C. for 3 hours. 2 mol/L hydrochloric acid (600 μL) was added to the reaction solution, the mixture was diluted with water, and then the precipitate was collected by filtration. The solid collected by filtration was dried under reduced pressure to obtain Example Compound 29 (yield 74.5 mg).

Example 30

[Chem. Fig. 71]

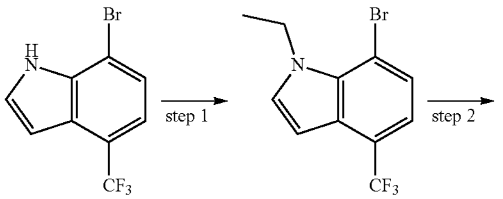

Ref.-113 Ref.-114

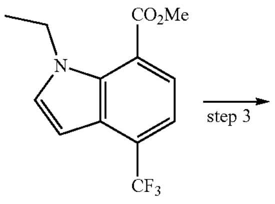

Ref.-115

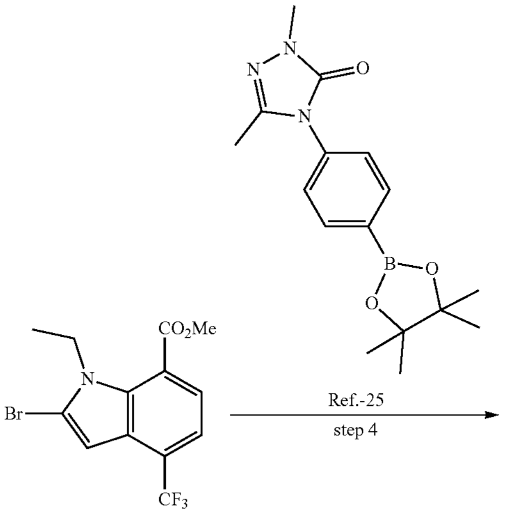

Ref.-116

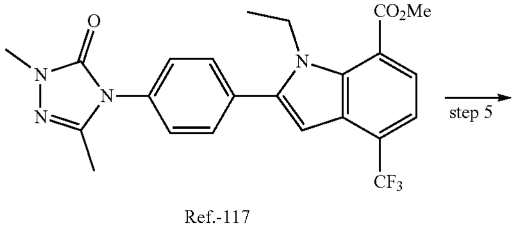

Ref.-117

-continued

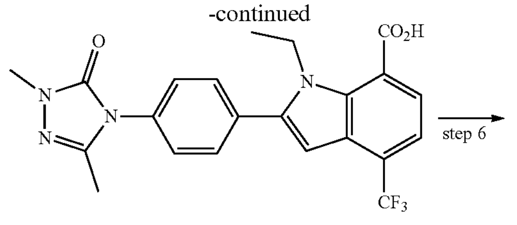

Ref.-118

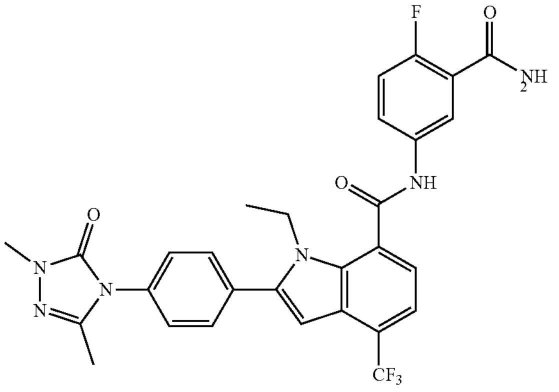

Ex.-30

Step 1

Reference synthesis example compound 113 (500 mg) and DMF (3.8 mL) were mixed, the mixture was ice-cooled, sodium hydride (60% in oil) (98.4 mg, 2.46 mmol) was added, and the mixture was stirred for 10 minutes. Ethyl iodide (0.21 mL, 2.6 mmol) was added to the reaction solution, and the mixture was stirred at room temperature for 2 hours. The reaction solution was added dropwise to an ice-cooled saturated aqueous ammonium chloride solution, water was added, and the mixture was extracted using ethyl acetate. Normal hexane was added to the extract, and the mixture was washed successively with water and saturated brine, and dried over anhydrous sodium sulfate. The solvent was distilled off under reduced pressure, and then the residue was purified by silica gel column chromatography to obtain reference synthesis example compound 114 (yield 356 mg).

Step 2

Reference synthesis example compound 114 (356 mg, 1.22 mmol) and MTBE (4 mL) were mixed and then cooled to −78° C., and then 2.56 mol/L of n-butyllithium/n-hexane (0.72 mL) was added, followed by stirring for 1 hour. A solution of methyl chloroformate (230 mg, 2.43 mmol) in MTBE was added dropwise, the mixture was warmed to room temperature, and stirred for 3 hours. The reaction solution was added dropwise to an ice-cooled saturated aqueous ammonium chloride solution, water was added, and the mixture was extracted using ethyl acetate. The extract was dried over anhydrous sodium sulfate, and the solvent was distilled off under reduced pressure. The residue was purified by silica gel column chromatography to obtain reference synthesis example compound 115 (yield 254 mg).

Step 3

A solution of N,N-diisopropylamine (0.39 mL, 2.8 mmol) in THF (3.7 mL) was cooled to −78° C., 2.56 mol/L n-butyllithium/n-hexane (0.73 mL) was added, the temperature was raised to 0° C., and the mixture was stirred for 15 minutes. After cooling to −78° C., reference synthesis example compound 115 (254 mg, 0.935 mmol) was added and stirred for 1 hour, a solution of carbontetrabromide (0.3 g, 0.9 mmol) in THF (368 μL) was added dropwise, and the mixture was warmed to room temperature and stirred for 3 hours. The reaction solution was added dropwise to an ice-cooled saturated aqueous ammonium chloride solution, water was added, and the mixture was extracted using ethyl acetate. The extract was dried over anhydrous sodium sulfate, and the solvent was distilled off under reduced pressure. The residue was purified by silica gel column chromatography to obtain reference synthesis example compound 116 (yield 176 mg).

Step 4

Reference synthesis example compound 116 (174 mg, 0.496 mmol), reference synthesis example compound 25 (234 mg, 0.742 mmol) and 1,4-dioxane (5 mL) were mixed, and then cesium carbonate (323 mg, 0.991 mmol) and APhos-Pd-G3 (15.8 mg, 0.0249 mmol) were added, followed by stirring at 140° C. for 1 hour under microwave irradiation. Water was added to the cooled reaction solution, and the mixture was extracted using ethyl acetate. The extract was neutralized with dilute hydrochloric acid and dried over anhydrous sodium sulfate, and the solvent was distilled off under reduced pressure. The residue was purified by silica gel column chromatography to obtain reference synthesis example compound 117 (yield 22.3 mg).

Step 5

Reference synthesis example compound 117 (22.3 mg, 0.0486 mmol), methanol (2.4 mL) and THF (0.6 mL) were mixed, and then 4 mol/L aqueous sodium hydroxide (0.24 mL) was added under ice-cooling, followed by stirring at room temperature for 1 hour. After the reaction solution was neutralized, the solvent was distilled off under reduced pressure to obtain reference synthetic example compound 118 as a sodium chloride mixture (yield 78.5 mg).

Step 6

A sodium chloride mixture (39 mg) of reference synthesis example compound 118 obtained by the method described in Step 5, 5-amino-2-fluorobenzamide (5.6 mg, 0.036 mmol), and acetonitrile (0.2 mL) were mixed, 1-methylimidazole (5.9 μL, 0.074 mmol) and TCFH (10.8 mg, 0.0385 mmol) were added, and the mixture was stirred at room temperature for 4 hours. Water was added, the mixture was extracted using ethyl acetate, and the extract was dried over anhydrous sodium sulfate. The solvent was distilled off under reduced pressure, and then the residue was purified by silica gel column chromatography and preparative TLC successively to obtain Example Compound 30 (yield 4.2 mg).

Example 31

[Chem. Fig. 72]

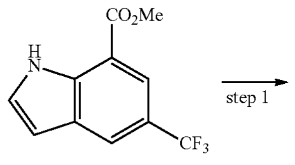

Ref.-58

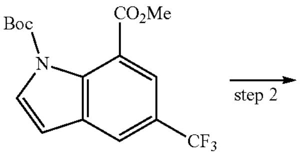

Ref.-119

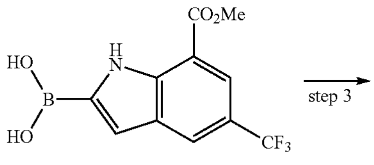

Ref.-120

-continued

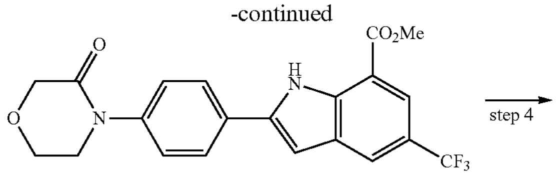

Ref.-121

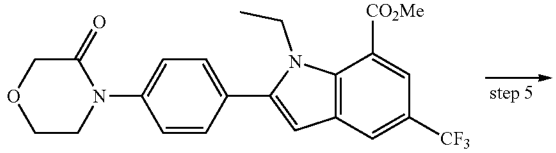

Ref.-122

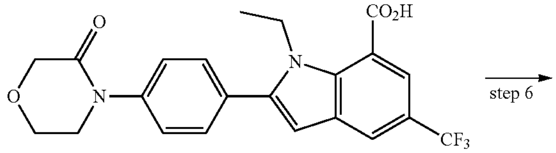

Ref.-123

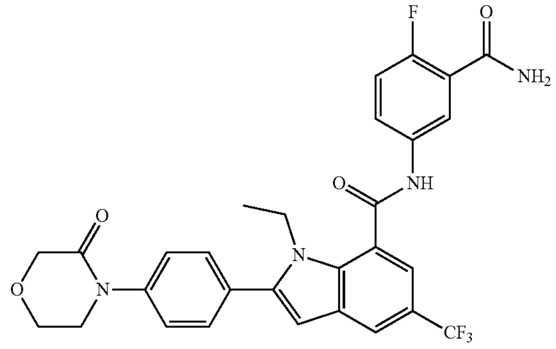

Ex.-31

Step 1

Reference synthesis example compound 58 (1.00 g, 4.11 mmol) and THF (21 mL) were mixed, and then DMAP (50.3 mg, 0.412 mmol) and di-tert-butyl dicarbonate (1.17 g, 5.36 mmol) were added, followed by stirring at room temperature for 16 hours. The solvent was distilled off under reduced pressure, and then the residue was purified by silica gel column chromatography to obtain reference synthesis example compound 119 (yield 1.16 g).

Step 2

1.8 mol/L LDA/n-hexane-THF (1.2 mL) was added to reference synthesis example compound 119 (600 mg, 1.75 mmol) and triisopropyl borate (0.64 mL, 2.8 mmol) in THF (1.2 mL), and the mixture was stirred at 0° C. for 1 hour. 2 mol/L HCl was added to the reaction solution, and the mixture was extracted using ethyl acetate. The extract was washed successively with water and saturated brine, and then dried over anhydrous sodium sulfate. The solvent was distilled off under reduced pressure to obtain reference synthesis example compound 120 (yield 317 mg).

Step 3

Reference synthesis example compound 120 (134 mg, 0.467 mmol), 4-(4-bromophenyl) morpholin-3-one (80.0 mg, 0.312 mmol), 1,4-dioxane (1.6 mL), and water (0.63 mL) were mixed, then cesium carbonate (153 mg, 0.470 mmol), XPhos (14.9 mg, 0.0313 mmol), and XPhos-palladium (crotyl) chloride (21.1 mg, 0.0313 mmol) were added, and the mixture was stirred at 90° C. for 2 hours. The reaction solution was allowed to cool, water was added, and the mixture was extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 121 (yield 129 mg).

Step 4

Ice-cooled reference synthesis example compound 121 (129 mg, 0.308 mmol) and DMF (3.1 mL) were mixed, sodium hydride (60% in oil) (16.0 mg, 0.400 mmol) was added, and the mixture was stirred at 0° C. for 30 minutes. Ethyl iodide (74 μL, 0.93 mmol) was added, and the mixture was stirred at room temperature for 2 hours, and then heated to 50° C. and stirred for 3 hours. The reaction solution was ice-cooled, saturated aqueous ammonium chloride solution was added, and the mixture was extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 122 partially containing impurity (yield 108 mg).

Step 5

Reference synthesis example compound 122 (129 mg) containing an impurity obtained by the method described in Step 4, methanol (1.4 mL) and THF (1.4 mL) were mixed, and then 4 mol/L aqueous sodium hydroxide (0.72 mL) was added, followed by stirring at room temperature for 16 hours. 6 mol/L hydrochloric acid (0.53 mL) was added to the reaction solution, and the solvent was distilled off under reduced pressure to obtain reference synthetic example compound 123 as a mixture of sodium chloride (yield 284 mg).

Step 6

A sodium chloride mixture (40.0 mg) of reference synthesis example compound 123 obtained by the method described in Step 5, 5-amino-2-fluorobenzamide (12.1 mg, 0.0785 mmol) and acetonitrile (393 μL) were mixed, 1-methylimidazole (14 μL, 0.18 mmol) and TCFH (24.3 mg, 0.0866 mmol) were added, and then the mixture was stirred at room temperature for 16 hours. Water was added to the reaction solution, followed by extraction using ethyl acetate. The extract was washed successively with water and saturated brine, and then dried over anhydrous sodium sulfate. The solvent was distilled off under reduced pressure, and then the residue was purified by silica gel column chromatography to obtain Example Compound 31 (yield 9.6 mg).

Example Compounds 15 to 128 in the following table were produced according to the methods shown in Examples 15 to 31 described above or similar methods. Furthermore, $^1$H-NMR data and/or LC/MS data of these Example compounds are shown in the table.

TABLE 2-1

| Ex. | Structure | Data |
|---|---|---|
| 15 | 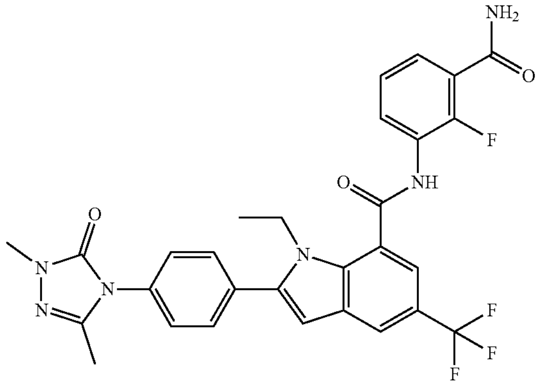 [SMILES: CCn1c(-c2ccc(-n3c(C)nn(C)c3=O)cc2)cc2cc(C(F)(F)F)cc(C(=O)Nc3cccc(C(N)=O)c3F)c21] | $^1$H-NMR (400 MHz, $CDCl_3$) δ: 1.08 (3H, t, J = 7.1 Hz), 2.25 (3H, s), 3.52 (3H, s), 4.42 (2H, q, J = 7.1 Hz), 5.84 (1H, s), 6.52-6.54 (1H, m), 6.76 (1H, s), 7.38 (1H, t, J = 8.0 Hz), 7.45 (2H, d, J = 8.5 Hz), 7.63 (2H, d, J = 8.5 Hz), 7.70 (1H, d, J = 1.2 Hz), 7.91 (1H, dt, J = 1.7, 7.7 Hz), 8.04 (1H, d, J = 2.6 Hz), 8.10 (1H, s), 8.61 (1H, m). ESI-MS m/z: 581 $[M + H]^+$ |
| 16 | 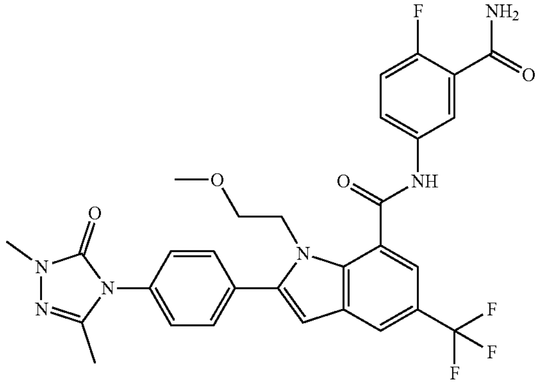 [SMILES: COCCn1c(-c2ccc(-n3c(C)nn(C)c3=O)cc2)cc2cc(C(F)(F)F)cc(C(=O)Nc3ccc(F)c(C(N)=O)c3)c21] | $^1$H-NMR (400 MHz, DMSO-$d_6$) δ: 2.15 (3H, s), 2.84 (3H, s), 3.35-3.37 (5H, m), 4.49 (2H, t, J = 5.4 Hz), 6.93 (1H, s), 7.32 (1H, t, J = 9.5 Hz), 7.60 (2H, d, J = 8.5 Hz), 7.69-7.75 (5H, m), 7.86-7.90 (1H, m), 8.06-8.08 (1H, m), 8.20 (1H, s), 11.00 (1H, s). ESI-MS m/z: 611 $[M + H]^+$ |

TABLE 2-1-continued

| Ex. | Structure | Data |
|---|---|---|
| 17 | 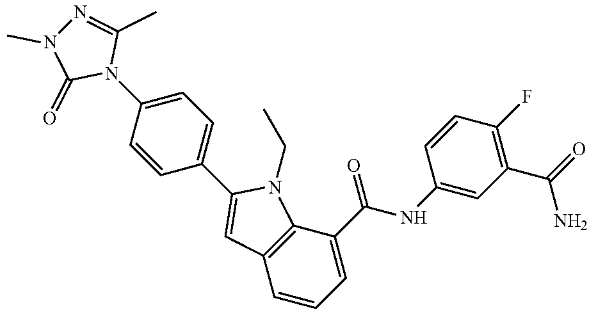 [SMILES: CCn1c(-c2ccc(-n3c(C)nn(C)c3=O)cc2)cc2cccc(C(=O)Nc3ccc(F)c(C(N)=O)c3)c21] | $^1$H-NMR (400 MHz, DMSO-$d_6$) δ: 0.98 (3H, t, J = 7.0 Hz), 2.16 (3H, s), 3.36 (3H, s), 4.28-4.33 (2H, m), 6.75 (1H, s), 7.20 (1H, t, J = 7.6 Hz), 7.30 (1H, t, J = 9.6 Hz), 7.38 (1H, d, J = 6.9 Hz), 7.59 (2H, d, J = 8.5 Hz), 7.69-7.78 (5H, m), 7.90 (1H, m), 8.10 (1H, m), 10.86 (1H, s). ESI-MS m/z: 513 [M + H]$^+$ |
| 18 | 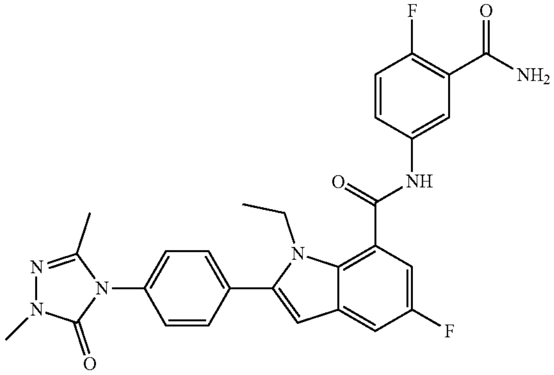 [SMILES: CCn1c(-c2ccc(-n3c(C)nn(C)c3=O)cc2)cc2cc(F)cc(C(=O)Nc3ccc(F)c(C(N)=O)c3)c21] | $^1$H-NMR (400 MHz, $CD_3OD$) δ: 1.36 (3H, t, J = 7.4 Hz), 2.20 (3H, s), 3.46 (3H, s), 4.35 (2H, q, J = 7.10 Hz), 6.69 (1H, s), 7.20-7.29 (2H, m), 7.45 (1H, dd, J = 2.5, 8.9 Hz), 7.54 (2H, d, J = 8.5 Hz), 7.72 (2H, d, J = 8.5 Hz), 7.97 (1H, m), 8.16 (1H, dd, J = 2.8, 6.5 Hz). ESI-MS m/z: 531 [M + H]$^+$ |
| 19 | 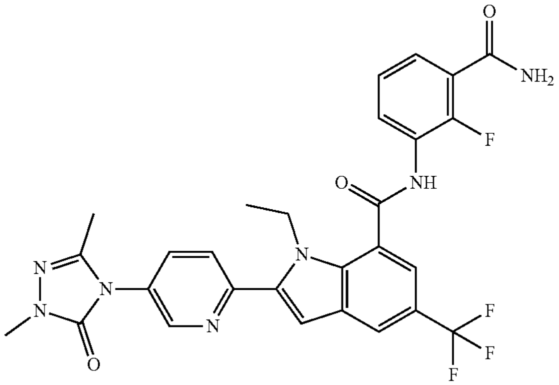 [SMILES: CCn1c(-c2ccc(-n3c(C)nn(C)c3=O)cn2)cc2cc(C(F)(F)F)cc(C(=O)Nc3cccc(C(N)=O)c3F)c21] | $^1$H-NMR (400 MHz, DMSO-$d_6$) δ: 1.21 (3H, t, J = 7.0 Hz), 2.20 (3H, s), 3.38 (3H, s), 4.80 (2H, q, J = 6.9 Hz), 7.31-7.34 (2H, m), 7.51 (1H, m), 7.67-7.69 (2H, m), 7.84 (1H, br s), 7.92 (1H, m), 8.11 (2H, d, J = 1.6 Hz), 8.24 (1H, d, J = 0.9 Hz), 8.83 (1H, t, J = 1.6 Hz), 10.9 (1H, br s). ESI-MS m/z: 582 [M + H]$^+$ |

TABLE 2-2

| | | |
|---|---|---|
| 20 | 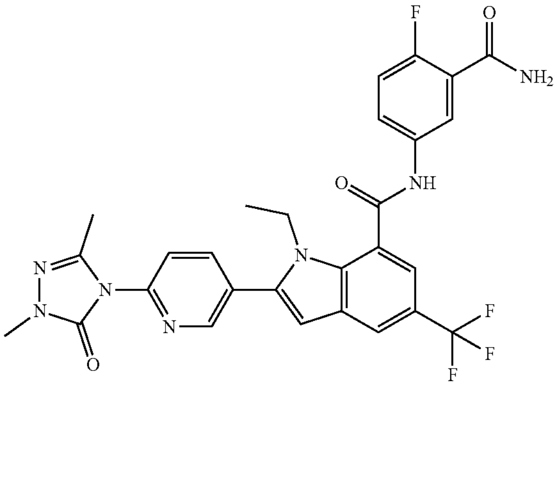 [SMILES: CCn1c(-c2ccc(-n3c(C)nn(C)c3=O)nc2)cc2cc(C(F)(F)F)cc(C(=O)Nc3ccc(F)c(C(N)=O)c3)c21] | $^1$H-NMR (400 MHz, DMSO-$d_6$) δ: 1.04 (3H, t, J = 7.2 Hz), 2.39 (3H, s), 3.38 (3H, s), 4.30 (2H, q, J = 6.9 Hz), 7.03 (1H, s), 7.33 (1H, dd, J = 9.0, 10.0 Hz), 7.69 (1H, d, J = 1.5 Hz), 7.72 (1H, br s), 7.74 (1H, br s), 7.89 (1H, m), 7.93 (1H, m), 8.08 (1H, dd, J = 2.8, 6.4 Hz,), 8.22 (1H, d, J = 1.0 Hz), 8.28 (1H, dd, J = 2.4, 8.4 Hz), 8.77 (1H, dd, J = 0.7, 2.4 Hz), 11.03 (1H, br s). ESI-MS m/z: 582 [M + H]$^+$ |

TABLE 2-2-continued

| | | |
|---|---|---|
| 21 | 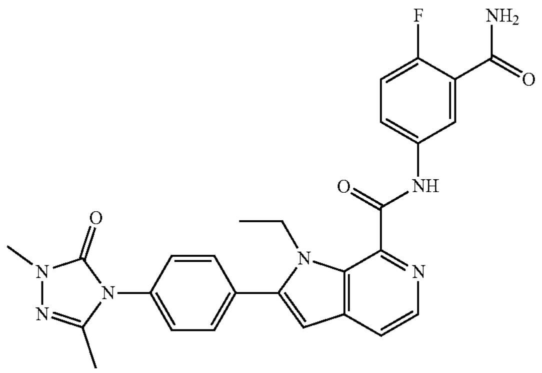 [SMILES: CCn1c(-c2ccc(-n3c(C)nn(C)c3=O)cc2)cc2ccnc(C(=O)Nc3ccc(F)c(C(N)=O)c3)c21] | $^1$H-NMR (400 MHz, DMSO-$d_6$) δ: 1.01 (3H, t, J = 7.1 Hz), 2.17 (3H, s), 3.37 (3H, s), 4.42-4.47 (2H, m), 6.85 (1H, s), 7.29-7.34 (1H, m), 7.64 (2H, d, J = 8.6 Hz), 7.70 (1H, br s), 7.75-7.82 (4H, m), 7.91-7.95 (1H, m), 8.16-8.18 (1H, m), 8.29 (1H, d, J = 5.3 Hz), 11.00 (1H, s). ESI-MS m/z: 514 [M + H]$^+$ |
| 22 | 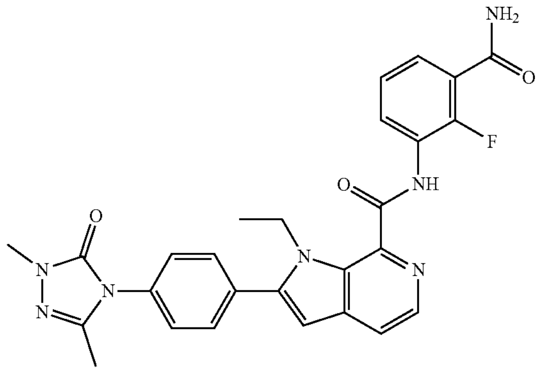 [SMILES: CCn1c(-c2ccc(-n3c(C)nn(C)c3=O)cc2)cc2ccnc(C(=O)Nc3cccc(C(N)=O)c3F)c21] | $^1$H-NMR (400 MHz, DMSO-$d_6$) δ: 1.04 (3H, t, J = 7.1 Hz), 2.17 (3H, s), 3.37 (3H, s), 4.52-4.58 (2H, m), 6.87 (1H, s), 7.32 (1H, t, J = 8.0 Hz), 7.45-7.49 (1H, m), 7.64 (2H, d, J = 8.6 Hz), 7.69 (1H, br s), 7.77 (2H, d, J = 8.6 Hz), 7.83-7.85 (2H, m), 8.02-8.05 (1H, m), 8.31-8.32 (1H, m), 10.70 (1H, s). ESI-MS m/z: 514 [M + H]$^+$ |
| 23 | 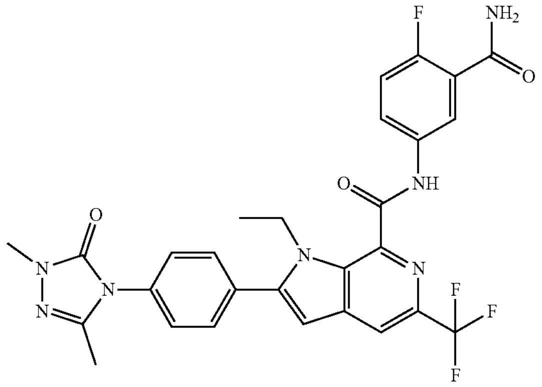 [SMILES: CCn1c(-c2ccc(-n3c(C)nn(C)c3=O)cc2)cc2cc(C(F)(F)F)nc(C(=O)Nc3ccc(F)c(C(N)=O)c3)c21] | $^1$H-NMR (400 MHz, DMSO-$d_6$) δ: 1.09 (3H, t, J = 7.1 Hz), 2.17 (3H, s), 3.37 (3H, s), 4.36-4.40 (2H, m), 7.03 (1H, s), 7.35 (1H, t, J = 9.0 Hz), 7.66 (2H, d, J = 8.6 Hz), 7.71 (1H, br s), 7.77-7.80 (3H, m), 7.91-7.94 (1H, m), 8.09-8.11 (1H, m), 8.31-8.34 (1H, m), 1.113 (1H, s). ESI-MS m/z: 582 [M + H]$^+$ |
| 24 | 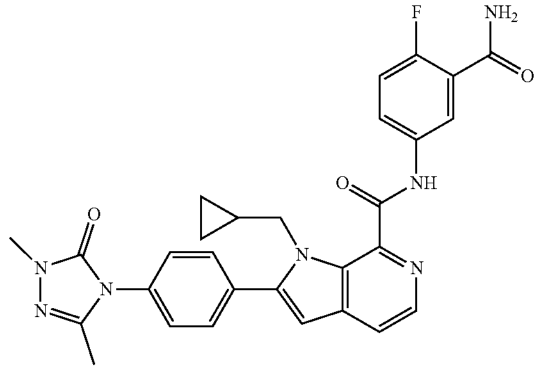 [SMILES: Cc1nn(C)c(=O)n1-c1ccc(-c2cc3ccnc(C(=O)Nc4ccc(F)c(C(N)=O)c4)c3n2CC2CC2)cc1] | $^1$H-NMR (400 MHz, DMSO-$d_6$) δ: −0.23-−0.22 (2H, m), 0.12-0.15 (2H, m), 0.76 (1H, m), 2.16 (3H, s), 3.37 (3H, s), 4.39 (2H, d, J = 7.3 Hz), 6.89 (1H, s), 7.32 (1H, t, J = 9.5 Hz), 7.62 (2H, d, J = 8.6 Hz), 7.69 (1H, m), 7.75-7.77 (3H, m), 7.83 (1H, d, J = 5.3 Hz), 7.95 (1H, m), 8.17 (1H, m), 8.32 (1H, d, J = 5.2 Hz), 11.04 (1H, s). ESI-MS m/z: 540 [M + H]$^+$ |

TABLE 2-3

| | | |
|---|---|---|
| 25 | 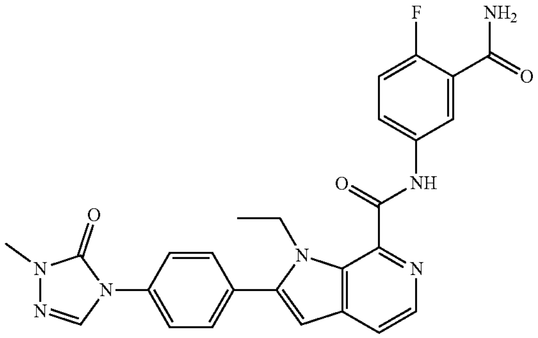 [SMILES: CCn1c(-c2ccc(-n3cnn(C)c3=O)cc2)cc2ccnc(C(=O)Nc3ccc(F)c(C(N)=O)c3)c21] | $^1$H-NMR (400 MHz, DMSO-$d_6$) δ: 0.99 (3H, t, J = 7.1 Hz), 3.43 (3H, s), 4.42 (2H, q, J = 6.9 Hz), 6.82 (1H, s), 7.32 (1H, t, J = 9.5 Hz), 7.70 (1H, s), 7.74-7.76 (3H, m), 7.81 (1H, d, J = 5.3 Hz), 7.90-7.95 (3H, m), 8.18 (1H, dd, J = 2.8, 6.5 Hz), 8.29 (1H, d, J = 5.3 Hz), 8.59 (1H, s), 11.00 (1H, s).<br>ESI-MS m/z: 500 $[M + H]^+$ |
| 26 | 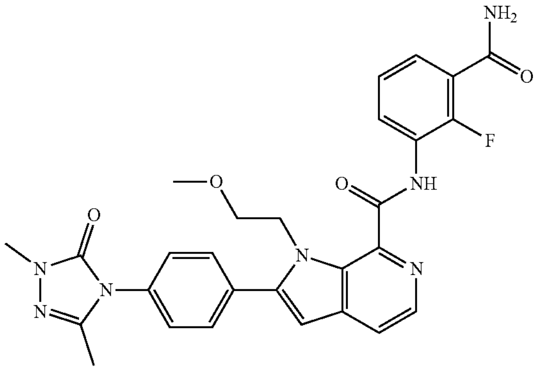 [SMILES: COCCn1c(-c2ccc(-n3c(C)nn(C)c3=O)cc2)cc2ccnc(C(=O)Nc3cccc(C(N)=O)c3F)c21] | $^1$H-NMR (400 MHz, DMSO-$d_6$) δ: 2.16 (3H, s), 2.85 (3H, s), 3.37-3.42 (5H, m), 4.76 (2H, t, J = 5.0 Hz), 6.87 (1H, s), 7.31 (1H, t, J = 7.9 Hz), 7.46 (1H, m), 7.63 (2H, d, J = 8.5 Hz), 7.70 (1H, br s), 7.78 (2H, d, J = 8.5 Hz), 7.83 (1H, br s), 7.86 (1H, d, J = 5.2 Hz), 8.05 (1H, m), 8.33 (1H, d, J = 5.2 Hz), 10.68 (1H, s).<br>ESI-MS m/z: 544 $[M + H]^+$ |
| 27 | 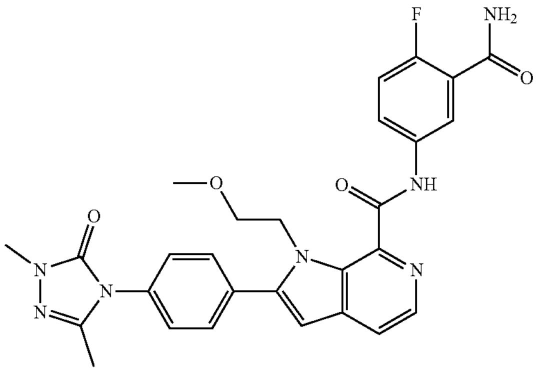 [SMILES: COCCn1c(-c2ccc(-n3c(C)nn(C)c3=O)cc2)cc2ccnc(C(=O)Nc3ccc(F)c(C(N)=O)c3)c21] | $^1$H-NMR (400 MHz, DMSO-$d_6$) δ: 2.16 (3H, s), 2.83 (3H, s), 3.33-3.37 (5H, m), 4.64-4.66 (2H, m), 6.85 (1H, s), 7.31 (1H, t, J = 9.5 Hz), 7.62 (2H, d, J = 8.5 Hz), 7.69 (1H, br s), 7.74-7.83 (4H, m), 7.92-7.95 (1H, m), 8.17-8.19 (1H, m), 8.31 (1H, d, J = 5.2 Hz), 10.98 (1H, s).<br>ESI-MS m/z: 544 $[M + H]^+$ |
| 28 | 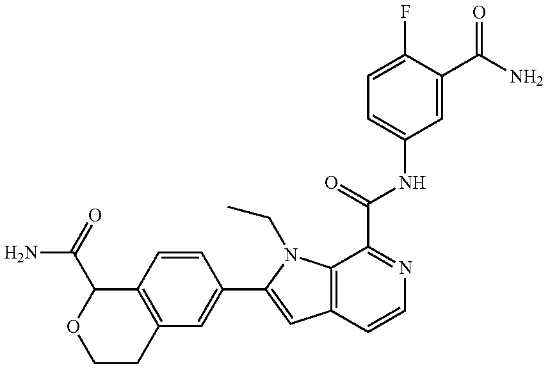 [SMILES: CCn1c(-c2ccc3c(c2)CCOC3C(N)=O)cc2ccnc(C(=O)Nc3ccc(F)c(C(N)=O)c3)c21] | $^1$H-NMR (400 MHz, DMSO-$d_6$) δ: 0.96 (3H, t, J = 7.1 Hz), 2.81-2.86 (1H, m), 2.97-3.05 (1H, m), 3.83-3.89 (1H, m), 4.13-4.19 (1H, m), 4.38-4.43 (2H, m), 5.15 (1H, s), 6.74 (1H, s), 7.29-7.41 (4H, m), 7.52 (1H, br s), 7.60 (1H, d, J = 8.0 Hz), 7.69 (1H, br s), 7.75 (1H, b r s), 7.79 (1H, d, J = 5.3 Hz), 7.90-7.94 (1H, m), 8.16-8.18 (1H, m), 8.27 (1H, d, J = 5.3 Hz), 10.99 (1H, s).<br>ESI-MS m/z: 502 $[M + H]^+$ |

TABLE 2-4
| | | |
|---|---|---|
| 29 | 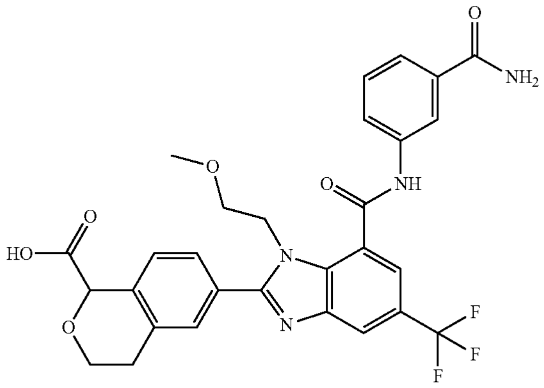 [SMILES: COCCn1c(-c2ccc3c(c2)CCOC3C(=O)O)nc2cc(C(F)(F)F)cc(C(=O)Nc3cccc(C(N)=O)c3)c21] | $^1$H-NMR (400 MHz, DMSO-$d_6$) δ: 2.83-2.98 (5H, m), 3.42 (2H, t, J = 5.2 Hz), 3.96-4.01 (1H, m), 4.14-4.19 (1H, m), 4.61 (2H, t, J = 4.9 Hz), 5.40 (1H, s), 7.40 (1H, br s), 7.47 (1H, t, J = 7.9 Hz), 7.55-7.66 (4H, m), 7.86-7.87 (1H, m), 7.90-7.92 (1H, m), 7.99 (1H, br s), 8.24-8.25 (2H, m), 11.04 (1H, s), 13.17 (1H, br s). ESI-MS m/z: 583 $[M + H]^+$ |
| 30 | 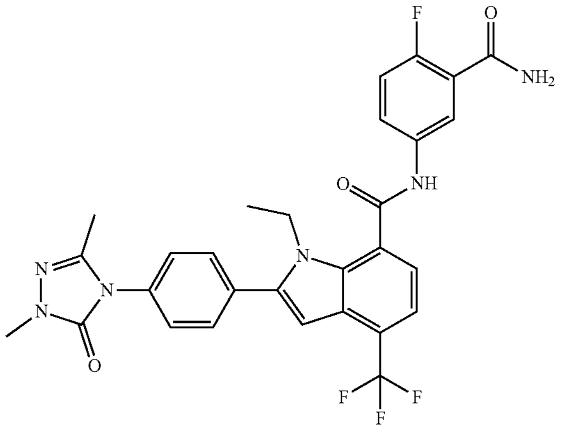 [SMILES: CCn1c(-c2ccc(-n3c(C)nn(C)c3=O)cc2)cc2c(C(F)(F)F)ccc(C(=O)Nc3ccc(F)c(C(N)=O)c3)c21] | $^1$H-NMR (400 MHz, $CD_3OD$) δ: 1.04 (3H, t, J = 7.1 Hz), 2.21 (3H, s), 3.47 (3H, s), 4.41 (2H, q, J = 7.1 Hz), 6.82 (1H, m), 7.27 (1H, dd, J = 9.0, 10.5 Hz), 7.50-7.59 (4H, m), 7.76 (2H, d, J = 8.5 Hz), 7.99 (1H, m), 8.16 (1H, dd, J = 2.8, 6.5 Hz). ESI-MS m/z: 581 $[M + H]^+$ |
| 31 | 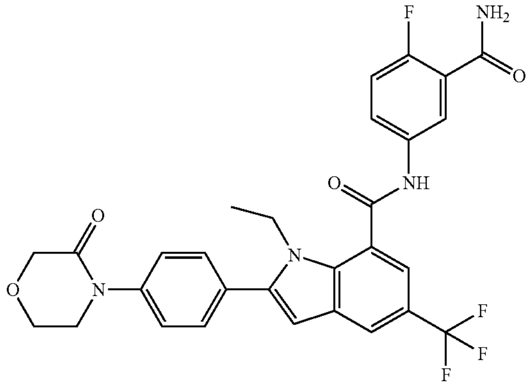 [SMILES: CCn1c(-c2ccc(N3CCOCC3=O)cc2)cc2cc(C(F)(F)F)cc(C(=O)Nc3ccc(F)c(C(N)=O)c3)c21] | $^1$H-NMR (400 MHz, $CD_3OD$) δ: 1.02 (3H, t, J = 7.1 Hz), 3.85-3.87 (2H, m), 4.06-4.09 (2H, m), 4.32 (2H, s), 4.39 (2H, q, J = 7.2 Hz), 6.80 (1H, s), 7.27 (1H, dd, J = 9.0, 10.5 Hz), 7.53-7.57 (2H, m), 7.61-7.64 (3H, m), 7.97 (1H, m), 8.08 (1H, m), 8.16 (1H, dd, J = 2.8, 6.4 Hz). ESI-MS m/z: 569 $[M + H]^+$ |
| 32 | 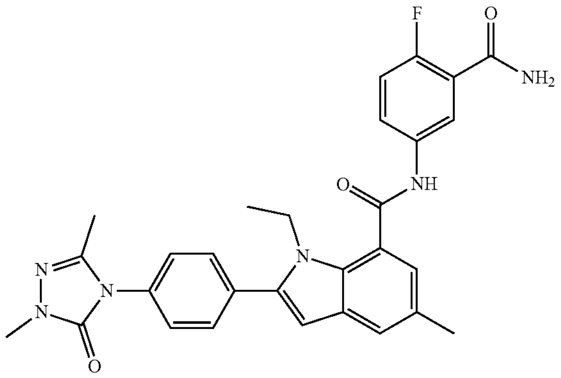 [SMILES: CCn1c(-c2ccc(-n3c(C)nn(C)c3=O)cc2)cc2cc(C)cc(C(=O)Nc3ccc(F)c(C(N)=O)c3)c21] | ESI-MS m/z: 527 $[M + H]^+$ |

TABLE 2-4-continued
| | | |
|---|---|---|
| 33 | 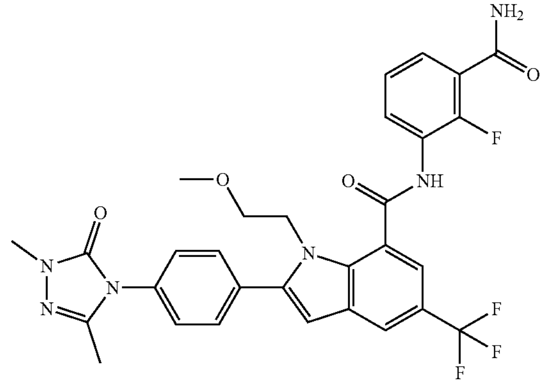 [SMILES: COCCn1c(-c2ccc(-n3c(C)nn(C)c3=O)cc2)cc2cc(C(F)(F)F)cc(C(=O)Nc3cccc(C(N)=O)c3F)c21] | $^1$H-NMR (400 MHz, $CDCl_3$) δ: 2.24 (3H, s), 2.98 (3H, s), 3.34 (2H, t, J = 5.2 Hz), 3.52 (3H, s), 4.61 (2H, t, J = 5.3 Hz), 5.82 (1H, s), 6.54 (1H, s), 6.77 (1H, s), 7.38 (1H, t, J = 8.0 Hz), 7.44 (2H, d, J = 8.5 Hz), 7.64-7.69 (3H, m), 7.90 (1H, dt, 1.8, 7.8 Hz), 8.08 (2H, br s), 8.57-8.62 (1H, m).<br>ESI-MS m/z: 611 [M + H]$^+$ |
TABLE 2-5
| | | |
|---|---|---|
| 34 | 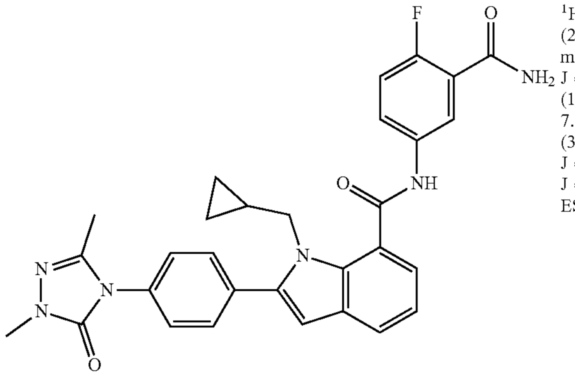 | $^1$H-NMR (400 MHz, DMSO-$d_6$) δ: −0.27-−0.25 (2H, m), 0.08-0.12 (2H, m), 0.80 (1H, m), 2.14 (3H, s), 3.36 (3H, s), 4.19 (2H, d, J = 6.7 Hz), 6.79 (1H, s), 7.22 (1H, m), 7.31 (1H, dd, J = 9.1, 9.9 Hz), 7.40 (1H, dd, J = 1.1, 7.3 Hz), 7.57 (2H, d, J = 8.5 Hz), 7.68-7.70 (3H, m), 7.73 (1H, br s), 7.79 (1H, dd, J = 1.1, 7.9 Hz), 7.89 (1H, m), 8.09 (1H, dd, J = 2.7, 6.5 Hz), 10.88 (1H, br s).<br>ESI-MS m/z: 539 [M + H]$^+$ |
| 35 | 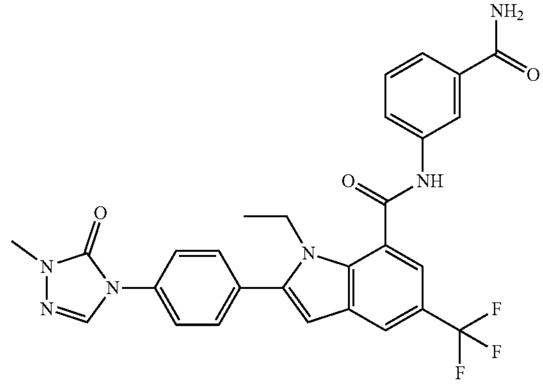 [SMILES: CCn1c(-c2ccc(-n3cnn(C)c3=O)cc2)cc2cc(C(F)(F)F)cc(C(=O)Nc3cccc(C(N)=O)c3)c21] | $^1$H-NMR (400 MHz, DMSO-$d_6$) δ: 1.00 (3H, t, J = 7.1 Hz), 3.42 (3H, s), 4.30 (2H, q, J = 7.4 Hz), 6.90 (1H, s), 7.40 (1H, br s), 7.46 (1H, t, J = 7.9 Hz), 7.63-7.65 (2H, m), 7.72 (2H, d, J = 8.7 Hz), 7.89-7.92 (3H, m), 7.99 (1H, br s), 8.17-8.18 (1H, m), 8.25-8.26 (1H, m), 8.58 (1H, s), 11.00 (1H, s).<br>ESI-MS m/z: 549 [M + H]$^+$ |

TABLE 2-5-continued
| | | |
|---|---|---|
| 36 | 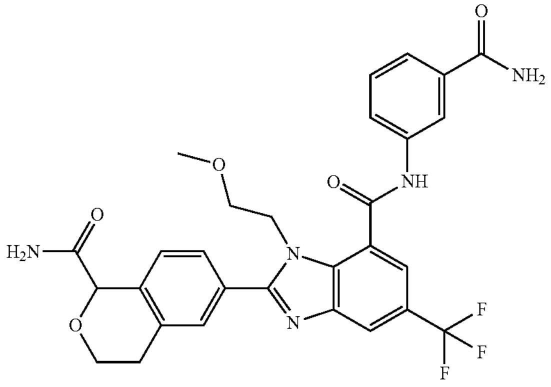 [SMILES: COCCn1c(-c2ccc3c(c2)CCOC3C(N)=O)nc2cc(C(F)(F)F)cc(C(=O)Nc3cccc(C(N)=O)c3)c21] | ESI-MS m/z: 582 $[M + H]^+$ |
| 37 | 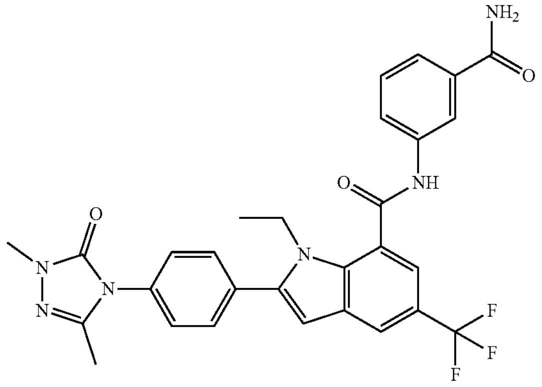 [SMILES: CCn1c(-c2ccc(-n3c(C)nn(C)c3=O)cc2)cc2cc(C(F)(F)F)cc(C(=O)Nc3cccc(C(N)=O)c3)c21] | $^1$H-NMR (400 MHz, DMSO-$d_6$) δ: 1.03 (3H, t, J = 7.1 Hz), 2.16 (3H, s), 3.37 (3H, s), 4.30-4.36 (2H, m), 6.93 (1H, s), 7.40 (1H, br s), 7.45-7.48 (1H, m), 7.61-7.65 (4H, m), 7.73 (2H, d, J = 8.5 Hz), 7.90-7.93 (1H, m), 7.98-8.00 (1H, m), 8.19 (1H, s), 8.25-8.26 (1H, m), 11.00 (1H, s). ESI-MS m/z: 563 $[M + H]^+$ |
| 38 | 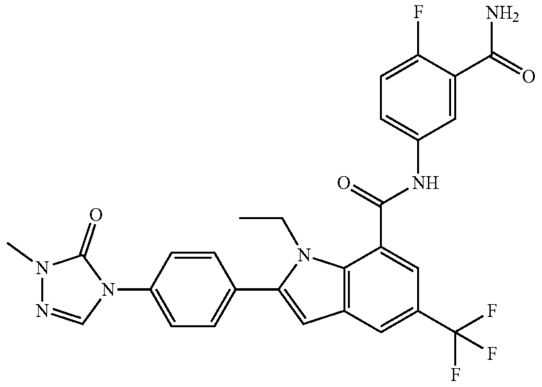 [SMILES: CCn1c(-c2ccc(-n3cnn(C)c3=O)cc2)cc2cc(C(F)(F)F)cc(C(=O)Nc3ccc(F)c(C(N)=O)c3)c21] | $^1$H-NMR (400 MHz, DMSO-$d_6$) δ: 1.00 (3H, t, J = 7.1 Hz), 3.42 (3H, s), 4.26-4.32 (2H, m), 6.90 (1H, s), 7.30-7.35 (1H, m), 7.64-7.65 (1H, m), 7.70-7.73 (4H, m), 7.87-7.91 (3H, m), 8.07-8.09 (1H, m), 8.18 (1H, br s), 8.58 (1H, s), 11.01 (1H, s). ESI-MS m/z: 567 $[M + H]^+$ |

TABLE 2-6
| | | |
|---|---|---|
| 39 | 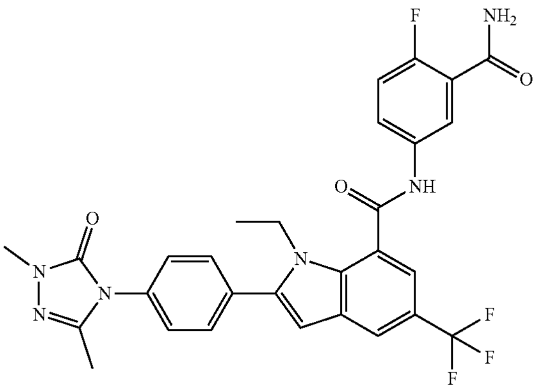 [SMILES: CCn1c(-c2ccc(-n3c(C)nn(C)c3=O)cc2)cc2cc(C(F)(F)F)cc(C(=O)Nc3ccc(F)c(C(N)=O)c3)c21] | $^1$H-NMR (400 MHz, DMSO-$d_6$) δ: 1.02 (3H, t, J = 7.2 Hz), 2.16 (3H, s), 3.37 (3H, s), 4.29-4.34 (2H, m), 6.93 (1H, s), 7.30-7.35 (1H, m), 7.61-7.66 (3H, m), 7.71-7.74 (4H, m), 7.87-7.91 (1H, m), 8.06-8.09 (1H, m), 8.19-8.20 (1H, m), 11.02 (1H, s). ESI-MS m/z: 581 $[M + H]^+$ |
| 40 | 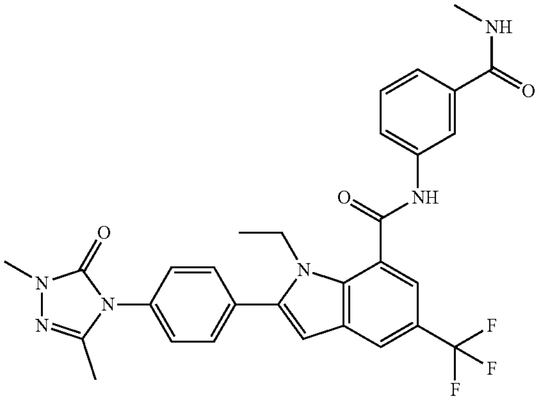 [SMILES: CCn1c(-c2ccc(-n3c(C)nn(C)c3=O)cc2)cc2cc(C(F)(F)F)cc(C(=O)Nc3cccc(C(=O)NC)c3)c21] | $^1$H-NMR (400 MHz, DMSO-$d_6$) δ: 1.03 (3H, t, J = 7.1 Hz), 2.16 (3H, s), 2.79 (3H, d, J = 4.5 Hz), 3.38 (3H, s), 4.30-4.35 (2H, m), 6.93 (1H, s), 7.45-7.49 (1H, m), 7.57-7.66 (4H, m), 7.72-7.74 (2H, m), 7.90-7.92 (1H, m), 8.18-8.19 (1H, m), 8.22-8.23 (1H, m), 8.44-8.47 (1H, m), 11.02 (1H, s). ESI-MS m/z: 577 $[M + H]^+$ |
| 41 | 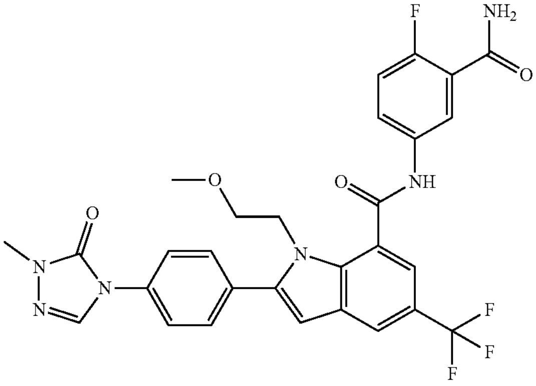 [SMILES: COCCn1c(-c2ccc(-n3cnn(C)c3=O)cc2)cc2cc(C(F)(F)F)cc(C(=O)Nc3ccc(F)c(C(N)=O)c3)c21] | $^1$H-NMR (400 MHz, DMSO-$d_6$) δ: 2.85 (3H, s), 3.30-3.34 (2H, m), 3.42 (3H, s), 4.46-4.49 (2H, m), 6.89 (1H, s), 7.30-7.35 (1H, m), 7.68-7.74 (5H, m), 7.87-7.90 (3H, m), 8.08 (1H, dd, J = 2.7, 6.4 Hz), 8.18-8.19 (1H, m), 8.58 (1H, s), 10.99 (1H, s). ESI-MS m/z: 597 $[M + H]^+$ |
| 42 | 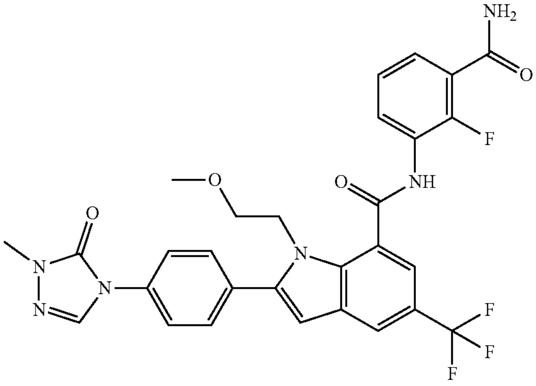 [SMILES: COCCn1c(-c2ccc(-n3cnn(C)c3=O)cc2)cc2cc(C(F)(F)F)cc(C(=O)Nc3cccc(C(N)=O)c3F)c21] | $^1$H-NMR (400 MHz, DMSO-$d_6$) δ: 2.89 (3H, s), 3.40-3.43 (5H, m), 4.51-4.53 (2H, m), 6.89 (1H, s), 7.29-7.33 (1H, m), 7.49-7.53 (1H, m), 7.70-7.74 (4H, m), 7.82-7.90 (4H, m), 8.20-8.21 (1H, m), 8.58 (1H, s), 10.80 (1H, s). ESI-MS m/z: 597 $[M + H]^+$ |

TABLE 2-6-continued
| | | |
|---|---|---|
| 43 | 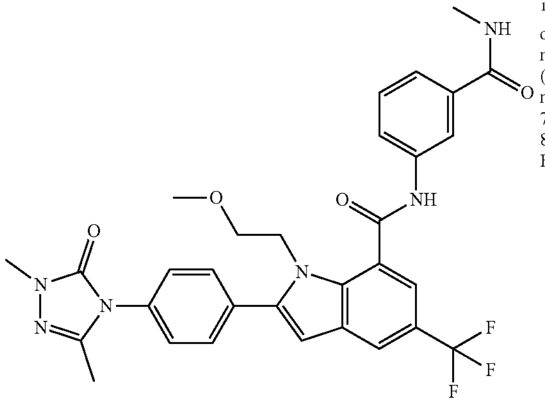 | $^1$H-NMR (400 MHz, DMSO-$d_6$) δ: 2.79 (3H, d, J = 4.6 Hz), 2.84 (3H, s), 3.30-3.35 (2H, m), 3.42 (3H, s), 4.47-4.49 (2H, m), 6.89 (1H, s), 7.45-7.48 (1H, m), 7.57-7.59 (1H, m), 7.66-7.67 (1H, m), 7.72-7.74 (2H, m), 7.87-7.91 (3H, m), 8.19-8.24 (2H, m), 8.43-8.46 (1H, m), 8.58 (1H, s), 10.99 (1H, s). ESI-MS m/z: 593 $[M + H]^+$ |
TABLE 2-7
| | | |
|---|---|---|
| 44 | 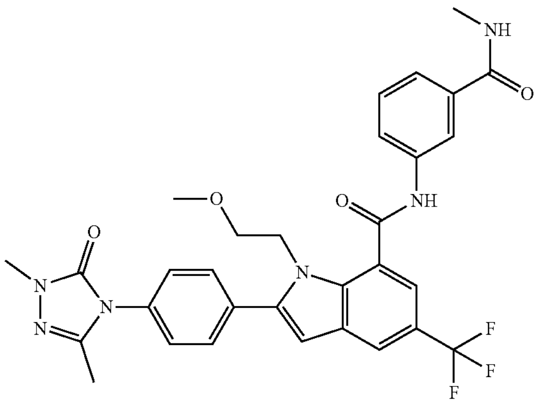 [SMILES: CNC(=O)c1cccc(NC(=O)c2cc(C(F)(F)F)cc3cc(-c4ccc(-n5c(C)nn(C)c5=O)cc4)n(CCOC)c23)c1] | $^1$H-NMR (400 MHz, DMSO-$d_6$) δ: 2.14 (3H, s), 2.79 (3H, d, J = 4.5 Hz), 2.83 (3H, s), 3.35-3.38 (5H, m), 4.49-4.51 (2H, m), 6.93 (1H, s), 7.45-7.49 (1H, m), 7.57-7.61 (3H, m), 7.67-7.68 (1H, m), 7.73-7.75 (2H, m), 7.89-7.92 (1H, m), 8.19-8.23 (2H, m), 8.43-8.47 (1H, m), 11.00 (1H, s). ESI-MS m/z: 607 $[M + H]^+$ |
| 45 | 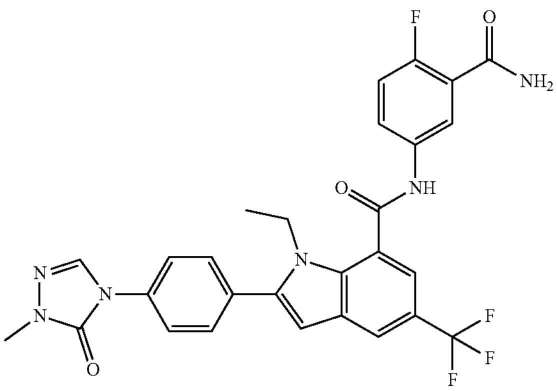 [SMILES: CCn1c(-c2ccc(-n3cnn(C)c3=O)cc2)cc2cc(C(F)(F)F)cc(C(=O)Nc3ccc(F)c(C(N)=O)c3)c21] | $^1$H-NMR (400 MHz, $CDCl_3$) δ: 1.01 (3H, t, J = 7.1 Hz), 3.41 (3H, s), 4.35 (2H, q, J = 7.1 Hz), 4.94 (1H, s), 6.59 (1H, d, J = 14.4 Hz), 6.71 (1H, s), 7.20 (1H, dd, J = 9.0, 11.4 Hz), 7.49 (2H, d, J = 8.7 Hz), 7.58 (1H, s), 7.69 (1H, d, J = 1.4 Hz), 8.02-8.04 (3H, m), 8.28 (1H, m), 8.62 (1H, m), 9.86 (1H, s). ESI-MS m/z: 567 $[M + H]^+$ |

TABLE 2-7-continued
46
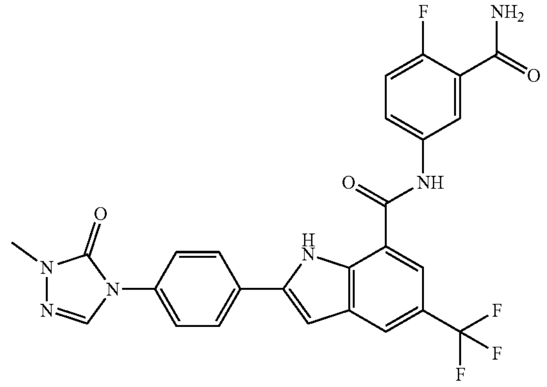 [SMILES: Cn1ncn(-c2ccc(-c3cc4cc(C(F)(F)F)cc(C(=O)Nc5ccc(F)c(C(N)=O)c5)c4[nH]3)cc2)c1=O]
ESI-MS m/z: 539 [M + H]$^+$
47
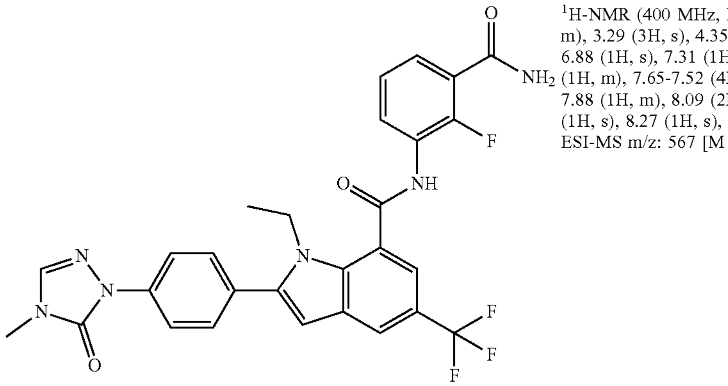
$^1$H-NMR (400 MHz, DMSO-$d_6$) δ: 1.05 (3H, m), 3.29 (3H, s), 4.35 (2H, q, J = 6.7 Hz), 6.88 (1H, s), 7.31 (1H, t, J = 7.9 Hz), 7.51 (1H, m), 7.65-7.52 (4H, m), 7.83 (1H, s), 7.88 (1H, m), 8.09 (2H, d, J = 8.8 Hz), 8.18 (1H, s), 8.27 (1H, s), 10.82 (1H, s).
ESI-MS m/z: 567 [M + H]$^+$
48
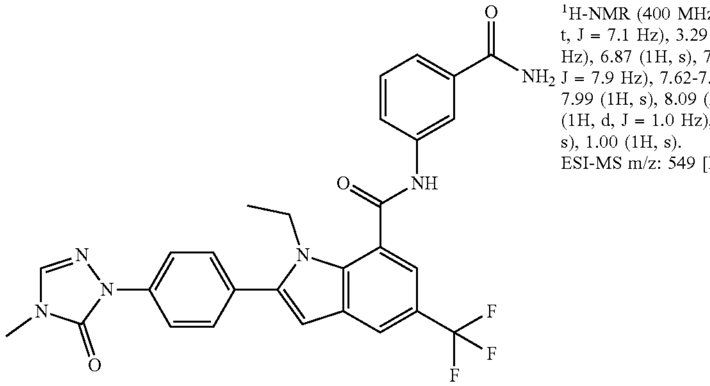
$^1$H-NMR (400 MHz, DMSO-$d_6$) δ: 1.00 (3H, t, J = 7.1 Hz), 3.29 (3H, s), 4.30 (2H, q, J = 7.0 Hz), 6.87 (1H, s), 7.40 (1H, s), 7.46 (1H, t, J = 7.9 Hz), 7.62-7.68 (4H, m), 7.91 (1H, m), 7.99 (1H, s), 8.09 (2H, d, J = 8.8 Hz), 8.16 (1H, d, J = 1.0 Hz), 8.25 (1H, m), 8.26 (1H, s), 1.00 (1H, s).
ESI-MS m/z: 549 [M + H]$^+$
49
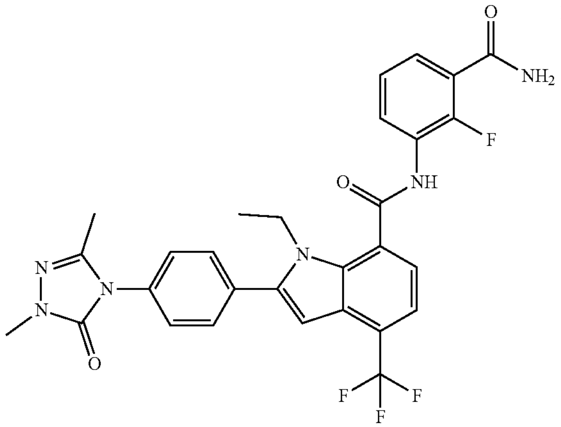 [SMILES: CCn1c(-c2ccc(-n3c(C)nn(C)c3=O)cc2)cc2c(C(F)(F)F)ccc(C(=O)Nc3cccc(C(N)=O)c3F)c21]
ESI-MS m/z: 581 [M + H]$^+$ TABLE 2-8
| | | |
|---|---|---|
| 50 | 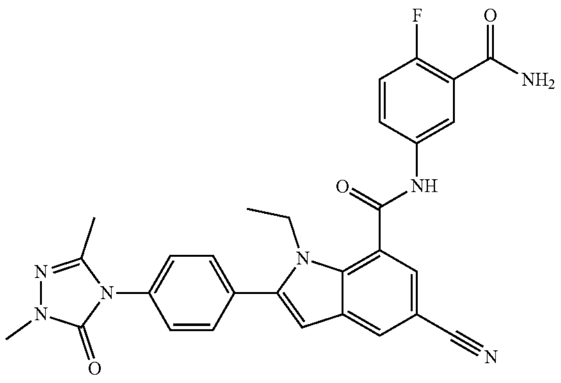 [SMILES: CCn1c(-c2ccc(-n3c(C)nn(C)c3=O)cc2)cc2cc(C#N)cc(C(=O)Nc3ccc(F)c(C(N)=O)c3)c21] | ESI-MS m/z: 538 [M + H]$^+$ |
| 51 | 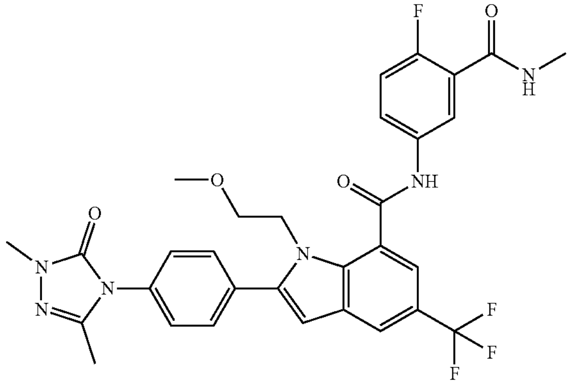 | $^1$H-NMR (400 MHz, DMSO-$d_6$) δ: 2.15 (3H, s), 2.79 (3H, d, J = 4.6 Hz), 2.84 (3H, s), 3.35-3.37 (5H, m), 4.49 (2H, t, J = 5.4 Hz), 6.93 (1H, s), 7.33 (1H, m), 7.60 (2H, d, J = 8.6 Hz), 7.69 (1H, d, J = 1.5 Hz), 7.74 (2H, d, J = 8.6 Hz), 7.87 (1H, m), 8.05 (1H, dd, J = 2.7, 6.5 Hz), 8.20 (1H, d, J = 1.0 Hz), 8.28 (1H, m), 11.01 (1H, s). ESI-MS m/z: 625 [M + H]$^+$ |
| 52 | 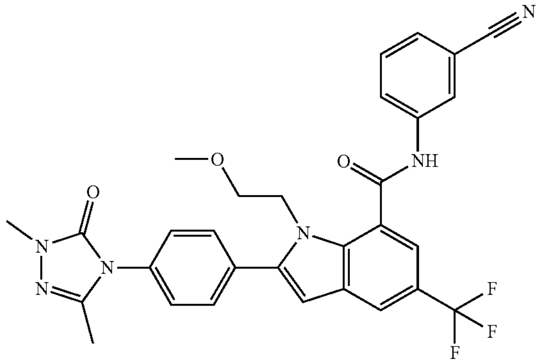 [SMILES: COCCn1c(-c2ccc(-n3c(C)nn(C)c3=O)cc2)cc2cc(C(F)(F)F)cc(C(=O)Nc3cccc(C#N)c3)c21] | ESI-MS m/z: 575 [M + H]$^+$ |
| 53 | 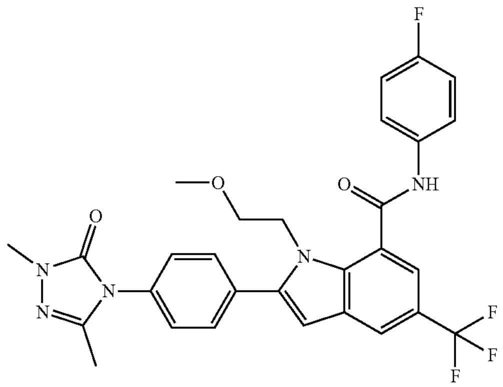 [SMILES: COCCn1c(-c2ccc(-n3c(C)nn(C)c3=O)cc2)cc2cc(C(F)(F)F)cc(C(=O)Nc3ccc(F)cc3)c21] | ESI-MS m/z: 568 [M + H]$^+$ |

TABLE 2-8-continued
| | | |
|---|---|---|
| 54 | 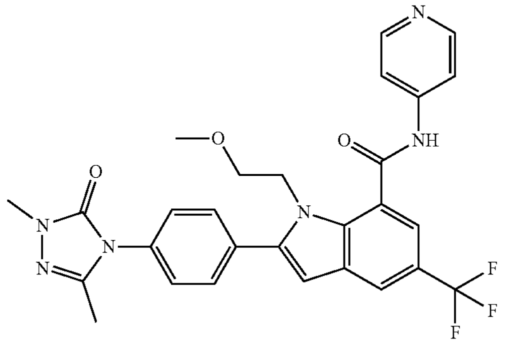 [SMILES: COCCn1c(-c2ccc(-n3c(C)nn(C)c3=O)cc2)cc2cc(C(F)(F)F)cc(C(=O)Nc3ccncc3)c21] | ESI-MS m/z: 551 [M + H]$^+$ |
| 55 | 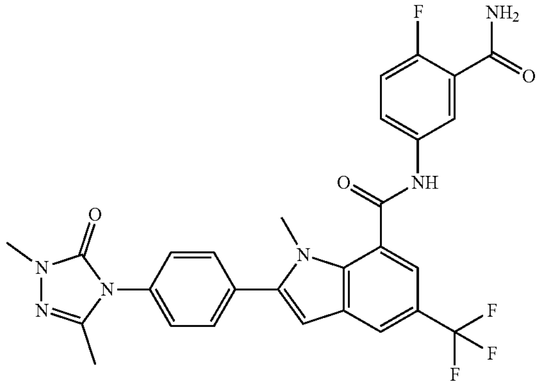 [SMILES: Cc1nn(C)c(=O)n1-c1ccc(-c2cc3cc(C(F)(F)F)cc(C(=O)Nc4ccc(F)c(C(N)=O)c4)c3n2C)cc1] | $^1$H-NMR (400 MHz, DMSO-$d_6$) δ: 2.16 (3H, s), 3.36 (3H, s), 3.74 (3H, s), 7.00 (1H, s), 7.32 (1H, t, J = 9.5 Hz), 7.61-7.79 (7H, m), 7.89-7.93 (1H, m), 8.10-8.12 (1H, m), 8.19-8.20 (1H, m), 10.98 (1H, s).<br>ESI-MS m/z: 567 [M + H]$^+$ |
TABLE 2-9
| | | |
|---|---|---|
| 56 | 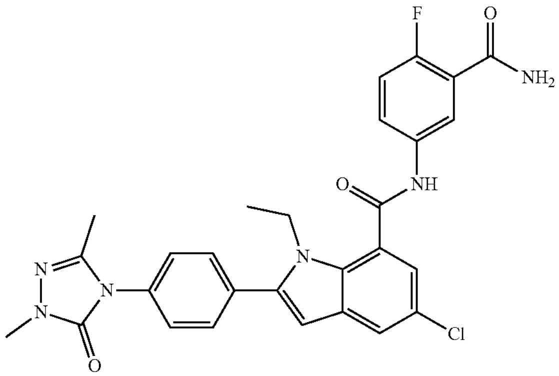 [SMILES: CCn1c(-c2ccc(-n3c(C)nn(C)c3=O)cc2)cc2cc(Cl)cc(C(=O)Nc3ccc(F)c(C(N)=O)c3)c21] | ESI-MS m/z: 545 [M − H]$^-$ |
| 57 | 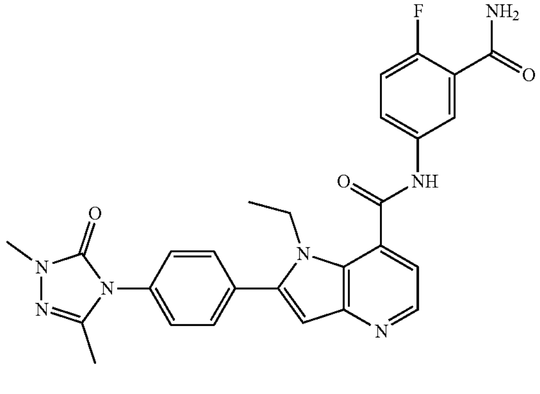 [SMILES: CCn1c(-c2ccc(-n3c(C)nn(C)c3=O)cc2)cc2nccc(C(=O)Nc3ccc(F)c(C(N)=O)c3)c21] | ESI-MS m/z: 514 [M + H]$^+$ |

TABLE 2-9-continued
| | | |
|---|---|---|
| 58 | 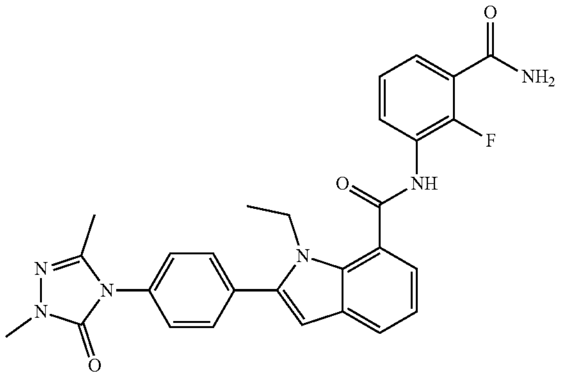 [SMILES: CCn1c(-c2ccc(-n3c(C)nn(C)c3=O)cc2)cc2cccc(C(=O)Nc3cccc(C(N)=O)c3F)c21] | $^1$H-NMR (400 MHz, $CD_3OD$) δ: 1.03 (3H, t, J = 7.1 Hz), 2.21 (3H, s), 3.47 (3H, s), 4.43 (2H, q, J = 7.2 Hz), 6.72 (1H, s), 7.22 (1H, t, J = 7.6 Hz), 7.34 (1H, t, J = 7.7 Hz), 7.50-7.56 (3H, m), 7.64 (1H, m), 7.74 (2H, d, J = 8.5 Hz), 7.79 (1H, dd, J = 1.1, 7.9 Hz), 8.05 (1H, m). ESI-MS m/z: 513 $[M + H]^+$ |
| 59 | 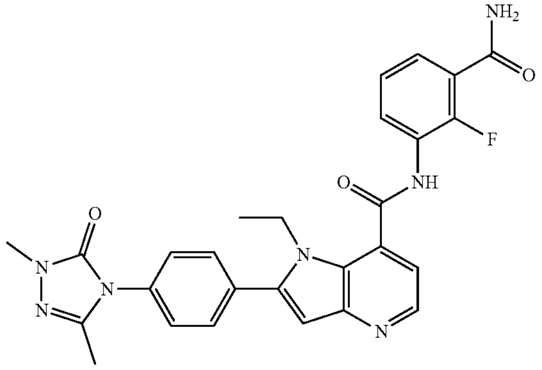 [SMILES: CCn1c(-c2ccc(-n3c(C)nn(C)c3=O)cc2)cc2nccc(C(=O)Nc3cccc(C(N)=O)c3F)c21] | ESI-MS m/z: 514 $[M + H]^+$ |
| 60 | 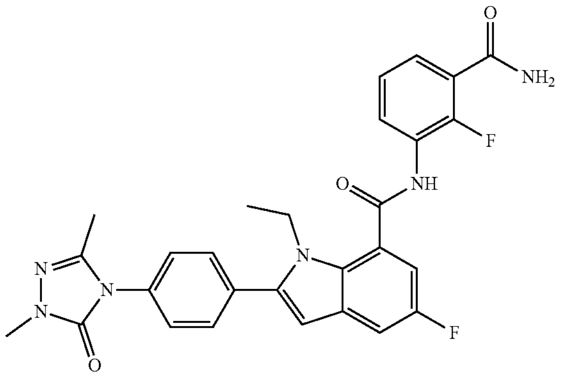 [SMILES: CCn1c(-c2ccc(-n3c(C)nn(C)c3=O)cc2)cc2cc(F)cc(C(=O)Nc3cccc(C(N)=O)c3F)c21] | $^1$H-NMR (400 MHz, $CD_3OD$) δ: 1.03 (3H, t, J = 7.1 Hz), 2.21 (3H, s), 3.47 (3H, s), 4.40 (2H, q, J = 7.0 Hz), 6.71 (1H, s), 7.28 (1H, dd, J = 2.5, 9.3 Hz), 7.35 (1H, t, J = 7.9 Hz), 7.48 (1H, dd, J = 2.5, 8.9 Hz), 7.55 (2H, d, J = 8.6 Hz), 7.65 (1H, m), 7.73 (2H, d, J = 8.5 Hz), 8.04 (1H, m). ESI-MS m/z: 531 $[M + H]^+$ |
| 61 | 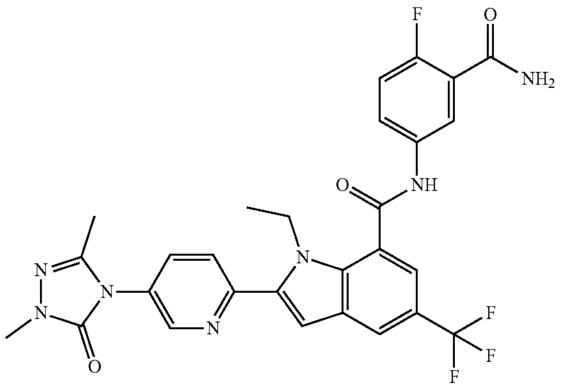 [SMILES: CCn1c(-c2ccc(-n3c(C)nn(C)c3=O)cn2)cc2cc(C(F)(F)F)cc(C(=O)Nc3ccc(F)c(C(N)=O)c3)c21] | $^1$H-NMR (400 MHz, DMSO-$d_6$) δ: 1.16 (3H, t, J = 7.0 Hz), 2.19 (3H, s), 3.38 (3H, s), 4.73 (2H, q, J = 7.0 Hz), 7.31-7.35 (2H, m), 7.67 (1H, m), 7.72 (1H, br s), 7.75 (1H, br s), 7.89 (1H, m), 8.07 (1H, dd, J = 2.8, 6.5 Hz), 8.10-8.11 (2H, m), 8.23 (1H, m), 8.82 (1H, t, J = 1.6 Hz), 11.05 (1H, br s). ESI-MS m/z: 582 $[M + H]^+$ |

TABLE 2-10
| | | |
|---|---|---|
| 62 | 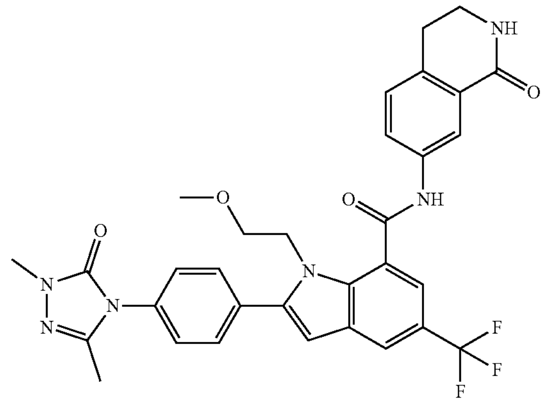 [SMILES: COCCn1c(-c2ccc(-n3c(C)nn(C)c3=O)cc2)cc2cc(C(F)(F)F)cc(C(=O)Nc3ccc4c(c3)C(=O)NCC4)c21] | ESI-MS m/z: 619 $[M + H]^+$ |
| 63 | 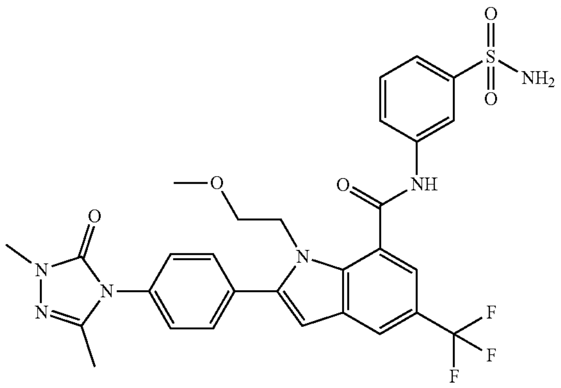 [SMILES: COCCn1c(-c2ccc(-n3c(C)nn(C)c3=O)cc2)cc2cc(C(F)(F)F)cc(C(=O)Nc3cccc(S(N)(=O)=O)c3)c21] | ESI-MS m/z: 629 $[M + H]^+$ |
| 64 | 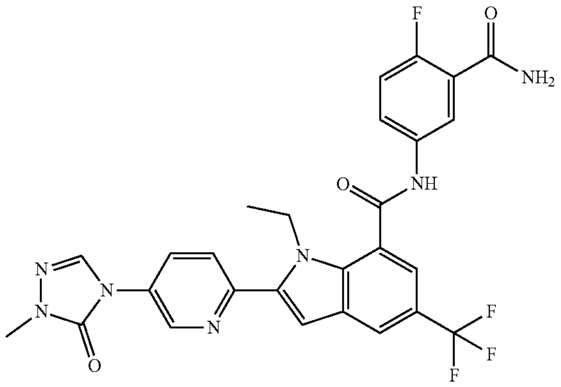 [SMILES: CCn1c(-c2ccc(-n3cnn(C)c3=O)cn2)cc2cc(C(F)(F)F)cc(C(=O)Nc3ccc(F)c(C(N)=O)c3)c21] | ESI-MS m/z: 568 $[M + H]^+$ |
| 65 | 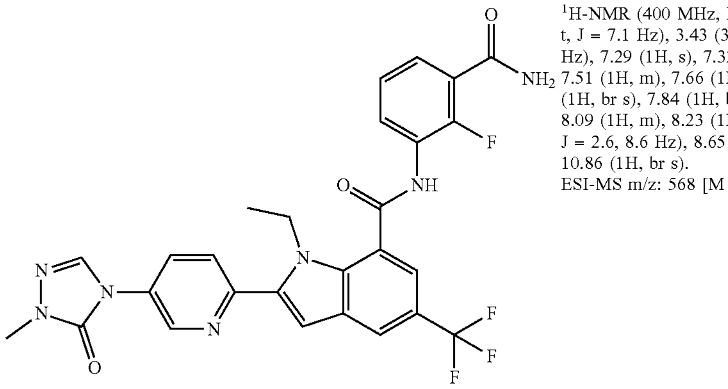 | $^1$H-NMR (400 MHz, DMSO-$d_6$) δ: 1.18 (3H, t, J = 7.1 Hz), 3.43 (3H, s), 4.78 (2H, q, J = 6.9 Hz), 7.29 (1H, s), 7.32 (1H, t, J = 7.8 Hz), 7.51 (1H, m), 7.66 (1H, d, J = 1.6 Hz), 7.68 (1H, br s), 7.84 (1H, br s), 7.92 (1H, m), 8.09 (1H, m), 8.23 (1H, m), 8.35 (1H, dd, J = 2.6, 8.6 Hz), 8.65 (1H, s), 9.09 (1H, m), 10.86 (1H, br s). ESI-MS m/z: 568 $[M + H]^+$ |

TABLE 2-10-continued
| | | |
|---|---|---|
| 66 | 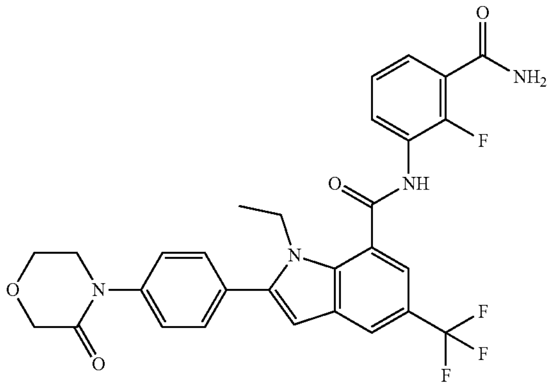 [SMILES: CCn1c(-c2ccc(N3CCOCC3=O)cc2)cc2cc(C(F)(F)F)cc(C(=O)Nc3cccc(C(N)=O)c3F)c21] | $^1$H-NMR (400 MHz, DMSO-$d_6$) δ: 1.06 (3H, t, J = 7.1 Hz), 3.82-3.85 (2H, m), 4.00-4.03 (2H, m), 4.25 (2H, s), 4.35 (2H, q, J = 7.0 Hz), 6.87 (1H, s), 7.31 (1H, t, J = 7.9 Hz), 7.51 (1H, m), 7.61-7.70 (6H, m), 7.83 (1H, br s), 7.88 (1H, m), 8.18 (1H, m), 10.82 (1H, br s).<br>ESI-MS m/z: 569 $[M + H]^+$ |
| 67 | 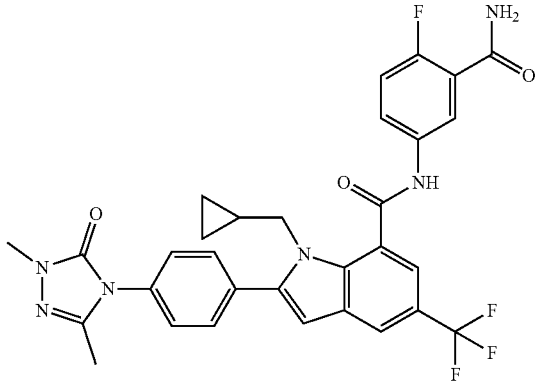 [SMILES: Cc1nn(C)c(=O)n1-c1ccc(-c2cc3cc(C(F)(F)F)cc(C(=O)Nc4ccc(F)c(C(N)=O)c4)c3n2CC2CC2)cc1] | $^1$H-NMR (400 MHz, DMSO-$d_6$) δ: −0.26-−0.24 (2H, m), 0.12-0.16 (2H, m), 0.81-0.88 (1H, m), 2.14 (3H, s), 3.36 (3H, s), 4.23 (2H, d, J = 7.0 Hz), 6.97 (1H, s), 7.31-7.36 (1H, m), 7.60-7.74 (7H, m), 7.86-7.91 (1H, m), 8.05-8.08 (1H, m), 8.20-8.21 (1H, m), 11.04 (1H, s).<br>ESI-MS m/z: 607 $[M + H]^+$ |
TABLE 2-11
| | | |
|---|---|---|
| 68 | 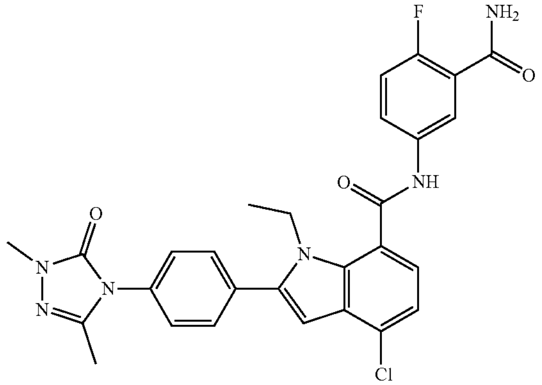 [SMILES: CCn1c(-c2ccc(-n3c(C)nn(C)c3=O)cc2)cc2c(Cl)ccc(C(=O)Nc3ccc(F)c(C(N)=O)c3)c21] | ESI-MS m/z: 547 $[M + H]^+$ |
| 69 | 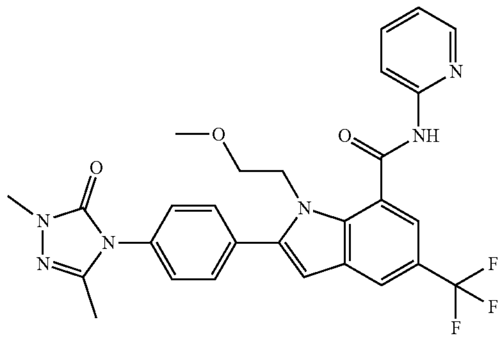 [SMILES: COCCn1c(-c2ccc(-n3c(C)nn(C)c3=O)cc2)cc2cc(C(F)(F)F)cc(C(=O)Nc3ccccn3)c21] | ESI-MS m/z: 551 $[M + H]^+$ |

TABLE 2-11-continued
| | | |
|---|---|---|
| 70 | 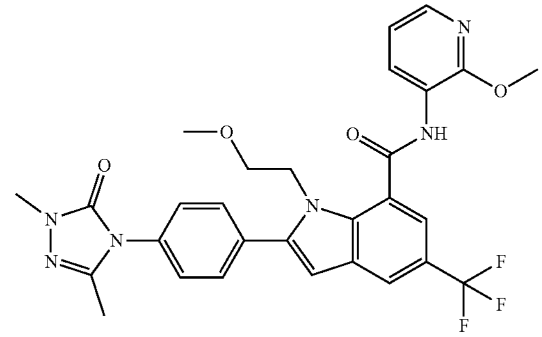 | ESI-MS m/z: 581 $[M + H]^+$ |
| 71 | 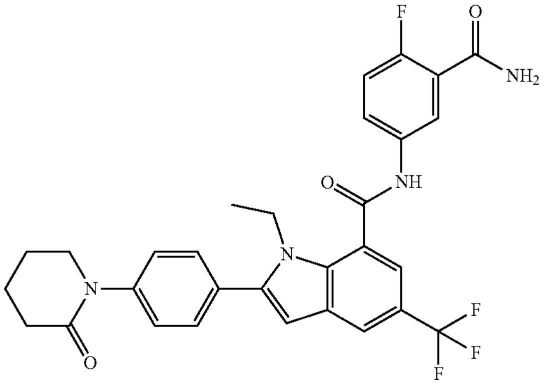 [SMILES: CCn1c(-c2ccc(N3CCCCC3=O)cc2)cc2cc(C(F)(F)F)cc(C(=O)Nc3ccc(F)c(C(N)=O)c3)c21] | $^1$H-NMR (400 MHz, DMSO-$d_6$) δ: 1.00 (3H, t, J = 7.1 Hz), 1.86-1.92 (4H, m), 2.43 (2H, t, J = 6.4 Hz), 3.69 (2H, t, J = 5.6 Hz), 4.29 (2H, q, J = 7.0 Hz), 6.86 (1H, s), 7.32 (1H, dd, J = 9.0, 10.0 Hz), 7.46-7.48 (2H, m), 7.56-7.58 (2H, m), 7.63 (1H, m), 7.71 (1H, br s), 7.74 (1H, br s), 7.89 (1H, m), 8.07 (1H, dd, J = 2.8, 6.4 Hz), 8.17 (1H, m), 11.01 (1H, br s).<br>ESI-MS m/z: 567 $[M + H]^+$ |
| 72 | 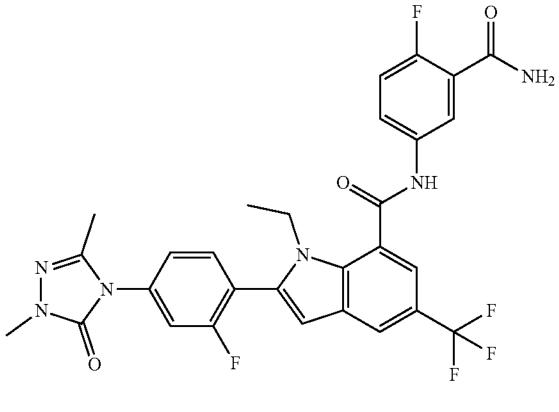 [SMILES: CCn1c(-c2ccc(-n3c(C)nn(C)c3=O)cc2F)cc2cc(C(F)(F)F)cc(C(=O)Nc3ccc(F)c(C(N)=O)c3)c21] | $^1$H-NMR (400 MHz, DMSO-$d_6$) δ: 1.02 (3H, t, J = 7.1 Hz), 2.20 (3H, s), 3.37 (3H, s), 4.17 (2H, q, J = 7.3 Hz), 6.97 (1H, s), 7.32 (1H, dd, J = 9.1, 9.9 Hz), 7.51 (1H, dd, J = 1.9, 8.2 Hz), 7.65-7.77 (5H, m), 7.88 (1H, m), 8.06 (1H, dd, J = 2.8, 6.5 Hz), 8.23 (1H, m), 11.03 (1H, br s).<br>ESI-MS m/z: 599 $[M + H]^+$ |
| 73 | 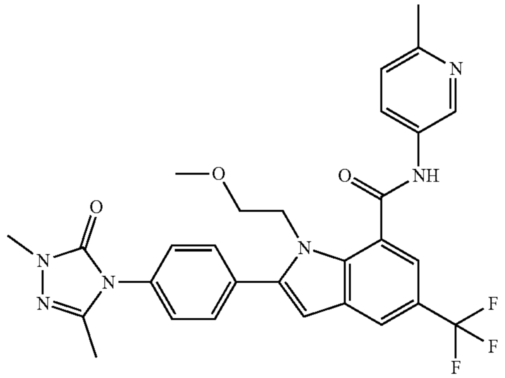 [SMILES: COCCn1c(-c2ccc(-n3c(C)nn(C)c3=O)cc2)cc2cc(C(F)(F)F)cc(C(=O)Nc3ccc(C)nc3)c21] | ESI-MS m/z: 565 $[M + H]^+$ |

TABLE 2-12
| | | |
|---|---|---|
| 74 | 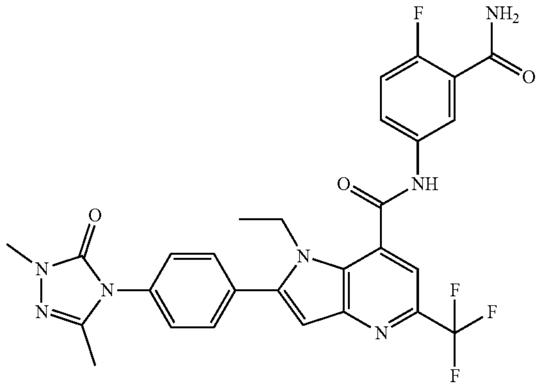 [SMILES: CCn1c(-c2ccc(-n3c(C)nn(C)c3=O)cc2)cc2nc(C(F)(F)F)cc(C(=O)Nc3ccc(F)c(C(N)=O)c3)c21] | ESI-MS m/z: 582 [M + H]$^+$ |
| 75 | 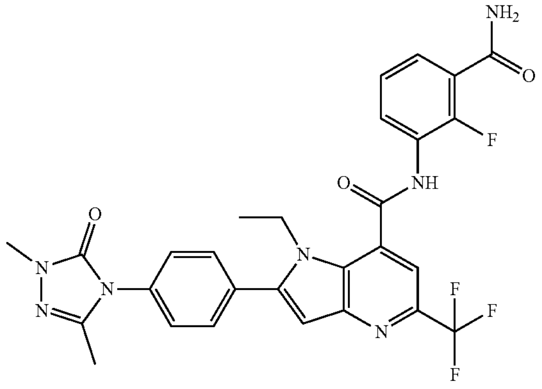 [SMILES: CCn1c(-c2ccc(-n3c(C)nn(C)c3=O)cc2)cc2nc(C(F)(F)F)cc(C(=O)Nc3cccc(C(N)=O)c3F)c21] | ESI-MS m/z: 582 [M + H]$^+$ |
| 76 | 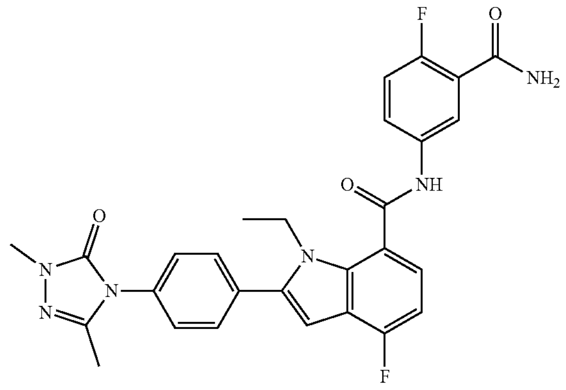 [SMILES: CCn1c(-c2ccc(-n3c(C)nn(C)c3=O)cc2)cc2c(F)ccc(C(=O)Nc3ccc(F)c(C(N)=O)c3)c21] | ESI-MS m/z: 531 [M + H]$^+$ |
| 77 | 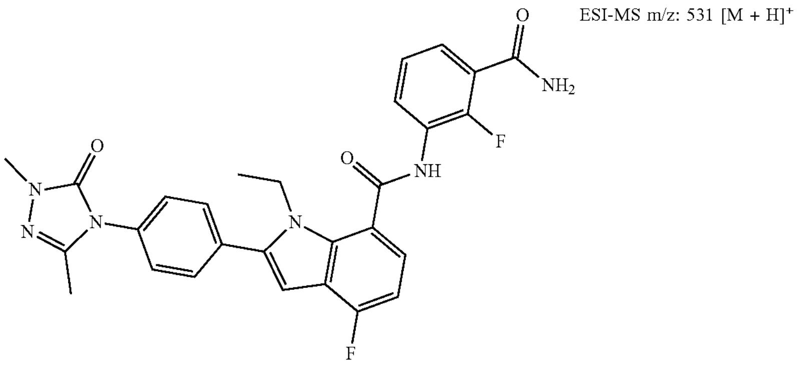 | ESI-MS m/z: 531 [M + H]$^+$ |

TABLE 2-12-continued
| | | |
|---|---|---|
| 78 | 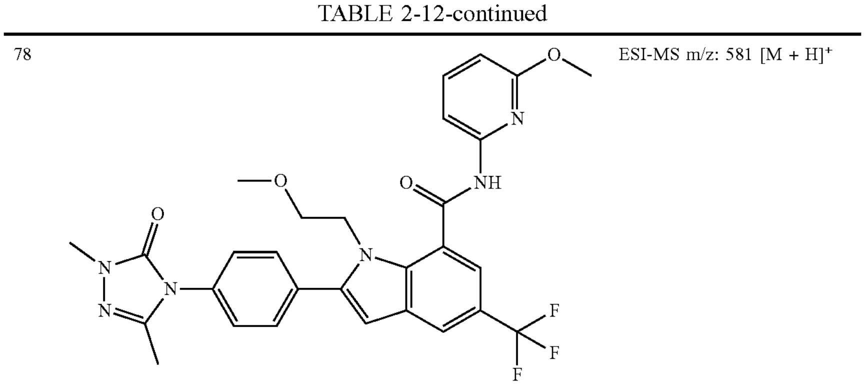 | ESI-MS m/z: 581 [M + H]+ |
| 79 | 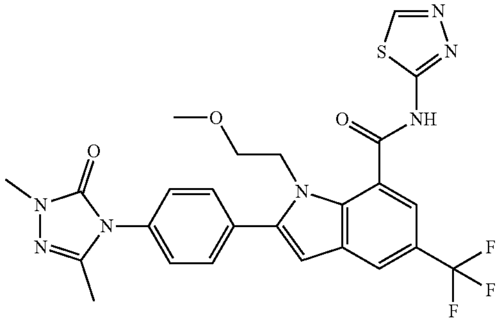 [SMILES: COCCn1c(-c2ccc(-n3c(C)nn(C)c3=O)cc2)cc2cc(C(F)(F)F)cc(C(=O)Nc3nncs3)c21] | ESI-MS m/z: 558 [M + H]+ |
| 80 | 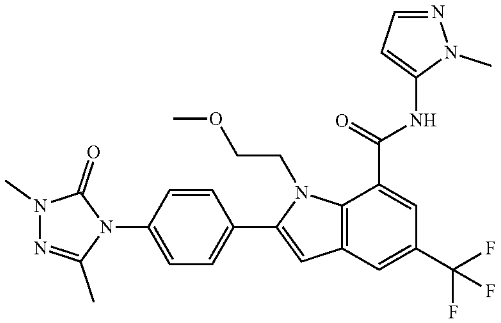 | ESI-MS m/z: 554 [M + H]+ |
TABLE 2-13
| | | |
|---|---|---|
| 81 | 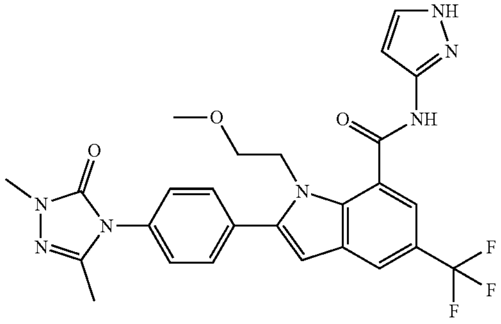 [SMILES: COCCn1c(-c2ccc(-n3c(C)nn(C)c3=O)cc2)cc2cc(C(F)(F)F)cc(C(=O)Nc3cc[nH]n3)c21] | ESI-MS m/z: 540 [M + H]+ |

TABLE 2-13-continued
| | | |
|---|---|---|
| 82 | 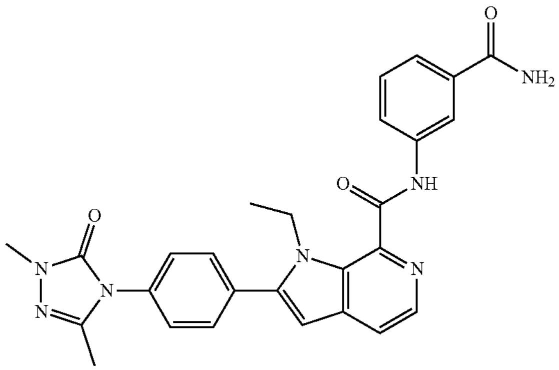 [SMILES: CCn1c(-c2ccc(-n3c(C)nn(C)c3=O)cc2)cc2ccnc(C(=O)Nc3cccc(C(N)=O)c3)c21] | $^{1}$H-NMR (400 MHz, $CD_3OD$) δ: 1.06 (3H, t, J = 7.1 Hz), 2.22 (3H, s), 3.47 (3H, s), 4.57 (2H, q, J = 7.1 Hz), 6.82 (1H, s), 7.50 (1H, t, J = 7.9 Hz), 7.60 (2H, d, J = 8.6 Hz), 7.67 (1H, m), 7.77-7.80 (3H, m), 8.00 (1H, m), 8.26 (1H, d, J = 5.4 Hz), 8.28 (1H, t, J = 1.8 Hz). ESI-MS m/z: 496 $[M + H]^+$ |
| 83 | 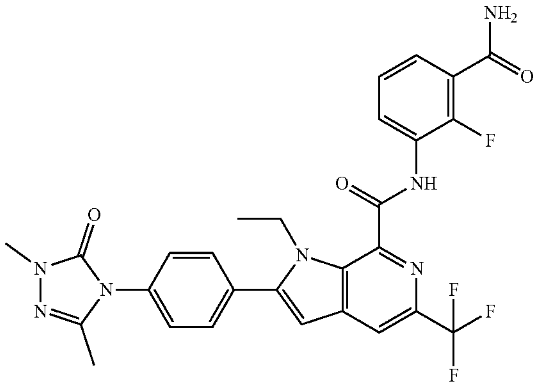 [SMILES: CCn1c(-c2ccc(-n3c(C)nn(C)c3=O)cc2)cc2cc(C(F)(F)F)nc(C(=O)Nc3cccc(C(N)=O)c3F)c21] | $^{1}$H-NMR (400 MHz, DMSO-$d_6$) δ: 1.13 (3H, t, J = 7.1 Hz), 2.17 (3H, s), 3.37 (3H, s), 4.45-4.50 (2H, m), 7.04 (1H, s), 7.32-7.35 (1H, m), 7.48-7.51 (1H, m), 7.65-7.69 (3H, m), 7.79-7.81 (2H, m), 7.85 (1H, br s), 8.02-8.06 (1H, m), 8.35 (1H, s), 10.86 (1H, s). ESI-MS m/z: 582 $[M + H]^+$ |
| 84 | 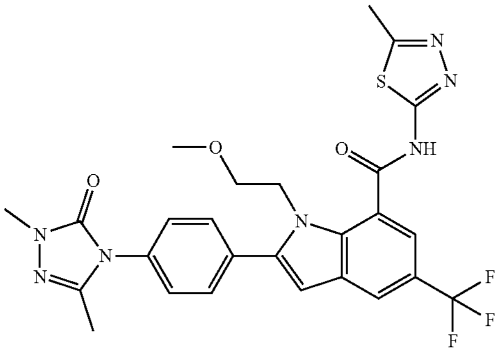 [SMILES: COCCn1c(-c2ccc(-n3c(C)nn(C)c3=O)cc2)cc2cc(C(F)(F)F)cc(C(=O)Nc3nnc(C)s3)c21] | ESI-MS m/z: 572 $[M + H]^+$ |
| 85 | 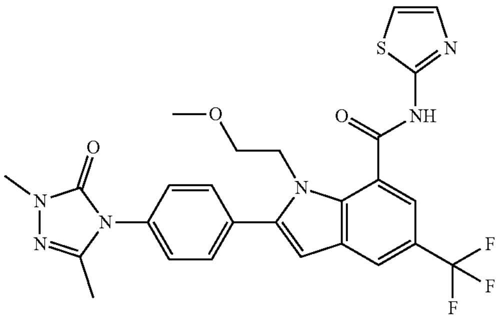 [SMILES: COCCn1c(-c2ccc(-n3c(C)nn(C)c3=O)cc2)cc2cc(C(F)(F)F)cc(C(=O)Nc3nccs3)c21] | ESI-MS m/z: 557 $[M + H]^+$ |

TABLE 2-13-continued
| | | |
|---|---|---|
| 86 | 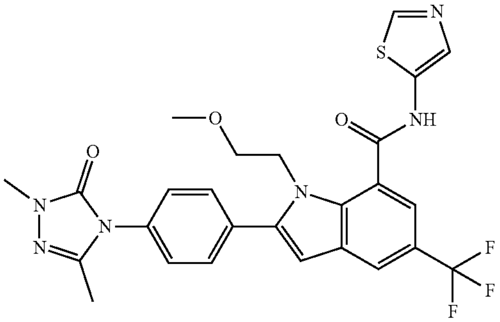 | ESI-MS m/z: 557 $[M + H]^+$ |
TABLE 2-14
| | | |
|---|---|---|
| 87 | 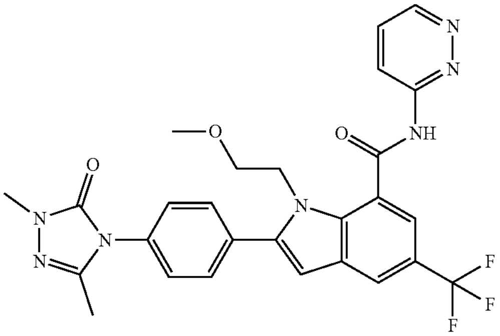 [SMILES: COCCn1c(-c2ccc(-n3c(C)nn(C)c3=O)cc2)cc2cc(C(F)(F)F)cc(C(=O)Nc3cccnn3)c21] | ESI-MS m/z: 552 $[M + H]^+$ |
| 88 | 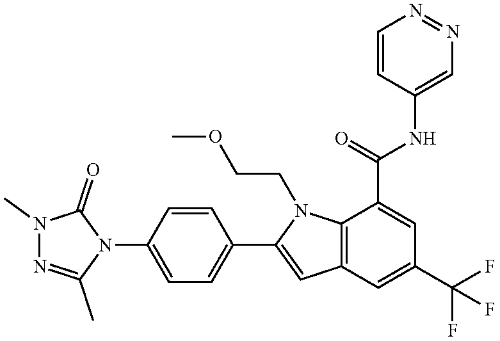 [SMILES: COCCn1c(-c2ccc(-n3c(C)nn(C)c3=O)cc2)cc2cc(C(F)(F)F)cc(C(=O)Nc3ccnnc3)c21] | ESI-MS m/z: 552 $[M + H]^+$ |
| 89 | 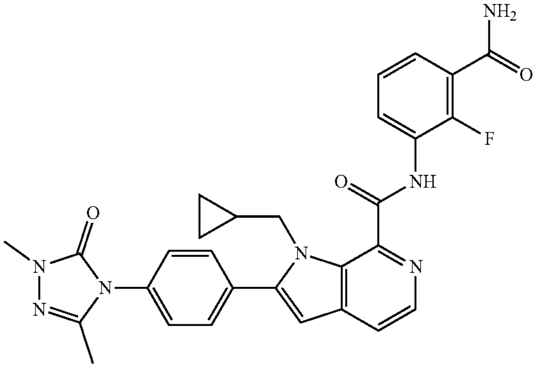 [SMILES: Cc1nn(C)c(=O)n1-c1ccc(-c2cc3ccnc(C(=O)Nc4cccc(C(N)=O)c4F)c3n2CC2CC2)cc1] | $^1$H-NMR (400 MHz, DMSO-$d_6$) δ: −0.19-−0.15 (2H, m), 0.14-0.19 (2H, m), 0.81 (1H, m), 2.16 (3H, s), 3.37 (3H, s), 4.50 (2H, d, J = 6.9 Hz), 6.92 (1H, s), 7.33 (1H, t, J = 7.8 Hz), 7.47 (1H, m), 7.63 (2H, d, J = 8.5 Hz), 7.69 (1H, s), 7.78 (2H, d, J = 8.5 Hz), 7.82 (1H, s), 7.88 (1H, d, J = 5.2 Hz), 8.05 (1H, m), 8.34 (1H, d, J = 5.2 Hz), 10.73 (1H, s). ESI-MS m/z: 540 $[M + H]^+$ |

TABLE 2-14-continued
| | | |
|---|---|---|
| 90 | 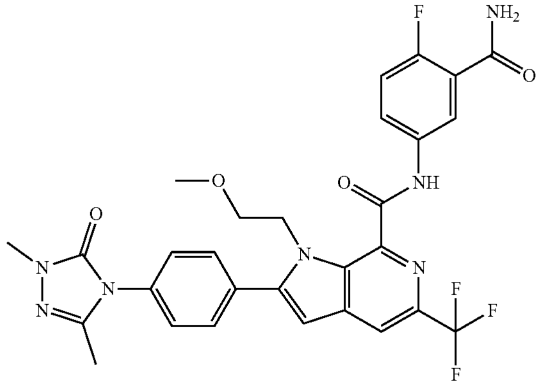 [SMILES: COCCn1c(-c2ccc(-n3c(C)nn(C)c3=O)cc2)cc2cc(C(F)(F)F)nc(C(=O)Nc3ccc(F)c(C(N)=O)c3)c21] | $^1$H-NMR (400 MHz, DMSO-$d_6$) δ: 2.17 (3H, s), 2.86 (3H, s), 3.37-3.42 (5H, m), 4.56-4.63 (2H, m), 7.03 (1H, s), 7.31-7.36 (1H, m), 7.63-7.66 (2H, m), 7.72 (1H, br s), 7.76-7.82 (3H, m), 7.92-7.96 (1H, m), 8.10-8.12 (1H, m), 8.35 (1H, s), 11.04 (1H, s). ESI-MS m/z: 612 $[M + H]^+$ |
| 91 | 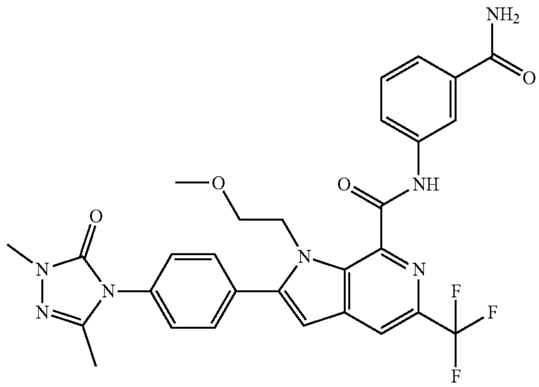 [SMILES: COCCn1c(-c2ccc(-n3c(C)nn(C)c3=O)cc2)cc2cc(C(F)(F)F)nc(C(=O)Nc3cccc(C(N)=O)c3)c21] | $^1$H-NMR (400 MHz, DMSO-$d_6$) δ: 2.16 (3H, s), 2.85 (3H, s), 3.37-3.41 (5H, m), 4.59-4.61 (2H, m), 7.03 (1H, s), 7.41 (1H, br s), 7.46-7.50 (1H, m), 7.63-7.66 (3H, m), 7.79-7.81 (2H, m), 7.93-7.96 (1H, m), 8.01 (1H, br s), 8.28-8.29 (1H, m), 8.34 (1H, s), 11.01 (1H, s). ESI-MS m/z: 594 $[M + H]^+$ |
| 92 | 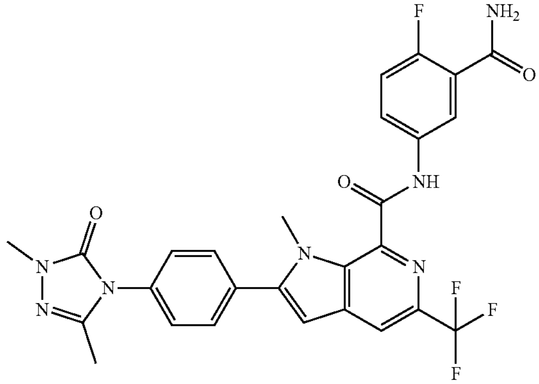 [SMILES: Cc1nn(C)c(=O)n1-c1ccc(-c2cc3cc(C(F)(F)F)nc(C(=O)Nc4ccc(F)c(C(N)=O)c4)c3n2C)cc1] | $^1$H-NMR (400 MHz, DMSO-$d_6$) δ: 2.16 (3H, s), 3.37 (3H, s), 3.84 (3H, s), 7.08 (1H, s), 7.32-7.37 (1H, m), 7.64-7.67 (2H, m), 7.71 (1H, br s), 7.77 (1H, br s), 7.84-7.86 (2H, m), 7.92-7.96 (1H, m), 8.12-8.15 (1H, m), 8.33 (1H, s), 11.08 (1H, s). ESI-MS m/z: 568 $[M + H]^+$ |

TABLE 2-15
| | | |
|---|---|---|
| 93 | 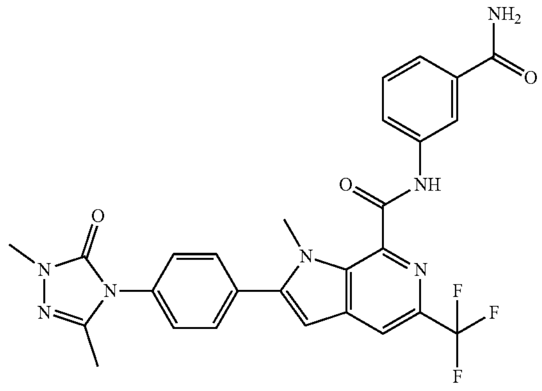 [SMILES: Cc1nn(C)c(=O)n1-c1ccc(-c2cc3cc(C(F)(F)F)nc(C(=O)Nc4cccc(C(N)=O)c4)c3n2C)cc1] | $^1$H-NMR (400 MHz, DMSO-$d_6$) δ: 2.16 (3H, s), 3.37 (3H, s), 3.86 (3H, s), 7.08 (1H, s), 7.40 (1H, br s), 7.49 (1H, t, d = 7.9 Hz), 7.65-7.67 (3H, m), 7.84-7.86 (2H, m), 7.95-7.97 (1H, m), 8.01 (1H, br s), 8.29-8.30 (1H, m), 8.33 (1H, s), 11.04 (1H, s). ESI-MS m/z: 550 $[M + H]^+$ |
| 94 | 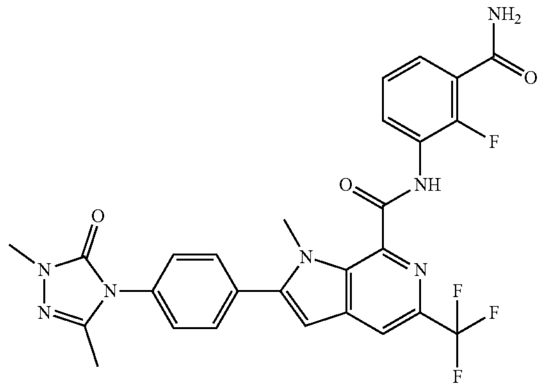 [SMILES: Cc1nn(C)c(=O)n1-c1ccc(-c2cc3cc(C(F)(F)F)nc(C(=O)Nc4cccc(C(N)=O)c4F)c3n2C)cc1] | $^1$H-NMR (400 MHz, DMSO-$d_6$) δ: 2.17 (3H, s), 3.37 (3H, s), 3.91 (3H, s), 7.09 (1H, s), 7.31-7.35 (1H, m), 7.47-7.51 (1H, m), 7.65-7.69 (3H, m), 7.85-7.87 (3H, m), 8.08-8.12 (1H, m), 8.34 (1H, s), 10.78 (1H, s). ESI-MS m/z: 568 $[M + H]^+$ |
| 95 | 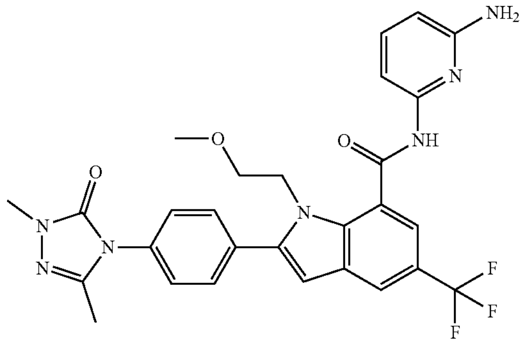 [SMILES: COCCn1c(-c2ccc(-n3c(C)nn(C)c3=O)cc2)cc2cc(C(F)(F)F)cc(C(=O)Nc3cccc(N)n3)c21] | ESI-MS m/z: 566 $[M + H]^+$ |
| 96 | 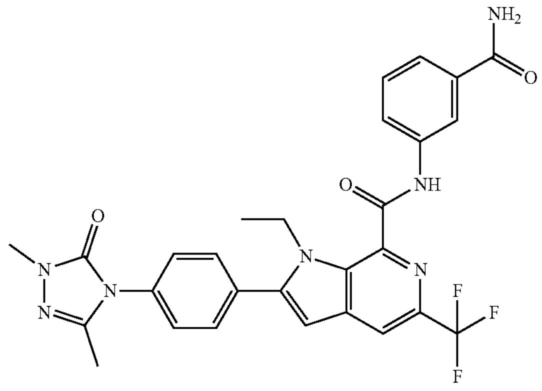 [SMILES: CCn1c(-c2ccc(-n3c(C)nn(C)c3=O)cc2)cc2cc(C(F)(F)F)nc(C(=O)Nc3cccc(C(N)=O)c3)c21] | $^1$H-NMR (400 MHz, DMSO-$d_6$) δ: 1.10 (3H, t, J = 7.1 Hz), 2.17 (3H, s), 3.37 (3H, s), 4.37-4.43 (2H, m), 7.03 (1H, s), 7.41 (1H, br s), 7.47-7.51 (1H, m), 7.65-7.67 (3H, m), 7.78-7.80 (2H, m), 7.94 (1H, d, J = 7.5 Hz), 8.02 (1H, br s), 8.27 (1H, s), 8.34 (1H, s), 11.09 (1H, s). ESI-MS m/z: 564 $[M + H]^+$ |

TABLE 2-15-continued
| | | |
|---|---|---|
| 97 | 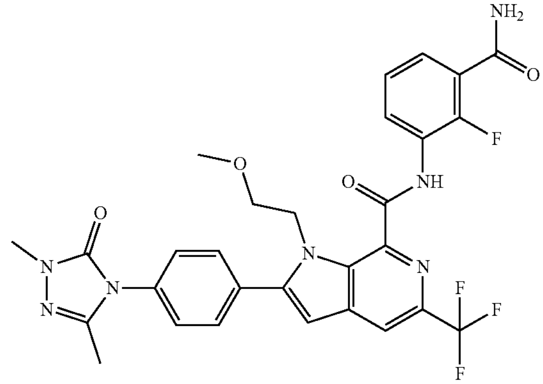 [SMILES: COCCn1c(-c2ccc(-n3c(C)nn(C)c3=O)cc2)cc2cc(C(F)(F)F)nc(C(=O)Nc3cccc(C(N)=O)c3F)c21] | $^1$H-NMR (400 MHz, DMSO-$d_6$) δ: 2.16 (3H, s), 2.88 (3H, s), 3.37 (3H, m), 3.45-3.47 (2H, m), 4.68-4.71 (2H, m), 7.04 (1H, s), 7.31-7.35 (1H, m), 7.47-7.51 (1H, m), 7.63-7.66 (2H, m), 7.69 (1H, br s), 7.79-7.81 (2H, m), 7.85 (1H, br s), 8.00-8.05 (1H, m), 8.37 (1H, s), 10.75 (1H, s). ESI-MS m/z: 612 [M + H]$^+$ |
| 98 | 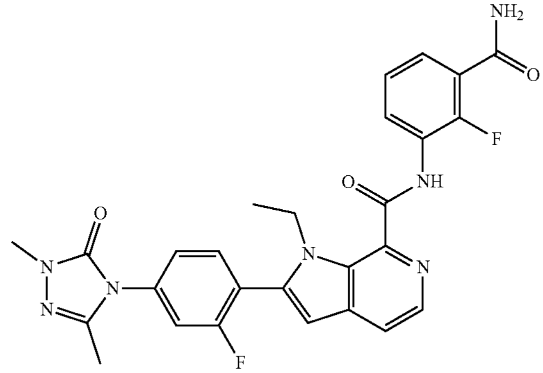 [SMILES: CCn1c(-c2ccc(-n3c(C)nn(C)c3=O)cc2F)cc2ccnc(C(=O)Nc3cccc(C(N)=O)c3F)c21] | ESI-MS m/z: 532 [M + H]$^+$ |
TABLE 2-16
| | | |
|---|---|---|
| 99 | 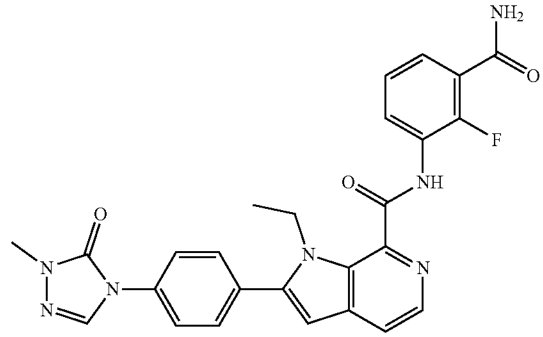 [SMILES: CCn1c(-c2ccc(-n3cnn(C)c3=O)cc2)cc2ccnc(C(=O)Nc3cccc(C(N)=O)c3F)c21] | $^1$H-NMR (400 MHz, DMSO-$d_6$) δ: 1.01 (3H, t, J = 7.1 Hz), 3.43 (3H, s), 4.53 (2H, q, J = 7.0 Hz), 6.84 (1H, s), 7.32 (1H, t, J = 7.9 Hz), 7.47 (1H, m), 7.69 (1H, s), 7.76 (2H, d, J = 8.6 Hz), 7.84 (2H, d, J = 5.2 Hz), 7.92 (2H, d, J = 8.6 Hz), 8.03 (1H, t, J = 7.0 Hz), 8.31 (1H, d, J = 5.2 Hz), 8.58 (1H, s), 10.70 (1H, s). ESI-MS m/z: 500 [M + H]$^+$ |
| 100 | 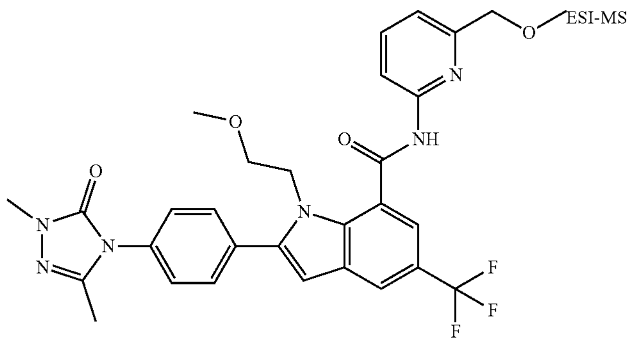 | ESI-MS m/z: 595 [M + H]$^+$ |

TABLE 2-16-continued
| | | |
|---|---|---|
| 101 | 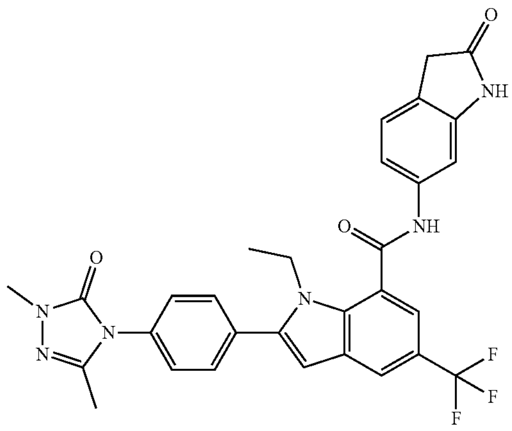 [SMILES: CCn1c(-c2ccc(-n3c(C)nn(C)c3=O)cc2)cc2cc(C(F)(F)F)cc(C(=O)Nc3ccc4c(c3)NC(=O)C4)c21] | ESI-MS m/z: 575 $[M + H]^+$ |
| 102 | 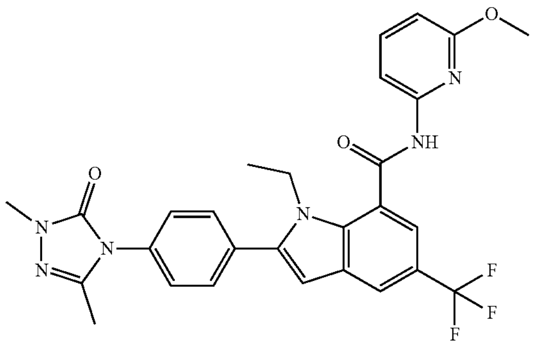 | ESI-MS m/z: 551 $[M + H]^+$ |
| 103 | 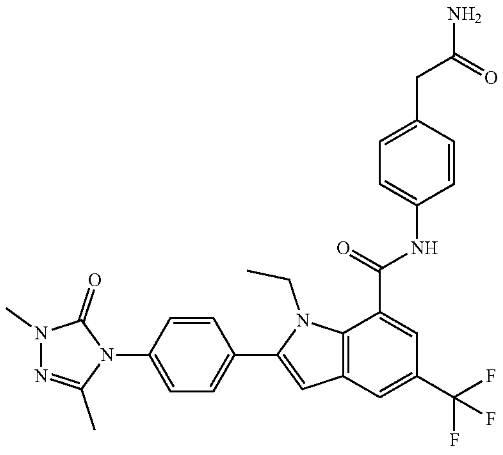 [SMILES: CCn1c(-c2ccc(-n3c(C)nn(C)c3=O)cc2)cc2cc(C(F)(F)F)cc(C(=O)Nc3ccc(CC(N)=O)cc3)c21] | ESI-MS m/z: 577 $[M + H]^+$ |

TABLE 2-17
| | | |
|---|---|---|
| 104 | 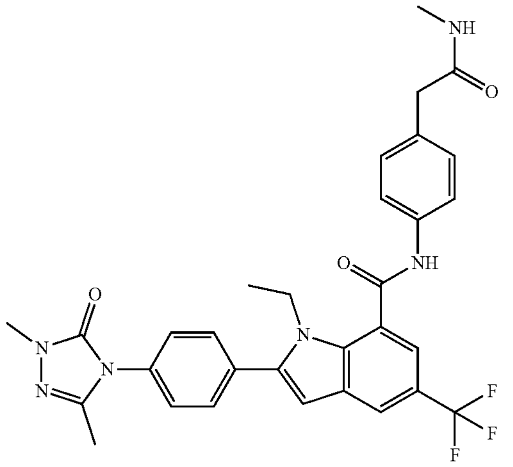 [SMILES: CCn1c(-c2ccc(-n3c(C)nn(C)c3=O)cc2)cc2cc(C(F)(F)F)cc(C(=O)Nc3ccc(CC(=O)NC)cc3)c21] | $^1$H-NMR (400 MHz, DMSO-$d_6$) δ: 1.03 (3H, t, J = 6.8 Hz), 2.16 (3H, s), 2.58 (3H, d, J = 4.4 Hz), 3.36 (3H, s), 3.37 (2H, s), 4.31 (2H, q, J = 6.8 Hz), 6.92 (1H, s), 7.25-7.27 (2H, m), 7.60-7.62 (3H, m), 7.66-7.69 (2H, m), 7.72-7.74 (2H, m), 7.90-7.94 (1H, m), 8.17 (1H, d, J = 0.8 Hz), 10.82 (1H, s). ESI-MS m/z: 591 $[M + H]^+$ |
| 105 | 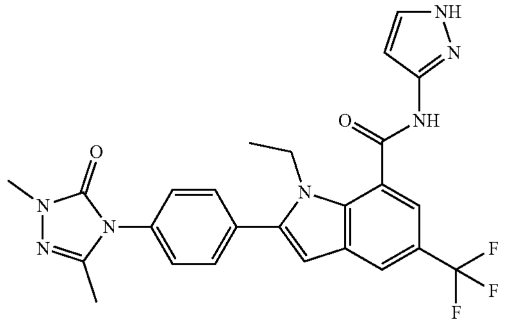 [SMILES: CCn1c(-c2ccc(-n3c(C)nn(C)c3=O)cc2)cc2cc(C(F)(F)F)cc(C(=O)Nc3cc[nH]n3)c21] | ESI-MS m/z: 510 $[M + H]^+$ |
| 106 | 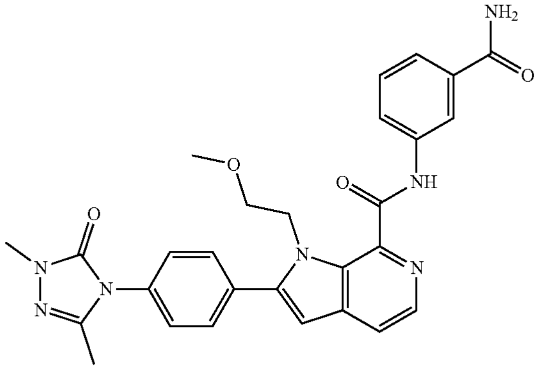 [SMILES: COCCn1c(-c2ccc(-n3c(C)nn(C)c3=O)cc2)cc2ccnc(C(=O)Nc3cccc(C(N)=O)c3)c21] | $^1$H-NMR (400 MHz, DMSO-$d_6$) δ: 2.16 (3H, s), 2.82 (3H, s), 3.35-3.37 (5H, m), 4.65-4.68 (2H, m), 6.85 (1H, s), 7.39 (1H, br s), 7.44-7.47 (1H, m), 7.61-7.63 (3H, m), 7.69 (1H, br s), 7.76-7.78 (1H, m), 7.81-7.82 (1H, m), 7.94-7.97 (2H, m), 8.30-8.32 (1H, m), 8.35-8.36 (1H, m), 10.93 (1H, s). ESI-MS m/z: 526 $[M + H]^+$ |
| 107 | 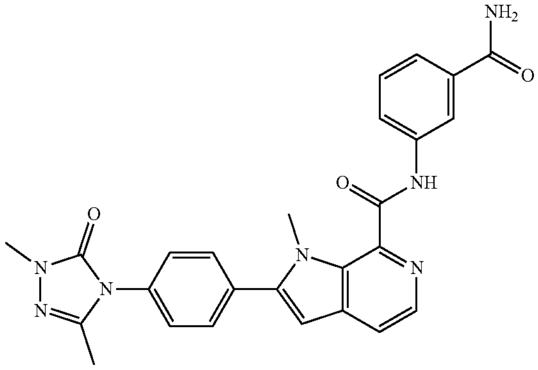 [SMILES: Cc1nn(C)c(=O)n1-c1ccc(-c2cc3ccnc(C(=O)Nc4cccc(C(N)=O)c4)c3n2C)cc1] | $^1$H-NMR (400 MHz, DMSO-$d_6$) δ: 2.17 (3H, s), 3.37 (3H, s), 3.83 (3H, s), 6.91 (1H, s), 7.39 (1H, br s), 7.44-7.48 (1H, m), 7.60-7.65 (3H, m), 7.80-7.84 (3H, m), 7.95-7.97 (2H, m), 8.28 (1H, d, J = 5.3 Hz), 8.37-8.38 (1H, m), 10.91 (1H, s). ESI-MS m/z: 482 $[M + H]^+$ |

TABLE 2-17-continued
| | | |
|---|---|---|
| 108 | 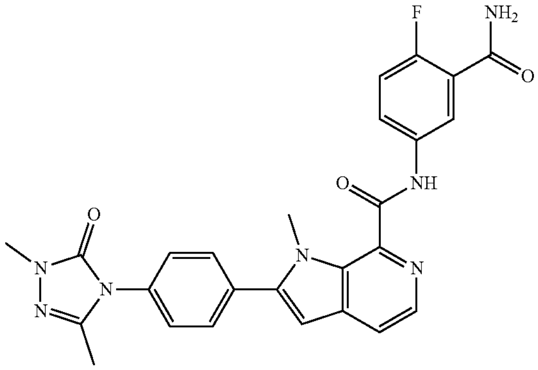 [SMILES: Cc1nn(C)c(=O)n1-c1ccc(-c2cc3ccnc(C(=O)Nc4ccc(F)c(C(N)=O)c4)c3n2C)cc1] | $^1$H-NMR (400 MHz, DMSO-$d_6$) δ: 2.16 (3H, s), 3.37 (3H, s), 3.81 (3H, s), 6.91 (1H, s), 7.28-7.33 (1H, m), 7.63 (2H, d, J = 8.6 Hz), 7.69 (1H, br s), 7.74 (1H, br s), 7.80-7.83 (3H, m), 7.92-7.97 (1H, m), 8.21-8.24 (1H, m), 8.28 (1H, d, J = 5.3 Hz), 10.98 (1H, s). ESI-MS m/z: 500 $[M + H]^+$ |
TABLE 2-18
| | | |
|---|---|---|
| 109 | 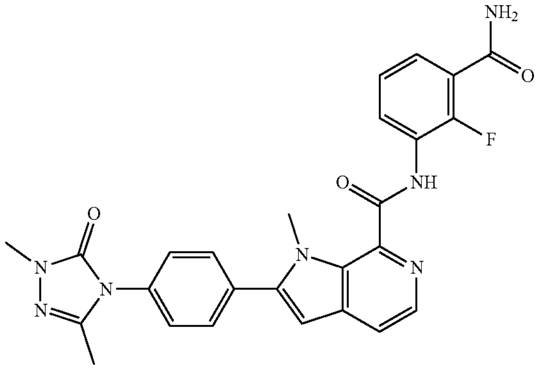 [SMILES: Cc1nn(C)c(=O)n1-c1ccc(-c2cc3ccnc(C(=O)Nc4cccc(C(N)=O)c4F)c3n2C)cc1] | $^1$H-NMR (400 MHz, DMSO-$d_6$) δ: 2.16 (3H, s), 3.37 (3H, s), 3.89 (3H, s), 6.93 (1H, s), 7.30-7.34 (1H, m), 7.44-7.48 (1H, m), 7.63-7.69 (3H, m), 7.82-7.85 (4H, m), 8.10-8.13 (1H, m), 8.30-8.31 (1H, m), 10.65 (1H, s). ESI-MS m/z: 500 $[M + H]^+$ |
| 110 | 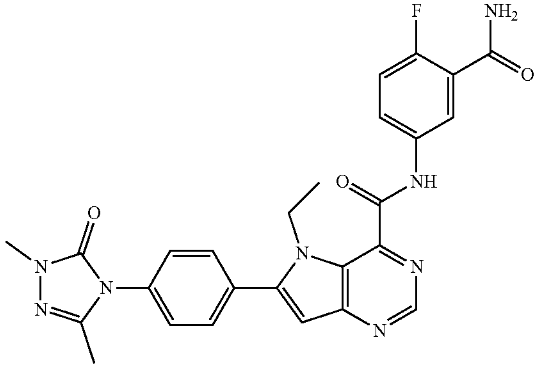 [SMILES: CCn1c(-c2ccc(-n3c(C)nn(C)c3=O)cc2)cc2ncnc(C(=O)Nc3ccc(F)c(C(N)=O)c3)c21] | ESI-MS m/z: 515 $[M + H]^+$ |
| 111 | 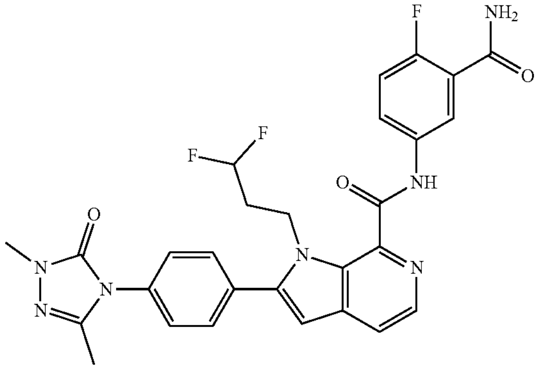 [SMILES: Cc1nn(C)c(=O)n1-c1ccc(-c2cc3ccnc(C(=O)Nc4ccc(F)c(C(N)=O)c4)c3n2CCC(F)F)cc1] | ESI-MS m/z: 564 $[M + H]^+$ |

TABLE 2-18-continued
| | | |
|---|---|---|
| 112 | 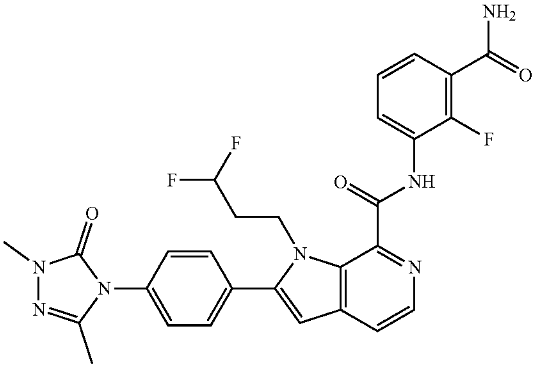 [SMILES: Cc1nn(C)c(=O)n1-c1ccc(-c2cc3ccnc(C(=O)Nc4cccc(C(N)=O)c4F)c3n2CCC(F)F)cc1] | ESI-MS m/z: 564 [M + H]$^+$ |
| 113 | 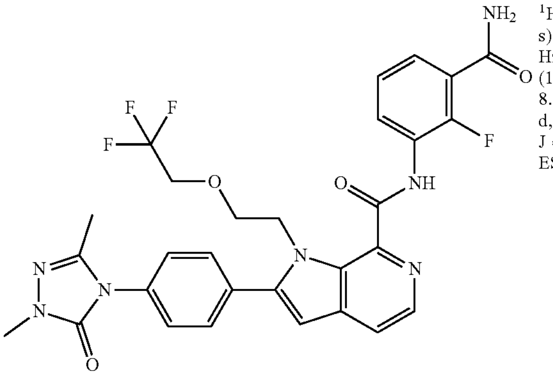 | $^1$H-NMR (400 MHz, $CD_3OD$) δ: 2.21 (3H, s), 3.45-3.54 (5H, m), 3.63 (2H, t, J = 5.1 Hz), 4.83-4.87 (2H, m), 6.82 (1H, s), 7.26 (1H, dd, J = 9.0, 10.5 Hz), 7.57 (2H, d, J = 8.6 Hz), 7.78 (2H, d, J = 8.5 Hz), 7.81 (1H, d, J = 5.3 Hz), 8.00 (1H, m), 8.25 (1H, dd, J = 2.8, 6.5 Hz), 8.29 (1H, d, J = 5.3 Hz). ESI-MS m/z: 612 [M + H]$^+$ |
| 114 | 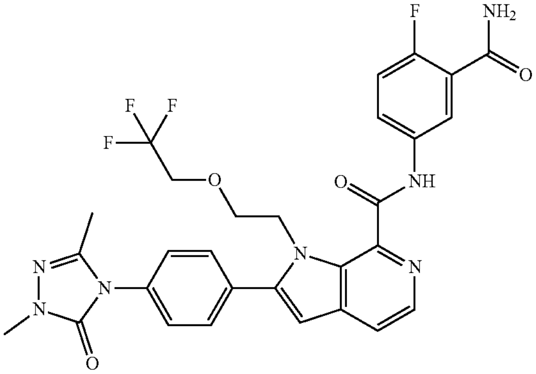 [SMILES: Cc1nn(C)c(=O)n1-c1ccc(-c2cc3ccnc(C(=O)Nc4ccc(F)c(C(N)=O)c4)c3n2CCOCC(F)(F)F)cc1] | ESI-MS m/z: 612 [M + H]$^+$ |
TABLE 2-19
| | | |
|---|---|---|
| 115 | 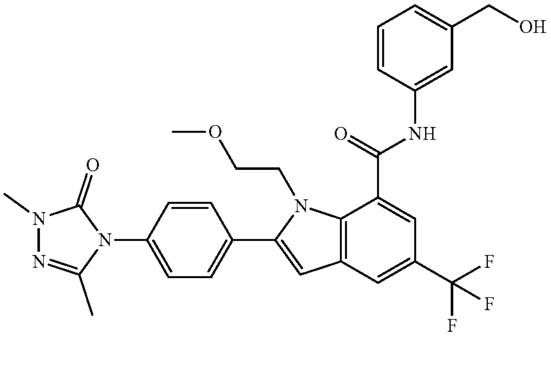 [SMILES: COCCn1c(-c2ccc(-n3c(C)nn(C)c3=O)cc2)cc2cc(C(F)(F)F)cc(C(=O)Nc3cccc(CO)c3)c21] | ESI-MS m/z: 580 [M + H]$^+$ |

TABLE 2-19-continued
| | | |
|---|---|---|
| 116 | 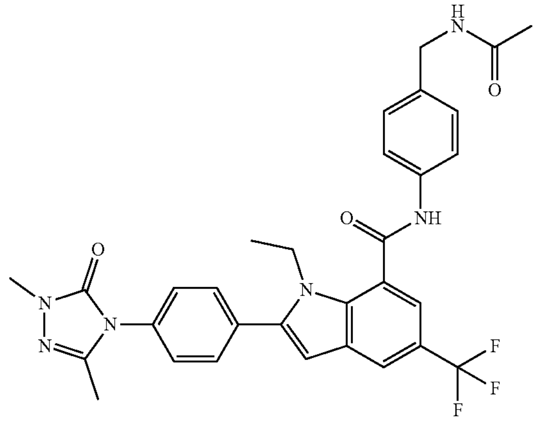 [SMILES: CCn1c(-c2ccc(-n3c(C)nn(C)c3=O)cc2)cc2cc(C(F)(F)F)cc(C(=O)Nc3ccc(CNC(C)=O)cc3)c21] | ESI-MS m/z: 591 $[M + H]^+$ |
| 117 | 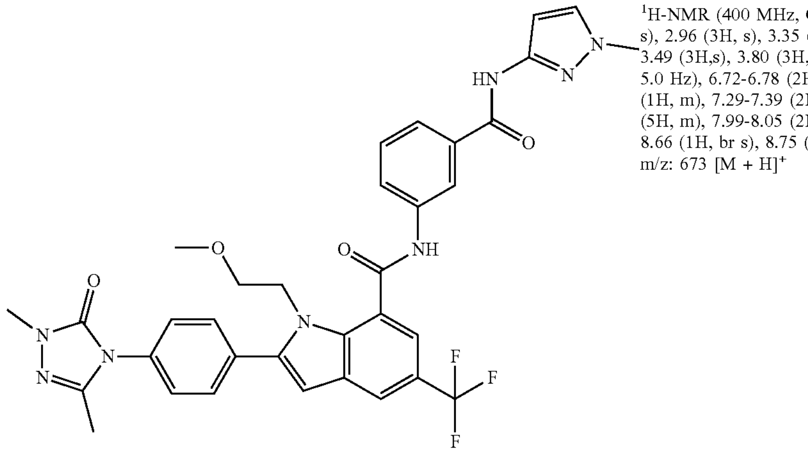 | $^1$H-NMR (400 MHz, $CDCl_3$) δ: 2.26 (3H, s), 2.96 (3H, s), 3.35 (2H, t, J = 5.2 Hz), 3.49 (3H,s), 3.80 (3H, s), 4.57 (2H, t, J = 5.0 Hz), 6.72-6.78 (2H, m), 7.24-7.28 (1H, m), 7.29-7.39 (2H, m), 7.48-7.72 (5H, m), 7.99-8.05 (2H, m), 8.19(1H, s), 8.66 (1H, br s), 8.75 (1H, br s). ESI-MS m/z: 673 $[M + H]^+$ |
| 118 | 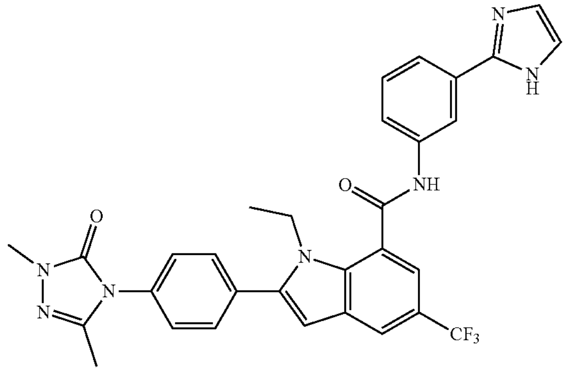 [SMILES: CCn1c(-c2ccc(-n3c(C)nn(C)c3=O)cc2)cc2cc(C(F)(F)F)cc(C(=O)Nc3cccc(-c4ncc[nH]4)c3)c21] | ESI-MS m/z: 586 $[M + H]^+$ |
| 119 | 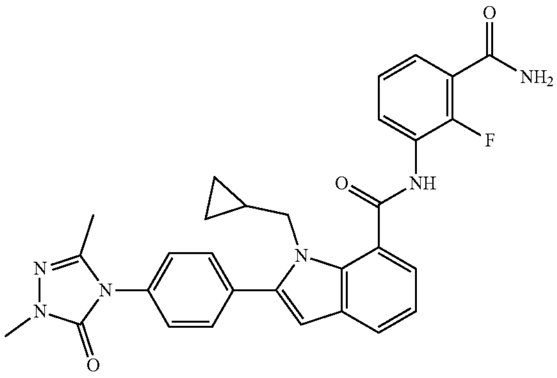 [SMILES: Cc1nn(C)c(=O)n1-c1ccc(-c2cc3cccc(C(=O)Nc4cccc(C(N)=O)c4F)c3n2CC2CC2)cc1] | $^1$H-NMR (400 MHz, DMSO-$d_6$) δ: −0.21- −0.18 (2H, m), 0.13-0.18 (2H, m), 0.85 (1H, m), 2.15 (3H, s), 3.34 (3H, s), 4.24 (2H, d, J = 6.7 Hz), 6.80 (1H, s), 7.23 (1H, m), 7.31 (1H, m), 7.44-7.50 (2H, m), 7.58 (2H, d, J = 8.6 Hz), 7.65-7.71 (3H, m), 7.77-7.81 (3H, m), 10.61 (1H, br s). ESI-MS m/z: 539 $[M + H]^+$ |

TABLE 2-19-continued
| | | |
|---|---|---|
| 120 | 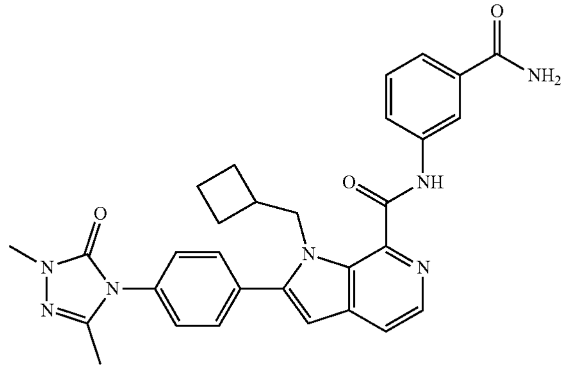 [SMILES: Cc1nn(C)c(=O)n1-c1ccc(-c2cc3ccnc(C(=O)Nc4cccc(C(N)=O)c4)c3n2CC2CCC2)cc1] | ESI-MS m/z: 536 $[M + H]^+$ |
TABLE 2-20
| | | |
|---|---|---|
| 121 | 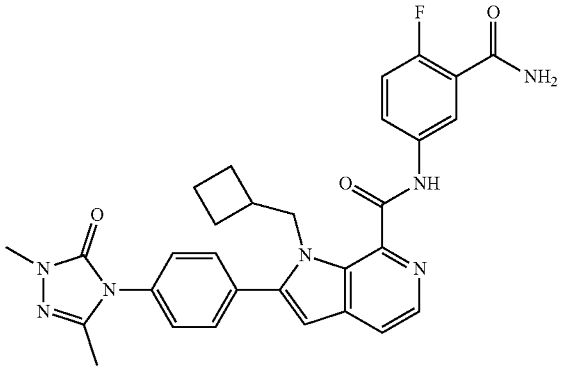 [SMILES: Cc1nn(C)c(=O)n1-c1ccc(-c2cc3ccnc(C(=O)Nc4ccc(F)c(C(N)=O)c4)c3n2CC2CCC2)cc1] | ESI-MS m/z: 554 $[M + H]^+$ |
| 122 | 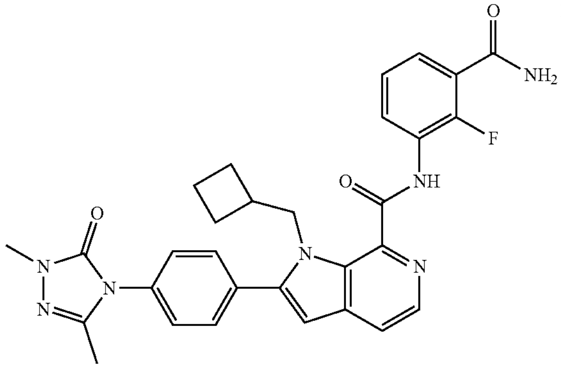 [SMILES: Cc1nn(C)c(=O)n1-c1ccc(-c2cc3ccnc(C(=O)Nc4cccc(C(N)=O)c4F)c3n2CC2CCC2)cc1] | ESI-MS m/z: 554 $[M + H]^+$ |
| 123 | 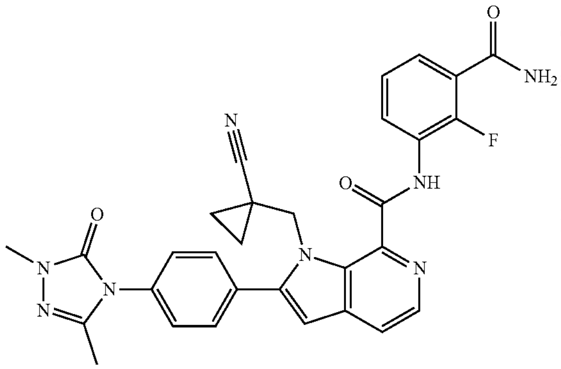 [SMILES: Cc1nn(C)c(=O)n1-c1ccc(-c2cc3ccnc(C(=O)Nc4cccc(C(N)=O)c4F)c3n2CC2(C#N)CC2)cc1] | $^1$H-NMR (400 MHz, $CDCl_3$) δ: 0.76-0.79 (2H, m), 0.97-1.00 (2H, m), 2.27 (3H, s), 3.53 (3H, s), 5.17 (2H, s), 5.85 (1H, s), 6.67 (1H, m), 6.86 (1H, s), 7.35 (1H, t, J = 8.0 Hz), 7.52 (2H, d, J = 8.5 Hz), 7.78 (2H, d, J = 8.5 Hz), 7.81 (1H, d, J = 5.1 Hz), 7.88 (1H, m), 8.41 (1H, d, J = 5.1 Hz), 8.69 (1H, dt, J = 1.7, 11.8 Hz), 10.85 (1H, m). ESI-MS m/z: 565 $[M + H]^+$ |

TABLE 2-20-continued
| | | |
|---|---|---|
| 124 | 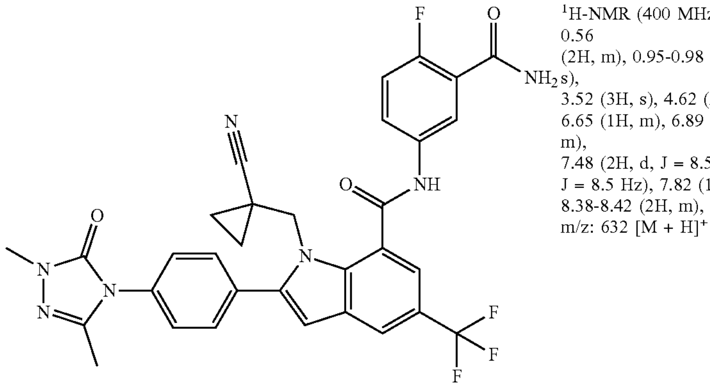 | $^1$H-NMR (400 MHz, $CDCl_3$) δ: 0.52-0.56 (2H, m), 0.95-0.98 (2H, m), 2.24 (3H, s), 3.52 (3H, s), 4.62 (2H, s), 5.50 (1H, s), 6.65 (1H, m), 6.89 (1H, s), 7.23 (1H, m), 7.48 (2H, d, J = 8.5 Hz), 7.68 (2H, d, J = 8.5 Hz), 7.82 (1H, s), 8.12 (1H, s), 8.38-8.42 (2H, m), 9.54 (1H, s). ESI-MS m/z: 632 [M + H]$^+$ |
| 125 | 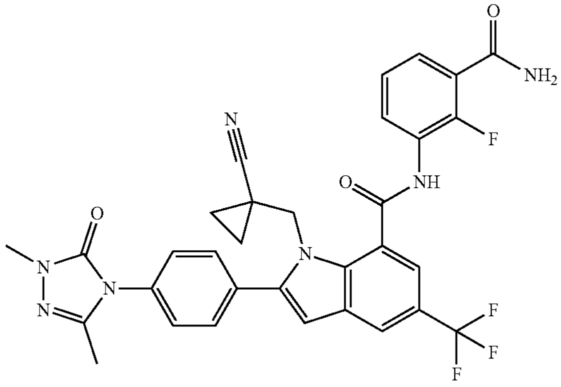 [SMILES: Cc1nn(C)c(=O)n1-c1ccc(-c2cc3cc(C(F)(F)F)cc(C(=O)Nc4cccc(C(N)=O)c4F)c3n2CC2(C#N)CC2)cc1] | $^1$H-NMR (400 MHz, $CDCl_3$) δ: 0.50-0.54 (2H, m), 0.98-1.01 (2H, m), 2.25 (3H, s), 3.52 (3H, s), 4.64 (2H, s), 5.85 (1H, s), 6.59 (1H, m), 6.89 (1H, s), 7.39 (1H, t, J = 7.9 Hz), 7.49 (2H, d, J = 8.5 Hz), 7.67 (2H, d, J = 8.5 Hz), 7.79 (1H, d, J = 1.3 Hz), 7.95 (1H, m), 8.14 (1H, m), 8.32 (1H, m), 8.52 (1H, m). ESI-MS m/z: 632 [M + H]$^+$ |
| 126 | 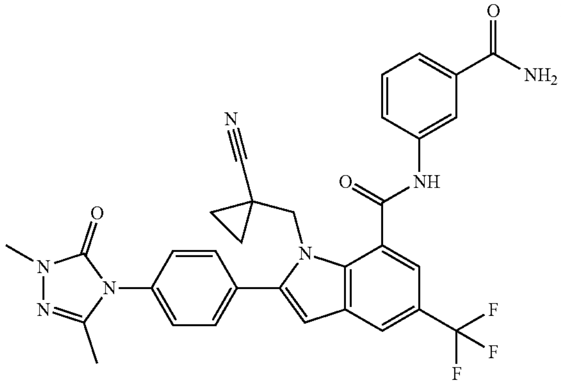 [SMILES: Cc1nn(C)c(=O)n1-c1ccc(-c2cc3cc(C(F)(F)F)cc(C(=O)Nc4cccc(C(N)=O)c4)c3n2CC2(C#N)CC2)cc1] | ESI-MS m/z: 614 [M + H]$^+$ |
TABLE 2-21
| | | |
|---|---|---|
| 127 | 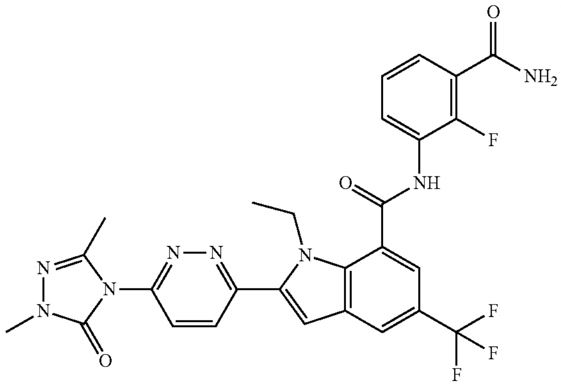 [SMILES: CCn1c(-c2ccc(-n3c(C)nn(C)c3=O)nn2)cc2cc(C(F)(F)F)cc(C(=O)Nc3cccc(C(N)=O)c3F)c21] | ESI-MS m/z: 583 [M + H]$^+$ |

TABLE 2-21-continued

| | | |
|---|---|---|
| 128 | 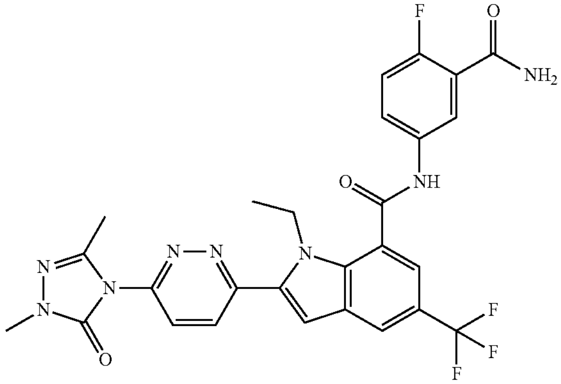 [SMILES: CCn1c(-c2ccc(-n3c(C)nn(C)c3=O)nn2)cc2cc(C(F)(F)F)cc(C(=O)Nc3ccc(F)c(C(N)=O)c3)c21] | ESI-MS m/z: 583 [M + H]+ |

Example 129

[Chem. Fig. 73]

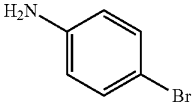

Ref.-124 step 1

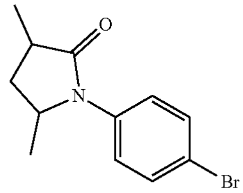

Ref.-125
1st peak
diastereomeric pure
racemate

+

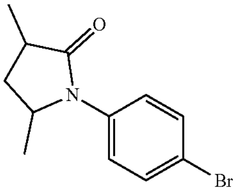

Ref.-126
2nd peak
diastereomeric pure
racemate

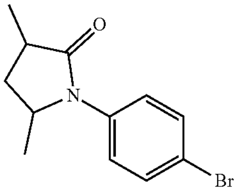

Ref.-126 step 2

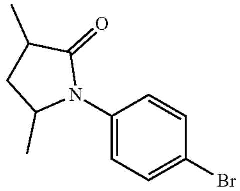

Ref.-127
1st peak
diastereomeric pure
enantiomeric pure

+

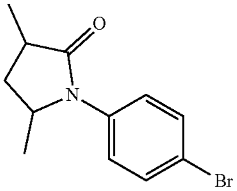

Ref.-128
2nd peak
diastereomeric pure
enantiomeric pure

-continued

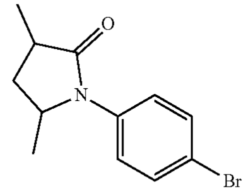

Ref.-127 step 3

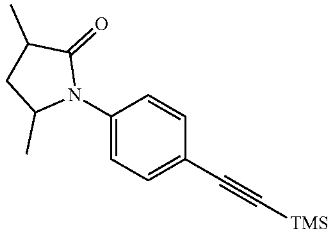

Ref.-129
diastereomeric pure
enantiomeric pure step 4

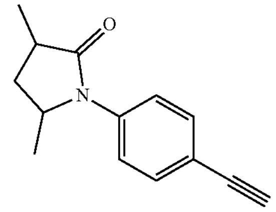

Ref.-130
diastereomeric pure
enantiomeric pure

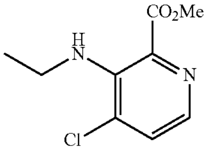

Ref.-69 step 5

-continued

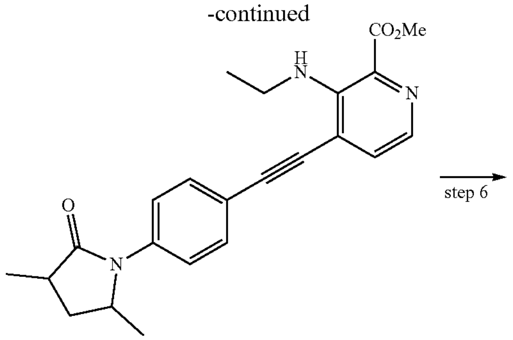

Ref.-131
diastereomeric pure
enantiomeric pure

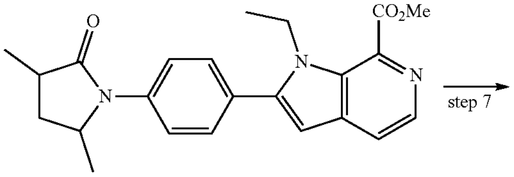

Ref.-132
diastereomeric pure
enantiomeric pure

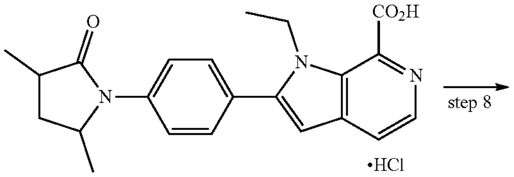

Ref.-133
diastereomeric pure
enantiomeric pure

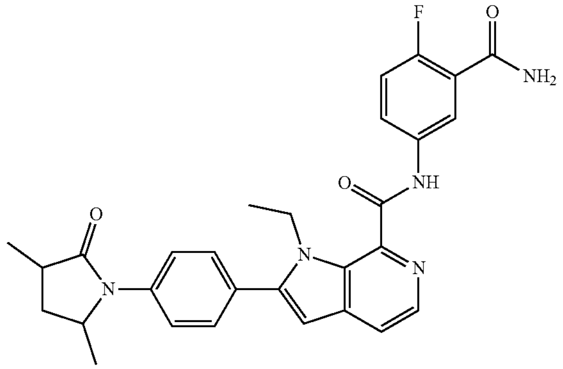

Ex.-129
diastereomeric pure
enantiomeric pure

Step 1

Indium(III) acetate (22.5 mg, 0.07 mmol) was added to a toluene solution (10 mL) of reference synthesis example compound 124 (1.32 g, 7.7 mmol), 2-methyl-oxopentanoic acid (1.0 g, 7.7 mmol), and phenylsilane (831 mg, 7.7 mmol), and the mixture was stirred at 110° C. for 20 hours under a nitrogen gas environment. The reaction solution was poured into a saturated aqueous solution of ammonium chloride, and extracted using ethyl acetate. The extract was dried over anhydrous sodium sulfate, and the solvent was distilled off under reduced pressure. The above reaction procedure was performed 15 times, and the obtained crude products were combined, purified by silica gel column chromatography (ethyl acetate/petrol ether=30/1) and simultaneously separated into diastereomers to obtain reference synthesis example compound 125 (first peak diastereomer) (yield 15 g) and reference synthesis example compound 126 (second peak diastereomer) (yield 7.0 g).

Step 2

A preparative chiral column (CHIRALART Celllose-SB, manufactured by YMC Co., Ltd.) was attached to a preparative LC system (LC-Forte/R, manufactured by YMC Co., Ltd.), and a mixed solution of n-heptane/2-propanol (9/1) was passed through the column at room temperature at a flow rate of 21 mL/min for equilibration. 2-propanol was added and dissolved in reference synthesis example compound 126 (3.55 g) to prepare a 50 mg/mL solution, and then n-heptane was added to the solution to obtain a solution (Solution A) of reference synthesis example compound 126 with a concentration of 5 mg/mL. About 30 mL of the solution A was injected, a first peak (retention time: about 14.5 minutes) and a second peak (retention time: about 18.8 minutes) were collected while observing a UV detector (detection wave length: 250 nm) (the operation was repeated until the whole amount of the solution A was injected). The solvent contained in the respective fractions was distilled off under reduced pressure to obtain reference synthesis example compound 127 (yield 1.72 g, optical pure>99.9% ee) from the fraction derived from the first peak and reference synthesis example compound 128 (yield 1.69 g, optical pure 99.4% ee) from the fraction derived from the second peak.

Step 3

Reference synthesis example compound 127 (1.40 g, 5.22 mmol) and THF (0.026 L) were mixed, then triethyl amine (2.2 mL), [1,1'-bis(diphenylphosphino)ferrocene]dichloropalladium (II) dichloromethane complex (0.426 g, 0.522 mmol), cuprous iodide (0.099 g, 0.52 mmol), and trimethylsilylacetylene (0.93 mL, 6.6 mmol) were sequentially added, and the mixture was stirred at 75° C. for 1.5 hours under an argon environment. After allowing to cool, the reaction solution was diluted with chloroform and filtered through Celite®. The filtrate was concentrated under reduced pressure, and the residue was purified by silica gel column chromatography to obtain reference synthesis example compound 129 (yield 1.38 g).

Step 4

Reference synthesis example compound 129 (1.39 g, 4.87 mmol) and THF (20.0 mL) were mixed, and then 1 mol/L TBAF/THE solution (7.8 mL, 7.8 mmol) were added, followed by stirring at room temperature for 30 minutes. The solvent was distilled off under reduced pressure, and then the residue was purified by silica gel column chromatography to obtain reference synthesis example compound 130 (yield 0.348 g).

Step 5

Palladium (II) acetate (18.3 mg, 0.0808 mmol) and XPhos (77.1 mg, 0.162 mmol) were suspended in degassed acetonitrile (4.0 mL), and the reference synthesis example compound 130 (0.345 g, 1.62 mmol), cesium carbonate (1.05 g, 3.22 mmol) and reference synthesis example compound 69 (0.694 g, 3.23 mmol) were added, followed by stirring at 95° C. for 1.5 hours under an argon environment. After allowing to cool, the reaction solution was diluted with water and then extracted using chloroform. The extract was dried over anhydrous sodium sulfate, and then the solvent was evaporated under reduced pressure. The residue was purified by silica gel column chromatography to obtain reference synthetic example compound 131 (yield 0.370 g).

Step 6

Reference synthesis example compound 131 (0.365 g, 0.932 mmol) and methanol (2.3 mL) were mixed, degassed, and the reactor was purged with argon. Then, chloro(triphenylphosphine) gold(I) (92.2 mg, 0.186 mmol) and silver bis(trifluoromethanesulfonyl)imide (72.3 mg, 0.186 mmol) were added, and the mixture was stirred at 80° C. for 2 hours. After cooling, the solvent was distilled off under reduced pressure. The residue was purified by silica gel column chromatography to obtain reference synthetic example compound 132 (yield 0.332 g).

Step 7

Reference synthesis example compound 132 (0.330 g, 0.843 mmol), THF (2.0 mL) and methanol (2.0 mL) were mixed, and then 4 mol/L aqueous sodium hydroxide (0.42 mL, 1.7 mmol) was added under ice-cooling, followed by stirring at room temperature for 5 hours. 2 mol/L hydrochloric acid (1.5 mL) was added dropwise to the reaction solution under ice-cooling, and the mixture was evaporated under reduced pressure. Toluene was added to the residue and stirred. The solvent was distilled off under reduced pressure to obtain reference synthesis example compound 133 as a mixture of sodium chloride (yield 0.447 g).

Step 8

A sodium chloride mixture (30.0 mg) of reference synthesis example compound 133 obtained by the method described in Step 7 was mixed with acetonitrile (0.57 mL), and then 5-amino-2-fluorobenzamide (17.4 mg, 0.113 mmol), 1-methylimidazole (22.3 μL, 0.282 mmol), and TCFH (31.7 mg, 0.113 mmol) were added, followed by stirring at room temperature for 15 hours. The mixture was diluted with water and extracted using chloroform. The extract was dried over anhydrous sodium sulfate, and the solvent was distilled off under reduced pressure. The residue was purified by silica gel column chromatography, and then ethanol (600 μL) was added to perform slurry washing. The solid was collected by filtration and dried under reduced pressure to obtain Example Compound 129 (yield 18.0 mg).

Example 130

[Chem. Fig. 74]

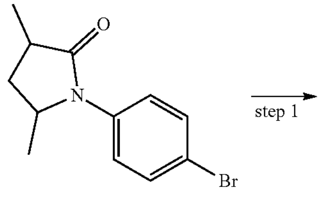

Ref.-126

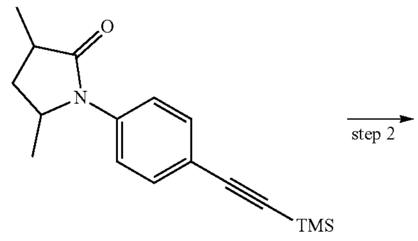

Ref.-134
diastereomeric pure
racemate

-continued

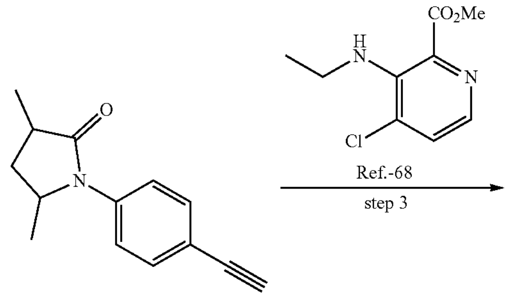

Ref.-135
diastereomeric pure
racemate

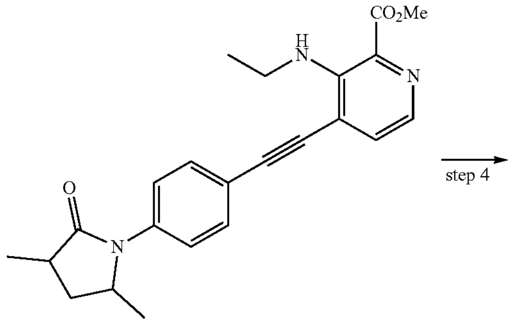

Ref.-136
diastereomeric pure
racemate

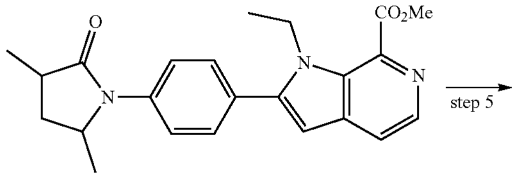

Ref.-137
diastereomeric pure
racemate

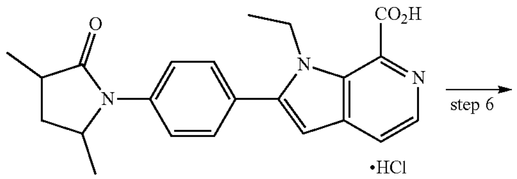

Ref.-138
diastereomeric pure
racemate

-continued

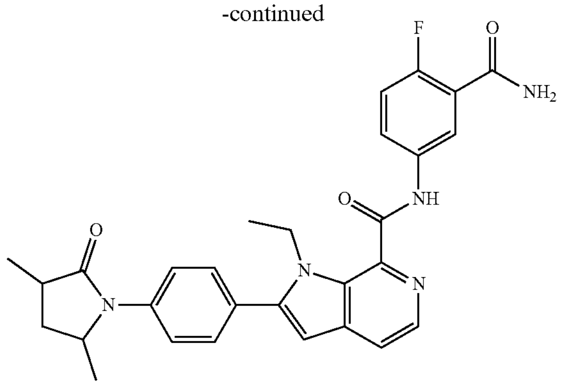

Ex.-130
diastereomeric pure
racemate

Step 1-6

Example Compound 130 (yield 11.3 mg) was obtained from reference synthesis example compound 126 by the same method as in Steps 3 to 8 of Example 129.

Example 131

[Chem. Fig. 75]

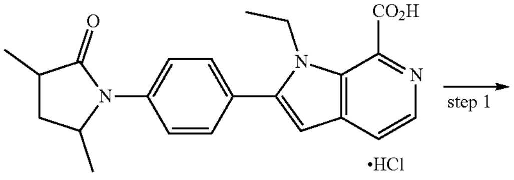

Ref.-138

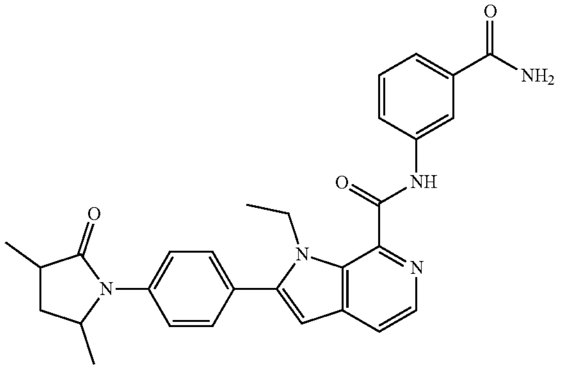

Ex.-131
(diastereomeric pure,
racemate)

Step 1

Example Compound 131 (yield 5.0 mg) was obtained from reference synthesis example compound 138 by the same method as in Step 8 of Example 129.

Example 132

[Chem. Fig. 76]

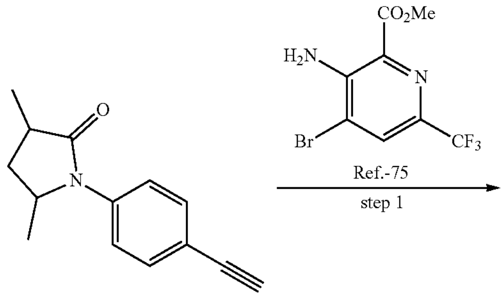

Ref.-135

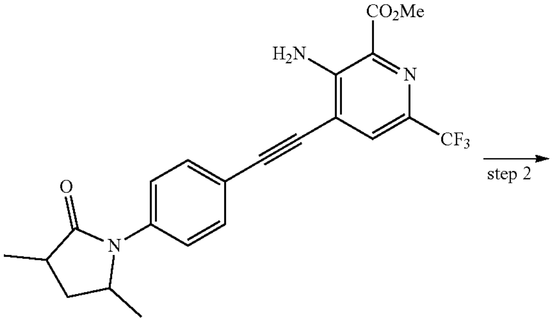

Ref.-139
diastereomeric pure
racemate

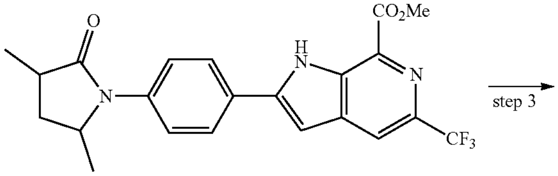

Ref.-140
diastereomeric pure
racemate

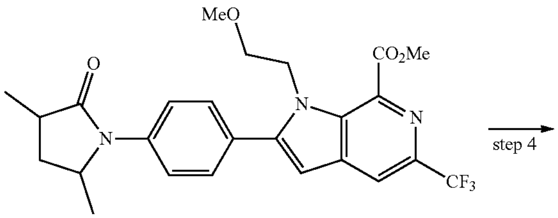

Ref.-141
diastereomeric pure
racemate

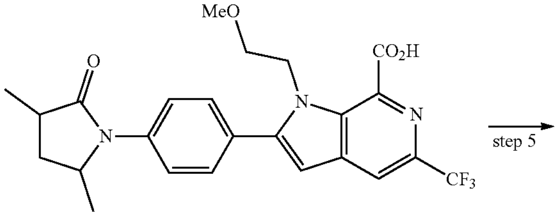

Ref.-142
diastereomeric pure
racemate

-continued

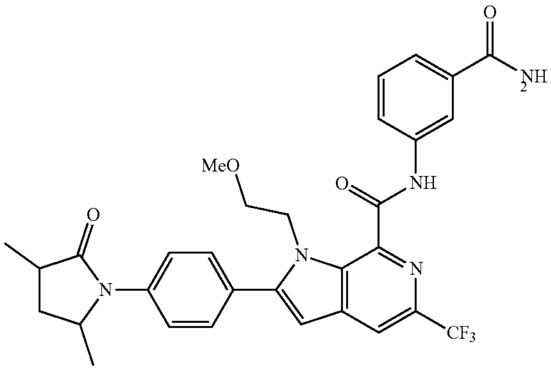

Ex.-132
diastereomeric pure
racemate

Step 1-5

Example Compound 132 (yield 16.6 mg) was obtained from reference synthesis example compound 135 and reference synthesis example compound 75 by the same method as in steps 3 to 7 of Example 23.

Example 133

[Chem. Fig. 77]

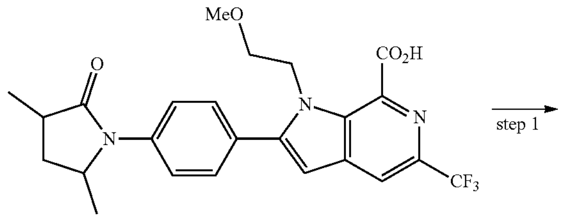

Ref.-142

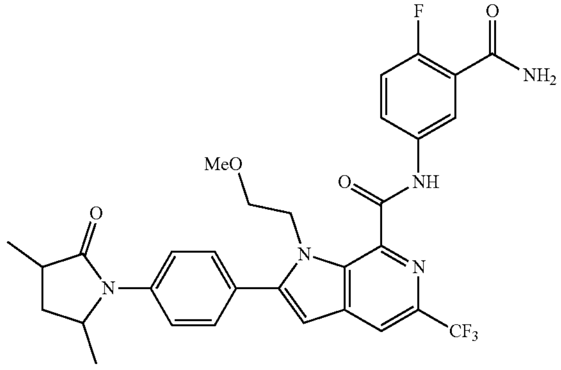

Ex.-133
diastereomeric pure
racemate

Step 1

Example Compound 133 (yield 18.4 mg) was obtained from reference synthesis example compound 142 by the same method as in Step 7 of Example 23.

Example 134

[Chem. Fig. 78]

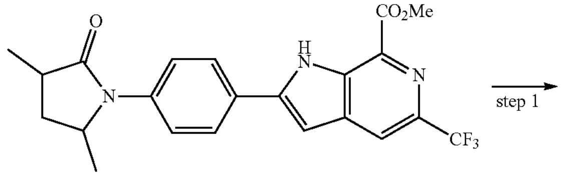

Ref.-140

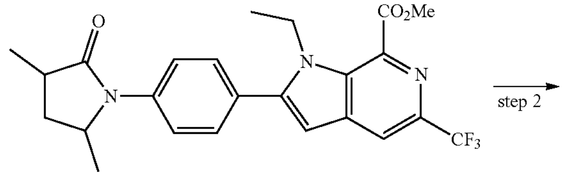

Ref.-143
diastereomeric pure
racemate

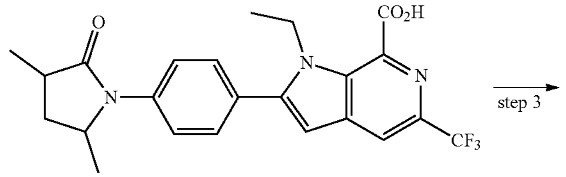

Ref.-144
diastereomeric pure
racemate

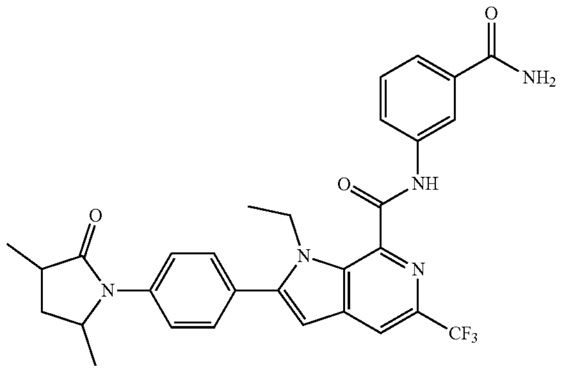

Ex.-134
diastereomeric pure
racemate

Step 1-3

Example Compound 134 (yield 23.3 mg) was obtained from reference synthesis example compound 140 by the same method as in steps 5 to 7 of Example 23.

Example 135

[Chem. Fig. 79]

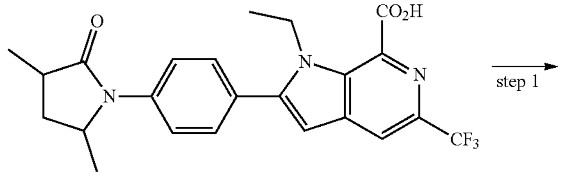

Ref.-144

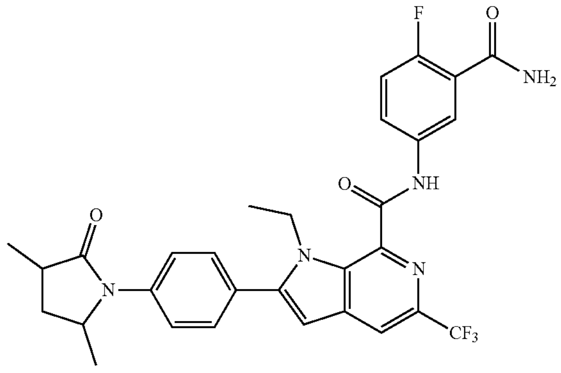

Ex.-135
diastereomeric pure
racemate

Step 1

Example Compound 135 (yield 18.4 mg) was obtained from reference synthesis example compound 144 by the same method as in Step 7 of Example 23.

Example 136

[Chem. Fig. 80]

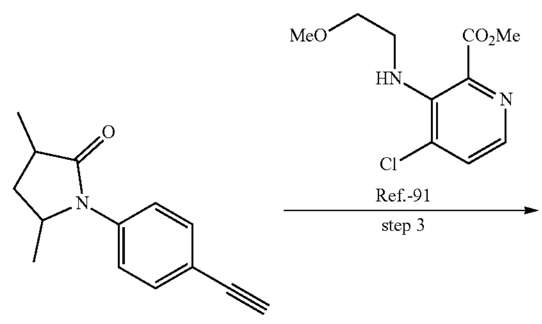

Ref.-135

-continued

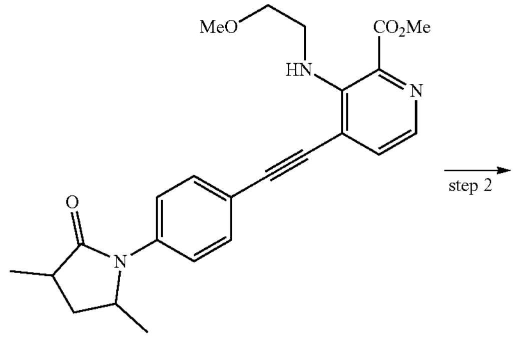

Ref.-145
diastereomeric pure
racemate

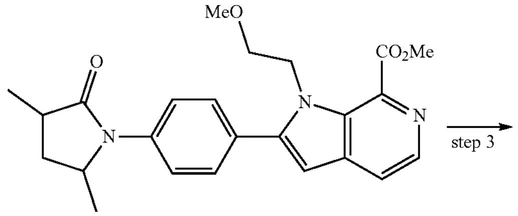

Ref.-146
diastereomeric pure
racemate

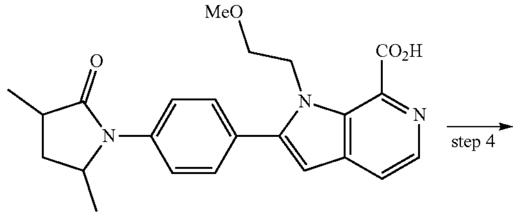

Ref.-147
diastereomeric pure
racemate

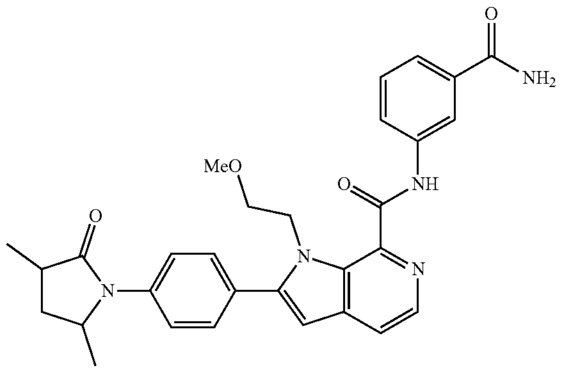

Ex.-136
diastereomeric pure
racemate

Step 1-4

Example Compound 136 (yield 8.6 mg) was obtained from reference synthesis example compound 135 and reference synthesis example compound 91 by the same method as in steps 2 to 5 of Example 26.

Example 137

[Chem. Fig. 81]

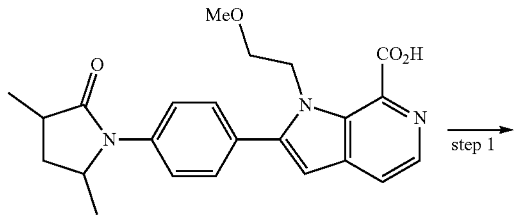

Ref.-147 step 1

-continued

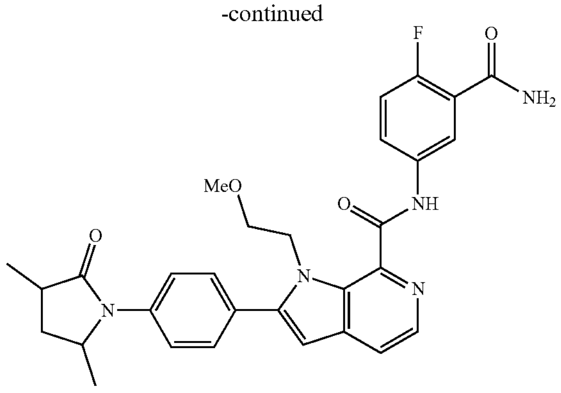

Ex.-137
diastereomeric pure
racemate

Step 1

Example Compound 137 (yield 9.5 mg) was obtained from reference synthesis example compound 147 by the same method as in Step 5 of Example 26.

Example Compounds 129 to 137 in the following table were produced according to the methods shown in Examples 129 to 137 described above, or similar methods. Furthermore, $^1$H-NMR data and/or LC/MS data of these Example compounds are shown in the table.

TABLE 3-1

| Ex. | Structure | Data |
|---|---|---|
| 129 | 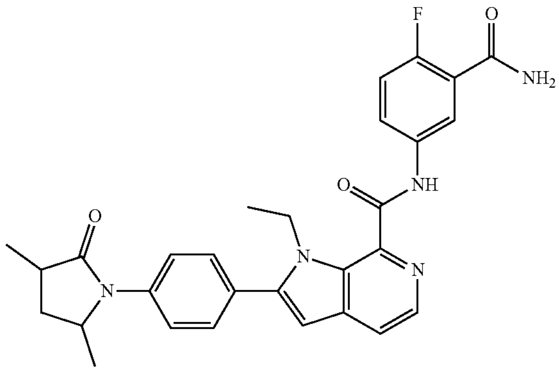 (diasrtereomeric pure, enantiomeric pure) | $^1$H-NMR (400 MHz, $CDCl_3$) δ: 0.96 (3H, t, J = 7.1 Hz), 1.30 (3H, d, J = 6.1 Hz), 1.36 (3H, d, J = 6.7 Hz), 1.39-1.47 (1H, m), 2.60-2.69 (2H, m), 4.24-4.30 (1H, m), 4.85 (2H, q, J = 7.1 Hz), 5.81 (1H, br s), 6.65 (1H, s), 6.72-6.75 (1H, m), 7.18-7.23 (1H, m), 7.47-7.59 (4H, m), 7.70-7.71 (1H, m), 8.19-8.22 (1H, m), 8.26-8.27 (1H, m), 8.30-8.34 (1H, m), 10.33 (1H, s). ESI-MS m/z: 514 $[M + H]^+$ |
| 130 | 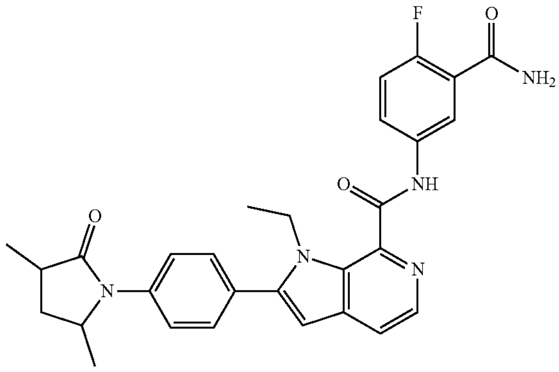 (diasrtereomeric pure, racemate) | $^1$H-NMR (400 MHz, DMSO-$d_6$) δ: 0.96-1.00 (3H, m), 1.15-1.35 (7H, m), 1.90-2.04 (1H, m), 2.55-2.86 (1H, m), 4.30-4.55 (3H, m), 6.76-6.78 (1H, m), 7.29-7.34 (1H, m), 7.55-7.83 (7H, m), 7.91-7.95 (1H, m), 8.16-8.18 (1H, m), 8.26-8.28 (1H, m), 10.98 (1H, s). ESI-MS m/z: 514 $[M + H]^+$ |

TABLE 3-1-continued
| Ex. | Structure | Data |
| --- | --- | --- |
| 131 | 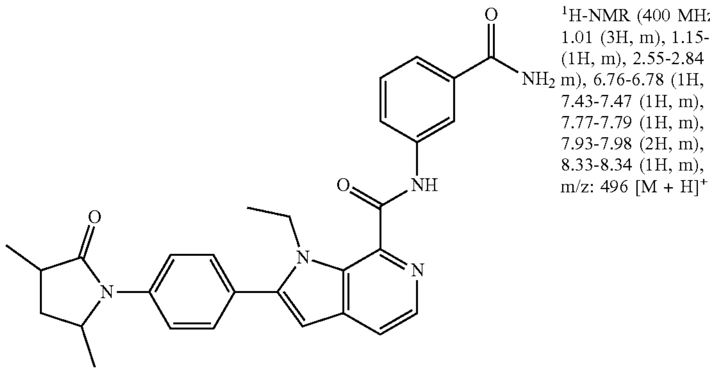 (diasrtereomeric pure, racemate) | $^{1}H$-NMR (400 MHz, DMSO-$d_6$) δ: 0.98-1.01 (3H, m), 1.15-1.35 (7H, m), 1.90-2.05 (1H, m), 2.55-2.84 (1H, m), 4.32-4.52 (3H, m), 6.76-6.78 (1H, m), 7.38 (1H, br s), 7.43-7.47 (1H, m), 7.54-7.63 (4H, m), 7.77-7.79 (1H, m), 7.81-7.83 (1H, m), 7.93-7.98 (2H, m), 8.26-8.28 (1H, m), 8.33-8.34 (1H, m), 10.92 (1H, s). ESI-MS m/z: 496 $[M + H]^+$ |
| 132 | 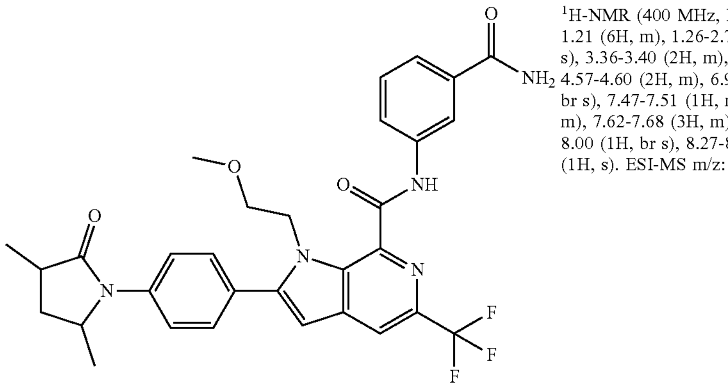 (diasrtereomeric pure, racemate) | $^{1}H$-NMR (400 MHz, DMSO-$d_6$) δ: 1.15-1.21 (6H, m), 1.26-2.73 (3H, m), 2.83 (3H, s), 3.36-3.40 (2H, m), 4.32-4.40 (1H, m), 4.57-4.60 (2H, m), 6.97 (1H, s), 7.00 (1H, br s), 7.47-7.51 (1H, m), 7.57-7.59 (2H, m), 7.62-7.68 (3H, m), 7.92-7.95 (1H, m), 8.00 (1H, br s), 8.27-8.31 (2H, m), 11.00 (1H, s). ESI-MS m/z: 594 $[M + H]^+$ |
| 133 | 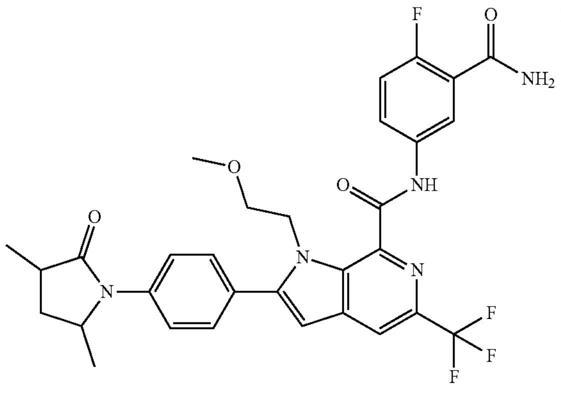 (diasrtereomeric pure, racemate) | ESI-MS m/z: 612 $[M + H]^+$ |

TABLE 3-2

| | | |
|---|---|---|
| 134 | 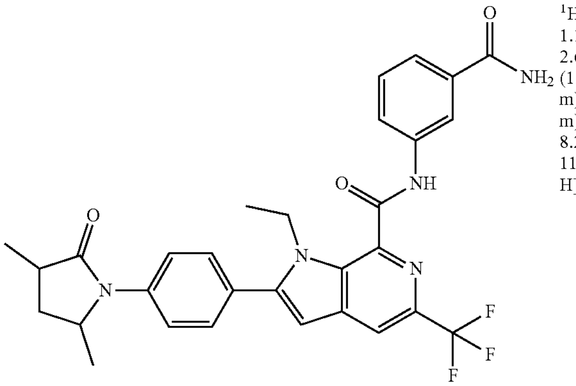<br>(diasrtereomeric pure, racemate) | $^1$H-NMR (400 MHz, DMSO-$d_6$) δ: 1.06-1.10 (3H, m), 1.17-1.22 (6H, m), 1.30-2.62 (3H, m), 4.32-4.41 (3H, m), 6.97 (1H, s), 7.40 (1H, br s), 7.45-7.51 (1H, m), 7.56-7.60 (2H, m), 7.62-7.68 (3H, m), 7.91-7.94 (1H, m), 8.01 (1H, br s), 8.25-8.27 (1H, m), 8.28-8.31 (1H, m), 11.08 (1H, s). ESI-MS m/z: 564 [M + H]$^+$ |
| 135 | 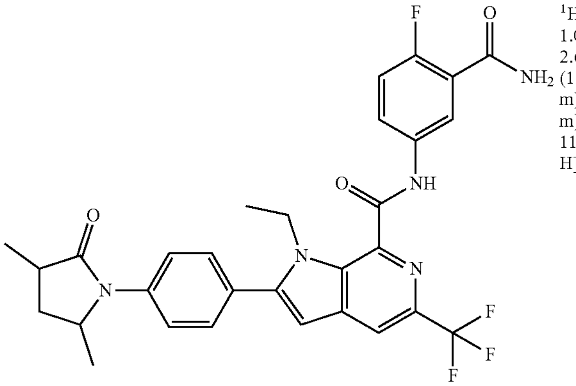<br>(diasrtereomeric pure, racemate) | $^1$H-NMR (400 MHz, DMSO-$d_6$) δ: 1.05-1.09(3H, m), 1.20-1.23 (6H, m), 1.31-2.63 (3H, m), 4.33-4.39 (3H, m), 6.97 (1H, s), 7.32-38 (1H, m), 7.58-7.67 (4H, m), 7.71-7.79 (2H, m), 7.90-7.95 (1H, m), 8.08-8.12 (1H, m), 8.30 (1H, s), 11.11 (1H, s). ESI-MS m/z: 582 [M + H]$^+$ |
| 136 | 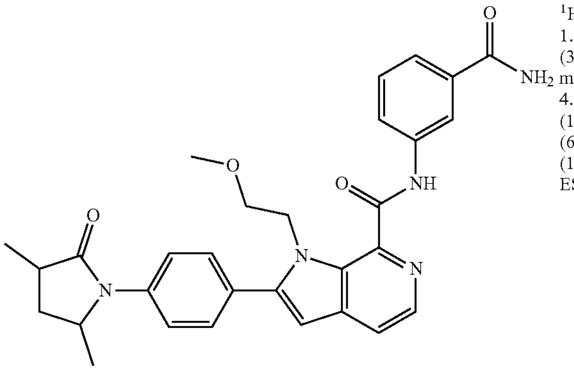<br>(diasrtereomeric pure, racemate) | $^1$H-NMR (400 MHz, DMSO-$d_6$) δ: 1.13-1.21 (6H, m), 1.29-2.62 (3H, m), 2.82 (3H, s), 3.35 (2H, m), 4.32-4.38 (1H, m),<br>4.62-4.68 (2H, m), 6.78 (1H, s), 7.38 (1H, br s), 7.43-7.48 (1H, m), 7.55-7.81 (6H, m), 7.93-7.99 (2H, m), 8.28-8.30 (1H, m), 8.34 (1H, s), 10.90 (1H, s). ESI-MS m/z: 526 [M + H]$^+$ |
| 137 | 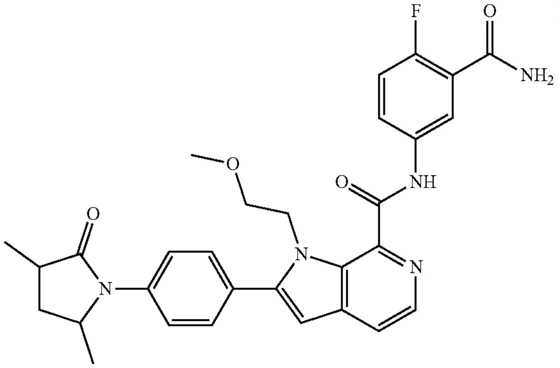<br>(diasrtereomeric pure, racemate) | ESI-MS m/z: 544 [M + H]$^+$ |

Example 138

[Chem Fig. 82]

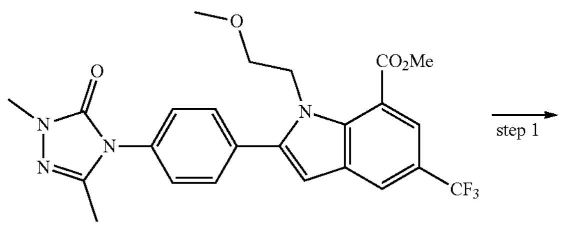

Ref.-35

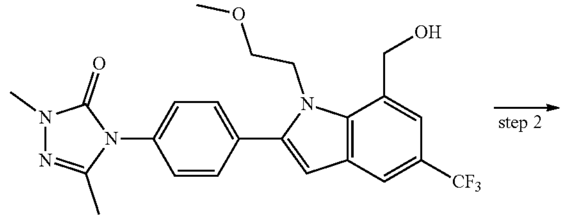

Ref.-148

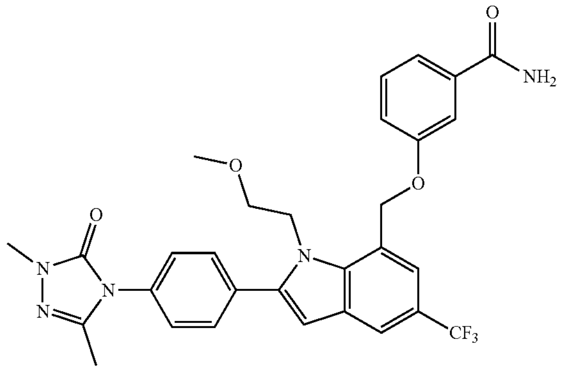

Ex.-138

Step 1

Reference synthesis example compound 35 (500 mg, 1.02 mmol) and THF (10 mL) were mixed, and then a 4 mol/L lithium borohydride/THF solution (1 mL) was added, followed by stirring at 60° C. for 4.5 hours. A saturated aqueous ammonium chloride solution and water were added to the cooled reaction solution, and the mixture was extracted using ethyl acetate. The extract was washed with saturated brine and dried over anhydrous sodium sulfate. The solvent was distilled off under reduced pressure, and then the residue was purified by silica gel column chromatography, slurry-washed with a mixed solution of ethylacetate/n-hexane (1/5), and the solid was collected by filtration to obtain reference synthesis example compound 148 (yield 405 mg).

Step 2

Reference synthesis example compound 148 (20.0 mg, 0.0434 mmol) and THF (220 μL) were mixed, and then 3-hydroxybenzamide (7.2 mg, 0.053 mmol), triphenylphosphine (13.7 mg, 0.0522 mmol) and 1.9 mol/L DIAD/toluene solution (27 μL) were added, and the mixture was stirred at room temperature for 16 hours. The solvent was distilled off under reduced pressure, the residue was purified by silica gel column chromatography, slurry-washed with ethyl acetate-normal hexane (1/3), and the precipitated solid was collected by filtration to obtain Example Compound 138 (yield 18.3 mg).

Example 139

[Chem. Fig. 83]

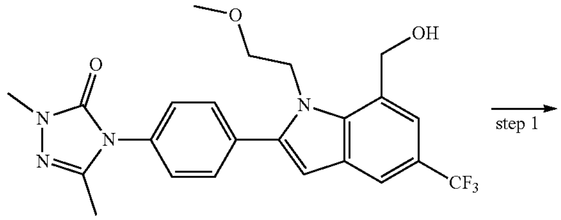

Ref.-148

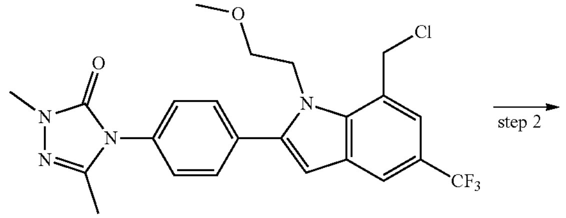

Ref.-149

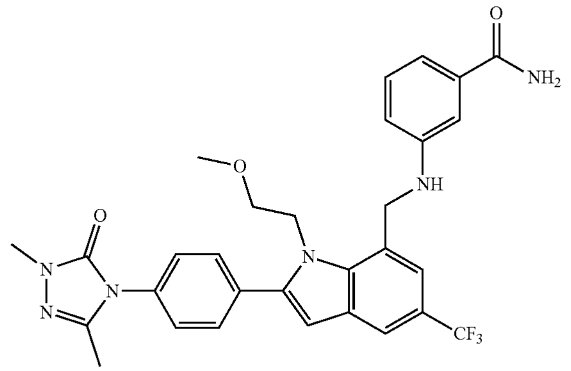

Ex.-139

Step 1

Reference synthetic example compound 148 (150 mg, 0.326 mmol) and dichloromethane (3.3 mL) were mixed, cooled with ice, triethyl amine (181 μL, 1.30 mmol) and methanesulfonylchloride (50.7 μL, 0.652 mmol) were added, and the mixture was stirred at room temperature for 16 hours. Water was added to the reaction solution, followed by extraction using chloroform. The extract was dried over anhydrous sodium sulfate, and the solvent was distilled off under reduced pressure. The residue was purified by silica gel column chromatography to obtain reference synthesis example compound 149 containing a portion of impurities (yield 165 mg).

Step 2

Reference synthesis example compound 149 (15 mg) obtained by the method described in Step 1 and partially containing an impurity was mixed with DMF (313 μL), triethylamine (13.1 μL, 0.0942 mmol) and 3-aminobenzamide (8.5 mg, 0.062 mmol) were added, and then the mixture was stirred at 80° C. for 16 hours. Water was added to the cooled reaction solution, and the mixture was extracted using ethyl acetate. The solvent was distilled off under reduced pressure, and then the residue was purified by silica gel column chromatography, slurry-washed with ethyl acetate/n-hexane (1/3), and the solid was collected by filtration to obtain Example Compound 139 (yield 6.2 mg).

Example Compounds 138 to 139 in the following table were produced according to the methods shown in Examples 138 to 139 described above. Furthermore, $^{1}$H-NMR data and LC/MS data of these example compounds are shown in the table.

TABLE 4
| Ex. | Structure | Data |
|---|---|---|
| 138 | 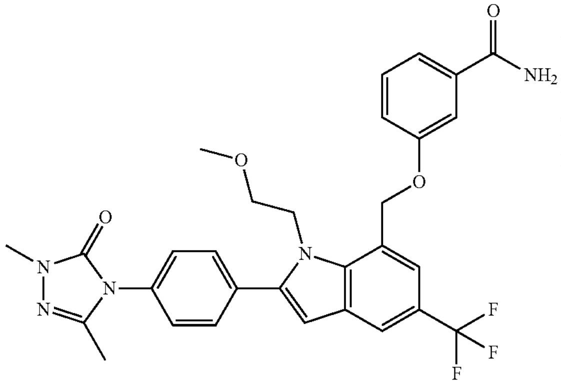 [SMILES: COCCn1c(-c2ccc(-n3c(C)nn(C)c3=O)cc2)cc2cc(C(F)(F)F)cc(COc3cccc(C(N)=O)c3)c21] | $^1$H-NMR (400 MHz, $CDCl_3$) δ: 2.23 (3H, s), 3.03 (3H, s), 3.35 (2H, t, J = 5.6 Hz), 3.51 (3H, s), 4.50 (2H, t, J = 5.7 Hz), 5.51 (2H, s), 5.58 (1H, s), 6.09 (1H, s), 6.71 (1H, s), 7.21 (1H, m), 7.40-7.45 (4H, m), 7.50 (1H, d, J = 1.5 Hz), 7.58 (1H, d, J = 1.6 Hz), 7.64 (2H, d, J = 8.4 Hz), 7.96 (1H, s). ESI-MS m/z: 580 [M + H]$^+$ |
| 139 | 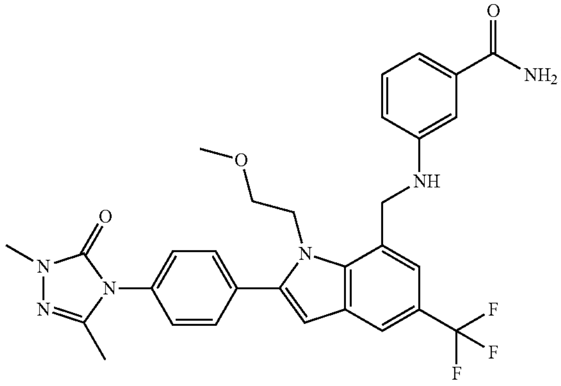 [SMILES: COCCn1c(-c2ccc(-n3c(C)nn(C)c3=O)cc2)cc2cc(C(F)(F)F)cc(CNc3cccc(C(N)=O)c3)c21] | $^1$H-NMR (400 MHz, $CDCl_3$) δ: 2.23 (3H, s), 3.05 (3H, s), 3.34 (2H, t, J = 5.6 Hz), 3.51 (3H, s), 4.31 (1H, s), 4.52 (2H, t, J = 5.6 Hz), 4.71 (2H, s), 5.53 (1H, s), 6.08 (1H, s), 6.71 (1H, s), 6.85 (1H, dd, J = 1.8, 8.1 Hz), 7.12 (1H, d, J = 7.6 Hz), 7.25-7.31(2H, m), 7.42-7.44 (3H, m), 7.63 (2H, d, J = 8.5 Hz), 7.91 (1H, s). ESI-MS m/z: 579 [M + H]$^+$ |
Example 140
[Chem. Fig. 84]
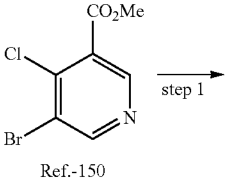
Ref.-150
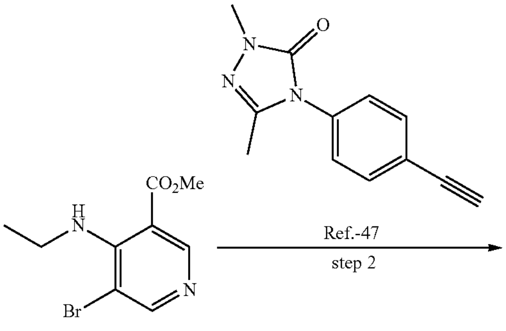
Ref.-151
-continued
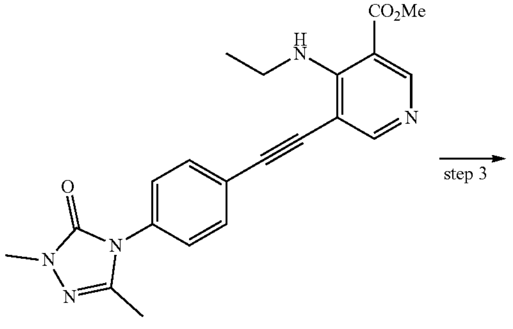
Ref.-152
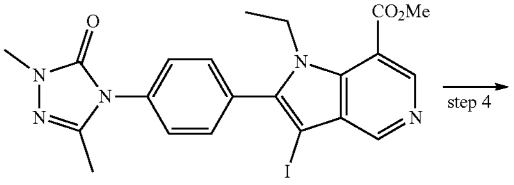
Ref.-153

-continued

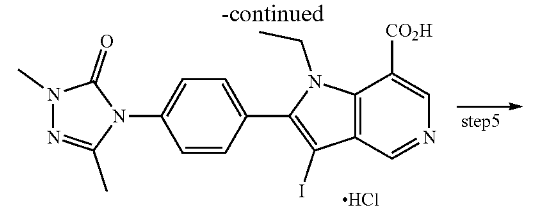

Ref.-154

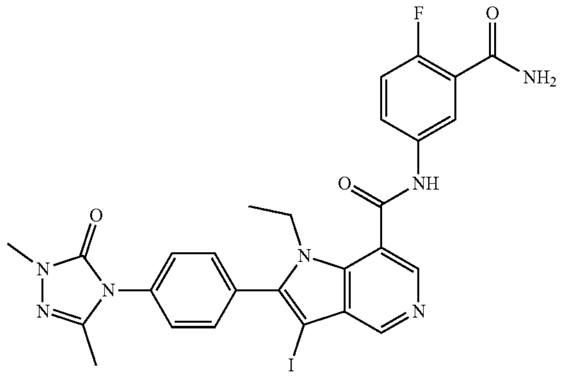

Ex.-140

Step 1

Reference synthesis example compound 150 (300 mg, 1.20 mmol) and DMSO (5 mL) were mixed, and then DIPEA (618 μL, 3.60 mmol) and 2.0 mol/L of ethylamine-THF (900 μL) were added, followed by stirring at 70° C. for 3 hours. Water was added to the cooled reaction solution, and the mixture was extracted using ethyl acetate. The extract was washed with saturated brine and dried over anhydrous sodium sulfate. The solvent was distilled off under reduced pressure to obtain reference synthesis example compound 151 partially containing an impurity (yield 319 mg).

Step 2

Reference synthesis example compound 151 (150 mg) containing an impurity obtained by the method described in Step 1 was mixed with THF (2.5 mL), and then reference synthesis example compound 47 (183 mg, 0.858 mmol), triethyl amine (241 μL, 1.73 mmol), cuprous iodide (11 mg, 0.058 mmol), and [1,1'-bis(diphenylphosphino)ferrocene] dichloropalladium (II) (21.2 mg, 0.029 mmol) were added, followed by stirring at 90° C. for 18 hours under an argon environment. Water was added to the cooled reaction solution, and the mixture was extracted using chloroform. The extract was dried over anhydrous sodium sulfate, and the solvent was distilled off under reduced pressure. The residue was purified by silica gel column chromatography to obtain reference synthesis example compound 152 (yield 224 mg).

Step 3

Reference synthesis example compound 152 (50.0 mg, 0.128 mmol) and DMF (1 mL) were mixed, then cuprous iodide (15 mg, 0.079 mmol) was added, and the mixture was stirred at 110° C. for 18 hours under an argon environment. Water was added to the cooled reaction solution, and the mixture was extracted using ethyl acetate. The extract was dried over anhydrous sodium sulfate, and the solvent was distilled off under reduced pressure. The residue was purified by silica gel column chromatography to obtain reference synthesis example compound 153 (yield 38 mg).

Step 4

Reference synthetic example compound 153 (34.0 mg, 0.0657 mmol), methanol (0.5 mL) and THF (0.5 mL) were mixed, then 4 mol/L aqueous sodium hydroxide (164 μL) was added, and the mixture was stirred at 60° C. for 4 hours.

2 mol/L HCl and water were added to the cooled reaction solution, and the solvent was distilled off under reduced pressure to obtain reference synthesis example compound 154 as a mixture with sodium chloride (yield 72 mg).

Step 5

A mixture (72 mg) of reference synthesis example compound 154 obtained by the method described in Step 4 and sodium chloride was mixed with acetonitrile (1 mL), and then 5-amino-2-fluorobenzamide (14.8 mg, 0.0960 mmol), 1-methylimidazole (30.3 μL, 0.384 mmol), and TCFH (35.9 mg, 0.128 mmol) were sequentially added, followed by stirring at 40° C. for 1.5 hours. The reaction solution was diluted with water, 1 mol/L HCl was added, and then extraction was performed using ethyl acetate. The extract was dried over anhydrous sodium sulfate, and the solvent was distilled off under reduced pressure. The residue was purified by silica gel column chromatography and then slurry-washed with a mixed solvent of n-hexane/ethyl acetate (3/1) to obtain Example Compound 140 (yield 30.1 mg).

Example 141

[Chem. Fig. 85]

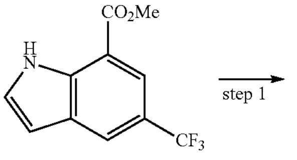

Ref.-32

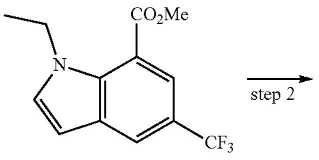

Ref.-155

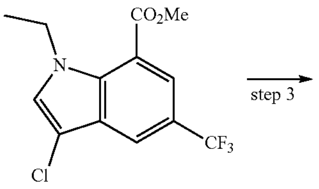

Ref.-156

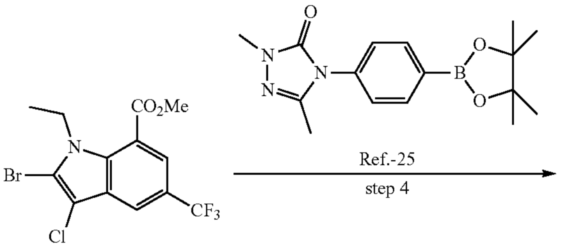

Ref.-157

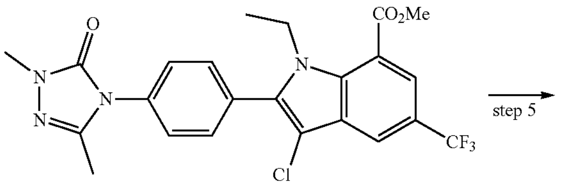

Ref.-158

-continued

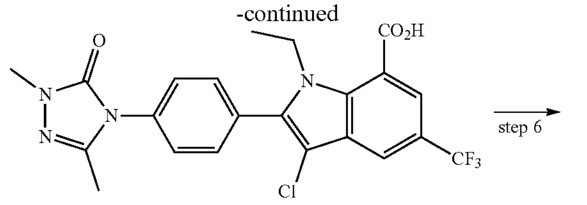

Ref.-159

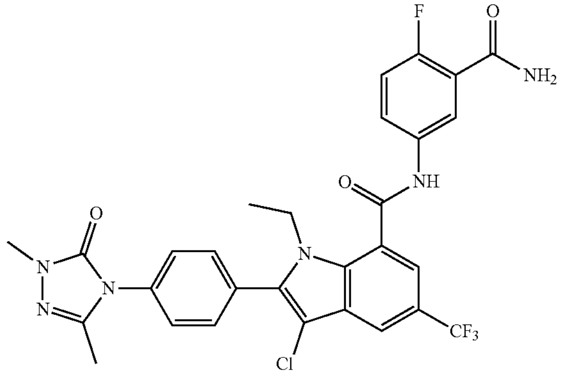

Ex.-141

Step 1

Reference synthesis example compound 32 (255 mg, 1.05 mmol) and DMF (5 mL) were mixed, the mixture was ice-cooled, sodium hydride (60% in oil) (54.5 mg, 1.36 mmol) was added, and the mixture was stirred for 10 minutes. Ethyl iodide (118 μL, 1.475 mmol) was added to the reaction solution, and the mixture was stirred at room temperature for 1 hour. The reaction solution was added dropwise to an ice-cooled saturated aqueous ammonium chloride solution, diluted with water, and extracted using ethyl acetate. Normal hexane was added to the extract, and the mixture was washed successively with water and saturated brine, and dried over anhydrous sodium sulfate. The solvent was distilled off under reduced pressure, and then the residue was purified by silica gel column chromatography to obtain reference synthesis example compound 155 (yield 214 mg).

Step 2

Reference synthesis example compound 155 (212 mg, 0.782 mmol) and dichloromethane (5 mL) were mixed, cooled with ice, and a solution of NCS (135 mg, 1.01 mmol) in dichloromethane (1 mL) was added dropwise, followed by stirring at room temperature for 3 hours. DMF (5 mL) was added, and the mixture was stirred at 60° C. for 3 hours. The cooled reaction solution was diluted with water and extracted using chloroform. The extract was dried over anhydrous sodium sulfate, and the solvent was distilled off under reduced pressure. The residue was purified by silica gel column chromatography to obtain reference synthesis example compound 156 (yield 170 mg).

Step 3

Reference synthetic example compound 156 (168 mg, 0.550 mmol) and tetrachloromethane (5 mL) were mixed, followed by ice-cooling, adding NBS (118 mg, 0.663 mmol), and stirring at 60° C. for 13 hours. Water was added to the cooled reaction solution, and the mixture was extracted using chloroform. The extract was dried over anhydrous sodium sulfate, and the solvent was distilled off under reduced pressure. The residue was purified by silica gel column chromatography to obtain reference synthesis example compound 157 (yield 117 mg).

Step 4-6

Example Compound 141 (yield 10.2 mg) was obtained from reference synthesis example compound 157 (115 mg, 0.300 mmol) by the same method as in Steps 5 to 7 of Example 17.

Example Compounds 140 to 143 in the following table were produced by the methods shown in Examples 140 to 141 described above, or a similar method. Furthermore, $^{1}$H-NMR data and/or LC/MS data of these Example 10 compounds are shown in the table.

TABLE 5

| Ex. | Structure | Data |
| --- | --- | --- |
| 140 | 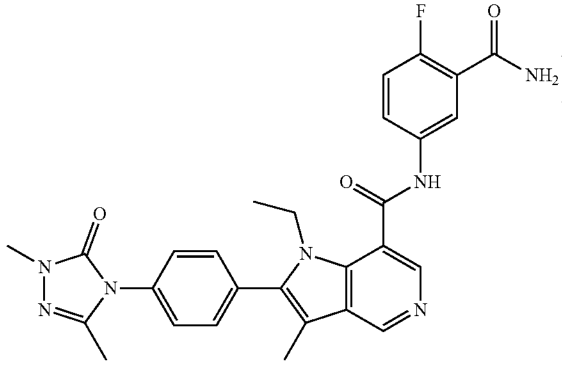 | $^{1}$H-NMR (400 MHz, DMSO-$d_6$) δ: 1.00-1.03 (3H, m), 2.18 (3H, s), 3.38 (3H, s), 4.19-4.24 (2H, m), 7.30-7.35 (1H, m), 7.68-7.74 (6H, m), 7.86-7.90 (1H, m), 8.06-8.08 (1H, m), 8.57 (1H, s), 8.77 (1H, s), 11.05 (1H, s). ESI-MS m/z: 640 [M + H]$^+$ |

TABLE 5-continued
| Ex. | Structure | Data |
|---|---|---|
| 141 | 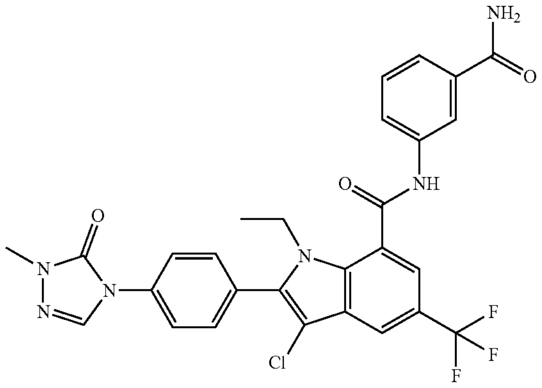 [SMILES: CCn1c(-c2ccc(-n3cnn(C)c3=O)cc2)c(Cl)c2cc(C(F)(F)F)cc(C(=O)Nc3cccc(C(N)=O)c3)c21] | $^{1}$H-NMR (400 MHz, DMSO-$d_6$) δ: 1.01 (3H, t, J = 7.1 Hz), 3.42 (3H, s), 4.20-4.24 (2H, m), 7.40 (1H, br s), 7.44-7.48 (1H, m), 7.64 (1H, d, J = 8.0 Hz), 7.72-7.75 (2H, m), 7.79-7.80 (1H, m), 7.89-7.91 (1H, m), 7.95-7.99 (3H, m), 8.05 (1H, br s), 8.23-8.24 (1H, m), 8.61 (1H, s), 11.06 (1H, s). ESI-MS m/z: 583 $[M + H]^+$ |
| 142 | 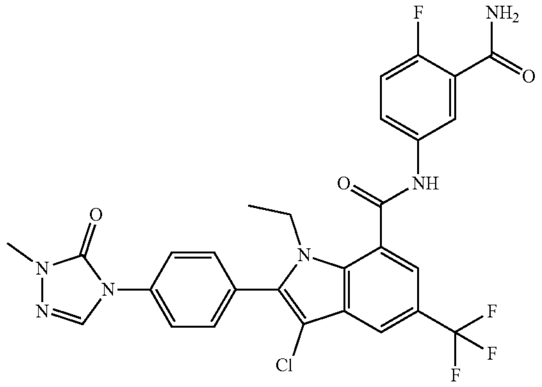 [SMILES: CCn1c(-c2ccc(-n3cnn(C)c3=O)cc2)c(Cl)c2cc(C(F)(F)F)cc(C(=O)Nc3ccc(F)c(C(N)=O)c3)c21] | $^{1}$H-NMR (400 MHz, DMSO-$d_6$) δ: 1.01 (3H, t, J = 7.1 Hz), 3.43 (3H, s), 4.19-4.23 (2H, m), 7.30-7.35 (1H, m), 7.72-7.74 (4H, m), 7.80-7.81 (1H, m), 7.86-7.89 (1H, m), 7.95-7.97 (2H, m), 8.06-8.07 (2H, m), 8.61 (1H, s), 11.07 (1H, s). ESI-MS m/z: 601 $[M + H]^+$ |
| 143 | 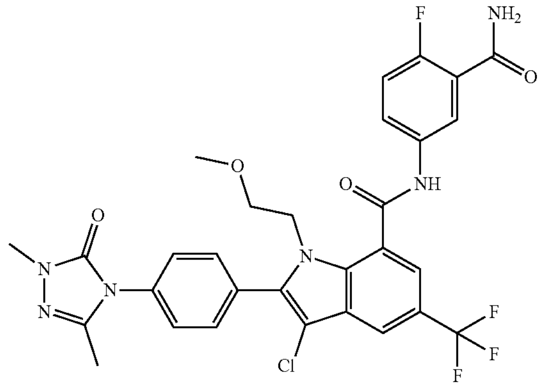 [SMILES: COCCn1c(-c2ccc(-n3c(C)nn(C)c3=O)cc2)c(Cl)c2cc(C(F)(F)F)cc(C(=O)Nc3ccc(F)c(C(N)=O)c3)c21] | ESI-MS m/z: 645 $[M + H]^+$ |

Example 144

[Chem. Fig. 86]

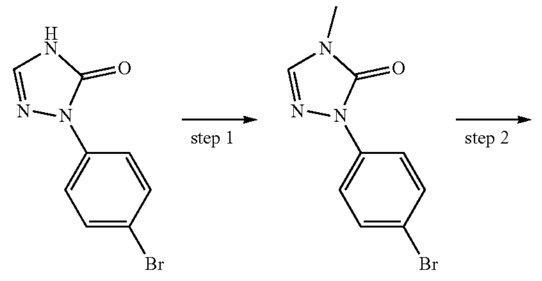

Ref.-160 Ref.-161

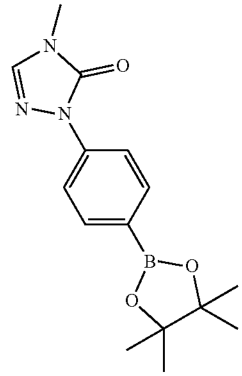

Ref.-162

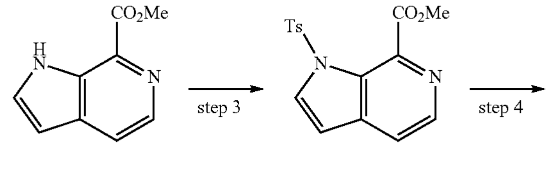

Ref.-163 Ref.-164

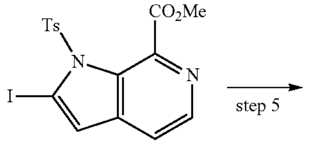

Ref.-165

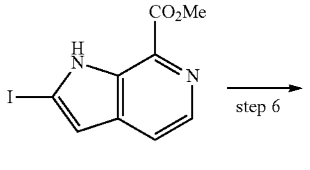

Ref.-166

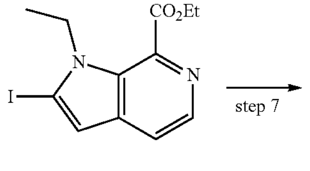

Ref.-167

-continued

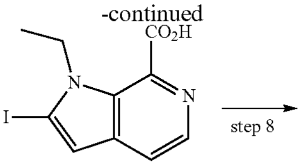

Ref.-168

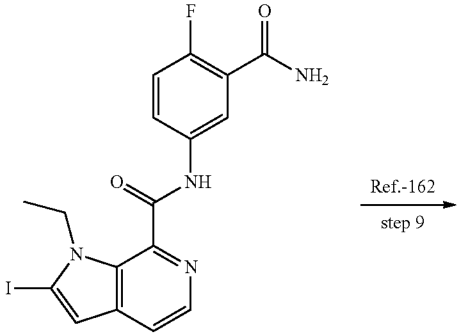

Ref.-169

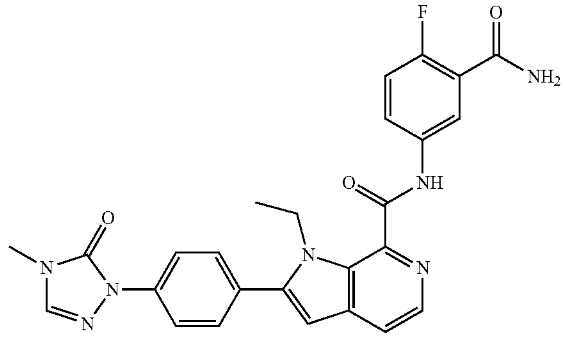

Ex.-144

Step 1-2

Reference synthesis example compound 162 was obtained from reference synthesis example compound 160 by the same method as in steps 1 and 2 of Example 15.

Step 3

Reference synthetic example compound 163 (3.00 g, 17.0 mmol) and DMF (85 mL) were mixed, the mixture was ice-cooled, sodium hydride (60% in oil) (885 mg, 22.1 mmol) was added, and the mixture was stirred for 30 minutes. p-toluenesulfonylchloride (4.87 g, 25.5 mmol) was added to the reaction solution, and then the mixture was stirred at room temperature for 2 hours. A saturated aqueous ammonium chloride solution was added to the ice-cooled reaction solution, and the mixture was extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 164 (yield 2.36 g).

Step 4

Reference synthesis example compound 164 (2.36 g, 7.14 mmol) and THF (36 mL) were mixed and then cooled to −78° C., and then LDA/n-hexane-THF (1.09 mol/L, 9.2 mL) was added, followed by stirring at −78° C. for 30 minutes. Iodine (2.72 g, 10.7 mmol) was added to the reaction solution, and the mixture was stirred at −78° C. for 30 minutes, warmed to room temperature, and stirred for 1 hour. The reaction solution was ice-cooled, saturated aqueous ammonium chloride solution was added, and the mixture was extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 165 (yield 1.53 g).

Step 5

Reference synthesis example compound 165 (1.20 g, 2.63 mmol) and THF (13 mL) were mixed, then cooled with ice, sodium methoxide/methanol (5 mol/L, 2.6 mL) was added, and the mixture was stirred under ice cooling for 1 hour. A saturated aqueous ammonium chloride solution was added to the reaction solution, and the mixture was extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 166 (yield 429 mg).

Step 6

Reference synthetic example compound 166 (429 mg) and DMF (14 mL) were mixed, the mixture was ice-cooled, sodium hydride (60% in oil) (85.2 mg, 2.13 mmol) was added, and the mixture was stirred under ice-cooling for 20 minutes. Ethyl iodide (341 μL, 4.26 mmol) was added to the reaction solution, and the mixture was stirred at room temperature for 2 hours. A saturated aqueous ammonium chloride solution was added to the ice-cooled reaction solution, and the mixture was extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 167 (yield 168 mg).

Step 7

Reference synthetic example compound 167 (168 mg, 0.488 mmol), methanol (1.2 mL) and THF (1.2 mL) were mixed, and then 4 mol/L aqueous sodium hydroxide (610 μL) was added, followed by stirring at room temperature for 12 hours. A 10% aqueous citric acid solution was added to the reaction solution and stirred, and then the solvent was distilled off under reduced pressure. A small amount of ethanol was added to the residue, and the precipitate was collected by filtration to obtain reference synthesis example compound 168 (yield 112 mg).

Step 8

Reference synthetic example compound 168 (100 mg, 0.316 mmol), 5-amino-2-fluorobenzamide (73.1 mg, 0.474 mmol), and acetonitrile (1.6 mL) were mixed, 1-methylimidazole (100 μL, 1.27 mmol) and TCFH (178 mg, 0.634 mmol) were added, and then the mixture was stirred at room temperature for 16 hours. Water was added to the reaction solution, and the precipitate was collected by filtration to obtain reference synthesis example compound 169 (yield 97.3 mg).

Step 9

Reference synthesis example compound 169 (20.0 mg, 0.0442 mmol), 1,4-dioxane (442 μL) and water (58 μL) were mixed, and then reference synthesis example compound 162 (20.0 mg, 0.0663 mmol), cesium carbonate (21.6 mg, 0.0663 mmol), XPhos (1.1 mg, 0.0023 mmol), and XPhos-palladium (crotyl) chloride (1.5 mg, 0.0022 mmol) were added, followed by stirring at 90° C. for 2 hours. Water was added to the cooled reaction solution, and the mixture was extracted using ethyl acetate. The extract was washed successively with water and saturated brine, and then dried over anhydrous sodium sulfate. The solvent was distilled off under reduced pressure, and then the residue was purified by silica gel column chromatography to obtain Example Compound 144 (yield 13.6 mg).

Example 145

[Chem. Fig. 87]

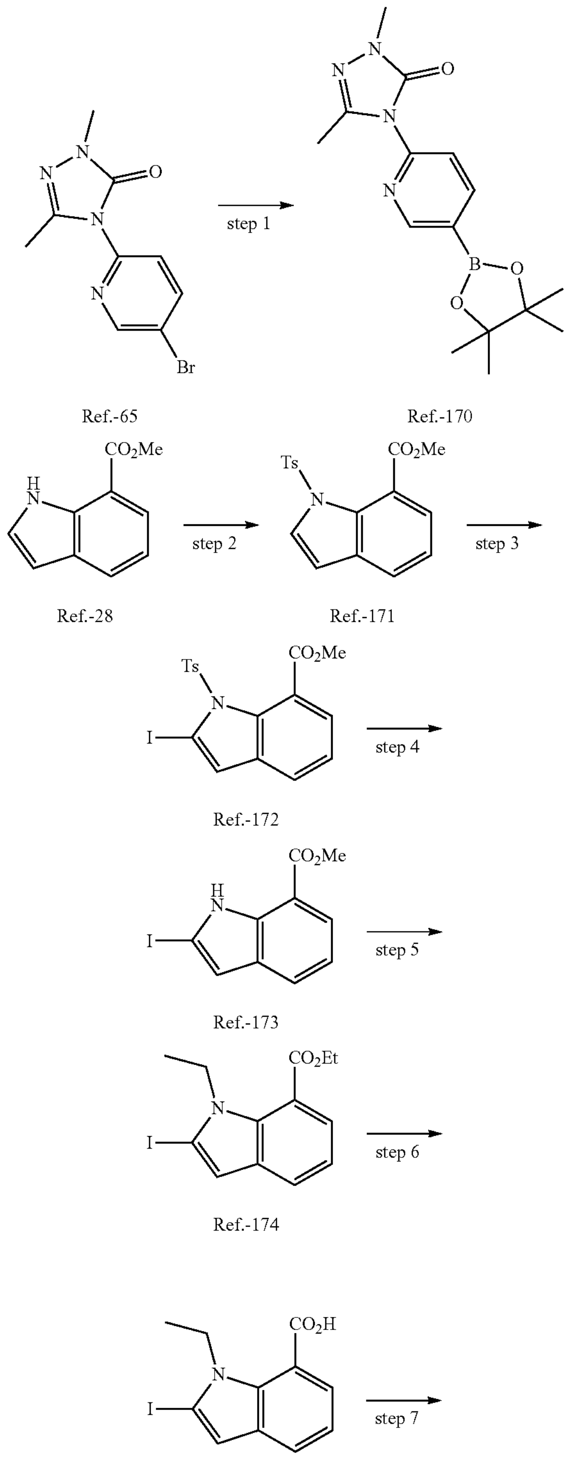

Ref.-65

Ref.-170

Ref.-28

Ref.-171

Ref.-172

Ref.-173

Ref.-174

Ref.-175

-continued
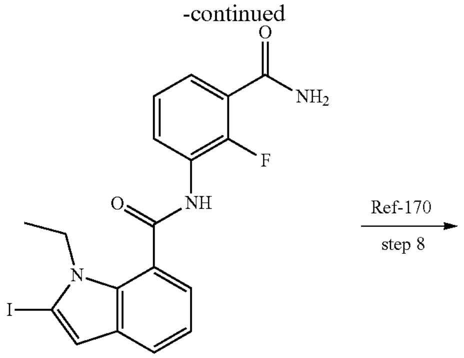
Ref.-176
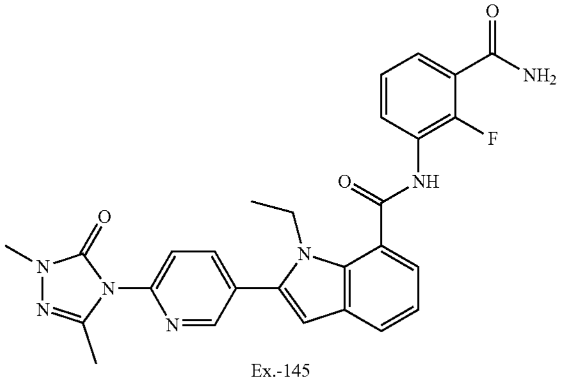
Ex.-145
Step 1
Reference synthesis example compound 170 (yield 110 mg) was obtained from reference synthesis example compound 65 (100 mg, 0.372 mmol) by the same method as in Step 2 of Example 15.
Step 2-8
Example Compound 145 (yield 15.6 mg) was obtained from reference synthesis example compound 28 by the same method as in steps 3 to 9 of Example 144.
Example 146
[Chem. Fig. 88]
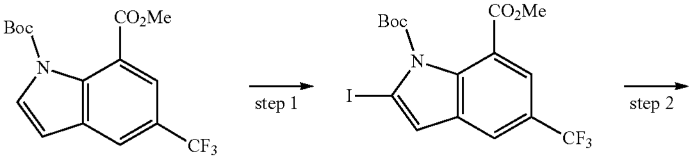
Ref.-119 Ref.-177
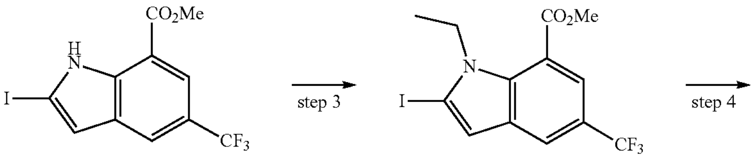
Ref.-178 Ref.-179
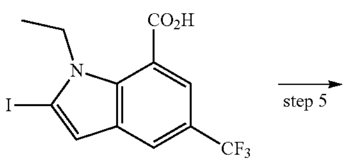
Ref.-180

-continued

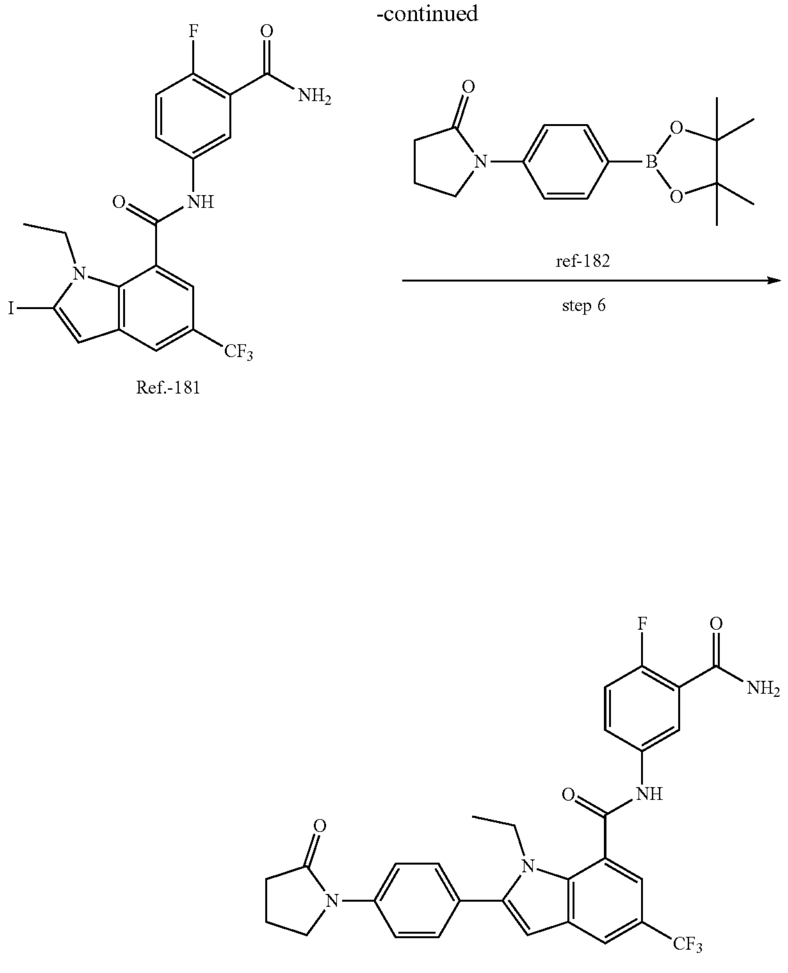

Ref.-181

Ex.-146

Step 1

Reference synthesis example compound 119 (10.0 g, 29.1 mmol) and THF (290 mL) were mixed and then cooled to −20° C., and LDA/n-hexane-THF (1.09 mol/L) (29 mL) was added, followed by stirring at −20° C. for 30 minutes. Iodine (8.87 g, 34.9 mmol) was added to the reaction solution, and the mixture was stirred at −20° C. for 1 hour, warmed to room temperature, and stirred for 2 hours. A saturated aqueous ammonium chloride solution was added to the reaction solution, and the mixture was extracted using ethyl acetate. The organic layer was washed successively with water and saturated brine, and dried over anhydrous sodium sulfate. The solvent was distilled off under reduced pressure, and then the residue was purified by silica gel column chromatography to obtain reference synthesis example compound 177 (yield 7.41 g).

Step 2

Reference synthesis example compound 177 (7.41 g, 15.8 mmol) and 1,1, 1,3,3,3-hexafluoro-2-propanol (34 mL) were mixed and stirred at 150° C. for 30 minutes under microwave irradiation. After allowing to cool, the solvent was distilled off under reduced pressure to obtain reference synthesis example compound 178 (yield 5.43 g).

Step 3

Reference synthetic example compound 178 (5.00 g, 13.5 mmol) and DMF (68 mL) were mixed, the mixture was ice-cooled, sodium hydride (60% in oil) (813 mg, 20.3 mmol) was added, and the mixture was stirred for 10 minutes. Ethyl iodide (5.4 mL, 68 mmol) was added to the reaction solution, and the mixture was stirred at room temperature for 2 hours. A saturated aqueous ammonium chloride solution was added to the ice-cooled reaction solution, and the mixture was extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 179 (yield 4.62 g).

Step 4-6

Example Compound 146 (yield 29.5 mg) was obtained from reference synthesis example compound 179 by the same method as in Steps 7 to 9 of Example 144.

Example 147

[Chem. Fig. 89]

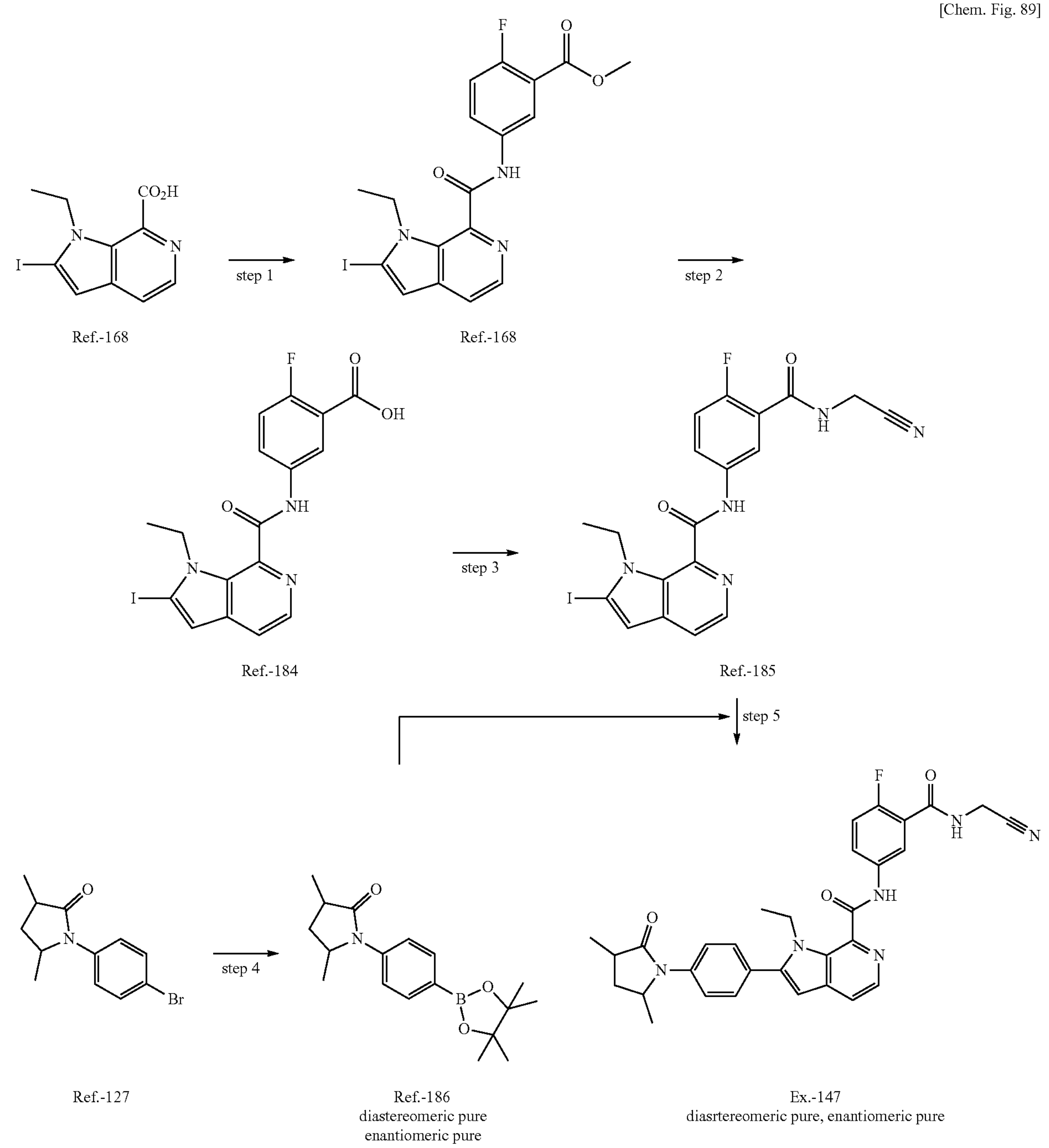

Ref.-168

Ref.-168

Ref.-184

Ref.-185

Ref.-127

Ref.-186
diastereomeric pure
enantiomeric pure

Ex.-147
diasrtereomeric pure, enantiomeric pure

Step 1

Reference synthesis example compound 183 (yield 142 mg) was obtained from reference synthesis example compound 168 and methyl 5-amino-2-fluorobenzoate by the same method as in Step 8 of Example 144.

Step 2

Reference synthetic example compound 183 (142 mg, 0.304 mmol), methanol (1.5 mL) and THF (1.5 mL) were mixed, and then 4 mol/L aqueous sodium hydroxide (380 μL) was added, followed by stirring at room temperature for 2 hours. 2 mol/L hydrochloric acid (1.2 mL) was added to the reaction solution, and the solvent was distilled off under reduced pressure to obtain reference synthesis example compound 184 as a mixture of sodium chloride (yield 254 mg).

Step 3

A sodium chloride mixture (254 mg) of reference synthesis example compound 184 obtained by the method of Step 2 was mixed with acetonitrile (5.0 mL), and 2-aminoacetonitrile hydrochloride (33.8 mg, 0.365 mmol), TCFH (171 mg, 0.609 mmol) and 1-methylimidazole (120 μL, 1.52 mmol) were added, followed by stirring at room temperature overnight. Water was added to the reaction solution, followed by extraction using ethyl acetate. The extract was washed with saturated brine and dried over anhydrous sodium sulfate. The solvent was distilled off under reduced pressure, and then the residue was purified by silica gel column chromatography to obtain reference synthesis example compound 185 (yield 114 mg).

Step 4

Reference synthesis example compound 186 (yield 103 mg) was obtained from reference synthesis example compound 127 (100 mg, 0.373 mmol) by the same method as in Step 2 of Example 144.

Step 5

Reference synthesis example compound 185 (15.0 mg, 0.0305 mmol), 1,4-dioxane (2.0 mL) and water (400 μL) were mixed and degassed, and then reference synthesis example compound 186 (19.2 mg, 0.0609 mmol), cesium carbonate (19.9 mg, 0.0611 mmol), and [1,1'-bis(diphenylphosphino)ferrocene]dichloropalladium (II) (4.5 mg, 0.0062 mmol) were added and stirred at 90° C. for 2 hours. A saturated aqueous ammonium chloride solution was added to the reaction solution, and the mixture was extracted using ethyl acetate. The extract was washed with saturated brine and dried over anhydrous sodium sulfate. The solvent was distilled off under reduced pressure, and then the residue was purified by silica gel column chromatography to obtain Example Compound 147 (yield 12.1 mg).

Example Compounds 144 to 156 in the following table were produced according to the methods shown in Examples 144 to 147 described above or a similar method. Furthermore, $^1$H-NMR data and/or LC/MS data of these Example compounds are shown in the table.

TABLE 6-1

| Ex. | Structure | Data |
|---|---|---|
| 144 | 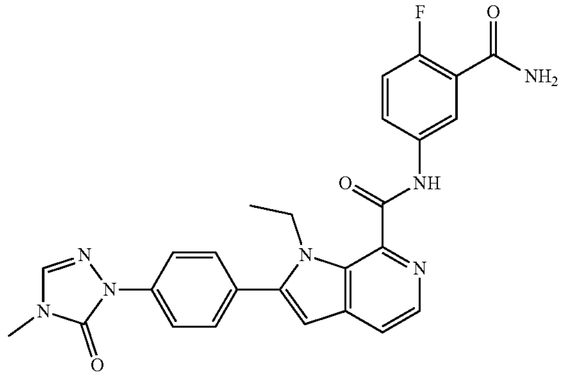 | $^1$H-NMR (400 MHz, DMSO-$d_6$) δ: 0.98 (3H, t, J = 7.1 Hz), 3.29 (3H, s), 4.42 (2H, q, J = 7.1 Hz), 6.79 (1H, s), 7.31 (1H, dd, J = 9.1, 9.9 Hz), 7.69-7.71 (3H, m), 7.75 (1H, br s), 7.79 (1H, d, J = 5.3 Hz), 7.93 (1H, m), 8.10 (2H, d, J = 8.8 Hz), 8.17 (1H, dd, J = 2.8, 6.4 Hz), 8.27-8.28 (2H, m), 10.99 (1H, br s). ESI-MS m/z: 500 [M + H]$^+$ |
| 145 | 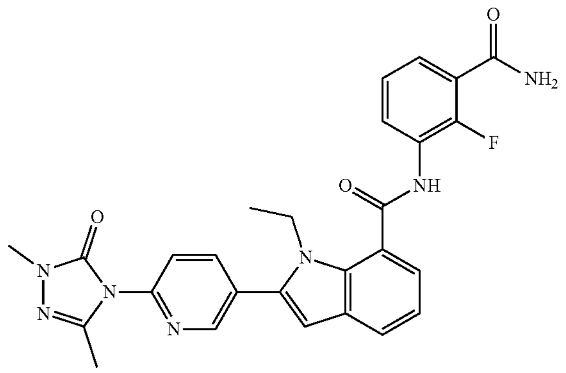 [SMILES: CCn1c(-c2ccc(-n3c(C)nn(C)c3=O)nc2)cc2cccc(C(=O)Nc3cccc(C(N)=O)c3F)c21] | $^1$H-NMR (400 MHz, DMSO-$d_6$) δ: 1.05 (3H, t, J = 6.9 Hz), 2.39 (3H, s), 3.38 (3H, s), 4.33 (2H, q, J = 6.9 Hz), 6.86 (1H, s), 7.23 (1H, m), 7.30 (1H, m), 7.44-7.50 (2H, m), 7.66 (1H, br s), 7.80-7.84 (3H, m), 7.90 (1H, d, J = 8.4 Hz), 8.24 (1H, dd, J = 2.4, 8.4 Hz), 8.75 (1H, m), 10.60 (1H, br s). ESI-MS m/z: 514 [M + H]$^+$ |
| 146 | 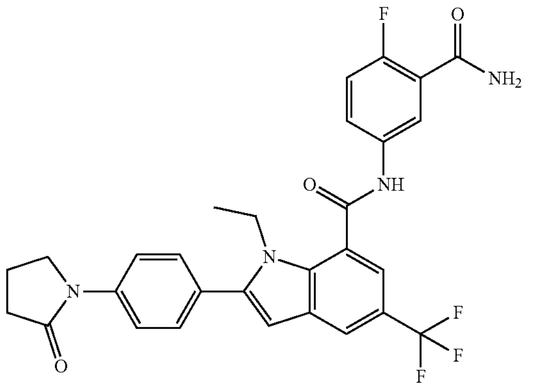 [SMILES: CCn1c(-c2ccc(N3CCCC3=O)cc2)cc2cc(C(F)(F)F)cc(C(=O)Nc3ccc(F)c(C(N)=O)c3)c21] | $^1$H-NMR (400 MHz, DMSO-$d_6$) δ: 0.98 (3H, t, J = 7.1 Hz), 2.06-2.13 (2H, m), 2.49-2.56 (2H, m), 3.90 (2H, t, J = 7.0 Hz), 4.27 (2H, q, J = 7.0 Hz), 6.83 (1H, s), 7.32 (1H, dd, J = 9.1, 10.0 Hz), 7.56-7.58 (2H, m), 7.62 (1H, d, J = 1.5 Hz), 7.70 (1H, br s), 7.73 (1H, br s), 7.83-7.90 (3H, m), 8.07 (1H, dd, J = 2.8, 6.4 Hz), 8.15 (1H, d, J = 1.0 Hz), 11.00 (1H, br s). ESI-MS m/z: 553 [M + H]$^+$ |

TABLE 6-1-continued
| Ex. | Structure | Data |
|---|---|---|
| 147 | 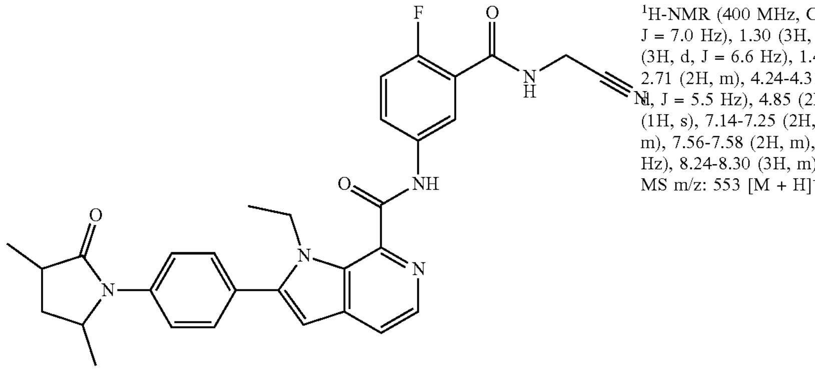 (diasrtereomeric pure, enantiomeric pure) | $^1$H-NMR (400 MHz, $CDCl_3$) δ: 0.96 (3H, t, J = 7.0 Hz), 1.30 (3H, d, J = 6.1 Hz), 1.36 (3H, d, J = 6.6 Hz), 1.40-1.47 (1H, m), 2.60-2.71 (2H, m), 4.24-4.31 (1H, m), 4.44 (2H, d, J = 5.5 Hz), 4.85 (2H, q, J = 7.0 Hz), 6.65 (1H, s), 7.14-7.25 (2H, m), 7.48-7.50 (2H, m), 7.56-7.58 (2H, m), 7.71 (1H, d, J = 5.1 Hz), 8.24-8.30 (3H, m), 10.37 (1H, s). ESI-MS m/z: 553 [M + H]$^+$ |
| 148 | 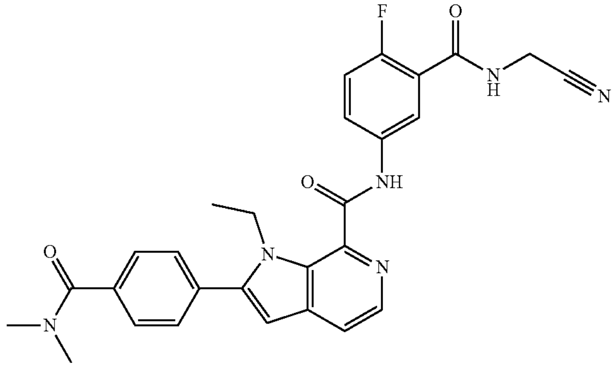 [SMILES: CCn1c(-c2ccc(C(=O)N(C)C)cc2)cc2ccnc(C(=O)Nc3ccc(F)c(C(=O)NCC#N)c3)c21] | ESI-MS m/z: 513 [M + H]$^+$ |
TABLE 6-2
| | | |
|---|---|---|
| 149 | 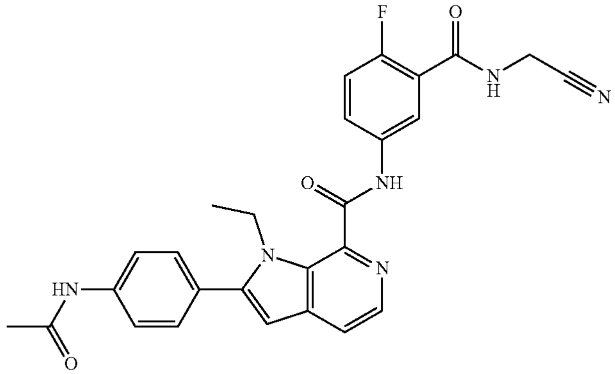 [SMILES: CCn1c(-c2ccc(NC(C)=O)cc2)cc2ccnc(C(=O)Nc3ccc(F)c(C(=O)NCC#N)c3)c21] | ESI-MS m/z: 499 [M + H]$^+$ |

TABLE 6-2-continued
| | | |
|---|---|---|
| 150 | 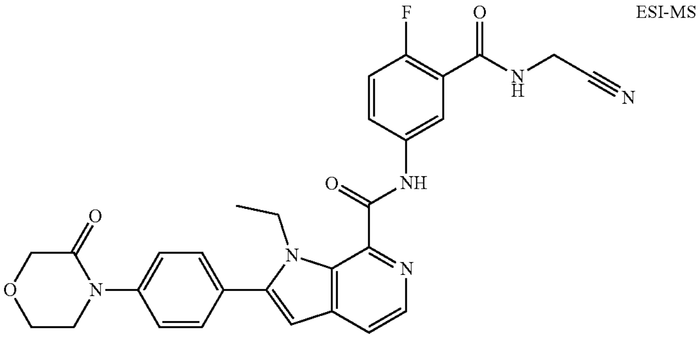 | ESI-MS m/z: 541 $[M + H]^+$ |
| 151 | 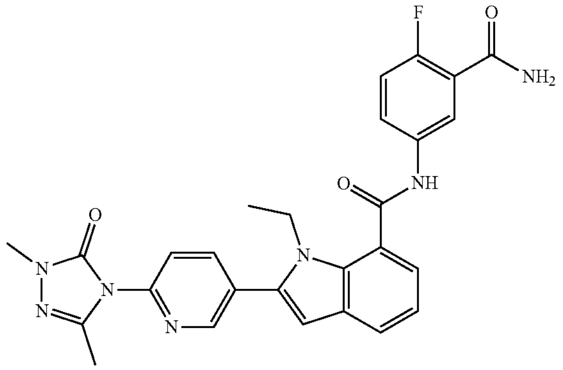 [SMILES: CCn1c(-c2ccc(-n3c(C)nn(C)c3=O)nc2)cc2cccc(C(=O)Nc3ccc(F)c(C(N)=O)c3)c21] | ESI-MS m/z: 514 $[M + H]^+$ |
| 152 | 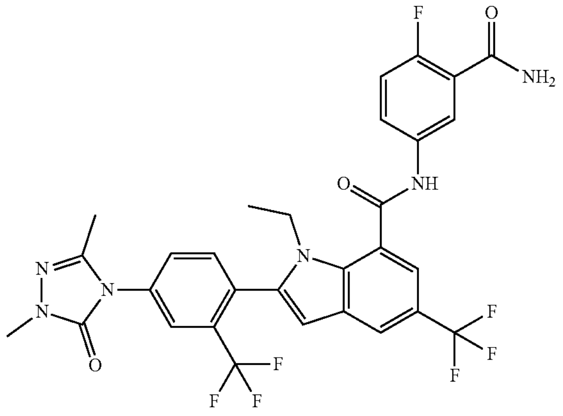 [SMILES: CCn1c(-c2ccc(-n3c(C)nn(C)c3=O)cc2C(F)(F)F)cc2cc(C(F)(F)F)cc(C(=O)Nc3ccc(F)c(C(N)=O)c3)c21] | ESI-MS m/z: 649 $[M + H]^+$ |
| 153 | 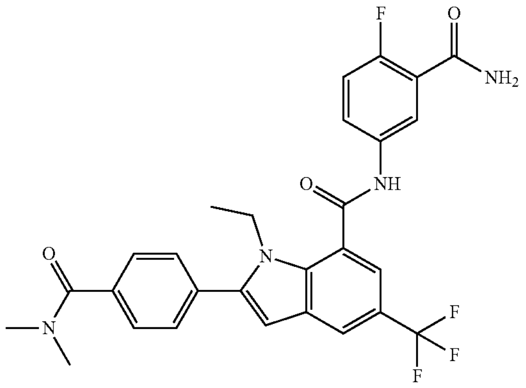 [SMILES: CCn1c(-c2ccc(C(=O)N(C)C)cc2)cc2cc(C(F)(F)F)cc(C(=O)Nc3ccc(F)c(C(N)=O)c3)c21] | $^1$H-NMR (400 MHz, DMSO-$d_6$) δ: 1.00 (3H, t, J = 7.1 Hz), 2.97-3.02 (6H, m), 4.29 (2H, q, J = 6.9 Hz), 6.91 (1H, s), 7.32 (1H, dd, J = 9.0, 10.0 Hz), 7.56-7.58 (2H, m), 7.62-7.65 (3H, m), 7.70 (1H, br s), 7.73 (1H, br s), 7.89 (1H, m), 8.07 (1H, dd, J = 2.7, 6.5 Hz), 8.18 (1H, m), 11.01 (1H, br s). ESI-MS m/z: 541 $[M + H]^+$ |

TABLE 6-2-continued
| | | |
|---|---|---|
| 154 | 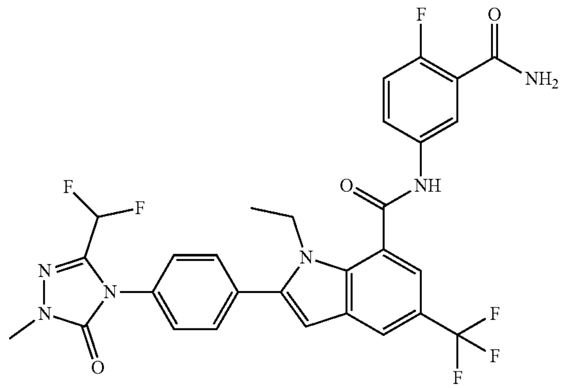 [SMILES: CCn1c(-c2ccc(-n3c(C(F)F)nn(C)c3=O)cc2)cc2cc(C(F)(F)F)cc(C(=O)Nc3ccc(F)c(C(N)=O)c3)c21] | $^1$H-NMR (400 MHz, DMSO-$d_6$) δ: 1.02 (3H, t, J = 7.1 Hz), 3.48 (3H, s), 4.31 (2H, q, J = 7.2 Hz), 6.95-7.21 (2H, m), 7.32 (1H, dd, J = 9.0, 10.0 Hz), 7.63-7.77 (7H, m), 7.89 (1H, m), 8.07 (1H, dd, J = 2.8, 6.4 Hz), 8.20 (1H, m), 11.02 (1H, br s). ESI-MS m/z: 617 [M + H]+ |
TABLE 6-3
| | | |
|---|---|---|
| 155 | 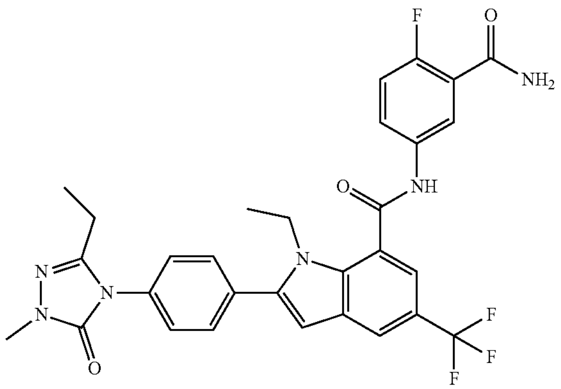 [SMILES: CCc1nn(C)c(=O)n1-c1ccc(-c2cc3cc(C(F)(F)F)cc(C(=O)Nc4ccc(F)c(C(N)=O)c4)c3n2CC)cc1] | ESI-MS m/z: 595 $[M + H]^+$ |
| 156 | 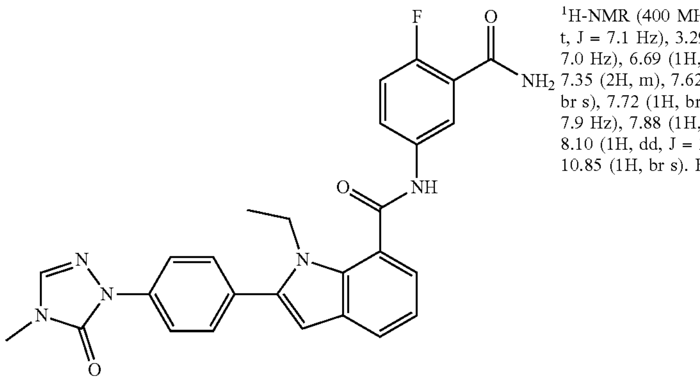 | $^1$H-NMR (400 MHz, DMSO-$d_6$) δ: 0.95 (3H, t, J = 7.1 Hz), 3.29 (3H, s), 4.26 (2H, q, J = 7.0 Hz), 6.69 (1H, s), 7.18 (1H, m), 7.27-7.35 (2H, m), 7.62-7.65 (2H, m), 7.69 (1H, br s), 7.72 (1H, br s), 7.75 (1H, dd, J = 1.1, 7.9 Hz), 7.88 (1H, m), 8.05-8.07 (2H, m), 8.10 (1H, dd, J = 2.8, 6.5 Hz), 8.25 (1H, s), 10.85 (1H, br s). ESI-MS m/z: 499 $[M + H]^+$ |

Example 157

[Chem. Fig. 90]

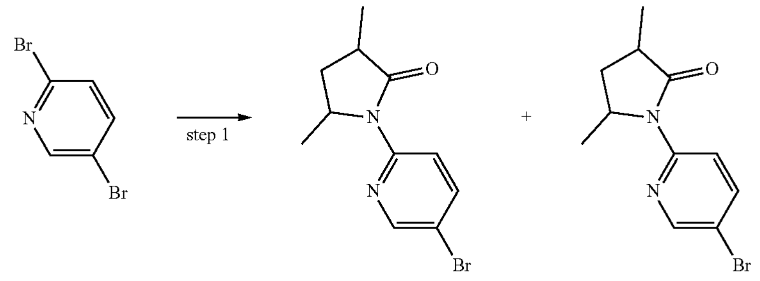

Ref.-187

Ref.-188
(1st peak
diastereomeric pure
racemate)

Ref.-189
(2nd peak
diastereomeric pure
racemate)

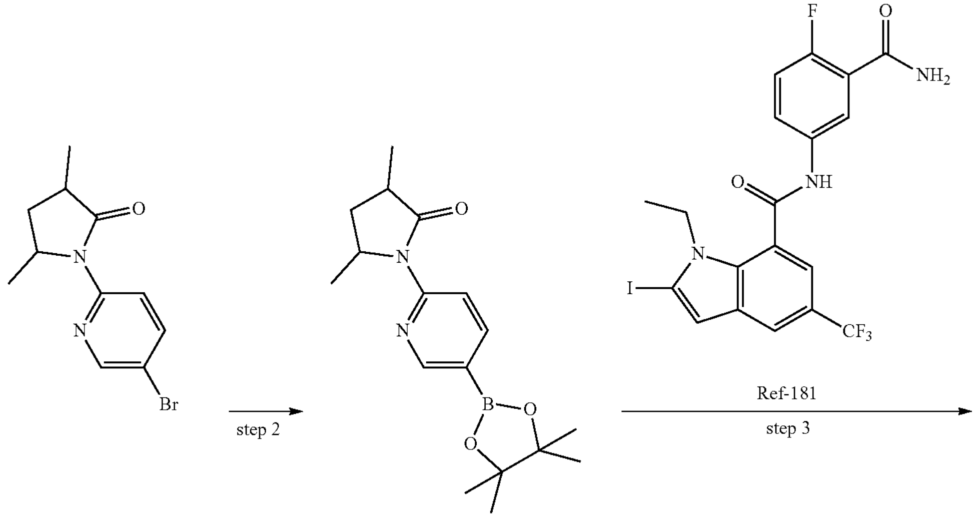

Ref.-189

Ref.-190
(diastereomeric pure
racemate)

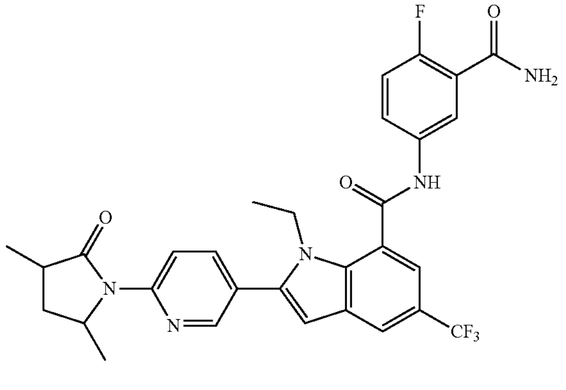

Ex.-157
(diasrtereomeric pure, racemate)

Reference synthesis example compound 187 (200 mg, 0.844 mmol) and 1,4-dioxane (2.8 mL) were mixed, and then 3,5-dimethylpyrrolidin-2-one (105 mg, 0.928 mmol), tripotassium phosphate (269 mg, 1.27 mmol), and Xantphos-PD-G3 (68.0 mg, 0.0845 mmol) were added, followed by stirring at 100° C. for 4 hours. Water was added to the cooled reaction solution, and the mixture was extracted using ethyl acetate. The extract was washed successively with water and saturated brine, and then dried over anhydrous sodium sulfate. The solvent was distilled off under reduced pressure, and then the residue was purified by silica gel column chromatography and the diastereomers were simultaneously separated to obtain reference synthesis example compound 188 (yield 86.3 mg) and reference synthesis example compound 189 (79.5 mg).

Step 2

Reference synthesis example compound 189 (50.0 mg, 0.186 mmol) and 1,4-dioxane (1.9 mL) were mixed, and then bis(pinacolato)diboron (70.8 mg, 0.279 mmol), potassium acetate (36.5 mg, 0.372 mmol), and [1,1'-bis(diphenylphosphino)ferrocene]dichloropalladium (II) (13.6 mg, 0.0186 mmol) were added and stirred at 100° C. for 3 hours. Water was added to the cooled reaction solution, and the mixture was extracted using ethyl acetate. The extract was washed successively with water and saturated brine, and then dried over anhydrous sodium sulfate. The solvent was distilled off under reduced pressure, and then the residue was purified by silica gel column chromatography to obtain reference synthesis example compound 190 (yield 53.6 mg).

Step 3

Reference synthesis example compound 181 (30.0 mg, 0.0578 mmol), 1,4-dioxane (578 μL) and water (58 μL) were mixed, and then reference synthesis example compound 190 (27.4 mg, 0.0867 mmol), cesium carbonate (28.2 mg, 0.0866 mmol), XPhos (1.4 mg, 0.0029 mmol), and XPhos-palladium (crotyl) chloride (2.0 mg, 0.0030 mmol) were added, followed by stirring at 90° C. for 2 hours. Water was added to the cooled reaction solution, and the mixture was extracted using ethyl acetate. The extract was washed successively with water and saturated brine, and then dried over anhydrous sodium sulfate. The solvent was distilled off under reduced pressure, and then the residue was purified by silica gel column chromatography to obtain Example Compound 157 (yield 22.5 mg).

Example 158

[Chem. Fig. 91]

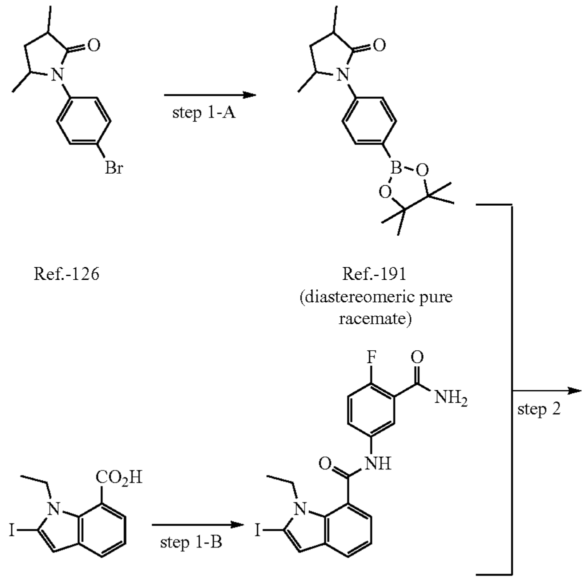

Ref.-126

Ref.-191
(diastereomeric pure racemate)

Ref.-175

Ref.-192

-continued

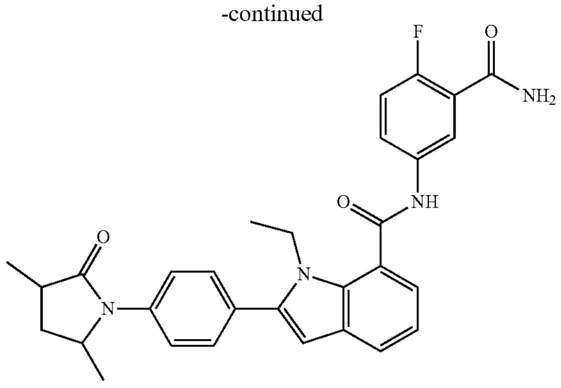

Ex.-158
(diasrtereomeric pure, racemate)

Step 1-A

Reference synthesis example compound 191 (yield 1.42 g) was obtained from reference synthesis example compound 126 (1.00 g, 3.73 mmol) by the same method as in Step 2 of Example 157.

Step 1-B

Reference synthesis example compound 192 (yield 38.8 mg) was obtained from reference synthesis example compound 175 (50.0 mg, 0.159 mmol) by the same method as in Step 7 of Example 145.

Step 2

Example Compound 158 (yield 18.9 mg) was obtained from reference synthesis example compound 191 (31.4 mg, 0.0996 mmol) and reference synthesis example compound 192 (30.0 mg, 0.0665 mmol) by the same method as in Step 3 of Example 157.

Example 159

[Chem. Fig. 92]

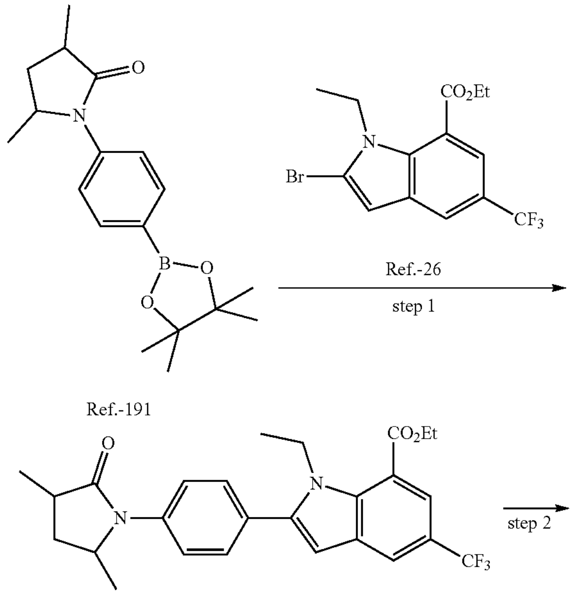

Ref.-191

Ref.-26

Ref.-193
(diasrtereomeric pure, racemate)

-continued

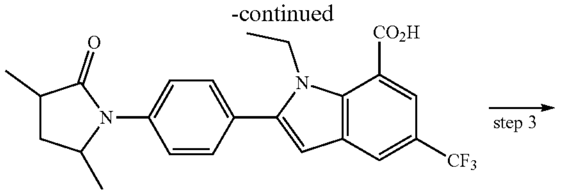

Ref.-194
(diasrtereomeric pure, racemate)

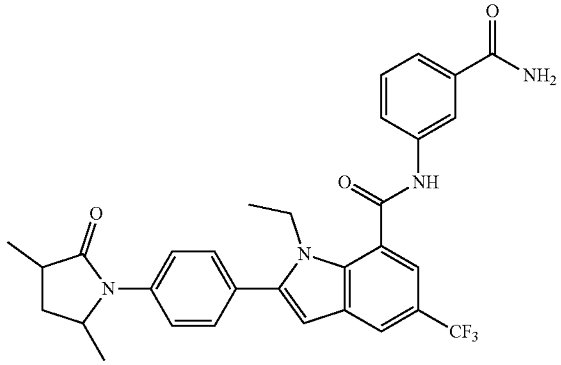

Ex.-159
(diasrtereomeric pure, racemate)

Step 1-3

Example Compound 159 (yield 10.6 mg) was obtained from reference synthesis example compound 191 by the same method as in steps 3 to 5 of Example 15.

Example 160

[Chem. Fig. 93]

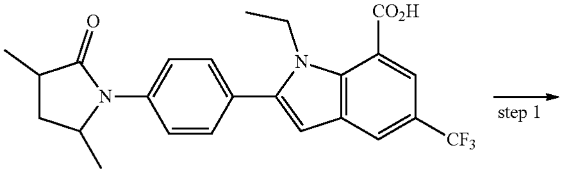

Ref.-194

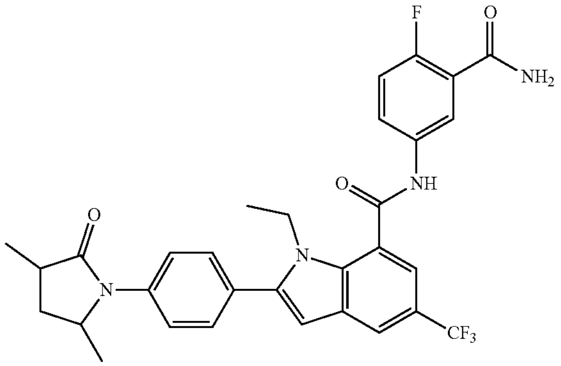

Ex.-160
(diasrtereomeric pure, racemate)

Step 1

Example Compound 160 (yield 17.2 mg) was obtained from reference synthesis example compound 194 (22 mg, 0.050 mmol) by the same method as in Step 5 of Example 15.

Example 161

[Chem. Fig. 94]

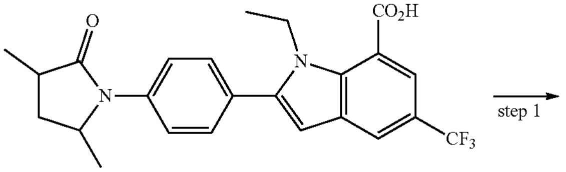

Ref.-194

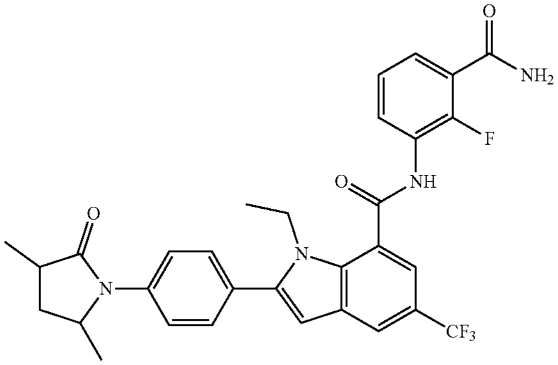

Ex.-161
(diasrtereomeric pure, racemate)

Step 1

Example Compound 161 (yield 5.4 mg) was obtained from reference synthesis example compound 194 (22 mg, 0.050 mmol) by the same method as in Step 5 of Example 15.

Example Compounds 157 to 161 in the following table were produced according to the methods shown in Examples 157 to 161 described above. Furthermore, $^1$H-NMR data and LC/MS data of these example compounds are shown in the table.

TABLE 7

| Ex. | Structure | Data |
|---|---|---|
| 157 | 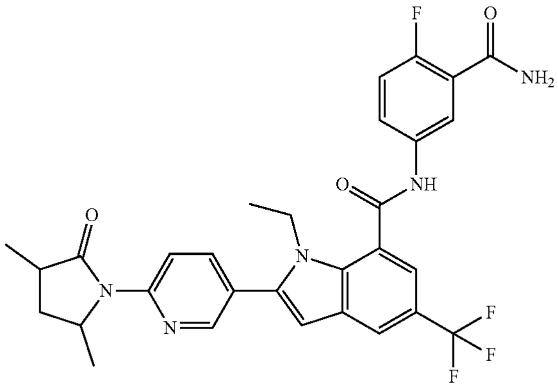 [SMILES: CCn1c(-c2ccc(N3C(=O)C(C)CC3C)nc2)cc2cc(C(F)(F)F)cc(C(=O)Nc3ccc(F)c(C(N)=O)c3)c21] (diasrtereomeric pure, racemate) | $^1$H-NMR (400 MHz, DMSO-$d_6$) δ: 1.01 (3H, t, J = 7.1 Hz), 1.24 (3H, d, J = 7.0 Hz), 1.34-1.41 (4H, m), 2.54-2.74 (2H, m), 4.26 (2H, q, J = 7.1 Hz), 4.57 (1H, m), 6.94 (1H, s), 7.32 (1H, dd, J = 9.1, 10.0 Hz), 7.65 (1H, d, J = 1.6 Hz), 7.71 (1H, br s), 7.73 (1H, br s), 7.88 (1H, m), 8.04-8.08 (2H, m), 8.14 (1H, m), 8.18 (1H, m), 8.62 (1H, m), 11.01 (1H, br s). ESI-MS m/z: 582 $[M + H]^+$ |
| 158 | 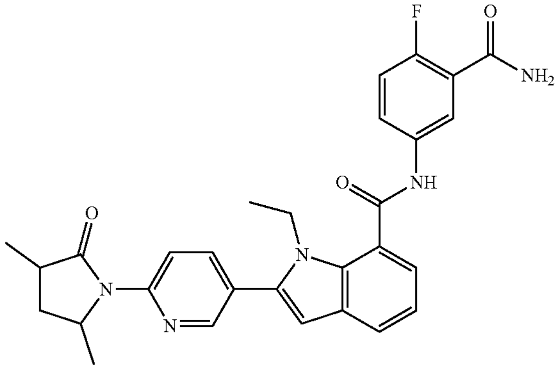 [SMILES: CCn1c(-c2ccc(N3C(=O)C(C)CC3C)nc2)cc2cccc(C(=O)Nc3ccc(F)c(C(N)=O)c3)c21] (diasrtereomeric pure, racemate) | $^1$H-NMR (400 MHz, DMSO-$d_6$) δ: 0.96 (3H, t, J = 7.1 Hz), 1.17-1.36 (7H, m), 2.54-2.70 (2H, m), 4.23-4.35 (3H, m), 6.68 (1H, s), 7.18 (1H, m), 7.30 (1H, dd, J = 9.1, 10.0 Hz), 7.34 (1H, dd, J = 1.2, 7.3 Hz), 7.50-7.57 (4H, m), 7.69 (1H, br s), 7.72 (1H, br s), 7.75 (1H, dd, J = 1.1, 7.9 Hz), 7.88 (1H, m), 8.10 (1H, dd, J = 2.8, 6.5 Hz), 10.84 (1H, br s). ESI-MS m/z: 513 $[M + H]^+$ |
| 159 | 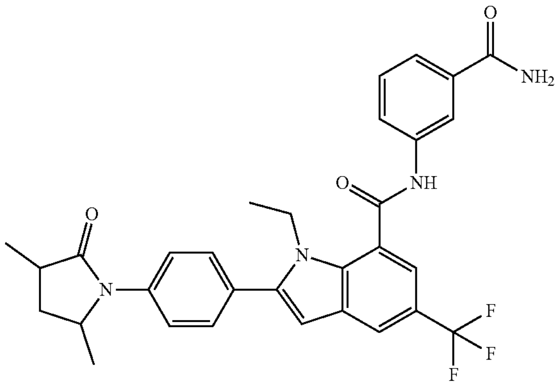 [SMILES: CCn1c(-c2ccc(N3C(=O)C(C)CC3C)cc2)cc2cc(C(F)(F)F)cc(C(=O)Nc3cccc(C(N)=O)c3)c21] (diasrtereomeric pure, racemate) | $^1$H-NMR (400 MHz, DMSO-$d_6$) δ: 0.99-1.03 (3H, m), 1.14-1.35 (6H, m), 1.89-2.05 (1H, m), 2.54-2.83 (2H, m), 4.27-4.50 (3H, m), 6.84-6.86 (1H, m), 7.31-7.32 (1H, m), 7.40 (1H, br s), 7.44-7.48 (1H, m), 7.63-7.82 (5H, m), 7.90-7.92 (1H, m), 7.99 (1H, br s), 8.16 (1H, br s), 8.25-8.26 (1H, m), 10.99 (1H, s). ESI-MS m/z: 563 $[M + H]^+$ |
| 160 | 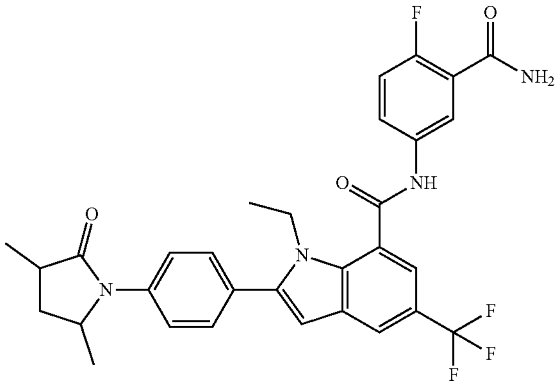 [SMILES: CCn1c(-c2ccc(N3C(=O)C(C)CC3C)cc2)cc2cc(C(F)(F)F)cc(C(=O)Nc3ccc(F)c(C(N)=O)c3)c21] (diasrtereomeric pure, racemate) | $^1$H-NMR (400 MHz, DMSO-$d_6$) δ: 0.98-1.02 (3H, m), 1.14-1.23 (6H, m), 1.28-2.61 (3H, m), 4.28-4.51 (3H, m), 6.85-6.86 (1H, m), 7.30-7.34 (1H, m), 7.63-7.81 (7H, m), 7.86-7.91 (1H, m), 8.06-8.08 (1H, m), 8.16 (1H, br s), 11.01 (1H, s). ESI-MS m/z: 581 $[M + H]^+$ |

TABLE 7-continued

| Ex. | Structure | Data |
|---|---|---|
| 161 | 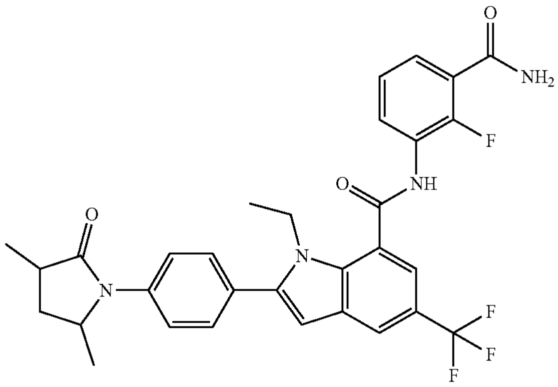 [SMILES: CCn1c(-c2ccc(N3C(=O)C(C)CC3C)cc2)cc2cc(C(F)(F)F)cc(C(=O)Nc3cccc(C(N)=O)c3F)c21]<br>(diasrtereomeric pure, racemate) | $^1$H-NMR (400 MHz, DMSO-$d_6$) δ: 1.04-1.07 (3H, m), 1.14-1.23 (6H, m), 1.28-2.63 (3H, m), 4.34-4.35 (2H, m), 5.24 (1H, m), 6.69-6.89 (2H, m), 7.29-7.33 (1H, m), 7.46-7.68 (6H, m), 7.80-7.82 (1H, m), 7.86-7.88 (1H, m), 8.17 (1H, br s), 10.81 (1H, s). ESI-MS m/z: 581 [M + H]$^+$ |

Example 162

[Chem. Fig. 95]

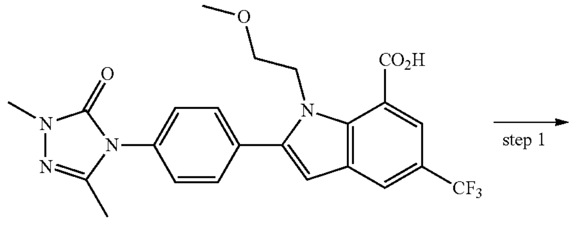

Ref.-36

-continued

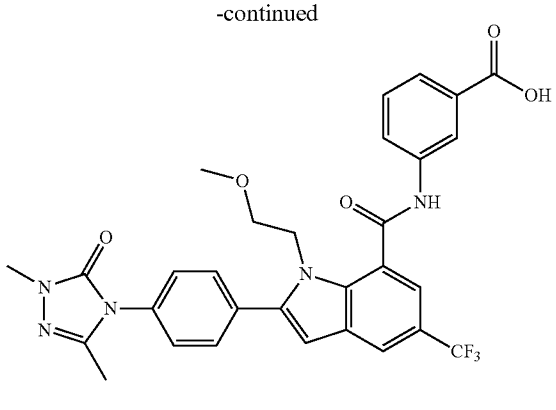

Ex.-162

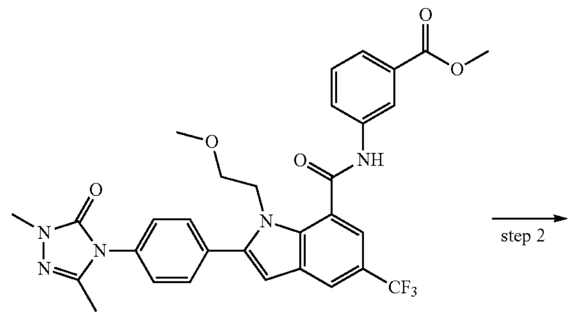

Ref.-195

Step 1

Acetonitrile (0.032 L), methyl 3-aminobenzoate (0.717 g, 4.74 mmol), 1-methylimidazole (1.0 mL, 13 mmol), and TCFH (1.33 g, 4.74 mmol) were sequentially added to reference synthesis example compound 36 (1.50 g, 3.16 mmol), and the mixture was stirred at room temperature for 16 hours. The solvent was distilled off under reduced pressure, and then ethylacetate and 1 mol/L hydrochloric acid were added and stirred, and then the organic layer was separated. The separated organic layer was washed with saturated brine and then dried over anhydrous sodium sulfate. The solvent was distilled off under reduced pressure, and then chloroform was added to the residue, followed by filtration. The filtrate was purified by silica gel column chromatography, slurry washing was performed with a mixed solution of ethyl acetate/normal hexane (1/3) (10 mL), and then the solid was collected by filtration to obtain reference synthesis example compound 195 (yield 1.56 g).

Step 2

THF (4.1 mL), methanol (4.1 mL), and 4 mol/L aqueous sodium hydroxide (1.7 mL, 6.8 mmol) were added to reference synthesis example compound 195 (407 mg, 0.670 mmol), and the mixture was stirred at room temperature for 5 hours. 2 mol/L hydrochloride (8 mL) was added dropwise to the reaction solution, the mixture was stirred, diluted with water, and then extracted using a chloroform/methanol (10/1) mixture. The extract was dried over anhydrous sodium sulfate, and evaporated under reduced pressure to obtain Example Compound 162 (397 mg yield).

Example 163

[Chem. Fig. 96]

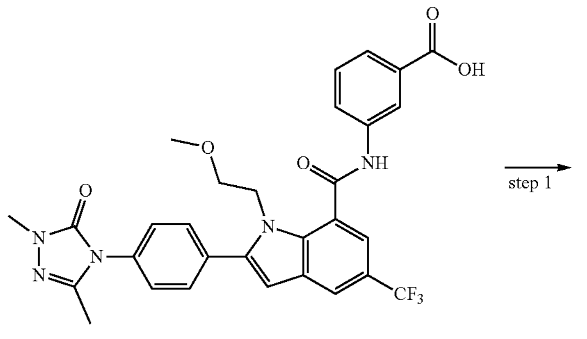

Ex.-162

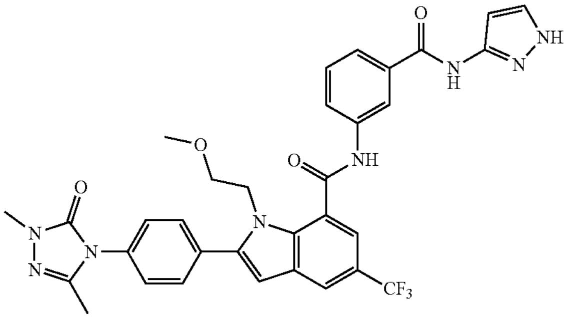

Ex.-163

Step 1

Acetonitrile (500 μL) and TCFH (9.5 mL, 0.034 mmol) were added to Example Compound 162 (10 mg, 0.017 mmol), stirred for 10 minutes, and then 1H-pyrazol-3-amine (2.8 mg, 0.034 mmol) and 1-methylimidazole (5.3 μL, 0.067 mmol) were added and stirred at 60° C. for 14 hours. The reaction solution was concentrated under reduced pressure, and the residue was purified by preparative thin-layer chromatography (silica gel) and silica gel column chromatography in this order to obtain example compound 163 (yield 9.1 mg).

Example 164

[Chem. Fig. 97]

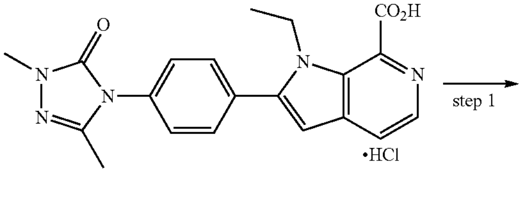

Ref.-72

-continued

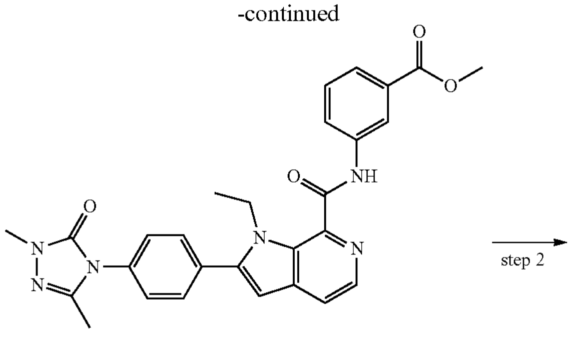

Ref.-196

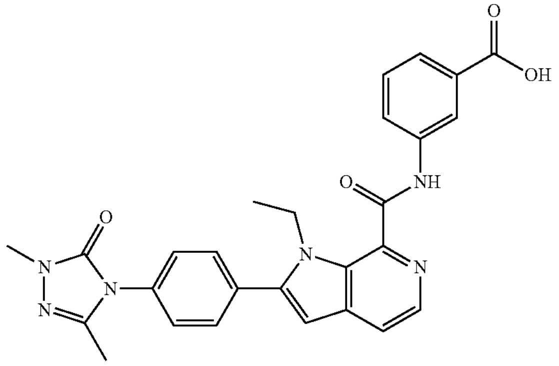

Ex.-164

Step 1

A sodium chloride mixture (50.0 mg) of reference synthesis example compound 72 obtained by the same method as in Step 4 of Example 21 was mixed with acetonitrile (0.77 mL), then methyl 3-aminobenzoate (23.3 mg, 0.154 mmol), 1-methylimidazole (30.5 μL, 0.386 mmol) and TCFH (43.3 mg, 0.154 mmol) were added, and then the mixture was stirred at room temperature for 15 hours. The reaction solution was diluted with chloroform and water, and then the organic layer was separated. The solvent was distilled off under reduced pressure, and then the residue was purified by silica gel column chromatography to obtain reference synthesis example compound 196 (yield 39.4 mg).

Step 2

Reference synthesis example compound 196 (0.340 g, 0.666 mmol) and THF (1.7 mL) were mixed, methanol (1.7 mL) and 4 mol/L aqueous sodium hydroxide (0.666 mL, 2.66 mmol) were added, and the mixture was stirred at room temperature for 2 hours. 2 mol/L hydrochloric acid (2.0 mL) was added dropwise to the reaction solution, the solvent was distilled off under reduced pressure, and a small amount of toluene was added for azeotropic dehydration. The residue was purified by silica gel column chromatography to obtain Example Compound 164 (yield 0.298 g).

Example 165

[Chem. Fig. 98]

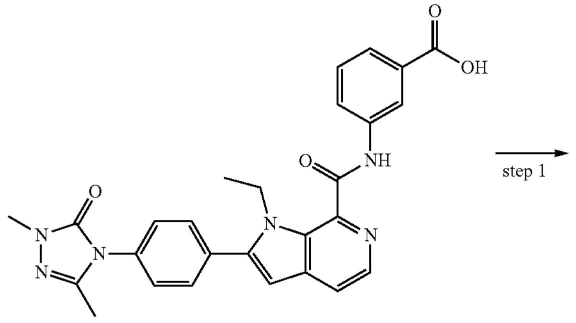

Ex.-164

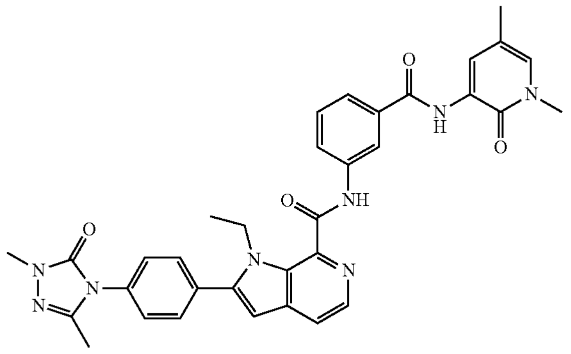

Ex.-165

Step 1

Example Compound 164 (13.0 mg, 0.0262 mmol) and acetonitrile (0.26 mL) were mixed, and then 3-amino-1,5-dimethyl-pyridin-2-one (3.6 mg, 0.026 mmol), 1-methylimidazole (10.3 L, 0.130 mmol) and TCFH (14.6 mg, 0.520 mmol) were added, followed by stirring at room temperature for 15 hours. The reaction solution was diluted with chloroform and water, and then the organic layer was separated. The solvent was distilled off under reduced pressure, and then the residue was purified by silica gel column chromatography to obtain Example Compound 165 (yield 10.2 mg).

Example 166

[Chem. Fig. 99]

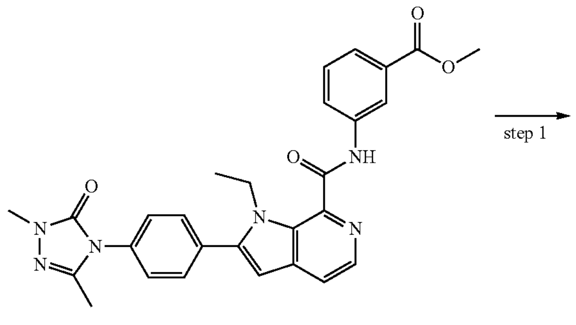

Ref.-196

-continued

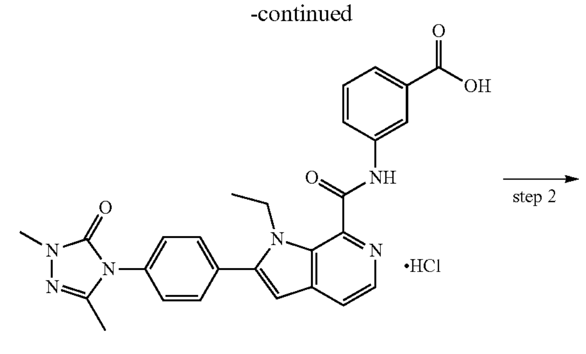

Ref.-197

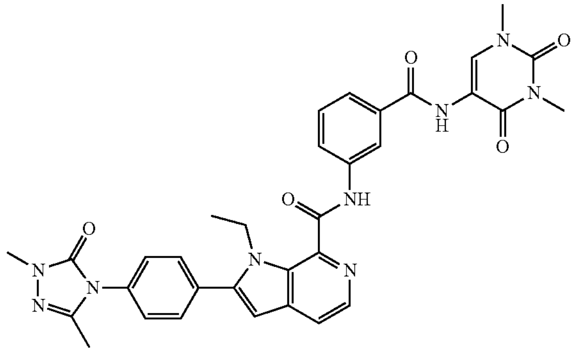

Ex.-166

Step 1

Reference synthesis example compound 196 (38.0 mg, 0.0744 mmol) and THF (0.19 mL) were mixed, methanol (0.19 mL) and 4 mol/L aqueous sodium hydroxide (74.4 µL, 0.298 mmol) were added, and the mixture was stirred at room temperature for 2 hours. 2 mol/L HCl (0.25 mL) was added dropwise to the reaction solution, and the mixture was evaporated under reduced pressure. Toluene was added to the residue for azeotropic dehydration, followed by drying under reduced pressure to obtain reference synthesis example compound 197 as a sodium chloride mixture (yield 51.2 mg).

Step 2

A sodium chloride mixture (25.0 mg) of reference synthesis example compound 197 was mixed with acetonitrile (0.33 mL), and then 5-amino-1,3-dimethyl-pyrimidine-2,4-dione (5.6 mg, 0.036 mmol), 1-methylimidazole (12.9 µL, 0.163 mmol), and TCFH (18.3 mg, 0.0652 mmol) were added, followed by stirring at room temperature for 15 hours. The reaction solution was diluted with chloroform and water, and then the organic layer was separated. The solvent was distilled off under reduced pressure, and then the residue was purified by silica gel column chromatography to obtain Example Compound 166 (yield 18.8 mg).

Example 167

[Chem. Fig. 100]

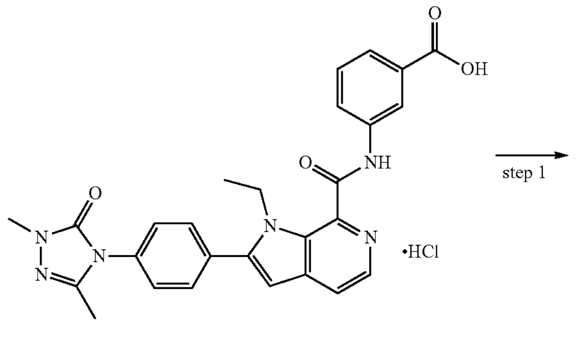

Ex.-197

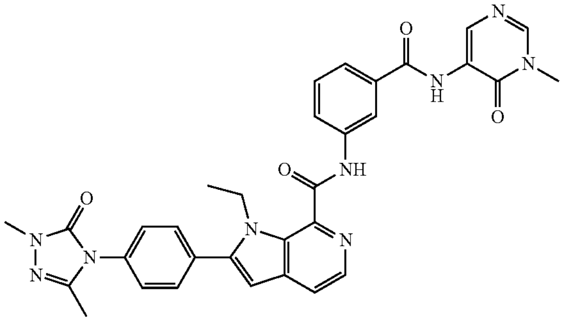

Ex.-167

Step 1

A sodium chloride mixture (20.0 mg) of reference synthetic example compound 197 obtained by the method of Step 2 of Example 166 was mixed with acetonitrile (0.26 mL), and then 5-amino-3-methyl-pyrimidin-4-one (3.9 mg, 0.031 mmol), 1-methylimidazole (10.3 μL, 0.130 mmol), and TCFH (14.6 mg, 0.0520 mmol) were added, followed by stirring at room temperature for 15 hours. The reaction solution was diluted with chloroform and water, and then the organic layer was separated. The solvent was distilled off under reduced pressure, and then the residue was purified by silica gel column chromatography to obtain Example Compound 167 (yield 9.3 mg).

Example 168

[Chem. Fig. 101]

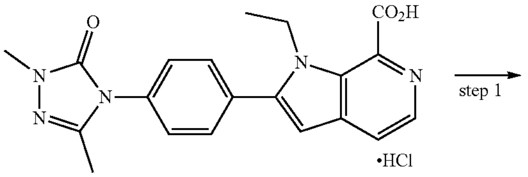

Ref.-72

-continued

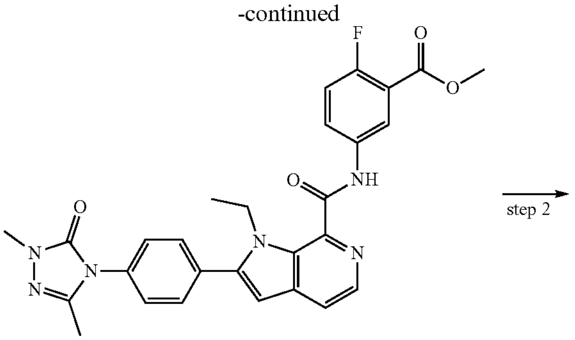

Ref.-198

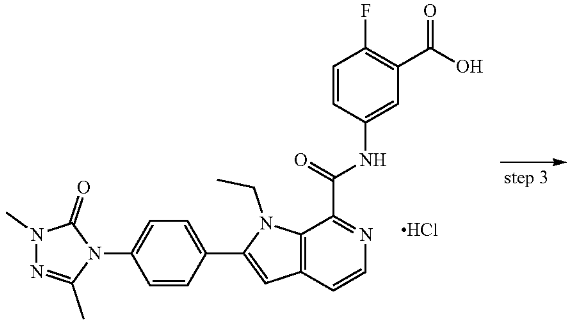

Ref.-199

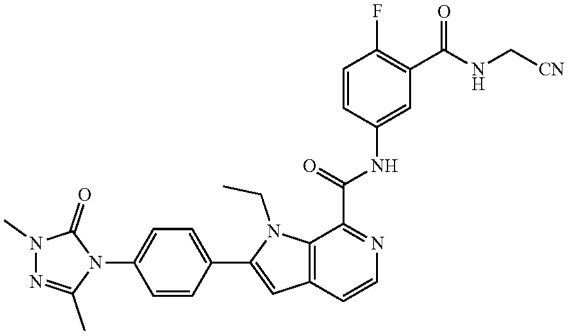

Ex.-168

Step 1

Acetonitrile (150 mg), methyl 5-amino-2-fluoro-benzoate (78.5 mL, 0.3 mg), 1-methylimidazole (183 μL, 2.463 mmol), and TCFH (130 mg, 0.463 mmol) were sequentially added to a sodium chloride mixture (32 mmol) of reference synthesis example compound 72 obtained by the same method as in Step 4 of Example 21, and the mixture was stirred at 40° C. for 15 hours. Water and ethyl acetate were added to the reaction solution and stirred, and then the organic layer was separated. The separated organic layer was dried over anhydrous sodium sulfate, and the solvent was distilled off under reduced pressure. The residue was purified by silica gel column chromatography to obtain reference synthesis example compound 198 partially containing an impurity (yield 127 mg).

Step 2

Reference synthesis example compound 198 (122 mg) containing an impurity obtained by the method of step 1, methanol (1.5 mL) and THF (1.5 mL) were mixed, and then 4 mol/L aqueous sodium hydroxide (346 μL) was added, followed by stirring at room temperature for 2 hours. 2 mol/L hydrochloric acid was added to the reaction solution to neutralize, and then the solvent was distilled off under reduced pressure. The obtained solid was dried under reduced pressure to obtain a sodium chloride mixture (yield 210 mg) of reference synthesis example compound 199.

Step 3

2-Aminoacetonitrile hydrochloride (39.30 mg, 0.0 mg), DMF (1.421 mmol), DIPEA (35 μL, 0.20 mmol) and HATU (25.3 mg, 0.0665 mmol) were sequentially added to a sodium chloride mixture (5 mL) of reference synthetic example compound 199 obtained by the method of Step 2, and the mixture was stirred at 55° C. for 4 hours and then at room temperature for 16 hours. Water and ethyl acetate were added, the mixture was stirred, and the organic layer was separated. The separated organic layer was dried over anhydrous sodium sulfate, and the solvent was distilled off under reduced pressure. After the residue was purified by silica gel column chromatography, the obtained solid was slurry-washed with a mixed solution of n-hexane/ethylacetate (4/1), and the solid was collected by filtration to obtain Example Compound 168 (yield 12.9 mg).

Example 169

[Chem. Fig. 102]

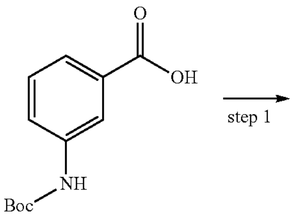

Ref.-200

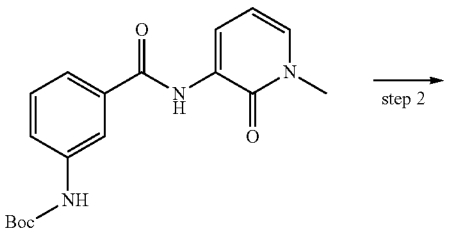

Ref.-201

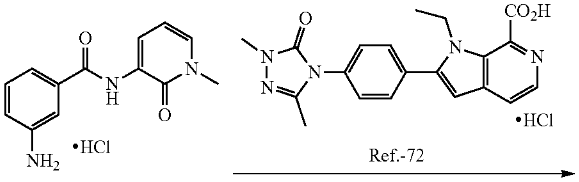

Ref.-202 step 3

-continued

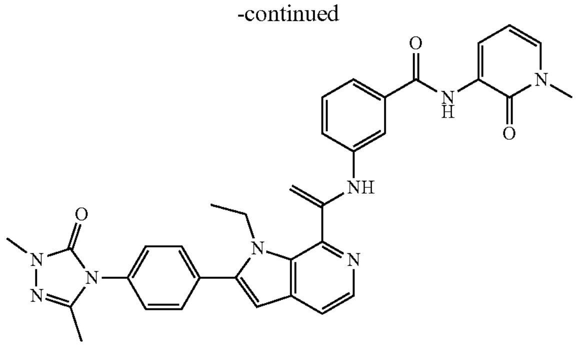

Ex.-169

Step 1

Acetonitrile (500 μL), TCFH (355 mg, 1.27 mmol) and 1-methylimidazole (200 μL, 2.53 mmol) were sequentially added to reference synthesis example compound 200 (200 mg, 0.843 mmol), and then the mixture was stirred for 10 minutes, followed by addition of 3-amino-1-methyl-pyridin-2-one (157 mg, 1.26 mmol) and stirring at 40° C. for 2 hours. Ethyl acetate and saturated brine were added and stirred, and then the organic layer was separated. The solvent was distilled off under reduced pressure, and then the residue was subjected to slurry washing with a mixed solution of ethyl acetate-normal hexane, and the solid was collected by filtration to obtain reference synthesis example compound 201 (yield 267 mg).

Step 2

4 mol/L hydrochloric acid/1,4-dioxane (5 mL) was added to reference synthetic example compound 201 (419 mg, 1.22 mmol) under ice-cooling, and then the mixture was stirred at room temperature for 2 hours. The solvent was distilled off under reduced pressure to obtain reference synthesis example compound 202 (yield 267 mg).

Step 3

Acetonitrile (500 μL), TCFH (13 mg, 0.046 mmol), and 1-methylimidazole (18.3 μL, 0.232 mmol) were sequentially added to a sodium chloride mixture (15 mg) of reference synthesis example compound 72 obtained by the same method as in Step 4 of Example 21, and then the mixture was stirred for 10 minutes. Reference synthetic example compound 202 (13 mg, 0.046 mmol) was added, and the mixture was stirred at 50° C. for 14 hours. The solvent was distilled off under reduced pressure, and then the residue was purified by preparative thin-layer chromatography (silica gel), and the resulting solid was slurry-washed with a mixture of n-hexane-ethyl acetate to obtain Example Compound 169 (yield 3.1 mg).

Example Compounds 162 to 202 in the following table were produced 5 according to the methods shown in Examples 162 to 169 described above or a similar method. Furthermore, $^1$H-NMR data and/or LC/MS data of these Example compounds are shown in the table.

TABLE 8-1
| Ex. | Structure | Data |
|---|---|---|
| 162 | 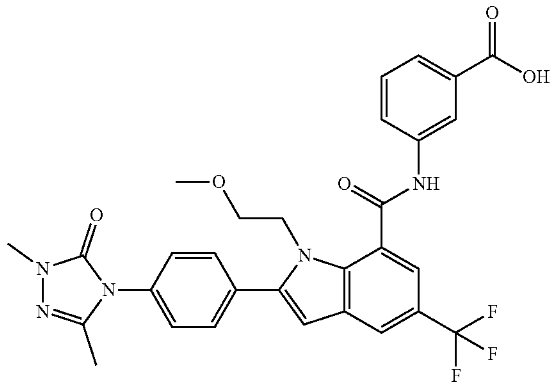 [SMILES: COCCn1c(-c2ccc(-n3c(C)nn(C)c3=O)cc2)cc2cc(C(F)(F)F)cc(C(=O)Nc3cccc(C(=O)O)c3)c21] | $^1$H-NMR (400 MHz, DMSO-$d_6$) δ: 2.15 (3H, s), 2.83 (3H, s), 3.36-3.38 (5H, m), 4.50 (2H, t, J = 5.4 Hz), 6.93 (1H, s), 7.52 (1H, t, J = 7.9 Hz), 7.60 (2H, d, J = 8.6 Hz), 7.72-7.75 (4H, m), 7.99 (1H, m), 8.20 (1H, d, J = 1.0 Hz), 8.43 (1H, t, J = 1.8 Hz), 11.04 (1H, s), 13.05 (1H, s). ESI-MS m/z: 594 [M + H]$^+$ |
| 163 | 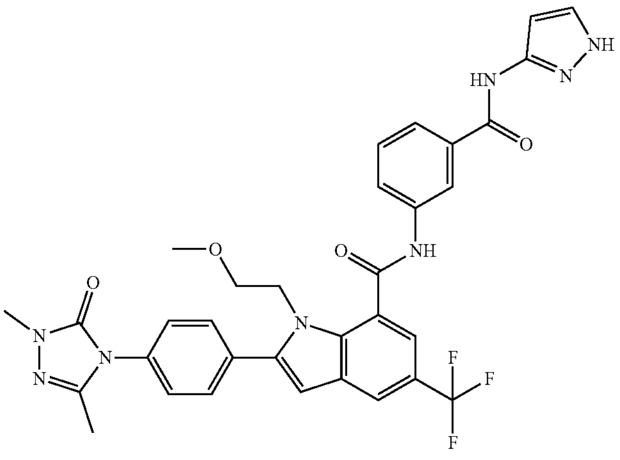 [SMILES: COCCn1c(-c2ccc(-n3c(C)nn(C)c3=O)cc2)cc2cc(C(F)(F)F)cc(C(=O)Nc3cccc(C(=O)Nc4cc[nH]n4)c3)c21] | $^1$H-NMR (400 MHz, $CDCl_3$) δ: 2.20 (3H, s), 2.89 (3H, s), 3.30 (2H, t, J = 5.1 Hz), 3.42 (3H, s), 4.43-4.57 (2H, m), 6.65 (1H, s), 6.70 (1H, s), 7.23-7.31 (3H, m), 7.34 (1H, m), 7.42 (1H, m), 7.50 (2H, d, J = 7.9 Hz), 7.57-7.70 (2H, m), 7.86 (1H, d, J = 8.2 Hz), 7.99 (1H, m), 8.18 (1H, m), 9.17 (1H, s), 10.24 (1H, s). ESI-MS m/z: 659 [M + H]$^+$ |
| 164 | 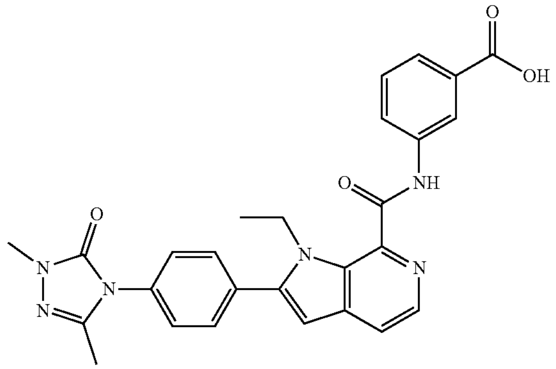 [SMILES: CCn1c(-c2ccc(-n3c(C)nn(C)c3=O)cc2)cc2ccnc(C(=O)Nc3cccc(C(=O)O)c3)c21] | $^1$H-NMR (400 MHz, DMSO-$d_6$) δ: 1.02 (3H, t, J = 7.2 Hz), 2.17 (3H, s), 3.37 (3H, s), 4.44 (2H, q, J = 6.9 Hz), 6.85 (1H, s), 7.51 (1H, t, J = 8.0 Hz), 7.64 (2H, d, J = 8.6 Hz), 7.72 (1H, d, J = 7.8 Hz), 7.76 (2H, d, J = 8.5 Hz), 7.81 (1H, d, J = 5.3 Hz), 8.03 (1H, m), 8.31 (1H, m), 8.53 (1H, m), 11.03 (1H, s), 13.03 (1H, m). ESI-MS m/z: 497 [M + H]$^+$ |

TABLE 8-1-continued

| Ex. | Structure | Data |
|---|---|---|
| 165 | 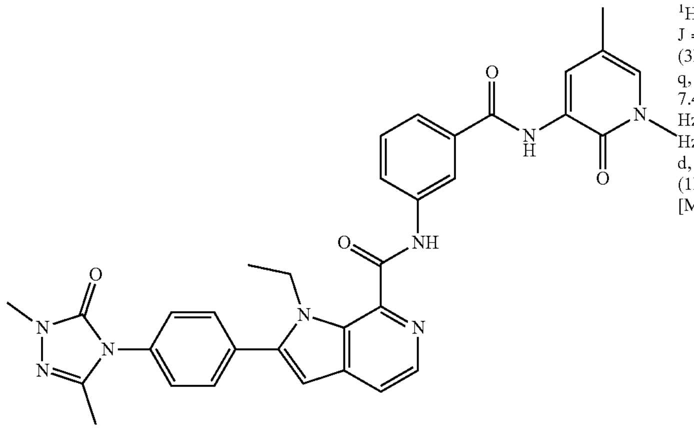 | $^1$H-NMR (400 MHz, $CDCl_3$) δ: 1.00 (3H, t, J = 7.0 Hz), 2.16 (3H, d, J = 0.8 Hz), 2.26 (3H, s), 3.53 (3H, s), 3.62 (3H, s), 4.89 (2H, q, J = 7.0 Hz), 6.70 (1H, s), 6.83 (1H, m), 7.48 (2H, d, J-8.5 Hz), 7.54 (1H, t, J = 7.9 Hz), 7.69-7.72 (3H, m), 7.74 (1H, d, J = 5.1 Hz), 8.16 (1H, m), 8.25 (1H, m), 8.32 (1H, d, J = 5.1 Hz), 8.47 (1H, d, J = 2.2 Hz), 9.29 (1H, s), 10.35 (1H, s). ESI-MS m/z: 617 $[M + H]^+$ |

TABLE 8-2

| | | |
|---|---|---|
| 166 | 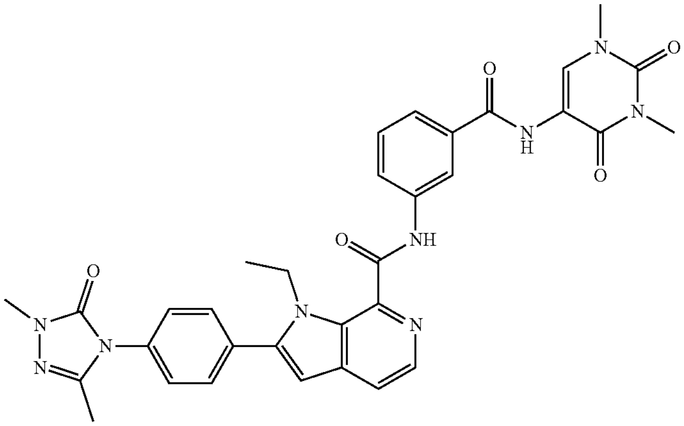 | $^1$H-NMR (400 MHz, $CDCl_3$) δ: 1.00 (3H, t, J = 7.0 Hz), 2.26 (3H, s), 3.46 (3H, s), 3.50 (3H, s), 3.53 (3H, s), 4.89 (2H, q, J = 7.0 Hz), 6.70 (1H, s), 7.48 (2H, d, J = 8.5 Hz), 7.54 (1H, t, J = 7.9 Hz), 7.62-7.64 (1H, m), 7.71 (2H, d, J = 8.4 Hz), 7.75 (1H, d, J = 5.1 Hz), 8.14 (1H, m), 8.23 (1H, m), 8.32 (1H, d, J = 5.1 Hz), 8.53 (1H, s), 8.71 (1H, s), 10.36 (1H, s). ESI-MS m/z: 634 $[M + H]^+$ |
| 167 | 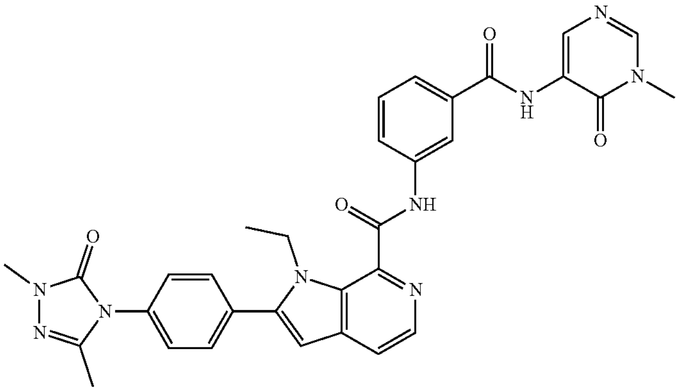 | $^1$H-NMR (400 MHz, $CDCl_3$) δ: 1.00 (3H, t, J = 7.0 Hz), 2.26 (3H, s), 3.53 (3H, s), 3.64 (3H, s), 4.89 (2H, q, J = 7.0 Hz), 6.70 (1H, s), 7.48 (2H, d, J = 8.5 Hz), 7.55 (1H, t, J = 7.9 Hz), 7.66-7.72 (3H, m), 7.74 (1H, d, J = 5.1 Hz), 7.95 (1H, s), 8.19 (1H, m), 8.25 (1H, m), 8.32 (1H, d, J-5.1 Hz), 8.88 (1H, s), 9.21 (1H, s), 10.37 (1H, s). ESI-MS m/z: 604 $[M + H]^+$ |

TABLE 8-2-continued
| | | |
|---|---|---|
| 168 | 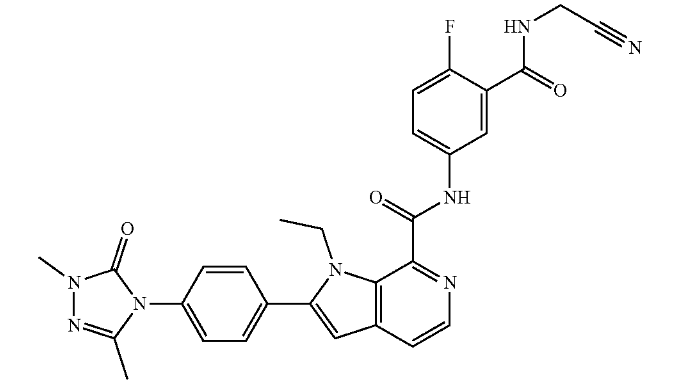 [SMILES: CCn1c(-c2ccc(-n3c(C)nn(C)c3=O)cc2)cc2ccnc(C(=O)Nc3ccc(F)c(C(=O)NCC#N)c3)c21] | $^1$H-NMR (400 MHz, $CDCl_3$) δ: 0.99 (3H, t, J = 7.0 Hz), 2.26 (3H, s), 3.53 (3H, s), 4.44 (2H, d, J = 5.6 Hz), 4.87 (2H, q, J = 7.1 Hz), 6.70 (1H, s), 7.11-7.16 (1H, m), 7.21-7.23 (1H, m), 7.48 (2H, d, J = 8.5 Hz), 7.69 (2H, d, J = 8.5 Hz), 7.74 (1H, d, J = 5.2 Hz), 8.25-8.32 (3H, m), 10.37 (1H, s). ESI-MS m/z: 553 $[M + H]^+$ |
| 169 | 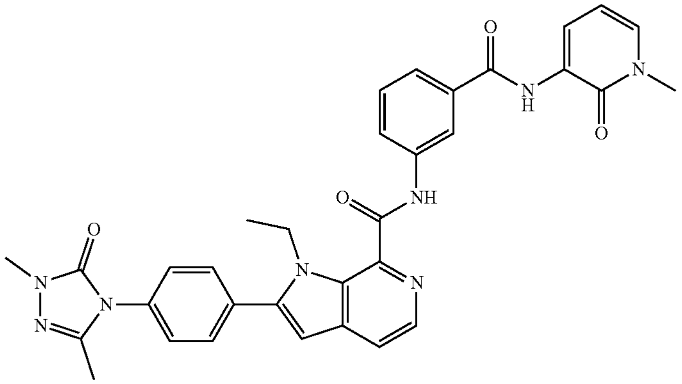 | $^1$H-NMR (400 MHz, $CDCl_3$) δ: 1.00 (3H, t, J = 7.0 Hz), 2.26 (3H, s), 3.53 (3H, s), 3.66 (3H, s), 4.89 (2H, t, J = 7.0 Hz), 6.31 (1H, t, J = 7.1 Hz), 6.70 (1H, s), 7.05 (1H, dd, J = 1.8, 6.8 Hz), 7.48 (2H, d, J = 8.5 Hz), 7.54 (1H, t, J = 7.9 Hz), 7.71 (4H, m), 8.18 (1H, t, J = 1.8 Hz), 8.23 (1H, d, J = 8.0 Hz), 8.31 (1H, d, J = 5.1 Hz), 8.57 (1H, dd, J = 7.4, 1.8 Hz), 9.28 (1H, s), 10.35 (1H, s). ESI-MS m/z: 603 $[M + H]^+$ |
| 170 | 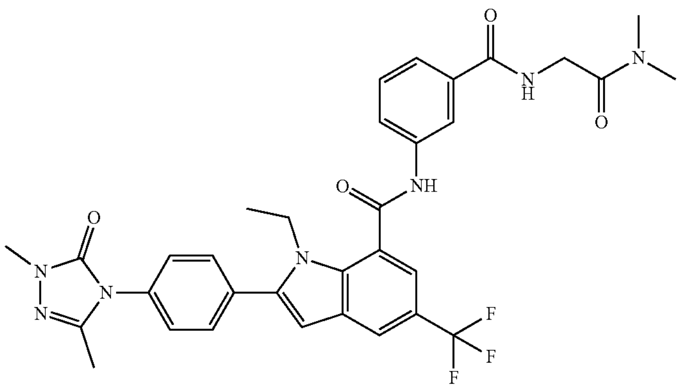 | ESI-MS m/z: 648 $[M + H]^+$ |

TABLE 8-3
| | | |
|---|---|---|
| 171 | 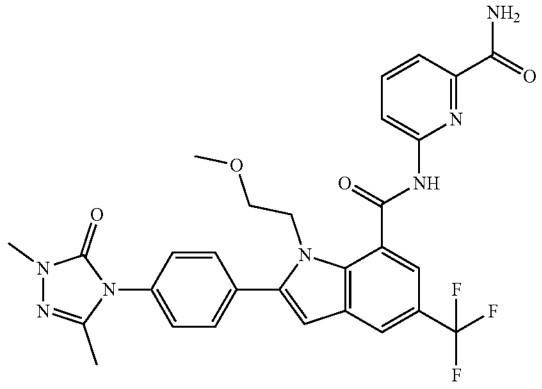 [SMILES: COCCn1c(-c2ccc(-n3c(C)nn(C)c3=O)cc2)cc2cc(C(F)(F)F)cc(C(=O)Nc3cccc(C(N)=O)n3)c21] | ESI-MS m/z: 594 [M + H]+ |
| 172 | 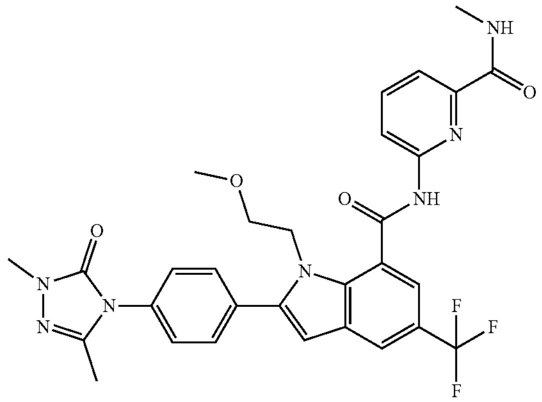 [SMILES: CNC(=O)c1cccc(NC(=O)c2cc(C(F)(F)F)cc3cc(-c4ccc(-n5c(C)nn(C)c5=O)cc4)n(CCOC)c23)n1] | ESI-MS m/z: 608 [M + H]+ |
| 173 | 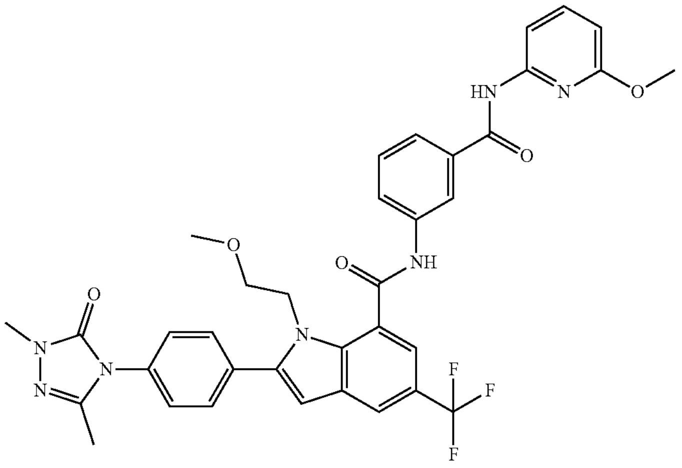 | ESI-MS m/z: 700 [M + H]+ |

TABLE 8-3-continued
| | | |
|---|---|---|
| 174 | 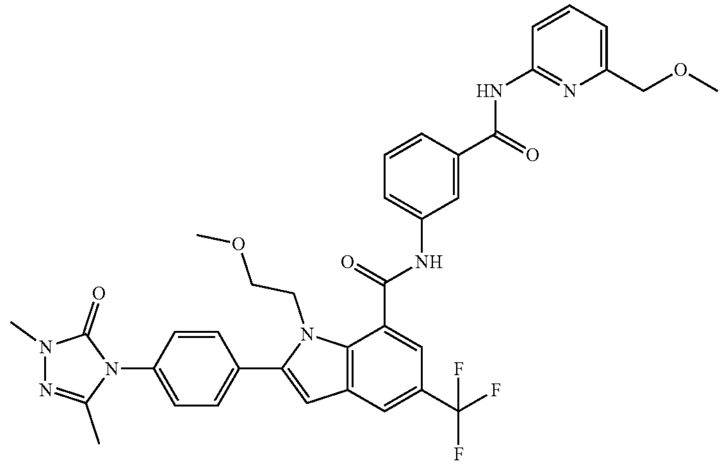 | $^1$H-NMR (400 MHz, $CDCl_3$) δ: 2.22 (3H, s), 2.97 (3H, s), 3.36 (2H, t, J = 5.2 Hz), 3.14 (3H, s), 3.51 (3H, s), 4.48 (2H, s), 4.58 (2H, t, J = 4.9 Hz), 6.74 (1H,s), 7.15 (1H, d, J = 7.4 Hz), 7.25-7.34 (2H, m), 7.51-7.60 (3H, m), 7.64-7.73 (3H, m), 8.01 (1H, s), 8.08-8.19 (2H, m), 8.22(1H, s), 8.67 (1H, s), 8.78 (1H, br s). ESI-MS m/z: 714 $[M + H]^+$ |
| 175 | 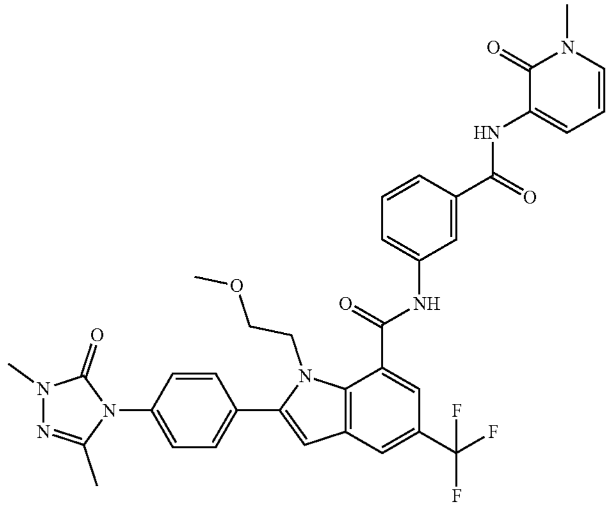 [SMILES: COCCn1c(-c2ccc(-n3c(C)nn(C)c3=O)cc2)cc2cc(C(F)(F)F)cc(C(=O)Nc3cccc(C(=O)Nc4cccn(C)c4=O)c3)c21] | $^1$H-NMR (400 MHz, $CDCl_3$) δ: 2.22 (3H, s), 2.97 (3H, s), 3.37 (2H, t, J = 5.2 Hz), 3.51 (3H, s), 3.63 (3H, s), 4.52-4.62 (2H, m), 6.24 (1H, m), 6.74 (1H, s), 7.02 (1H, d, J = 6.8 Hz), 7.30-7.38 (2H, m), 7.50-7.63 (3H, m), 7.64-7.72 (2H, m), 8.02 (1H, s), 8.07 (1H, s), 8.21 (1H, d, J =8.0 Hz), 8.43(1H, m), 8.68 (1H, br s), 9.24 (1H, s). ESI-MS m/z: 700 $[M + H]^+$ |
TABLE 8-4
| | | |
|---|---|---|
| 176 | 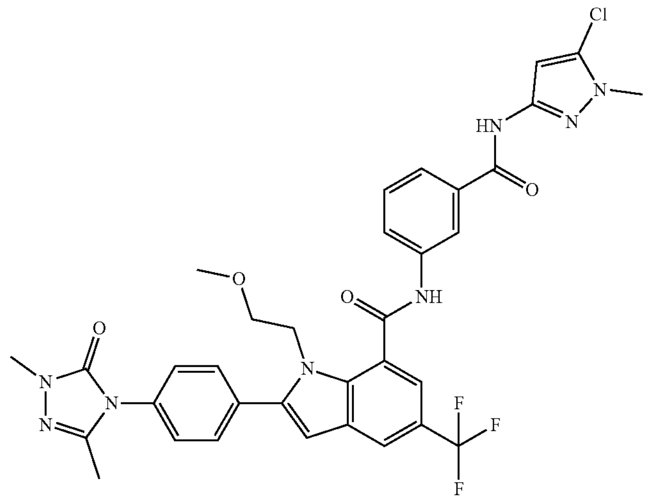 | $^1$H-NMR (400 MHz, $CDCl_3$) δ: 2.22 (3H, s), 2.95 (3H, s), 3.34 (2H, t, J = 5.2 Hz), 3.49 (3H, s), 3.74 (3H, s), 4.49-4.60 (2H, m), 6.70-6.77 (2H, m), 7.24-7.37 (2H, m), 7.46-7.59 (3H, m), 7.60-7.70 (2H, m), 7.98-8.09 (2H, m), 8.22(1H, s), 8.69 (1H, br s), 8.81 (1H, br s). ESI-MS m/z: 706 $[M - H]^-$ |

TABLE 8-4-continued
| | | |
|---|---|---|
| 177 | 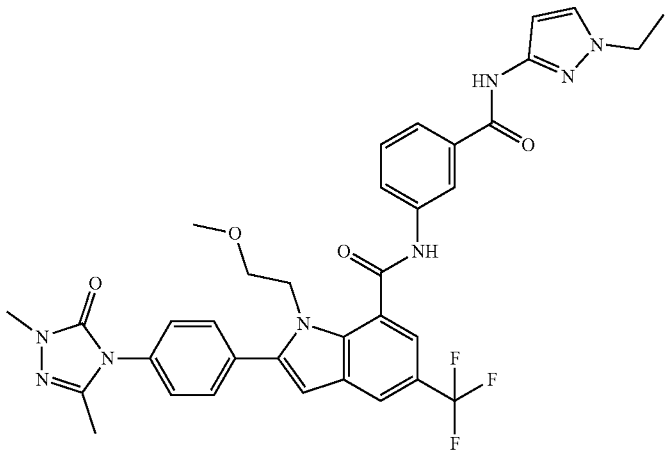 [SMILES: CCn1ccc(NC(=O)c2cccc(NC(=O)c3cc(C(F)(F)F)cc4cc(-c5ccc(-n6c(C)nn(C)c6=O)cc5)n(CCOC)c34)c2)n1] | $^1$H-NMR (400 MHz, $CDCl_3$) δ: 1.46 (3H, t, J = 7.3 Hz), 2.22 (3H, s), 2.95 (3H, s), 3.35 (2H, t, J = 5.3 Hz), 3.50 (3H, s), 4.05 (2H, q, J = 7.3 Hz), 4.50-4.60 (2H, m), 6.70-6.77 (2H, m), 7.24-7.38 (3H, m), 7.46-7.61 (3H, m), 7.62-7.70 (2H, m), 7.98-8.08 (2H, m), 8.20(1H, s), 8.62-8.85 (2H, m). ESI-MS m/z: 687 $[M + H]^+$ |
| 178 | 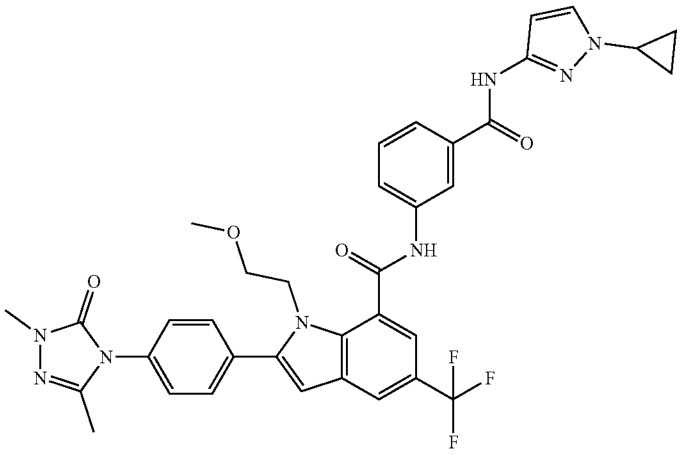 [SMILES: COCCn1c(-c2ccc(-n3c(C)nn(C)c3=O)cc2)cc2cc(C(F)(F)F)cc(C(=O)Nc3cccc(C(=O)Nc4ccn(C5CC5)n4)c3)c21] | $^1$H-NMR (400 MHz, $CDCl_3$) δ: 0.98 (2H, t, J = 6.9 Hz), 1.03-1.09 (2H, m), 2.22 (3H, s), 2.94 (3H, s), 3.35 (2H, t, J = 5.3 Hz), 3.44-3.54 (4H, m), 4.47-4.62 (2H, m), 6.68-6.77 (2H, m), 7.22-7.37 (3H, m), 7.45-7.60 (3H, m), 7.61-7.69 (2H, m), 7.99-8.08 (2H, m), 8.22(1H, s), 8.69-8.97 (2H, m). ESI-MS m/z: 699 $[M + H]^+$ |
| 179 | 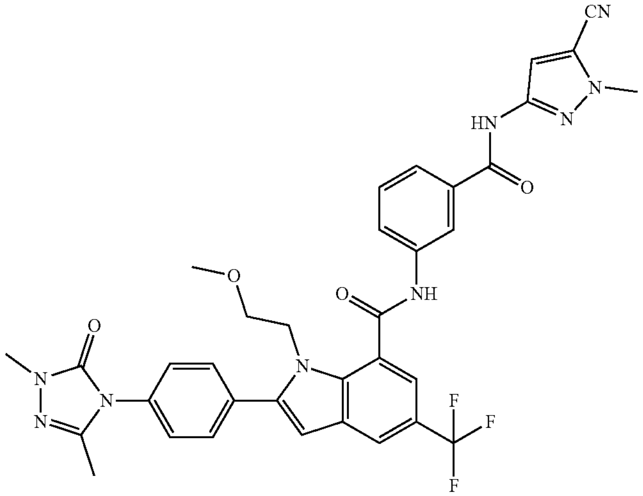 | $^1$H-NMR (400 MHz, $CDCl_3$) δ: 2.23 (3H, s), 2.99 (3H, s), 3.36 (2H, t, J = 5.2 Hz), 3.51 (3H, s), 3.96 (3H, s), 4.59 (2H, t, J = 5.2 Hz), 6.75 (1H, s), 7.15-7.21 (1H, m), 7.32-7.39 (2H, m), 7.55 (1H, t, J = 8.0 Hz), 7.58-7.65 (3H, m), 7.68 (1H, d, J = 7.4 Hz), 7.98-8.06 (2H, m), 8.30(1H, s), 8.65-8.80 (2H, m). ESI-MS m/z: 696 $[M - H]^-$ |

TABLE 8-4-continued
| | | |
|---|---|---|
| 180 | 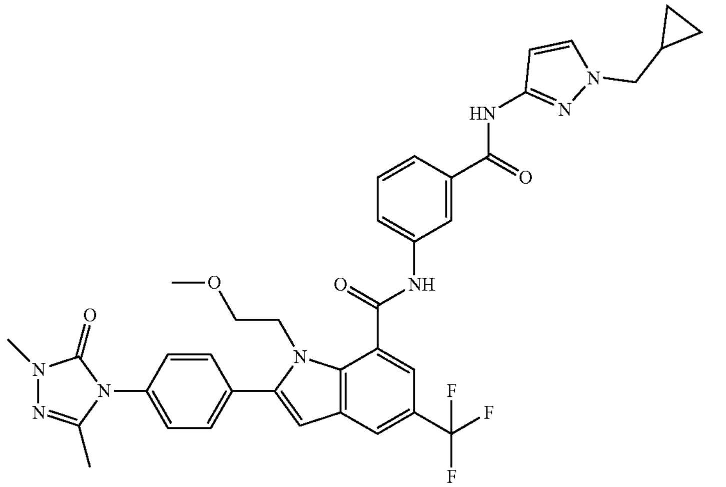 [SMILES: COCCn1c(-c2ccc(-n3c(C)nn(C)c3=O)cc2)cc2cc(C(F)(F)F)cc(C(=O)Nc3cccc(C(=O)Nc4ccn(CC5CC5)n4)c3)c21] | $^1$H-NMR (400 MHz, $CDCl_3$) δ: 0.32-0.38 (2H, m), 0.61-0.68 (2H, m), 1.25 (1H, m), 2.22 (3H, s) 2.95 (3H, s), 3.35 (2H, t, J = 5.2 Hz), 3.49 (3H, s), 3.86 (2H, d, J = 7.0 Hz), 4.48-4.63 (2H, m), 6.70-6.80 (2H, m), 7.28 (1H, m), 7.39 (1H, m), 7.55 (1H, t, J = 8.0 Hz), 7.46-7.60 (3H, m), 7.62-7.70 (2H, m), 7.99-8.07 (2H, m), 8.20(1H, s), 8.63-8.88 (2H, m). ESI-MS m/z: 713 $[M + H]^+$ |
TABLE 8-5
| | | |
|---|---|---|
| 181 | 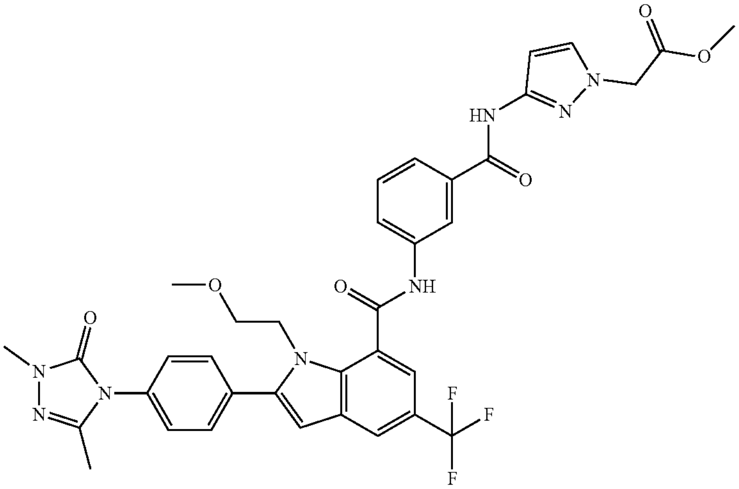 | $^1$H-NMR (400 MHz, $CDCl_3$) δ: 2.22 (3H, s), 2.95 (3H, s), 3.35 (2H, t, J = 5.3 Hz), 3.49 (3H, s), 3.77 (3H, s), 4.50-4.61 (2H, m), 4.80 (2H, s), 6.74 (1H, s), 6.87 (1H, m), 7.27-7.34 (2H, m), 7.37 (1H, m), 7.51 (1H, t, J = 7.8 Hz), 7.54-7.60 (2H, m), 7.62-7.69 (2H, m), 7.97-8.06 (2H, m), 8.19(1H, s), 8.63-8.81 (2H, m). ESI-MS m/z: 729 $[M - H]^-$ |
| 182 | 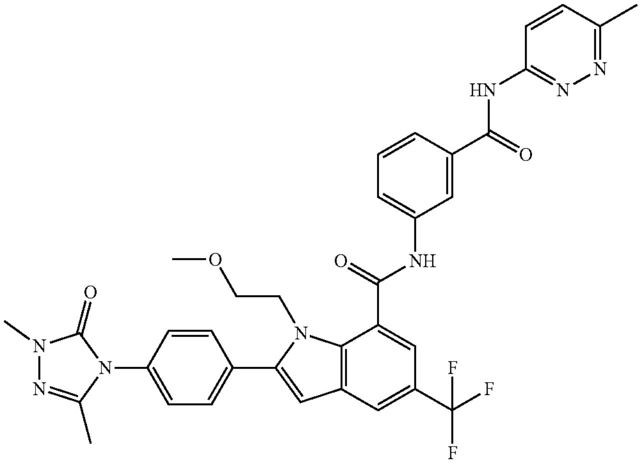 | $^1$H-NMR (400 MHz, $CDCl_3$) δ: 2.22 (3H, s), 2.65 (3H, s), 3.02 (3H, s), 3.40-3.47 (2H, m), 3.49 (3H, s), 4.53-4.65 (2H, m), 6.72 (1H, s), 7.29-7.44 (3H, m), 7.48-7.63 (4H, m), 7.77 (1H, d, J = 7.8 Hz), 7.99 (1H, m), 8.07 (1H, d, J = 7.8 Hz), 8.37 (1H, s), 8.50(1H, br s), 9.24 (1H, br s), 9.64 (1H, br s). ESI-MS m/z: 685 $[M + H]^+$ |

TABLE 8-5-continued
| | | |
|---|---|---|
| 183 | 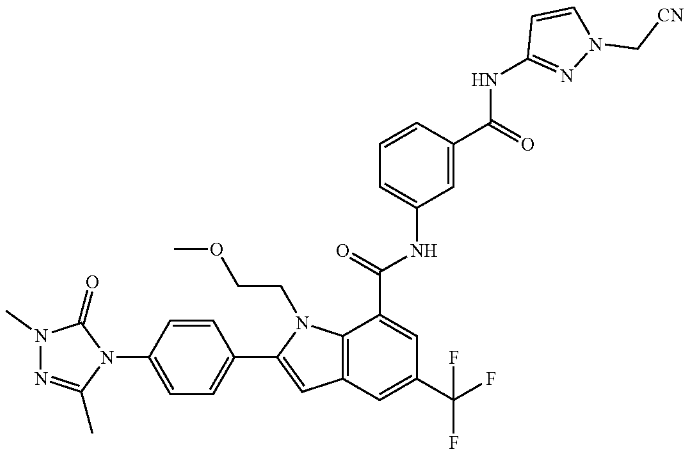 [SMILES: COCCn1c(-c2ccc(-n3c(C)nn(C)c3=O)cc2)cc2cc(C(F)(F)F)cc(C(=O)Nc3cccc(C(=O)Nc4ccn(CC#N)n4)c3)c21] | $^1$H-NMR (400 MHz, $CDCl_3$) δ: 2.22 (3H, s), 2.95 (3H, s), 3.35 (2H, t, J = 5.4 Hz), 3.49 (3H, s), 4.55 (2H, t, J = 5.3 Hz), 4.95 (2H, s), 6.74 (1H, s), 6.88 (1H, d, J = 2.4 Hz), 7.29 (2H, d, J = 8.4 Hz), 7.39 (1H, d, J = 2.5 Hz), 7.49-7.58 (3H, m), 7.64 (1H, m), 7.68 (1H, d, J = 7.9 Hz), 7.97-8.05 (2H, m) 8.26 (1H, m), 8.82-8.90 (2H, m). ESI-MS m/z: 698 $[M + H]^+$ |
| 184 | 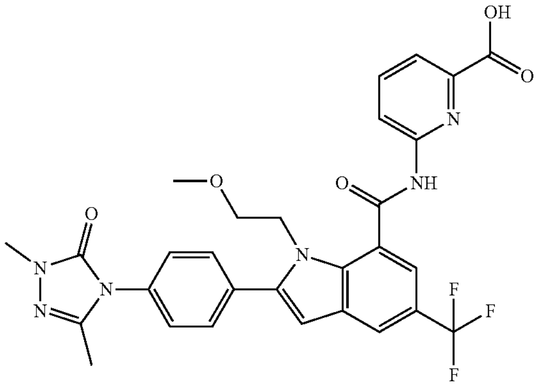 [SMILES: COCCn1c(-c2ccc(-n3c(C)nn(C)c3=O)cc2)cc2cc(C(F)(F)F)cc(C(=O)Nc3cccc(C(=O)O)n3)c21] | ESI-MS m/z: 595 $[M + H]^+$ |
| 185 | 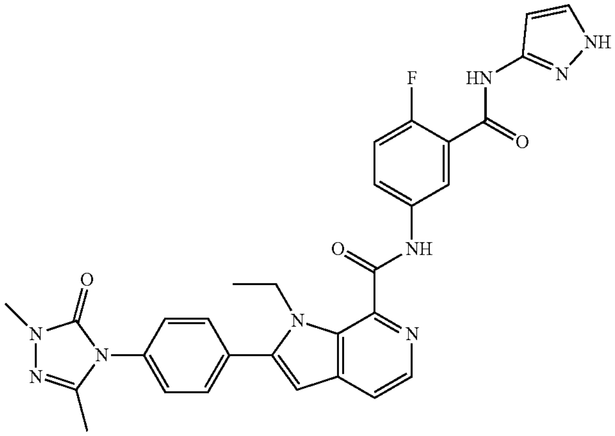 [SMILES: CCn1c(-c2ccc(-n3c(C)nn(C)c3=O)cc2)cc2ccnc(C(=O)Nc3ccc(F)c(C(=O)Nc4cc[nH]n4)c3)c21] | ESI-MS m/z: 580 $[M + H]^+$ |

TABLE 8-5-continued
| | | |
|---|---|---|
| 186 | 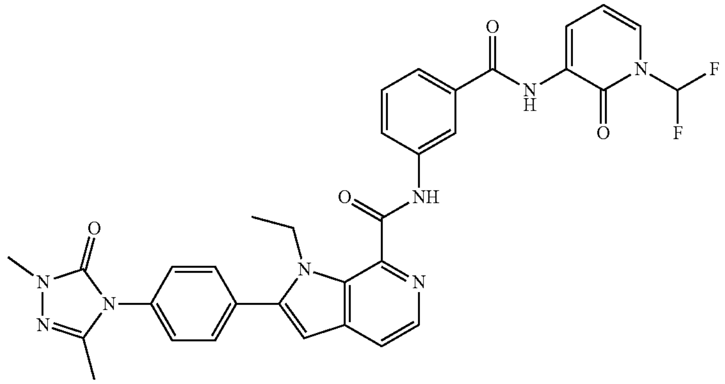 [SMILES: CCn1c(-c2ccc(-n3c(C)nn(C)c3=O)cc2)cc2ccnc(C(=O)Nc3cccc(C(=O)Nc4cccn(C(F)F)c4=O)c3)c21] | ESI-MS m/z: 639 $[M + H]^+$ |
TABLE 8-6
| | | |
|---|---|---|
| 187 | 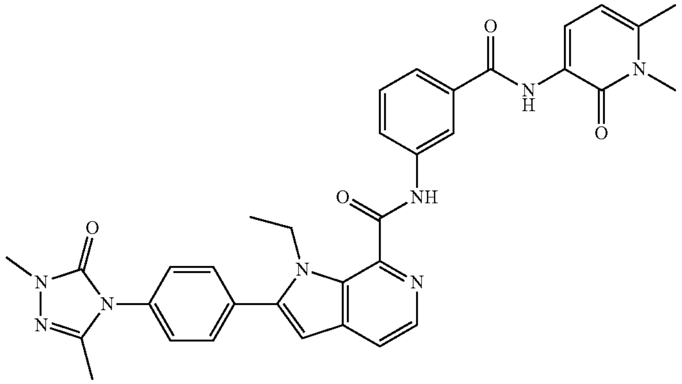 | $^1$H-NMR (400 MHz, $CDCl_3$) δ: 1.00 (3H, t, J = 7.0 Hz), 2.26 (3H, s), 2.39 (3H, s), 3.53 (3H, s), 3.64 (3H, s), 4.89 (2H, q, J = 7.0 Hz), 6.18 (1H, d, J = 8.2 Hz), 6.70 (1H, s), 7.48 (2H, d, J = 8.4 Hz), 7.54 (1H, t, J = 7.9 Hz), 7.69-7.74 (4H, m), 8.16 (1H, m), 8.24 (1H, m), 8.32 (1H, d, J = 5.1 Hz), 8.47 (1H, d, J = 7.6 Hz), 9.20 (1H, s), 10.34 (1H, s). ESI-MS m/z: 617 $[M + H]^+$ |
| 188 | 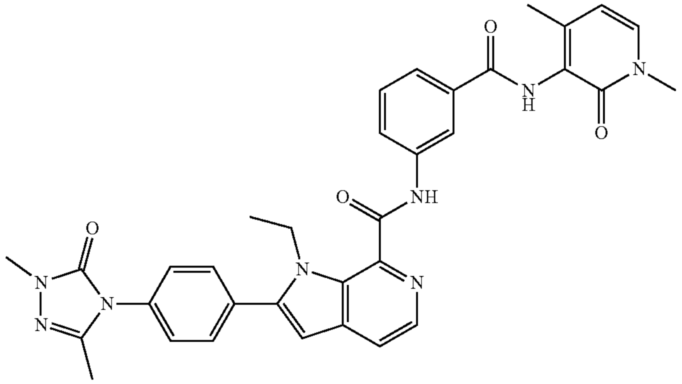 | ESI-MS m/z: 617 $[M + H]^+$ |

TABLE 8-6-continued
| | | |
|---|---|---|
| 189 | 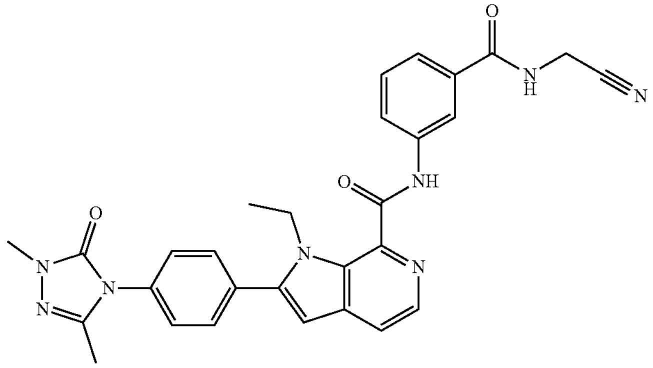 [SMILES: CCn1c(-c2ccc(-n3c(C)nn(C)c3=O)cc2)cc2ccnc(C(=O)Nc3cccc(C(=O)NCC#N)c3)c21] | $^{1}$H-NMR (400 MHz, $CDCl_3$) δ: 0.98 (3H, t, J = 7.0 Hz), 2.25 (3H, s), 3.53 (3H, s), 4.40 (2H, d, J = 5.7 Hz), 4.83 (2H, q, J = 7.0 Hz), 6.70 (1H, s), 7.02 (1H, t, J = 5.5 Hz), 7.46-7.50 (3H, m), 7.60 (1H, d, J = 7.9 Hz), 7.68 (2H, d, J = 8.4 Hz), 7.72 (1H, d, J = 5.2 Hz), 7.90 (1H, m), 8.25 (1H, d, J = 5.1 Hz), 8.32 (1H, m), 10.46 (1H, s). ESI-MS m/z: 535 $[M + H]^+$ |
| 190 | 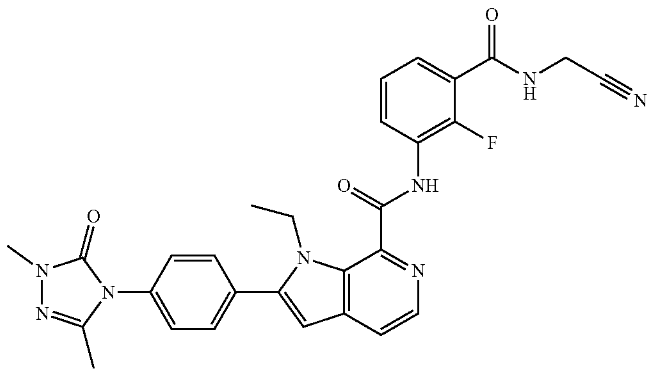 [SMILES: CCn1c(-c2ccc(-n3c(C)nn(C)c3=O)cc2)cc2ccnc(C(=O)Nc3cccc(C(=O)NCC#N)c3F)c21] | $^{1}$H-NMR (400 MHz, $CDCl_3$) δ: 1.00 (3H, t, J = 7.0 Hz), 2.26 (3H, s), 3.53 (3H, s), 4.45 (2H, d, J-4.9 Hz), 4.88 (2H, q, J = 7.0 Hz), 6.71 (1H, s), 7.06 (1H, m), 7.37 (1H, t, J = 8.0 Hz), 7.48 (2H, d, J = 8.5 Hz), 7.70 (2H, d, J = 8.5 Hz), 7.76 (1H, d, J = 5.1 Hz), 7.85 (1H, m), 8.32 (1H, d, J = 5.1 Hz), 8.75 (1H, dt, J = 1.7, 11.9 Hz), 10.63 (1H, m). ESI-MS m/z: 553 $[M + H]^+$ |
| 191 | 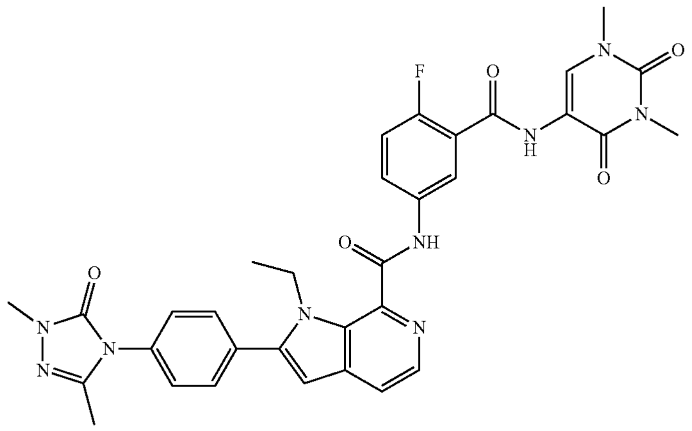 | $^{1}$H-NMR (400 MHz, $CDCl_3$) δ: 0.99 (3H, t, J = 7.0 Hz), 2.26 (3H, s), 3.46 (3H, s), 3.49 (3H, s), 3.53 (3H, s), 4.88 (2H, q, J = 7.0 Hz), 6.70 (1H, s), 7.26 (1H, m), 7.48 (2H, d, J = 8.4 Hz), 7.70 (2H, d, J = 8.4 Hz), 7.74 (1H, d, J = 5.1 Hz), 8.20 (1H, m), 8.30-8.33 (2H, m), 8.73 (1H, s), 9.19 (1H, d, J = 14.4 Hz), 10.35 (1H, s). ESI-MS m/z: 652 $[M + H]^+$ |

TABLE 8-7

| | | |
|---|---|---|
| 192 | 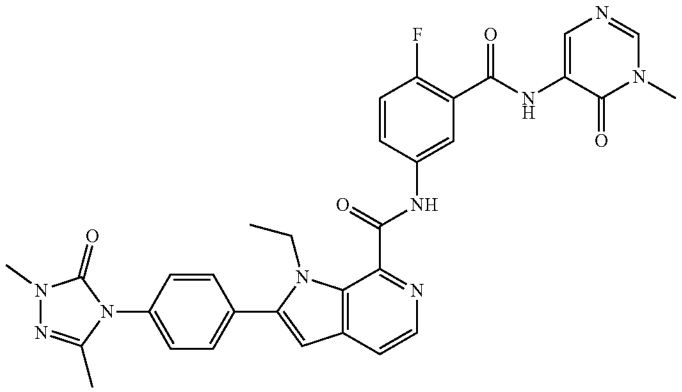 | $^1$H-NMR (400 MHz, $CDCl_3$) 1.01 (3H, t, J = 7.0 Hz), 2.26 (3H, s), 3.53 (3H, s), 3.65 (3H, s), 4.89 (2H, q, J = 7.0 Hz), 6.71 (1H, s), 7.38 (1H, t, J = 8.0 Hz), 7.48 (2H, d, J = 8.5 Hz), 7.71 (2H, d, J = 8.5 Hz), 7.76 (1H, d, J = 5.1 Hz), 7.86 (1H, m), 7.97 (1H, s), 8.34 (1H, d, J = 5.1 Hz), 8.83 (1H, m), 9.22 (1H, s), 9.46 (1H, d, J = 13.8 Hz), 10.73 (1H, m). ESI-MS m/z: 622 $[M + H]^+$ |
| 193 | 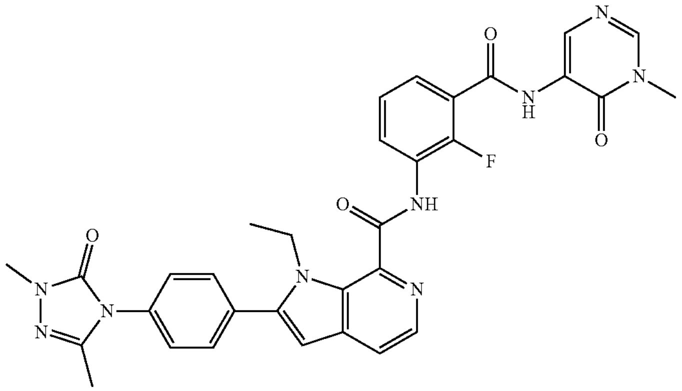 | $^1$H-NMR (400 MHz, $CDCl_3$) δ: 0.99 (3H, t, J = 7.0 Hz), 2.26 (3H, s), 3.53 (3H, s), 3.64 (3H, s), 4.88 (2H, q, J = 7.0 Hz), 6.70 (1H, s), 7.26 (1H, m), 7.48 (2H, d, J = 8.5 Hz), 7.70 (2H, d, J = 8.5 Hz), 7.74 (1H, d, J = 5.2 Hz), 7.96 (1H, s), 8.26-8.33 (3H, m), 9.22 (1H, s), 9.50 (1H, d, J = 15.0 Hz), 10.37 (1H, s). ESI-MS m/z: 622 $[M + H]^+$ |
| 194 | 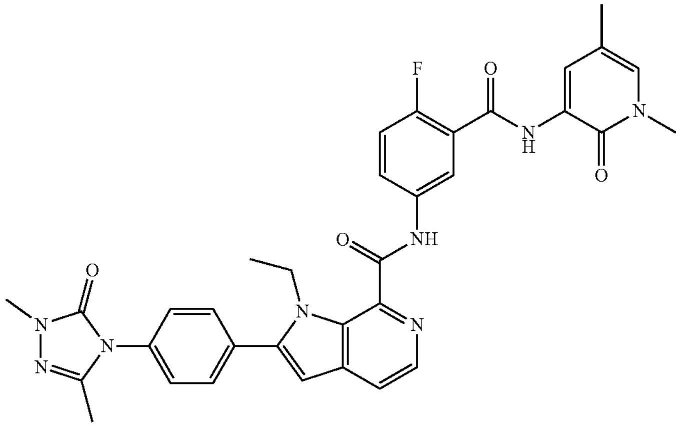 | $^1$H-NMR (400 MHz, $CDCl_3$) δ: 0.99 (3H, t, J = 7.0 Hz), 2.16 (3H, s), 2.26 (3H, s), 3.53 (3H, s), 3.61 (3H, s), 4.88 (2H, q, J = 7.0 Hz), 6.70 (1H, s), 6.84 (1H, m), 7.26 (1H, m), 7.48 (2H, d, J = 8.5 Hz), 7.70 (2H, d, J = 8.4 Hz), 7.74 (1H, d, J = 5.2 Hz), 8.23 (1H, m), 8.29-8.31 (2H, m), 8.49 (1H, d, J = 2.2 Hz), 9.84 (1H, d, J = 14.0 Hz), 10.32 (1H, s). ESI-MS m/z: 635 $[M + H]^+$ |
| 195 | 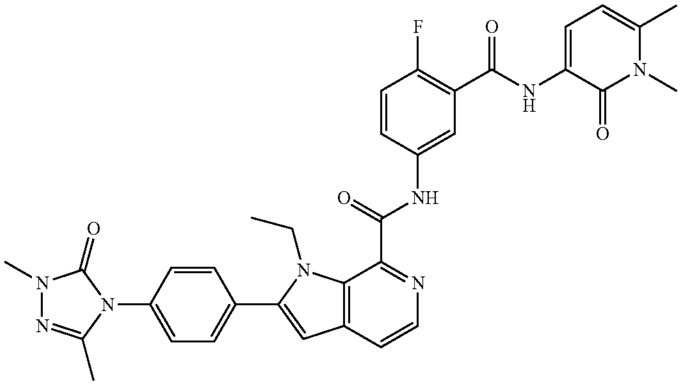 | $^1$H-NMR (400 MHz, $CDCl_3$) δ: 0.99 (3H, t, J = 7.0 Hz), 2.26 (3H, s), 2.38 (3H, s), 3.53 (3H, s), 3.64 (3H, s), 4.88 (2H, q, J = 7.0 Hz), 6.17 (1H, d, J = 8.3 Hz), 6.70 (1H, s), 7.26 (1H, m), 7.48 (2H, d, J = 8.5 Hz), 7.70 (2H, d, J = 8.5 Hz), 7.73 (1H, d, J = 5.2 Hz), 8.23-8.31 (3H, m), 8.48 (1H, d, J = 7.6 Hz), 9.77 (1H, d, J = 13.6 Hz), 10.32 (1H, s). ESI-MS m/z: 635 $[M + H]^+$ |

TABLE 8-8
| | | |
|---|---|---|
| 196 | 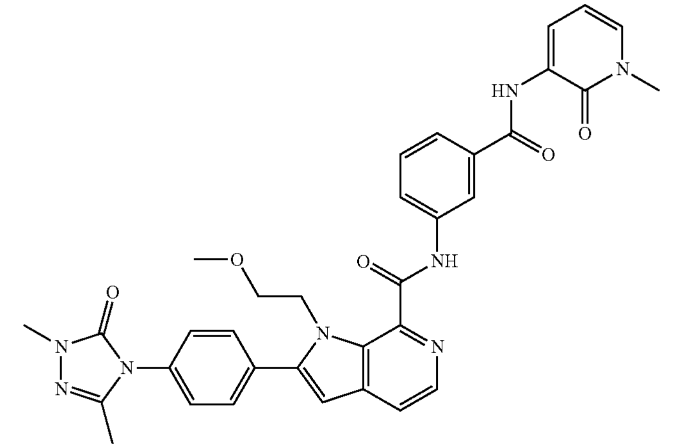 | $^1$H-NMR (400 MHz, $CDCl_3$) δ: 2.26 (3H, s), 2.94 (3H, s), 3.40 (2H, t, J = 5.1 Hz), 3.53 (3H, s), 3.66 (3H, s), 5.07 (2H, t, J = 5.1 Hz), 6.31 (1H, t, J = 7.1 Hz), 6.89 (1H, s), 7.04-7.06 (1H, m), 7.46 (2H, d, J = 8.4 Hz), 7.54 (1H, t, J = 7.8 Hz), 7.68-7.75 (4H, m), 8.16-8.17 (1H, m), 8.21-8.24 (1H, m), 8.32 (1H, d, J = 5.1 Hz), 8.55-8.58 (1H, m), 8.28 (1H, s), 10.39 (1H, s). ESI-MS m/z: 633 $[M + H]^+$ |
| 197 | 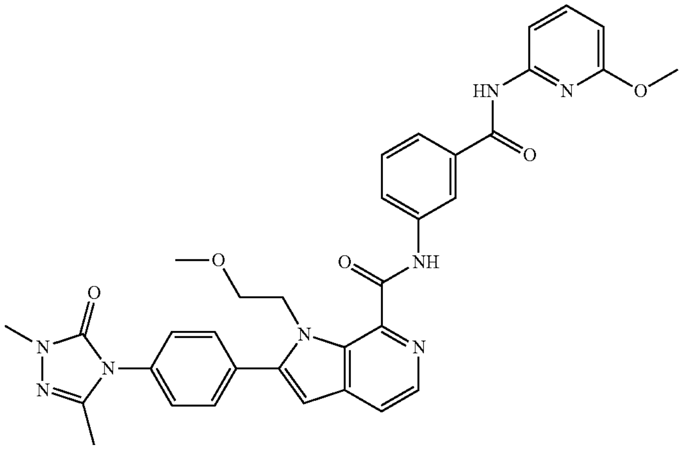 | $^1$H-NMR (400 MHz, $CDCl_3$) δ: 2.27 (3H, s), 2.95 (3H, s), 3.40 (2H, t, J = 5.1 Hz), 3.53 (3H, s), 3.92 (3H, s), 5.07 (2H, t, J = 5.1 Hz), 6.54 (1H, t, J = 8.1 Hz), 6.70 (1H, s), 7.46 (2H, d, J = 8.5 Hz), 7.55 (1H, t, J = 7.9 Hz), 7.65-7.76 (5H, m), 7.95 (1H, d, J = 7.6 Hz), 8.08-8.10 (1H, m), 8.31-8.36 (3H, m), 10.38 (1H, s). ESI-MS m/z: 633 $[M + H]^+$ |
| 198 | 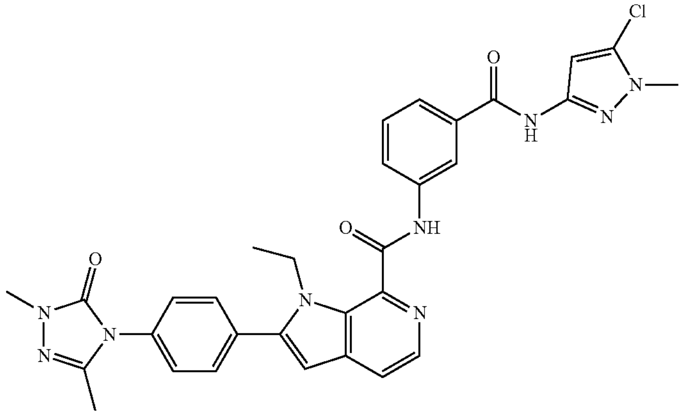 | $^1$H-NMR (400 MHz, $CDCl_3$) δ: 1.00 (3H, t, J = 7.0 Hz), 2.26 (3H, s), 3.53 (3H, s), 3.77 (3H, s), 4.89 (2H, q, J = 7.0 Hz), 6.70 (1H, s), 6.87 (1H, s), 7.45-7.56 (3H, m), 7.63-7.76 (4H, m), 7.99 (1H, dd, J = 8.0, 1.2 Hz), 8.30 (1H, d, J = 5.1 Hz), 8.37 (1H, t, J = 1.8 Hz), 8.58 (1H, m), 10.37 (1H, s). ESI-MS m/z: 610 $[M + H]^+$ |

TABLE 8-8-continued

| | | |
|---|---|---|
| 199 | 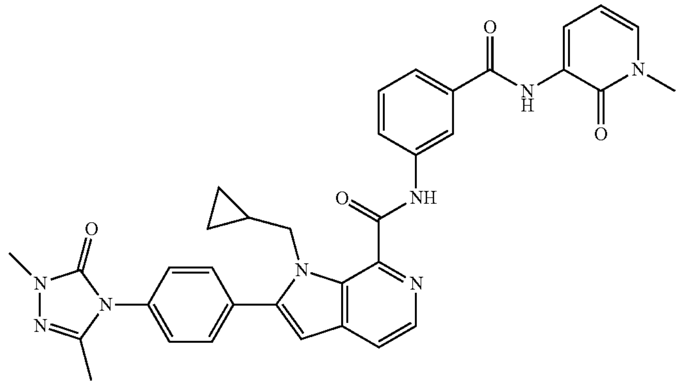 | $^1$H-NMR (400 MHz, $CDCl_3$) δ: −0.13-−0.09(2H, m), 0.14-0.19 (2H, m), 0.73 (1H, m), 2.26 (3H, s), 3.53 (3H, s), 3.66 (3H, s), 4.74 (2H, d, J = 6.9 Hz), 6.31 (1H, t, J = 7.1 Hz), 6.74 (1H, s), 7.05 (1H, dd, J = 1.8, 6.8 Hz), 7.47 (2H, d, J = 8.4 Hz), 7.55 (1H, t, J = 8.0 Hz), 7.69-7.73 (3H, m), 7.75 (1H, d, J = 5.2 Hz), 8.17 (1H, s), 8.28 (1H, m), 8.33 (1H, d, J = 5.2 Hz), 8.57 (1H, dd, J = 1.7, 7.5 Hz), 9.29 (1H, s), 10.41 (1H, s). ESI-MS m/z: 629 [M + H]$^+$ |

TABLE 8-9

| | | |
|---|---|---|
| 200 | 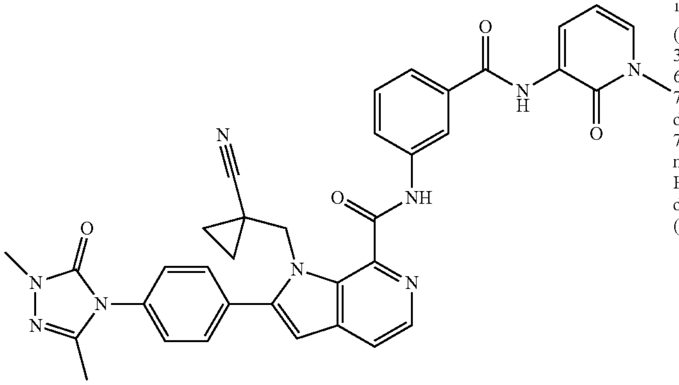 | $^1$H-NMR (400 MHz, $CDCl_3$) δ: 0.84-0.90 (2H, m), 0.97-1.00 (2H, m), 2.27 (3H, s), 3.53 (3H, s), 3.66 (3H, s), 5.19 (2H, s), 6.32 (1H, t, J = 7.1 Hz), 6.85 (1H, s), 7.06 (1H, dd, J = 1.8, 6.9 Hz), 7.51 (2H, d, J = 8.5 Hz), 7.56 (1H, d, J = 7.9 Hz), 7.72 (1H, d, J = 8.1 Hz), 7.79-7.81 (3H, m), 8.15 (1H, m), 8.27 (1H, t, J = 1.8 Hz), 8.40 (1H, d, J = 5.1 Hz), 8.57 (1H, dd, J = 1.8, 7.4 Hz), 9.29 (1H, s), 10.64 (1H, s). ESI-MS m/z: 654 [M + H]$^+$ |
| 201 | 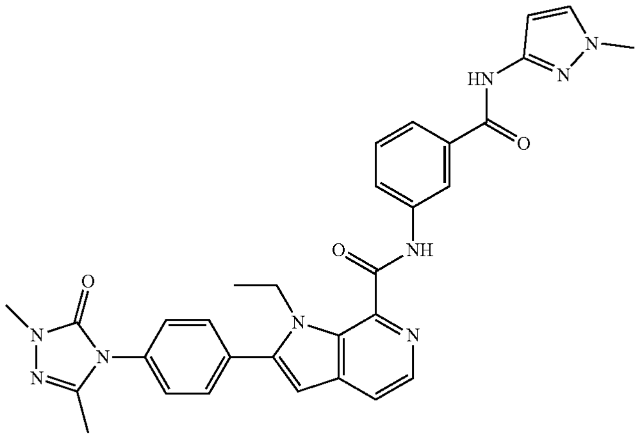 | $^1$H-NMR (400 MHz, $CDCl_3$) δ: 1.00 (3H, t, J = 7.0 Hz), 2.26 (3H, s), 3.53 (3H, s), 3.84 (3H, s), 4.89 (2H, q, J = 7.1 Hz), 6.70 (1H, s), 6.86 (1H, d, J = 2.2 Hz), 7.31 (1H, d, J = 2.3 Hz), 7.46-7.54 (3H, m), 7.66-7.74 (4H, m), 7.89-8.00 (1H, m), 8.31 (1H, d, J = 5.1 Hz), 8.38 (1H, t, J = 1.9 Hz), 8.61 (1H, br s), 10.35 (1H, s). ESI-MS m/z: 576 [M + H]$^+$ |

TABLE 8-9-continued

| | | |
|---|---|---|
| 202 | 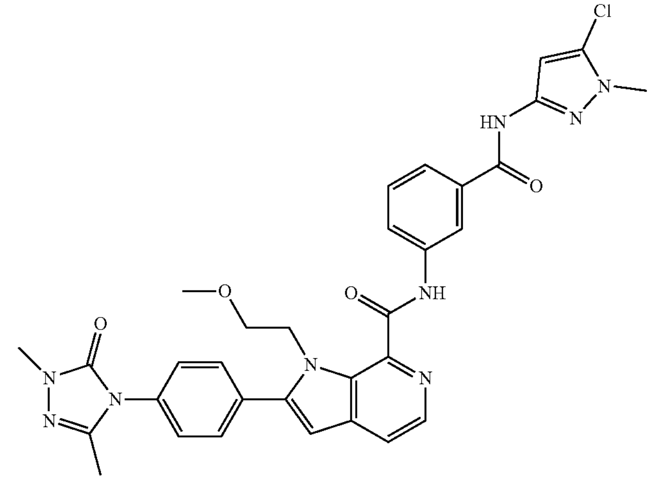 | $^1$H-NMR (400 MHz, $CDCl_3$) δ: 2.18 (3H, s), 2.94 (3H, s), 3.40 (2H, t, J = 5.1 Hz), 3.53 (3H, s), 3.79 (3H, s), 5.07 (2H, t, J = 4.5 Hz), 6.70 (1H, s), 6.87 (1H, s), 7.45-7.47 (2H, m), 7.52 (1H, t, J = 7.9 Hz), 7.64 (1H, d, J = 7.6 Hz), 7.72-7.75 (3H, m), 7.98-8.01 (1H, m), 8.31 (1H, d, J = 5.1 Hz), 8.36-8.39 (2H, m), 10.40 (1H, s). ESI-MS m/z: 640 [M + H]$^+$ |

Example 203

[Chem. Fig. 103]

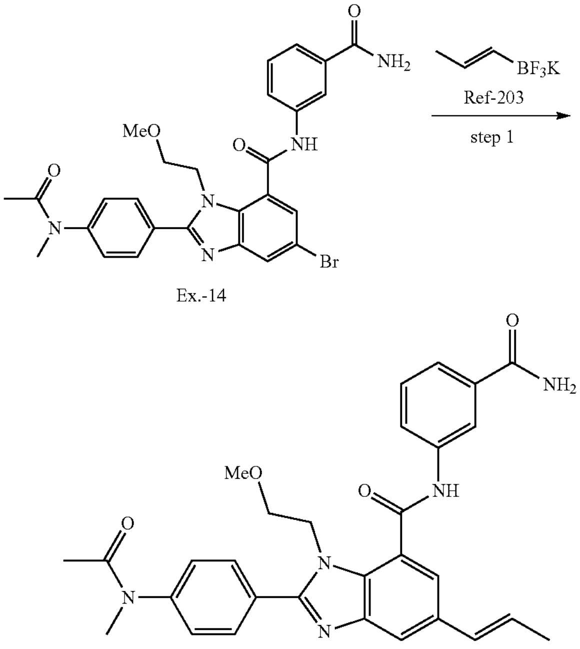

Ex.-14
Ex.-203

Step 1

Example Compound 14 (39.8 mg, 0.0705 mmol), reference synthesis example compound 203 (54.3 mg, 0.367 mmol), 1,4-dioxane (700 μL), and water (64 μL) were mixed, and then cesium carbonate (33.2 mg, 0.102 mmol), XPhos (3.9 mg, 0.0082 mmol), and XPhos-palladium (crotyl) chloride (4.7 mg, 0.0070 mmol) were added, followed by stirring at 100° C. for 2 hours. Water was added to the cooled reaction solution, and the mixture was extracted using ethyl acetate. The solvent was distilled off under reduced pressure, and then the residue was purified by silica gel column chromatography to obtain Example Compound 203 (yield 33.6 mg).

Example 204

[Chem. Fig. 104]

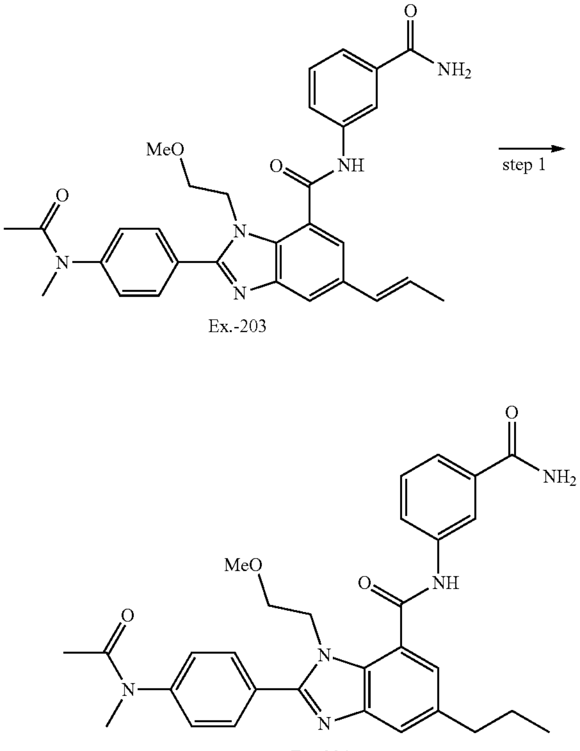

Ex.-203
Ex.-204

Step 1

Example Compound 203 (23.0 mg, 0.0438 mmol) and methanol (1 mL) were mixed, 20% palladium hydroxide-carbon (4.8 mg) was added, and then the mixture was stirred at room temperature for 17 hours under a hydrogen environment. The reaction solution was filtered through Celite®, and evaporated under reduced pressure to obtain Example Compound 204 (yield 18.6 mg).

Example 205

[Chem. Fig. 105]

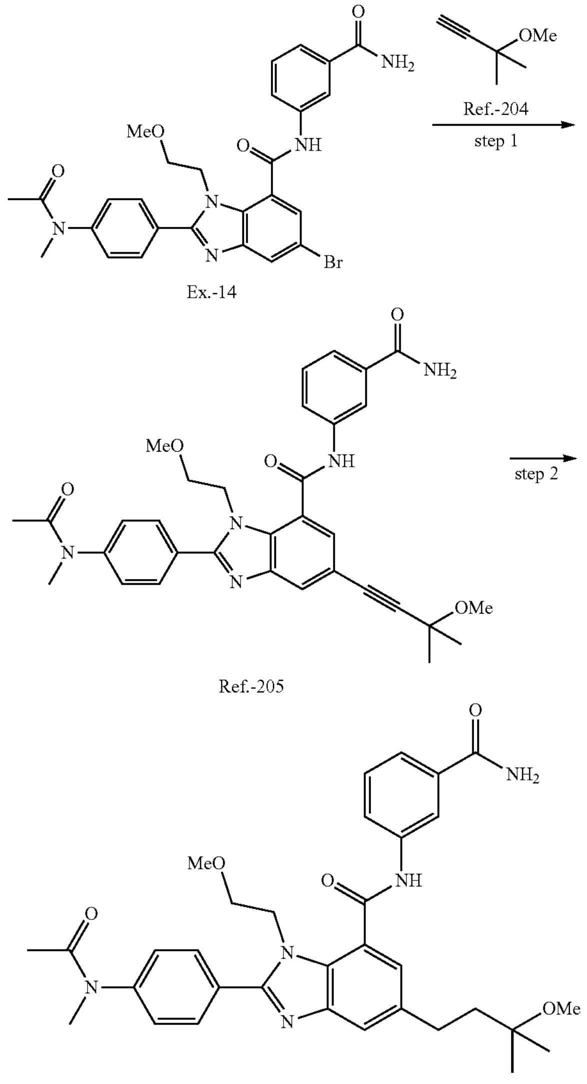

Ex.-14

Ref.-205

Ex.-205

Step 1

Example Compound 14 (50.3 mg, 0.0891 mmol) and 1,4-dioxane (886 μL) were mixed, and then reference synthesis example compound 204 (46.9 mg, 0.478 mmol), [1,1'-bis(diphenylphosphino)ferrocene] dichloropalladium (II) (13.1 mg, 0.0179 mmol), cuprous iodide (4.0 mg, 0.021 mmol), and triethyl amine (25 μL, 0.179 mmol) were added, and the mixture was stirred at 100° C. for 3 hours under an argon environment. Water was added to the cooled reaction solution, and the mixture was extracted using ethyl acetate. The solvent was distilled off under reduced pressure, and then the residue was purified by silica gel column chromatography to obtain reference synthesis example compound 205 (yield 22.0 mg).

Step 2

Reference synthesis example compound 205 (18.0 mg, 0.0309 mmol) and methanol (1 mL) were mixed, 20% palladium hydroxide-carbon (3.5 mg) was added, and the mixture was stirred at room temperature for 17 hours under a hydrogen environment (ambient pressure). The reaction solution was filtered through Celite®, and evaporated under reduced pressure to give Example Compound 205 (yield 18.2 mg).

Example 206

[Chem. Fig. 106]

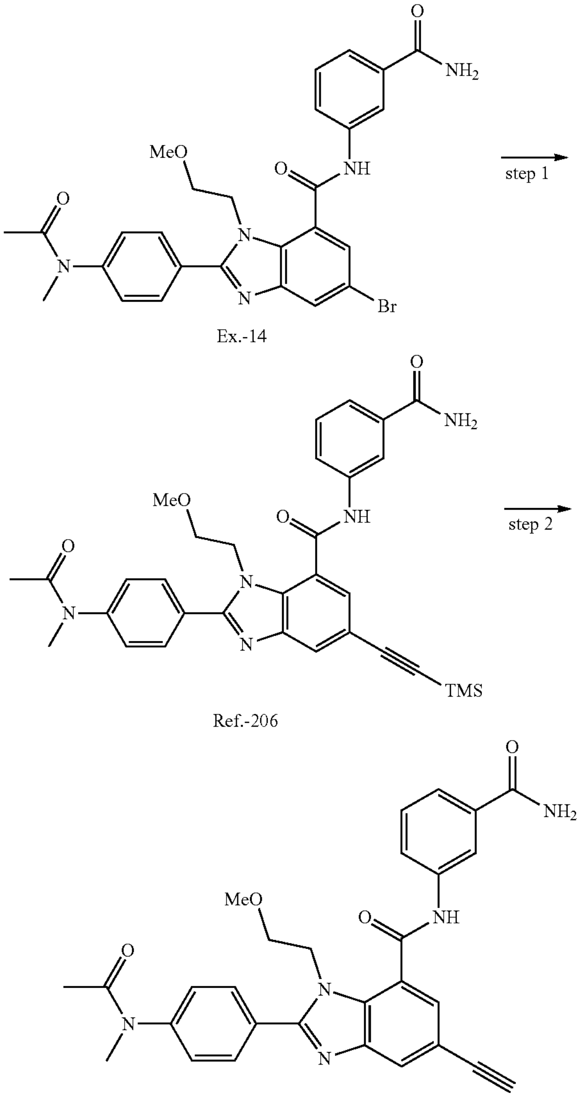

Ex.-14

Ref.-206

Ex.-206

Step 1

Example Compound 14 (39.7 mg, 0.0703 mmol) and 1,4-dioxane (700 μL) were mixed, then trimethylsilylacetylene (50 μL, 0.35 mmol), dichlorobis(triphenylphosphine) palladium(II) (5.8 mg, 0.0083 mmol), cuprous iodide (3.3 mg, 0.017 mmol), and triethylamine (19.8 μL, 0.142 mmol) were added, and the mixture was stirred at 100° C. for 3 hours under an argon environment. Water was added to the cooled reaction solution, and the mixture was extracted using ethyl acetate. The solvent was distilled off under reduced pressure, and then the residue was purified by silica gel column chromatography to obtain reference synthesis example compound 206 (yield 11.3 mg).

Step 2

Reference synthesis example compound 206 (7.0 mg, 0.012 mmol) and THF (0.4 mL) were mixed, and TBAF/THF (1.00 mol/L) (24 μL) was added, followed by stirring at room temperature for 2 hours. The reaction solution was concentrated under reduced pressure, and then the residue was purified by silica gel column chromatography to obtain Example Compound 206 (yield 6.0 mg).

Example Compounds 203 to 212 in the following table were produced by the methods shown in Examples 203 to 206 described above or a similar method. Furthermore, $^1$H-NMR data and/or LC/MS data of these Example compounds are shown in the table.

TABLE 9-1

| Ex. | Structure | Data |
|---|---|---|
| 203 | 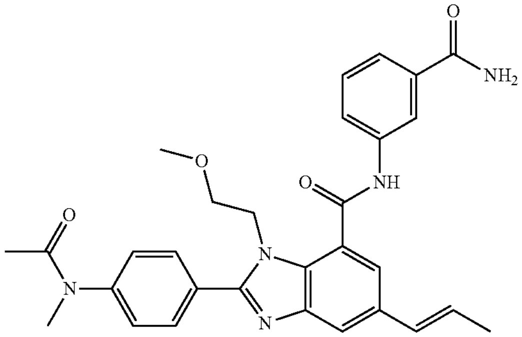 [SMILES: C/C=C/c1cc(C(=O)Nc2cccc(C(N)=O)c2)c2c(c1)nc(-c1ccc(N(C)C(C)=O)cc1)n2CCOC] | $^1$H-NMR (400 MHz, DMSO-$d_6$) δ: 1.89-1.90 (6H, m), 2.87 (3H, s), 3.24 (3H, s), 3.40-3.45 (2H, m), 4.52-4.59 (2H, m), 6.43 (1H, m), 6.61 (1H, m), 7.39-7.62 (6H, m), 7.82-7.98 (5H, m), 8.27 (1H, m), 10.88 (1H, m). ESI-MS m/z: 526 [M + H]$^+$ |
| 204 | 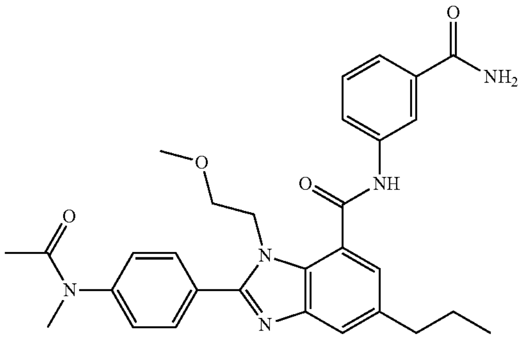 [SMILES: CCCc1cc(C(=O)Nc2cccc(C(N)=O)c2)c2c(c1)nc(-c1ccc(N(C)C(C)=O)cc1)n2CCOC] | $^1$H-NMR (400 MHz, $CDCl_3$) δ: 0.94-1.01 (3H, m), 1.71-1.73 (2H, m), 1.95 (3H, s), 2.69-2.78 (2H, m), 3.01 (3H, s), 3.32 (3H, s), 3.47-3.53 (2H, m), 4.65-4.73 (2H, m), 5.45 (1H, m), 6.28 (1H, m), 7.34-7.35 (2H, m), 7.45-7.51 (3H, m), 7.73 (1H, s), 7.82-7.83 (2H, m), 8.15-8.22 (2H, m), 9.07 (1H, m). ESI-MS m/z: 528 [M + H]$^+$ |
| 205 | 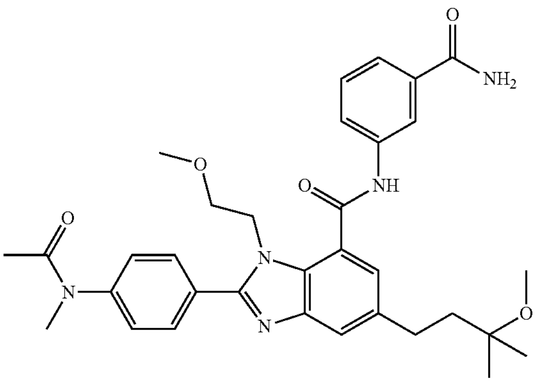 [SMILES: COCCn1c(-c2ccc(N(C)C(C)=O)cc2)nc2cc(CCC(C)(C)OC)cc(C(=O)Nc3cccc(C(N)=O)c3)c21] | ESI-MS m/z: 586 [M + H]$^+$ |

TABLE 9-1-continued
| Ex. | Structure | Data |
| --- | --- | --- |
| 206 | 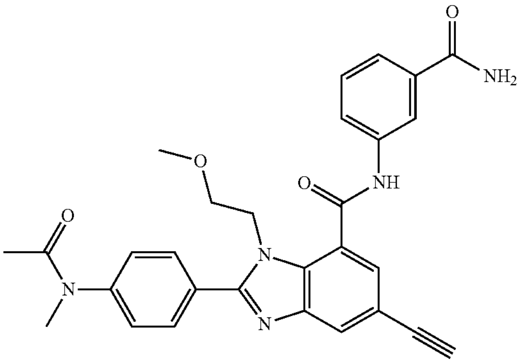 [SMILES: C#Cc1cc(C(=O)Nc2cccc(C(N)=O)c2)c2c(c1)nc(-c1ccc(N(C)C(C)=O)cc1)n2CCOC] | $^1$H-NMR (400 MHz, DMSO-$d_6$) δ: 1.90 (3H, s), 2.87 (3H, s), 3.25 (3H, s), 3.40-3.45 (2H, m), 4.22 (1H, s), 4.54-4.61 (2H, m), 7.40-7.48 (2H, m), 7.55 (2H, d, J = 6.8 Hz), 7.63-7.65 (2H, m), 7.83-7.91 (3H, m), 7.95-8.02 (2H, m), 8.25 (1H, m), 10.94 (1H, m). ESI-MS m/z: 510 $[M + H]^+$ |
| 207 | 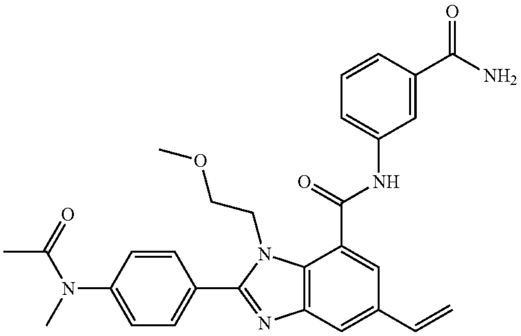 [SMILES: C=Cc1cc(C(=O)Nc2cccc(C(N)=O)c2)c2c(c1)nc(-c1ccc(N(C)C(C)=O)cc1)n2CCOC] | ESI-MS m/z: 512 $[M + H]^+$ |
TABLE 9-2
| | | |
| --- | --- | --- |
| 208 | 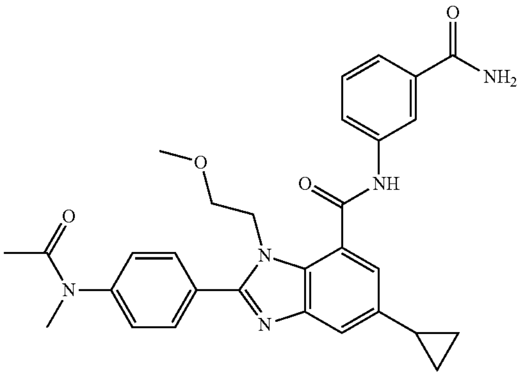 [SMILES: COCCn1c(-c2ccc(N(C)C(C)=O)cc2)nc2cc(C3CC3)cc(C(=O)Nc3cccc(C(N)=O)c3)c21] | ESI-MS m/z: 526 $[M + H]^+$ |
| 209 | 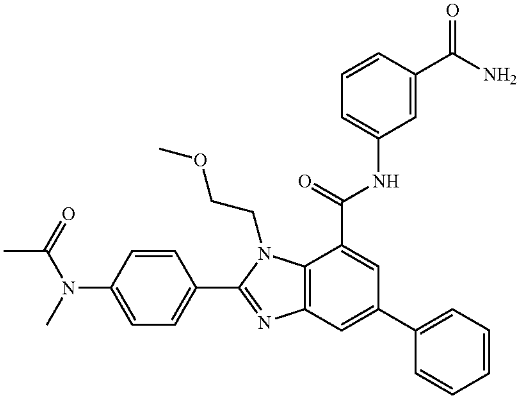 [SMILES: COCCn1c(-c2ccc(N(C)C(C)=O)cc2)nc2cc(-c3ccccc3)cc(C(=O)Nc3cccc(C(N)=O)c3)c21] | ESI-MS m/z: 562 $[M + H]^+$ |

TABLE 9-2-continued
| | | |
|---|---|---|
| 210 | 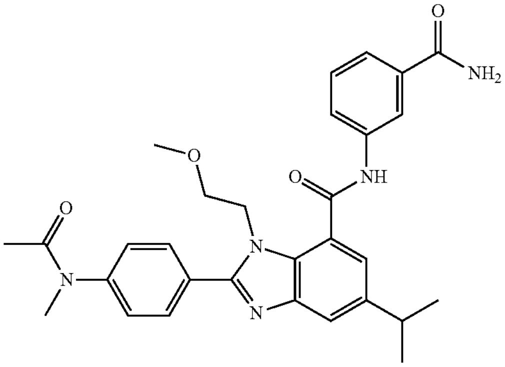 [SMILES: COCCn1c(-c2ccc(N(C)C(C)=O)cc2)nc2cc(C(C)C)cc(C(=O)Nc3cccc(C(N)=O)c3)c21] | $^1$H-NMR (400 MHz, $CDCl_3$) δ: 1.25-1.33 (6H, m), 1.97 (3H, s), 3.03 (3H, s), 3.09 (1H, m), 3.33 (3H, s), 3.48-3.56 (2H, m), 4.70-4.77 (2H, m), 5.50 (1H, m), 6.30 (1H, m), 7.36-7.53 (5H, m), 7.81-7.92 (3H, m), 8.13-8.20 (2H, m), 9.07 (1H, m). ESI-MS m/z: 528 [M + H]$^+$ |
| 211 | 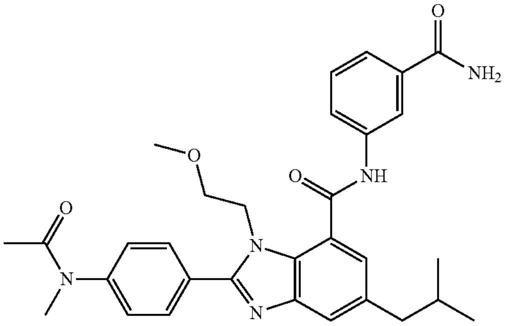 [SMILES: COCCn1c(-c2ccc(N(C)C(C)=O)cc2)nc2cc(CC(C)C)cc(C(=O)Nc3cccc(C(N)=O)c3)c21] | ESI-MS m/z: 542 [M + H]$^+$ |
| 212 | 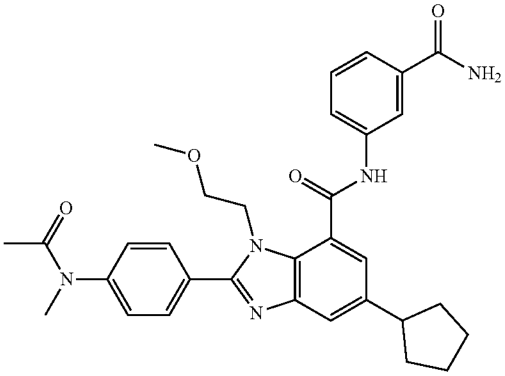 [SMILES: COCCn1c(-c2ccc(N(C)C(C)=O)cc2)nc2cc(C3CCCC3)cc(C(=O)Nc3cccc(C(N)=O)c3)c21] | ESI-MS m/z: 554 [M + H]$^+$ |
Example 213
[Chem. Fig. 107]
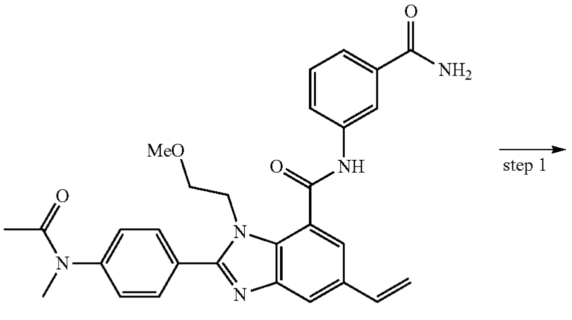
Ex.-207
-continued
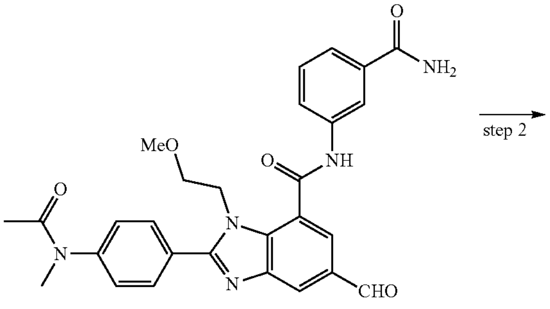
Ref.-207

-continued

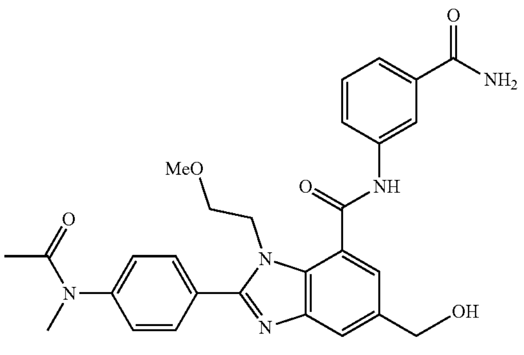

Ex.-213

Step 1

Example Compound 207 (280 mg, 0.547 mmol) and 1,4-dioxane (5.5 mL) were mixed, then, under ice-cooling, water (1.8 mL), 2,6-dimethylpyridine (127 μL, 1.09 mmol), sodium periodate (470 mg, 2.20 mmol), and osmic tetraoxide/tert-butyl alcohol (2.5 w/v %) (280 μL) were sequentially added, and the mixture was stirred at room temperature for 1.5 hours. A saturated aqueous sodium thiosulfate solution was added to the reaction solution, and the mixture was extracted using ethyl acetate. The solvent was distilled off under reduced pressure, and then the residue was purified by silica gel column chromatography to obtain reference synthesis example compound 207 (yield 280 mg).

Step 2

Reference synthetic example compound 207 (19.3 mg, 0.0376 mmol) and methanol (390 μL) were mixed, cooled with ice, sodium borohydride (14.7 mg, 0.389 mmol) was added, and then the mixture was stirred at room temperature for 7 hours. A saturated aqueous ammonium chloride solution was added to the reaction solution, and the mixture was extracted using ethyl acetate. The solvent was distilled off under reduced pressure, and then the residue was purified by silica gel column chromatography to obtain Example Compound 213 (yield 9.6 mg).

Example 214

[Chem. Fig. 108]

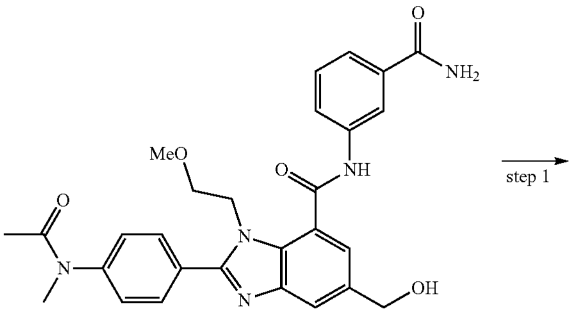

Ex.-213

-continued

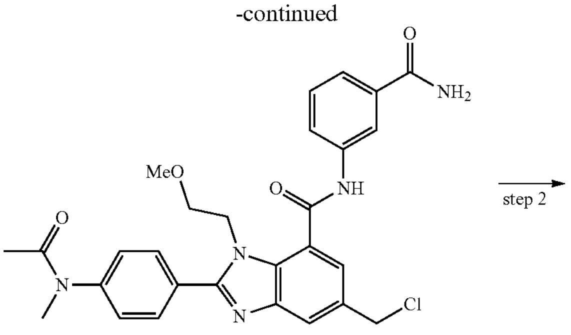

Ref.-208

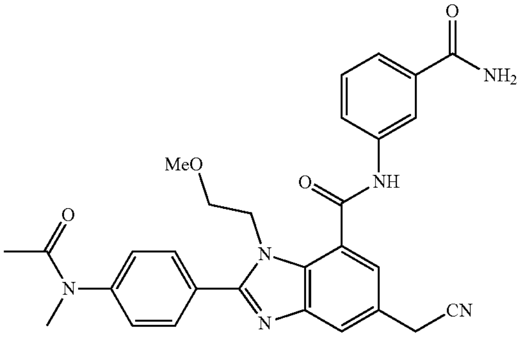

Ex.-214

Step 1

Example Compound 213 (73 mg, 0.14 mmol) and dichloromethane (1.4 mL) were mixed, ice-cooled, triethylamine (118 μL, 0.849 mmol) and methanesulfonylchloride (44 μL, 0.57 mmol) were added, and the mixture was stirred at room temperature for 23 hours. Water was added to the reaction solution, followed by extraction using chloroform. The extract was dried over anhydrous sodium sulfate, and the solvent was distilled off under reduced pressure. The residue was purified by silica gel column chromatography to obtain reference synthesis example compound 208 (yield 38.5 mg).

Step 2

Reference synthesis example compound 208 (9.8 mg, 0.018 mmol) and DMSO (370 μL) were mixed, sodium cyanide (5.1 mg, 0.10 mmol) was added, and the mixture was stirred at room temperature for 2 hours. Water was added to the reaction solution, followed by extraction using ethyl acetate. The solvent was distilled off under reduced pressure, and then the residue was purified by silica gel column chromatography and then slurry-washed with a mixed solution of ethylacetate/n-hexane (1/4) to obtain Example Compound 214 (yield 4.1 mg).

Example 215

[Chem. Fig. 109]

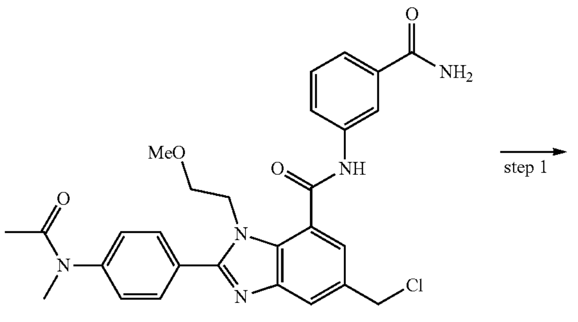

Ref.-208

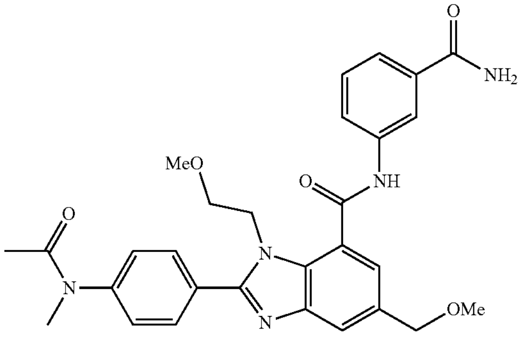

Ex.-215

Step 1

Reference synthesis example compound 208 (18.7 mg, 0.0350 mmol) and methanol (700 μL) were mixed, sodium methoxide (5.9 mg, 0.11 mmol) was added, and the mixture was stirred at room temperature for 48 hours. A saturated aqueous ammonium chloride solution was added to the reaction solution, and the mixture was extracted using chloroform. The solvent was distilled off under reduced pressure, and then the residue was purified by silica gel column chromatography to obtain Example Compound 215 (yield 2.1 mg).

Example 216

[Chem. Fig. 110]

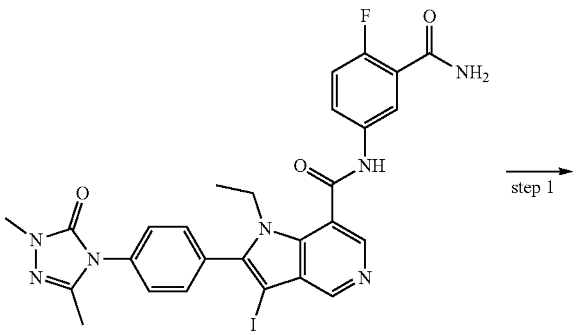

Ex.-140

-continued

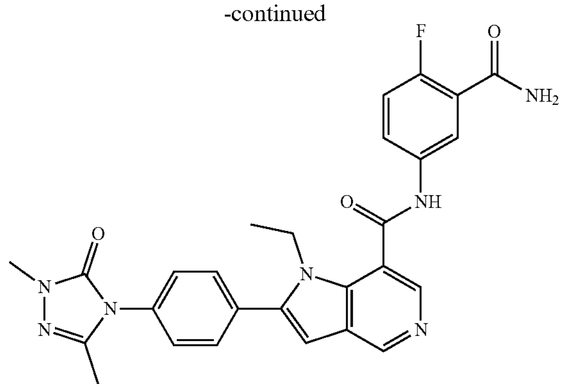

Ex-216

Step 1

Example Compound 140 (25.4 mg, 0.0397 mmol), ethanol (1 mL), and THF (1 mL) were mixed, 20% palladium hydroxide-carbon (2 mg) was added thereto, and the mixture was stirred at room temperature for 2 hours under a hydrogen environment. The reaction solution was filtered, the solvent was distilled under reduced pressure, and then the residue was purified by silica gel column chromatography to obtain Example Compound 216 (yield 17.2 mg).

Example 217

[Chem. Fig. 111]

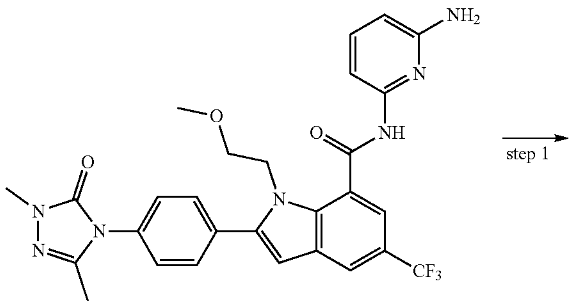

Ex.-95

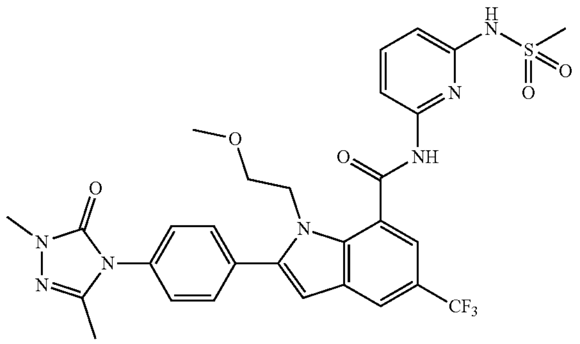

Ex.-217

Step 1

Example Compound 95 (20 mg, 0.035 mmol) and pyridine (500 μL) were mixed, and then methanesulfonylchloride (4 μL, 0.05 mmol) was added, followed by stirring at room temperature for 4 hours. Water was added to the reaction solution and the mixture was extracted using ethyl acetate. The extract was washed with saturated brine and dried over anhydrous sodium sulfate. The solvent was distilled off under reduced pressure, and then the residue was purified by silica gel column chromatography to obtain Example Compound 217 (yield 12.7 mg).

Example Compounds 213 to 217 in the following table were produced by the methods shown in Examples 213 to 217 described above. Furthermore, $^{1}$H-NMR data and/or LC/MS data of these Example compounds are shown in the table.

TABLE 10

| Ex. | Structure | Data |
|---|---|---|
| 213 | 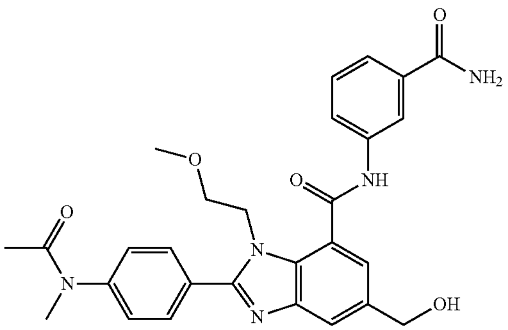 [SMILES: COCCn1c(-c2ccc(N(C)C(C)=O)cc2)nc2cc(CO)cc(C(=O)Nc3cccc(C(N)=O)c3)c21] | $^{1}$H-NMR (400 MHz, $CD_3OD$) δ: 1.94 (3H, s), 2.98 (3H, s), 3.31 (3H, s), 3.46-3.53 (2H, m), 4.65-4.72 (2H, m), 4.89-4.84 (2H, m), 7.49-7.54 (3H, m), 7.65-7.67 (2H, m), 7.85-7.94 (4H, m), 8.24 (1H, m). ESI-MS m/z: 516 $[M + H]^+$ |
| 214 | 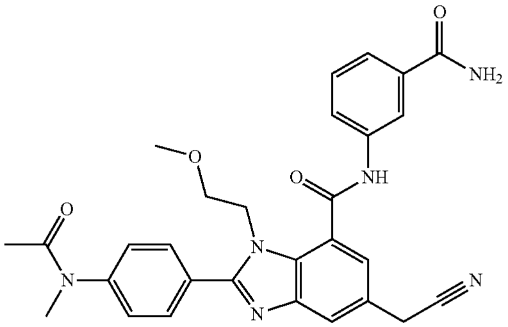 [SMILES: COCCn1c(-c2ccc(N(C)C(C)=O)cc2)nc2cc(CC#N)cc(C(=O)Nc3cccc(C(N)=O)c3)c21] | $^{1}$H-NMR (400 MHz, $CDCl_3$) δ: 1.93 (3H, s), 3.03 (3H, s), 3.32 (3H, s), 3.45-3.53 (2H, m), 3.82-3.88 (2H, m), 4.65-4.74 (2H, m), 5.56 (1H, m), 6.25 (1H, m), 7.34-7.46 (2H, m), 7.47-7.52 (3H, m), 7.74-7.80 (3H, m), 8.08 (1H, m), 8.18 (1H, m), 9.25 (1H, m). ESI-MS m/z: 525 $[M + H]^+$ |
| 215 | 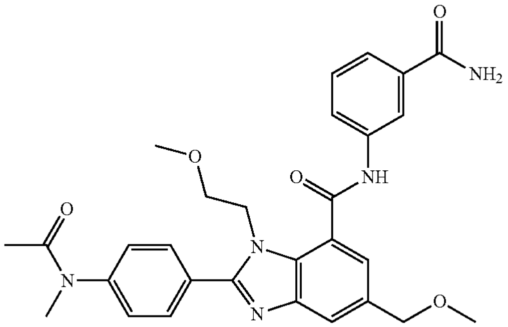 [SMILES: COCCn1c(-c2ccc(N(C)C(C)=O)cc2)nc2cc(COC)cc(C(=O)Nc3cccc(C(N)=O)c3)c21] | ESI-MS m/z: 530 $[M + H]^+$ |
| 216 | 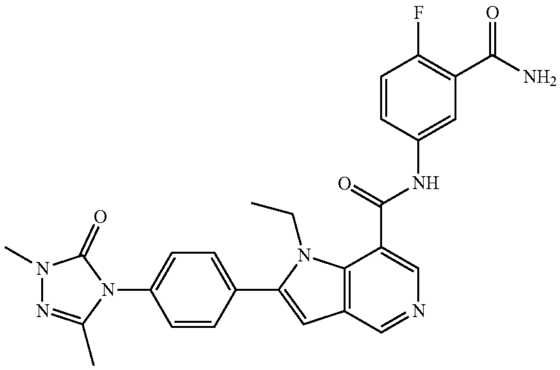 [SMILES: CCn1c(-c2ccc(-n3c(C)nn(C)c3=O)cc2)cc2cncc(C(=O)Nc3ccc(F)c(C(N)=O)c3)c21] | $^{1}$H-NMR (400 MHz, DMSO-$d_6$) δ: 1.02-1.05 (3H, m), 2.16 (3H, s), 3.37 (3H, s), 4.28-4.33 (2H, m), 6.91 (1H, s), 7.30-7.35 (1H, m), 7.61-7.63 (2H, m), 7.71-7.75 (4H, m), 7.87-7.91 (1H, m), 8.08-8.10 (1H, m), 8.46 (1H, s), 9.01 (1H, s), 11.02 (1H, s). ESI-MS m/z: 514 $[M + H]^+$ |

TABLE 10-continued
| Ex. | Structure | Data |
|---|---|---|
| 217 | 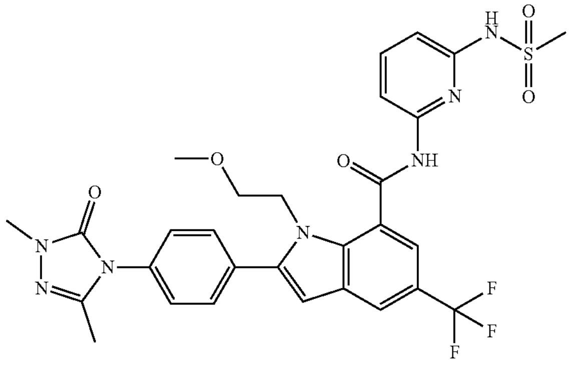 | $^1$H-NMR (400 MHz, DMSO-$d_6$) δ: 2.15 (3H,s), 2.83 (3H, s), 3.36-3.39 (5H, m), 3.47 (3H, s), 4.44-4.47 (2H, m), 6.66-6.67 (1H, m), 6.92 (1H, s), 7.59-7.61 (2H, m), 7.64-7.65 (1H, m), 7.73-7.82 (4H, m), 8.19 (1H, s), 10.55 (1H, br s), 11.31 (1H, s). ESI-MS m/z: 644 $[M + H]^+$ |
Example 218
[Chem. Fig. 112]
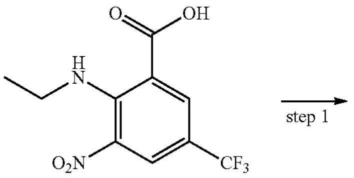
Ref.-2
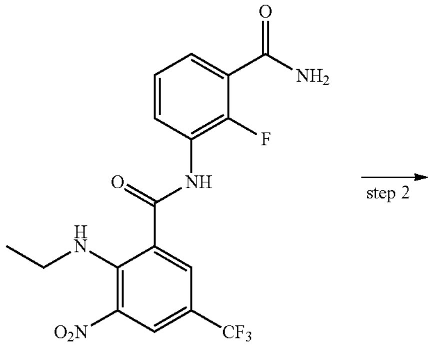
Ref.-209
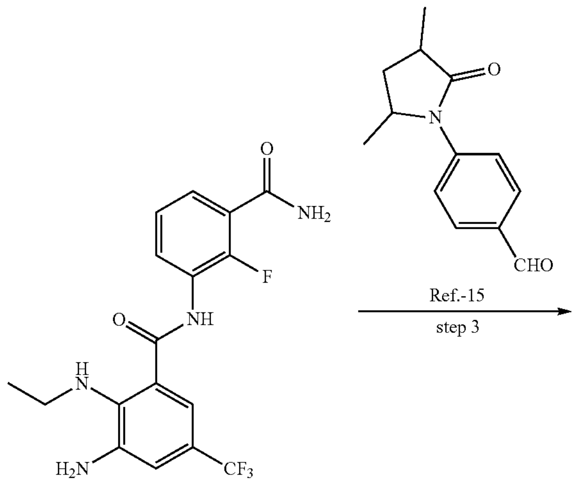
Ref.-210
-continued
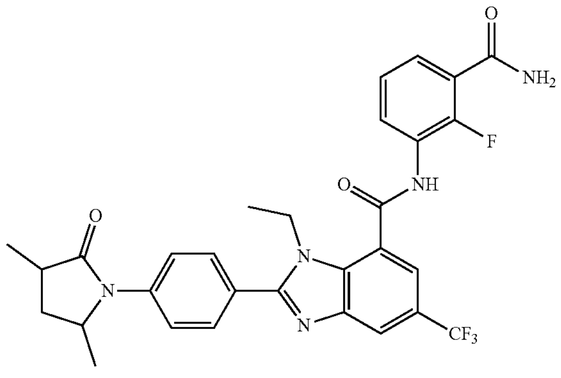
Ex.-218
(diasrtereomeric pure, racemate)
Step 1-3
Example Compound 218 (yield 27.0 mg) was obtained from reference synthesis example compound 2 by the same method as in steps 2 to 4 of Example 11.
Examples 219, 220
[Chem. Fig. 113]
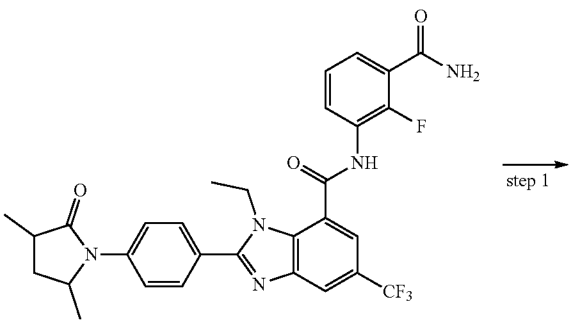
Ex.-218

-continued

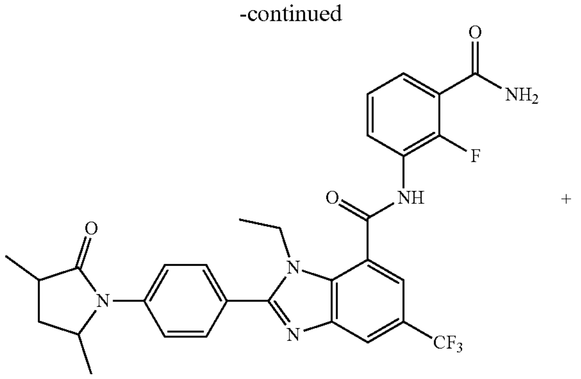

Ex.-219
(1st peak,
diasrtereomeric pure,
enantiomeric pure)

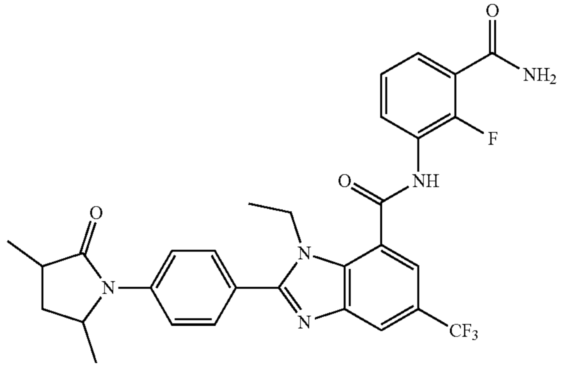

Ex.-220
(2nd peak,
diasrtereomeric pure,
enantiomeric pure)

Step 1

A preparative chiral column (CHIRALPAK IC, manufactured by Daicel Corporation) was attached to a preparative LC system (LC-Forte/R, manufactured by YMC Co., Ltd.), and a mixed solution of ethanol/normal hexane (1/1) was passed through the column at room temperature and a flow rate of 8.0 mL/min for equilibration. Example Compound 218 (12.8 mg, 0.0220 mmol) was dissolved in ethanol (8 mL) to obtain solution A. Solution A (4 mL) was injected, and the first peak (retention time: about 24 minutes) and the second peak (retention time: about 37 minutes) were collected while observing the UV detector (the operation was performed twice). Example Compound 219 (yield 4.9 mg) was obtained from the fraction derived from the first peak, and Example Compound 220 (yield 4.5 mg) was obtained from the fraction derived from the second peak, by distilling off the solvents contained in the respective fractions under reduced pressure.

Examples 221 and 222

[Chem. Fig. 114]

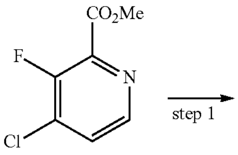

Ref.-68

-continued

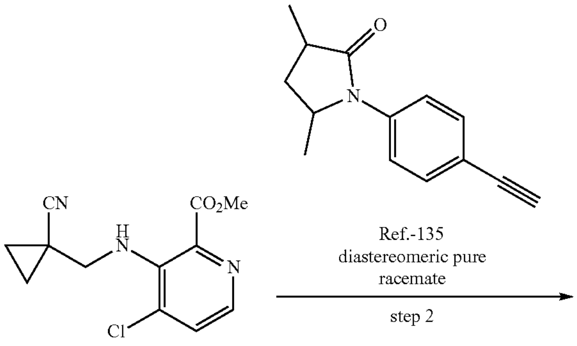

Ref.-211

Ref.-135
diastereomeric pure
racemate

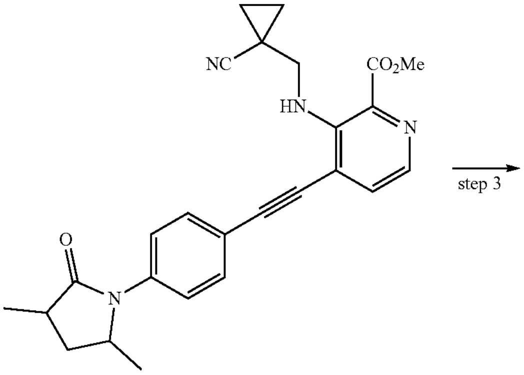

Ref.-214
diastereomeric pure
racemate

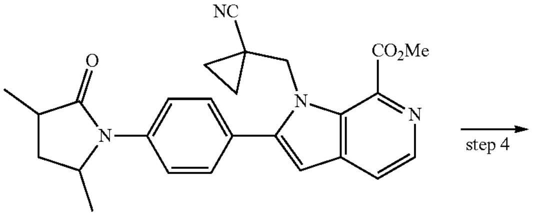

Ref.-213
diastereomeric pure
racemate

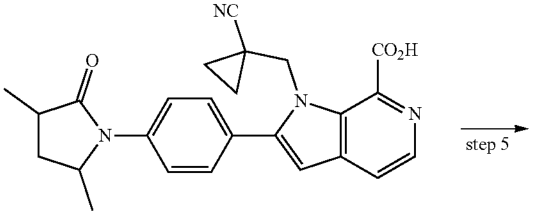

Ref.-214
diastereomeric pure
racemate

-continued

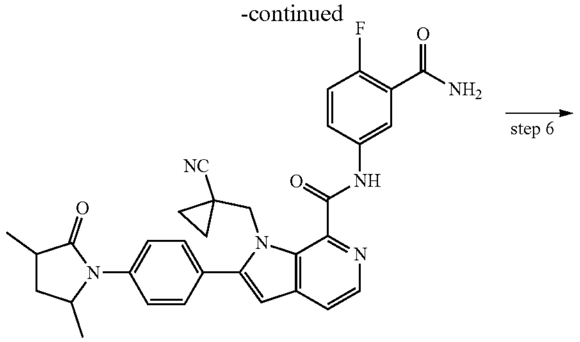

Ref.-215
diastereomeric pure
racemate

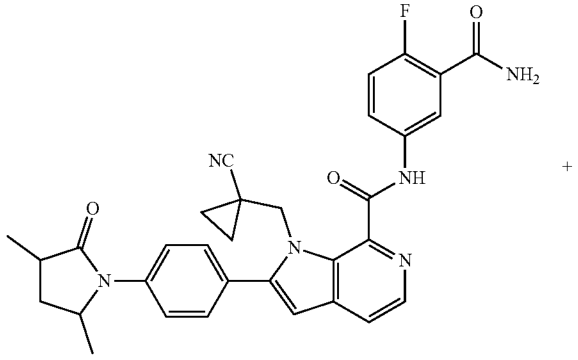

Ex.-221
1st peak
diastereomeric pure
enantiomeric pure

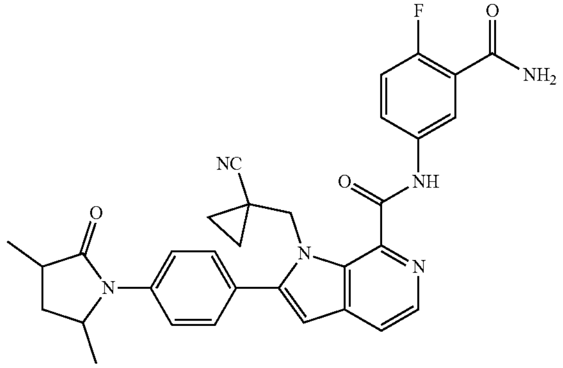

Ex.-222
2nd peak
diastereomeric pure
enantiomeric pure

Step 1-5

Reference synthesis example compound 215 (yield 26.2 mg) was obtained from reference synthesis example compound 68 by the same method as in steps 1 to 5 of Example 21.

Step 6

A preparative chiral column (CHIRALPAK IC, manufactured by Daicel Corporation) was attached to a preparative LC system (LC-Forte/R, manufactured by YMC Co., Ltd.), and a mixed solution of ethanol/normal hexane (4/1) was passed through the column at room temperature and a flow rate of 20.0 mL/min for equilibration. Reference synthetic example compound 215 (26.2 mg, 0.0427 mmol) was dissolved in ethanol (5.2 mL) to prepare Solution A. Solution A (2 to 3 mL) was injected, and the first peak (retention time: about 11.5 minutes) and the second peak (retention time: about 14.0 minutes) were collected while observing the UV detector (the operation was performed twice). Example Compound 221 (yield 12.0 mg) was obtained from the fraction derived from the first peak, and Example Compound 222 (yield 11.4 mg) was obtained from the fraction derived from the second peak, by distilling off the solvents contained in the respective fractions under reduced pressure.

Examples 223 and 224

[Chem. Fig. 115]

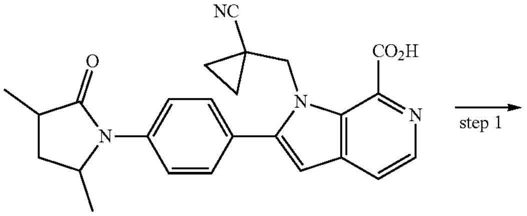

Ref.-214

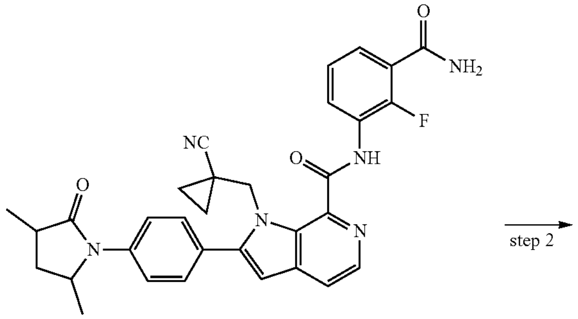

Ref.-216
diastereomeric pure
racemate

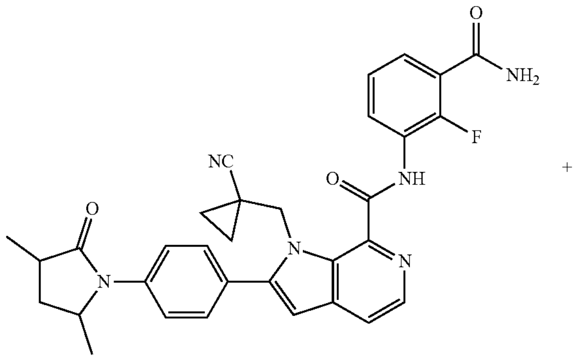

Ex.-223
1st peak
diastereomeric pure
enantiomeric pure

-continued

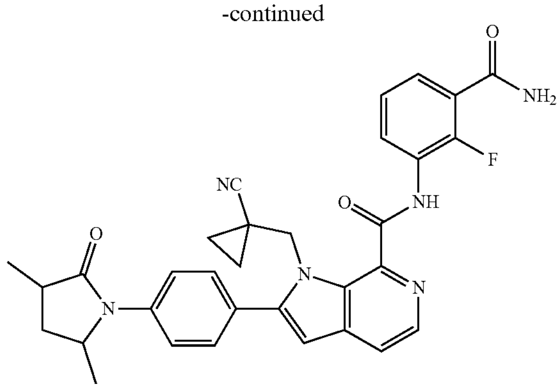

Ex.-224
2nd peak
diastereomeric pure
enantiomeric pure

Step 1

Reference synthesis example compound 216 (yield 31.2 mg) was obtained from reference synthesis example compound 214 by the same method as in Step 5 of Example 21.

Step 2

A preparative chiral column (CHIRALPAK IC, manufactured by Daicel Corporation) was attached to a preparative LC system (LC-Forte/R, manufactured by YMC Co., Ltd.), and a mixed solution of ethanol/normal hexane (4/1) was passed through the column at room temperature and a flow rate of 20.0 mL/min for equilibration. Reference synthetic example compound 216 (31.2 mg, 0.0431 mmol) was dissolved in ethanol (6.2 mL) to prepare Solution A. Solution A (about 3 mL) was injected, and the first peak (retention time: about 11.0 minutes) and the second peak (retention time: about 13.5 minutes) were collected while observing the UV detector (this operation was performed twice). Example Compound 223 (yield 10.8 mg) was obtained from the fraction derived from the first peak, and Example Compound 224 (yield 11.4 mg) was obtained from the fraction derived from the second peak, by distilling off the solvents contained in the respective fractions under reduced pressure.

Example Compounds 218 to 224 in the following table were produced by the methods shown in Examples 218 to 224 described above. Furthermore, $^1$H-NMR data and/or LC/MS data of these Example compounds are shown in the table.

TABLE 11-1

| Ex. | Structure | Data |
|---|---|---|
| 218 | 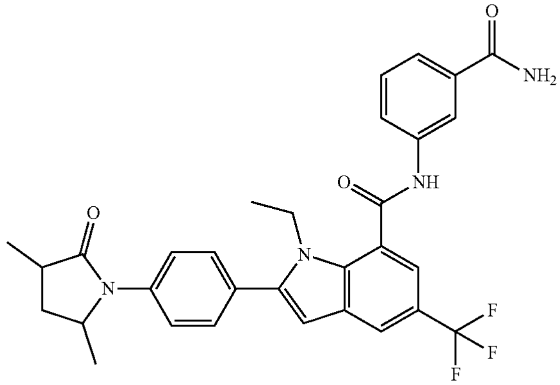 (diasrtereomeric pure, racemate) | ESI-MS m/z: 582 $[M + H]^+$ |
| 219 | 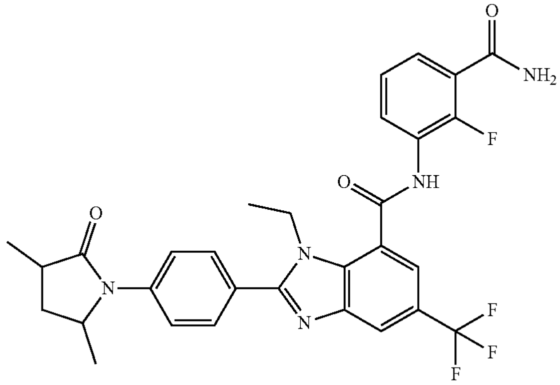 [SMILES: CCn1c(-c2ccc(N3C(=O)C(C)CC3C)cc2)nc2cc(C(F)(F)F)cc(C(=O)Nc3cccc(C(N)=O)c3F)c21] diasrtereomeric pure enantiomeric pure | $^1$H-NMR (400 MHz, DMSO-$d_6$) δ: 1.17-1.35 (10H, m), 2.59-2.62 (2H, m), 4.37-4.49 (3H, m), 7.32 (1H, t, J = 7.8 Hz), 7.51 (1H, t, J = 6.4 Hz), 7.62 (2H, d, J = 8.7 Hz), 7.68 (1H, br s), 7.82 (2H, d, J = 8.7 Hz), 7.85-7.92 (2H, m), 8.06-8.08 (1H, m), 8.26 (1H, s), 10.88 (1H, s). ESI-MS m/z: 582 $[M + H]^+$ |

TABLE 11-1-continued
| Ex. | Structure | Data |
|---|---|---|
| 220 | 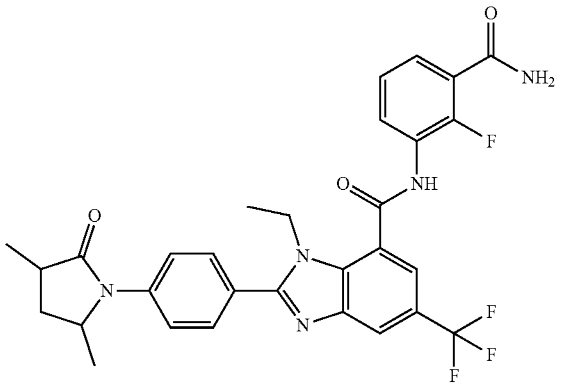 [SMILES: CCn1c(-c2ccc(N3C(=O)C(C)CC3C)cc2)nc2cc(C(F)(F)F)cc(C(=O)Nc3cccc(C(N)=O)c3F)c21]<br>diasrtereomeric pure<br>enantiomeric pure | ESI-MS m/z: 582 $[M + H]^+$ |
| 221 | 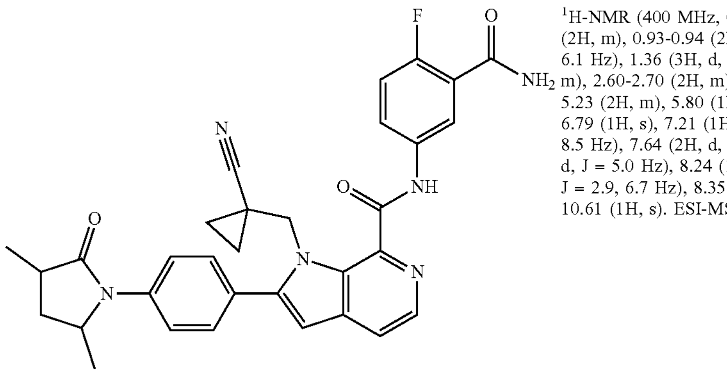<br>diasrtereomeric pure<br>enantiomeric pure | $^1$H-NMR (400 MHz, $CDCl_3$) δ: 0.65-0.73 (2H, m), 0.93-0.94 (2H, m), 1.30 (3H, d, J = 6.1 Hz), 1.36 (3H, d, J = 6.6 Hz), 1.43 (1H, m), 2.60-2.70 (2H, m), 4.29 (1H, m), 5.11-5.23 (2H, m), 5.80 (1H, s), 6.73 (1H, m), 6.79 (1H, s), 7.21 (1H, m), 7.52 (2H, d, J = 8.5 Hz), 7.64 (2H, d, J = 8.4 Hz), 7.76 (1H, d, J = 5.0 Hz), 8.24 (1H, m), 8.31 (1H, dd, J = 2.9, 6.7 Hz), 8.35 (1H, d, J = 5.0 Hz), 10.61 (1H, s). ESI-MS m/z: 565 $[M + H]^+$ |
TABLE 11-2
| | | |
|---|---|---|
| 222 | 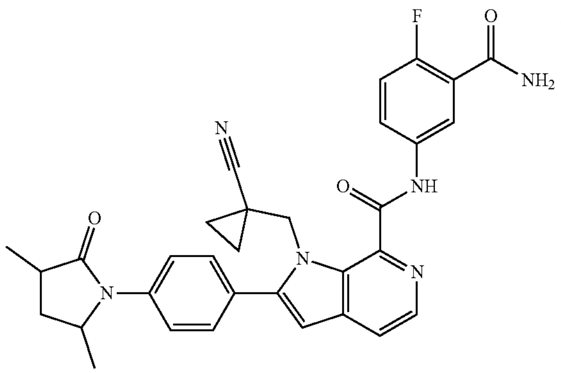 [SMILES: CC1CC(C)N(c2ccc(-c3cc4ccnc(C(=O)Nc5ccc(F)c(C(N)=O)c5)c4n3CC3(C#N)CC3)cc2)C1=O]<br>diasrtereomeric pure<br>enantiomeric pure | ESI-MS m/z: 565 $[M + H]^+$ |

TABLE 11-2-continued

| | | |
|---|---|---|
| 223 | 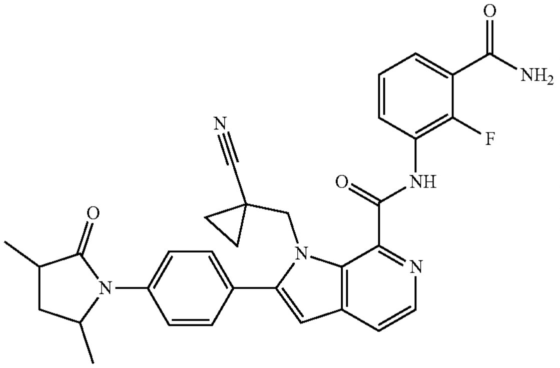 [SMILES: CC1CC(C)N(c2ccc(-c3cc4ccnc(C(=O)Nc5cccc(C(N)=O)c5F)c4n3CC3(C#N)CC3)cc2)C1=O]<br>diasrtereomeric pure<br>enantiomeric pure | $^1$H-NMR (400 MHz, $CDCl_3$) δ: 0.63-0.73 (2H, m), 0.92-0.98 (2H, m), 1.30 (3H, d, J = 6.1 Hz), 1.36 (3H, d, J = 6.6 Hz), 1.44 (1H, m), 2.60-2.70 (2H, m), 4.28 (1H, m), 5.10-5.23 (2H, m), 5.84 (1H, s), 6.67 (1H, m), 6.80 (1H, s), 7.34 (1H, t, J = 8.0 Hz), 7.53 (2H, d, J = 8.6 Hz), 7.64 (2H, d, J = 8.6 Hz), 7.78 (1H, d, J = 5.1 Hz), 7.87 (1H, m), 8.38 (1H, d, J = 5.1 Hz), 8.70 (1H, dt, J = 1.7, 11.8 Hz), 10.84 (1H, m). ESI-MS m/z: 565 $[M + H]^+$ |
| 224 | 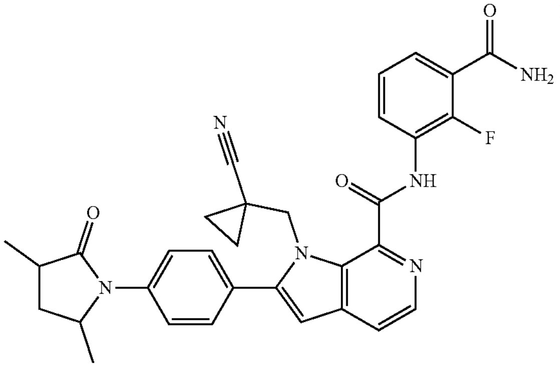 [SMILES: CC1CC(C)N(c2ccc(-c3cc4ccnc(C(=O)Nc5cccc(C(N)=O)c5F)c4n3CC3(C#N)CC3)cc2)C1=O]<br>diasrtereomeric pure<br>enantiomeric pure | ESI-MS m/z: 565 $[M + H]^+$ |

Test Example 1: Measurement of Binding Inhibitory Activity Between Human STAT6/pIL-p 4Rα by Fluorescence Polarization Method 1) Construction of Histidine Tag-Fused Recombinant Human STAT6 (123 to 658 Region)

A histidine tag-fused recombinant human STAT6 (hereinafter referred to as rhSTAT6) expression vector [plasmid DNA in which a nucleic acid sequence containing human STAT6 (123-658 region) was inserted into a pET28a(+) vector (Novagen)] was inserted into *E. coli*, and the cells were cultured overnight under culturing conditions at 17° C. with IPTG treatment. After disrupting *E. coli* with a high-pressure homogenizer (EmulsiFlex-C3, manufactured by AVESTIN, Inc.), affinity purification using Ni-NTA agarose (manufactured by Qiagen), cation exchange chromatography using HiTrap® CM-FF (manufactured by GE healthcare), and gel filtration chromatography using Superdex® 200 10/300GL (manufactured by GE healthcare) were performed to obtain rhSTAT6.

2) Measurement of Binding Inhibitory Activity Between Human STAT6/pIL-4Rα by Fluorescence Polarization Method A DMSO solution of the example compound was diluted with an assay buffer [for example, a buffer containing 50 mmol/L NaCl, 10 mmol/L HEPES (pH 7.0), 1 mmol/L DTT, 1 mmol/L EDTA, and 0.01 vol % NP-40, and the like] to prepare a compound-added solution. The DMSO concentration in the compound addition solution was adjusted to 1 or 2 vol %. 10 μL of the compound addition solution and an assay buffer containing 1 or 2 vol % DMSO were added to each well of a 384-well plate. 5 μL of an assay buffer solution containing rhSTAT6 (rhSTAT6 concentration: for example, 1 μmol/L) or an assay buffer was added to each well of a 384-well plate. After leaving the plate at room temperature for 30 minutes in the dark, 5 μL of an assay buffer solution (FAM-pIL-4Rp concentration: for example, 80 nmol/L) containing FAM-labeled phosphorylated IL-4Rα peptide (sequence: FAM-Ala-pTyr-Lys-Pro-Phe-Gln-Asp-Leu-11e-$NH_2$) (hereinafter, FAM-pIL-4Rp) or an assay buffer containing 2 vol % DMSO was added to each well of the 384-well plate. The mixture was left to stand at room temperature for 30 minutes in the dark, and then centrifuged (200 g, 1 minute, room temperature). Fluorescence polarization values were measured using Infinite (registered trademark) F500 (manufactured by Tecan Japan Co., Ltd.) (Excitation: 485 nm, Emission: 535 nm). The inhibition rate of each Example compound was calculated according to the following formula using the fluorescence polarization value (A) when rhSTAT6 and FAM-pIL-4Rp were added without adding the Example compound, the fluorescence polarization value (B) when FAM-pIL-4Rp was added without adding the Example compound and rhSTAT6, and the fluorescence polarization value (C) when each Example compound, rhSTAT6, and FAM-pIL-4Rp were added.

$$\text{Inhibition rate (\%)} = ((A-C)/(A-B)) \times 100$$

In the evaluation of each example compound, the 50% inhibitory concentration ($IC_{50}$) of each example compound was calculated from a linear function equation of a straight line connecting two points sandwiching 50%. The $IC_{50}$ values of the example compounds are shown in the table below. Furthermore, as a comparative example, the $IC_{50}$ value of the compound PM-301H in the present evaluation system (reference: WO2014/182928) is also shown.

TABLE 12-1

| Example compound | IC 50 (μmol/L) |
|---|---|
| Ex.1 | 0.39 |
| Ex.2 | 0.49 |
| Ex.3 | 2.28 |
| Ex.4 | 0.74 |
| Ex.5 | 0.66 |
| Ex.6 | 1.14 |
| Ex.7 | 0.86 |
| Ex.8 | 0.41 |
| Ex.9 | 0.45 |
| Ex.10 | 3.26 |
| Ex.11 | 0.44 |
| Ex.12 | 0.35 |
| Ex.13 | 9.09 |
| Ex.14 | 0.59 |
| Ex.15 | 0.25 |
| Ex.16 | 0.24 |
| Ex.17 | 0.35 |
| Ex.18 | 0.35 |
| Ex.19 | 0.36 |
| Ex.20 | 0.66 |
| Ex.21 | 0.38 |
| Ex.22 | 0.32 |
| Ex.23 | 0.24 |
| Ex.24 | 0.32 |
| Ex.25 | 0.28 |
| Ex.26 | 0.39 |
| Ex.27 | 0.35 |
| Ex.28 | 0.41 |
| Ex.29 | 0.84 |
| Ex.30 | 0.27 |
| Ex.31 | 0.46 |
| Ex.32 | 0.42 |
| Ex.33 | 0.10 |
| Ex.34 | 0.61 |
| Ex.35 | 0.35 |
| Ex.36 | 0.40 |
| Ex.37 | 0.25 |
| Ex.38 | 0.33 |
| Ex.39 | 1.20 |
| Ex.40 | 0.29 |
| Ex.41 | 0.28 |
| Ex.42 | 0.26 |
| Ex.43 | 0.25 |
| Ex.44 | 0.17 |
| Ex.45 | 0.25 |
| Ex.46 | 0.45 |
| Ex.47 | 1.00 |
| Ex.48 | 0.34 |
| Ex.49 | 0.31 |
| Ex.50 | 0.56 |
| Ex.51 | 0.49 |
| Ex.52 | 0.19 |
| Ex.53 | 3.97 |
| Ex.54 | 3.39 |
| Ex.55 | 2.57 |
| Ex.56 | 0.27 |
| Ex.57 | 0.49 |
| Ex.58 | 0.55 |
| Ex.59 | 0.39 |
| Ex.60 | 0.47 |
| Ex.61 | 0.47 |
| Ex.62 | 0.45 |
| Ex.63 | 2.53 |
| Ex.64 | 2.62 |

TABLE 12-2

| Example compound | IC 50 (μmol/L) |
|---|---|
| Ex.65 | 0.44 |
| Ex.66 | 0.32 |
| Ex.67 | 0.58 |
| Ex.68 | 0.35 |

TABLE 12-2-continued

| Example compound | IC 50 (μmol/L) |
|---|---|
| Ex.69 | 0.29 |
| Ex.70 | 0.76 |
| Ex.71 | 1.18 |
| Ex.72 | 0.34 |
| Ex.73 | 0.37 |
| Ex.74 | 0.48 |
| Ex.75 | 0.36 |
| Ex.76 | 0.36 |
| Ex.77 | 0.59 |
| Ex.78 | 0.34 |
| Ex.79 | 1.90 |
| Ex.80 | 0.40 |
| Ex.81 | 2.27 |
| Ex.82 | 1.14 |
| Ex.83 | 0.37 |
| Ex.84 | 0.24 |
| Ex.85 | 0.34 |
| Ex.86 | 1.78 |
| Ex.87 | 1.00 |
| Ex.88 | 0.42 |
| Ex.89 | 0.94 |
| Ex.90 | 0.28 |
| Ex.91 | 0.25 |
| Ex.92 | 0.23 |
| Ex.93 | 0.28 |
| Ex.94 | 0.31 |
| Ex.95 | 0.28 |
| Ex.96 | 1.89 |
| Ex.97 | 0.29 |
| Ex.98 | 0.31 |
| Ex.99 | 0.38 |
| Ex.100 | 0.30 |
| Ex.101 | 4.06 |
| Ex.102 | 2.82 |
| Ex.103 | 2.66 |
| Ex.104 | 0.73 |
| Ex.105 | 0.78 |
| Ex.106 | 1.97 |
| Ex.107 | 0.29 |
| Ex.108 | 0.46 |
| Ex.109 | 0.43 |
| Ex.110 | 0.43 |
| Ex.111 | 0.55 |
| Ex.112 | 0.40 |
| Ex.113 | 0.44 |
| Ex.114 | 0.33 |
| Ex.115 | 0.43 |
| Ex.116 | 2.07 |
| Ex.117 | 0.32 |
| Ex.118 | 0.23 |
| Ex.119 | 0.38 |
| Ex.120 | 0.50 |
| Ex.121 | 0.42 |
| Ex.122 | 0.69 |
| Ex.123 | 0.50 |
| Ex.124 | 0.45 |
| Ex.125 | 0.26 |
| Ex.126 | 0.24 |
| Ex.127 | 0.25 |
| Ex.128 | 0.57 |
| Ex.129 | 0.59 |
| Ex.130 | 0.36 |
| Ex.131 | 0.51 |
| Ex.132 | 0.52 |

TABLE 12-3

| Example compound | IC 50 (μmol/L) |
|---|---|
| Ex.133 | 0.23 |
| Ex.134 | 0.37 |
| Ex.135 | 0.53 |
| Ex.136 | 0.48 |

TABLE 12-3-continued

| Example compound | IC 50 (μmol/L) |
|---|---|
| Ex.137 | 0.28 |
| Ex.138 | 0.37 |
| Ex.139 | 1.94 |
| Ex.140 | 2.72 |
| Ex.141 | 0.91 |
| Ex.142 | 0.30 |
| Ex.143 | 0.39 |
| Ex.144 | 0.37 |
| Ex.145 | 0.28 |
| Ex.146 | 0.75 |
| Ex.147 | 0.78 |
| Ex.148 | 0.33 |
| Ex.149 | 0.33 |
| Ex.150 | 0.24 |
| Ex.151 | 0.61 |
| Ex.152 | 0.65 |
| Ex.153 | 0.94 |
| Ex.154 | 0.28 |
| Ex.155 | 0.38 |
| Ex.156 | 0.40 |
| Ex.157 | 0.31 |
| Ex.158 | 0.73 |
| Ex.159 | 0.53 |
| Ex.160 | 0.41 |
| Ex.161 | 0.87 |
| Ex.162 | 0.30 |
| Ex.163 | 0.27 |
| Ex.164 | 0.32 |
| Ex.165 | 0.20 |
| Ex.166 | 0.35 |
| Ex.167 | 0.24 |
| Ex.168 | 0.35 |
| Ex.169 | 0.40 |
| Ex.170 | 0.40 |
| Ex.171 | 0.33 |
| Ex.172 | 0.38 |
| Ex.173 | 0.34 |
| Ex.174 | 0.68 |
| Ex.175 | 0.40 |
| Ex.176 | 0.28 |
| Ex.177 | 0.30 |
| Ex.178 | 0.28 |
| Ex.179 | 0.32 |
| Ex.180 | 0.30 |
| Ex.181 | 0.31 |
| Ex.182 | 0.35 |
| Ex.183 | 0.23 |
| Ex.184 | 0.27 |
| Ex.185 | 0.47 |
| Ex.186 | 0.33 |
| Ex.187 | 0.34 |
| Ex.188 | 0.32 |
| Ex.189 | 0.38 |
| Ex.190 | 0.41 |
| Ex.191 | 0.29 |
| Ex.192 | 0.34 |
| Ex.193 | 0.42 |
| Ex.194 | 0.42 |
| Ex.195 | 0.29 |
| Ex.196 | 0.27 |
| Ex.197 | 0.25 |
| Ex.198 | 0.41 |
| Ex.199 | 0.27 |
| Ex.200 | 0.23 |

TABLE 12-4

| Example compound | IC 50 (μmol/L) | Comparative example compound | IC 50 (μmol/L) |
|---|---|---|---|
| Ex.201 | 0.31 | PM-301H | 0.27 |
| Ex.202 | 0.34 | | |
| Ex.203 | 7.06 | | |
| Ex.204 | 2.35 | | |

TABLE 12-4-continued

| Example compound | IC 50 (μmol/L) | Comparative example compound | IC 50 (μmol/L) |
|---|---|---|---|
| Ex.205 | 8.44 | | |
| Ex.206 | 3.62 | | |
| Ex.207 | 2.95 | | |
| Ex.208 | 2.08 | | |
| Ex.209 | 6.60 | | |
| Ex.210 | 2.74 | | |
| Ex.211 | 4.98 | | |
| Ex.212 | 9.03 | | |
| Ex.213 | 3.47 | | |
| Ex.214 | 3.98 | | |
| Ex.215 | 2.94 | | |
| Ex.216 | 0.43 | | |
| Ex.217 | 0.59 | | |
| Ex.218 | 0.68 | | |
| Ex.219 | 0.28 | | |
| Ex.220 | 9.60 | | |
| Ex.221 | 0.36 | | |
| Ex.222 | 3.10 | | |
| Ex.223 | 0.32 | | |
| Ex.224 | 1.59 | | |

Test Example 2: Measurement of Human STAT6 Dependent Reporter Activity

1) Construction of Human STAT6-HEK293 Cells

HEK 293 cells maintenance cultured by [Penicillin-Streptomycin (Thermo Fisher Scientific) and FBS, 1 vol % and 10 vol % respectively added to DMEM high glucose (Thermo Fisher Scientific)] (manufactured by ATCC) were collected, and suspended in 10 mL of 0.5% BSA/PBS. $1\times10^6$ cells were collected, the supernatant was removed by centrifuging, and the cells were suspended in 100 μL of Nucleofector solution V (manufactured by Lonza K.K.). 2 μg of STAT6 vector [plasmid DNAs incorporating human STAT6 sequences in pcDNA3.1 (Invitrogen)] was added, and the STAT6 vector was introduced into the HEK293 cells using the program Q-001 initially registered in the Nucleofector® 2b. A cell line (STAT6-HEK293 cells) consistently expressing STAT6 was acquired by selecting resistant cells in a medium containing Geneticin® (manufactured by Thermo Fisher Scientific).

2) STAT6 Reporter Assay Using STAT6-HEK293 Cells $3\times10^6$ STAT6-HEK293 cells maintained in assay medium [culture medium supplemented with 1 vol % Geneticin®] were harvested and seeded in a 10 cm dish. 3 μg of a STAT6 reporter vector [plasmid in which a sequence containing a STAT6 binding sequence and a C/EBP binding sequence in tandem was incorporated into pGL4.27 (manufactured by Promega Corporation)] and 9 μL of FuGENE® HD transfection reagent (manufactured by Promega Corporation) were added to 500 UL of Opti-MEM® (manufactured by Thermo Fisher Scientific) to prepare transfection solutions. The transfection solution was vortexed and left to stand for about 5 minutes, then added dropwise to the STAT6-HEK293 cells, which were then cultured overnight in a $CO_2$ incubator to produce STAT6 reporter cells.

The prepared STAT6 reporter cells were seeded on B&W isoplate-96 TC (PerkinElmer Japan Co., Ltd.) ($3\times10^4$ cells/50 μL/well) and cultured overnight in a $CO_2$ incubator (37° C., 5% $CO_2$). 50 μL of assay medium was added to each well instead of the STAT6 reporter cells. The compound addition solution was prepared by diluting the DMSO solution of the example compound 250-fold using the assay medium. 20 μL of compound addition solution or 0.4 vol % DMSO-containing assay medium was added to the plate, and the plate was then cultured in a $CO_2$ incubator for 1 hour. 10 μL of 80 ng/ml human IL-4 solution (Peprotech) or assay medium was added to each well, and the cells were cultured in a $CO_2$ incubator for 6 hours.

The viable cell rate was measured using CellTiter-Fluor® Cell Viability Assay (manufactured by Promega Corporation). After adding 20 μL of the diluted CellTiter Reagent to each well, the cells were cultured in a $CO_2$ incubator for 1 hour, and the fluorescence value was measured using Infinite® F500 (Excitation: 340 nm, Emission: 495 nm). The cell viability of each Example compound was calculated by the following formula using the fluorescence value (D) under conditions where IL-4 stimulation was performed without addition of the Example compound, the fluorescence value (E) under the condition where STAT6 reporter cells were not seeded, and the fluorescence value (F) under conditions where IL-4 stimulation was performed after treatment with each Example compound.

$$\text{Viability }(\%)=[(F-E)/(D-E)]\times 100$$

STAT6 reporter activity was measured using the Bright-Glo® Luciferase Assay System (Promega). 100 μL of Bright-Glo® reagent was added to each well, and luciferase activity was measured using Infinite® F500. The inhibition rate of each Example compound was calculated by the following formula using the luciferase activity value (G) when no Example compound was added and stimulation with IL-4 was performed, the luciferase activity value (H) when no Example compound was added and stimulation with IL-4 was not performed, and the luciferase activity value (I) when each Example compound was treated and stimulation with IL-4 was performed.

$$\text{Inhibition rate }(\%)=[(G-I)/(G-H)]\times 100$$

The inhibition rate (%) when the concentration of each example compound was 1 μmol/L and 0.1 μmol/L is shown in Table 13. Note that the viable cell rate under each condition was 70% or more, and it was determined that the luciferase activity inhibitory activity of each example compound was appropriately evaluated.

TABLE 13-1

| Examples | Inhibition rate (%) | |
|---|---|---|
| Compound | 1 μmol/L | 0.1 μmol/L |
| Ex.1 | 93 | 22 |
| Ex.2 | 72 | 14 |
| Ex.4 | 64 | 12 |
| Ex.5 | 63 | 8 |
| Ex.6 | 52 | −1 |
| Ex.7 | 56 | 1 |
| Ex.8 | 43 | 2 |
| Ex.9 | 76 | 10 |
| Ex.11 | 92 | 43 |
| Ex.12 | 94 | 47 |
| Ex.15 | 100 | 97 |
| Ex.16 | 100 | 72 |
| Ex.17 | 99 | 81 |
| Ex.18 | 99 | 80 |
| Ex.19 | 98 | 42 |
| Ex.20 | 98 | 50 |
| Ex.21 | 98 | 73 |
| Ex.22 | 99 | 89 |
| Ex.23 | 100 | 86 |
| Ex.24 | 98 | 54 |
| Ex.25 | 97 | 64 |
| Ex.26 | 98 | 63 |
| Ex.27 | 96 | 52 |
| Ex.28 | 93 | 43 |
| Ex.30 | 100 | 76 |
| Ex.31 | 97 | 80 |
| Ex.32 | 100 | 91 |
| Ex.33 | 100 | 75 |
| Ex.34 | 96 | 39 |

TABLE 13-1-continued

| Examples | Inhibition rate (%) | |
|---|---|---|
| Compound | 1 μmol/L | 0.1 μmol/L |
| Ex.35 | — | 100 |
| Ex.37 | 100 | 96 |
| Ex.38 | 100 | 99 |
| Ex.39 | 99 | 84 |
| Ex.40 | 100 | 92 |
| Ex.41 | 100 | 92 |
| Ex.42 | 100 | 90 |
| Ex.43 | 100 | 93 |
| Ex.44 | 100 | 93 |
| Ex.45 | 100 | 63 |
| Ex.46 | 100 | 81 |
| Ex.47 | 95 | 43 |
| Ex.48 | 100 | 84 |
| Ex.49 | 100 | 97 |
| Ex.50 | 99 | 42 |
| Ex.51 | 82 | 13 |
| Ex.52 | 100 | 52 |
| Ex.56 | 100 | 94 |
| Ex.57 | 100 | 89 |
| Ex.59 | 99 | 83 |
| Ex.61 | 100 | 93 |
| Ex.62 | 99 | 59 |
| Ex.65 | 98 | 50 |
| Ex.66 | 99 | 58 |
| Ex.67 | 96 | 56 |
| Ex.68 | 100 | 59 |
| Ex.69 | 100 | 61 |
| Ex.70 | 45 | −6 |
| Ex.72 | 97 | 65 |
| Ex.73 | 100 | 72 |
| Ex.74 | 91 | 21 |
| Ex.75 | 93 | 36 |
| Ex.76 | 94 | 31 |

TABLE 13-2

| Examples | Inhibition rate (%) | |
|---|---|---|
| Compound | 1 μmol/L | 0.1 μmol/L |
| Ex.77 | 99 | 73 |
| Ex.78 | 100 | 89 |
| Ex.80 | 61 | 4 |
| Ex.83 | 98 | 68 |
| Ex.84 | 100 | 93 |
| Ex.85 | 73 | 11 |
| Ex.88 | 76 | 9 |
| Ex.90 | 99 | 63 |
| Ex.91 | 99 | 67 |
| Ex.92 | 99 | 74 |
| Ex.93 | 96 | 67 |
| Ex.94 | — | 79 |
| Ex.95 | — | 74 |
| Ex.97 | — | 89 |
| Ex.98 | 100 | 60 |
| Ex.99 | 95 | 51 |
| Ex.100 | — | 85 |
| Ex.102 | 60 | — |
| Ex.107 | — | 67 |
| Ex.108 | 97 | 52 |
| Ex.109 | — | 62 |
| Ex.110 | — | 65 |
| Ex.111 | 80 | 25 |
| Ex.112 | 93 | 38 |
| Ex.113 | 96 | 44 |
| Ex.114 | 97 | 57 |
| Ex.115 | 95 | 54 |
| Ex.118 | — | 95 |
| Ex.119 | — | 95 |
| Ex.120 | — | 74 |
| Ex.121 | 97 | 40 |
| Ex.122 | 89 | 23 |
| Ex.123 | 96 | 40 |

TABLE 13-2-continued

| Examples | Inhibition rate (%) | |
|---|---|---|
| Compound | 1 μmol/L | 0.1 μmol/L |
| Ex.124 | 99 | 57 |
| Ex.125 | 99 | 52 |
| Ex.126 | — | 62 |
| Ex.127 | 99 | 38 |
| Ex.129 | 75 | 8 |
| Ex.130 | 96 | 74 |
| Ex.131 | 92 | 56 |
| Ex.132 | 96 | 70 |
| Ex.133 | — | 80 |
| Ex.134 | 99 | 48 |
| Ex.135 | — | 85 |
| Ex.136 | — | 61 |
| Ex.137 | — | 62 |
| Ex.138 | 93 | 35 |
| Ex.139 | 69 | 8 |
| Ex.140 | 45 | 3 |
| Ex.142 | 100 | 94 |
| Ex.143 | 99 | 87 |
| Ex.144 | 99 | 48 |
| Ex.145 | 97 | 53 |
| Ex.146 | 87 | 55 |
| Ex.147 | 91 | 48 |
| Ex.148 | — | 86 |
| Ex.149 | 84 | 25 |
| Ex.150 | 89 | 38 |
| Ex.151 | 77 | 26 |
| Ex.152 | 84 | 38 |
| Ex.153 | 93 | 25 |
| Ex.154 | 99 | 52 |
| Ex.155 | 100 | 69 |
| Ex.156 | 99 | 46 |
| Ex.157 | — | 62 |
| Ex.158 | 96 | 44 |

TABLE 13-3

| Examples | Inhibition rate (%) | |
|---|---|---|
| Compound | 1 μmol/L | 0.1 μmol/L |
| Ex.159 | 95 | 50 |
| Ex.160 | 100 | 93 |
| Ex.161 | 99 | 86 |
| Ex.163 | 99 | 60 |
| Ex.165 | 100 | 86 |
| Ex.166 | 99 | 76 |
| Ex.167 | 99 | 90 |
| Ex.168 | 99 | 60 |
| Ex.169 | 99 | 81 |
| Ex.170 | 99 | 49 |
| Ex.171 | 95 | 29 |
| Ex.172 | 83 | 17 |
| Ex.173 | 100 | 43 |
| Ex.174 | — | 70 |
| Ex.175 | — | 65 |
| Ex.176 | — | 93 |
| Ex.177 | — | 99 |
| Ex.178 | — | 100 |
| Ex.179 | — | 93 |
| Ex.180 | — | 100 |
| Ex.181 | — | 94 |
| Ex.182 | 100 | 52 |
| Ex.183 | — | 86 |
| Ex.185 | 96 | 34 |
| Ex.186 | 96 | 43 |
| Ex.187 | — | 88 |
| Ex.188 | 97 | 44 |
| Ex.189 | 97 | 72 |
| Ex.190 | 97 | 66 |
| Ex.191 | — | 63 |
| Ex.192 | — | 71 |
| Ex.193 | 98 | 67 |
| Ex.194 | 98 | 68 |

TABLE 13-3-continued

| Examples | Inhibition rate (%) | |
|---|---|---|
| Compound | 1 μmol/L | 0.1 μmol/L |
| Ex.195 | — | 56 |
| Ex.196 | — | 81 |
| Ex.197 | — | 73 |
| Ex.198 | — | 96 |
| Ex.199 | — | 67 |
| Ex.200 | 99 | 53 |
| Ex.201 | — | 99 |
| Ex.202 | — | 95 |
| Ex.216 | 42 | 7 |
| Ex.218 | 89 | 38 |
| Ex.219 | 96 | 32 |
| Ex.221 | 94 | 60 |
| Ex.223 | — | 67 |

INDUSTRIAL APPLICABILITY

The compounds of the present invention or pharmaceutically acceptable salts thereof have excellent STAT6 inhibitory activity and are useful as active ingredients in therapeutic agents and/or prophylactic agents for various diseases associated with STAT6. For example, a medicament containing the compound of the present invention or a pharmaceutically acceptable salt thereof as an active ingredient is useful as a therapeutic agent for an inflammatory disease such as atopic dermatitis and for allergic diseases.

The invention claimed is:

1. A compound selected from the group consisting of:

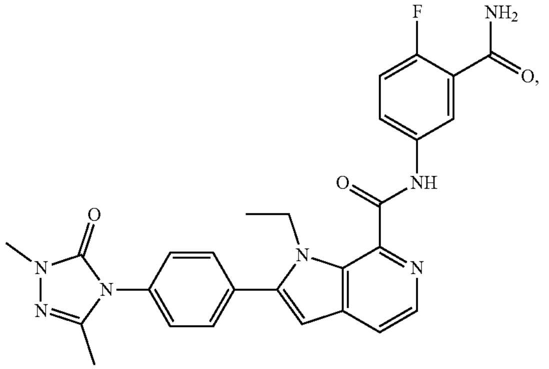 [SMILES: CCn1c(-c2ccc(-n3c(C)nn(C)c3=O)cc2)cc2ccnc(C(=O)Nc3ccc(F)c(C(N)=O)c3)c21]

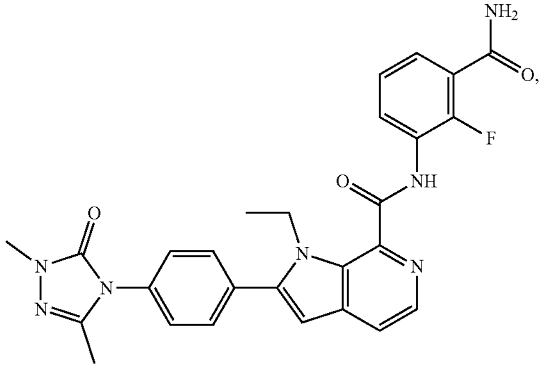 [SMILES: CCn1c(-c2ccc(-n3c(C)nn(C)c3=O)cc2)cc2ccnc(C(=O)Nc3cccc(C(N)=O)c3F)c21]

-continued
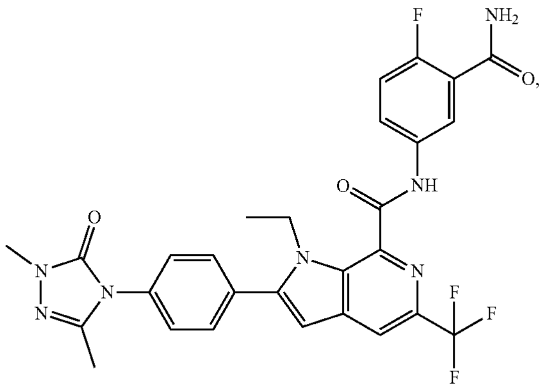 [SMILES: CCn1c(-c2ccc(-n3c(C)nn(C)c3=O)cc2)cc2cc(C(F)(F)F)nc(C(=O)Nc3ccc(F)c(C(N)=O)c3)c21]
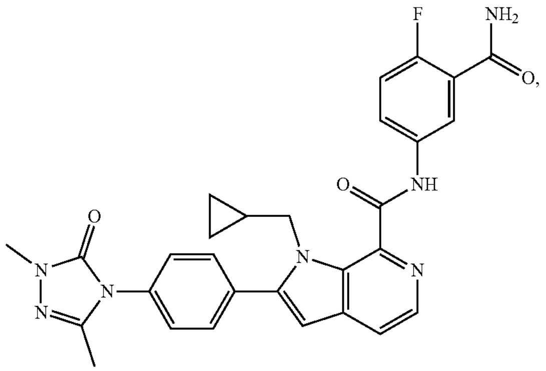 [SMILES: Cc1nn(C)c(=O)n1-c1ccc(-c2cc3ccnc(C(=O)Nc4ccc(F)c(C(N)=O)c4)c3n2CC2CC2)cc1]
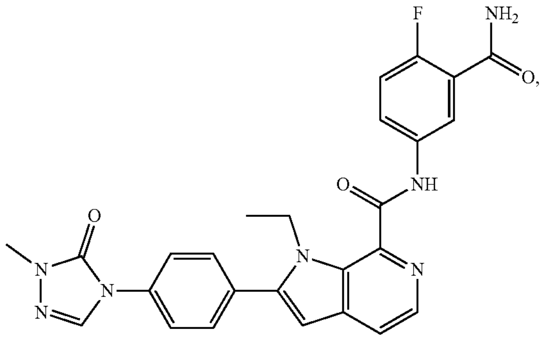
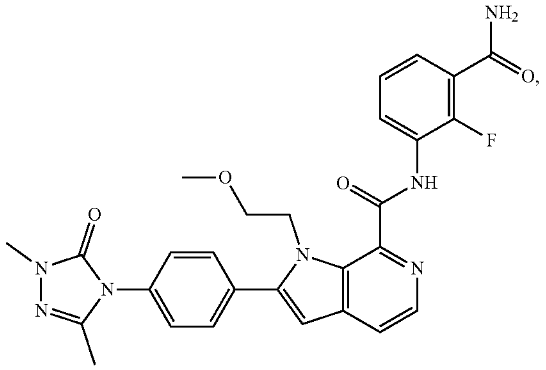
-continued
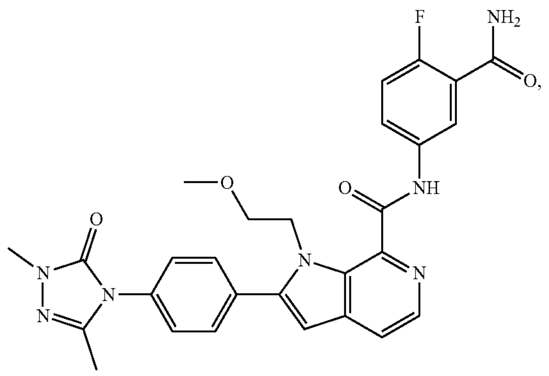
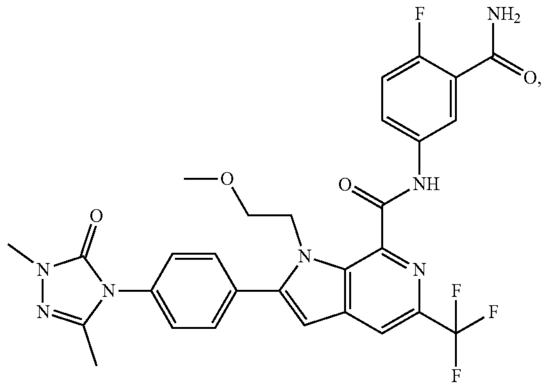
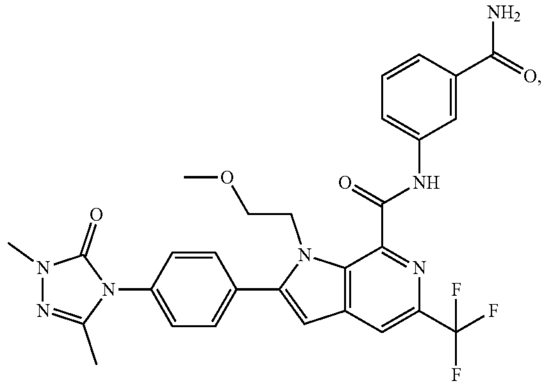
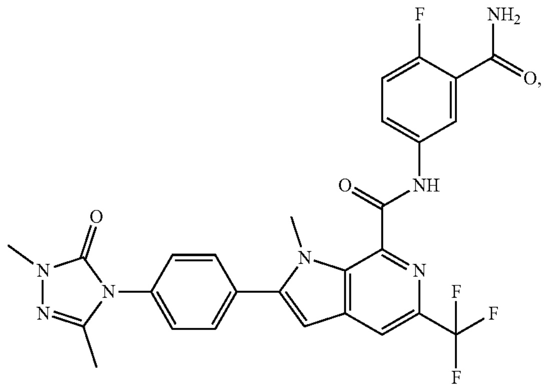

-continued
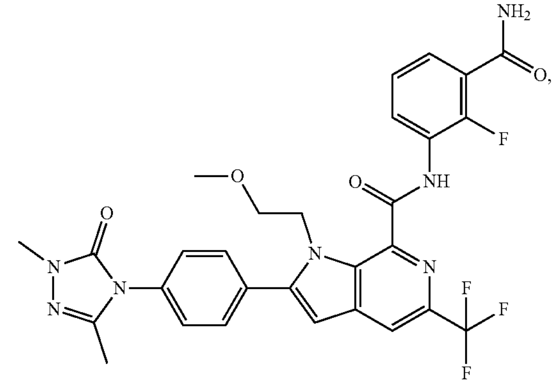
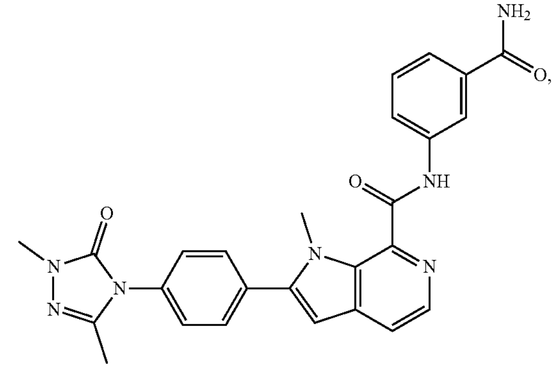
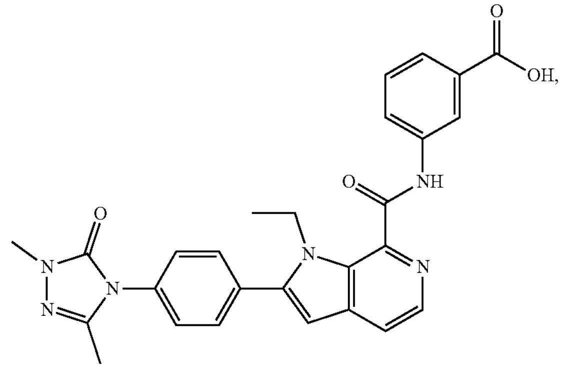
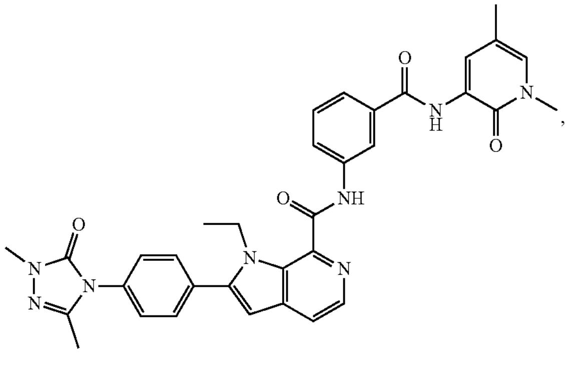
-continued
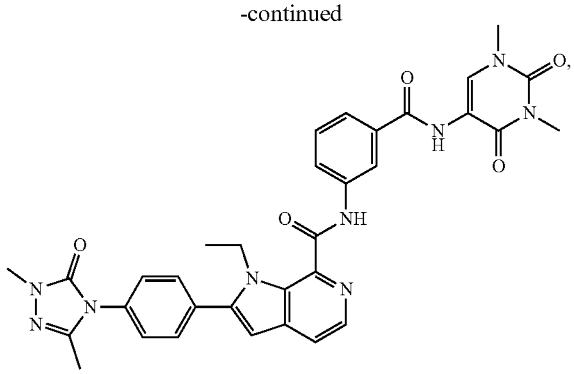
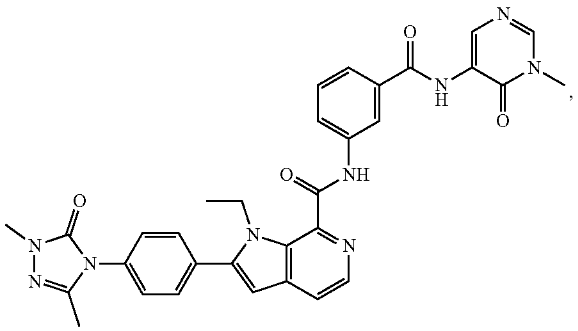
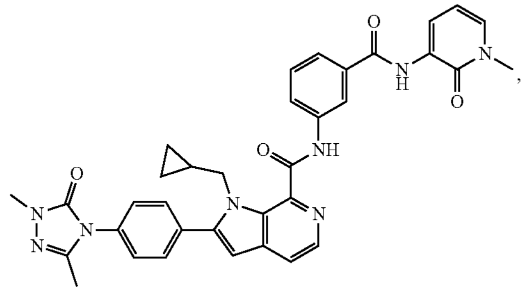
and
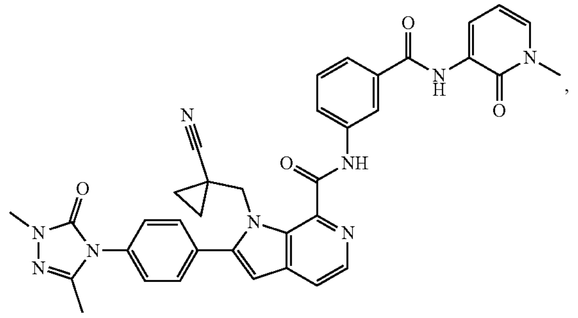
or a pharmaceutically acceptable salt thereof.
2. The compound of claim 1, wherein the compound is selected from the group consisting of:

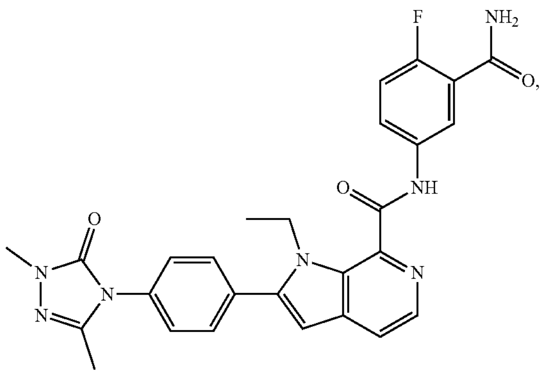
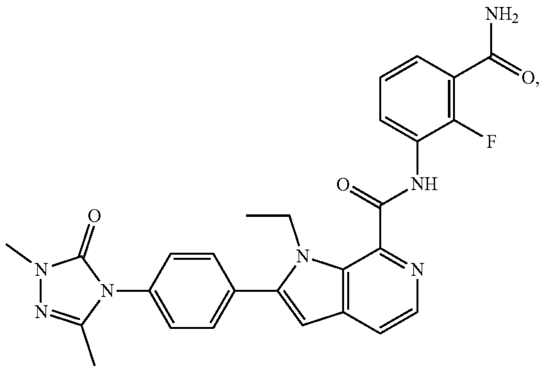
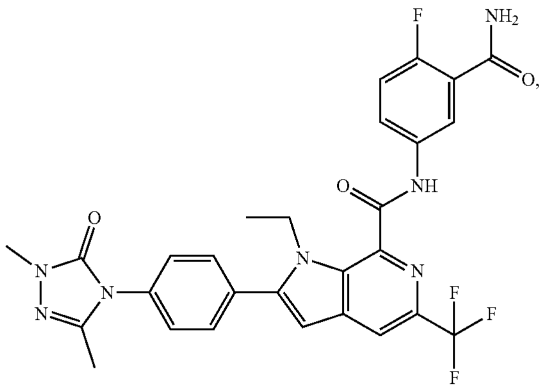
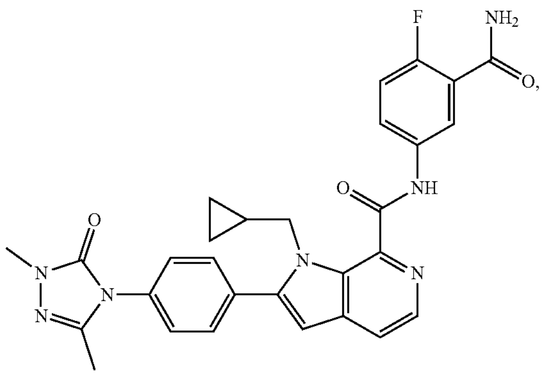
-continued
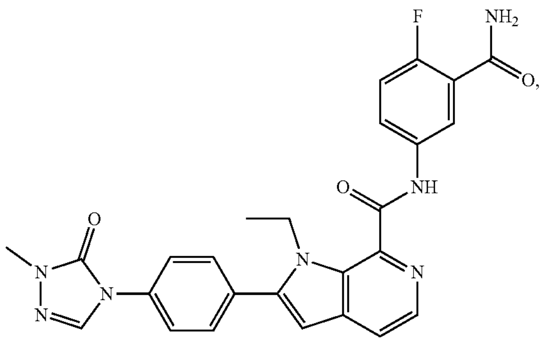
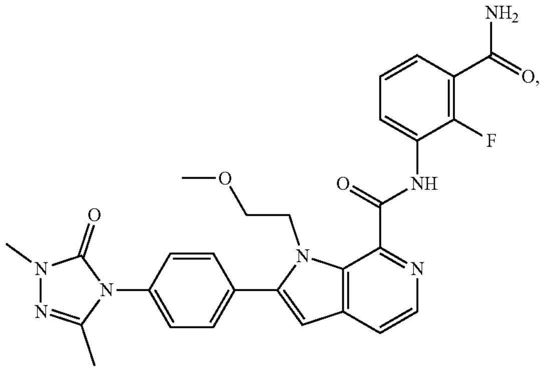
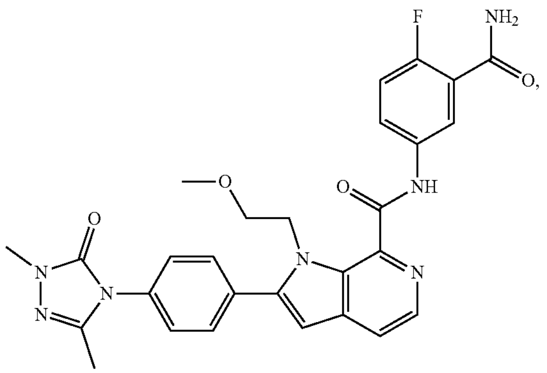
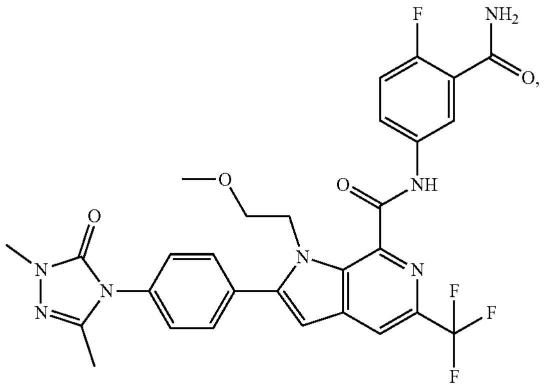

-continued
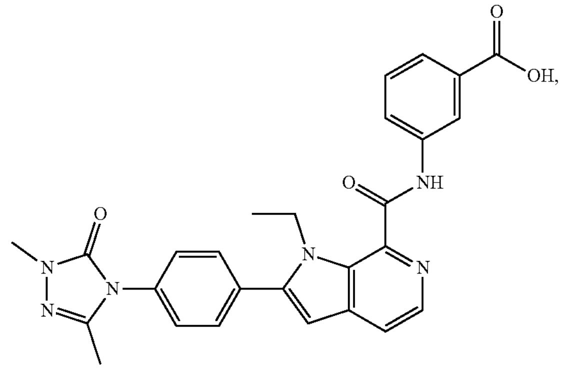
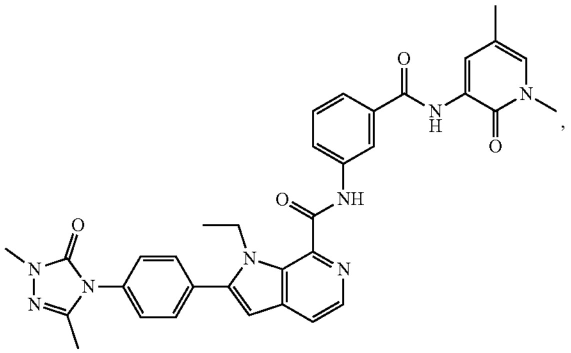
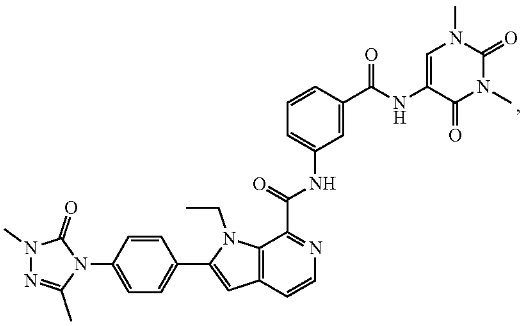
and
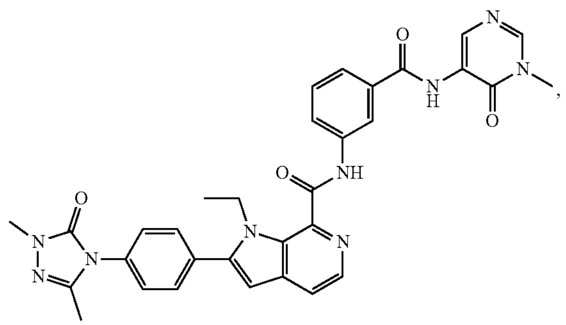
or a pharmaceutically acceptable salt thereof.
3. The compound of claim 2, wherein the compound
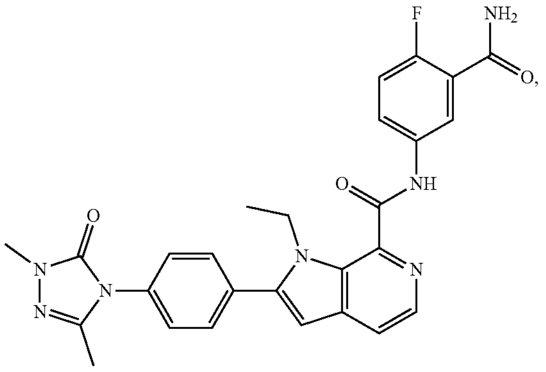
or a pharmaceutically acceptable salt thereof.
4. The compound of claim 2, wherein the compound is:
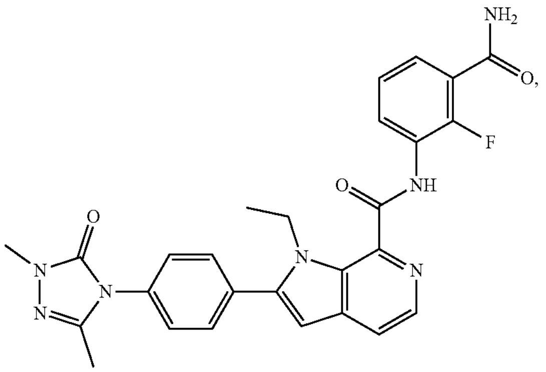
or a pharmaceutically acceptable salt thereof.
5. The compound of claim 2, wherein the compound is:
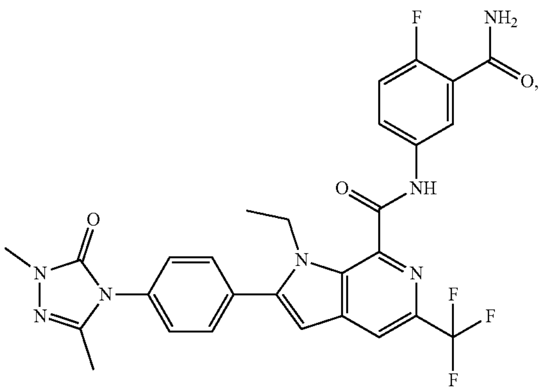
or a pharmaceutically acceptable salt thereof.

6. The compound of claim 2, wherein the compound is:

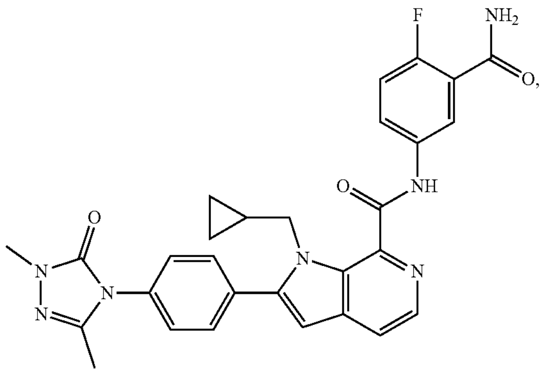

or a pharmaceutically acceptable salt thereof.

7. The compound of claim 2, wherein the compound

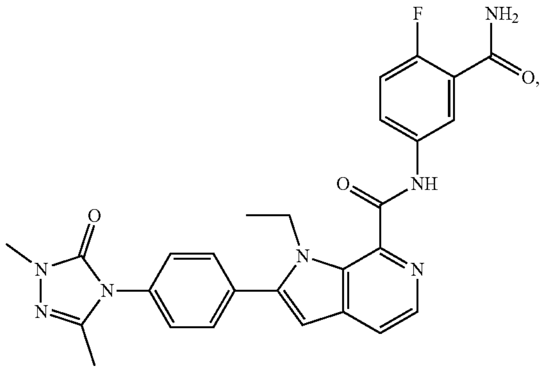 [SMILES: CCn1c(-c2ccc(-n3c(C)nn(C)c3=O)cc2)cc2ccnc(C(=O)Nc3ccc(F)c(C(N)=O)c3)c21]

or a pharmaceutically acceptable salt thereof.

8. The compound of claim 2, wherein the compound is:

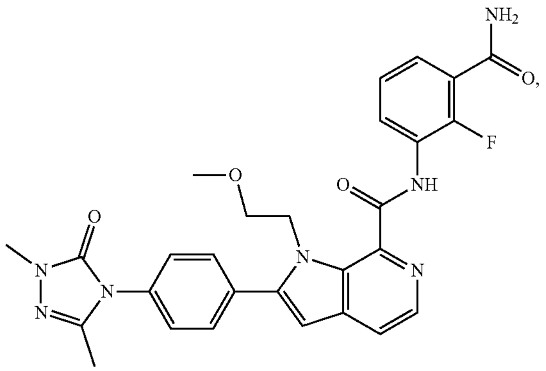 [SMILES: COCCn1c(-c2ccc(-n3c(C)nn(C)c3=O)cc2)cc2ccnc(C(=O)Nc3cccc(C(N)=O)c3F)c21]

or a pharmaceutically acceptable salt thereof.

9. The compound of claim 2, wherein the compound is:

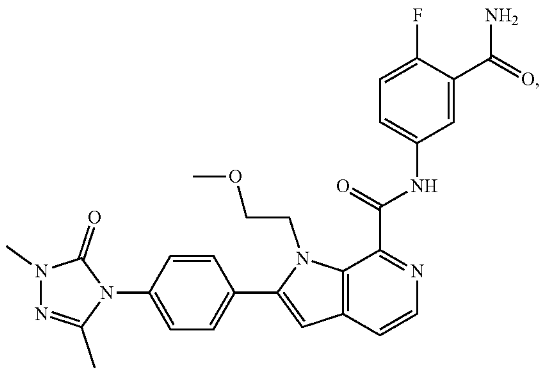 [SMILES: COCCn1c(-c2ccc(-n3c(C)nn(C)c3=O)cc2)cc2ccnc(C(=O)Nc3ccc(F)c(C(N)=O)c3)c21]

or a pharmaceutically acceptable salt thereof.

10. The compound of claim 2, wherein the compound is:

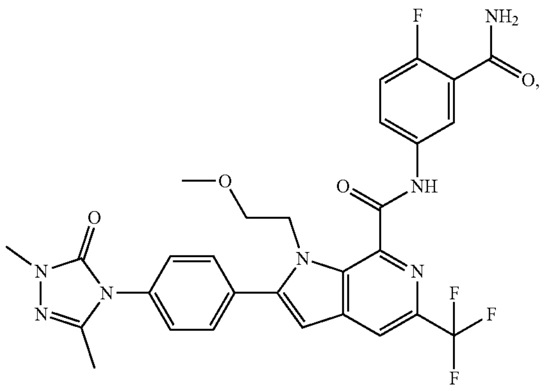 [SMILES: COCCn1c(-c2ccc(-n3c(C)nn(C)c3=O)cc2)cc2cc(C(F)(F)F)nc(C(=O)Nc3ccc(F)c(C(N)=O)c3)c21]

or a pharmaceutically acceptable salt thereof.

11. The compound of claim 2, wherein the compound is:

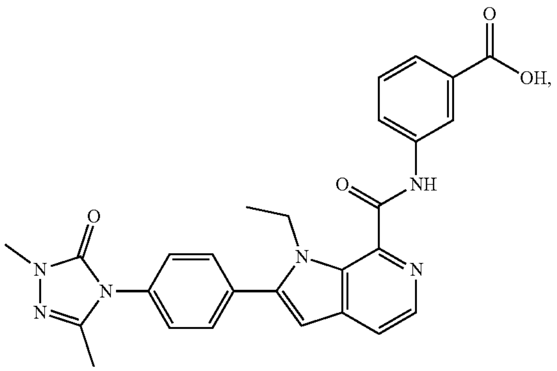 [SMILES: CCn1c(-c2ccc(-n3c(C)nn(C)c3=O)cc2)cc2ccnc(C(=O)Nc3cccc(C(=O)O)c3)c21]

or a pharmaceutically acceptable salt thereof.

12. The compound of claim 2, wherein the compound is:

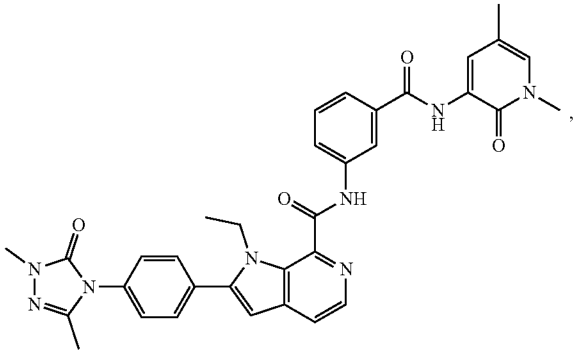

or a pharmaceutically acceptable salt thereof.

13. The compound of claim 2, wherein the compound is:

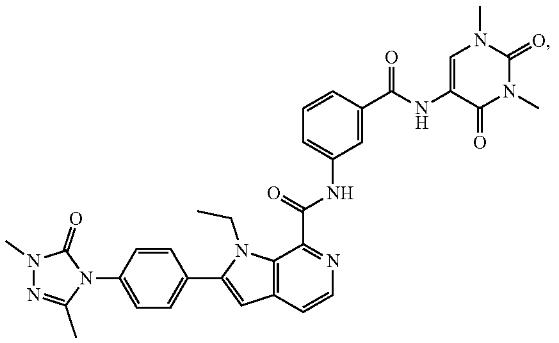

or a pharmaceutically acceptable salt thereof.

14. The compound of claim 2, wherein the compound is:

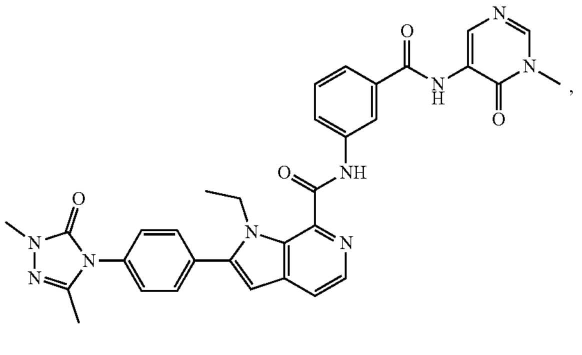

or a pharmaceutically acceptable salt thereof.

15. The compound of claim 1, wherein the compound is selected from the group consisting of:

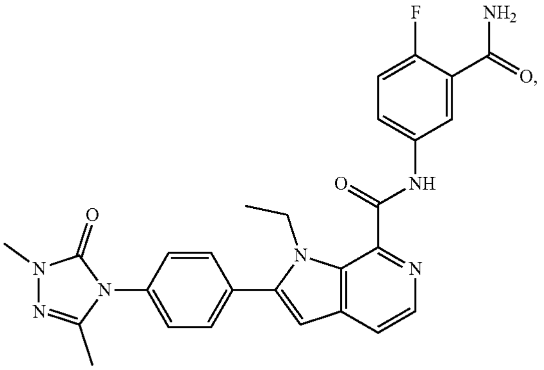

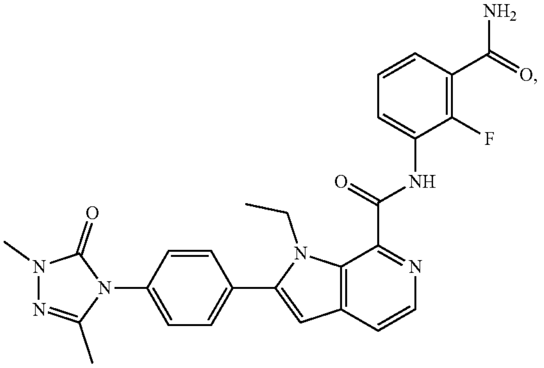

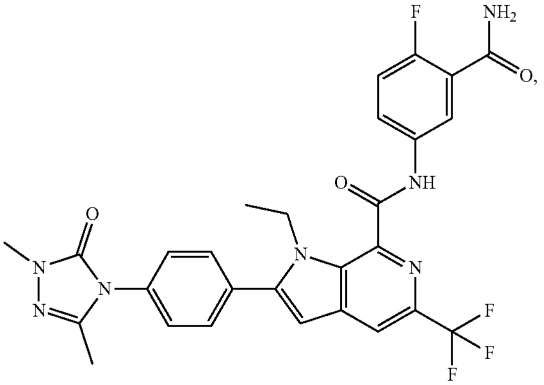

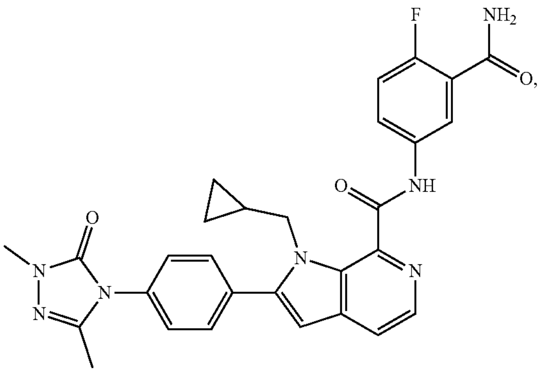

-continued
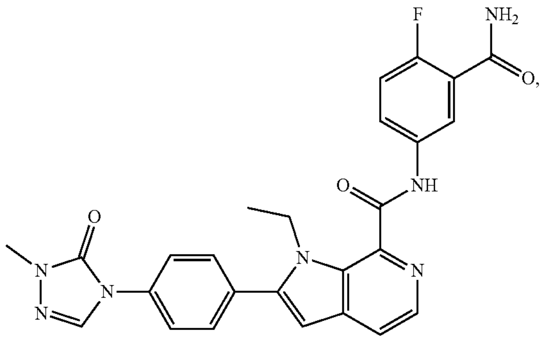
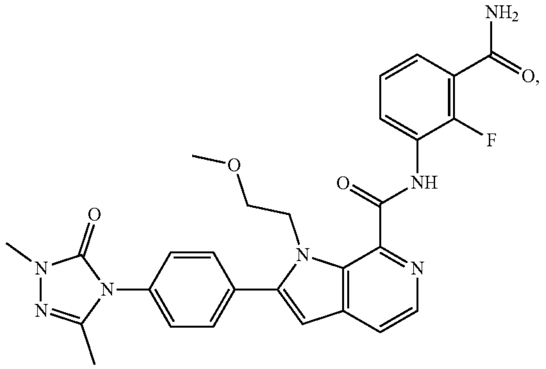
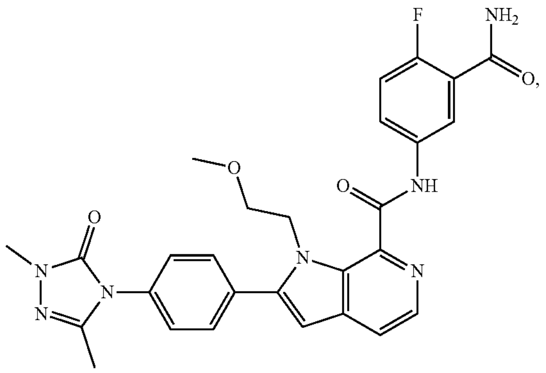
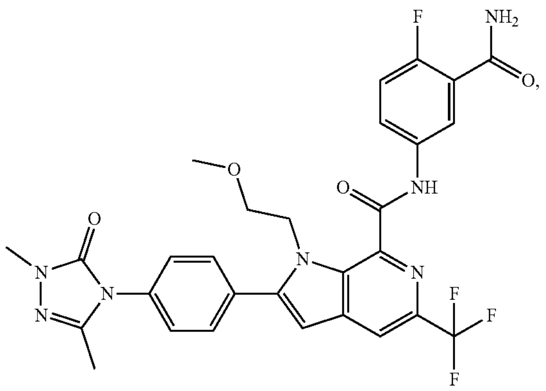
-continued
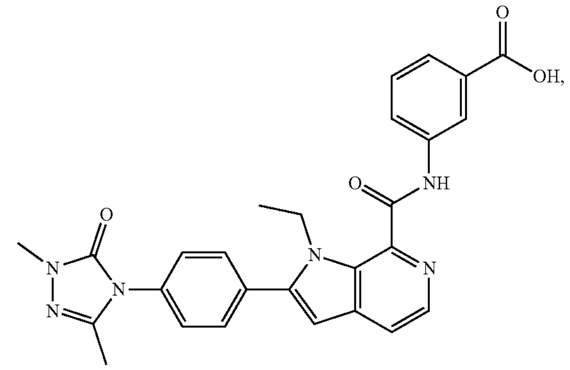
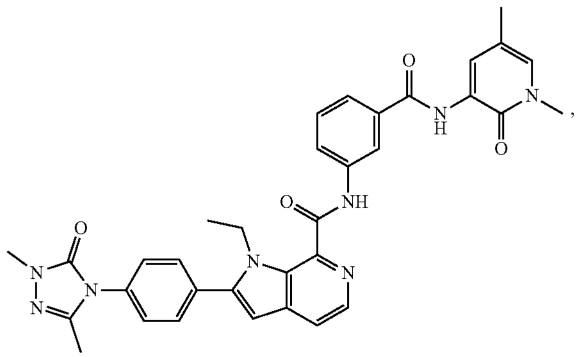
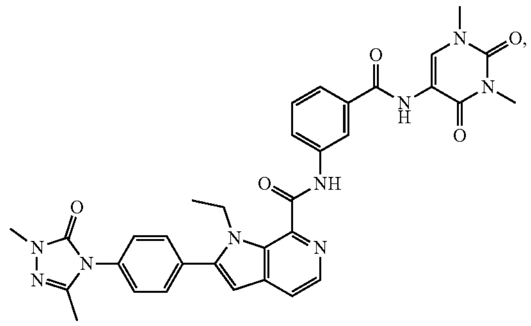
and
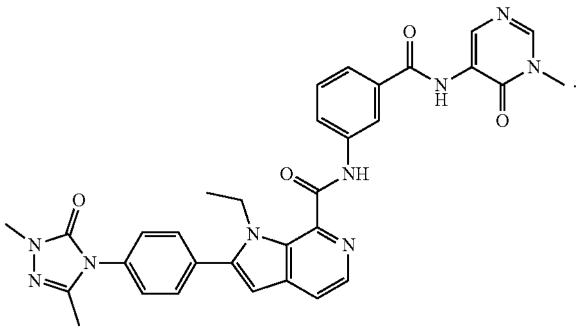

16. The compound of claim 15, wherein the compound is:
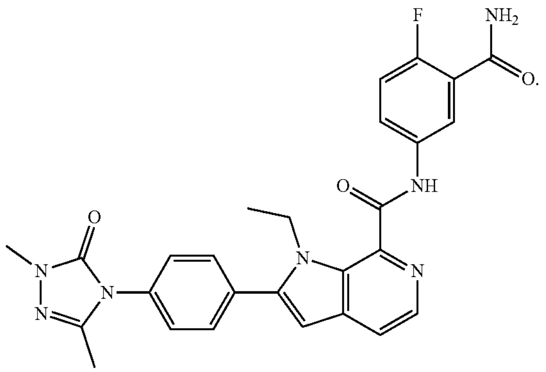 [SMILES: CCn1c(-c2ccc(-n3c(C)nn(C)c3=O)cc2)cc2ccnc(C(=O)Nc3ccc(F)c(C(N)=O)c3)c21]
17. The compound of claim 15, wherein the compound is:
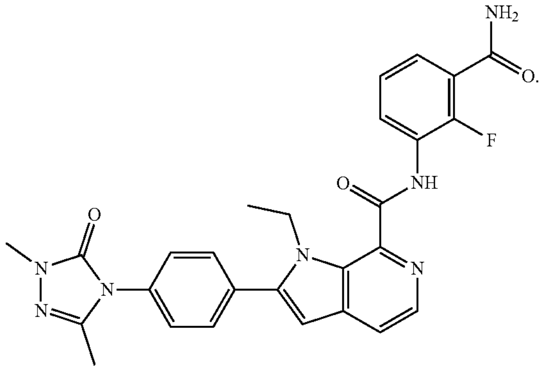 [SMILES: CCn1c(-c2ccc(-n3c(C)nn(C)c3=O)cc2)cc2ccnc(C(=O)Nc3cccc(C(N)=O)c3F)c21]
18. The compound of claim 15, wherein the compound is:
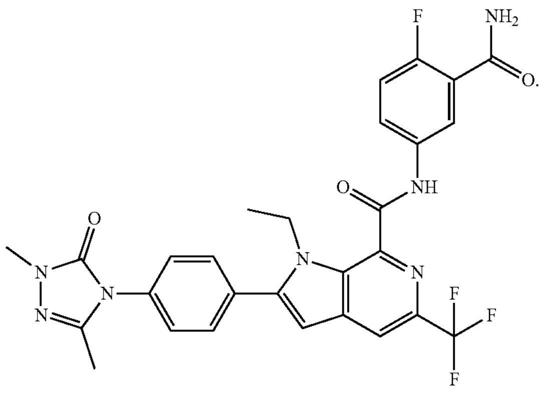 [SMILES: CCn1c(-c2ccc(-n3c(C)nn(C)c3=O)cc2)cc2cc(C(F)(F)F)nc(C(=O)Nc3ccc(F)c(C(N)=O)c3)c21]
19. The compound of claim 15, wherein the compound is:
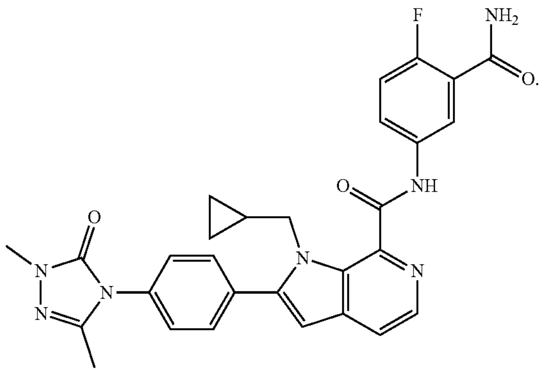 [SMILES: Cc1nn(C)c(=O)n1-c1ccc(-c2cc3ccnc(C(=O)Nc4ccc(F)c(C(N)=O)c4)c3n2CC2CC2)cc1]
20. The compound of claim 15, wherein the compound is:
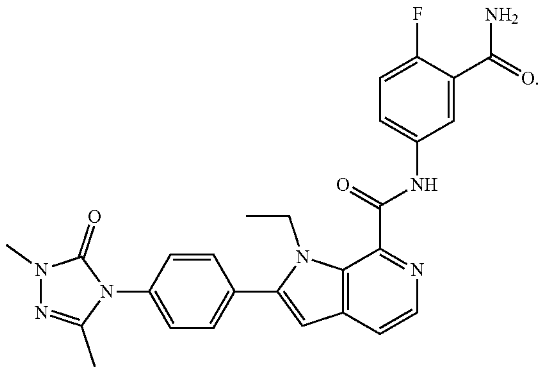 [SMILES: CCn1c(-c2ccc(-n3c(C)nn(C)c3=O)cc2)cc2ccnc(C(=O)Nc3ccc(F)c(C(N)=O)c3)c21]
21. The compound of claim 15, wherein the compound is:
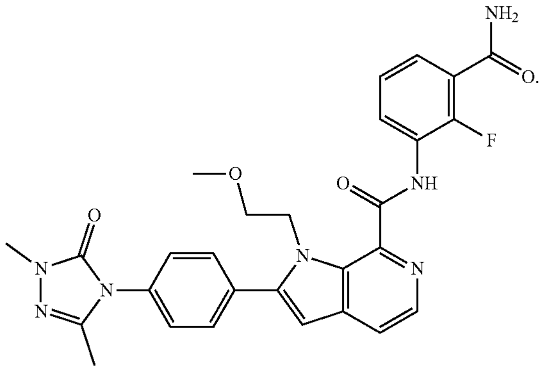 [SMILES: COCCn1c(-c2ccc(-n3c(C)nn(C)c3=O)cc2)cc2ccnc(C(=O)Nc3cccc(C(N)=O)c3F)c21]

22. The compound of claim 15, wherein the compound is:

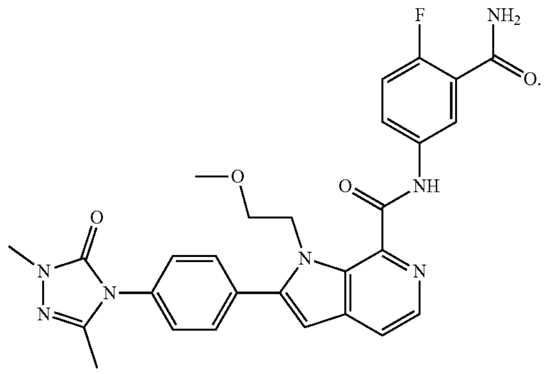 [SMILES: COCCn1c(-c2ccc(-n3c(C)nn(C)c3=O)cc2)cc2ccnc(C(=O)Nc3ccc(F)c(C(N)=O)c3)c21]

23. The compound of claim 15, wherein the compound is:

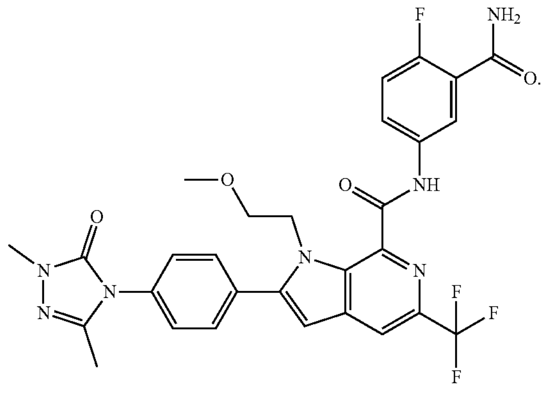 [SMILES: COCCn1c(-c2ccc(-n3c(C)nn(C)c3=O)cc2)cc2cc(C(F)(F)F)nc(C(=O)Nc3ccc(F)c(C(N)=O)c3)c21]

24. The compound of claim 15, wherein the compound is:

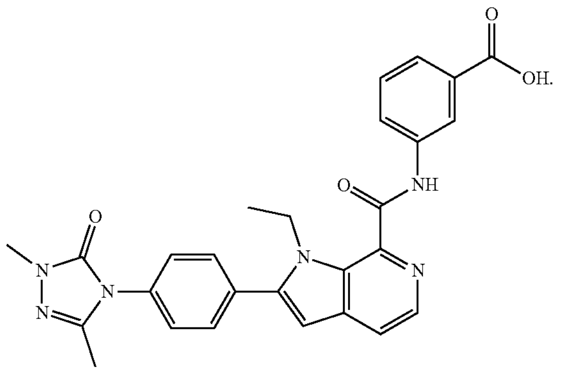 [SMILES: CCn1c(-c2ccc(-n3c(C)nn(C)c3=O)cc2)cc2ccnc(C(=O)Nc3cccc(C(=O)O)c3)c21]

25. The compound of claim 15, wherein the compound is:

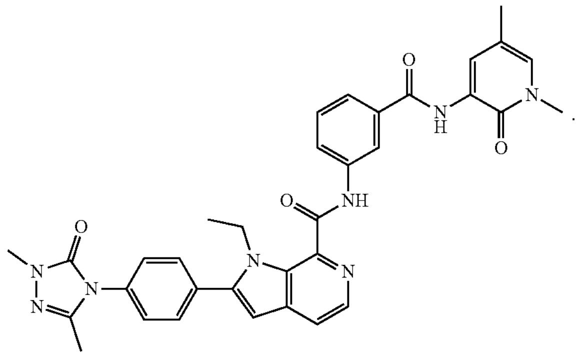

26. The compound of claim 15, wherein the compound is:

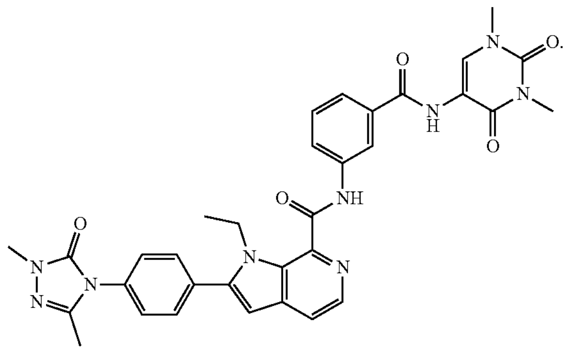

27. The compound of claim 15, wherein the compound is:

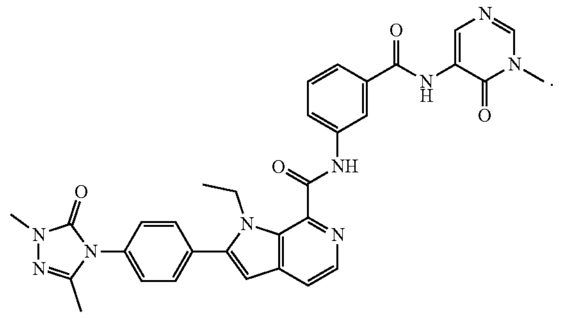

28. A medicament comprising the compound according to claim 1, or a pharmaceutically acceptable salt thereof, with a pharmaceutically acceptable carrier.

29. A medicament comprising the compound according to claim 2, or a pharmaceutically acceptable salt thereof, with a pharmaceutically acceptable carrier.

30. A medicament comprising the compound according to claim 15 with a pharmaceutically acceptable carrier.

* * * * *